(12) United States Patent
Blaquiere et al.

(10) Patent No.: US 11,597,733 B2
(45) Date of Patent: Mar. 7, 2023

(54) COMPOUNDS AND COMPOSITIONS FOR THE TREATMENT OF PARASITIC DISEASES

(71) Applicant: Novartis AG, Basel (CH)

(72) Inventors: Nicole Alice Blaquiere, Oakland, CA (US); Richard Yichong Huang, El Cerrito, CA (US); Thomas Martin Kirrane, Jr., San Ramon, CA (US); Andreas Kordikowski, Binningen (CH); Anne-Catherine Mata, Berkeley, CA (US); Christopher Ronald Sarko, San Ramon, CA (US); Benjamin Robert Taft, Lafayette, CA (US); Grace Lamprecht Waldron, Rancho Palos Verdes, CA (US); Fumiaki Yokokawa, Dublin, CA (US); Tingying Zhu, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/076,126

(22) Filed: Oct. 21, 2020

(65) Prior Publication Data

US 2021/0115065 A1  Apr. 22, 2021

Related U.S. Application Data

(60) Provisional application No. 62/923,915, filed on Oct. 21, 2019.

(51) Int. Cl.

| | |
|---|---|
| *C07D 513/04* | (2006.01) |
| *C07D 519/00* | (2006.01) |
| *A61K 31/4545* | (2006.01) |
| *A61K 31/433* | (2006.01) |
| *A61K 31/496* | (2006.01) |
| *A61K 45/06* | (2006.01) |
| *A61K 31/4439* | (2006.01) |
| *A61K 31/5386* | (2006.01) |
| *A61K 31/438* | (2006.01) |
| *A61K 31/5355* | (2006.01) |
| *A61K 31/499* | (2006.01) |
| *A61K 31/454* | (2006.01) |

(52) U.S. Cl.
CPC .......... *C07D 513/04* (2013.01); *A61K 31/433* (2013.01); *A61K 31/438* (2013.01); *A61K 31/4439* (2013.01); *A61K 31/454* (2013.01); *A61K 31/4545* (2013.01); *A61K 31/496* (2013.01); *A61K 31/499* (2013.01); *A61K 31/5355* (2013.01); *A61K 31/5386* (2013.01); *A61K 45/06* (2013.01); *C07D 519/00* (2013.01)

(58) Field of Classification Search
CPC .. C07D 285/02; C07D 285/12; A61K 31/433; A61K 31/4545; A61K 31/4439
See application file for complete search history.

(56) References Cited

U.S. PATENT DOCUMENTS

| | | |
|---|---|---|
| 4,444,770 A | 4/1984 | Meyer et al. |
| 4,585,873 A | 4/1986 | Ingendoh et al. |
| 2017/0291894 A1 | 10/2017 | Patil et al. |

FOREIGN PATENT DOCUMENTS

| | | | |
|---|---|---|---|
| AU | 2009275544 A1 | 2/2010 | |
| AU | 2010231162 A1 | 11/2011 | |
| AU | 2013292529 A1 | 2/2015 | |
| DK | 113283 A | 9/1983 | |
| EP | 0238070 A2 | 9/1987 | |
| PT | 73058 A | 6/1981 | |
| WO | 2009040552 A2 | 4/2009 | |
| WO | 2010012345 A1 | 2/2010 | |
| WO | 2010112874 A1 | 10/2010 | |
| WO | 12020215 A1 | 2/2012 | |
| WO | 12020217 A1 | 2/2012 | |
| WO | WO-2012020215 A1 * | 2/2012 | ........... C07D 513/04 |
| WO | 2014015167 A3 | 1/2014 | |
| WO | 2014078813 A1 | 5/2014 | |
| WO | 18022802 A1 | 2/2018 | |

OTHER PUBLICATIONS

Darter, T.A. et al. "Inhibition of drug-resistant mutants of ABL, KIT, and EGF receptor kinases," Proc. Natl. Acad. Sci. USA 102, 11011-11016 (2005).
Fabian, M.A. et al. "A small molecule-kinase interaction map for clinical kinase inhibitors," Nat. Biotechnol. 23, 329-336 (2005).

(Continued)

*Primary Examiner* — Theodore R. Howell
*Assistant Examiner* — George W Kosturko
(74) *Attorney, Agent, or Firm* — Emily T. Wu

(57) ABSTRACT

The present invention provides a compound of formula (Ia) or a pharmaceutically acceptable salt thereof;

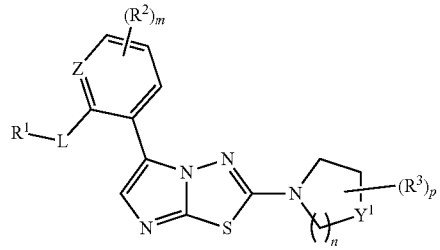

a method for manufacturing the compounds of the invention, solid forms, combinations of pharmacologically active agents, pharmaceutical compositions and methods of using such compounds and solid forms thereof to treat or prevent parasitic diseases, for example malaria.

12 Claims, 8 Drawing Sheets

(56) References Cited

OTHER PUBLICATIONS

Hill, A.V. The possible effects of the aggregation of the molecules of haemoglobin on its dissociation curves. J. Physiol., 1910, 40, iv-vii.
Karaman, M.W. et al. "A quantitative analysis of kinase inhibitor selectivity," Nat. Biotechnol. 26, 127-132 (2008).
"Levenberg, K., ""A Method for the Solution of Certain Non-Linearproblems in Least Squares,"" A Q. Appl. Math. 2, 164-168 (1944)".
Saulnier et al., "An efficient method for the synthesis of guanidino prodrugs," (1994), Bioorganic and Medicinal Chemistry Letters, vol. 4, p. 1985.
Derbyshire, et al., "Chemical Interrogation of the Malaria Kinome," ChemBioChem, vol. 15, Aug. 2014, pp. 1920-1930.
Arang, et al., "Identifying host regulators and inhibitors of liver stage malaria infection using kinase activity profiles," Nature Communications, vol. 8, Article No. 1232 (2017).

\* cited by examiner

COMPOUNDS AND COMPOSITIONS FOR THE TREATMENT OF PARASITIC DISEASES

This application claims priority to U.S. provisional application Ser. No. 62/923,915, filed 21 Oct. 2019, which is hereby incorporated in its entirety.

BACKGROUND OF THE INVENTION

Field of the Invention

The invention provides a class of compounds, pharmaceutical compositions comprising such compounds and methods of using such compounds to treat or prevent parasitic diseases, such as malaria.

Background

Malaria is an infectious disease caused by four protozoan parasites: *Plasmodium falciparum*; *Plasmodium vivax*; *Plasmodium ovale*; and *Plasmodium malaria*. These four parasites are typically transmitted by the bite of an infected female Anopheles mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

International patent applications WO 2012/020215 and WO 2012/020217 disclose various amino-imidazolothiadiazoles for use as protein or lipid kinase inhibitors. However, for the treatment of malaria, there is a need for targeted therapies which may be selective (i.e. may inhibit a certain targeted molecule more selectively as compared to other molecular targets, e.g. protein or lipid kinases, e.g. as described hereinafter), which may have the benefit of reducing side effects and may also have a benefit that malaria can be treated selectively.

In view of the foregoing, there remains a need to develop novel compounds as selective antiparasitic agents. The invention provides such compounds, pharmaceutically acceptable salts thereof, solid forms thereof, pharmaceutical compositions thereof and combinations thereof. The invention further provides methods of treating, preventing, or ameliorating parasitic disease, comprising administering to a subject in need thereof an effective amount of a compound of the invention.

SUMMARY OF THE INVENTION

In one aspect, the present invention provides a compound selected from Formula Ia:

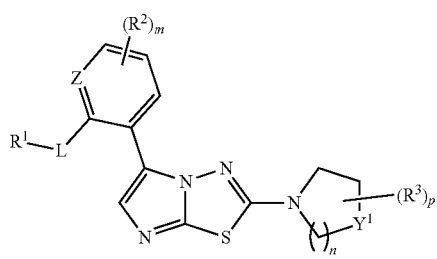

Ia in which:

L is each independently selected from $NCH_3$, O and S;

Z is each independently selected from N and $CR^2$;

$Y^1$ is each independently selected from $C(R^3)_2$, O, $NR^3$ and S;

$R^1$ is each independently selected from $—C_{1-4}alkyl$; hydroxy-$C_{1-4}alkyl$-, alkoxy-$C_{1-4}alkyl$-, halo-$C_{1-4}alkyl$-, and $—X^1—C_{3-6}$-cycloalkyl;

$R^2$ is each independently selected from -hydrogen, $—C_{1-4}$ alkyl, $—C_{1-4}alkoxy$, halo-$C_{1-4}alkyl$-, -halo, and a saturated 3-6 membered carbocyclic ring or heterocyclic ring containing up to three heteroatoms selected from N, S and O, wherein carbocyclic or heterocyclic ring of $R^2$ is unsubstituted or substituted with 1 or 2 $C_{1-4}alkoxy$; or $R^1$ and a $R^2$ together with the atoms through which $R^1$ and $R^2$ are connected form a saturated, unsaturated or partially unsaturated 3-6 member heterocyclic ring containing up to three heteroatoms selected from N, S and O;

$R^3$ is each independently selected from hydrogen, $C_{1-4}$alkyl, amino, $—X^1—R^{3a}$, $—NH—X^1—R^{3a}$, hydroxy-substituted-$C_{1-4}alkyl$; $C_{1-4}alkoxy$-substituted-$C_{1-4}alkyl$; hydroxy, oxo, halo, $—X^1—CO_2H$, $—X^1—CO_2NH_2$, $—X^1—SO_2C_{1-4}$ alkyl, $—X^1—SO_2N(C_{1-4}alkyl)_2$, $—X^1—C_{3-6}$-cycloalkyl;

$R^{3a}$ is each independently selected amino, $—CO—C_{1-4}$ alkyl, and 3-6 member, saturated, unsaturated or partially unsaturated heterocyclic ring containing up to three heteroatoms selected from N, $NR_{30}$, $S(O)_{0-2}$ and O, wherein the heterocyclic ring of $R^{3a}$ is unsubstituted or substituted with 1 or 2 hydroxy or amino; or any two $R^3$ together with the atoms through which $R^3$ are connected form a saturated, unsaturated or partially unsaturated 3-6 member carbocyclic or heterocyclic ring containing up to three heteroatoms selected from N, $NR^4$, $S(O)_{0-2}$ and O; wherein the $C_{3-6}$cycloalkyl of $R^3$ is unsubstituted or substituted with 1 to 4 $R^4$ independently selected from $C_{1-4}alkyl$, amino, amino-$C_{1-4}alkyl$, $C_{1-4}alkoxy$, hydroxy, $—X^1CO_2R^{4a}$, $—X^1COR^{4a}$, $—X^1C(O)NR^{4a}R^{4b}$, $—X^1$-cycloalkyl-$R^{4a}$, $R^{4a}$ and $R^{4b}$ are each independently selected from hydrogen, amino, and aminosubstituted-$C_{1-4}alkyl$;

$X^1$ is each independently selected from a bond and $C_{1-4}$alkylene;

n is each independently selected from 0, 1 and 2;

m is each independently selected from 0, 1, 2, and 3;

p is each independently selected from 0, 1, 2, 3 and 4; or individual isomers and mixture of isomers thereof; or a pharmaceutically acceptable salt thereof.

In a second aspect, the present invention provides a solid form of the compound 4-(aminomethyl)-1-(5-(6-isopropyl-2-methoxypyridin-3-yl)imidazo[2,1-b][1,3,4]thiadiazol-2-yl)piperidin-4-ol, and salts thereof.

In a third aspect, the present invention provides a pharmaceutical composition which contains a compound selected from Formula Ia, individual isomers and mixture of isomers thereof; or a pharmaceutically acceptable salt thereof, solid forms thereof in admixture with one or more suitable excipients.

In a fourth aspect, the present invention provides a method of treating a disease in an animal in which a compound of the invention can prevent, inhibit or ameliorate the pathology and/or symptomology of disease caused by a parasite (such as, for example, *Plasmodium falciparum, Plasmodium vivax, Plasmodium ovale, Plasmodium malaria, Trypanosoma cruzi* or a parasite of the *Leishmania* genus such as, for example, *Leishmania donovani*) which method comprises administering to the animal a therapeutically effective amount of a compound selected from Formula Ia, individual isomers or mixture of isomers thereof, or a pharmaceutically acceptable salt thereof.

In a fifth aspect, the present invention provides the use of a compound selected from Formulae Ia, Ib, Ic, Id, Ie, If, Ig, Ih, Ii or Ij or a compound of the Examples in the manufacture of a medicament for treating a disease caused by a parasite in an animal. The disease may be malaria.

In a sixth aspect, the present invention provides a process for preparing compounds selected from Formula Ia, prodrug derivatives, individual isomers or mixture of isomers thereof, or a pharmaceutically acceptable salt thereof.

Other aspects of the invention will become evident from the following more detailed description of the invention and the claims.

DETAILED DESCRIPTION OF THE INVENTION

Definitions

Figure 1:
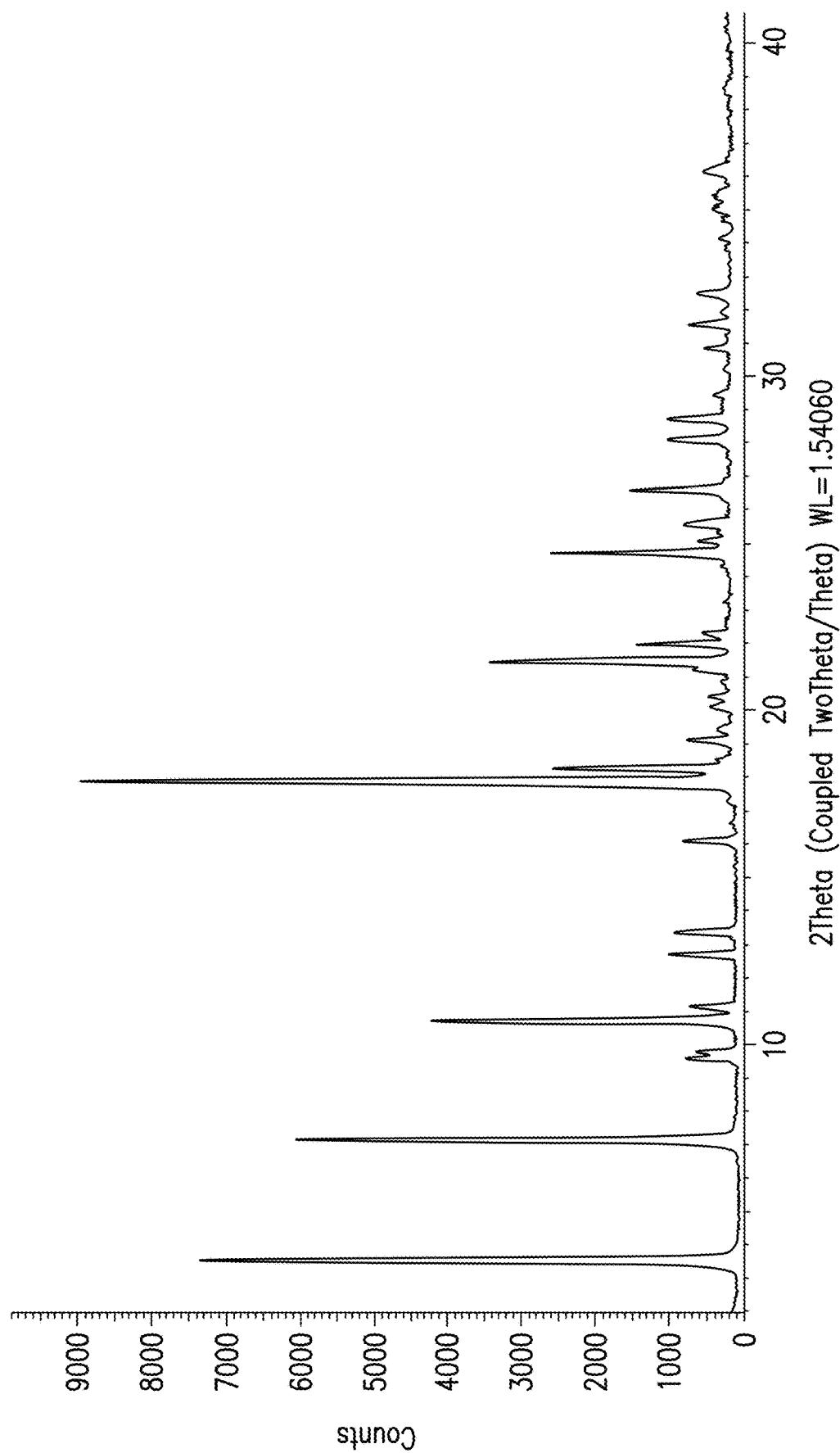
FIG. 1 provides the X-ray diffraction pattern for crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

As used herein, the term "$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, isopropoxy, butoxy, isobutoxy, pentoxy, and hexoxy.

As used herein, the term "$C_{1-6}$alkoxy$C_{1-6}$alkyl" refers to a radical of the formula —$R_a$—O—$R_a$ where each $R_a$ is independently a $C_{1-6}$alkyl radical as defined above. The oxygen atom may be bonded to any carbon atom in either alkyl radical. Examples of $C_{1-6}$alkoxy $C_{1-6}$alkyl include, but are not limited to, methoxy-methyl, methoxy-ethyl, ethoxy-ethyl, 1-ethoxy-propyl and 2-methoxy-butyl.

As used herein, the term "hydroxy$C_{1-6}$alkyl" refers to a $C_{1-6}$alkyl radical as defined above, wherein one of the hydrogen atoms of the $C_{1-6}$alkyl radical is replaced by OH. Examples of hydroxy$C_{1-6}$alkyl include, but are not limited to, hydroxy-methyl, 2-hydroxy-ethyl, 2-hydroxy-propyl, 3-hydroxy-propyl and 5-hydroxy-pentyl.

As used herein, the term "amino$C_{1-6}$alkyl" refers to a $C_{1-6}$alkyl radical as defined above, wherein one of the hydrogen atoms of the $C_{1-6}$alkyl group is replaced by a primary amino group. Representative examples of amino$C_{1-6}$alkyl include, but are not limited to, amino-methyl, 2-amino-ethyl, 2-amino-propyl, 3-amino-propyl, 3-amino-pentyl and 5-amino-pentyl.

As used herein, the term "$C_{1-4}$alkylamino" refers to a radical of the formula —NH—$R_a$ where $R_a$ is a $C_{1-4}$alkyl radical as defined above.

As used herein, the term "$C_{3-8}$cycloalkyl$C_{0-6}$alkyl" refers to a stable monocyclic saturated hydrocarbon radical consisting solely of carbon and hydrogen atoms, having from three to eight carbon atoms, and which is attached to the rest of the molecule by a single bond or by a $C_{1-6}$alkyl radical as defined above. Examples of $C_{3-8}$cycloalkyl$C_{0-6}$alkyl include, but are not limited to, cyclopropyl, cyclopropyl-methyl, cyclobutyl, cyclobutyl-ethyl, cyclopentyl, cyclopentyl-propyl, cyclohexyl, cyclohepty and cyclooctyl.

"Heterocyclic", "heterocyclyl" or "heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, 3-8 member heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" refers to bromo, chloro, fluoro or iodo.

As used herein, the term "halogen$C_{1-6}$alkyl" refers to $C_{1-6}$alkyl radical, as defined above, substituted by one or more halo radicals, as defined above. Examples of halogen$C_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "heterocyclyl" or "heterocyclic" refers to a stable 4-, 5-, 6- or 7-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

As used herein, the term "heterocyclylC$_{0-6}$alkyl" refers to a heterocyclic ring as defined above which is attached to the rest of the molecule by a single bond or by a C$_{1-6}$alkyl radical as defined above.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

DESCRIPTION OF THE EMBODIMENTS

The invention provides a novel class of compounds, pharmaceutical compositions comprising such compounds and methods of using such compounds to treat or prevent diseases or disorders associated with a parasite. In particular, the compounds can be used to treat malaria.

In one embodiment, with reference to compounds of Formula Ia:

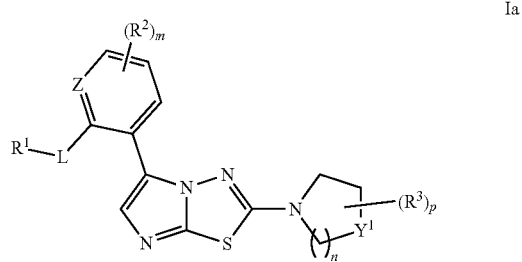

L is each independently selected from NCH$_3$, O and S;

Z is each independently selected from N and CR$^2$;

Y$^1$ is each independently selected from C(R$^3$)$_2$; O, NR$^3$ and S;

R$^1$ is each independently selected from —C$_{1-4}$alkyl; hydroxy-C$_{1-4}$alkyl-, alkoxy-C$_{1-4}$alkyl-, halo-C$_{1-4}$alkyl-, and —X$^1$—C$_{3-6}$-cycloalkyl;

R$^2$ is each independently selected from -hydrogen, —C$_{1-4}$alkyl, —C$_{1-4}$alkoxy, halo-C$_{1-4}$alkyl-, -halo, and a saturated 3-6 membered carbocyclic ring or heterocyclic ring containing up to three heteroatoms selected from N, S and O, wherein carbocyclic or heterocyclic ring of R$^2$ is unsubstituted or substituted with 1 or 2 C$_{1-4}$alkoxy; or R$^1$ and a R$^2$ together with the atoms through which R$^1$ and R$^2$ are connected form a saturated, unsaturated or partially unsaturated 3-6 member heterocyclic ring containing up to three heteroatoms selected from N, S and O;

R$^3$ is each independently selected from hydrogen, C$_{1-4}$alkyl, amino, —X$^1$—R$^{3a}$, —NH—X$^1$—R$^{3a}$, hydroxy-substituted-C$_{1-4}$alkyl; C$_{1-4}$alkoxy-substituted-C$_{1-4}$alkyl; hydroxy, oxo, halo, —X$^1$—CO$_2$H, —X$^1$—CO$_2$NH$_2$, —X$^1$—SO$_2$C$_{1-4}$alkyl, —X$^1$—SO$_2$N(C$_{1-4}$alkyl)$_2$, —X$^1$—C$_{3-6}$-cycloalkyl;

R$^{3a}$ is each independently selected amino, —CO—C$_{1-4}$alkyl, and 3-6 member, saturated, unsaturated or partially unsaturated heterocyclic ring containing up to three heteroatoms selected from N, NR$_{30}$, S(O)$_{0-2}$ and O, wherein the heterocyclic ring of R$^{3a}$ is unsubstituted or substituted with 1 or 2 hydroxy or amino; or any two R$^3$ together with the atoms through which R$^3$ are connected form a saturated, unsaturated or partially unsaturated 3-6 member carbocyclic or heterocyclic ring containing up to three heteroatoms selected from N, NR$^4$, S(O)$_{0-2}$ and O; wherein the C$_{3-6}$cycloalkyl of R$^3$ is unsubstituted or substituted with 1 to 4 R$^4$ independently selected from C$_{1-4}$alkyl, amino, amino-C$_{1-4}$alkyl, C$_{1-4}$alkoxy, hydroxy, —X$^1$CO$_2$R$^{4a}$, —X$^1$COR$^{4a}$, —X$^1$C(O)NR$^{4a}$R$^{4b}$, —X$^1$-cycloalkyl-R$^{4a}$, R$^{4a}$ and R$^{4b}$ are each independently selected from hydrogen, amino, and aminosubstituted-C$_{1-4}$alkyl;

X$^1$ is each independently selected from a bond and C$_{1-4}$alkylene;

n is each independently selected from 0, 1 and 2;

m is each independently selected from 0, 1, 2, and 3;

p is each independently selected from 0, 1, 2, 3 and 4; or a pharmaceutically acceptable salt thereof.

In another embodiment, the compound has Formula Ib:

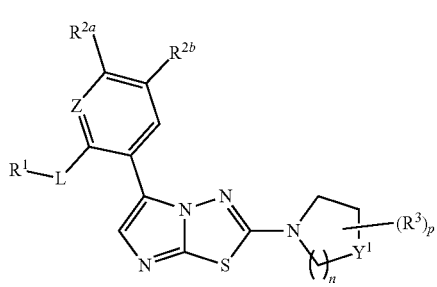

Ib wherein:

$R^{2a}$ and $R^{2b}$ is each independently selected from -hydrogen, —$C_{1-4}$alkyl, —$C_{1-4}$alkoxy, halo-$C_{1-4}$alkyl-, -halo, and a saturated 3-6 membered carbocyclic ring or heterocyclic ring containing up to three heteroatoms selected from N, S and O, wherein carbocyclic or heterocyclic ring of $R^2$ is unsubstituted or substituted with 1 or 2 $C_{1-4}$alkoxy.

In another embodiment, L is O. In another embodiment, L is NCH$_3$. In another embodiment, L is S;

In another embodiment, Z is N. In another embodiment, Z is $CR^2$.

In another embodiment, $Y^1$ is $C(R^3)_2$. In another embodiment, $Y^1$ is O. In another embodiment, $Y^1NR^3$. In another embodiment, $Y^1$ is S.

In another embodiment, $R^1$ is —$C_{1-4}$alkyl. In another embodiment, $R^1$ is hydroxy-$C_{1-4}$alkyl-. In another embodiment, $R^1$ is alkoxy-$C_{1-4}$alkyl-. In another embodiment, $R^1$ is halo-$C_{1-4}$alkyl-. In another embodiment, $R^1$ is —$X^1$—$C_{3-6}$-cycloalkyl.

In another embodiment, $R^2$ is -hydrogen. In another embodiment, $R^2$ is —$C_{1-4}$alkyl. In another embodiment, $R^2$ is —$C_{1-4}$alkoxy. In another embodiment, $R^2$ is halo-$C_{1-4}$alkyl-. In another embodiment, $R^2$ is -halo. In another embodiment, $R^2$ is a saturated 3-6 membered carbocyclic ring. In another embodiment, $R^2$ is heterocyclic ring containing up to three heteroatoms selected from N, S and O. In another embodiment, $R^2$ is carbocyclic or heterocyclic ring of $R^2$ is unsubstituted. In another embodiment, $R^2$ is substituted with 1 or 2 $C_{1-4}$alkoxy.

In another embodiment, $R^1$ and a $R^2$ together with the atoms through which $R^1$ and $R^2$ are connected form a saturated, unsaturated or partially unsaturated 3-6 member heterocyclic ring containing up to three heteroatoms selected from N, S and O.

In another embodiment, $X^1$ is bond. In another embodiment, $X^1$ is $C_{1-4}$alkylene.

In another embodiment, n is 0. In another embodiment, n is 1. In another embodiment, n is 2.

In another embodiment, m is 0. In another embodiment, m is 1. In another embodiment, m is 2. In another embodiment, m is 3.

In another embodiment, p is 0. In another embodiment, p is 1. In another embodiment, p is 2. In another embodiment, p is 3. In another embodiment, p is 4.

In another embodiment, the compound has Formula Ic:

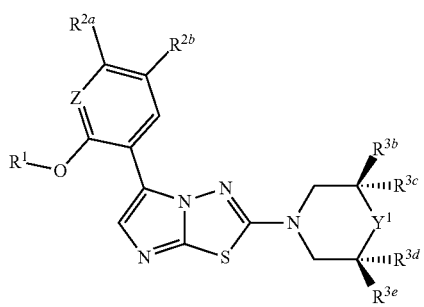

Ic $R^{3b}$, $R^{3c}$, $R^{3e}$, and $R^{3e}$ is each independently selected from hydrogen, $C_{1-4}$alkyl, amino, —$X^1$—$R^{3a}$, —NH—$X^1$—$R^{3a}$, hydroxy-substituted-$C_{1-4}$alkyl; $C_{1-4}$alkoxy-substituted-$C_{1-4}$alkyl; hydroxy, oxo, halo, —$X^1$—$CO_2H$, —$X^1$—$CO_2NH_2$, —$X^1$—$SO_2C_{1-4}$alkyl, —$X^1$—$SO_2N(C_{1-4}$alkyl$)_2$, and —$X^1$—$C_{3-6}$-cycloalkyl.

In another embodiment, the compound has Formula Id:

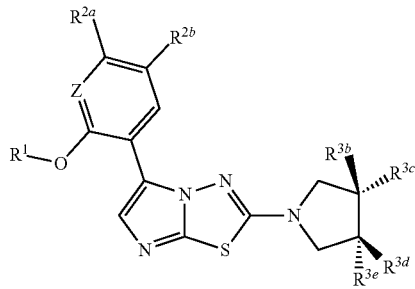

Id wherein:

$R^{3b}$, $R^{3c}$, $R^{3e}$, and $R^{3e}$ is each independently selected from hydrogen, $C_{1-4}$alkyl, amino, —$X^1$—$R^{3a}$, —NH—$X^1$—$R^{3a}$, hydroxy-substituted-$C_{1-4}$alkyl; $C_{1-4}$alkoxy-substituted-$C_{1-4}$alkyl; hydroxy, oxo, halo, —$X^1$—$CO_2H$, —$X^1$—$CO_2NH_2$, —$X^1$—$SO_2C_{1-4}$alkyl, —$X^1$—$SO_2N(C_{1-4}$alkyl$)_2$, and —$X^1$—$C_{3-6}$-cycloalkyl.

In another embodiment, the compound has Formula Ie:

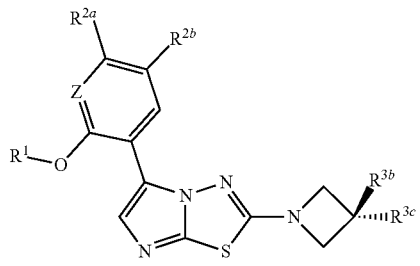

Ie wherein:

$R^{3b}$, and $R^{3c}$, is each independently selected from hydrogen, $C_{1-4}$alkyl, amino, —$X^1$—$R^{3a}$, —NH—$X^1$—$R^{3a}$, hydroxy-substituted-$C_{1-4}$alkyl; $C_{1-4}$alkoxy-substituted-$C_{1-4}$alkyl; hydroxy, oxo, halo, —$X^1$—$CO_2H$, —$X^1$—$CO_2NH_2$, —$X^1$—$SO_2C_{1-4}$alkyl, —$X^1$—$SO_2N(C_{1-4}$alkyl$)_2$, and —$X^1$—$C_{3-6}$-cycloalkyl.

In another embodiment, the compound has Formula If:

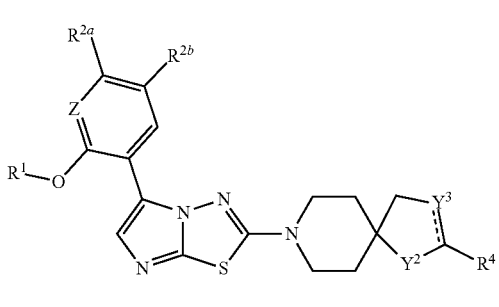

If wherein:

$Y^2$ is each independently selected from $C(R^4)_2$; O, $NR^4$ and S;

$Y^3$ is each independently selected from $C(R^4)_2$; O, $NR^4$ and S; and the dashed line represents that the bond is a single or double bond.

In another embodiment, the compound has Formula Ig:

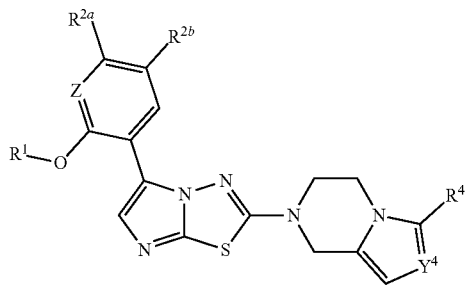

Ig wherein:

$Y^4$ is each independently selected from $C(R^4)_2$; O, $NR^4$ and S.

In another embodiment, the compound has Formula Ih:

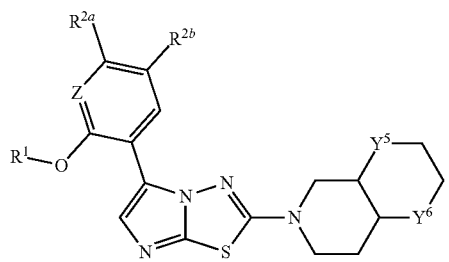

Ih wherein:

$Y^5$ is each independently selected from $C(R^4)_2$; O, $NR^4$ and S; and $Y^6$ is each independently selected from $C(R^4)_2$; O, $NR^4$ and S.

In another embodiment, m is 0. In another embodiment, m is 1. In another embodiment, m is 2. In another embodiment, m is 3.

In another embodiment, the compound has Formula Ii:

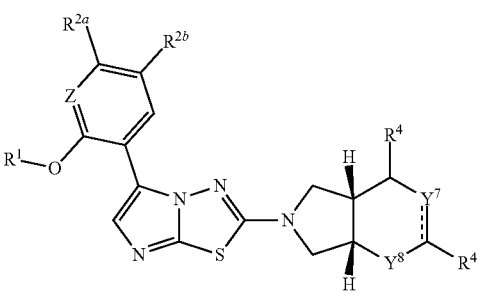

Ii wherein:

$Y^7$ is each independently selected from $C(R^4)_2$; O, $NR^4$ and S; and $Y^8$ is each independently selected from $C(R^4)_2$; O, $NR^4$ and S.

In another embodiment, the compound has Formula Ij:

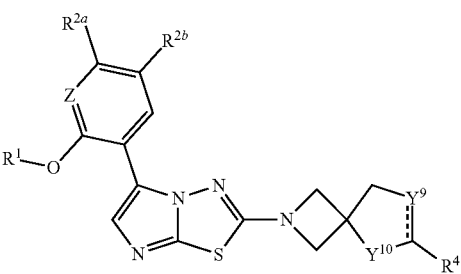

Ij wherein:

$Y^9$ is each independently selected from $C(R^4)_2$; O, $NR^4$ and S; and $Y^{10}$ is each independently selected from $C(R^4)_2$; O, $NR^4$ and S.

In another embodiment, Y is $C(OH)CH_2NH_2$.

In another embodiment, $R^3$ is hydrogen. In another embodiment, $R^3$ is $C_{1-4}$alkyl. In another embodiment, $R^3$ is amino. In another embodiment, $R^3$ is $-X^1-R^{3a}$. In another embodiment, $R^3$ is $-NH-X^1-R^{3a}$. In another embodiment, $R^3$ is hydroxy-substituted-$C_{1-4}$alkyl. In another embodiment, $R^3$ is $C_{1-4}$alkoxy-substituted-$C_{1-4}$alkyl. In another embodiment, $R^3$ is hydroxy. In another embodiment, $R^3$ is oxo. In another embodiment, $R^3$ is halo. In another embodiment, $R^3$ is $-X^1-CO_2H$. In another embodiment, $R^3$ is $-X^1-CO_2NH_2$. In another embodiment, $R^3$ is $-X^1-SO_2C_{1-4}$alkyl. In another embodiment, $R^3$ is $-X^1-SO_2N(C_{1-4}$alkyl$)_2$. In another embodiment, $R^3$ is $-X^1-C_{3-6}$-cycloalkyl.

In another embodiment, any two $R^3$ together with the atoms through which $R^3$ are connected form a saturated, unsaturated or partially unsaturated 3-6 member carbocyclic or heterocyclic ring containing up to three heteroatoms selected from N, $NR^4$, $S(O)_{0-2}$ and O. In another embodiment, the $C_{3-6}$cycloalkyl of $R^3$ is unsubstituted. In another embodiment, the $C_{3-6}$cycloalkyl of $R^3$ is substituted with 1 to 4 $R^4$ independently selected from $C_{1-4}$alkyl, amino, amino-$C_{1-4}$alkyl, $C_{1-4}$alkoxy, hydroxy, $-X^1CO_2R^{4a}$, $-X^1-COR^{4a}$, $-XC(O)NR^{4a}R^{4b}$, and $-X^1$-cycloalkyl-$R^{4a}$.

In another embodiment, $R^{3a}$ is amino. In another embodiment, $R^{3a}$ is —CO—$C_{1-4}$alkyl. In another embodiment, $R^{3a}$ is 3-6 member, saturated, unsaturated or partially unsaturated heterocyclic ring containing up to three heteroatoms selected from N, $NR_{30}$, $S(O)_{0-2}$ and O. In another embodiment, the heterocyclic ring of $R^{3a}$ is unsubstituted. In another embodiment, the heterocyclic ring of $R^{3a}$ is substituted with 1 or 2 hydroxy or amino.

In another embodiment, $R^{4a}$ is hydrogen. In another embodiment, $R^{4a}$ is amino. In another embodiment, $R^{4a}$ is aminosubstituted-$C_{1-4}$alkyl. In another embodiment, $R^{4b}$ is hydrogen. In another embodiment, $R^{4b}$ is amino. In another embodiment, $R^{4b}$ is aminosubstituted-$C_{1-4}$alkyl.

In a further embodiment are compounds selected from any one of Examples 4-0 to 58-2: 4-(aminomethyl)-1-(5-(6-isopropyl-2-methoxypyridin-3-yl)imidazo[2,1-b][1,3,4]thiadiazol-2-yl)piperidin-4-ol; 3-(aminomethyl)-1-(5-(2-methoxy-4-methylphenyl)imidazo[2,1-b][1,3,4]thiadiazol-2-yl)pyrrolidin-3-ol; (4-(5-(2-methoxy-4-methylphenyl)imidazo[2,1-b][1,3,4]thiadiazol-2-yl)piperazin-2-yl)methanol; (4-amino-1-(5-(2-methoxy-4-methylphenyl)imidazo[2,1-b][1,3,4]thiadiazol-2-yl)piperidin-4-yl)methanol; (3S,5S)-5-amino-1-(5-(4-fluoro-2-methoxyphenyl)imidazo[2,1-b][1,3,4]thiadiazol-2-yl)piperidin-3-ol; 3-(aminomethyl)-1-(5-(6-isopropyl-2-methoxypyridin-3-yl)imidazo[2,1-b][1,3,4]thiadiazol-2-yl)azetidin-3-ol; 4-(aminomethyl)-1-(5-(5-chloro-4-fluoro-2-methoxyphenyl)imidazo[2,1-b][1,3,4]thiadiazol-2-yl)piperidin-4-ol; 4-(aminomethyl)-1-(5-(2-ethoxy-5-methylphenyl)imidazo[2,1-b][1,3,4]thiadiazol-2-yl)piperidin-4-ol; 2-(5-(4-fluoro-2-methoxyphenyl)imidazo[2,1-b][1,3,4]thiadiazol-2-yl)-5-oxa-2,8-diazaspiro[3.5]nonane; 8-(5-(2-methoxy-4-methylphenyl)imidazo[2,1-b][1,3,4]thiadiazol-2-yl)-1-oxa-8-azaspiro[4.5]decan-3-amine; 4-(aminomethyl)-1-(5-(5-fluoro-2-methoxyphenyl)imidazo[2,1-b][1,3,4]thiadiazol-2-yl)piperidin-4-ol; 9-(5-(4-fluoro-2-methoxyphenyl)imidazo[2,1-b][1,3,4]thiadiazol-2-yl)-1-oxa-4,9-diazaspiro[5.5]undecane; 4-(aminomethyl)-1-(5-(2-methoxy-6-methylpyridin-3-yl)imidazo[2,1-b][1,3,4]thiadiazol-2-yl)piperidin-4-ol; 4-(aminomethyl)-1-(5-(3-chloro-2-methoxyphenyl)imidazo[2,1-b][1,3,4]thiadiazol-2-yl)piperidin-4-ol; 4-(aminomethyl)-1-(5-(4-cyclopropyl-2-methoxyphenyl)imidazo[2,1-b][1,3,4]thiadiazol-2-yl)piperidin-4-ol; (3S,4R)-4-amino-1-(5-(4-fluoro-2-methoxyphenyl)imidazo[2,1-b][1,3,4]thiadiazol-2-yl)piperidin-3-ol; (3R,4S)-4-amino-1-(5-(4-fluoro-2-methoxyphenyl)imidazo[2,1-b][1,3,4]thiadiazol-2-yl)piperidin-3-ol; 4-(aminomethyl)-1-(5-(3,5-difluoro-2-methoxyphenyl)imidazo[2,1-b][1,3,4]thiadiazol-2-yl)piperidin-4-ol; 4-(aminomethyl)-1-(5-(2,3-dihydrobenzofuran-7-yl)imidazo[2,1-b][1,3,4]thiadiazol-2-yl)piperidin-4-ol; 4-(aminomethyl)-1-(5-(2-methoxy-3-methylphenyl)imidazo[2,1-b][1,3,4]thiadiazol-2-yl)piperidin-4-ol; (R)-1-(1-(5-(6-isopropyl-2-methoxypyridin-3-yl)imidazo[2,1-b][1,3,4]thiadiazol-2-yl)pyrrolidin-3-yl)cyclopropan-1-amine; (4-((cyclopropylmethyl)amino)-1-(5-(2-methoxy-4-methylphenyl)imidazo[2,1-b][1,3,4]thiadiazol-2-yl)piperidin-4-yl)methanol; 4-(aminomethyl)-1-(5-(2-methoxy-3-(trifluoromethyl)phenyl)imidazo[2,1-b][1,3,4]thiadiazol-2-yl)piperidin-4-ol; 2-(4-(5-(2-methoxy-4-methylphenyl)imidazo[2,1-b][1,3,4]thiadiazol-2-yl)piperazin-2-yl)ethan-1-ol; 3-(aminomethyl)-1-(5-(2-methoxy-4-methylphenyl)imidazo[2,1-b][1,3,4]thiadiazol-2-yl)azetidin-3-ol; (3S,4R)-3-fluoro-1-(5-(4-fluoro-2-methoxyphenyl)imidazo[2,1-b][1,3,4]thiadiazol-2-yl)piperidin-4-amine; (3R,4S)-3-fluoro-1-(5-(4-fluoro-2-methoxyphenyl)imidazo[2,1-b][1,3,4]thiadiazol-2-yl)piperidin-4-amine; (3S,4R)-4-amino-1-(5-(6-isopropyl-2-methoxypyridin-3-yl)imidazo[2,1-b][1,3,4]thiadiazol-2-yl)pyrrolidin-3-ol; (4-(5-(6-isopropyl-2-methoxypyridin-3-yl)imidazo[2,1-b][1,3,4]thiadiazol-2-yl)piperazin-2-yl)methanol; 8-(5-(6-isopropyl-2-methoxypyridin-3-yl)imidazo[2,1-b][1,3,4]thiadiazol-2-yl)-1-oxa-8-azaspiro[4.5]decan-3-amine; 8-(5-(4-fluoro-2-methoxyphenyl)imidazo[2,1-b][1,3,4]thiadiazol-2-yl)-1-oxa-8-azaspiro[4.5]decan-3-amine; 4-(aminomethyl)-1-(5-(2-ethoxy-4-(trifluoromethyl)phenyl)imidazo[2,1-b][1,3,4]thiadiazol-2-yl)piperidin-4-ol; 3-(aminomethyl)-1-(5-(2-methoxy-6-methylpyridin-3-yl)imidazo[2,1-b][1,3,4]thiadiazol-2-yl)pyrrolidin-3-ol; 4-(aminomethyl)-1-(5-(4-chloro-2-(2-methoxyethoxy)phenyl)imidazo[2,1-b][1,3,4]thiadiazol-2-yl)piperidin-4-ol; (S)-3-(aminomethyl)-1-(5-(4-fluoro-2-methoxyphenyl)imidazo[2,1-b][1,3,4]thiadiazol-2-yl)pyrrolidin-3-ol; (R)-3-(aminomethyl)-1-(5-(4-fluoro-2-methoxyphenyl)imidazo[2,1-b][1,3,4]thiadiazol-2-yl)pyrrolidin-3-ol; 4-(aminomethyl)-1-(5-(4-fluoro-2-(trifluoromethoxy)phenyl)imidazo[2,1-b][1,3,4]thiadiazol-2-yl)piperidin-4-ol; 4-(aminomethyl)-1-(5-(3-fluoro-2-methoxy-4-methylphenyl)imidazo[2,1-b][1,3,4]thiadiazol-2-yl)piperidin-4-ol; 4-(aminomethyl)-1-(5-(2-(cyclopropylmethoxy)-4-fluorophenyl)imidazo[2,1-b][1,3,4]thiadiazol-2-yl)piperidin-4-ol; 4-(aminomethyl)-1-(5-(4-fluoro-2-methoxyphenyl)imidazo[2,1-b][1,3,4]thiadiazol-2-yl)piperidin-4-ol; 4-(aminomethyl)-1-(5-(4-fluoro-5-isopropyl-2-methoxyphenyl)imidazo[2,1-b][1,3,4]thiadiazol-2-yl)piperidin-4-ol; 8-(5-(2-methoxy-6-methylpyridin-3-yl)imidazo[2,1-b][1,3,4]thiadiazol-2-yl)-1-oxa-8-azaspiro[4.5]decan-3-amine; (4-amino-1-(5-(4-chloro-2-methoxyphenyl)imidazo[2,1-b][1,3,4]thiadiazol-2-yl)piperidin-4-yl)methanol; 4-(aminomethyl)-1-(5-(2,3-dihydrobenzo[b][1,4]dioxin-5-yl)imidazo[2,1-b][1,3,4]thiadiazol-2-yl)piperidin-4-ol; 2-(5-(4-fluoro-2-methoxyphenyl)imidazo[2,1-b][1,3,4]thiadiazol-2-yl)-2-azaspiro[3.3]heptan-5-amine; (4-(aminomethyl)-1-(5-(4-fluoro-2-methoxyphenyl)imidazo[2,1-b][1,3,4]thiadiazol-2-yl)piperidin-4-yl)methanol; 4-(aminomethyl)-1-(5-(2-ethoxyphenyl)imidazo[2,1-b][1,3,4]thiadiazol-2-yl)piperidin-4-ol; 4-(aminomethyl)-1-(5-(2-methoxypyridin-3-yl)imidazo[2,1-b][1,3,4]thiadiazol-2-yl)piperidin-4-ol; (S)-(3-amino-1-(5-(4-fluoro-2-methoxyphenyl)imidazo[2,1-b][1,3,4]thiadiazol-2-yl)pyrrolidin-3-yl)methanol; (R)-(3-amino-1-(5-(4-fluoro-2-methoxyphenyl)imidazo[2,1-b][1,3,4]thiadiazol-2-yl)pyrrolidin-3-yl)methanol; (3R,5R)-5-fluoro-1-(5-(4-fluoro-2-methoxyphenyl)imidazo[2,1-b][1,3,4]thiadiazol-2-yl)piperidin-3-amine; (3R,4R)-4-amino-1-(5-(4-fluoro-2-methoxyphenyl)imidazo[2,1-b][1,3,4]thiadiazol-2-yl)piperidin-3-ol; (3S,4S)-4-amino-1-(5-(4-fluoro-2-methoxyphenyl)imidazo[2,1-b][1,3,4]thiadiazol-2-yl)piperidin-3-ol; 1-(5-(2-methoxy-4-methylphenyl)imidazo[2,1-b][1,3,4]thiadiazol-2-yl)-3-methylpyrrolidin-3-amine; 1-(5-(2-methoxy-6-methylpyridin-3-yl)imidazo[2,1-b][1,3,4]thiadiazol-2-yl)-3-methylpyrrolidin-3-amine; 1-(5-(6-isopropyl-2-methoxypyridin-3-yl)imidazo[2,1-b][1,3,4]thiadiazol-2-yl)-3-methylpyrrolidin-3-amine; 2-((1-(5-(6-isopropyl-2-methoxypyridin-3-yl)imidazo[2,1-b][1,3,4]thiadiazol-2-yl)piperidin-4-yl)amino)ethan-1-ol; 4-(aminomethyl)-1-(5-(2-methoxy-4-(trifluoromethyl)phenyl)imidazo[2,1-b][1,3,4]thiadiazol-2-yl)piperidin-4-ol; 4-amino-1-(5-(4-fluoro-2-methoxyphenyl)imidazo[2,1-b][1,3,4]thiadiazol-2-yl)pyrrolidin-3-ol; 4-(aminomethyl)-1-(5-(3,4-difluoro-2-methoxyphenyl)imidazo[2,1-b][1,3,4]thiadiazol-2-yl)piperidin-4-ol; (3S,4R)-4-amino-1-(5-(4-fluoro-2-methoxyphenyl)imidazo[2,1-b][1,3,4]thiadiazol-2-yl)pyrrolidin-3-ol; (3S,4R)-4-amino-1-(5-(4-fluoro-2-methoxyphenyl)imidazo[2,1-b][1,3,4]thiadiazol-2-yl)pyrrolidin-3-ol; 4-(aminomethyl)-1-(5-(4-chloro-2- methoxyphenyl)imidazo[2,1-b][1,3,4]thiadiazol-2-yl)piperidin-4-ol; 4-(aminomethyl)-1-(5-(4,5-difluoro-2-methoxyphenyl)imidazo[2,1-b][1,3,4]thiadiazol-2-yl)piperidin-4-ol; (R)-(3-amino-1-(5-(2-ethoxy-4-fluorophenyl)imidazo[2,1-b][1,3,4]thiadiazol-2-yl)pyrrolidin-3-yl)methanol; (S)-(3-amino-1-(5-(2-ethoxy-4-fluorophenyl)imidazo[2,1-b][1,3,4]thiadiazol-2-yl)pyrrolidin-3-yl)methanol; 4-(aminomethyl)-1-(5-(2-methoxy-4,5-dimethylphenyl)imidazo[2,1-b][1,3,4]thiadiazol-2-yl)piperidin-4-ol; (3S,4R)-3-amino-1-(5-(4-fluoro-2-methoxyphenyl)imidazo[2,1-b][1,3,4]thiadiazol-2-yl)piperidin-4-ol; (3R,4S)-3-amino-1-(5-(4-fluoro-2-methoxyphenyl)imidazo[2,1-b][1,3,4]thiadiazol-2-yl)piperidin-4-ol; 2-(4-(5-(6-isopropyl-2-methoxypyridin-3-yl)imidazo[2,1-b][1,3,4]thiadiazol-2-yl)piperazin-1-yl)ethan-1-ol; 3-(aminomethyl)-1-(5-(6-isopropyl-2-methoxypyridin-3-yl)imidazo[2,1-b][1,3,4]thiadiazol-2-yl)pyrrolidin-3-ol; 4-(aminomethyl)-1-(5-(2-methoxy-4-(tetrahydro-2H-pyran-4-yl)phenyl)imidazo[2,1-b][1,3,4]thiadiazol-2-yl)piperidin-4-ol; 4-(2-(4-(aminomethyl)-4-hydroxypiperidin-1-yl)imidazo[2,1-b][1,3,4]thiadiazol-5-yl)-3-methoxybenzonitrile; 4-(aminomethyl)-1-(5-(2,6-dimethoxypyridin-3-yl)imidazo[2,1-b][1,3,4]thiadiazol-2-yl)piperidin-4-ol; (4-amino-1-(5-(4-chloro-2-(2-methoxyethoxy)phenyl)imidazo[2,1-b][1,3,4]thiadiazol-2-yl)piperidin-4-yl)methanol; 3-(aminomethyl)-1-(5-(4-fluoro-2-methoxyphenyl)imidazo[2,1-b][1,3,4]thiadiazol-2-yl)azetidin-3-ol; 4-(aminomethyl)-1-(5-(2-ethoxy-4-fluorophenyl)imidazo[2,1-b][1,3,4]thiadiazol-2-yl)piperidin-4-ol; 4-(aminomethyl)-1-(5-(6-isopropyl-2-(2-methoxyethoxy)pyridin-3-yl)imidazo[2,1-b][1,3,4]thiadiazol-2-yl)piperidin-4-ol; 4-(aminomethyl)-1-(5-(3-fluoro-2-methoxyphenyl)imidazo[2,1-b][1,3,4]thiadiazol-2-yl)piperidin-4-ol; 4-(aminomethyl)-1-(5-(3-methoxynaphthalen-2-yl)imidazo[2,1-b][1,3,4]thiadiazol-2-yl)piperidin-4-ol; (3S,4S)-3-amino-1-(5-(4-fluoro-2-methoxyphenyl)imidazo[2,1-b][1,3,4]thiadiazol-2-yl)piperidin-4-ol; (3R,4R)-3-amino-1-(5-(4-fluoro-2-methoxyphenyl)imidazo[2,1-b][1,3,4]thiadiazol-2-yl)piperidin-4-ol; (4aR,8aR)-6-(5-(2-methoxy-4-methylphenyl)imidazo[2,1-b][1,3,4]thiadiazol-2-yl)octahydro-2H-pyrido[4,3-b][1,4]oxazine; 1'-(5-(6-isopropyl-2-methoxypyridin-3-yl)imidazo[2,1-b][1,3,4]thiadiazol-2-yl)-[1,3'-biazetidin]-3-ol; (4-amino-1-(5-(6-isopropyl-2-methoxypyridin-3-yl)imidazo[2,1-b][1,3,4]thiadiazol-2-yl)piperidin-4-yl)methanol; 4-(aminomethyl)-1-(5-(5-chloro-2-methoxyphenyl)imidazo[2,1-b][1,3,4]thiadiazol-2-yl)piperidin-4-ol; 4-(aminomethyl)-1-(5-(2-methoxyphenyl)imidazo[2,1-b][1,3,4]thiadiazol-2-yl)piperidin-4-ol; 4-(aminomethyl)-1-(5-(4-fluoro-2-isopropoxyphenyl)imidazo[2,1-b][1,3,4]thiadiazol-2-yl)piperidin-4-ol; 4-(1-(5-(6-isopropyl-2-methoxypyridin-3-yl)imidazo[2,1-b][1,3,4]thiadiazol-2-yl)piperidin-4-yl)morpholine; 4-(aminomethyl)-1-(5-(2-(trifluoromethoxy)phenyl)imidazo[2,1-b][1,3,4]thiadiazol-2-yl)piperidin-4-ol; 3-(aminomethyl)-1-(5-(2-ethoxy-4-fluorophenyl)imidazo[2,1-b][1,3,4]thiadiazol-2-yl)pyrrolidin-3-ol; 1-(1-(5-(6-isopropyl-2-methoxypyridin-3-yl)imidazo[2,1-b][1,3,4]thiadiazol-2-yl)piperidin-4-yl)azetidin-3-ol; 4-(aminomethyl)-1-(5-(2-methoxy-6-(trifluoromethyl)pyridin-3-yl)imidazo[2,1-b][1,3,4]thiadiazol-2-yl)piperidin-4-ol; (4-(aminomethyl)-1-(5-(2-methoxy-4-methylphenyl)imidazo[2,1-b][1,3,4]thiadiazol-2-yl)piperidin-4-yl)methanol; 4-(1-(5-(6-isopropyl-2-methoxypyridin-3-yl)imidazo[2,1-b][1,3,4]thiadiazol-2-yl)piperidin-4-yl)thiomorpholine 1,1-dioxide; (4-amino-1-(5-(2-methoxy-6-methylpyridin-3-yl)imidazo[2,1-b][1,3,4]thiadiazol-2-yl)piperidin-4-yl)methanol; (4-amino-1-(5-(4-fluoro-2-methoxyphenyl)imidazo[2,1-b][1,3,4]thiadiazol-2-yl)piperidin-4-yl)methanol; 4-(aminomethyl)-1-(5-(4-fluoro-2-methoxy-5-methylphenyl)imidazo[2,1-b][1,3,4]thiadiazol-2-yl)piperidin-4-ol; (4-amino-1-(5-(2-ethoxy-4-fluorophenyl)imidazo[2,1-b][1,3,4]thiadiazol-2-yl)piperidin-4-yl)methanol; 4-(aminomethyl)-1-(5-(2,4-dimethoxyphenyl)imidazo[2,1-b][1,3,4]thiadiazol-2-yl)piperidin-4-ol; N-((3aR,7aR)-2-(5-(4-fluoro-2-methoxyphenyl)imidazo[2,1-b][1,3,4]thiadiazol-2-yl)octahydro-3aH-pyrrolo[3,4-c]pyridin-3a-yl)acetamide; 2-(5-(2-methoxy-4-methylphenyl)imidazo[2,1-b][1,3,4]thiadiazol-2-yl)-5-oxa-2,7-diazaspiro[3.4]oct-6-en-6-amine; 8-(5-(4-fluoro-2-methoxyphenyl)imidazo[2,1-b][1,3,4]thiadiazol-2-yl)-1-oxa-3,8-diazaspiro[4.5]dec-2-en-2-amine; 8-(5-(4-fluoro-2-methoxyphenyl)imidazo[2,1-b][1,3,4]thiadiazol-2-yl)-3-oxa-1,8-diazaspiro[4.5]dec-1-en-2-amine; 8-(5-(2-methoxy-4-methylphenyl)imidazo[2,1-b][1,3,4]thiadiazol-2-yl)-1-oxa-3,8-diazaspiro[4.5]dec-2-en-2-amine; (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol; (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol; (3aS,5S,6S,7aR)-6-amino-2-(5-(4-fluoro-2-methoxyphenyl)imidazo[2,1-b][1,3,4]thiadiazol-2-yl)octahydro-1H-isoindol-5-ol; (9-(5-(4-fluoro-2-methoxyphenyl)imidazo[2,1-b][1,3,4]thiadiazol-2-yl)-2-oxa-9-azaspiro[5.5]undecan-3-yl)methanamine; (3-amino-1-(5-(6-isopropyl-2-methoxypyridin-3-yl)imidazo[2,1-b][1,3,4]thiadiazol-2-yl)azetidin-3-yl)methanol; (3-fluoro-1-(5-(4-fluoro-2-methoxyphenyl)imidazo[2,1-b][1,3,4]thiadiazol-2-yl)piperidin-3-yl)methanamine; (8-(5-(4-fluoro-2-methoxyphenyl)imidazo[2,1-b][1,3,4]thiadiazol-2-yl)-1-oxa-8-azaspiro[4.5]decan-2-yl)methanamine; 2-(5-(4-fluoro-2-methoxyphenyl)imidazo[2,1-b][1,3,4]thiadiazol-2-yl)-5-oxa-2-azaspiro[3.4]octan-7-amine; (3S,4S)-8-(5-(4-fluoro-2-methoxyphenyl)imidazo[2,1-b][1,3,4]thiadiazol-2-yl)-3-methyl-2-oxa-8-azaspiro[4.5]decan-4-amine; 4-(aminomethyl)-1-(5-(2-(dimethylamino)-6-methylpyridin-3-yl)imidazo[2,1-b][1,3,4]thiadiazol-2-yl)piperidin-4-ol; 4-(aminomethyl)-1-(5-(6-methyl-2-(methylthio)pyridin-3-yl)imidazo[2,1-b][1,3,4]thiadiazol-2-yl)piperidin-4-ol; 3-(aminomethyl)-1-(5-(4-fluoro-2-methoxyphenyl)imidazo[2,1-b][1,3,4]thiadiazol-2-yl)piperidin-3-ol; 8-(5-(4-fluoro-2-methoxyphenyl)imidazo[2,1-b][1,3,4]thiadiazol-2-yl)-2-oxa-8-azaspiro[4.5]decan-4-amine; 3-amino-1-(9-(5-(4-fluoro-2-methoxyphenyl)imidazo[2,1-b][1,3,4]thiadiazol-2-yl)-1,4,9-triazaspiro[5.5]undecan-4-yl)-3-methylbutan-1-one; 5-(6-isopropyl-2-methoxypyridin-3-yl)-2-(1,4,9-triazaspiro[5.5]undecan-9-yl)imidazo[2,1-b][1,3,4]thiadiazole; 5-(4-fluoro-2-methoxyphenyl)-2-(1,4,9-triazaspiro[5.5]undecan-9-yl)imidazo[2,1-b][1,3,4]thiadiazole; 1-(5-(4-fluoro-2-methoxyphenyl)imidazo[2,1-b][1,3,4]thiadiazol-2-yl)-4-(morpholinomethyl)piperidin-4-amine; 7-(5-(4-fluoro-2-methoxyphenyl)imidazo[2,1-b][1,3,4]thiadiazol-2-yl)-5,6,7,8-tetrahydroimidazo[1,5-a]pyrazin-3-amine; (1-(5-(4-fluoro-2-methoxyphenyl)imidazo[2,1-b][1,3,4]thiadiazol-2-yl)-4-((oxetan-3-ylmethyl)amino)piperidin-4-yl)methanol; (1-(5-(4-fluoro-2-methoxyphenyl)imidazo[2,1-b][1,3,4]thiadiazol-2-yl)-4-((2-morpholinoethyl)amino)piperidin-4-yl)methanol; 4-((3-aminopropyl)amino)-1-(5-(4-fluoro-2-methoxyphenyl)imidazo[2,1-b][1,3,4]thiadiazol-2-yl)piperidin-4-yl)methanol; 6-(aminomethyl)-2-(5-(4-fluoro-2-methoxyphenyl)imidazo[2,1-b][1,3,4]thiadiazol-2-yl)-2-azaspiro[3.3]heptan-6-ol; (S)-3-(aminomethyl)-1-(5-(6-isopropyl-2-methoxypyridin-3-yl)imidazo[2,1-b][1,3,4]thiadiazol-2-yl)pyrrolidin-3-ol; (R)-3-(aminomethyl)-1-(5-

(6-isopropyl-2-methoxypyridin-3-yl)imidazo[2,1-b][1,3,4]thiadiazol-2-yl)pyrrolidin-3-ol; (S)-3-(aminomethyl)-1-(5-(2-methoxy-6-methylpyridin-3-yl)imidazo[2,1-b][1,3,4]thiadiazol-2-yl)pyrrolidin-3-ol; (R)-3-(aminomethyl)-1-(5-(2-methoxy-6-methylpyridin-3-yl)imidazo[2,1-b][1,3,4]thiadiazol-2-yl)pyrrolidin-3-ol; 3-(aminomethyl)-1-(5-(6-isopropyl-2-methoxypyridin-3-yl)imidazo[2,1-b][1,3,4]thiadiazol-2-yl)pyrrolidin-3-ol; (3S,4S)-4-amino-1-(5-(2-methoxy-4-methylphenyl)imidazo[2,1-b][1,3,4]thiadiazol-2-yl)-4-methylpiperidin-3-ol; (3R,4R)-4-amino-1-(5-(2-methoxy-4-methylphenyl)imidazo[2,1-b][1,3,4]thiadiazol-2-yl)-4-methylpiperidin-3-ol; (3R,4R)-4-amino-1-(5-(6-isopropyl-2-methoxypyridin-3-yl)imidazo[2,1-b][1,3,4]thiadiazol-2-yl)-4-methylpiperidin-3-ol; (3S,4S)-4-amino-1-(5-(6-isopropyl-2-methoxypyridin-3-yl)imidazo[2,1-b][1,3,4]thiadiazol-2-yl)-4-methylpiperidin-3-ol; (3R,4R)-4-amino-1-(5-(4-fluoro-2-methoxyphenyl)imidazo[2,1-b][1,3,4]thiadiazol-2-yl)-4-methylpiperidin-3-ol; (3S,4S)-4-amino-1-(5-(4-fluoro-2-methoxyphenyl)imidazo[2,1-b][1,3,4]thiadiazol-2-yl)-4-methylpiperidin-3-ol; (3R,4R)-4-amino-1-(5-(2-methoxy-6-methylpyridin-3-yl)imidazo[2,1-b][1,3,4]thiadiazol-2-yl)-4-methylpiperidin-3-ol; (3S,4S)-4-amino-1-(5-(2-methoxy-6-methylpyridin-3-yl)imidazo[2,1-b][1,3,4]thiadiazol-2-yl)-4-methylpiperidin-3-ol; (3S,4S)-3-amino-1-(5-(4-fluoro-2-methoxyphenyl)imidazo[2,1-b][1,3,4]thiadiazol-2-yl)-4-methylpiperidin-4-ol; (3R,4R)-3-amino-1-(5-(4-fluoro-2-methoxyphenyl)imidazo[2,1-b][1,3,4]thiadiazol-2-yl)-4-methylpiperidin-4-ol; (3R,4R)-4-amino-1-(5-(4-fluoro-2-methoxyphenyl)imidazo[2,1-b][1,3,4]thiadiazol-2-yl)-4-methylpiperidin-3-ol; 4-(aminomethyl)-1-(5-(4-fluoro-2-methoxyphenyl)imidazo[2,1-b][1,3,4]thiadiazol-2-yl)piperidine-4-carboxamide; N-((1-aminocyclopropyl)methyl)-4-(aminomethyl)-1-(5-(4-fluoro-2-methoxyphenyl)imidazo[2,1-b][1,3,4]thiadiazol-2-yl)piperidine-4-carboxamide; N-(2-amino-2-methylpropyl)-8-(5-(4-fluoro-2-methoxyphenyl)imidazo[2,1-b][1,3,4]thiadiazol-2-yl)-1-thia-8-azaspiro[4.5]decane-4-carboxamide 1,1-dioxide; 2-(4-amino-1-(5-(4-fluoro-2-methoxyphenyl)imidazo[2,1-b][1,3,4]thiadiazol-2-yl)piperidin-4-yl)propan-2-ol; 2-(4-amino-1-(5-(4-fluoro-2-methoxyphenyl)imidazo[2,1-b][1,3,4]thiadiazol-2-yl)piperidin-4-yl)propan-2-ol; 4-(aminomethyl)-1-(5-(4-(1-hydroxycyclobutyl)-2-methoxyphenyl)imidazo[2,1-b][1,3,4]thiadiazol-2-yl)piperidin-4-ol; ((1-(5-(4-fluoro-2-methoxyphenyl)imidazo[2,1-b][1,3,4]thiadiazol-2-yl)-4-((methylsulfonyl)methyl)piperidin-4-yl)methanamine; 1-(4-(aminomethyl)-1-(5-(4-fluoro-2-methoxyphenyl)imidazo[2,1-b][1,3,4]thiadiazol-2-yl)piperidin-4-yl)-N,N-dimethylmethanesulfonamide; ((3R,5S)-5-amino-1-(5-(4-fluoro-2-methoxyphenyl)imidazo[2,1-b][1,3,4]thiadiazol-2-yl)piperidin-3-ol; (4S,4aR,7aS)-6-(5-(2-ethoxy-6-isopropylpyridin-3-yl)imidazo[2,1-b][1,3,4]thiadiazol-2-yl)octahydropyrano[2,3-c]pyrrol-4-amine; (4S,4aR,7aS)-6-(5-(2-methoxy-4-(trifluoromethyl)phenyl)imidazo[2,1-b][1,3,4]thiadiazol-2-yl)octahydropyrano[2,3-c]pyrrol-4-amine; (4R,4aS,7aR)-6-(5-(2-methoxy-4-(trifluoromethyl)phenyl)imidazo[2,1-b][1,3,4]thiadiazol-2-yl)octahydropyrano[2,3-c]pyrrol-4-amine; (4S,4aR,7aS)-6-(5-(6-isopropyl-2-methoxypyridin-3-yl)imidazo[2,1-b][1,3,4]thiadiazol-2-yl)octahydropyrano[2,3-c]pyrrol-4-amine; (4R,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (4S,4aR,7aS)-6-(5-(4-fluoro-2-methoxyphenyl)imidazo[2,1-b][1,3,4]thiadiazol-2-yl)octahydropyrano[2,3-c]pyrrol-4-amine; (4R,4aS,7aR)-6-(5-(4-fluoro-2-methoxyphenyl)imidazo[2,1-b][1,3,4]thiadiazol-2-yl)octahydropyrano[2,3-c]pyrrol-4-amine; ((4S,4aS,7aR)-6-(5-(4-fluoro-2-methoxyphenyl)imidazo[2,1-b][1,3,4]thiadiazol-2-yl)octahydropyrano[2,3-c]pyrrol-4-amine; (4S,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (4R,4aR,7aS)-6-(5-(6-isopropyl-2-methoxypyridin-3-yl)imidazo[2,1-b][1,3,4]thiadiazol-2-yl)octahydropyrano[2,3-c]pyrrol-4-amine; 4S,4aR,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (3aS,5R,7R,7aR)-7-amino-2-(5-(6-isopropyl-2-methoxypyridin-3-yl)imidazo[2,1-b][1,3,4]thiadiazol-2-yl)octahydro-TH-isoindol-5-ol; (3aR,4S,5S,7aS)-4-amino-2-(5-(6-isopropyl-2-methoxypyridin-3-yl)imidazo[2,1-b][1,3,4]thiadiazol-2-yl)octahydro-H-isoindol-5-ol; (3aR,4S,5R,7aS)-4-amino-2-(5-(2-methoxy-6-methylpyridin-3-yl)imidazo[2,1-b][1,3,4]thiadiazol-2-yl)octahydro-TH-isoindol-5-ol; (3aR,4S,5R,7aS)-4-amino-2-(5-(6-isopropyl-2-methoxypyridin-3-yl)imidazo[2,1-b][1,3,4]thiadiazol-2-yl)octahydro-H-isoindol-5-ol; (3aR,4S,5R,7aS)-4-amino-2-(5-(4-fluoro-2-methoxyphenyl)imidazo[2,1-b][1,3,4]thiadiazol-2-yl)octahydro-1H-isoindol-5-ol; (3aR,4R,7aS)-2-(5-(6-isopropyl-2-methoxypyridin-3-yl)imidazo[2,1-b][1,3,4]thiadiazol-2-yl)-2,3,3a,4,7,7a-hexahydro-1H-isoindol-4-amine: 4-(aminomethyl)-1-(5-(4-chloro-5-fluoro-2-methoxyphenyl)imidazo[2,1-b][1,3,4]thiadiazol-2-yl)piperidin-4-ol; 4-(aminomethyl)-1-(5-(2-isopropoxy-6-isopropylpyridin-3-yl)imidazo[2,1-b][1,3,4]thiadiazol-2-yl)piperidin-4-ol; 4-(aminomethyl)-1-(5-(2-ethoxy-6-isopropylpyridin-3-yl)imidazo[2,1-b][1,3,4]thiadiazol-2-yl)piperidin-4-ol; (4-amino-1-(5-(2-ethoxy-6-isopropylpyridin-3-yl)imidazo[2,1-b][1,3,4]thiadiazol-2-yl)piperidin-4-yl)methanol; 3-(aminomethyl)-1-(5-(2-ethoxy-6-isopropylpyridin-3-yl)imidazo[2,1-b][1,3,4]thiadiazol-2-yl)azetidin-3-ol; (4-amino-1-(5-(4-(1,2-difluoroethyl)-2-methoxyphenyl)imidazo[2,1-b][1,3,4]thiadiazol-2-yl)piperidin-4-yl)methanol; 4-(aminomethyl)-1-(5-(2-(2-hydroxyethoxy)-6-isopropylpyridin-3-yl)imidazo[2,1-b][1,3,4]thiadiazol-2-yl)piperidin-4-ol; (4-amino-1-(5-(4-(1,2-difluoroethyl)-2-methoxyphenyl)imidazo[2,1-b][1,3,4]thiadiazol-2-yl)piperidin-4-yl)methanol; 4-(aminomethyl)-1-(5-(4-(1,2-difluoroethyl)-2-methoxyphenyl)imidazo[2,1-b][1,3,4]thiadiazol-2-yl)piperidin-4-ol; 4-(aminomethyl)-1-(5-(2-(2,2-difluoroethoxy)phenyl)imidazo[2,1-b][1,3,4]thiadiazol-2-yl)piperidin-4-ol; 4-(aminomethyl)-1-(5-(4-isopropyl-2-methoxyphenyl)imidazo[2,1-b][1,3,4]thiadiazol-2-yl)piperidin-4-ol; 4-(aminomethyl)-1-(5-(2-ethoxy-4-isopropylphenyl)imidazo[2,1-b][1,3,4]thiadiazol-2-yl)piperidin-4-ol; 4-(aminomethyl)-1-(5-(2-methoxy-4-(tetrahydrofuran-3-yl)phenyl)imidazo[2,1-b][1,3,4]thiadiazol-2-yl)piperidin-4-ol; 4-(aminomethyl)-1-(5-(2-methoxy-4-(1-methoxycyclopropyl)phenyl)imidazo[2,1-b][1,3,4]thiadiazol-2-yl)piperidin-4-ol; 4-(aminomethyl)-1-(5-(2-methoxy-4-(1-methoxycyclobutyl)phenyl)imidazo[2,1-b][1,3,4]thiadiazol-2-yl)piperidin-4-ol; (4-amino-1-(5-(2-(2-fluoroethoxy)phenyl)imidazo[2,1-b][1,3,4]thiadiazol-2-yl)piperidin-4-yl)methanol; 4-(aminomethyl)-1-(5-(2-(2-fluoroethoxy)phenyl)imidazo[2,1-b][1,3,4]thiadiazol-2-yl)piperidin-4-ol; (4-amino-1-(5-(2-(2,2-difluoroethoxy)phenyl)imidazo[2,1-b][1,3,4]thiadiazol-2-yl)piperidin-4-yl)methanol; 4-(aminomethyl)-1-(5-(2-(2,2-difluoroethoxy)phenyl)imidazo[2,1-b][1,3,4]thiadiazol-2-yl)piperidin-4-ol; (4-amino-1-(5-(2-(2,3-difluoropropoxy)phenyl)imidazo[2,1-b][1,3,4]thiadiazol-2-yl)piperidin-4-yl)methanol; 4-(aminomethyl)-1-(5-(2-(2,3-difluoropropoxy)phenyl)imidazo[2,1-b][1,3,4]thiadiazol-2-yl)piperidin-4-ol; 4-(aminomethyl)-1-(5-(4-chloro-5-isopropyl-2-methoxyphenyl)imidazo[2,1-b][1,3,4]thiadiazol-2-yl)piperidin-4-ol; 4-amino-8-(5-(6- isopropyl-2-methoxypyridin-3-yl)imidazo[2,1-b][1,3,4]thiadiazol-2-yl)-1-thia-8-azaspiro[4.5]decane 1,1-dioxide; 1-(5-(4-fluoro-2-methoxyphenyl)imidazo[2,1-b][1,3,4]thiadiazol-2-yl)-4-(methoxymethyl)piperidin-4-amine; 2-(3-amino-1-(5-(4-fluoro-2-methoxyphenyl)imidazo[2,1-b][1,3,4]thiadiazol-2-yl)pyrrolidin-3-yl)propan-2-ol; 3-amino-1-(5-(4-fluoro-2-methoxyphenyl)imidazo[2,1-b][1,3,4]thiadiazol-2-yl)-4-methylpiperidin-4-ol; (3R,4r,5S)-4-amino-1-(5-(4-fluoro-2-methoxyphenyl)imidazo[2,1-b][1,3,4]thiadiazol-2-yl)-4-methylpiperidine-3,5-diol; and ((3S,4S)-4-amino-1-(5-(4-fluoro-2-methoxyphenyl)imidazo[2,1-b][1,3,4]thiadiazol-2-yl)piperidin-3-yl)methanol.

Crystal Forms of Compound I

In one aspect, the present invention relates to crystal form K' of 4-(7-Hydroxy-2-isopropyl-4-oxo-4H-quinazolin-3-yl)-benzonitrile (compound I) having an X ray diffraction pattern having three or more peaks at 2θ values selected from 5.3, 12.3, and 22.5±0.2°2θ. In some embodiments, crystal form K' of compound I is characterized by an X ray diffraction pattern having three or more peaks at 2θ values selected from 5.3, 10.6, 12.3, 21.2, 22.5, and 23.0±0.2°2θ. In some embodiments, crystal form K' is characterized by an X-ray diffraction pattern having 3 or more, 4 or more, 5 or more, 6 or more, or 7 or more peaks at 2θ values selected from 5.3, 10.6, 12.3, 17.0, 17.3, 19.4, 20.3, 21.2, 22.5, 23.0, 24.8, 27.1, 32.0±0.2°2θ. In some embodiments, the present invention relates to a method of preparing a crystal form K' of compound I, comprising evaporating a solution of compound I in about 1:1 (v/v) n-butanol/dichloromethane, to crystallize compound I as crystal form K'.

In one embodiment, a crystal form K' of compound I is provided in substantially pure form. This crystal form K' of compound I in substantially pure form may be employed in pharmaceutical compositions, e.g., ophthalmic formulations as described herein. In some embodiments, the disclosure provides for pharmaceutical formulations including compound I in crystal form K'. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form K'.

In one aspect, the present invention relates to crystal form M of 4-(7-Hydroxy-2-isopropyl-4-oxo-4H-quinazolin-3-yl)-benzonitrile (compound I) having an X ray diffraction pattern having three or more peaks at 2θ values selected from 11.1, 18.5, 19.1±0.2°2θ. In particular embodiments, crystal form M of compound I is characterized by an X ray diffraction pattern having three or more peaks at 2θ values selected from 11.1, 12.1, 18.5, 19.1, 20.1, 21.4±0.2°2θ. In some embodiments, crystal form M is characterized by an X-ray diffraction pattern having 3 or more, 4 or more, 5 or more, 6 or more, or 7 or more peaks at 2θ values selected from 11.1, 12.1, 18.5, 19.1, 20.1, 21.4, 21.7, 22.2, 23.1, 26.4, 273, 29.7±0.2°2θ. In some embodiments, the invention relates to a method of preparing a crystal form M of compound I, comprising slurrying compound I in crystal form B in acetone at room temperature for at least 24 hours, at least 2 days, at least 3 days, at least 4 days, or at least 5 days. Alternatively, crystal form M may be obtained by slurrying crystal form B of compound I in acetone, ethanol, 1:1 ethanol/water, methanol or 1:1 methanol/water at 50° C. for 2 weeks.

In one embodiment, a crystal form M of compound I is provided in substantially pure form. This crystal form M of compound I in substantially pure form may be employed in pharmaceutical compositions, e.g., ophthalmic formulations as described herein. In some embodiments, the disclosure provides for pharmaceutical formulations including compound I in crystal form M. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form M.

In one aspect, the present invention relates to crystalline Hydrate $H_B$ of 4-(7-Hydroxy-2-isopropyl-4-oxo-4H-quinazolin-3-yl)-benzonitrile (compound I) having an X ray diffraction pattern having three or more peaks at 2θ values selected from 6.6, 12.2, 15.8 0.2°2θ. In particular embodiments, the crystalline Hydrate $H_B$ of compound I is characterized by an X ray diffraction pattern having three or more peaks at 2θ values selected from 6.6, 12.2, 14.6, 15.8, 16.1, 18.5, 20.9, 24.7±0.2°2θ. In some embodiments, Hydrate $H_B$ is characterized by an X-ray diffraction pattern having 3 or more, 4 or more, 5 or more, 6 or more, or 7 or more peaks at 2θ values selected from 6.6, 11.7, 12.2, 14.6, 15.8, 16.1, 18.5, 19.7, 20.9, 24.7, 26.5, 27.7, 29.3±0.2°2θ. In some embodiments, the present invention relates to a method of preparing crystalline hydrate $H_B$ of compound I, comprising slurrying compound I in crystal form B in a about 1:1 mixture of acetone and water at room temperature for at least 5 days, at least 6 days, or at least 7 days, to provide compound I as crystalline Hydrate $H_B$.

In one embodiment, a Hydrate $H_B$ of compound I is provided in substantially pure form. This Hydrate $H_B$ of compound I in substantially pure form may be employed in pharmaceutical compositions, e.g., ophthalmic formulations as described herein. In some embodiments, the disclosure provides for pharmaceutical formulations including compound I as Hydrate $H_B$. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as Hydrate $H_B$.

In one aspect, the present invention relates to crystal form Q of 4-(7-Hydroxy-2-isopropyl-4-oxo-4H-quinazolin-3-yl)-benzonitrile (compound I) having an X ray diffraction pattern having three or more peaks at 2θ values selected from 11.2, 12.2, 19.1±0.2°2θ. In particular embodiments, crystal form Q of compound I is characterized by an X ray diffraction pattern having three or more peaks at 2θ values selected from 11.2, 12.2, 18.5, 19.1, 20.1, 22.0, 22.5, 23.3, 26.5±0.2°2θ. In some embodiments, crystal form A is characterized by an X-ray diffraction pattern having 3 or more, 4 or more, 5 or more, 6 or more, or 7 or more peaks at 2θ values selected from 11.2, 12.2, 17.7, 18.5, 19.1, 20.1, 22.0, 22.5, 23.3, 24.2, 24.6, 26.5, 28.5±0.2°2θ. In some embodiments, the present invention relates to a method of preparing a crystal form Q of compound I according to claims 10-11, comprising slurrying compound I in crystal form B in about 1:1 (v/v) n-butanol/dichloromethane, to obtain compound I as crystal form Q.

In one embodiment, a crystal form Q of compound I is provided in substantially pure form. This crystal form Q of compound I in substantially pure form may be employed in pharmaceutical compositions, e.g., ophthalmic formulations as described herein. In some embodiments, the disclosure provides for pharmaceutical formulations including compound I in crystal form Q. In some embodiments, the present disclosure provides ophthalmic suspensions of compound I, wherein at least 10%, at least about 20%, at least about 30%, at least about 40%, at least about 50%, at least about 60%, at least about 70%, at least about 80%, or at least 90% of compound I is present as crystal form Q.

In a further embodiment of the invention is a method for treating a *Plasmodium* related disease in a subject to prevent, inhibit or ameliorate the pathology and/or symptamology of the *Plasmodium* related disease, comprising administering to a subject, in vivo or in vitro, a therapeutically effective amount of a compound of the invention alone or in combination with a second agent.

In a further embodiment is a method for treating a *Plasmodium* related disease in a subject to prevent, inhibit or ameliorate the pathology and/or symptamology of the *Plasmodium* related disease, comprising administering to a subject, in vivo or in vitro, a therapeutically effective amount of a compound of any of the embodiments herein, alone or in combination with a second agent.

In a further embodiment, the *Plasmodium* related disease is malaria.

In a further embodiment, the second agent is selected from a kinase inhibitor, an anti-malarial drug and an anti-inflammatory agent. The anti-malarial drug is selected from proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, KAE-609 and KAF-156.

In a further embodiment, the compounds of the invention can be administered prior to, simultaneously with, or after the second agent.

In a further embodiment, the subject is a human.

Pharmacology and Utility

Compounds of the invention are useful in the treatment and/or prevention of infections such as those caused by *Plasmodium falciparum*; *Plasmodium vivax*; *Plasmodium ovale*; and *Plasmodium malaria*, *Trypanosoma cruzi* and parasites of the *Leishmania* genus, such as, for example, *Leishmania donovani*.

Malaria is an infectious disease caused by four protozoan parasites: *Plasmodium falciparum*; *Plasmodium vivax*; *Plasmodium ovale*; and *Plasmodium malaria*. These four parasites are typically transmitted by the bite of an infected female Anopheles mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

The phylum, Apicomplexa, contains many members that are human or animal pathogens including, but not limited to, *Plasmodium* spp. (Malaria), *Toxoplasma gondii* (congenital neurological defects in humans), *Eimeria* spp. (poultry and cattle pathogens), *Cryptosporidia* (opportunistic human and animal pathogens), *Babesia* (cattle parasites) and *Theileria* (cattle parasites). The pathogenesis associated with these parasitic diseases is due to repeated cycles of host-cell invasion, intracellular replication and host-cell lysis. Therefore, understanding parasite proliferation is essential for development of novel drugs and vaccines, for example, to treat malaria.

In vertebrate hosts, the parasite undergoes two main phases of development, the hepathocytic and erythrocytic phases, but it is the erythrocytic phase of its life cycle that causes severe pathology. During the erythrocytic phase, the parasite goes through a complex but well synchronized series of stages, suggesting the existence of tightly regulated signaling pathways.

Calcium serves as an intracellular messenger to control synchronization and development in the erythrocytic life phase. The *Plasmodium* spp. genomes reveal many sequence identities with calcium binding/sensing protein motifs that include Pf39, calmodulin, and calcium dependent protein kinases (CDPKs). *Plasmodium* CDPKs, *Plasmodium* CDPK3 and 4, have been shown to be involved in mosquito infection. CDPK4 has been demonstrated to be essential for the sexual reproduction in the midgut of mosquito by translating the calcium signal into a cellular response and regulating cell cycle progression in the male gametocyte. CDPK3 regulates ookinete gliding motility and penetration of the layer covering the midgut epithelium. *P. falciparum* CDPKI1 (PfCDPK1) is expressed during late schizogony of blood stage and in the infectious sporozoite stage and is secreted to the parasitophorous vacuole by an acylation-dependent mechanism. It can be myristoylated and is abundantly found in detergent-resistant membrane fractions isolated from schizogony-phase parasites. Ontology based pattern identification analysis reveals that PfCDPK1 is clustered with genes associated with either parasite egress or erythrocyte invasion. Direct inhibition of PfCDPK1 can arrest the parasite erythrocytic life cycle progression in the late schizogony phase.

Therefore, kinase activity is distributed in all the stages of *P. falciparum* parasite maturation and kinase inhibitors of the present invention can be used for treating *Plasmodium* related diseases. In particular, kinase inhibitors of the present invention can be a route for treating malaria by inhibiting the kinase PfCDPK1. The in vitro cellular assay, infra, can be used to assess the activity of compounds of the invention against a variety of malarial parasite strains.

Compounds of the invention are relatively inactive against certain protein kinases, e.g. receptor-type tyrosine-protein kinase or fetal liver kinase-2 (FLT3), phosphatidylinositol 3-kinase (PIK3CA), Proto-Oncogene, Serine/Threonine Kinase (PIM1), mitogen-activated protein kinase-activated protein kinase 2 (MapKap2 or MK-2); and cannabinoid receptor 1 (CB1).

In accordance with the foregoing, the present invention further provides a method for preventing or treating malaria in a subject in need of such treatment, which method comprises administering to said subject a therapeutically effective amount of a compound selected from Formula Ia to Formula Ij, a compound of the Examples or a pharmaceutically acceptable salt thereof. The required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). Non-limiting examples of compounds which can be used in combination with compounds of the invention are known anti-malarial drugs, for example, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, KAE-609 and KAF-156, etc.

Where the compounds of the invention are administered in conjunction with other therapies, dosages of the co-administered compounds will of course vary depending on the type of co-drug employed, on the specific drug employed, on the condition being treated and so forth.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula Ia can be prepared by proceeding as in the Reaction Scheme 1; wherein L, Z, $Y^1$, $R^1$, $R^2$, $R^3$, n, m are as defined in the Summary of the Invention. The following reaction schemes are given to be illustrative, not limiting, descriptions of the synthesis of compounds of the invention:

Reaction Scheme 1: General Synthetic Route

The compounds of the invention can be produced by organic synthesis methods known to one of ordinary skill in the art with reference to the following reaction schemes and examples. General methods for synthesis of compounds of Formula (Ia) are provided in Scheme I below.

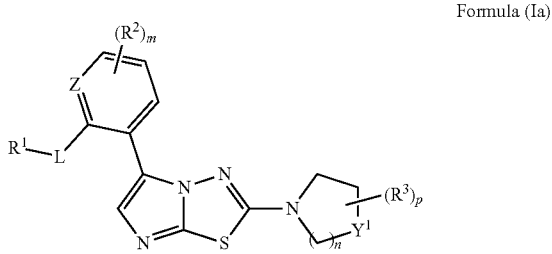

Formula (Ia)

Scheme (I). General method for synthesis of compounds of Formula (Ia).

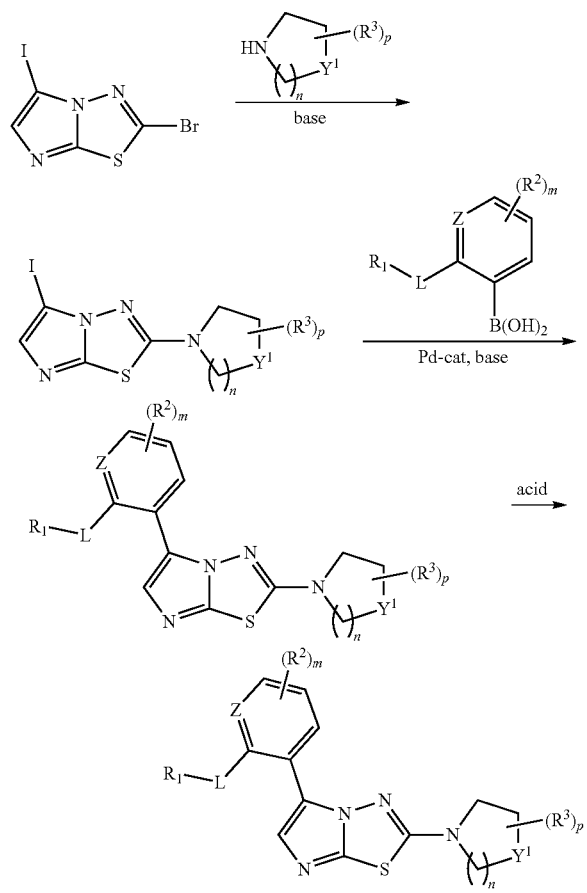

Scheme I shows a general method for synthesizing many compounds of Formula (Ia) from commercially available intermediates described heron. The iodo-bromo-imidazothi- adiazole core can be selective reacted at the bromo-position with secondary cyclic amines under typical SnAr conditions in the presence of base. The secondary amines can contain various functional groups, $R^3$, for example hydroxyl or fluoro. The intermediates from the SnAr reaction can be further reacted with aryl- and heteroaryl-boronic acids under typical Suzuki-coupling conditions using a palladium catalyst and base. The boronic acid compounds contain an ortho-substitution and can also have one-to-two additional substituents such as methyl, isopropyl, alkoxy, or fluoro. Finally, the amine is de-protected using typical conditions for removing an N-Boc group such as trifluoro acetic acid, hydrochloric acid, or formic acid.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention, for example, fumarate salts, can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamoylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

In summary, the compounds of Formula Ia can be made by a process, which involves:
  (a) that of reaction scheme 1; and
  (b) optionally converting a compound of the invention into a pharmaceutically acceptable salt;
  (c) optionally converting a salt form of a compound of the invention to a non-salt form;
  (d) optionally resolving an individual isomer of a compound of the invention from a mixture of isomers;
  (e) optionally converting a non-derivatized compound of the invention into a pharmaceutically acceptable prodrug derivative; and
  (f) optionally converting a prodrug derivative of a compound of the invention to its non-derivatized form.

The invention further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present invention and intermediates can also be converted into each other according to methods generally known to those skilled in the art. Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

List of Abbreviations

AcOH Acetic acid
Alloc-Cl Allyl chloroformate
$B_2Pin_2$ Bis(pinacolato)diboron
br broad signal
BnBr Benzyl bromide
$BnNH_2$ Benzylamine
BnOH Benzyl alcohol
$B(O^iPr)_3$ Triisopropyl borate
$B(OMe)_3$ Trimethyl borate
$(Boc)_2O$ Di-tert-butyl dicarbonate
Cbz-Cl Benzyl chloroformate
$CDCl_3$ Chloroform-d
d Doublet
DAST Diethylaminosulfur trifluoride
DCM Dichloromethane
DEA Diethylamine
DIBAL Diisobutylaluminum hydride
DIPEA Diisopropylethylamine
DMAP 4-Dimethylaminopyridine
DME 1,2-dimethoxyethane
DMF Dimethyl formamide
DMP Dess-Martin periodinane
DMSO Dimethylsulfoxide
DPPA Diphenylphosphoryl azide
equiv. Equivalent(s)
$Et_3N$ Triethylamine
$Et_2O$ Diethyl ether
EtMgBr Ethyl magnesium bromide
EtOAc Ethyl acetate
EtOH Ethanol
$Fe(acac)_3$ Tis(acetylacetonato) iron (III)
Fmoc Fluorenylmethyloxycarbonyl
Grubbs II (1,3-Bis(2,4,6-trimethylphenyl)-2-imidazolidinylidene)dichloro(phenylmethylene)(tricyclohexylphosphine)ruthenium
h Heptet
$H_2O$ Water
HATU 1-[Bis(dimethylamino)methylene]-1H-1,2,3-triazolo[4,5-b]pyridinium 3-oxide hexafluorophosphate
$I_2$ Iodine
IPA 2-Propanol
IPAm Isopropylamine
i-PrMgCl Isopropylmagnesium Chloride
KHMDS Potassium bis(trimethylsilyl)amide
$KHSO_4$ Potassium bisulfate
$K_2CO_3$ Potassium carbonate
$K_2OsO_4$ Potassium osmate (VI)
$K_2S_2O_4$ Potassium dithionite
$K_3Fe(CN)_6$ Potassium ferricyanide
$K_3PO_4$ Potassium phosphate tribasic
KI Potassium iodide
KOAc Potassium acetate
KOH Potassium hydroxide
$KO^tBu$ Potassium tert-butoxide
LDA Lithium diisopropylamide
$LiAlH_4$ Lithium aluminium hydride
$LiBH_4$ Lithium borohydride
LiHMDS Lithium hexamethyldisilazide
LiOH Lithium hydroxide
m Multiplet mCPBA Meta-Chloroperbenzoic Acid
Me$_2$NH Dimethylamine
MeCN Acetonitrile
MeMgBr Methylmagnesium bromide
MeI Methyl iodide
MeOH Methanol
MeSO$_2$NH$_2$ Methanesulfonamide
MTBE Methyl tert-butyl ether
MS Mass spectrometry
MsCl Methanesulfonyl chloride
MW Microwave
N Normality
N$_2$ Nitrogen
NBS N-bromo succinimide
n-BuLi n-Butyllithium
Na$_2$CO$_3$ Sodium carbonate
NaBH(OAc)$_3$ Sodium triacetoxyborohydride
NaCN Sodium cyanide
NaH Sodium hydride
NaHCO$_3$ Sodium bicarbonate
NaN$_3$ Sodium azide
Na$_2$SO$_4$ Sodium Sulphate
NCS N-Chlorosuccinimide
NH$_4$Cl Ammonium Chloride
(NH$_4$)$_2$CO$_3$ Ammonium carbonate
NH$_4$HCO$_2$ Ammonium formate
NH$_4$OH Ammonium hydroxide
NMO 4-Methylmorpholine N-oxide
NMP N-Methyl-2-pyrrolidone
NMR Nuclear magnetic resonance spectrometry
OsO$_4$ Osmium tetroxide
p Pentet
Pd/C Palladium on carbon
Pd(dppf)Cl$_2$ 1,1'-Bis(diphenylphosphino)ferrocene] palladium (II) dichloride
Pd(dtbpf)Cl$_2$ [1,1'-Bis(di-tert-butylphosphino)ferrocene] dichloropalladium(II)
Pd(PPh$_3$)$_4$ Tetrakis(triphenylphosphine)palladium(0)
Ph$_3$P Triphenyl phosphine
PhMe Toluene
q quartet
s singlet
Red-Al Sodium bis(2-methoxyethoxy)aluminum dihydride
Rf Retention factor
Rochelle salt Potassium sodium tartrate tetrahydrate
RockPhos 2-Di(tert-butyl)phosphino-2',4',6'-triisopropyl-3-methoxy-6-methylbiphenyl
t Triplet
TBAB Tetra-n-butylammonium bromide
TBDMS-Cl tert-Butyldimethylsilyl chloride
t-BuLi tert-Butyllithium
t-BuOH tert-Butyl alcohol
T$_3$P 1-Propanephosphonic anhydride
TBAF Tetra-n-butylammonium fluoride
TMEDA N,N,N',N'-Tetramethylethylenediamine
TFA Trifluoroacetic acid
THF Tetrahydrofuran
Ti(OEt)$_4$ Titanium (IV) ethoxide
TLC Thin layer chromatography
TsCl 4-Toluenesulfonyl chloride
Zn Zinc metal
General Synthesis Procedures The compounds as described herein may be synthesized by the general synthetic routes below, specific examples of which are described in more detail in the Examples.

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21).

Compounds of the present invention are prepared from commonly available compounds using procedures known to those skilled in the art in view of the examples and schemes provided herein.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F $^{31}$P, $^{32}$P, $^{35}$S, $^{36}$C, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

Intermediates and final products can be worked up and/or purified according to standard methods, e.g., using chromatographic methods, distribution methods, (re-) crystallization, and the like.

CHIRAL HPLC METHODS:

| Chiral HPLC Method | Conditions |
|---|---|
| 1 | Column: ChiralCel—OD-H, SFC (21 mm × 250 mm)<br>Mobile phase: CO2 (A) in MeOH (B)<br>Flow rate: 100 mL/minute<br>Isocratic: 80/20 (A:B) |
| 2 | Column: ChiralCel—OD-H, SFC (21 mm × 250 mm)<br>Mobile phase: CO2 (A) in MeOH (B)<br>Flow rate: 100 mL/minute<br>Isocratic: 75/25 (A:B) |
| 3 | Column: ChiralPak—IC, SFC (21 mm × 250 mm)<br>Mobile phase: CO2 (A) in MeOH + 0.1% DEA (B)<br>Flow rate: 100 mL/minute<br>Isocratic: 80/20 (A:B) |
| 4 | Column: ChiralPak—AD (21 mm × 250 mm)<br>Mobile phase: heptane (A) in EtOH (B)<br>Flow rate: 20 mL/minute<br>Isocratic: 80/20 (A:B) |
| 5 | Column: ChiralPak—AD (21 mm × 250 mm)<br>Mobile phase: heptane (A) in IPA (B)<br>Flow rate: 20 mL/minute<br>Isocratic: 80/20 (A:B) |
| 6 | Column: ChiralPak—AD (21 mm × 250 mm)<br>Mobile phase: heptane (A) in EtOH (B)<br>Flow rate: 20 mL/minute<br>Isocratic: 80/20 (A:B) |
| 7 | Column: ChiralPak—AD-H (21 mm × 250 mm)<br>Mobile phase: CO2 (A) in MeOH (B)<br>Flow rate: 100 mL/minute<br>Isocratic: 60/40 (A:B) |
| 8 | Column: ChiralPak—AD-H (21 mm × 250 mm)<br>Mobile phase: CO2 (A) in MeOH (B)<br>Flow rate: 100 mL/minute<br>Isocratic: 70/30 (A:B) |
| 9 | Column: ChiralPak—AS-H (30 mm × 250 mm)<br>Mobile phase: CO2 (A) in 50% MeOH (0.1% NH4OH) |

| Chiral HPLC Method | Conditions |
|---|---|
| 10 | Column: ChiralPak—AD-H (30 mm × 250 mm)<br>Mobile phase: CO2 (A) in 55% MeOH (0.1% NH4OH) |
| 11 | Column: ChiralPak—IC-H (30 mm × 250 mm)<br>Mobile phase: CO2 (A) in 40% MeOH (0.1% NH4OH) |
| 12 | Column: C-4<br>Mobile phase: n-hexane (A)/EtOH (B)<br>Flow rate: 19 mL/minute<br>Isocratic: 70-30 (A:B) |
| 13 | Column: C-4<br>Mobile phase: n-hexane (A)/EtOH (B)<br>Flow rate: 20 mL/minute<br>Isocratic: 85-15 |
| 14 | Column: ChiralPak IC (10 mm × 250 mm, 5 micron)<br>Mobile phase: CO2 (A) 0.1% DEA in IPA(B)<br>Flow rate: 13 mL/minute<br>Isocratic: 87:13 (A:B) |

X-Ray Diffraction

The X-ray powder diffraction (XRPD) patterns described herein were recorded on a Bruker D8 Advance diffractometer using $CuK_\alpha$ radiation. The XRPD pattern was recorded between 2° and 40° (2-theta).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and wavelength of X-ray radiation used. The agreement in the 2-theta-diffraction angles between specimen and reference is within 0.2° for the same crystal form and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Thermogravimetric Method

The TGA instruments used to test the crystalline forms was a TA Discovery TGA. Samples of 10 to 20 milligrams were analyzed at a heating rate of 10° C. per minute in the temperature range between 30° C. and about 300° C.

Differential Scanning Calorimetry (DSC)

The DSC instrument used to test the crystalline forms was a TA Discovery DSC. The DSC cell/sample chamber was purged with 20-50 ml/min of ultra-high purity nitrogen gas. The instrument was calibrated with high purity indium. The sample was placed into an open aluminum DSC pan and measured against an empty reference pan. About 1-3 mg of sample powder was placed into the bottom of the pan and lightly tapped down to make contact with the pan. The weight of the sample was measured accurately and recorded to a hundredth of a milligram. The instrument was programmed to heat at 10° C. per minute in the temperature range between 0° C. and 300° C.

The invention is further illustrated by the following examples, which should not be construed as limiting. The assays used throughout the Examples are well established in the art: demonstration of efficacy in these assays is generally regarded as predictive of efficacy in subjects.

Examples 1-3: Intermediates

Compound-1-0: 2-bromo-5-iodoimidazo[2,1-b][1,3,4]thiadiazole

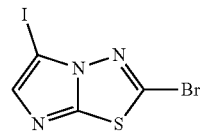

Compound 1-0 was prepared in the following way:

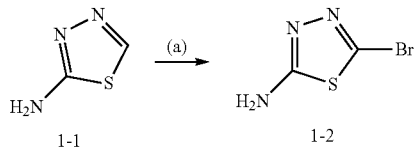 [SMILES: Nc1nncs1 ; Nc1nnc(Br)s1]

Compound 1-1 (500 g, 4.95 mol) in MeOH (5 L), $NaHCO_3$ (830.9 g, 9.89 mol) was added at room temperature, the mixture was cooled to 0-5° C., bromine (792.0 g, 4.95 mol) was added dropwise over a period of 1 hour, then the mixture was warmed to room temperature and stirred for 3 hours, the solid was filtered and washed with MeOH (500 mL), then the solid was slurry in $H_2O$ (10 L) for 1 hours, the solid was collected and washed with $H_2O$ (1 L), the solid was slurry in MeOH (1.5 L) and filtered, washed with MTBE (1 L) to afford 554.0 g of Compound 1-2 as a solid. $^1$H NMR (400 MHz, DMSO-$d_6$): δ ppm 7.51 (brs, 2H). LC-MS=179.9 $[M+H]^+$.

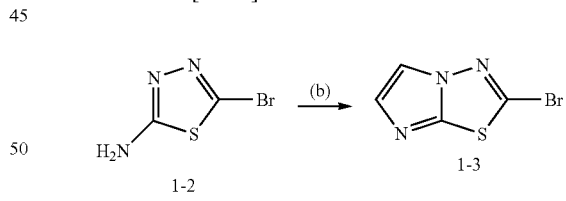

Compound 1-2 (500 g, 2.78 mol) in $H_2O$ and EtOH (1:1; 5 L) and then to it was added 44% aq. solution of 2-chloroacetaldehyde (1425.9 g, 7.78 mol) over a period of 15 minutes at room temperature. The reaction mixture was heated at reflux over a period of 1 hour and stirred for 48 hours. After completion of the reaction, the reaction mixture was quenched with 8% aq. solution of $NaHCO_3$ (5 L) and EtOAc (10 L) was added to it. The mixture was stirred for 10 minutes at room temperature. The reaction mixture was filtered through CELITE pad and the pad was washed with EtOAc (1 L). The organic layer was separated and aqueous layer was extracted with EtOAc (1 L×2). The combined organic layers were concentrated and purified by normal phase chromatography with a running gradient of 16.7-25%

EtOAc/heptane to afford 88.5 g of Compound 1-3 as a solid. $^{1}$H NMR (300 MHz, DMSO-$d_6$): δ ppm 8.22 (d, J=1.2 Hz, 1H), 7.39 (d, J=0.8 Hz, 1H). LC-MS=203.9 [M+H]$^{+}$.

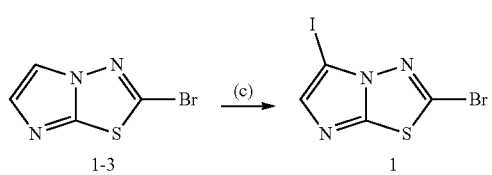 [SMILES: Brc1nn2ccnc2s1 ; Brc1nn2c(I)cnc2s1]

Compound 1-3 (50.0 g, 245 mmol) in DMF (500 mL), NIS (66.1 g, 294 mmol) was added at one portion, the resulting mixture was stirred for 2.5 hours, another NIS (11.0 g, 49 mmol) was added and stirred for another 1.5 hours, the reaction mixture was diluted with EtOAc (2.0 L), and then the reaction mixture was washed with aqueous $Na_2S_2O_3$ solution (500 mL). The organic layer was washed with ice cooled $H_2O$ (3×250 mL) and further washed with brine (250 mL), dried over $Na_2SO_4$, filtered and concentrated and the residue was stirred in MeCN (100 mL) for 30 minutes, the solid was filtered and washed with MeCN (50 mL) to afford 40.4 g of Compound 1 as a solid. $^{1}$H NMR (400 MHz, DMSO-$d_6$): δ ppm 7.43 (s, 1H). LC-MS=329.7 [M+H]$^{+}$.

Compound 2-0a: tert-butyl ((4-hydroxypiperidin-4-yl)methyl)carbamate

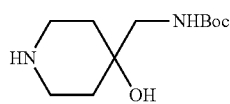

Compound 2-0a was prepared in the following way:

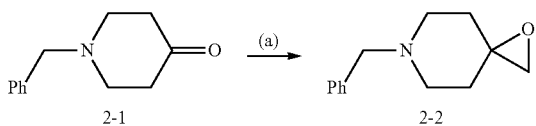

NaH (27.5 g, 687.5 mmol) was added in portion to DMSO (1000 mL) at 18° C. under $N_2$, trimethylsulfoxonium iodide (127.9 g, 581.1 mmol) was added in portion slowly within 1 hour, the resulting solution was raised to room temperature and kept for 1 hour, Compound 2-1 (100 g, 528.3 mmol) in DMSO (100 mL) was added at 18° C. and stirred at room temperature for 2 hours, then the solution was quenched with sat. $NH_4Cl$ solution (500 mL) at 10° C., extracted with MTBE (1 L×4), the combined organic layers were washed with $H_2O$ (300 mL×3), brine (200 mL×2) and concentrated to afford 120.2 g of Compound 2-2 as a yellowish liquid. $^{1}$H NMR (400 MHz, DMSO-$d_6$): δ ppm 7.26-7.38 (m, 5H), 3.59 (s, 2H), 2.55-2.67 (m, 5H), 1.82-1.89 (m, 2H), 1.57-1.60 (m, 2H). LC-MS=204.1 [M+H]$^{+}$.

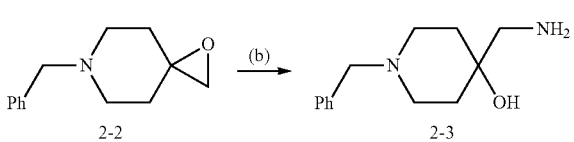 [SMILES: c1ccc(CN2CCC3(CC2)CO3)cc1 ; NCC1(O)CCN(Cc2ccccc2)CC1]

Compound 2-2 (120.2 g, 514 mmol) in MeOH (720 mL), aqueous ammonia (1440 mL, 28%) was added dropwise at 0° C., then the resulting mixture was stirred at room temperature for 16 hours, the mixture was extracted with DCM (800 mL×3), the combined organic layers were washed with NaOH (1 N, 200 mL×2), brine (200 mL), dried on $Na_2SO_4$, concentrated to afford 144.2 g of Compound 2-3 as a solid, which was used for the next step without further purification.

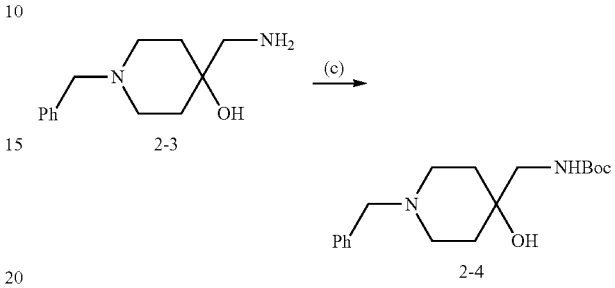

Compound 2-3 (144.2 g, crude) was dissolved in DCM (1.4 L), (Boc)$_2$O (140.4 g, 644 mmol) was added dropwise at room temperature, the resulting solution was stirred for 3 hours. The reaction mixture was concentrated and was purified by normal phase chromatography to afford 129.6 g of Compound 2-4 as a solid. $^{1}$H NMR (400 MHz, CDCl$_3$): δ ppm 7.24-7.32 (brs, 5H), 4.90 (s, 1H), 3.53 (s, 2H), 3.15 (d, J=6.0 Hz, 2H), 2.59-2.62 (m, 2H), 2.30-2.40 (m, 3H), 1.56-1.67 (m, 4H), 1.44 (s, 9H). LC-MS=321.2 [M+H]$^{+}$.

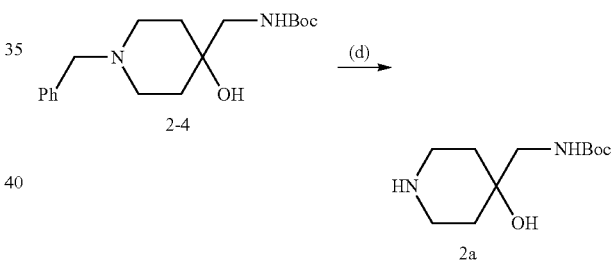

Compound 2.4 (69.0 g, 215.3 mmol) was dissolved in EtOH (510 mL), Pd(OH)$_2$ (21.0 g, 10%) was added under $N_2$, the resulting mixture was exchanged with $H_2$, the mixture was stirred for 18 hours, the mixture was filtered through CELITE pad, washed with DCM (100 mL), concentrated and stirred in MTBE (100 mL), filtered to afford compound 35.2 g of Compound 2a as a solid. $^{1}$H NMR (400 MHz, CDCl$_3$): δ ppm 4.95 (brs, 1H), 3.13-3.21 (d, J=6.0 Hz, 2H), 2.91-2.97 (m, 2H), 2.82-2.87 (m, 2H), 2.08 (brs, 2H), 1.47-1.54 (m, 4H), 1.43 (s, 9H). LC-MS=231.1 [M+H]$^{+}$.

Compound 2-0b: tert-butyl (4-(hydroxymethyl)piperidin-4-yl)carbamate

Compound 2-0b was prepared in the following way:

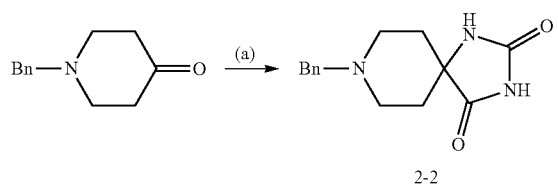 [SMILES: O=C1CCN(Cc2ccccc2)CC1 ; O=C1NC(=O)C2(CCN(Cc3ccccc3)CC2)N1]

To a solution of 1-benzylpiperidin-4-one (20.0 g, 105.6 mmol) in EtOH:H₂O (280 mL, 1:1), was added (NH$_4$)$_2$CO$_3$ (101.4 g, 1056.7 mmol) followed by NaCN (15.5 g, 316.8 mmol). The reaction mixture was heated at 60° C. for 16 hours. The reaction mixture was cooled to room temperature, diluted with H$_2$O and then filtered off. The filtrate was washed with H$_2$O and EtOH, was dried under vacuum to afford 25 g of Compound 2-2 as a solid. The crude compound was used to the next step without further purification. ¹H NMR (300 MHz, DMSO-d$_6$) δ 8.33 (s, 1H), 7.38-7.06 (m, 5H), 3.46 (s, 2H), 2.67 (dt, J=11.5, 4.0, 4.0 Hz, 2H), 2.34-2.15 (m, 2H), 1.79 (td, J=12.4, 11.9, 4.1 Hz, 2H), 1.47 (d, J=13.2 Hz, 2H). LC-MS=260.1 [M+H]⁺, retention time=0.35 minutes (Method P).

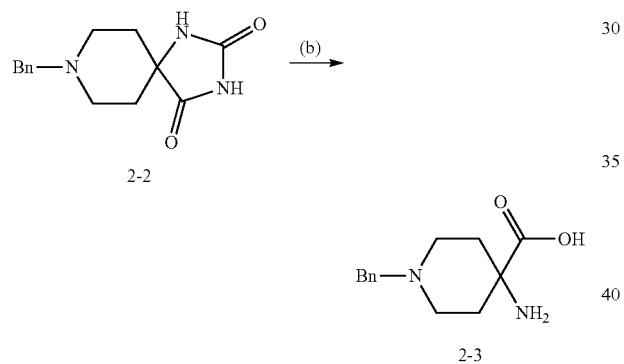

To a solution of KOH (75.0 g, 1532.9 mmol) in H$_2$O (320 mL), Compound 2-2 (26.5 g, 102.1 mmol) was added and the reaction mixture was heated at 100° C. for 24 hours. The reaction mixture was cooled to 0° C., pH was adjusted to 6 using 6 N HCl solution. The precipitated product was filtered and washed with H$_2$O and MTBE and dried under vacuum. The resulting product was co-distilled with PhMe to afford 18 g of Compound 2-3 as a solid. LC-MS=234.9 [M+H]⁺, retention time=0.13 minutes; HPLC: 96.66%, retention time=2.62 minutes (Method P).

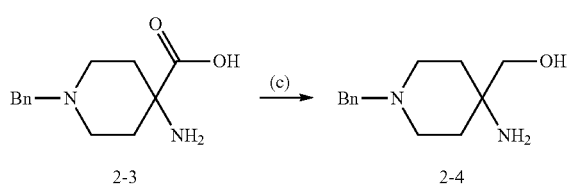 [SMILES: NC1(C(=O)O)CCN(Cc2ccccc2)CC1 ; NC1(CO)CCN(Cc2ccccc2)CC1]

To a solution of Compound 2-3 (18 g, 76.9 mmol) in anhydrous THF (600 mL), LiAlH$_4$ (9.71 g, 256.08 mmol) was added in portionwise at 0° C. and heated at 66° C. for 3 hours. The reaction mixture was quenched with H$_2$O and 1 N NaOH solution and filtered off. The resulting solid was washed with EtOAc and solvent concentrated to afford 14 g of Compound 2-4 as an oil. ¹H NMR (400 MHz, DMSO-d$_6$) δ 7.44-7.02 (m, 5H), 4.51 (s, 1H), 3.44 (s, 2H), 3.11 (s, 1H), 2.46-2.23 (m, 3H), 1.46 (ddd, J=15.9, 8.0, 3.0 Hz, 2H), 1.27-1.18 (m, 2H). LC-MS=234.9 [M+H]⁺, retention time=0.13 minutes.

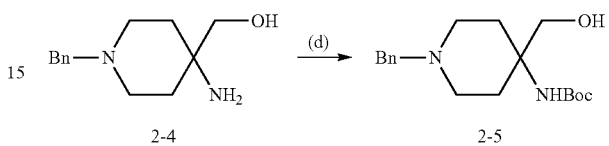

To a stirred solution of Compound 2-4 (14 g, 63.54 mmol) in anhydrous DCM (200 mL) was added (Boc)$_2$O (15.2 g, 69.89 mmol) dropwise and heated at room temperature for 16 hours. The reaction mixture was concentrated and crude compound was purified by normal phase chromatography with a running gradient of 5-10% MeOH/DCM. The resulting product was washed with pentane and filtered to afford 9.3 g of Compound 2-5 as a solid. ¹H NMR (300 MHz, CDCl$_3$) δ 7.39-7.17 (m, 5H), 4.53 (s, 1H), 3.68 (s, 1H), 3.55 (d, J=20.6 Hz, 2H), 2.62 (ddd, J=17.5, 6.6, 4.4 Hz, 2H), 2.36-2.11 (m, 1H), 1.98-1.77 (m, 2H), 1.78-1.64 (m, 2H), 1.44 (s, 9H). LC-MS=221.0 [M+H]⁺, retention time=0.13 minutes.

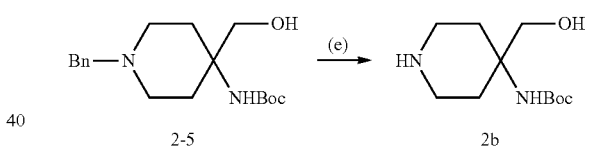

To a stirred solution of Compound 2-5 in MeOH (150 mL) HCOONH$_4$ (11.0 g, 174.14 mmol) was added followed by 10% Pd/C (0.93 g, 10% w.w) and heated at 60° C. for 2 hours. The reaction mixture was filtered through the CELITE pad, washed with MeOH and concentrated to afford 7 g of Compound 2b as a solid. ¹H NMR (300 MHz, DMSO-d$_6$) δ 6.11 (s, 1H), 4.71-4.40 (m, 1H), 3.35-3.30 (m, 4H), 2.64-2.52 (m, 4H), 1.82 (d, J=13.1 Hz, 2H), 1.36 (s, 9H), 1.35-1.31 (m, 1H). LC-MS=321.1 [M+H]⁺, retention time=1.27 minutes.

Compound 3-0: tert-butyl((4-hydroxy-1-(5-iodoimidazo[2,1-b][1,3,4]thiadiazol-2-yl)piperidin-4-yl)methyl)carbamate

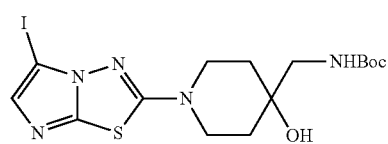 [SMILES: CC(C)(C)OC(=O)NCC1(O)CCN(c2nn3c(I)cnc3s2)CC1]

Compound 3-0 was prepared in the following way:

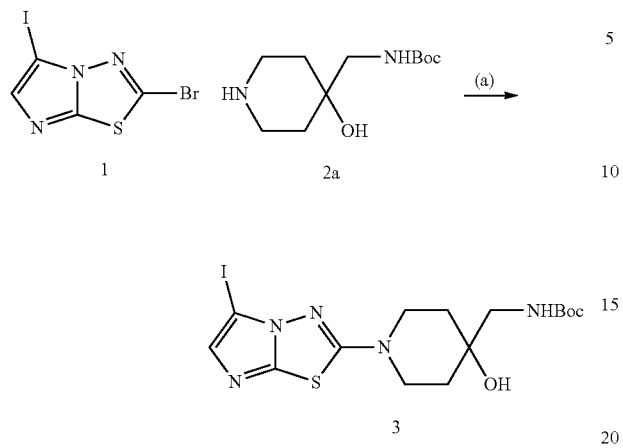

Compound 2a (83.8 g, 363.7 mmol) and Compound 1 (80 g, 242.5 mmol) was dissolved in DMSO (800 mL), DIPEA (62.6 g, 485 mmol) was added dropwise, the resulting mixture was heated to 110° C., the mixture was stirred for 3 hours, the mixture was cooled to room temperature and added H$_2$O (800 mL), extracted with EtOAc (1 L×4), the combined organic layers were washed with H$_2$O (200 mL×3), brine (200 mL×3), dried on Na$_2$SO$_4$, concentrated and the residue was stirred in MeCN:MeOH (10:1, 500 mL) to afford 67.1 g of Compound 3 as a solid. $^1$H NMR (400 MHz, MeOD-d$_4$): δ ppm 7.06 (s, 1H), 2.69-3.72 (m, 2H), 3.45-3.52 (m, 2H), 3.11 (s, 2H), 1.63-1.76 (m, 4H), 1.44 (s, 9H). LC-MS=480.0 [M+H]$^+$.

Example 4-0: 4-(aminomethyl)-1-(5-(6-isopropyl-2-methoxypyridin-3-yl)imidazo[2,1-b][1,3,4]thiadiazol-2-yl)piperidin-4-ol

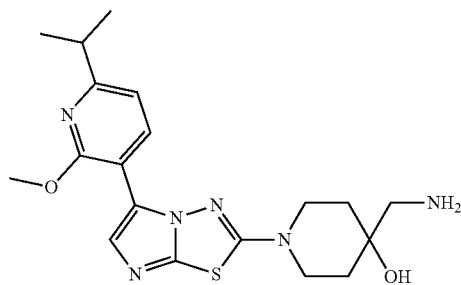 [SMILES: COc1nc(C(C)C)ccc1-c1cnc2sc(N3CCC(O)(CN)CC3)nn12]

Compound 4-0 was prepared in the following way:

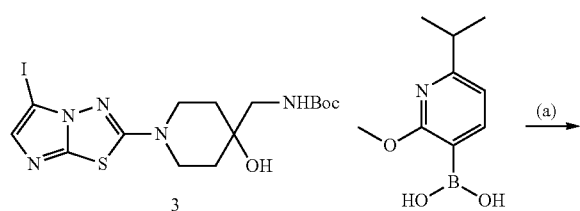

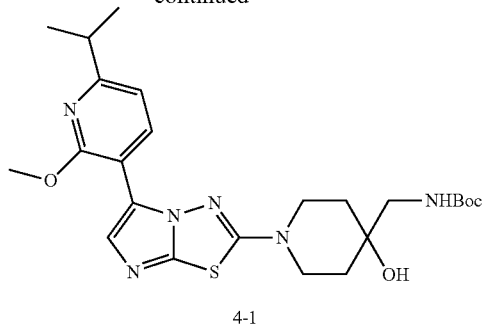

A mixture of Compound 3 (40 mg, 0.083 mmol), (6-isopropyl-2-methoxypyridin-3-yl)boronic acid (32.5 mg, 0.167 mmol), PdCl$_2$(dppf)-DCM complex (3.41 mg, 4.17 μmol), and K$_3$PO$_4$ (53.1 mg, 0.250 mmol) in anhydrous dioxane (1 mL) and H$_2$O (0.2 mL) was flushed with N$_2$ for a few minutes, then sealed and heated to 80° C. for 3 hours. The crude material was purified by normal phase chromatography (4 g column) with a running gradient of 0-50% (3:1 EtOAc:EtOH)/heptane to afford 39.4 mg of Compound 4-1 as a solid. LC-MS=503.3 [M+H]$^+$.

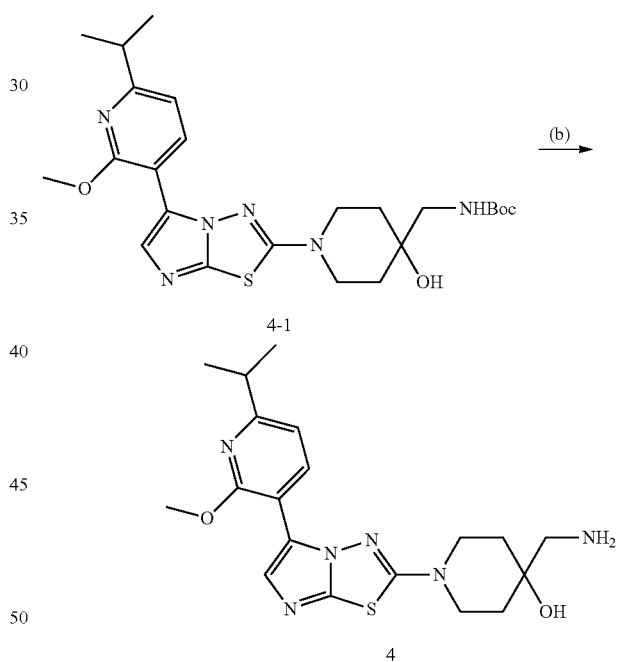

N-Boc De-Protection Methods:
Route A via TFA conditions: Compound 4-1 (148 mg, 0.294 mmol) was dissolved in DCM (1 mL) and TFA (0.5 mL, 6.53 mmol) was added. The reaction was stirred at room temperature for 30 minutes. The mixture was concentrated in vacuo, then redissolved in DCM and a sat. solution of Na$_2$CO$_3$ was added. The aqueous layer was extracted twice with DCM, then twice with EtOAc. The combined organic layers were dried over Na$_2$SO$_4$, and concentrated. The crude material was purified by prep-HPLC to afford 63.7 mg of Compound 4-2 as a solid.
Route B Via HCl Conditions:
To a solution of Compound 4-1 (39 mg, 0.078 mmol) in MeOH (0.5 mL) was added HCl 4 M in dioxane (0.5 mL, 2.0 mmol). The reaction was stirred at room temperature for 1 hour. The mixture was concentrated in vacuo, then was purified by prep-HPLC to afford 18.2 mg of Compound 4-2 as a solid.

Route C Via TFA (Free Base) Conditions:

To a solution of Compound 4-1 (150 mg, 0.298 mmol) in DCM (10 mL) was added TFA (0.6 mL) at 0° C., then the reaction mixture was stirred at room temperature for 2 hours. The reaction was concentrated in vacuo. The residue was treated with 10% NaHCO$_3$ for 2 hours at room temperature and then the product was extracted with 5% MeOH in DCM. The combined organic layers were washed with 10% NaHCO$_3$, brine, dried over Na$_2$SO$_4$ and concentrated in vacuo. The resulting solid was triturated in pentane, filtered and dried to give the desired product as a free base.

Preparation and Characterization of 4-(aminomethyl)-1-(5-(6-isopropyl-2-methoxypyridin-3-yl)imidazo[2,1-b][1,3,4]thiadiazol-2-yl)piperidin-4-ol (2:1) Adipic Acid Salt and Solid Forms 3.0 g of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt (7.45 mmol) was added to a mixture of 30 mL of acetonitrile and 5 mL water in a reactor. A solution of 0.549 g of adipic acid (3.75 mmol) in 15 mL of acetonitrile/water (80:20) was added at 50° C. within 90 minutes. The resulting suspension was kept under stirring at 50° C. for 2 hours and subsequently cooled to 25° C. with further stirring for another 12 hours. After filtration, and washing with dry acetonitrile, the residue was dried at 40° C. for eight hours under vacuum. 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt was obtained as a solid.

Solid form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt can be obtained by 1) thermal conversion of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt or solid form B by heating a sample to at least 10° C. above the melting point and cooling; or 2) equilibrating a slurry of about 40 mg to about 100 mg of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt or solid form B at 25° C. to 50° C. in about 0.5 ml to about 1 ml of a solvent listed in Table 1 below for at least about 24 hours to about 28 days and filtering and drying the solids in air for about 10 min. Solid form A is slightly hygroscopic, absorbing about 0.4% of moisture at 95% RH.

TABLE 1

Powder X-Ray Diffraction Peaks 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt form A
Solvent 1,4-Dioxane
2-Methyl-2-butanol
Acetone
Acetonitrile
Anisole
Benzyl alcohol
Dichloromethane
Chloroform
Cyclopentanone TABLE 1-continued Powder X-Ray Diffraction Peaks 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt form A
Solvent Ethanol
Heptane
Isopropyl Acetate
Methanol
MIBK
MTBE
Nitromethane
Pyridine
Toluene
Tetrahydrofuran
Water
Methanol/water (97:3) (aw = 0.1)
Methanol/water (90:10) (aw = 0.3)
Methanol/water (78:22) (aw = 0.5)
Methanol/water (57:43) (aw = 0.7)
Methanol/water (33:67) (aw = 0.9)
1-Propanol/water (99:1) (aw = 0.15)
Acetonitrile/water (98:2) (aw = 0.3)
2-Propanol/water (96:4) (aw = 0.4)
Acetone/water (94:6) (aw = 0.6)
Tetrahydrofuran/water (95:5) (aw = 0.8)

Figure 2:
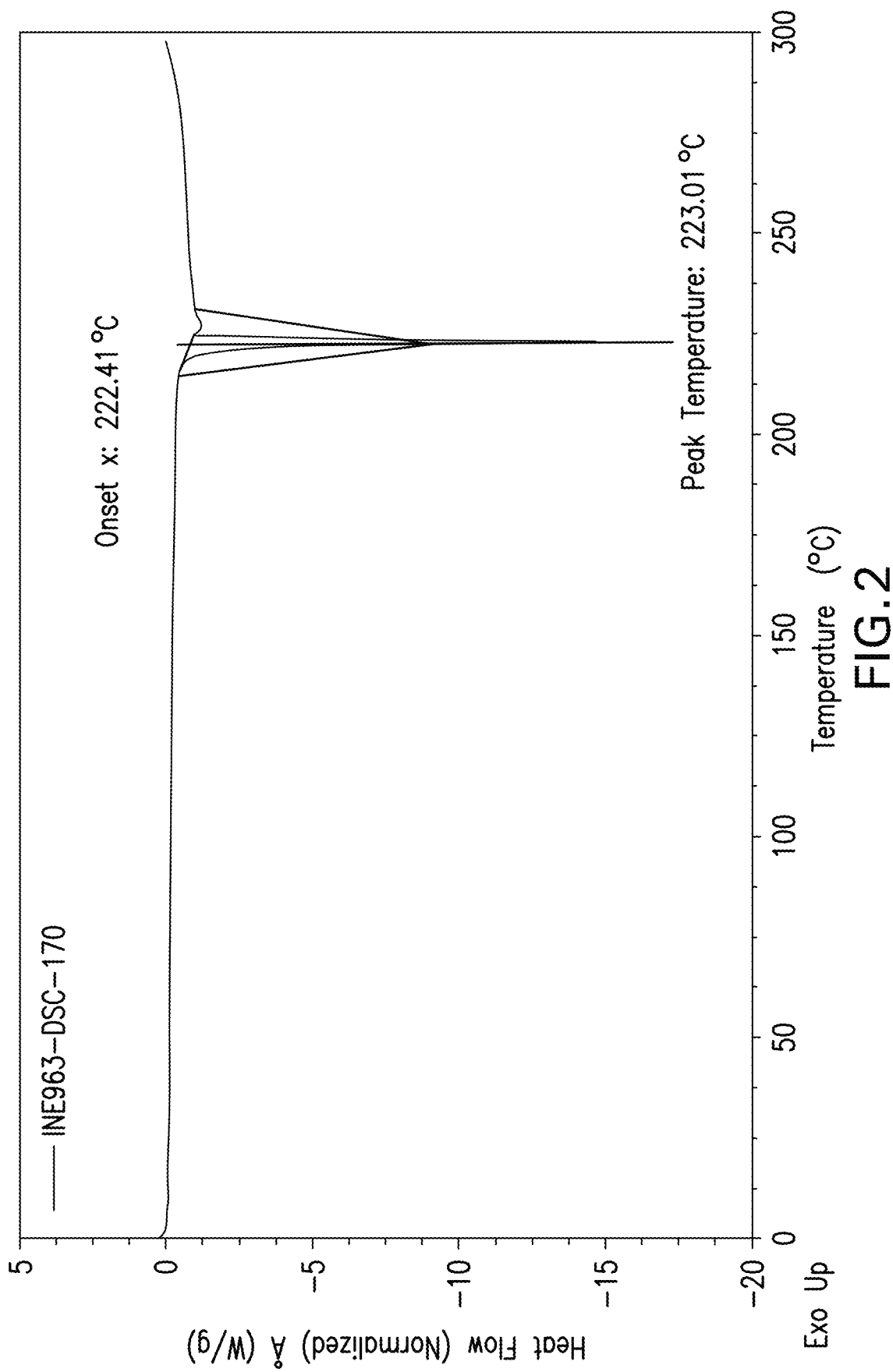
FIG. 2 provides the differential scanning calorimetry (DSC) thermogram scan of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.
Figure 3:
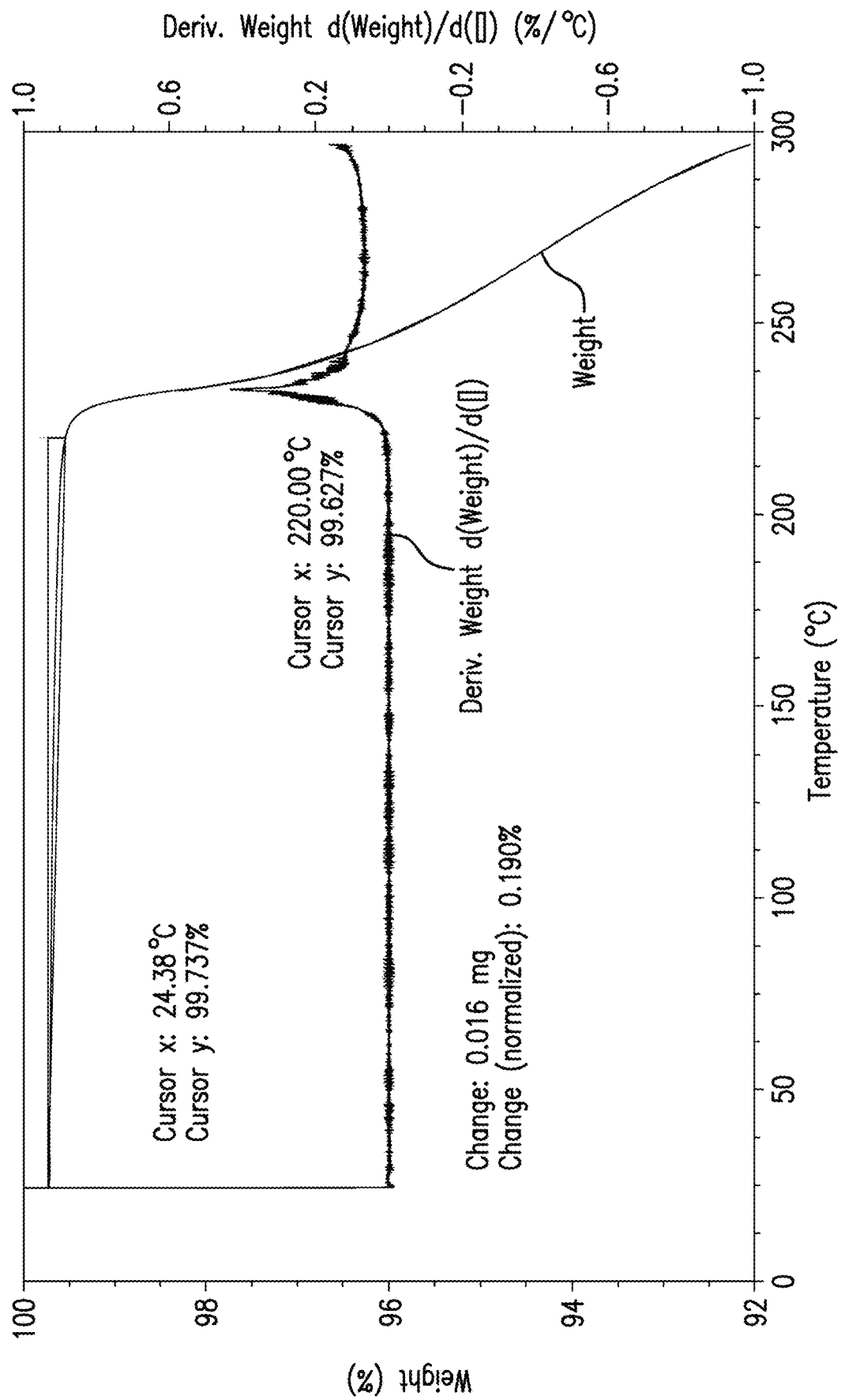
FIG. 3 provides the TGA thermogram scan of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.
Figure 4:
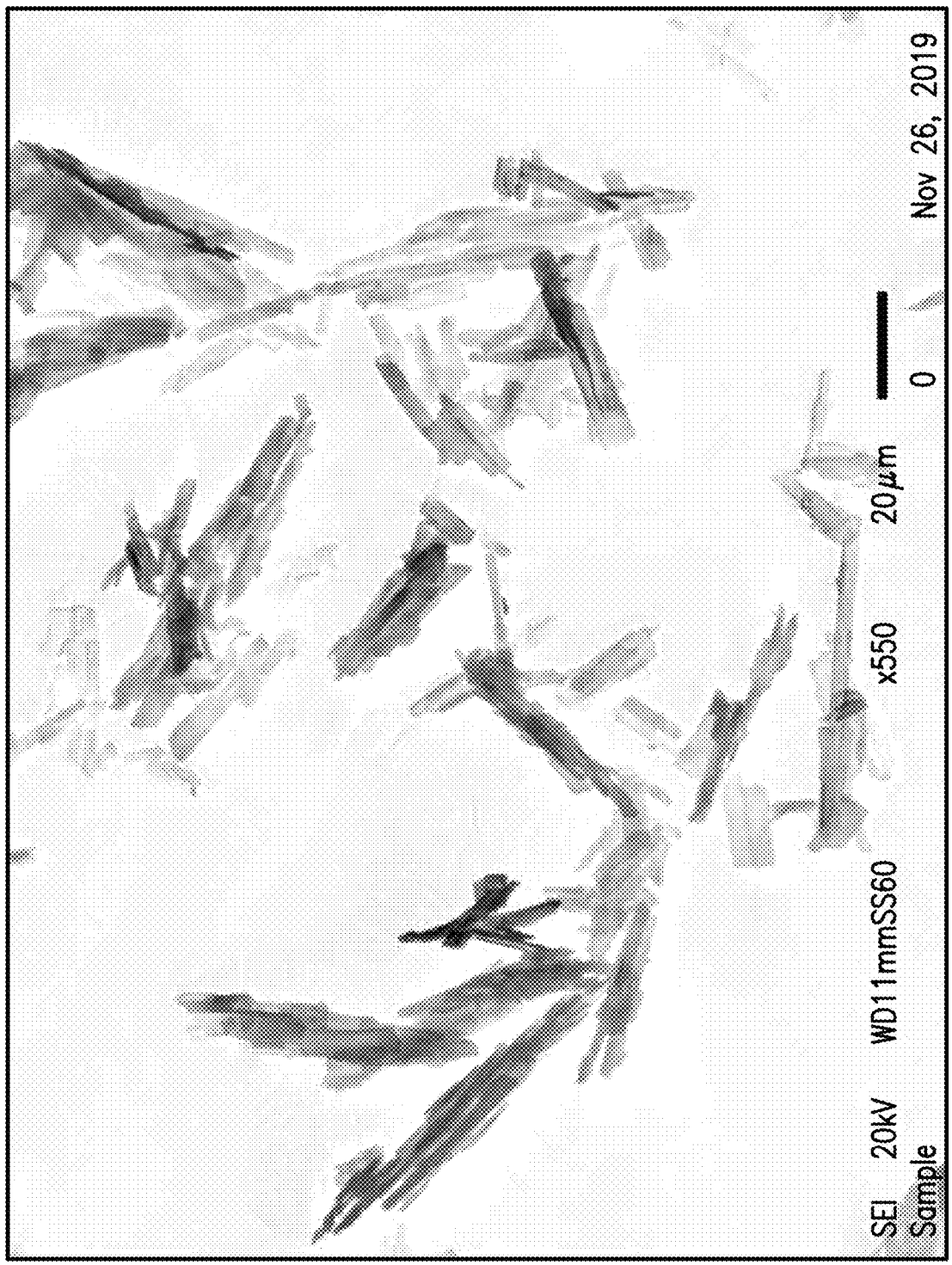
FIG. 4 provides shows the scanning electron microscope (SEM) photograph of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.

FIG. 1 provides the X-ray diffraction pattern for crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt and the peak listing is as shown. FIG. 2 provides the differential scanning calorimetry (DSC) thermogram scan of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt. FIG. 3 provides the TGA thermogram scan of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt. FIG. 4 shows the scanning electron microscope (SEM) photograph of crystal form A of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.

TABLE 2

Powder X-Ray Diffraction Peaks 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt form A

| Angle (2-theta) | d-spacing (Å) | Intensity (Net) | Intensity (Relative) |
| --- | --- | --- | --- |
| 3.555 | 24.832 | 7239.566 | 82 |
| 7.146 | 12.360 | 5908.563 | 67 |
| 10.718 | 8.247 | 4118.988 | 46 |
| 11.151 | 7.929 | 620.816 | 7 |
| 12.715 | 6.956 | 869.004 | 10 |
| 13.373 | 6.616 | 803.501 | 9 |
| 16.098 | 5.501 | 696.916 | 8 |
| 17.874 | 4.959 | 8862.471 | 100 |
| 18.277 | 4.850 | 2394.394 | 27 |
| 19.115 | 4.639 | 578.956 | 7 |
| 21.459 | 4.138 | 3180.716 | 36 |
| 22.006 | 4.036 | 1217.298 | 14 |
| 24.731 | 3.597 | 2403.704 | 27 |
| 25.583 | 3.479 | 561.0364 | 6 |
| 26.609 | 3.347 | 1312.784 | 15 |
| 28.120 | 3.171 | 818.253 | 9 |
| 28.737 | 3.104 | 805.523 | 9 |
| 31.603 | 2.829 | 482.870 | 5 |

Figure 5:
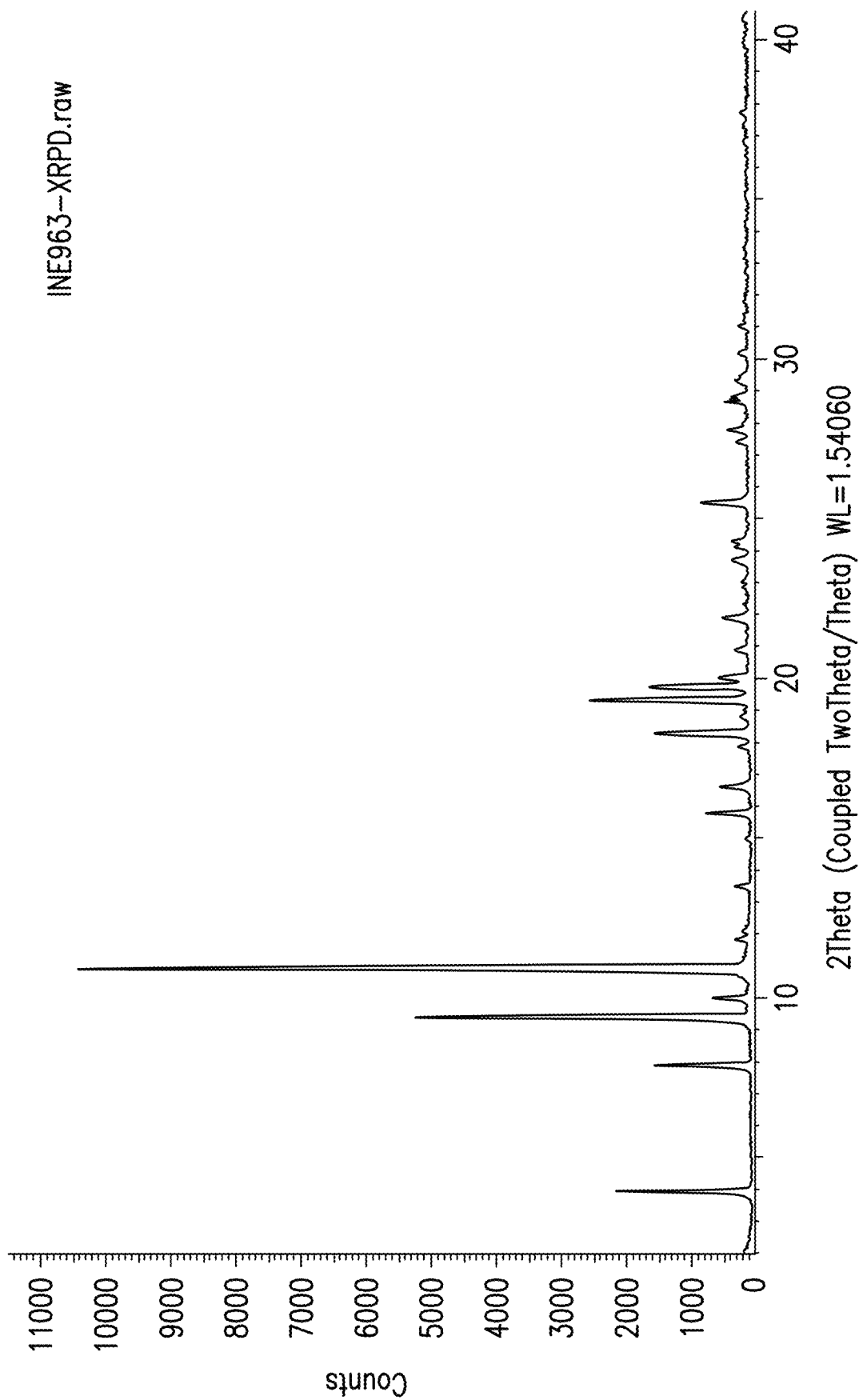
FIG. 5 provides the X-ray diffraction pattern for crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.
Figure 6:
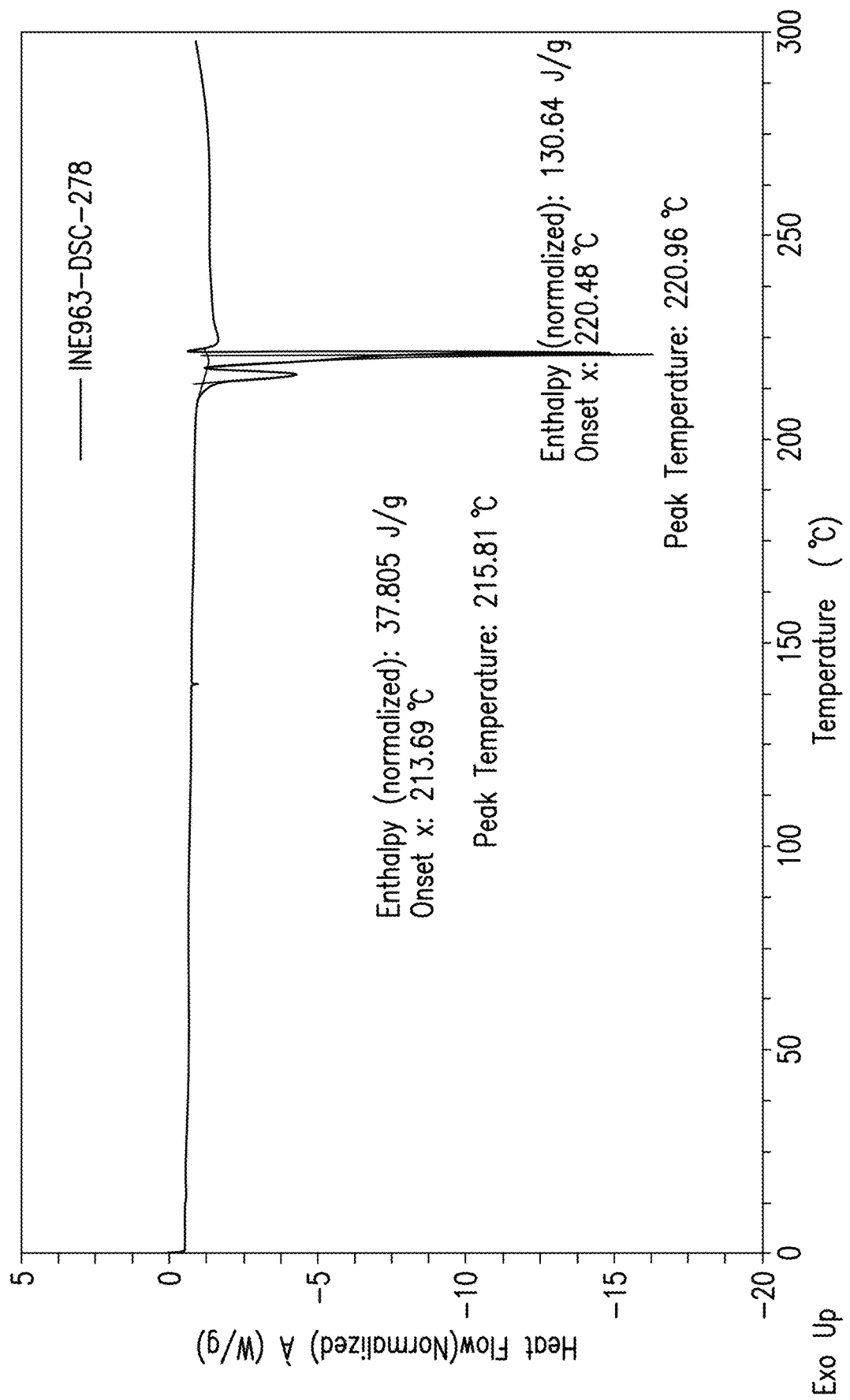
FIG. 6 provides the differential scanning calorimetry (DSC) thermogram scan of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.
Figure 7:
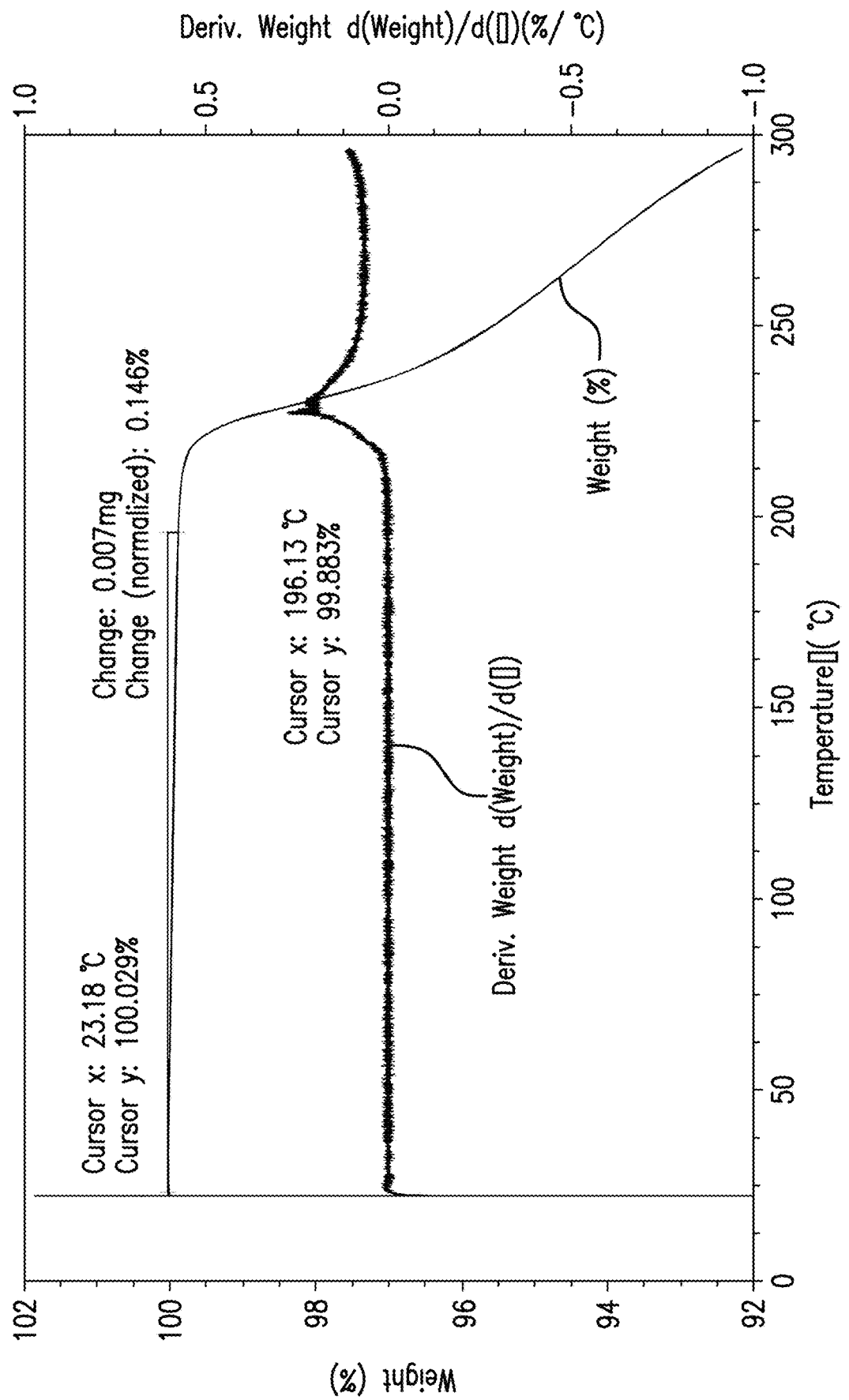
FIG. 7 provides the TGA thermogram scan of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.
Figure 8:
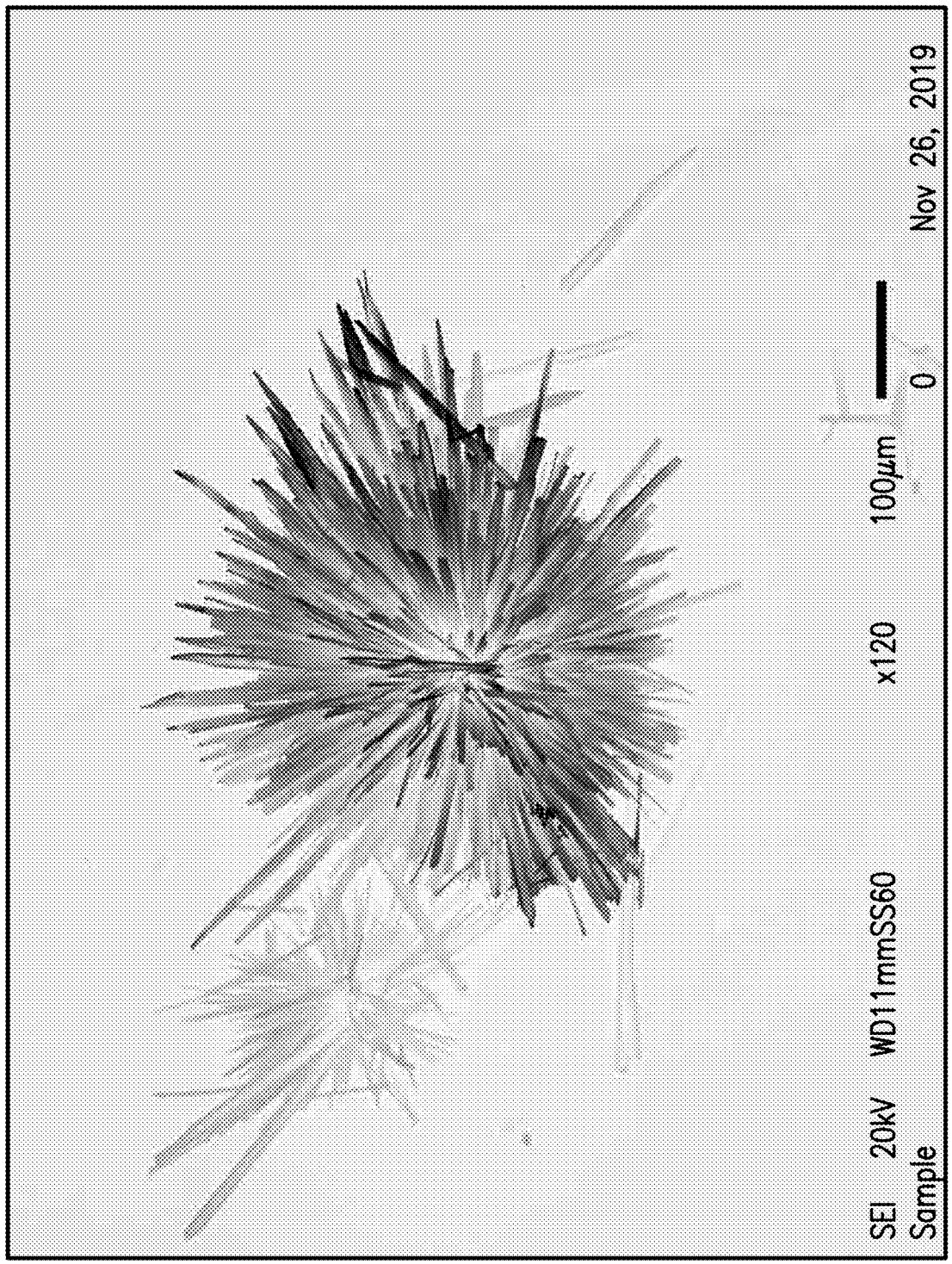
FIG. 8 provides shows the scanning electron microscope (SEM) photograph of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.

Solid form B was obtained by recrystallizing solid form A from 1) the minimal amount of acetone to dissolve solid form A at 60° C., cooling and agitating the solution in a nice bath, and filtering and drying the solids in air for about 10 min; 2) recrystallizing solid form A from the minimal amount of 1:1 methanol/water to dissolve solid form A at 60° C., cooling and agitating the solution in a nice bath, and filtering and drying the solids in air for about 10 ml; 3) precipitation by the addition of DMSO to a benzyl alcohol solution of 4-(aminomethyl)-1-(5-(6-isopropyl-2-methoxypyridin-3-yl)imidazo[2,1-b][1,3,4]thiadiazol-2-yl)piperidin-4-ol (2:1) adipate salt; and 4) precipitation by the addition of methanol to a benzyl alcohol solution of 4-(aminomethyl)-1-(5-(6-isopropyl-2-methoxypyridin-3-yl)imidazo[2,1-b][1,3,4]thiadiazol-2-yl)piperidin-4-ol (2:1) adipate salt. Solid form B is a highly crystalline material with an approximate melting point of 214° C. Solid form B is only slightly hygroscopic absorbing about 0.30% of moisture at 95% RH. FIG. 5 provides the X-ray diffraction pattern for crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt and the peak listing is as shown in Table 3 FIG. 6 provides the differential scanning calorimetry (DSC) thermogram scan of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt. FIG. 7 provides the TGA thermogram scan of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt. FIG. 8 shows the scanning electron microscope (SEM) photograph of crystal form B of 4-(aminomethyl)-1-(5-(6-isopropyl-2-methoxypyridin-3-yl)imidazo[2,1-b][1,3,4]thiadiazol-2-yl)piperidin-4-ol (2:1) adipic acid salt.

TABLE 3

Powder X-Ray Diffraction Peaks
4-(aminomethyl)-1-(5-(6-isopropyl-2-methoxypyridin-3-yl)imidazo[2,1-b][1,3,4]thiadiazol-2-yl)piperidin-4-ol
(2:1) adipic acid salt form B

| Angle (2-theta) | d-spacing (Å) | Intensity (Net) | Intensity (Relative) |
|---|---|---|---|
| 3.936 | 22.430 | 2013.049 | 20 |
| 7.893 | 11.193 | 1443.807 | 14 |
| 9.399 | 9.402 | 5080.186 | 49 |
| 9.994 | 8.843 | 535.937 | 5 |
| 10.928 | 8.090 | 10301.53 | 100 |
| 13.481 | 6.563 | 233.091 | 2 |
| 15.780 | 5.611 | 661.829 | 6 |
| 16.607 | 5.334 | 402.436 | 4 |
| 18.283 | 4.849 | 1441.511 | 14 |
| 19.327 | 4.589 | 2338.473 | 23 |
| 19.752 | 4.491 | 1474.368 | 14 |
| 20.019 | 4.432 | 446.352 | 4 |
| 21.884 | 4.058 | 367.028 | 4 |
| 23.690 | 3.753 | 206.162 | 2 |
| 25.501 | 3.490 | 704.429 | 7 |
| 27.781 | 3.209 | 279.555 | 3 |

The following compounds were prepared by the general synthesis route (I) and exemplified by Compound 4-0, using appropriate commercially available starting materials. All starting materials, and intermediates which are not commercially available, and/or do not have published synthetic routes, are exemplified by compounds herein. Compounds containing stereocenter(s) were prepared from the appropriate chiral commercial starting material, or were purified using chiral prep-HPLC methods listed below as the N-Boc intermediate prior to N-Boc deprotection.

| Example/Compound Number | Structure | NMR | LC-MS | Chiral HPLC Method |
|---|---|---|---|---|
| 4-0 | 4-(aminomethyl)-1-(5-(6-isopropyl-2-methoxypyridin-3-yl)imidazo[2,1-b][1,3,4]thiadiazol-2-yl)piperidin-4-ol | $^1$H NMR (500 MHz, DMSO-$d_6$) δ 8.54 (d, J = 7.8 Hz, 1H), 7.56 (s, 1H), 6.99 (d, J = 7.8 Hz, 1H), 3.99 (s, 3H), 3.65 (m, m, 2H), 3.43 (m, m, 2H), 2.94 (m, 1H), 2.47 (s, 2H), 1.58 (m, 4H), 1.25 (d, J = 5.0 Hz, 6H). | MS m/z calcd for $C_{19}H_{26}N_6O_2S$ 402.2 found 403.2 [M + H]$^+$ | |

-continued

| Example/Compound Number | Structure | NMR | LC-MS | Chiral HPLC Method |
|---|---|---|---|---|
| 4-2 | 3-(aminomethyl)-1-(5-(2-methoxy-4-methylphenyl)imidazo[2,1-b][1,3,4]thiadiazol-2-yl)pyrrolidin-3-ol | $^1$H NMR (500 MHz, DMSO-d$_6$) δ 8.09 (d, J = 7.9 Hz, 1H), 7.93 (s, 3H), 7.53 (s, 1H), 7.02-6.98 (m, 1H), 6.88 (ddd, J = 7.9, 1.7, 0.8 Hz, 1H), 3.89 (s, 3H), 3.68-3.63 (m, 2H), 3.62-3.51 (m, 2H), 3.19-3.01 (m, 2H), 2.37 (s, 3H), 2.19-2.05 (m, 2H). | MS m/z calcd for C$_{17}$H$_{21}$N$_5$O$_2$S 359.1 found 360.1 [M + H]$^+$ | |
| 4-3 | (4-(5-(2-methoxy-4-methylphenyl)imidazo[2,1-b][1,3,4]thiadiazol-2-yl)piperazin-2-yl)methanol | $^1$H NMR (500 MHz, DMSO-d$_6$) δ 9.36-8.86 (m, 2H), 8.02 (d, J = 7.9 Hz, 1H), 7.54 (s, 1H), 7.00 (d, J = 1.6 Hz, 1H), 6.91-6.87 (m, 1H), 4.02-3.95 (m, 2H), 3.89 (s, 3H), 3.73 (dd, J = 11.8, 4.4 Hz, 1H), 3.66 (dd, J = 11.7, 5.3 Hz, 1H), 3.53-3.27 (m, 5H), 2.37 (s, 3H). | MS m/z calcd for C$_{17}$H$_{21}$N$_5$O$_2$S 359.1 found 360.1 [M + H]$^+$ | |
| 4-4 | (4-amino-1-(5-(2-methoxy-4-methylphenyl)imidazo[2,1-b][1,3,4]thiadiazol-2-yl)piperidin-4-yl)methanol | $^1$H NMR (500 MHz, DMSO-d$_6$) δ 8.04 (d, J = 7.8 Hz, 1H), 7.94 (s, 2H), 7.49 (s, 1H), 6.99 (d, J = 1.6 Hz, 1H), 6.88 (dt, J = 8.6, 1.1 Hz, 1H), 3.89 (s, 3H), 3.72-3.66 (m, 2H), 3.64 (s, 2H), 3.53-3.47 (m, 2H), 2.37 (s, 3H), 1.97-1.89 (m, 2H), 1.80 (ddd, J = 13.6, 9.2, 4.4 Hz, 2H). | MS m/z calcd for C$_{18}$H$_{23}$N$_5$O$_2$S 373.2 found 374.2 [M + H]$^+$ | |
| 4-5 | (3S,5S)-5-amino-1-(5-(4-fluoro-2-methoxyphenyl)imidazo[2,1-b][1,3,4]thiadiazol-2-yl)piperidin-3-ol | $^1$H NMR (500 MHz, MeOD-d$_4$) δ 8.27 (dd, J = 8.7, 6.5 Hz, 1H), 7.90 (s, 1H), 7.06 (dd, J = 11.0, 2.4 Hz, 1H), 6.90 (td, J = 8.4, 2.5 Hz, 1H), 4.50-4.41 (m, 1H), 4.28 (d, J = 4.7 Hz, 1H), 3.99 (s, 3H), 3.87-3.75 (m, 1H), 3.71-3.60 (m, 2H), 3.40 (dd, J = 13.0, 10.3 Hz, 1H), 2.28 (d, J = 13.3 Hz, 1H), 1.95 (ddd, J = 13.5, 11.1, 2.8 Hz, 1H). | MS m/z calcd for C$_{16}$H$_{18}$FN$_5$O$_2$S 363.1 found 364.3 [M + H]$^+$ | |

| Example/ Compound Number | Structure | NMR | LC-MS | Chiral HPLC Method |
|---|---|---|---|---|
| 4-6 | 3-(aminomethyl)-1-(5-(6-isopropyl-2-methoxypyridin-3-yl)imidazo[2,1-b][1,3,4]thiadiazol-2-yl)azetidin-3-ol | $^1$H NMR (500 MHz, DMSO-d$_6$) δ 8.47 (d, J = 7.7 Hz, 1H), 7.86 (s, 1H), 7.58 (s, 1H), 6.99 (d, J = 7.8 Hz, 1H), 4.26 (d, J = 8.7 Hz, 2H), 4.05 (d, J = 8.9 Hz, 2H), 3.99 (s, 3H), 3.22 (s, 2H), 3.02-2.91 (m, 1H), 1.26 (d, J = 6.9 Hz, 6H). | MS m/z calcd for C$_{17}$H$_{22}$N$_6$O$_2$S 374.2, found 375.2 [M + H]$^+$ | |
| 4-7 | 4-(aminomethyl)-1-(5-(5-chloro-4-fluoro-2-methoxyphenyl)imidazo[2,1-b][1,3,4]thiadiazol-2-yl)piperidin-4-ol | $^1$H NMR (300 MHz, MeOD-d$_4$) δ 8.44 (dd, J = 8.3, 5.6 Hz, 1H), 7.96 (s, 1H), 7.22 (d, J = 11.1 Hz, 1H), 3.99 (s, 3H), 3.83 (s, 2H), 3.76-3.52 (m, 2H), 2.98 (s, 2H), 1.93-1.74 (m, 4H). | MS m/z calcd for C$_{17}$H$_{19}$ClFN$_5$O$_2$S 411.1 found 412.2 [M + H]$^+$ | |
| 4-8 | 4-(aminomethyl)-1-(5-(2-ethoxy-5-methylphenyl)imidazo[2,1-b][1,3,4]thiadiazol-2-yl)piperidin-4-ol | $^1$H NMR (500 MHz, DMSO-d$_6$) δ 8.00 (d, J = 2.2 Hz, 1H), 7.81 (t, J = 5.6 Hz, 3H), 7.61 (s, 1H), 7.13 (dd, J = 8.4, 2.2 Hz, 1H), 7.04 (d, J = 8.4 Hz, 1H), 4.12 (q, J = 6.9 Hz, 2H), 3.70 (dt, J = 13.2, 4.2 Hz, 2H), 3.51 (ddd, J = 13.6, 9.9, 4.4 Hz, 2H), 2.86 (q, J = 5.8 Hz, 2H), 2.32 (s, 3H), 1.73 (tdd, J = 13.0, 10.2, 4.4 Hz, 4H), 1.40 (t, J = 6.9 Hz, 3H). | MS m/z calcd for C$_{19}$H$_{25}$N$_5$O$_2$S 387.2 found 388.2 [M + H]$^+$ | |
| 4-9 | 2-(5-(4-fluoro-2-methoxyphenyl)imidazo[2,1-b][1,3,4]thiadiazol-2-yl)-5-oxa-2,8-diazaspiro[3.5]nonane | $^1$H NMR (500 MHz, DMSO-d$_6$) δ 9.09 (s, 2H), 8.15 (dd, J = 8.7, 6.9 Hz, 1H), 7.53 (s, 1H), 7.09 (dd, J = 11.4, 2.6 Hz, 1H), 6.91 (td, J = 8.4, 2.6 Hz, 1H), 4.27 (d, J = 9.2 Hz, 2H), 4.14 (d, J = 9.2 Hz, 2H), 3.91 (s, 3H), 3.90-3.86 (m, 2H), 3.45 (s, 2H), 3.14 (s, 2H). | MS m/z calcd for C$_{17}$H$_{18}$FN$_5$O$_2$S 375.1 found 376.1 [M + H]$^+$ | |

-continued

| Example/Compound Number | Structure | NMR | LC-MS | Chiral HPLC Method |
|---|---|---|---|---|
| 4-10 | 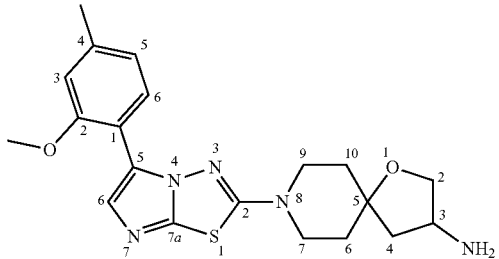<br>8-(5-(2-methoxy-4-methylphenyl)imidazo[2,1-b][1,3,4]thiadiazol-2-yl)-1-oxa-8-azaspiro[4.5]decan-3-amine | $^1$H NMR (500 MHz, DMSO-d$_6$) δ 8.16-8.07 (m, 3H), 8.05 (d, J = 7.9 Hz, 1H), 7.62 (s, 1H), 7.01 (t, J = 1.0 Hz, 1H), 6.91 (ddd, J = 7.9, 1.6, 0.8 Hz, 1H), 3.99 (dd, J = 10.0, 6.0 Hz, 1H), 3.89 (s, 4H), 3.79 (dd, J = 10.0, 4.1 Hz, 1H), 3.62 (ddt, J = 18.0, 13.1, 4.7 Hz, 2H), 3.55-3.42 (m, 2H), 2.37 (s, 3H), 2.24 (dd, J = 13.8, 8.3 Hz, 1H), 1.90 (dd, J = 8.1, 4.5 Hz, 2H), 1.82-1.68 (m, 3H). | MS m/z calcd for C$_{20}$H$_{25}$N$_5$O$_2$S 399.2 found 400.2 [M + H]$^+$ | |
| 4-11 | 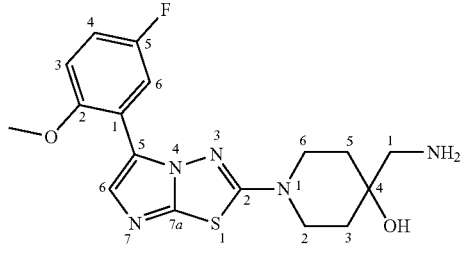<br>4-(aminomethyl)-1-(5-(5-fluoro-2-methoxyphenyl)imidazo[2,1-b][1,3,4]thiadiazol-2-yl)piperidin-4-ol | $^1$H NMR (500 MHz, DMSO-d$_6$) δ 8.12 (ddd, J = 10.4, 2.5, 1.0 Hz, 1H), 7.85 (d, J = 6.7 Hz, 3H), 7.72 (s, 1H), 7.21-7.12 (m, 2H), 3.92 (s, 3H), 3.70 (dt, J = 13.2, 4.2 Hz, 2H), 3.52 (ddd, J = 13.6, 9.8, 4.6 Hz, 2H), 2.87 (q, J = 5.7 Hz, 2H), 1.74 (h, J = 9.2 Hz, 4H). | MS m/z calcd for C$_{17}$H$_{20}$FN$_5$O$_2$S 377.1 found 378.1 [M + H]$^+$ | |
| 4-12 | 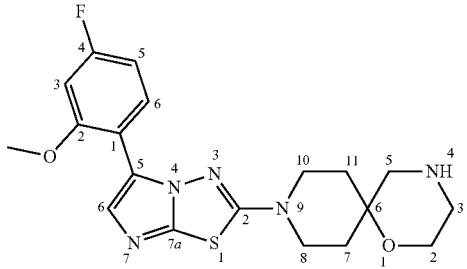<br>9-(5-(4-fluoro-2-methoxyphenyl)imidazo[2,1-b][1,3,4]thiadiazol-2-yl)-1-oxa-4,9-diazaspiro[5.5]undecane | 1H NMR (500 MHz, DMSO-d$_6$) δ 8.96 (s, 2H), 8.19 (dd, J = 8.7, 6.8 Hz, 1H), 7.53 (s, 1H), 7.08 (dd, J = 11.4, 2.6 Hz, 1H), 6.91 (td, J = 8.5, 2.6 Hz, 1H), 3.91 (s, 3H), 3.83 (t, J = 5.0 Hz, 2H), 3.68 (dt, J = 13.4, 3.9 Hz, 2H), 3.37 (td, J = 12.6, 2.9 Hz, 2H), 3.09 (d, J = 9.2 Hz, 4H), 2.06 (d, J = 13.5 Hz, 2H), 1.74 (dq, J = 13.7, 4.6 Hz, 2H). | MS m/z calcd for C$_{19}$H$_{22}$FN$_5$O$_2$S 403.2 found 404.1 [M + H]$^+$ | |
| 4-13 | 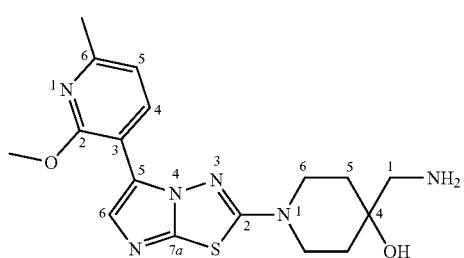<br>4-(aminomethyl)-1-(5-(2-methoxy-6-methylpyridin-3-yl)imidazo[2,1-b][1,3,4]thiadiazol-2-yl)piperidin-4-ol | $^1$H NMR (500 MHz, DMSO-d$_6$) δ 8.55 (d, J = 7.7 Hz, 1H), 7.82 (s, 3H), 7.65 (s, 1H), 7.00 (d, J = 7.7 Hz, 1H), 4.00 (s, 3H), 3.72 (dt, J = 13.3, 4.1 Hz, 2H), 3.50 (ddd, J = 13.6, 9.7, 4.7 Hz, 2H), 2.86 (q, J = 5.8 Hz, 2H), 2.45 (s, 3H), 1.72 (q, J = 4.5 Hz, 4H). | MS m/z calcd for C$_{17}$H$_{22}$N$_6$O$_2$S 374.2 found 375.2 [M + H]$^+$ | |

| Example/Compound Number | Structure | NMR | LC-MS | Chiral HPLC Method |
|---|---|---|---|---|
| 4-14 | 4-(aminomethyl)-1-(5-(3-chloro-2-methoxyphenyl)imidazo[2,1-b][1,3,4]thiadiazol-2-yl)piperidin-4-ol | $^1$H NMR (300 MHz, MeOD-d$_4$) δ 8.17 (dd, J = 7.9, 1.6 Hz, 1H), 7.99 (s, 1H), 7.56 (dd, J = 8.1, 1.6 Hz, 1H), 7.29 (t, J = 8.0, 8.0 Hz, 1H), 3.90-3.80 (m, 2H), 3.82 (s, 3H), 3.80-3.60 (m, 2H), 2.98 (s, 2H), 1.95-1.80 (m, 4H). | MS m/z calcd for C$_{17}$H$_{16}$FN$_7$OS 393.1 found 394.1 [M + H]$^+$ | |
| 4-15 | 4-(aminomethyl)-1-(5-(4-cyclopropyl-2-methoxyphenyl)imidazo[2,1-b][1,3,4]thiadiazol-2-yl)piperidin-4-ol | $^1$H NMR (400 MHz, MeOD-d$_4$) δ 8.14 (d, J = 8.1 Hz, 1H), 7.82 (s, 1H), 6.89 (d, J = 1.6 Hz, 1H), 6.79 (dd, J = 8.2, 1.7 Hz, 1H), 3.94 (s, 3H), 3.88-3.80 (m, 2H), 3.68-3.58 (m, 2H), 2.97 (s, 2H), 2.03-1.93 (m, 1H), 1.87-1.75 (m, 4H), 1.07-1.00 (m, 2H), 0.80-0.73 (m, 2H). | MS m/z calcd for C$_{20}$H$_{25}$N$_5$O$_2$S 399.1 found 400.1 [M + H]$^+$ | |
| 4-16 | (3S,4R)-4-amino-1-(5-(4-fluoro-2-methoxyphenyl)imidazo[2,1-b][1,3,4]thiadiazol-2-yl)piperidin-3-ol | $^1$H NMR (400 MHz, MeOD-d$_4$) δ 8.27 (dd, J = 6.5, 8.7 Hz, 1H), 7.89 (s, 1H), 7.03 (dd, J = 2.4, 11.0 Hz, 1H), 6.89 (dt, J = 2.4, 8.4 Hz, 1H), 4.22-4.14 (m, 2H), 3.97 (s, 4H), 3.65-3.53 (m, 2H), 3.49-3.36 (m, 1H), 2.18 (dq, J = 4.6, 12.5 Hz, 1H), 2.01-1.88 (m, 1H). | MS m/z calcd for C$_{20}$H$_{25}$N$_5$O$_2$S 399.2 found 400.1 [M + H]$^+$ | 9 |
| 4-17 | (3R,4S)-4-amino-1-(5-(4-fluoro-2-methoxyphenyl)imidazo[2,1-b][1,3,4]thiadiazol-2-yl)piperidin-3-ol | $^1$H NMR (400 MHz, MeOD-d$_4$) δ 8.27 (dd, J = 6.6, 8.7 Hz, 1H), 7.89 (s, 1H), 7.03 (dd, J = 2.4, 10.9 Hz, 1H), 6.89 (dt, J = 2.4, 8.4 Hz, 1H), 4.23-4.13 (m, 2H), 3.97 (s, 4H), 3.65-3.52 (m, 2H), 3.51-3.36 (m, 1H), 2.25-2.11 (m, 1H), 1.94 (br d, J = 12.7 Hz, 1H). | MS m/z calcd for C$_{16}$H$_{18}$FN$_5$O$_2$S 363.1 found 364.3 [M + H]$^+$ | 9 |

| Example/Compound Number | Structure | NMR | LC-MS | Chiral HPLC Method |
|---|---|---|---|---|
| 4-18 | 4-(aminomethyl)-1-(5-(3,5-difluoro-2-methoxyphenyl)imidazo[2,1-b][1,3,4]thiadiazol-2-yl)piperidin-4-ol | $^1$H NMR (400 MHz, MeOD-d$_4$) δ 8.04 (s, 1H), 7.99-7.92 (m, 1H), 7.25-7.16 (m, 1H), 3.98 (d, J = 1.8, 0.5 Hz, 3H), 3.92-3.83 (m, 2H), 3.74-3.68 (m, 2H), 3.00 (s, 2H), 1.90-1.81 (m, 4H). | MS m/z calcd for C$_{17}$H$_{19}$F$_2$N$_5$O$_2$S 395.1 found 395.75 [M + H]$^+$ | |
| 4-19 | 4-(aminomethyl)-1-(5-(2,3-dihydrobenzofuran-7-yl)imidazo[2,1-b][1,3,4]thiadiazol-2-yl)piperidin-4-ol | $^1$H NMR (500 MHz, DMSO-d$_6$) δ 8.15 (d, J = 7.9 Hz, 1H), 7.98 (s, 3H), 7.68 (s, 1H), 7.25 (d, J = 7.2 Hz, 1H), 6.99 (t, J = 7.6 Hz, 1H), 4.70 (t, J = 8.8 Hz, 2H), 3.77-3.73 (m, 2H), 3.52 (dt, J = 13.9, 7.6 Hz, 2H), 3.28 (t, J = 8.7 Hz, 2H), 2.85 (q, J = 5.9 Hz, 2H), 1.74 (dd, J = 7.6, 4.2 Hz, 4H). | MS m/z calcd for C$_{18}$H$_{21}$N$_5$O$_2$S 371.1 found 372.3 [M + H]$^+$ | |
| 4-20 | 4-(aminomethyl)-1-(5-(2-methoxy-3-methylphenyl)imidazo[2,1-b][1,3,4]thiadiazol-2-yl)piperidin-4-ol | $^1$H NMR (500 MHz, DMSO-d$_6$) δ 8.02 (dd, J = 7.8, 1.7 Hz, 1H), 7.83 (d, J = 5.8 Hz, 3H), 7.64 (s, 1H), 7.27-7.22 (m, 1H), 7.16 (t, J = 7.6 Hz, 1H), 3.70 (dt, J = 13.1, 4.1 Hz, 2H), 3.62 (s, 3H), 3.49 (ddd, J = 13.7, 9.9, 4.7 Hz, 2H), 2.86 (q, J = 5.8 Hz, 2H), 2.33 (s, 3H), 1.79-1.64 (m, 4H). | MS m/z calcd for C$_{18}$H$_{23}$N$_5$O$_2$S 373.2 found 374.2 [M + H]$^+$ | |
| 4-21 | (R)-1-(1-(5-(6-isopropyl-2-methoxypyridin-3-yl)imidazo[2,1-b][1,3,4]thiadiazol-2-yl)pyrrolidin-3-yl)cyclopropan-1-amine | $^1$H NMR (500 MHz, DMSO-d$_6$) δ 8.57 (d, J = 7.7 Hz, 1H), 8.25 (s, 3H), 7.60 (s, 1H), 6.99 (d, J = 7.8 Hz, 1H), 4.01 (s, 3H), 3.74 (dd, J = 9.9, 7.9 Hz, 1H), 3.62 (t, J = 9.0 Hz, 1H), 3.49 (td, J = 9.7, 6.7 Hz, 1H), 3.26 (t, J = 9.8 Hz, 1H), 2.98 (p, J = 6.9 Hz, 1H), 2.80-2.65 (m, 1H), 2.13 (dt, J = 12.7, 6.5 Hz, 1H), 1.87-1.74 (m, 1H), 1.27 (d, J = 6.9 Hz, 6H), 0.91 (s, 4H). | MS m/z calcd for C$_{20}$H$_{26}$N$_6$OS 398.2 found 399.2 [M + H]$^+$ | |

| Example/Compound Number | Structure | NMR | LC-MS | Chiral HPLC Method |
|---|---|---|---|---|
| 4-22 | 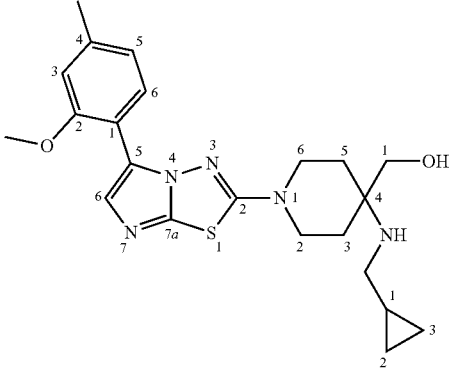<br>(4-((cyclopropylmethyl)amino)-1-(5-(2-methoxy-4-methylphenyl)imidazo[2,1-b][1,3,4]thiadiazol-2-yl)piperidin-4-yl)methanol | $^1$H NMR (500 MHz, DMSO-$d_6$) δ 8.38 (s, 2H), 8.04 (d, J = 7.9 Hz, 1H), 7.53 (s, 1H), 7.00 (d, J = 1.6 Hz, 1H), 6.89 (ddd, J = 7.8, 1.6, 0.8 Hz, 1H), 3.89 (s, 3H), 3.84-3.78 (m, 2H), 3.77 (s, 2H), 3.41-3.34 (m, 2H), 2.84 (q, J = 7.1 Hz, 2H), 2.37 (s, 3H), 2.02 (d, J = 13.3 Hz, 2H), 1.87 (td, J = 12.8, 4.9 Hz, 2H), 1.01 (ddd, J = 12.4, 8.1, 4.8 Hz, 1H), 0.63-0.58 (m, 2H), 0.35-0.32 (m, 2H). | MS m/z calcd for $C_{22}H_{29}N_5O_2S$ 427.2 found 428.2 [M + H]$^+$ | |
| 4-23 | 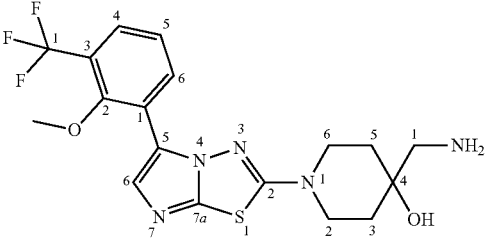<br>4-(aminomethyl)-1-(5-(2-methoxy-3-(trifluoromethyl)phenyl)imidazo[2,1-b][1,3,4]thiadiazol-2-yl)piperidin-4-ol | $^1$H NMR (500 MHz, DMSO-$d_6$) δ 8.40 (d, J = 7.9 Hz, 1H), 7.80 (t, J = 5.9 Hz, 3H), 7.66 (d, J = 7.7 Hz, 1H), 7.62 (s, 1H), 7.45 (t, J = 7.9 Hz, 1H), 3.70 (dt, J = 13.1, 4.1 Hz, 2H), 3.64 (s, 3H), 3.49 (ddd, J = 13.9, 9.9, 4.5 Hz, 2H), 2.85 (q, J = 5.8 Hz, 2H), 1.77-1.64 (m, 4H). | MS m/z calcd for $C_{18}H_{20}F_3N_5O_2S$ 427.1 found 428.1 [M + H]$^+$ | |
| 4-24 | 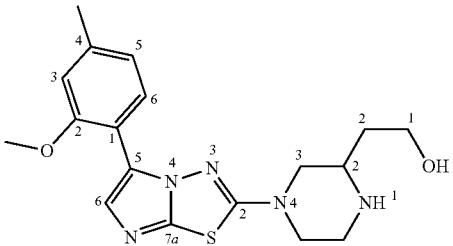<br>2-(4-(5-(2-methoxy-4-methylphenyl)imidazo[2,1-b][1,3,4]thiadiazol-2-yl)piperazin-2-yl)ethan-1-ol | $^1$H NMR (500 MHz, DMSO-$d_6$) δ 8.02 (d, J = 7.9 Hz, 1H), 7.50 (s, 1H), 6.98 (d, J = 1.6 Hz, 1H), 6.88-6.85 (m, 1H), 4.03 (d, J = 13.4 Hz, 1H), 3.95 (d, J = 13.8 Hz, 1H), 3.87 (s, 3H), 3.61 (t, J = 5.9 Hz, 2H), 3.54 (s, 1H), 3.44 (dd, J = 20.3, 9.7 Hz, 2H), 3.30 (dd, J = 13.8, 10.7 Hz, 2H), 2.35 (s, 3H), 1.80 (t, J = 6.1 Hz, 2H). | MS m/z calcd for $C_{18}H_{23}N_5O_2S$ 373.2 found 374.2 [M + H]$^+$ | |

| Example/Compound Number | Structure | NMR | LC-MS | Chiral HPLC Method |
|---|---|---|---|---|
| 4-25 | 3-(aminomethyl)-1-(5-(2-methoxy-4-methylphenyl)imidazo[2,1-b][1,3,4]thiadiazol-2-yl)azetidin-3-ol | $^1$H NMR (500 MHz, DMSO-d$_6$) δ 8.02 (d, J = 7.8 Hz, 1H), 7.92 (s, 3H), 7.53 (s, 1H), 7.00 (d, J = 1.6 Hz, 1H), 6.94-6.86 (m, 1H), 4.27 (d, J = 8.8 Hz, 3H), 4.06 (d, J = 8.9 Hz, 2H), 3.89 (s, 3H), 3.24 (q, J = 5.7 Hz, 2H), 2.37 (s, 3H). | MS m/z calcd for C$_{16}$H$_{19}$N$_5$O$_2$S 345.1 found 346.1 [M + H]$^+$ | |
| 4-26 | (3S,4R)-3-fluoro-1-(5-(4-fluoro-2-methoxyphenyl)imidazo[2,1-b][1,3,4]thiadiazol-2-yl)piperidin-4-amine | $^1$H NMR (400 MHz, MeOD-d$_4$) δ 8.22-8.06 (m, 1H), 7.81 (br s, 1H), 6.93 (br d, J = 10.9 Hz, 1H), 6.79 (dt, J = 2.1, 8.3 Hz, 1H), 5.17-4.94 (m, 1H), 4.33 (br t, J = 13.3 Hz, 1H), 4.09 (br d, J = 13.2 Hz, 1H), 3.87 (s, 3H), 3.78-3.51 (m, 2H), 3.50-3.34 (m, 1H), 2.13-1.92 (m, 2H). | MS m/z calcd for C$_{16}$H$_{17}$F$_2$N$_5$OS 365.1 found 366.3 [M + H]$^+$ | 10 |
| 4-27 | (3R,4S)-3-fluoro-1-(5-(4-fluoro-2-methoxyphenyl)imidazo[2,1-b][1,3,4]thiadiazol-2-yl)piperidin-4-amine | $^1$H NMR (400 MHz, MeOD-d$_4$) δ 8.30-8.18 (m, 1H), 7.92 (s, 1H), 7.09-6.97 (m, 1H), 6.89 (dt, J = 2.3, 8.4 Hz, 1H), 5.29-5.05 (m, 1H), 4.48-4.37 (m, 1H), 4.24-4.12 (m, 1H), 3.97 (s, 3H), 3.88-3.64 (m, 2H), 3.58-3.45 (m, 1H), 2.26-2.04 (m, 2H). | MS m/z calcd for C$_{16}$H$_{17}$F$_2$N$_5$OS 365.1 found 366.3 [M + H]$^+$ | 10 |
| 4-28 | (3S,4R)-4-amino-1-(5-(6-isopropyl-2-methoxypyridin-3-yl)imidazo[2,1-b][1,3,4]thiadiazol-2-yl)pyrrolidin-3-ol | $^1$H NMR (400 MHz, DMSO-d$_6$) δ 8.56 (d, J = 7.7 Hz, 1H), 8.20 (d, J = 5.2 Hz, 3H), 7.62 (s, 1H), 7.01 (d, J = 7.8 Hz, 1H), 4.54 (q, J = 4.3 Hz, 1H), 4.01 (s, 3H), 3.95 (d, J = 15.1 Hz, 1H), 3.81 (ddd, J = 2.7, 10.4, 6.1 Hz, 2H), 3.59-3.43 (m, 2H), 2.98 (p, J = 6.8 Hz, 1H), 1.28 (d, J = 6.8 Hz, 6H). | MS m/z calcd for C$_{17}$H$_{22}$N$_6$O$_2$S 374.1 found 375.2 [M + H]$^+$ | |

| Example/Compound Number | Structure | NMR | LC-MS | Chiral HPLC Method |
|---|---|---|---|---|
| 4-29 | 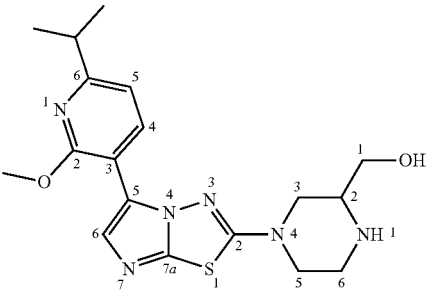<br>(4-(5-(6-isopropyl-2-methoxypyridin-3-yl)imidazo[2,1-b][1,3,4]thiadiazol-2-yl)piperazin-2-yl)methanol | ¹H NMR (500 MHz, DMSO-d₆) δ 9.32 (s, 1H), 8.92 (d, J = 11.4 Hz, 1H), 8.53 (d, J = 7.7 Hz, 1H), 7.63 (s, 1H), 6.99 (d, J = 7.7 Hz, 1H), 4.01 (s, 5H), 3.78-3.62 (m, 2H), 3.38 (tt, J = 3.8, 11.2 Hz, 5H), 2.98 (p, J = 6.8 Hz, 1H), 1.27 (d, J = 7.6 Hz, 6H). | MS m/z calcd for $C_{18}H_{24}N_6O_2S$ 388.2 found 389.2 [M + H]⁺ | |
| 4-30 | 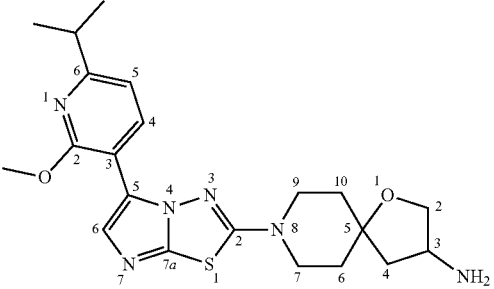<br>8-(5-(6-isopropyl-2-methoxypyridin-3-yl)imidazo[2,1-b][1,3,4]thiadiazol-2-yl)-1-oxa-8-azaspiro[4.5]decan-3-amine | ¹H NMR (500 MHz, DMSO-d₆) δ 8.55 (d, J = 7.7 Hz, 1H), 8.02 (d, J = 5.2 Hz, 3H), 7.62 (s, 1H), 7.01 (d, J = 7.8 Hz, 1H), 4.04-3.96 (m, 4H), 3.91 (s, 1H), 3.78 (dd, J = 10.0, 4.0 Hz, 1H), 3.64 (ddt, J = 18.3, 13.1, 4.7 Hz, 2H), 3.49 (dddd, J = 24.1, 13.3, 9.4, 4.4 Hz, 2H), 2.98 (p, J = 6.8 Hz, 1H), 2.24 (dd, J = 13.8, 8.3 Hz, 1H), 1.93-1.87 (m, 2H), 1.83-1.69 (m, 3H), 1.28 (d, J = 6.9 Hz, 6H). | MS m/z calcd for $C_{21}H_{28}N_6O_2S$ 428.2 found 429.2 [M + H]⁺ | |
| 4-31 | 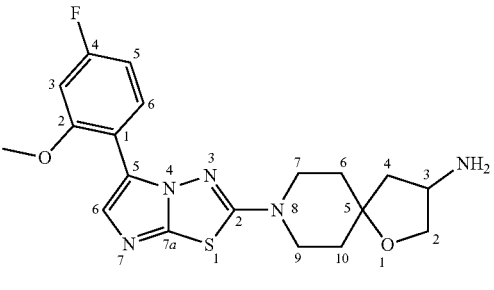<br>8-(5-(4-fluoro-2-methoxyphenyl)imidazo[2,1-b][1,3,4]thiadiazol-2-yl)-1-oxa-8-azaspiro[4.5]decan-3-amine | ¹H NMR (400 MHz, MeOD-d₄) δ 8.27 (dd, J = 8.8, 6.6 Hz, 1H), 7.86 (s, 1H), 7.02 (dd, J = 11.0, 2.5 Hz, 1H), 6.90-6.82 (m, 1H), 4.13-4.06 (m, 1H), 4.02-3.97 (m, 1H), 3.96 (s, 3H), 3.90 (dd, J = 10.4, 3.2 Hz, 1H), 3.85-3.70 (m, 2H), 3.64-3.53 (m, 2H), 2.41-2.33 (m, 1H), 2.02-1.87 (m, 3H), 1.88-1.73 (m, 2H). | MS m/z calcd for $C_{19}H_{22}FN_5O_2S$ 403.2 found 404.2 [M + H]⁺ | |

-continued

| Example/Compound Number | Structure | NMR | LC-MS | Chiral HPLC Method |
|---|---|---|---|---|
| 4-32 | 4-(aminomethyl)-1-(5-(2-ethoxy-4-(trifluoromethyl)phenyl)imidazo[2,1-b][1,3,4]thiadiazol-2-yl)piperidin-4-ol | $^1$H NMR (500 MHz, DMSO-d$_6$) δ 8.54 (d, J = 8.2 Hz, 1H), 7.84 (t, J = 5.8 Hz, 3H), 7.77 (s, 1H), 7.44 (dd, J = 8.3, 1.7 Hz, 1H), 7.39 (d, J = 1.8 Hz, 1H), 4.28 (q, J = 6.9 Hz, 2H), 3.74 (dt, J = 13.1, 4.1 Hz, 2H), 3.51 (ddd, J = 13.6, 9.6, 4.9 Hz, 2H), 2.87 (q, J = 5.8 Hz, 2H), 1.73 (q, J = 4.7 Hz, 4H), 1.47 (t, J = 6.9 Hz, 3H). | MS m/z calcd for C$_{19}$H$_{22}$F$_3$N$_5$O$_2$S 441.1 found 442.2 [M + H]$^+$ | |
| 4-33 | 3-(aminomethyl)-1-(5-(2-methoxy-6-methylpyridin-3-yl)imidazo[2,1-b][1,3,4]thiadiazol-2-yl)pyrrolidin-3-ol | $^1$H NMR (500 MHz, DMSO-d$_6$) δ 8.56 (d, J = 7.7 Hz, 1H), 7.93 (s, 3H), 7.62 (s, 1H), 6.98 (d, J = 7.9 Hz, 1H), 4.00 (s, 3H), 3.70-3.65 (m, 2H), 3.64-3.52 (m, 2H), 3.18-3.04 (m, 2H), 2.46 (s, 3H), 2.20-2.08 (m, 2H). | MS m/z calcd for C$_{16}$H$_{20}$N$_6$O$_2$S 360.1 found 361.1 [M + H]$^+$ | |
| 4-34 | 4-(aminomethyl)-1-(5-(4-chloro-2-(2-methoxyethoxy)phenyl)imidazo[2,1-b][1,3,4]thiadiazol-2-yl)piperidin-4-ol | $^1$H NMR (500 MHz, DMSO-d$_6$) δ 8.33 (d, J = 8.5 Hz, 1H), 7.81 (s, 3H), 7.69 (s, 1H), 7.25 (d, J = 2.1 Hz, 1H), 7.15 (dd, J = 8.4, 2.1 Hz, 1H), 4.30-4.26 (m, 2H), 3.80-3.75 (m, 2H), 3.72 (dt, J = 13.2, 4.1 Hz, 2H), 3.50 (ddd, J = 13.4, 9.7, 4.5 Hz, 2H), 3.36 (s, 3H), 2.86 (q, J = 5.8 Hz, 2H), 1.76-1.68 (m, 4H). | MS m/z calcd for C$_{19}$H$_{24}$ClN$_5$O$_3$S 437.1 found 438.1 [M + H]$^+$ | |

-continued

| Example/ Compound Number | Structure | NMR | LC-MS | Chiral HPLC Method |
|---|---|---|---|---|
| 4-35 | (S)-3-(aminomethyl)-1-(5-(4-fluoro-2-methoxyphenyl)imidazo[2,1-b][1,3,4]thiadiazol-2-yl)pyrrolidin-3-ol | $^1$H NMR (500 MHz, DMSO-d$_6$) δ 8.33 (d, J = 8.5 Hz, 1H), 7.81 (s, 3H), 7.69 (s, 1H), 7.25 (d, J = 2.1 Hz, 1H), 7.15 (dd, J = 8.4, 2.1 Hz, 1H), 4.30-4.26 (m, 2H), 3.80-3.75 (m, 2H), 3.72 (dt, J = 13.2, 4.1 Hz, 2H), 3.50 (ddd, J = 13.4, 9.7, 4.5 Hz, 2H), 3.36 (s, 3H), 2.86 (q, J = 5.8 Hz, 2H), 1.76-1.68 (m, 4H). | MS m/z calcd for C$_{16}$H$_{18}$FN$_5$O$_2$S 363.1 found 364.3 [M + H]$^+$ | 3 |
| 4-36 | (R)-3-(aminomethyl)-1-(5-(4-fluoro-2-methoxyphenyl)imidazo[2,1-b][1,3,4]thiadiazol-2-yl)pyrrolidin-3-ol | $^1$H NMR (500 MHz, DMSO-d$_6$) δ 8.20 (t, J = 7.8 Hz, 1H), 8.08 (s, 3H), 7.64 (s, 1H), 7.12 (d, J = 11.2 Hz, 1H), 6.93 (t, J = 8.5 Hz, 1H), 3.92 (d, J = 1.7 Hz, 3H), 3.70-3.51 (m, 4H), 3.10 (tt, J = 13.2, 6.4 Hz, 2H), 2.20-2.02 (m, 2H). | MS m/z calcd for C$_{16}$H$_{18}$FN$_5$O$_2$S•HCl 363.1 found 364.3 [M + H]$^+$ | 3 |
| 4-37 | 4-(aminomethyl)-1-(5-(4-fluoro-2-(trifluoromethoxy)phenyl)imidazo[2,1-b][1,3,4]thiadiazol-2-yl)piperidin-4-ol | $^1$H NMR (500 MHz, DMSO-d$_6$) δ 8.23 (dd, J = 8.9, 6.4 Hz, 1H), 7.84 (t, J = 5.8 Hz, 3H), 7.53 (ddq, J = 9.3, 2.9, 1.5 Hz, 1H), 7.49-7.36 (m, 2H), 3.69 (dt, J = 13.1, 4.1 Hz, 2H), 3.53-3.42 (m, 2H), 2.86 (q, J = 5.8 Hz, 2H), 1.70 (p, J = 4.5 Hz, 4H). | MS m/z calcd for C$_{17}$H$_{17}$F$_4$N$_5$O$_2$S 431.1 found 432.11 [M + H]$^+$ | |

| Example/ Compound Number | Structure | NMR | LC-MS | Chiral HPLC Method |
|---|---|---|---|---|
| 4-38 | 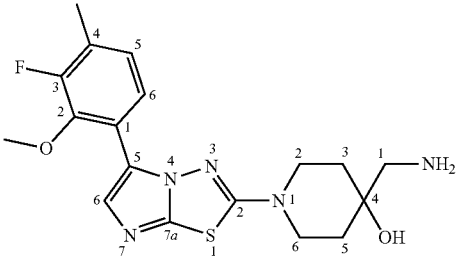<br>4-(aminomethyl)-1-(5-(3-fluoro-2-methoxy-4-methylphenyl)imidazo[2,1-b][1,3,4]thiadiazol-2-yl)piperidin-4-ol | $^1$H NMR (300 MHz, MeOD-d$_4$) δ 7.87 (dd, J = 8.0, 1.5 Hz, 2H), 7.10 (t, J = 7.7 Hz, 1H), 3.97 (d, J = 2.1 Hz, 3H), 3.92-3.77 (m, 2H), 3.73-3.57 (m, 2H), 2.97 (s, 2H), 2.34 (d, J = 2.5 Hz, 3H), 1.83 (dd, J = 7.6, 4.0 Hz, 4H). | MS m/z calcd for C$_{18}$H$_{22}$FN$_5$O$_2$S 391.2 found 392.3 [M + H]$^+$ | |
| 4-39 | 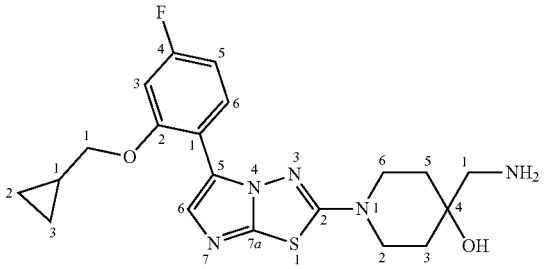<br>4-(aminomethyl)-1-(5-(2-(cyclopropylmethoxy)-4-fluorophenyl)imidazo[2,1-b][1,3,4]thiadiazol-2-yl)piperidin-4-ol | $^1$H NMR (500 MHz, DMSO-d$_6$) δ 8.28 (dd, J = 8.7, 6.9 Hz, 1H), 7.81 (s, 3H), 7.66 (s, 1H), 7.03 (dd, J = 11.4, 2.6 Hz, 1H), 6.90 (td, J = 8.4, 2.5 Hz, 1H), 3.99 (d, J = 7.1 Hz, 2H), 3.71 (dt, J = 13.3, 4.2 Hz, 2H), 3.49 (ddd, J = 13.5, 9.8, 4.7 Hz, 2H), 2.86 (q, J = 5.7 Hz, 2H), 1.75-1.67 (m, 4H), 1.38-1.25 (m, 1H), 0.66-0.61 (m, 2H), 0.40-0.35 (m, 2H). | MS m/z calcd for C$_{20}$H$_{24}$FN$_5$O$_2$S 417.2 found 418.2 [M + H]$^+$ | |
| 4-40 | 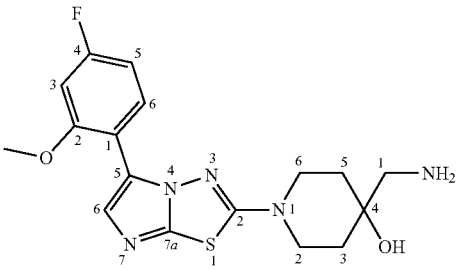<br>4-(aminomethyl)-1-(5-(4-fluoro-2-methoxyphenyl)imidazo[2,1-b][1,3,4]thiadiazol-2-yl)piperidin-4-ol | $^1$H NMR (500 MHz, DMSO-d$_6$) δ 8.21 (dd, J = 8.7, 6.8 Hz, 1H), 8.04 (t, J = 5.7 Hz, 3H), 7.72 (s, 1H), 7.13 (dd, J = 11.3, 2.5 Hz, 1H), 6.97 (td, J = 8.5, 2.5 Hz, 1H), 3.92 (s, 3H), 3.71 (dt, J = 13.5, 4.1 Hz, 2H), 3.49 (ddd, J = 13.9, 9.4, 5.4 Hz, 2H), 2.84 (q, J = 5.8 Hz, 2H), 1.72 (q, J = 4.6 Hz, 4H). | MS m/z calcd for C$_{17}$H$_{20}$FN$_5$O$_2$S 377.1 found 378.3 [M + H]$^+$ | |

| Example/Compound Number | Structure | NMR | LC-MS | Chiral HPLC Method |
|---|---|---|---|---|
| 4-41 | 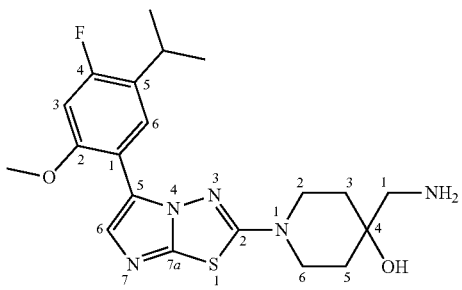<br>4-(aminomethyl)-1-(5-(4-fluoro-5-isopropyl-2-methoxyphenyl)imidazo[2,1-b][1,3,4]thiadiazol-2-yl)piperidin-4-ol | $^1$H NMR (300 MHz, DMSO-d$_6$) δ 8.23 (d, J = 8.8 Hz, 1H), 8.05 (br s, 2H), 7.72 (s, 1H), 7.05 (d J = 12.5 Hz, 1H), 3.80-3.65 (m, 2H), 3.58-3.41 (m, 2H), 3.20-3.11 (m, 1H), 2.82 (d, J = 5.9 Hz, 2H), 1.78-1.64 (m, 4H), 1.22 (d, J = 6.8 Hz, 6H). | MS m/z calcd for C$_{20}$H$_{26}$FN$_5$O$_2$S 419.2 found 420.2 [M + H]$^+$ | |
| 4-42 | 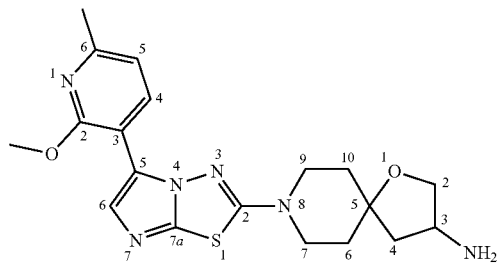<br>8-(5-(2-methoxy-6-methylpyridin-3-yl)imidazo[2,1-b][1,3,4]thiadiazol-2-yl)-1-oxa-8-azaspiro[4.5]decan-3-amine | $^1$H NMR (500 MHz, DMSO-d$_6$) δ 8.53 (d, J = 7.6 Hz, 1H), 8.02 (s, 3H), 7.61 (s, 1H), 7.02-6.97 (m, 1H), 4.00 (s, 4H), 3.89 (d, J = 14.3 Hz, 1H), 3.78 (dd, J = 10.0, 4.1 Hz, 1H), 3.64 (ddt, J = 17.7, 12.9, 4.6 Hz, 2H), 3.49 (dddd, J = 26.5, 13.2, 9.3, 4.3 Hz, 2H), 2.45 (s, 3H), 2.31-2.20 (m, 1H), 1.93-1.87 (m, 2H), 1.82-1.68 (m, 3H). | MS m/z calcd for C$_{19}$H$_{24}$N$_6$O$_2$S 400.2, found 401.2 [M + H]$^+$ | |
| 4-43 | 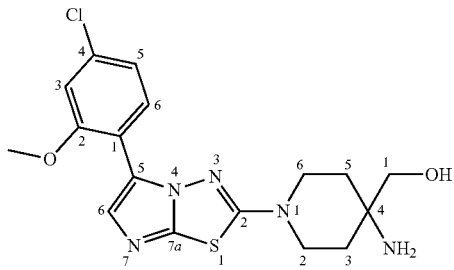<br>(4-amino-1-(5-(4-chloro-2-methoxyphenyl)imidazo[2,1-b][1,3,4]thiadiazol-2-yl)piperidin-4-yl)methanol | $^1$H NMR (400 MHz, MeOD-d4) δ 8.31 (d, J = 8.4 Hz, 1H), 7.98 (s, 1H), 7.28 (d, J = 2.0 Hz, 1H), 7.17 (dd, J = 8.5, 2.0 Hz, 1H), 4.01 (s, 3H), 3.89 (dt, J = 13.8, 5.1, 5.1 Hz, 2H), 3.81 (s, 2H), 3.65 (ddt, J = 15.7, 9.8, 4.9 Hz, 2H), 2.15 (dt, J = 14.1, 4.6, 4.6 Hz, 2H), 2.06-1.90 (m, 2H). | MS m/z calcd for C$_{17}$H$_{20}$ClN$_5$O$_2$S 393.1 found 394.1 [M + H]$^+$ | |

| Example/ Compound Number | Structure | NMR | LC-MS | Chiral HPLC Method |
|---|---|---|---|---|
| 4-44 | 4-(aminomethyl)-1-(5-(2,3-dihydrobenzo[b][1,4]dioxin-5-yl)imidazo[2,1-b][1,3,4]thiadiazol-2-yl)piperidin-4-ol | $^1$H NMR (500 MHz, DMSO-d$_6$) δ 7.83 (d, J = 5.8 Hz, 3H), 7.77 (dd, J = 7.8, 1.6 Hz, 1H), 7.62 (s, 1H), 7.01-6.81 (m, 2H), 4.42-4.36 (m, 2H), 4.34-4.28 (m, 2H), 3.71 (dt, J = 13.2, 4.2 Hz, 2H), 3.55-3.44 (m, 2H), 2.86 (q, J = 5.8 Hz, 2H), 1.75-1.66 (m, 4H). | MS m/z calcd for C$_{18}$H$_{21}$N$_5$O$_3$S 387.1 found 388.1 [M + H]$^+$ | |
| 4-45 | 2-(5-(4-fluoro-2-methoxyphenyl)imidazo[2,1-b][1,3,4]thiadiazol-2-yl)-2-azaspiro[3.3]heptan-5-amine | $^1$H NMR (500 MHz, DMSO-d$_6$) δ 8.41 (s, 3H), 8.15 (dd, J = 8.7, 6.8 Hz, 1H), 7.60 (s, 1H), 7.11 (dd, J = 11.4, 2.6 Hz, 1H), 6.94 (td, J = 8.4, 2.6 Hz 1H), 4.49 (d, J = 8.9 Hz, 1H), 4.25 (d, J = 8.4 Hz, 1H), 4.10 (dd, J = 28.4, 8.7 Hz, 2H), 3.92 (s, 3H), 3.78 (d, J = 7.9 Hz, 1H), 2.27 (t, J = 10.0 Hz, 1H), 2.22-2.07 (m, 2H), 2.05-1.88 (m, 1H). | MS m/z calcd for C$_{17}$H$_{18}$FN$_5$OS 359.1 found 360.4 [M + H]$^+$ | |
| 4-46 | (4-(aminomethyl)-1-(5-(4-fluoro-2-methoxyphenyl)imidazo[2,1-b][1,3,4]thiadiazol-2-yl)piperidin-4-yl)methanol | $^1$H NMR (400 MHz, MeOD-d$_4$) δ 8.27 (dd, J = 8.8, 6.6 Hz, 1H), 7.74 (s, 1H), 7.00 (dd, J = 11.0, 2.5 Hz, 1H), 6.84 (td, J = 8.4, 2.5 Hz, 1H), 3.97 (s, 3H), 3.76 (s, 2H), 3.73-3.54 (m, 4H), 3.50 (q, J = 7.1 Hz, 1H), 3.11 (s, 2H), 1.91-1.65 (m, 4H), 1.19 (t, J = 7.0 Hz, 1H). | MS m/z calcd for C$_{18}$H$_{22}$FN$_5$O$_2$S 391.2 found 392.1 [M + H]$^+$ | |
| 4-47 | 4-(aminomethyl)-1-(5-(2-ethoxyphenyl)imidazo[2,1-b][1,3,4]thiadiazol-2-yl)piperidin-4-ol | $^1$H NMR (400 MHz, MeOD-d$_4$) δ 8.30 (d, 1H), 7.98 (s, 1H), 7.47 (t, J = 8.8, 7.5, 1.7 Hz, 1H), 7.20 (d, J = 8.4 Hz, 1H), 7.12 (t, J = 7.6, 7.6 Hz, 1H), 4.24 (q, J = 6.9 Hz, 2H), 3.95-3.83 (m, 2H), 3.74-3.63 (m, 2H), 3.00 (s, 2H), 1.89-1.82 (m, 4H), 1.50 (t, J = 7.0, 7.0 Hz, 3H). | MS m/z calcd for C$_{18}$H$_{23}$N$_5$O$_2$S 373.2 found 374.05 [M + H]$^+$ | |

| Example/Compound Number | Structure | NMR | LC-MS | Chiral HPLC Method |
|---|---|---|---|---|
| 4-48 | 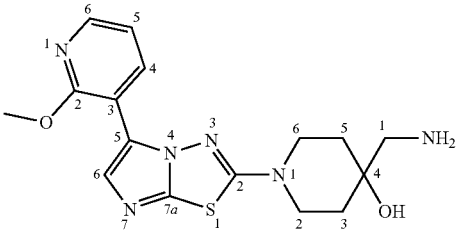<br>4-(aminomethyl)-1-(5-(2-methoxypyridin-3-yl)imidazo[2,1-b][1,3,4]thiadiazol-2-yl)piperidin-4-ol | $^1$H NMR (500 MHz, DMSO-d$_6$) δ 7.83 (d, J = 5.8 Hz, 3H), 7.77 (dd, J = 7.8, 1.6 Hz, 1H), 7.62 (s, 1H), 7.01-6.81 (m, 2H), 4.42-4.36 (m, 2H), 4.34-4.28 (m, 2H), 3.71 (dt, J = 13.2, 4.2 Hz, 2H), 3.55-3.44 (m, 2H), 2.86 (q, J = 5.8 Hz, 2H), 1.75-1.66 (m, 4H). | MS m/z calcd for C$_{16}$H$_{20}$N$_6$O$_2$S 360.1 found 361.1 [M + H]$^+$ | |
| 4-49 | 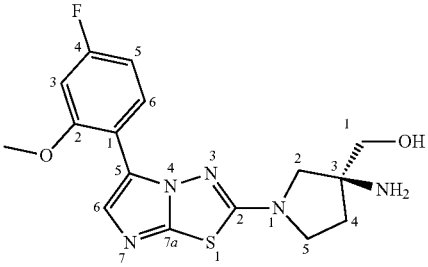<br>(S)-3-amino-1-(5-(4-fluoro-2-methoxyphenyl)imidazo[2,1-b][1,3,4]thiadiazol-2-yl)pyrrolidin-3-yl)methanol | $^1$H NMR (500 MHz, DMSO-d$_6$) δ 8.52 (s, 3H), 8.21 (dd, J = 8.7, 6.8 Hz, 1H), 7.67 (s, 1H), 7.12 (dd, J = 11.3, 2.5 Hz, 1H), 6.95 (td, J = 8.5, 2.5 Hz, 1H), 3.93 (s, 3H), 3.80-3.61 (m, 6H), 3.57 (s, 1H), 2.34-2.15 (m, 2H). | MS m/z calcd for C$_{16}$H$_{18}$FN$_5$O$_2$S 363.1 found 364.3 [M + H]$^+$ | 4 |
| 4-50 | 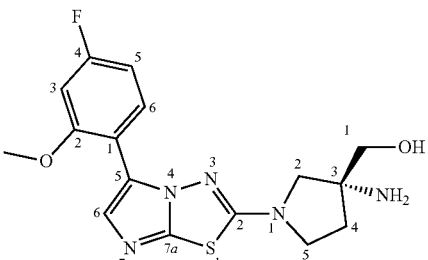<br>(R)-3-amino-1-(5-(4-fluoro-2-methoxyphenyl)imidazo[2,1-b][1,3,4]thiadiazol-2-yl)pyrrolidin-3-yl)methanol | $^1$H NMR (500 MHz, DMSO-d$_6$) δ 8.53 (s, 3H), 8.21 (dd, J = 8.7, 6.8 Hz, 1H), 7.68 (s, 1H), 7.13 (dd, J = 11.3, 2.5 Hz, 1H), 6.95 (td, J = 8.4, 2.5 Hz, 1H), 3.93 (s, 3H), 3.78 (q, J = 8.3 Hz, 1H), 3.73-3.59 (m, 5H), 2.35-2.20 (m, 2H). | MS m/z calcd for C$_{16}$H$_{18}$FN$_5$O$_2$S 363.1 found 364.3 [M + H]$^+$ | 4 |

| Example/Compound Number | Structure | NMR | LC-MS | Chiral HPLC Method |
|---|---|---|---|---|
| 4-51 | 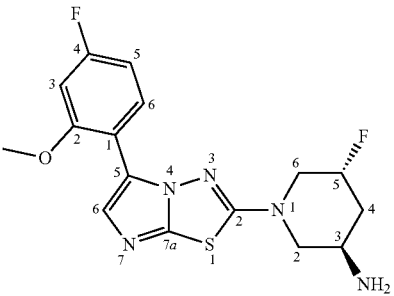<br>(3R,5R)-5-fluoro-1-(5-(4-fluoro-2-methoxyphenyl)imidazo[2,1-b][1,3,4]thiadiazol-2-yl)piperidin-3-amine | $^1$H NMR (500 MHz, DMSO-d$_6$) δ 8.53-8.28 (m, 3H), 8.18 (dd, J = 8.7, 6.8 Hz, 1H), 7.62 (s, 1H), 7.12 (dd, J = 11.3, 2.4 Hz, 1H), 6.94 (td, J = 8.4, 2.4 Hz, 1H), 5.16 (d, J = 45.7 Hz, 1H), 4.33-4.22 (m, 1H), 4.03 (t, J = 13.5 Hz, 1H), 3.92 (s, 3H), 3.62-3.45 (m, 2H), 3.31 (t, J = 11.8 Hz, 1H), 2.43 (d, J = 10.1 Hz, 1H), 1.96 (dt, J = 41.7, 13.0 Hz, 1H). | MS m/z calcd for C$_{16}$H$_{17}$F$_2$N$_5$OS 365.1 found 366.3 [M + H]$^+$ | |
| 4-52 | 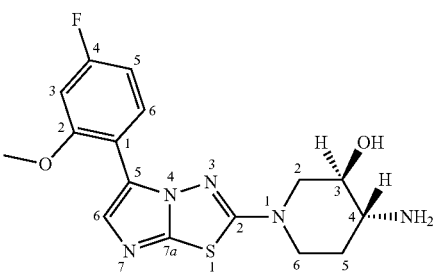<br>(3R,4R)-4-amino-1-(5-(4-fluoro-2-methoxyphenyl)imidazo[2,1-b][1,3,4]thiadiazol-2-yl)piperidin-3-ol | $^1$H NMR (400 MHz, MeOD-d$_4$) δ 8.25 (dd, J = 6.5, 8.7 Hz, 1H), 7.90 (s, 1H), 7.04 (dd, J = 2.4, 10.9 Hz, 1H), 6.88 (dt, J = 2.4, 8.4 Hz, 1H), 4.23-4.14 (m, 1H), 4.03 (td, J = 2.2, 13.6 Hz, 1H), 3.97 (s, 3H), 3.80-3.70 (m, 1H), 3.42 (dt, J = 2.8, 13.1 Hz, 1H), 3.27-3.21 (m, 1H), 3.17 (dd, J = 10.5, 12.8 Hz, 1H), 2.23 (br dd, J = 3.8, 13.0 Hz, 1H), 1.87 (dd, J = 4.6, 12.6 Hz, 1H). | MS m/z calcd for C$_{16}$H$_{18}$FN$_5$O$_2$S 363.1 found 364.1 [M + H]$^+$ | 10 |
| 4-53 | 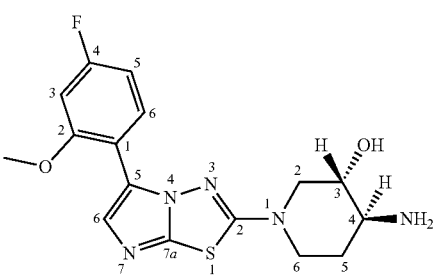<br>(3S,4S)-4-amino-1-(5-(4-fluoro-2-methoxyphenyl)imidazo[2,1-b][1,3,4]thiadiazol-2-yl)piperidin-3-ol | $^1$H NMR (400 MHz, MeOD-d$_4$) δ 8.25 (dd, J = 6.5, 8.8 Hz, 1H), 7.90 (s, 1H), 7.04 (dd, J = 2.4, 10.9 Hz, 1H), 6.88 (dt, J = 2.4, 8.4 Hz, 1H), 4.22-4.14 (m, 1H), 4.03 (td, J = 2.3, 13.6 Hz, 1H), 3.97 (s, 3H), 3.74 (dt, J = 5.1, 10.2 Hz, 1H), 3.50-3.37 (m, 1H), 3.26-3.21 (m, 1H), 3.16 (dd, J = 10.6, 13.0 Hz, 1H), 2.28-2.18 (m, 1H), 1.86 (dq, J = 4.8, 12.6 Hz, 1H). | MS m/z calcd for C$_{16}$H$_{18}$FN$_5$O$_2$S 363.1 found 364.1 [M + H]$^+$ | 10 |

-continued

| Example/ Compound Number | Structure | NMR | LC-MS | Chiral HPLC Method |
|---|---|---|---|---|
| 4-54 | 1-(5-(2-methoxy-4-methylphenyl)imidazo[2,1-b][1,3,4]thiadiazol-2-yl)-3-methylpyrrolidin-3-amine | $^1$H NMR (500 MHz, DMSO-d$_6$) δ 8.26 (s, 3H), 8.11 (d, J = 7.9 Hz, 1H), 7.57 (s, 1H), 7.01 (d, J = 1.6 Hz, 1H), 6.89 (dt, J = 8.1, 1.2 Hz, 1H), 3.89 (s, 3H), 3.73 (m, 2H), 3.62-3.58 (m, 2H), 2.37 (s, 3H), 2.33-2.21 (m, 2H), 1.50 (s, 3H). | MS m/z calcd for C$_{17}$H$_{21}$N$_5$OS 343.2 found 344.1 [M + H]$^+$ | |
| 4-55 | 1-(5-(2-methoxy-6-methylpyridin-3-yl)imidazo[2,1-b][1,3,4]thiadiazol-2-yl)-3-methylpyrrolidin-3-amine | $^1$H NMR (500 MHz, DMSO-d$_6$) δ 8.58 (d, J = 7.7 Hz, 1H), 8.26 (s, 3H), 7.66 (s, 1H), 7.00 (dd, J = 7.7, 0.7 Hz, 1H), 4.01 (s, 3H), 3.78-3.59 (m, 4H), 2.46 (s, 3H), 2.28 (ddt, J = 17.3, 13.4, 8.7 Hz, 2H), 1.51 (s, 3H). | MS m/z calcd for C$_{16}$H$_{20}$N$_6$OS 344.1 found 345.1 [M + H]$^+$ | |
| 4-56 | 1-(5-(6-isopropyl-2-methoxypyridin-3-yl)imidazo[2,1-b][1,3,4]thiadiazol-2-yl)-3-methylpyrrolidin-3-amine | $^1$H NMR (500 MHz, DMSO-d$_6$) δ 8.58 (d, J = 7.7 Hz, 1H), 8.26 (s, 3H), 7.65 (s, 1H), 7.01 (d, J = 7.8 Hz, 1H), 4.02 (s, 3H), 3.78-3.59 (m, 4H), 2.99 (h, J = 6.9 Hz, 1H), 2.28 (ddt, J = 16.8, 13.4, 8.6 Hz, 2H), 1.51 (s, 3H), 1.28 (d, J = 6.8 Hz, 6H). | MS m/z calcd for C$_{18}$H$_{24}$N$_6$OS 372.2 found 373.2 [M + H]$^+$ | |

| Example/ Compound Number | Structure | NMR | LC-MS | Chiral HPLC Method |
|---|---|---|---|---|
| 4-57 | 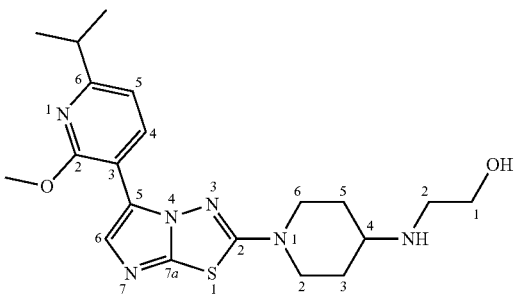<br>2-((1-(5-(6-isopropyl-2-methoxypyridin-3-yl)imidazo[2,1-b][1,3,4]thiadiazol-2-yl)piperidin-4-yl)amino)ethan-1-ol | $^1$H NMR (400 MHz, DMSO-d$_6$) δ 8.64-8.43 (m, 3H), 7.59 (s, 1H), 7.00 (d, J = 7.6 Hz, 1H), 3.98 (s, 3H), 3.41 (s, 2H), 3.24 (t, J = 12.8 Hz, 2H), 3.07 (s, 2H), 2.98 (p, J = 7.0 Hz, 1H), 2.17 (d, J = 12.5 Hz, 2H), 1.70 (d, J = 12.6 Hz, 2H), 1.27 (d, J = 6.8 Hz, 6H). | MS m/z calcd for C$_{20}$H$_{28}$N$_6$O$_2$S 416.2 found 417.2 [M + H]$^+$ | |
| 4-58 | 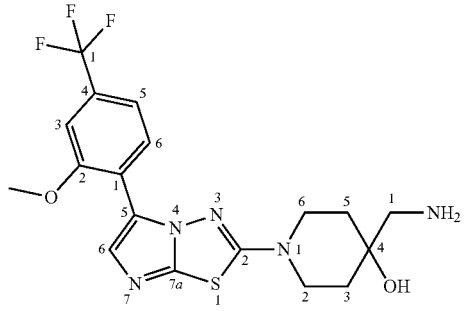<br>4-(aminomethyl)-1-(5-(2-methoxy-4-(trifluoromethyl)phenyl)imidazo[2,1-b][1,3,4]thiadiazol-2-yl)piperidin-4-ol | $^1$H NMR (300 MHz, MeOD-d$_4$) δ 8.56 (d, J = 8.2 Hz, 1H), 8.06 (s, 1H), 7.48-7.38 (m, 2H), 4.05 (s, 3H), 3.96-3.82 (m, 2H), 3.75-3.59 (m, 2H), 2.98 (s, 2H), 1.92-1.74 (m, 4H). | MS m/z calcd for C$_{18}$H$_{20}$F$_3$N$_5$O$_2$S 427.1 found 427.8 [M + H]$^+$ | |
| 4-59 | 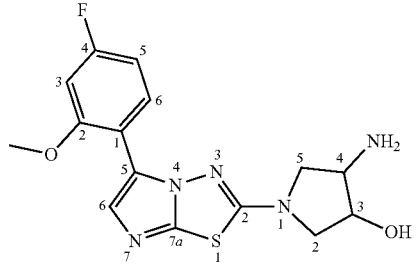<br>4-amino-1-(5-(4-fluoro-2-methoxyphenyl)imidazo[2,1-b][1,3,4]thiadiazol-2-yl)pyrrolidin-3-ol | $^1$H NMR (500 MHz, DMSO-d$_6$) δ 8.37 (d, J = 5.5 Hz, 3H), 8.20 (dd, J = 8.7, 6.7 Hz, 1H), 7.66 (s, 1H), 7.12 (dd, J = 11.4, 2.6 Hz, 1H), 6.96 (td, J = 8.5, 2.6 Hz, 1H), 4.54 (t, J = 4.1 Hz, 1H), 3.92 (s, 3H), 3.85 (dd, J = 10.1, 7.4 Hz, 1H), 3.77 (dd, J = 10.6, 4.8 Hz, 1H), 3.57 (dd, J = 10.2, 6.7 Hz, 1H), 3.50 (dd, J = 10.7, 3.1 Hz, 1H). | MS m/z calcd for C$_{15}$H$_{16}$FN$_5$O$_2$S 349.1 found 350.3 [M + H]$^+$ | |

-continued

| Example/Compound Number | Structure | NMR | LC-MS | Chiral HPLC Method |
|---|---|---|---|---|
| 4-60 | 4-(aminomethyl)-1-(5-(3,4-difluoro-2-methoxyphenyl)imidazo[2,1-b][1,3,4]thiadiazol-2-yl)piperidin-4-ol | $^1$H NMR (300 MHz, MeOD-d$_4$) δ 8.00-7.90 (m, 1H), 7.87 (s, 1H), 7.21-7.12 (m, 1H), 4.06 (d, J = 2.7 Hz, 3H), 3.89-3.97 (m, 2H), 3.69-3.58 (m, 2H), 2.97 (s, 3H), 1.86-1.78 (m, 4H). | MS m/z calcd for C$_{17}$H$_{19}$F$_2$N5O$_2$S 395.1 found 396.3 [M + H]$^+$ | |
| 4-61 | (3S,4R)-4-amino-1-(5-(4-fluoro-2-methoxyphenyl)imidazo[2,1-b][1,3,4]thiadiazol-2-yl)pyrrolidin-3-ol | $^1$H NMR (500 MHz, DMSO-d$_6$) δ 8.39 (d, J = 5.0 Hz, 3H), 8.20 (t, J = 7.8 Hz, 1H), 7.67 (s, 1H), 7.13 (d, J = 11.3 Hz, 1H), 6.96 (t, J = 8.6 Hz, 1H), 4.54 (d, J = 4.8 Hz, 1H), 3.92 (s, 3H), 3.85 (d, J = 9.7 Hz, 1H), 3.77 (dd, J = 10.6, 4.7 Hz, 1H), 3.57 (t, J = 8.5 Hz, 1H), 3.50 (d, J = 10.5 Hz, 1H). | MS m/z calcd for C$_{15}$H$_{16}$FN5O$_2$S 349.1 found 350.3 [M + H]$^+$ | 5 |
| 4-62 | (3S,4R)-4-amino-1-(5-(4-fluoro-2-methoxyphenyl)imidazo[2,1-b][1,3,4]thiadiazol-2-yl)pyrrolidin-3-ol | $^1$H NMR (500 MHz, DMSO-d$_6$) δ 8.35 (d, J = 5.4 Hz, 3H), 8.20 (t, J = 7.7 Hz, 1H), 7.64 (s, 1H), 7.12 (d, J = 11.3 Hz, 1H), 6.96 (dt, J = 9.6, 4.8 Hz, 1H), 4.54 (s, 1H), 3.92 (s, 3H), 3.84 (d, J = 8.0 Hz, 1H), 3.76 (dd, J = 10.7, 4.7 Hz, 1H), 3.57 (t, J = 8.6 Hz, 1H), 3.52-3.46 (m, 1H). | MS m/z calcd for C$_{15}$H$_{16}$FN5O$_2$S 349.1 found 350.3 [M + H]$^+$ | 5 |
| 4-63 | 4-(aminomethyl)-1-(5-(4-chloro-2-methoxyphenyl)imidazo[2,1-b][1,3,4]thiadiazol-2-yl)piperidin-4-ol | $^1$H NMR (500 MHz, DMSO-d$_6$) δ 8.25 (d, J = 8.4 Hz, 1H), 8.01 (s, 3H), 7.72 (s, 1H), 7.27 (d, J = 2.1 Hz, 1H), 7.18 (dd, J = 8.4, 2.1 Hz, 1H), 3.95 (s, 3H), 3.72 (dt, J = 13.0, 4.2 Hz, 2H), 3.50 (dt, J = 13.6, 7.5 Hz, 2H), 2.84 (t, J = 6.0 Hz, 2H), 1.82-1.59 (m, 4H). | MS m/z calcd for C$_{17}$H$_{20}$ClN5O$_2$S 393.1 found 394.2 [M + H]$^+$ | |

| Example/Compound Number | Structure | NMR | LC-MS | Chiral HPLC Method |
|---|---|---|---|---|
| 4-64 | 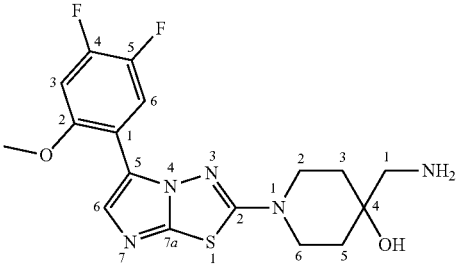<br>4-(aminomethyl)-1-(5-(4,5-difluoro-2-methoxyphenyl)imidazo[2,1-b][1,3,4]thiadiazol-2-yl)piperidin-4-ol | $^1$H NMR (300 MHz, MeOD-d$_4$) δ 8.38-8.29 (m, 1H), 7.98 (s, 1H), 7.27-7.19 (m, 1H), 3.97 (s, 3H), 3.91-3.83 (m, 2H), 3.72-3.61 (m, 2H), 2.98 (s, 2H), 1.89-1.81 (m, 4H). | MS m/z calcd for C$_{17}$H$_{20}$ClF$_2$N$_5$O$_2$S 395.1 found 395.8 [M + H]$^+$ | |
| 4-65 | 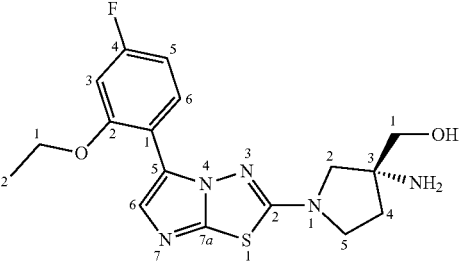<br>(R)-(3-amino-1-(5-(2-ethoxy-4-fluorophenyl)imidazo[2,1-b][1,3,4]thiadiazol-2-yl)pyrrolidin-3-yl)methanol | $^1$H NMR (400 MHz, DMSO-d$_6$) δ 8.50 (s, 3H), 8.24 (dd, J = 8.8, 6.8 Hz, 1H), 7.68 (s, 1H), 7.08 (dd, J = 11.4, 2.5 Hz, 1H), 6.91 (td, J = 8.4, 2.5 Hz, 1H), 4.16 (q, J = 6.9 Hz, 2H), 3.80-3.58 (m, 6H), 2.33-2.16 (m, 2H), 1.40 (t, J = 6.9 Hz, 3H). | MS m/z calcd for C$_{17}$H$_{20}$FN$_5$O$_2$S 377.1 found 378.3 [M + H]$^+$ | 6 |
| 4-66 | 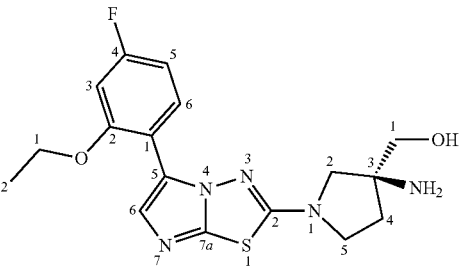<br>(S)-(3-amino-1-(5-(2-ethoxy-4-fluorophenyl)imidazo[2,1-b][1,3,4]thiadiazol-2-yl)pyrrolidin-3-yl)methanol | $^1$H NMR (400 MHz, DMSO-d$_6$) δ 8.47 (s, 3H), 8.24 (dd, J = 8.8, 6.8 Hz, 1H), 7.66 (s, 1H), 7.07 (dd, J = 11.4, 2.5 Hz, 1H), 6.91 (td, J = 8.5, 2.5 Hz, 1H), 4.15 (q, J = 7.0 Hz, 2H), 3.79-3.70 (m, 2H), 3.71-3.58 (m, 2H), 3.55 (s, 2H), 2.35-2.11 (m, 2H), 1.40 (t, J = 6.9 Hz, 3H). | MS m/z calcd for C$_{17}$H$_{20}$FN$_5$O$_2$S 377.1 found 378.3 [M + H]$^+$ | 6 |

| Example/ Compound Number | Structure | NMR | LC-MS | Chiral HPLC Method |
|---|---|---|---|---|
| 4-67 | 4-(aminomethyl)-1-(5-(2-methoxy-4,5-dimethylphenyl)imidazo[2,1-b][1,3,4]thiadiazol-2-yl)piperidin-4-ol | ¹H NMR (400 MHz, MeOD-d₄) δ 7.99 (s, 1H), 7.84 (s, 1H), 6.98 (s, 1H), 3.91 (s, 3H), 3.87-3.80 (m, 2H), 3.69-3.62 (m, 2H), 2.98 (s, 2H), 2.34 (s, 3H), 2.27 (s, 3H), 1.86-1.80 (m, 4H). | MS m/z calcd for $C_{19}H_{25}N_5O_2S$ 387.2 found 388.3 $[M+H]^+$ | |
| 4-68 | (3S,4R)-3-amino-1-(5-(4-fluoro-2-methoxyphenyl)imidazo[2,1-b][1,3,4]thiadiazol-2-yl)piperidin-4-ol | ¹H NMR (400 MHz, MeOD-d₄) δ 8.25 (dd, J = 6.5, 8.7 Hz, 1H), 7.89 (s, 1H), 7.04 (dd, J = 2.4, 10.9 Hz, 1H), 6.94-6.83 (m, 1H), 4.24-4.19 (m, 1H), 4.03 (dd, J = 4.2, 13.1 Hz, 1H), 3.97 (s, 3H), 3.85-3.69 (m, 2H), 3.63-3.55 (m, 2H), 2.09-1.92 (m, 2H). | MS m/z calcd for $C_{16}H_{18}FN_5O_2S$ 363.1 found 364.0 $[M+H]^+$ | 11 |
| 4-69 | (3R,4S)-3-amino-1-(5-(4-fluoro-2-methoxyphenyl)imidazo[2,1-b][1,3,4]thiadiazol-2-yl)piperidin-4-ol | ¹H NMR (400 MHz, MeOD-d₄) δ 8.26 (dd, J = 6.5, 8.7 Hz, 1H), 7.90 (s, 1H), 7.03 (dd, J = 2.4, 11.0 Hz, 1H), 6.88 (br d, J = 2.3 Hz, 1H), 4.25-4.18 (m, 1H), 4.03 (dd, J = 4.3, 13.2 Hz, 1H), 3.97 (s, 3H), 3.86-3.70 (m, 2H), 3.64-3.54 (m, 2H), 2.02 (td, J = 5.5, 10.7 Hz, 2H). | MS m/z calcd for $C_{16}H_{18}FN_5O_2S$ 363.1 found 364.0 $[M+H]^+$ | 11 |

| Example/Compound Number | Structure | NMR | LC-MS | Chiral HPLC Method |
|---|---|---|---|---|
| 4-70 | 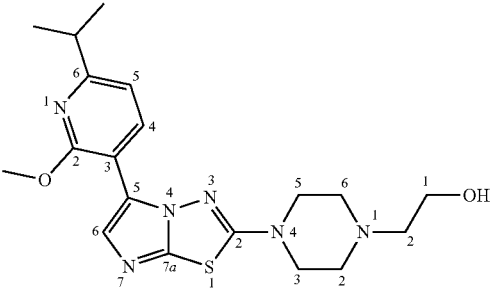 2-(4-(5-(6-isopropyl-2-methoxypyridin-3-yl)imidazo[2,1-b][1,3,4]thiadiazol-2-yl)piperidin-1-yl)ethan-1-ol | NA | MS m/z calcd for $C_{19}H_{26}N_6O_2S$ 402.2 found 403.2 $[M + H]^+$ | |
| 4-71 | 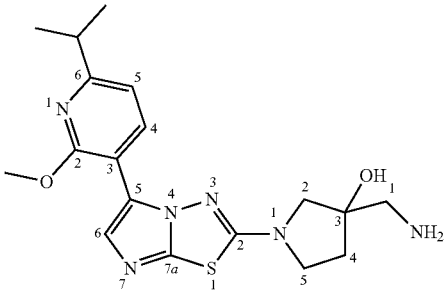 3-(aminomethyl)-1-(5-(6-isopropyl-2-methoxypyridin-3-yl)imidazo[2,1-b][1,3,4]thiadiazol-2-yl)pyrrolidin-3-ol | $^1$H NMR (500 MHz, DMSO-$d_6$) δ 8.57 (d, J = 7.7 Hz, 1H), 7.92 (s, 3H), 7.59 (s, 1H), 6.99 (d, J = 7.7 Hz, 1H), 4.02 (s, 3H), 3.67 (m, 2H), 3.62 (d, J = 10.8 Hz, 1H), 3.53 (d, J = 10.7 Hz, 1H), 3.17-3.05 (m, 2H), 2.99 (p, J = 6.9 Hz, 1H), 2.18-2.08 (m, 2H), 1.28 (d, J = 6.9 Hz, 6H). | MS m/z calcd for $C_{18}H_{24}N_6O_2S$ 388.2 found 389.2 $[M + H]^+$ | |
| 4-72 | 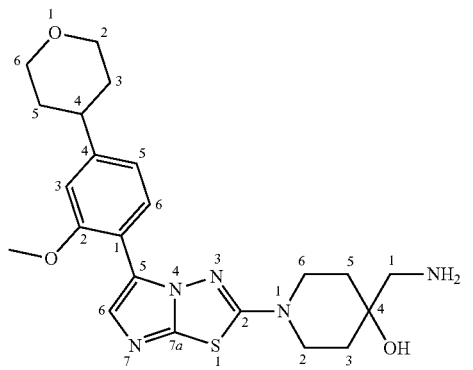 4-(aminomethyl)-1-(5-(2-methoxy-4-(tetrahydro-2H-pyran-4-yl)phenyl)imidazo[2,1-b][1,3,4]thiadiazol-2-yl)piperidin-4-ol | $^1$H NMR (400 MHz, MeOD-$d_4$) δ 8.22 (d, J = 8.0 Hz, 1H), 7.89 (s, 1H), 7.06 (s, 1H), 7.02 (d, J = 8.0, 1H), 4.08-4.04 (m, 2H), 3.96 (s, 3H), 3.86-3.80 (m, 2H), 3.70-3.54 (m, 4H), 2.97 (s, 2H), 2.95-2.86 (m, 1H), 1.96-1.78 (m, 8H). | MS m/z calcd for $C_{22}H_{29}N_5O_3S$ 443.2 found 444.1 $[M + H]^+$ | |

| Example/Compound Number | Structure | NMR | LC-MS | Chiral HPLC Method |
|---|---|---|---|---|
| 4-73 | 4-(2-(4-(aminomethyl)-4-hydroxypiperidin-1-yl)imidazo[2,1-b][1,3,4]thiadiazol-5-yl)-3-methoxybenzonitrile | $^1$H NMR (500 MHz, DMSO-d$_6$) δ 8.05 (d, J = 7.8 Hz, 1H), 7.82 (s, 3H), 7.58 (s, 1H), 7.01 (d, J = 1.6 Hz, 1H), 6.96-6.83 (m, 1H), 3.89 (s, 3H), 3.70 (dt, J = 13.4, 4.2 Hz, 2H), 3.50 (ddd, J = 13.6, 9.6, 4.8 Hz, 2H), 2.86 (q, J = 5.8 Hz, 2H), 2.37 (s, 3H), 1.76-1.65 (m, 4H). | MS m/z calcd for C$_{18}$H$_{23}$N$_5$O$_2$S 373.2 found 374.2 [M + H]$^+$ | |
| 4-74 | 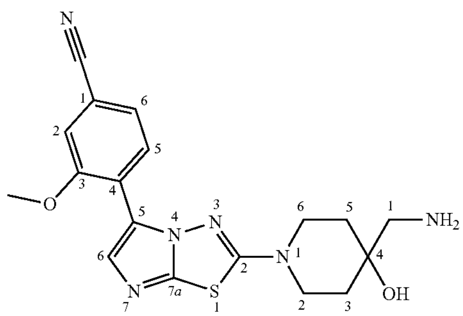 [SMILES: COc1cc(C#N)ccc1-c1cnc2sc(N3CCC(O)(CN)CC3)nn12] | $^1$H NMR (500 MHz, DMSO-d$_6$) δ 8.53 (d, J = 8.1 Hz, 1H), 7.81 (d, J = 5.5 Hz, 4H), 7.62 (d, J = 1.6 Hz, 1H), 7.55 (dd, J = 8.1, 1.6 Hz, 1H), 4.01 (s, 3H), 3.73 (dt, J = 13.1, 4.1 Hz, 2H), 3.52 (ddd, J = 13.6, 9.8, 4.7 Hz, 2H), 2.87 (d, J = 5.8 Hz, 2H), 1.73 (q, J = 4.6 Hz, 4H). | MS m/z calcd for C$_{18}$H$_{20}$N$_6$O$_2$S 384.1 found 385.1 [M + H]$^+$ | |
| 4-75 | 4-(aminomethyl)-1-(5-(2,6-dimethoxypyridin-3-yl)imidazo[2,1-b][1,3,4]thiadiazol-2-yl)piperidin-4-ol | $^1$H NMR (500 MHz, DMSO-d$_6$) δ 8.57 (d, J = 8.3 Hz, 1H), 7.84 (s, 3H), 7.59 (s, 1H), 6.57 (d, J = 8.3 Hz, 1H), 4.03 (s, 3H), 3.93 (s, 3H), 3.72 (dt, J = 13.1, 4.1 Hz, 2H), 3.50 (ddd, J = 13.0, 9.3, 5.3 Hz, 2H), 2.86 (q, J = 5.7 Hz, 2H), 1.72 (t, J = 4.8 Hz, 4H). | MS m/z calcd for C$_{17}$H$_{22}$N$_6$O$_3$S 390.2 found 391.1 [M + H]$^+$ | |
| 4-76 | (4-amino-1-(5-(4-chloro-2-(2-methoxyethoxy)phenyl)imidazo[2,1-b][1,3,4]thiadiazol-2-yl)piperidin-4-yl)methanol | $^1$H NMR (400 MHz, MeOD-d$_4$) δ 8.40 (d, J = 8.5 Hz, 1H), 8.12 (s, 1H), 7.28 (d, J = 2.0 Hz, 1H), 7.18 (dd, J = 8.5, 2.0 Hz, 1H), 4.36-4.26 (m, 2H), 3.90 (dt, J = 13.8, 5.0, 5.0 Hz, 2H), 3.86-3.92 (m, 2H), 3.81 (s, 2H), 3.66 (ddd, J = 13.7, 9.7, 3.9 Hz, 2H), 3.47 (s, 3H), 2.16 (dt, J = 14.0, 4.7 Hz, 2H), 2.00 (ddd, J = 14.1, 9.7, 4.7 Hz, 2H). | MS m/z calcd for C$_{19}$H$_{24}$ClN$_5$O$_3$S 437.1 found 438.1 [M + H]$^+$ | |

| Example/Compound Number | Structure | NMR | LC-MS | Chiral HPLC Method |
|---|---|---|---|---|
| 4-77 | 3-(aminomethyl)-1-(5-(4-fluoro-2-methoxyphenyl)imidazo[2,1-b][1,3,4]thiadiazol-2-yl)azetidin-3-ol | $^1$H NMR (500 MHz, DMSO-d$_6$) δ 8.13 (dd, J = 8.7, 6.8 Hz, 1H), 8.08 (s, 3H), 7.62 (s, 1H), 7.11 (dd, J = 11.4, 2.6 Hz, 1H), 6.95 (td, J = 8.5, 2.6 Hz, 1H), 4.30 (d, J = 8.9 Hz, 2H), 4.08 (d, J = 8.9 Hz, 2H), 3.92 (s, 3H), 3.21 (d, J = 5.8 Hz, 2H). | MS m/z calcd for C$_{15}$H$_{16}$FN$_5$O$_2$S 349.1 found 350.3 [M + H]$^+$ | |
| 4-78 | 4-(aminomethyl)-1-(5-(2-ethoxy-4-fluorophenyl)imidazo[2,1-b][1,3,4]thiadiazol-2-yl)piperidin-4-ol | $^1$H NMR (500 MHz, DMSO-d$_6$) δ 8.24 (dd, J = 8.7, 6.9 Hz, 1H), 7.85 (t, J = 5.7 Hz, 3H), 7.63 (s, 1H), 7.07 (dd, J = 11.4, 2.5 Hz, 1H), 6.92 (td, J = 8.4, 2.5 Hz, 1H), 4.19 (q, J = 6.9 Hz, 2H), 3.71 (dt, J = 13.2, 4.1 Hz, 2H), 3.50 (ddd, J = 13.1, 9.1, 5.5 Hz, 2H), 2.86 (q, J = 5.8 Hz, 2H), 1.76-1.67 (m, 4H), 1.42 (t, J = 6.9 Hz, 3H). | MS m/z calcd for C$_{18}$H$_{22}$FN$_5$O$_2$S 391.2 found 392.1 [M + H]$^+$ | |
| 4-79 | 4-(aminomethyl)-1-(5-(6-isopropyl-2-(2-methoxyethoxy)pyridin-3-yl)imidazo[2,1-b][1,3,4]thiadiazol-2-yl)piperidin-4-ol | $^1$H NMR (500 MHz, DMSO-d$_6$) δ 8.61 (d, J = 7.7 Hz, 1H), 7.83 (s, 3H), 7.70 (s, 1H), 7.02 (d, J = 7.8 Hz, 1H), 4.60-4.49 (m, 2H), 3.80-3.68 (m, 4H), 3.51 (ddd, J = 14.0, 9.7, 4.9 Hz, 2H), 3.36 (s, 3H), 2.97 (h, J = 6.9 Hz, 1H), 2.86 (q, J = 5.8 Hz, 2H), 1.76-1.66 (m, 4H), 1.27 (d, J = 6.9 Hz, 6H). | MS m/z calcd for C$_{21}$H$_{30}$N$_6$O$_3$S 446.2 found 447.2 [M + H]$^+$ | |
| 4-80 | 4-(aminomethyl)-1-(5-(3-fluoro-2-methoxyphenyl)imidazo[2,1-b][1,3,4]thiadiazol-2-yl)piperidin-4-ol | $^1$H NMR (500 MHz, DMSO-d$_6$) δ 8.05 (s, 3H), 7.98 (d, J = 7.9 Hz, 1H), 7.73 (d, J = 6.9 Hz, 1H), 7.29 (dtd, J = 31.2, 8.3, 6.0 Hz, 2H), 3.91 (d, J = 1.8 Hz, 3H), 3.72 (dt, J = 13.0, 4.1 Hz, 2H), 3.50 (dq, J = 13.9, 6.8, 6.0 Hz, 2H), 2.84 (t, J = 6.0 Hz, 2H), 1.72 (q, J = 4.4 Hz, 4H). | MS m/z calcd for C$_{17}$H$_{20}$FN$_5$O$_2$S 377.1 found 378.3 [M + H]$^+$ | |

| Example/Compound Number | Structure | NMR | LC-MS | Chiral HPLC Method |
|---|---|---|---|---|
| 4-81 | 4-(aminomethyl)-1-(5-(3-methoxynaphthalen-2-yl)imidazo[2,1-b][1,3,4]thiadiazol-2-yl)piperidin-4-ol | $^1$H NMR (500 MHz, DMSO-$d_6$) δ 8.76 (s, 1H), 7.91 (d, J = 8.1 Hz, 1H), 7.86 (d, J = 8.2 Hz, 1H), 7.81 (s, 3H), 7.69 (s, 1H), 7.53-7.48 (m, 2H), 7.40 (ddd, J = 8.1, 6.8, 1.2 Hz, 1H), 4.03 (s, 3H), 3.78-3.74 (m, 2H), 3.54 (td, J = 10.2, 5.1 Hz, 2H), 2.87 (q, J = 5.7 Hz, 2H), 1.81-1.69 (m, 4H). | MS m/z calcd for $C_{21}H_{23}N_5O_2S$ 409.2 found 410.2 [M + H]$^+$ | |
| 4-82 | (3S,4S)-3-amino-1-(5-(4-fluoro-2-methoxyphenyl)imidazo[2,1-b][1,3,4]thiadiazol-2-yl)piperidin-4-ol | 1H NMR (400 MHz, MeOD-$d_4$) δ 8.24 (dd, J = 6.5, 8.7 Hz, 1H), 7.89 (s, 1H), 7.04 (dd, J = 2.4, 10.9 Hz, 1H), 6.88 (dt, J = 2.4, 8.4 Hz, 1H), 4.40 (br dd, J = 2.9, 12.8 Hz, 1H), 3.97 (s, 3H), 3.92-3.80 (m, 2H), 3.50-3.39 (m, 2H), 3.28-3.21 (m, 1H), 2.20 (br dd, J = 4.2, 13.2 Hz, 1H), 1.86-1.75 (m, 1H) | MS m/z calcd for $C_{16}H_{18}FN_5O_2S$ 363.1 found 364.2 [M + H]$^+$ | 10 |
| 4-83 | (3R,4R)-3-amino-1-(5-(4-fluoro-2-methoxyphenyl)imidazo[2,1-b][1,3,4]thiadiazol-2-yl)piperidin-4-ol | 1H NMR (400 MHz, MeOD-$d_4$) δ 8.26 (dd, J = 6.5, 8.7 Hz, 1H), 7.91 (s, 1H), 7.04 (dd, J = 2.3, 11.0 Hz, 1H), 6.89 (dt, J = 2.4, 8.4 Hz, 1H), 4.40 (br dd, J = 3.5, 13.0 Hz, 1H), 4.00-3.78 (m, 5H), 3.53-3.34 (m, 2H), 3.27-3.21 (m, 1H), 2.25-2.15 (m, 1H), 1.86-1.75 (m, 1H). | MS m/z calcd for $C_{16}H_{18}FN_5O_2S$ 363.1 found 364.2 [M + H]$^+$ | 10 |

| Example/Compound Number | Structure | NMR | LC-MS | Chiral HPLC Method |
|---|---|---|---|---|
| 4-84 | (4aR,8aR)-6-(5-(2-methoxy-4-methylphenyl)imidazo[2,1-b][1,3,4]thiadiazol-2-yl)octahydro-2H-pyrido[4,3-b][1,4]oxazine | ¹H NMR (400 MHz, DMSO-d₆) δ 9.30 (d, J = 17.9 Hz, 2H), 8.00 (d, J = 7.9 Hz, 1H), 7.50 (s, 1H), 6.99 (s, 1H), 6.87 (d, J = 7.9 Hz, 1H), 4.04-4.02 (m, 2H), 3.96 (m, 1H), 3.88 (s, 3H), 3.74 (m, 3H), 3.60-3.57 (m, 1H), 3.42-3.28 (m, 2H), 3.10 (d, J = 12.9 Hz, 1H), 2.36 (s, 3H), 1.97 (dd, J = 10.3, 4.6 Hz, 2H). | MS m/z calcd for $C_{19}H_{23}N_5O_2S$ 385.2 found 386.2 $[M + H]^+$ | |
| 4-85 | 1'-(5-(6-isopropyl-2-methoxypyridin-3-yl)imidazo[2,1-b][1,3,4]thiadiazol-2-yl)-[1,3'-biazetidin]-3-ol | ¹H NMR (400 MHz, DMSO-d₆) δ 8.54 (d, J = 7.7 Hz, 1H), 8.04 (s, 3H), 7.60 (s, 1H), 6.99 (d, J = 7.7 Hz, 1H), 4.06 (d, J = 9.2 Hz, 2H), 4.01 (s, 3H), 3.61 (s, 1H), 3.51-3.44 (m, 2H), 3.34 (dd, J = 12.9, 9.0 Hz, 1H), 2.98 (p, J = 6.9 Hz, 1H), 2.00 (d, J = 12.6 Hz, 1H), 1.82 (t, J = 10.9 Hz, 1H), 1.28 (d, J = 6.8 Hz, 6H). | MS m/z calcd for $C_{18}H_{24}N_6O_2S$ 388.2 found 389.2 $[M + H]^+$ | |
| 4-86 | 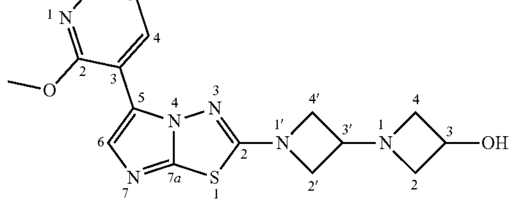 | ¹H NMR (500 MHz, DMSO-d₆) δ 8.48 (d, J = 7.7 Hz, 1H), 7.55 (s, 1H), 6.98 (d, J = 7.7 Hz, 1H), 4.22 (t, J = 6.2 Hz, 1H), 4.16 (t, J = 7.7 Hz, 2H), 3.99 (s, 3H), 3.92 (dd, J = 8.4, 4.5 Hz, 2H), 3.68 (tt, J = 7.2, 4.5 Hz, 1H), 3.50 (td, J = 6.2, 1.9 Hz, 2H), 2.96 (dq, J = 13.6, 6.6 Hz, 1H), 2.89 (td, J = 6.1, 1.9 Hz, 2H), 1.26 (d, J = 6.9 Hz, 6H). | MS m/z calcd for $C_{19}H_{24}N_6O_2S$ 400.2 found 401.2 $[M + H]^+$ | |

| Example/ Compound Number | Structure | NMR | LC-MS | Chiral HPLC Method |
|---|---|---|---|---|
| 4-87 | (4-amino-1-(5-(6-isopropyl-2-methoxypyridin-3-yl)imidazo[2,1-b][1,3,4]thiadiazol-2-yl)piperidin-4-yl)methanol | $^1$H NMR (300 MHz, MeOD-$d_4$) δ 8.58 (dd, J = 8.1, 2.1 Hz, 1H), 7.61 (s, 1H), 6.91 (d, J = 7.8 Hz, 1H), 4.06 (s, 3H), 3.91-3.72 (m, 4H), 3.66-3.50 (m, 2H), 3.08-2.90 (m, 1H), 2.17-2.02 (m, 2H), 2.00-1.85 (m, 2H), 1.32 (s, 3H), 1.30 (s, 3H). | MS m/z calcd for $C_{19}H_{26}N_6O_2S$ 402.2, found 403.2 [M + H]$^+$ | |
| 4-88 | 4-(aminomethyl)-1-(5-(5-chloro-2-methoxyphenyl)imidazo[2,1-b][1,3,4]thiadiazol-2-yl)piperidin-4-ol | $^1$H NMR (300 MHz, MeOD-$d_4$) δ 8.37 (d, J = 2.6 Hz, 1H), 8.02 (s, 1H), 7.45 (dd, J = 8.9, 2.5 Hz, 1H), 7.20 (d, J = 9.0 Hz, 1H), 3.98 (s, 3H), 3.90-3.80 (m, 2H), 3.74-3.62 (m, 2H), 2.99 (s, 2H), 1.92-1.79 (m, 4H). | MS m/z calcd for $C_{17}H_{20}ClN_5O_2S$ 393.1 found 394.3 [M + H]$^+$ | |
| 4-89 | 4-(aminomethyl)-1-(5-(2-methoxyphenyl)imidazo[2,1-b][1,3,4]thiadiazol-2-yl)piperidin-4-ol | $^1$H NMR (500 MHz, DMSO-$d_6$) δ 8.20 (d, J = 7.6 Hz, 1H), 7.77 (s, 3H), 7.56 (s, 1H), 7.33 (t, J = 7.8 Hz, 1H), 7.16 (d, J = 8.3 Hz, 1H), 7.07 (t, J = 7.6 Hz, 1H), 3.90 (s, 3H), 3.69 (d, J = 13.8 Hz, 2H), 3.52-3.41 (m, 2H), 2.85 (q, J = 5.8 Hz, 2H), 1.71 (dt, J = 8.6, 4.3 Hz, 4H). | MS m/z calcd for $C_{17}H_{21}N_5O_2S$ 359.1 found 360.3 [M + H]$^+$ | |
| 4-89 | 4-(aminomethyl)-1-(5-(4-fluoro-2-isopropoxyphenyl)imidazo[2,1-b][1,3,4]thiadiazol-2-yl)piperidin-4-ol | $^1$H NMR (500 MHz, DMSO-$d_6$) δ 8.22 (dd, J = 8.7, 6.9 Hz, 1H), 7.84 (s, 3H), 7.62 (s, 1H), 7.11 (dd, J = 11.7, 2.6 Hz, 1H), 6.90 (td, J = 8.4, 2.5 Hz, 1H), 4.82 (p, J = 6.0 Hz, 1H), 3.78-3.66 (m, 2H), 3.50 (ddd, J = 13.5, 9.3, 5.3 Hz, 2H), 2.86 (d, J = 5.9 Hz, 2H), 1.72 (q, J = 4.6 Hz, 4H), 1.35 (d, J = 6.0 Hz, 6H). | MS m/z calcd for $C_{19}H_{24}FN_5O_2S$ 405.2 found 406.2 [M + H]$^+$ | |

| Example/Compound Number | Structure | NMR | LC-MS | Chiral HPLC Method |
|---|---|---|---|---|
| 4-90 | 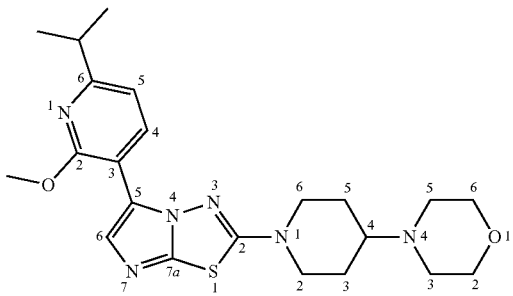<br>4-(1-(5-(6-isopropyl-2-methoxypyridin-3-yl)imidazo[2,1-b][1,3,4]thiadiazol-2-yl)piperidin-4-yl)morpholine | NA | MS m/z calcd for $C_{22}H_{30}N_6O_2S$ 442.2 found 443.2 [M + H]$^+$ | |
| 4-91 | 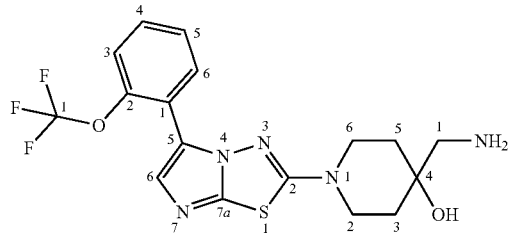<br>4-(aminomethyl)-1-(5-(2-(trifluoromethoxy)phenyl)imidazo[2,1-b][1,3,4]thiadiazol-2-yl)piperidin-4-ol | $^1$H NMR (300 MHz, MeOD-d$_4$) δ 8.12 (dd, J = 8.0, 1.8 Hz, 1H), 7.84 (s, 1H), 7.69-7.59 (m, 1H), 7.60-7.51 (m, 2H), 3.88-3.76 (m, 2H), 3.72-3.60 (m, 2H), 2.97 (s, 2H), 1.87-1.73 (m, 4H). | MS m/z calcd for $C_{17}H_{18}F_3N_5O_2S$ 413.1 found 414.3 [M + H]$^+$ | |
| 4-92 | 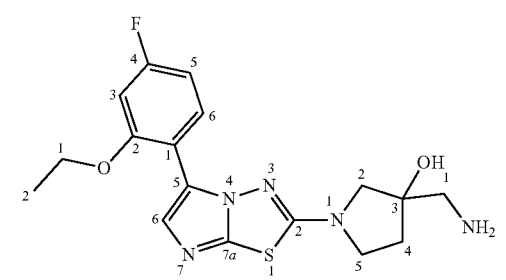<br>3-(aminomethyl)-1-(5-(2-ethoxy-4-fluorophenyl)imidazo[2,1-b][1,3,4]thiadiazol-2-yl)pyrrolidin-3-ol | $^1$H NMR (500 MHz, DMSO-d$_6$) δ 8.26 (dd, J = 8.7, 6.8 Hz, 1H), 8.11 (d, J = 7.6 Hz, 3H), 7.70 (s, 1H), 7.10 (dd, J = 11.4, 2.5 Hz, 1H), 6.92 (td, J = 8.4, 2.5 Hz, 1H), 4.20 (t, J = 6.9 Hz, 2H), 3.70-3.54 (m, 4H), 3.10 (tq, J = 13.1, 6.4 Hz, 2H), 2.19-2.10 (m, 2H), 1.42 (t, J = 6.9 Hz, 3H). | MS m/z calcd for $C_{17}H_{20}FN_5O_2S$ 377.1 found 378.3 [M + H]$^+$ | |

| Example/ Compound Number | Structure | NMR | LC-MS | Chiral HPLC Method |
|---|---|---|---|---|
| 4-93 | 1-(1-(5-(6-isopropyl-2-methoxypyridin-3-yl)imidazo[2,1-b][1,3,4]thiadiazol-2-yl)piperidin-4-yl)azetidin-3-ol | $^1$H NMR (500 MHz, DMSO-$d_6$) δ 8.54 (dd, J = 7.7, 2.3 Hz, 1H), 7.60 (s, 1H), 7.01 (d, J = 7.8 Hz, 1H), 4.51 (d, J = 6.8 Hz, 1H), 4.37 (m, 2H), 4.02 (s, 3H), 4.00-3.93 (m, 2H), 3.22 (m, J = 12.1 Hz, 4H), 2.98 (m, 1H), 2.10 (m, 1H), 1.48 (m, 2H), 1.23-1.30 (m, 2H), 1.28 (d, J = 6.9 Hz, 6H). | MS m/z calcd for $C_{21}H_{28}N_6O_2S$ 428.2, found 429.2 [M + H]$^+$ | |
| 4-94 | 4-(aminomethyl)-1-(5-(2-methoxy-6-(trifluoromethyl)pyridin-3-yl)imidazo[2,1-b][1,3,4]thiadiazol-2-yl)piperidin-4-ol | $^1$H NMR (500 MHz, DMSO-$d_6$) δ 8.96 (d, J = 7.8 Hz, 1H), 7.92-7.78 (m, 4H), 7.65 (d, J = 7.9 Hz, 1H), 4.09 (s, 3H), 3.76 (dt, J = 13.2, 4.1 Hz, 2H), 3.52 (ddd, J = 13.6, 9.6, 4.9 Hz, 2H), 2.87 (q, J = 5.8 Hz, 2H), 1.80-1.68 (m, 4H). | MS m/z calcd for $C_{17}H_{19}F_3N_6O_2S$ 428.1 found 429.1 [M + H]$^+$ | |
| 4-95 | (4-(aminomethyl)-1-(5-(2-methoxy-4-methylphenyl)imidazo[2,1-b][1,3,4]thiadiazol-2-yl)piperidin-4-yl)methanol | $^1$H NMR (400 MHz, MeOD-$d_4$) δ 8.14 (d, J = 7.9 Hz, 1H), 7.75 (s, 1H), 7.01 (d, J = 1.3 Hz, 1H), 6.94-6.88 (m, 1H), 3.95 (s, 3H), 3.76 (s, 2H), 3.65 (ddd, J = 19.4, 7.6, 4.7 Hz, 4H), 3.50 (q, J = 7.0 Hz, 2H), 3.12 (s, 2H), 2.42 (s, 3H), 1.94-1.60 (m, 4H). | MS m/z calcd for $C_{19}H_{25}N_5O_2S$ 387.2 found 388.2 [M + H]$^+$ | |

| Example/ Compound Number | Structure | NMR | LC-MS | Chiral HPLC Method |
|---|---|---|---|---|
| 4-96 | 4-(1-(5-(6-isopropyl-2-methoxypyridin-3-yl)imidazo[2,1-b][1,3,4]thiadiazol-2-yl)piperidin-4-yl)thiomorpholin 1,1-dioxide | $^1$H NMR (500 MHz, DMSO-$d_6$) δ 8.55 (d, J = 7.7 Hz, 1H), 7.60 (s, 1H), 7.02 (d, J = 7.8 Hz, 1H), 4.02 (s, 3H), 3.93 (s, 2H), 3.24-3.09 (m, 10H), 2.98 (d, J = 6.8 Hz, 1H), 1.90 (d, J = 12.4 Hz, 2H), 1.65 (d, J = 13.0 Hz, 2H), 1.28 (d, J = 6.9 Hz, 6H). | MS m/z calcd for $C_{22}H_{30}N_6O_3S_2$ 490.2 found 491.2 [M + H]$^+$ | |
| 4-97 | (4-amino-1-(5-(2-methoxy-6-methylpyridin-3-yl)imidazo[2,1-b][1,3,4]thiadiazol-2-yl) piperidin-4-yl)methanol | $^1$H NMR (500 MHz, MeOD-$d_4$) δ 8.61 (d, J = 7.7 Hz, 1H), 7.62 (s, 1H), 6.92 (d, J = 7.7 Hz, 1H), 4.07 (s, 3H), 3.66 (dt, J = 7.3, 4.6 Hz, 4H), 3.49 (s, 2H), 2.48 (s, 3H), 1.86 (ddd, J = 14.0, 9.0, 5.3 Hz, 2H), 1.66 (dt, J = 13.9, 4.5 Hz, 2H). | MS m/z calcd for $C_{17}H_{22}N_6O_2S$ 374.1 found 375.2 [M + H]$^+$ | |
| 4-98 | (4-amino-1-(5-(4-fluoro-2-methoxyphenyl)imidazo[2,1-b][1,3,4]thiadiazol-2-yl)piperidin-4-yl)methanol | $^1$H NMR (500 MHz, DMSO-$d_6$) δ 8.24-8.07 (m, 4H), 7.64 (s, 1H), 7.11 (d, J = 11.2 Hz, 1H), 6.93 (t, J = 8.3 Hz, 1H), 3.92 (s, 3H), 3.75 (dt, J = 12.1, 5.5 Hz, 2H), 3.62 (s, 2H), 3.53 (ddd, J = 13.1, 8.8, 3.9 Hz, 2H), 1.97-1.77 (m, 4H). | MS m/z calcd for $C_{17}H_{20}FN_5O_2S$ 377.1 found 378.3 [M + H]$^+$ | |

| Example/Compound Number | Structure | NMR | LC-MS | Chiral HPLC Method |
|---|---|---|---|---|
| 4-99 | 4-(aminomethyl)-1-(5-(4-fluoro-2-methoxy-5-methylphenyl)imidazo[2,1-b][1,3,4]thiadiazol-2-yl)piperidin-4-ol | $^1$H NMR (400 MHz, DMSO-d$_6$) δ 8.02-7.90 (m, 4H), 7.61 (s, 1H), 7.06 (d, J = 11.9 Hz, 1H), 3.87 (s, 3H), 3.56-3.40 (m, 5H), 2.84 (q, J = 6.0, 5.5, 5.5 Hz, 2H), 2.23 (s, 3H), 1.75-1.65 (m, 4H). | MS m/z calcd for C$_{18}$H$_{22}$FN$_5$O$_2$S 391.2 found 391.8 [M + H]$^+$ | |
| 4-100 | (4-amino-1-(5-(2-ethoxy-4-fluorophenyl)imidazo[2,1-b][1,3,4]thiadiazol-2-yl)piperidin-4-yl)methanol | $^1$H NMR (500 MHz, DMSO-d$_6$) δ 8.23 (dd, J = 8.7, 6.8 Hz, 1H), 8.15 (s, 3H), 7.67 (s, 1H), 7.09 (dd, J = 11.4 2.6 Hz, 1H), 6.92 (td, J = 8.4, 2.5 Hz, 1H), 4.18 (q, J = 6.9 Hz, 2H), 3.75 (dt, J = 13.7, 5.4 Hz, 2H), 3.62 (s, 2H), 3.53 (ddd, J = 13.3, 8.8, 4.0 Hz, 2H), 1.99-1.76 (m, 4H), 1.41 (t, J = 6.9 Hz, 3H). | MS m/z calcd for C$_{18}$H$_{22}$FN$_5$O$_2$S 391.2 found 392.4 [M + H]$^+$ | |
| 4-101 | 4-(aminomethyl)-1-(5-(2,4-dimethoxyphenyl)imidazo[2,1-b][1,3,4]thiadiazol-2-yl)piperidin-4-ol | $^1$H NMR (500 MHz, DMSO-d$_6$) δ 8.08 (d, J = 8.6 Hz, 1H), 7.81 (d, J = 5.9 Hz, 3H), 7.50 (s, 1H), 6.72 (d, J = 2.4 Hz, 1H), 6.68 (dd, J = 8.6, 2.4 Hz, 1H), 3.89 (s, 3H), 3.83 (s, 3H), 3.70 (dt, J = 13.3, 4.2 Hz, 2H), 3.49 (ddd, J = 13.6, 9.6, 4.7 Hz, 2H), 2.86 (q, J = 5.8 Hz, 2H), 1.75-1.64 (m, 4H). | MS m/z calcd for C$_{18}$H$_{23}$N$_5$O$_3$S 389.2 found 390.152 [M + H]$^+$ | |

| Example/ Compound Number | Structure | NMR | LC-MS | Chiral HPLC Method |
|---|---|---|---|---|
| 4-102 | 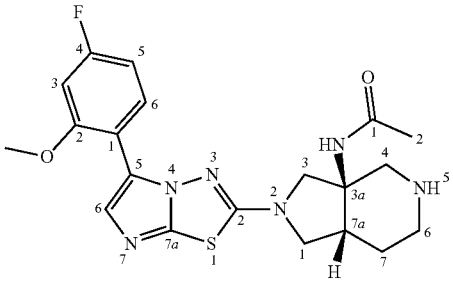<br>N-((3aR,7aR)-2-(5-(4-fluoro-2-methoxyphenyl)imidazo[2,1-b][1,3,4]thiadiazol-2-yl)octahydro-3aH-pyrrolo[3,4-c]pyridin-3a-yl)acetamide | $^1$H NMR (500 MHz, DMSO-$d_6$) δ 8.86 (s, 1H), 8.67 (d, J = 9.9 Hz, 1H), 8.37 (s, 1H), 8.23 (dd, J = 8.7, 6.9 Hz, 1H), 7.63 (s, 1H), 7.11 (dd, J = 11.4, 2.6 Hz, 1H), 6.95 (td, J = 8.5, 2.6 Hz, 1H), 3.99 (d, J = 10.9 Hz, 1H), 3.93 (s, 3H), 3.79-3.64 (m, 2H), 3.60 (dd, J = 10.4, 7.9 Hz, 2H), 3.29-3.06 (m, 3H), 2.75 (td, J = 8.2, 4.2 Hz, 1H), 2.13 (qt, J = 12.2, 6.1 Hz, 1H), 1.91 (s, 3H), 1.78 (q, J = 4.7 Hz, 1H). | MS m/z calcd for $C_{20}H_{23}FN_6O_2S$ 430.2 found 431.2 [M + H]$^+$ | |

Example 5-0: 2-(5-(2-methoxy-4-methylphenyl)imidazo[2,1-b][1,3,4]thiadiazol-2-yl)-5-oxa-2,7-diazaspiro[3.4]oct-6-en-6-amine

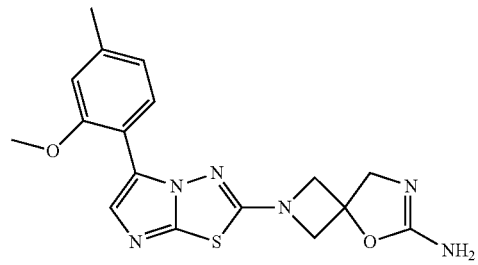 [SMILES: COc1cc(C)ccc1-c1cnc2sc(N3CC4(CN=C(N)O4)C3)nn12]

Compound 5-0 was prepared by the same route used to prepare Compound 4-0, using tert-butyl ((3-hydroxyazetidin-3-yl)methyl)carbamate, Compound 1 and (2-methoxy-4-methylphenyl)boronic acid, followed by cyclization.

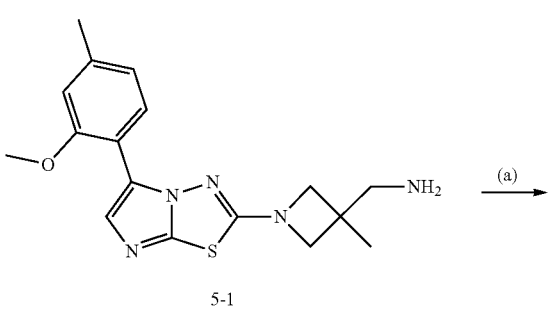

5-1

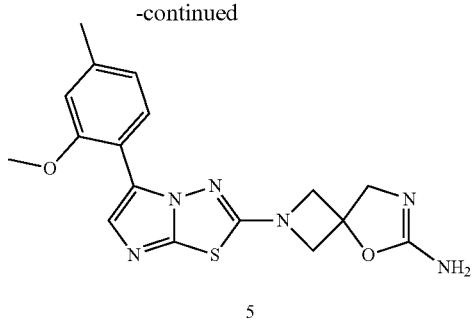

5

Compound 5-1 (38 mg, 0.091 mmol) and $K_2CO_3$ (50.2 mg, 0.363 mmol) were stirred in anhydrous DMSO (1 mL), followed by an addition of cyanogen bromide (14.43 mg, 0.136 mmol), the reaction was stirred at room temperature for 1 hour. Then the reaction mixture was filtered and purified by prep-HPLC. The resulting fractions in formic acid solution, was treated with aqueous $Na_2CO_3$ until pH was highly basic (pH>11). Then the solution was extracted twice with EtOAc, washed with brine, dried over $Na_2SO_4$ and concentrated to afford 6.3 mg of Compound 5-0 as a solid. $^1$H NMR (500 MHz, DMSO-$d_6$) δ 7.98 (d, J=7.8 Hz, 1H), 7.45 (s, 1H), 6.97 (s, 1H), 6.87 (d, J=7.7 Hz, 1H), 6.13 (s, 2H), 4.50-4.21 (m, 4H), 3.86 (s, 5H), 2.35 (s, 3H). LC-MS=371.1 [M+H]$^+$.

The following compounds were prepared by the same route used to prepare Compound 5-0, using appropriate starting materials.

| Example/Compound Number | Structure | NMR | LC-MS |
|---|---|---|---|
| 5-0 | 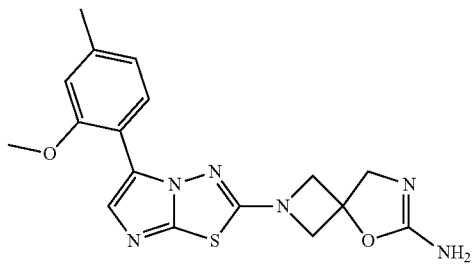<br>2-(5-(2-methoxy-4-methylphenyl)imidazo[2,1-b][1,3,4]thiadiazol-2-yl)-5-oxa-2,7-diazaspiro[3.4]oct-6-en-6-amine | $^1$H NMR (500 MHz, DMSO-$d_6$) δ 7.98 (d, J = 7.8 Hz, 1H), 7.45 (s, 1H), 6.97 (s, 1H), 6.87 (d, J = 7.7 Hz, 1H), 6.13 (s, 2H), 4.50-4.21 (m, 4H), 3.86 (s, 5H), 2.35 (s, 3H). | MS m/z calcd for $C_{17}H_{18}N_6O_2S$ 370.1 found 371.1 [M + H]$^+$ |
| 5-2 | 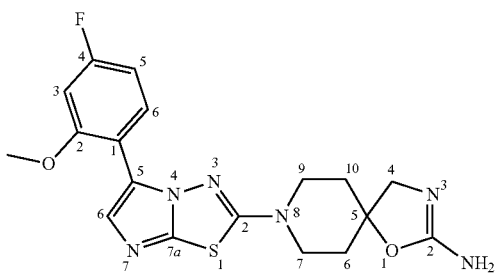<br>8-(5-(4-fluoro-2-methoxyphenyl)imidazo[2,1-b][1,3,4]thiadiazol-2-yl)-1-oxa-3,8-diazaspiro[4.5]dec-2-en-2-amine | $^1$H NMR (500 MHz, DMSO-$d_6$) δ 8.19 (dd, J = 8.7, 6.9 Hz, 1H), 7.51 (s, 1H), 7.09 (dd, J = 11.4, 2.5 Hz, 1H), 6.93 (dd, J = 8.4, 2.5 Hz, 1H), 4.03 (s, 2H), 3.92 (s, 3H), 3.52-3.46 (m, 4H), 2.28 (d, J = 13.9 Hz, 2H), 2.24-2.13 (m, 2H). | MS m/z calcd for $C_{18}H_{19}FN_6O_2S$ 402.1 found 403.1 [M + H]$^+$ |
| 5-3 | 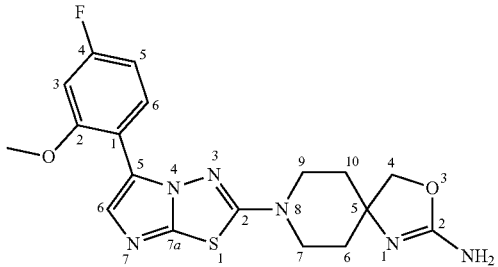<br>8-(5-(4-fluoro-2-methoxyphenyl)imidazo[2,1-b][1,3,4]thiadiazol-2-yl)-3-oxa-1,8-diazaspiro[4.5]dec-1-en-2-amine | $^1$H NMR (500 MHz, DMSO-$d_6$) δ 8.18 (dd, J = 8.7, 6.9 Hz, 1H), 7.46 (s, 1H), 7.05 (dd, J = 11.4, 2.6 Hz, 1H), 6.91 (td, J = 8.5, 2.6 Hz, 1H), 5.95 (s, 1H), 3.90 (d, J = 3.7 Hz, 5H), 3.63-3.51 (m, 4H), 1.73 (ddd, J = 13.6, 8.7, 5.2 Hz, 2H), 1.63-1.57 (m, 2H). | MS m/z calcd for $C_{18}H_{19}FN_6O_2S$ 402.1 found 403.1 [M + H]$^+$ |
| 5-4 | 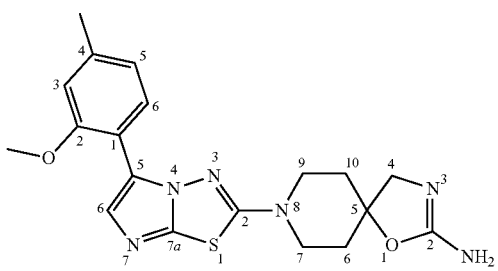<br>8-(5-(2-methoxy-4-methylphenyl)imidazo[2,1-b][1,3,4]thiadiazol-2-yl)-1-oxa-3,8-diazaspiro[4.5]dec-2-en-2-amine | $^1$H NMR (500 MHz, DMSO-$d_6$) δ 8.03 (d, J = 8.0 Hz, 1H), 7.45 (s, 1H), 6.93 (d, J = 4.7 Hz, 2H), 3.88 (s, 3H), 3.66 (d, J = 11.8 Hz, 2H), 3.52-3.43 (m, 4H), 2.36 (s, 3H), 1.92 (s, 4H). | MS m/z calcd for $C_{19}H_{22}N_6O_2S$ 398.2 found 399.2 [M + H]$^+$ |

Example 6-0: (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol

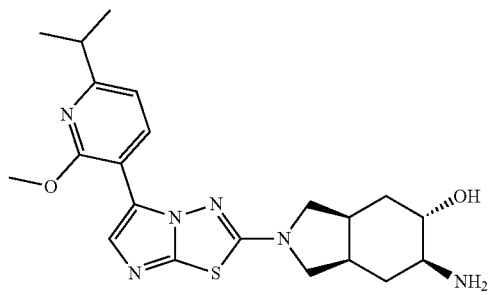 [SMILES: COc1nc(C(C)C)ccc1-c1cnc2sc(N3C[C@H]4C[C@H](O)[C@@H](N)C[C@H]4C3)nn12]

Compound 6-0 was prepared in the following way:

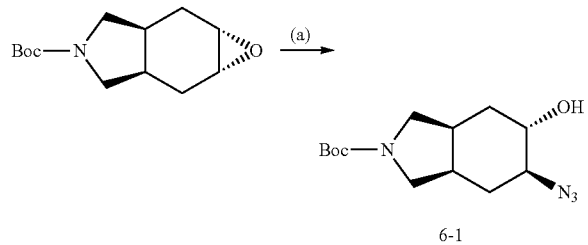

A solution of tert-butyl (1aR,2aR,5aS,6aS)-octahydro-4H-oxireno[2,3-f]isoindole-4-carboxylate (500 mg, 2.089 mmol) in MeOH (10 mL) and H$_2$O (2 mL) was treated with NaN$_3$ (679 mg, 10.45 mmol) and NH$_4$Cl (224 mg, 4.18 mmol). The reaction was warmed to 65° C. for 18 hours and then cooled to room temperature, concentrated to remove MeOH and extracted with DCM. The combined organic layers were passed through a phase separator and concentrated in vacuo to give an oil that crystallized upon standing. The residue was taken up in Et$_2$O and the resulting solid was isolated by filtration and dried to afford 289 mg of Compound 6-1. $^1$H NMR (500 MHz, DMSO-d$_6$) δ 5.15 (d, J=5.7 Hz, 1H), 3.53 (td, J=10.4, 5.3 Hz, 1H), 3.31-3.20 (m, 3H), 3.06 (dd, J=11.2, 5.9 Hz, 2H), 2.36 (s, 1H), 2.17 (dd, J=11.5, 6.2 Hz, 1H), 1.89 (t, J=9.8 Hz, 1H), 1.78 (d, J=12.1 Hz, 1H), 1.52 (d, J=13.1 Hz, 1H), 1.39 (s, 9H), 1.17-1.04 (m, 1H).

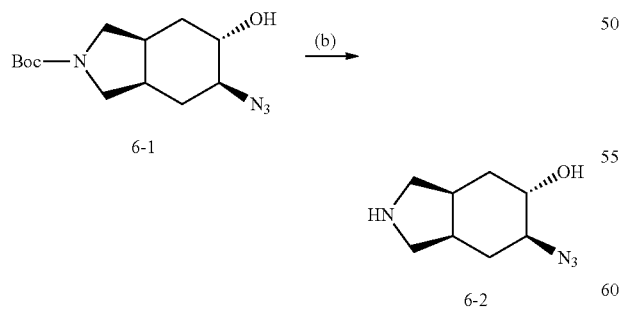

Compound 6-1 (289 mg, 1.024 mmol) was treated with HCl (1 M in dioxane) (4 mL, 4.00 mmol). The reaction was sealed and stirred at 20° C. for 3 hours. The reaction was concentrated in vacuo under a stream of N$_2$ to afford 222 mg of Compound 6-2.

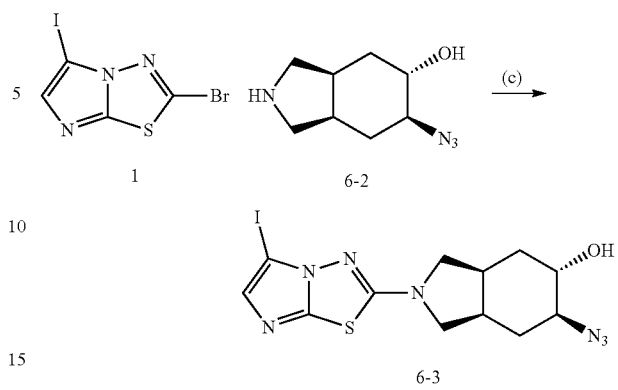

To a solution of Compound 1 (335 mg, 1.015 mmol) and Compound 6-2 (222 mg, 1.015 mmol) in MeCN (4 mL) was added DIPEA (0.544 mL, 3.05 mmol). The reaction was sealed and stirred at 100° C. for 2 hours, then was cooled to room temperature and purified by normal phase chromatography with a running gradient of 0-100% EtOAc/heptane to afford 349 mg of Compound 6-3. $^1$H NMR (500 MHz, DMSO-d$_6$) δ 7.08 (s, 1H), 5.27-5.12 (m, 1H), 3.59 (dd, J=3.3, 9.1 Hz, 2H), 3.43 (dt, J=5.6, 10.2 Hz, 2H), 3.25 (d, J=10.0 Hz, 2H), 2.61 (s, 1H), 2.41 (s, 1H), 1.97 (s, 1H), 1.92-1.77 (m, 1H), 1.61 (d, J=13.1 Hz, 1H), 1.31-1.16 (m, 1H). LC-MS=432.1 [M+H]$^+$.

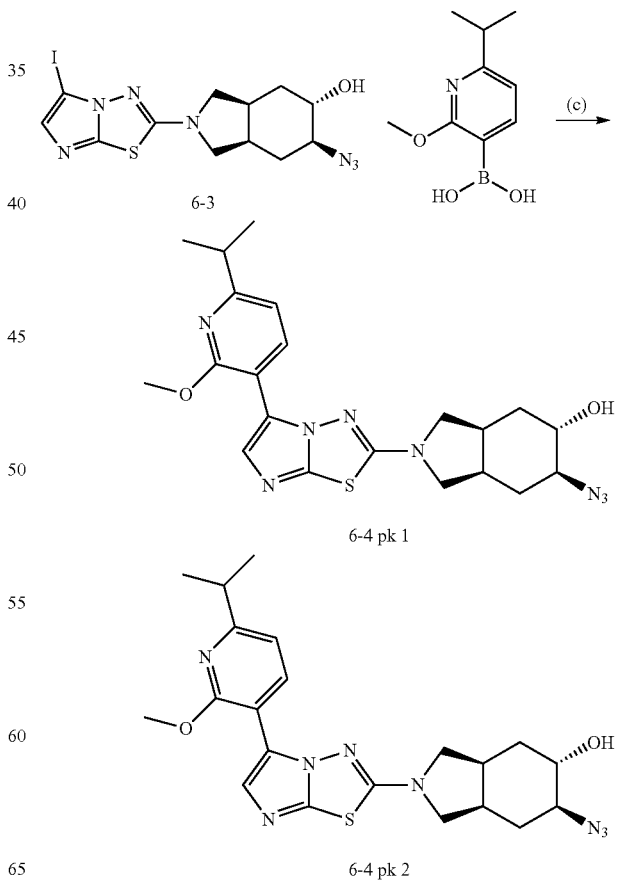

A mixture of Compound 6-3 (149 mg, 0.346 mmol), (6-isopropyl-2-methoxypyridin-3-yl)boronic acid (135 mg, 0.691 mmol), PdCl$_2$(dppf)-DCM complex (28.2 mg, 0.035 mmol), and K$_3$PO$_4$ (220 mg, 1.037 mmol) was flushed with N$_2$ for a few minutes, then dioxane (2.5 mL) and H$_2$O (0.5 mL) were added. The vial was flushed with N$_2$ for an additional minute, then sealed and heated to 80° C. for 3 hours. The reaction was concentrated in vacuo and was purified by normal phase chromatography (24 g column) with a running gradient of 0-60% (3:1 EtOAc:EtOH)/heptane. Fractions were combined, concentrated in vacuo, then triturated from DCM/heptane twice, then MeOH/heptane. The resulting product was separated by chiral separation (Method 8) to afford 18.2 mg of Compound 6-4 Peak 1 and 17.3 mg of Compound 6-4 Peak 2.

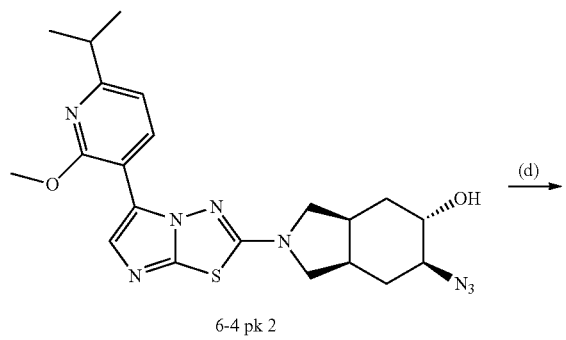

6-4 pk 2

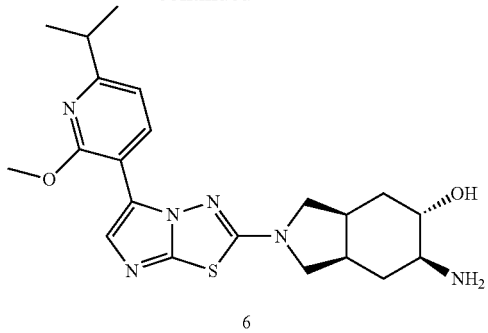

6

A solution of single stereoisomer Compound 6-4 pk2 (17.3 mg, 0.038 mmol) in THF (1 mL) and H$_2$O (0.2 mL) was added Ph$_3$P (15 mg, 0.057 mmol. The reaction was then heated to 40° C. for 2 hours. Additional Ph$_3$P (15 mg, 0.057 mmol) was added and heated to 50° C. for 12 hours. The reaction was concentrated in vacuo and was purified by prep-HPLC to afford 9.5 mg of Compound 6. $^1$H NMR (500 MHz, DMSO-d$_6$) δ 8.60 (d, J=7.7 Hz, 1H), 7.83 (d, J=5.1 Hz, 3H), 7.62 (s, 1H), 7.01 (d, J=7.8 Hz, 1H), 4.02 (s, 3H), 3.64 (qd, J=9.7, 8.7, 4.0 Hz, 3H), 3.44-3.31 (m, 2H), 2.98 (h, J=6.9 Hz, 1H), 2.89 (s, 1H), 2.72 (s, 1H), 2.48 (dd, J=12.4, 5.8 Hz, 1H), 2.09 (q, J=6.0, 4.8 Hz, 1H), 2.03-1.94 (m, 1H), 1.69-1.60 (m, 1H), 1.35 (q, J=12.8 Hz, 1H), 1.28 (d, J=6.9 Hz, 6H). LC-MS=429.2 [M+H]$^+$.

The following compounds were prepared by the same route used to prepare Compound 6-0, using appropriate starting materials:

| Example/Compound Number | Structure | NMR | LC-MS |
| --- | --- | --- | --- |
| 6-5 | (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol | $^1$H NMR (500 MHz, DMSO-d$_6$) δ 8.60 (d, J = 7.7 Hz, 1H), 7.83 (d, J = 5.0 Hz, 3H), 7.63 (s, 1H), 7.01 (d, J = 7.8 Hz, 1H), 4.02 (s, 3H), 3.63 (dq, J = 9.0, 4.6, 3.4 Hz, 3H), 3.41-3.31 (m, 2H), 2.98 (m, 1H), 2.89 (s, 1H), 2.72 (s, 1H), 2.47 (dt, J = 11.1, 5.6 Hz, 1H), 2.13-2.04 (m, 1H), 1.98 (dt, J = 13.3, 4.6 Hz, 1H), 1.64 (ddd, J = 13.7, 11.3, 5.4 Hz, 1H), 1.35 (d, J = 12.8 Hz, 1H), 1.28 (d, J = 6.9 Hz, 6H). | MS m/z calcd for C$_{21}$H$_{28}$N$_6$O$_2$S 428.2 found 429.2 [M + H]$^+$ |

| Example/Compound Number | Structure | NMR | LC-MS |
|---|---|---|---|
| 6-6 | (3aS,5S,6S,7aR)-6-amino-2-(5-(4-fluoro-2-methoxyphenyl)imidazo[2,1-b][1,3,4]thiadiazol-2-yl)octahydro-1H-isoindol-5-ol | $^1$H NMR (500 MHz, DMSO-$d_6$) δ 8.26 (dd, J = 8.7, 6.8 Hz, 1H), 7.84 (s, 3H), 7.59 (s, 1H), 7.10 (dd, J = 11.4, 2.5 Hz, 1H), 6.93 (td, J = 8.4, 2.6 Hz, 1H), 3.93 (s, 3H), 3.64 (dp, J = 15.4, 5.6 Hz, 3H), 3.40-3.31 (m, 2H), 2.89 (s, 1H), 2.72 (s, 1H), 2.48 (dd, J = 12.4, 5.7 Hz, 1H), 2.14-2.03 (m, 1H), 1.98 (dt, J = 13.1, 4.6 Hz, 1H), 1.64 (ddd, J = 13.7, 11.3, 5.4 Hz, 1H), 1.35 (q, J = 12.8 Hz, 1H). | MS m/z calcd for $C_{19}H_{22}FN_5O_2S$ 403.2 found 404.1 [M + H]$^+$ |

Example 7-0: (9-(5-(4-fluoro-2-methoxyphenyl)imidazo[2,1-b][1,3,4]thiadiazol-2-yl)-2-oxa-9-azaspiro[5.5]undecan-3-yl)methanamine

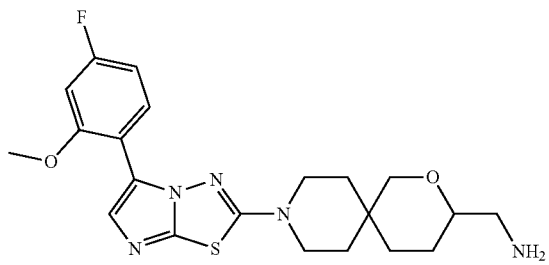 [SMILES: COc1cc(F)ccc1-c1cnc2sc(N3CCC4(CCC(CN)OC4)CC3)nn12]

The Compound 7-0 was prepared in the following way:

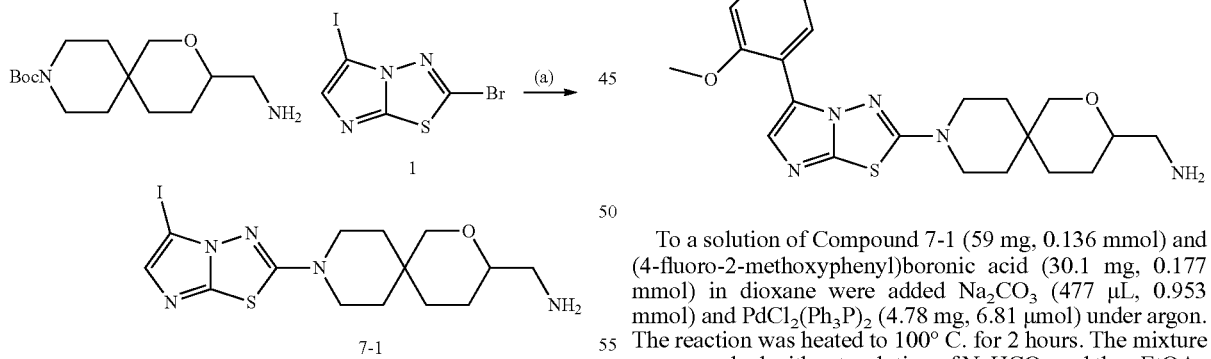

To solution of tert-butyl 3-(aminomethyl)-2-oxa-9-azaspiro[5.5]undecane-9-carboxylate (100 mg, 0.352 mmol) in MeOH (1 mL) was added HCl 4 M in dioxane (1.319 mL, 5.27 mmol) and was stirred for 1 hour. The resulting white suspension was concentrated in vacuo, then was partially dissolved in EtOH (1 mL) and Compound 1 (116 mg, 0.352 mmol) and DIPEA (0.184 mL, 1.055 mmol) were added. The resulting suspension was heated to 80° C. for 18 hours. The mixture was quenched with sat. solution of NaHCO$_3$ and was extracted twice with EtOAc. The combined organic layers were dried over MgSO$_4$, filtered and concentrated in vacuo. The product was purified by normal phase chromatography (4 g column), with a running gradient of 0-20% (DCM/(DCM/MeOH 8/2)) to afford 59 mg of Compound 7-1 as a beige foam. $^1$H NMR (500 MHz, MeOD-$d_4$) δ 7.04 (s, 1H), 3.87 (dd, J=11.5, 2.7 Hz, 1H), 3.55-3.42 (m, 4H), 3.33 (dt, J=8.3, 3.6 Hz, 1H), 3.24 (d, J=11.5 Hz, 1H), 2.76-2.62 (m, 2H), 1.91 (dt, J=13.3, 3.2 Hz, 1H), 1.86-1.75 (m, 2H), 1.52-1.46 (m, 2H), 1.45-1.35 (m, 3H). LC-MS=434.2 [M+H]$^+$.

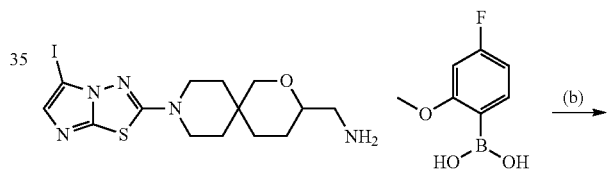

To a solution of Compound 7-1 (59 mg, 0.136 mmol) and (4-fluoro-2-methoxyphenyl)boronic acid (30.1 mg, 0.177 mmol) in dioxane were added Na$_2$CO$_3$ (477 μL, 0.953 mmol) and PdCl$_2$(Ph$_3$P)$_2$ (4.78 mg, 6.81 μmol) under argon. The reaction was heated to 100° C. for 2 hours. The mixture was quenched with sat. solution of NaHCO$_3$ and then EtOAc was added. The organic layer was separated and the aqueous layer was extracted twice with EtOAc. The combined organic layers were dried over MgSO$_4$, filtered and concentrated in vacuo. The crude material was purified by prep-HPLC to afford 7.1 mg of Compound 7-0 as a solid. $^1$H NMR (500 MHz, DMSO-$d_6$) δ 8.21 (dd, J=8.7, 6.9 Hz, 1H), 7.83 (s, 3H), 7.53 (s, 1H), 7.09 (dd, J=11.4, 2.6 Hz, 1H), 6.92 (td, J=8.4, 2.6 Hz, 1H), 3.92 (s, 3H), 3.90 (d, J=5.2 Hz, 1H), 3.89-3.86 (m, 3H), 3.56-3.43 (m, 8H), 3.19 (d, J=11.5 Hz, 1H), 3.03-2.92 (m, 1H), 2.89-2.79 (m, 1H), 1.91 (d, J=12.9 Hz, 1H), 1.76 (t, J=4.9 Hz, 2H), 1.55-1.34 (m, 5H). LC-MS=432.4 [M+H]$^+$.

The following compounds were prepared by the same route used to prepare Compound 7-0, using appropriate starting materials:

| Example/ Compound Number | Structure | NMR | LC-MS |
|---|---|---|---|
| 7-2 | 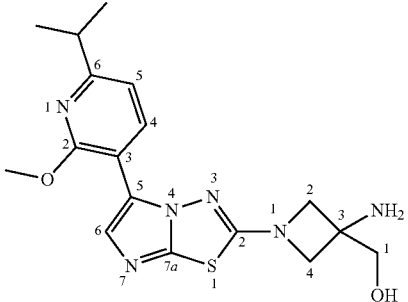<br>(3-amino-1-(5-(6-isopropyl-2-methoxypyridin-3-yl)imidazo[2,1-b][1,3,4]thiadiazol-2-yl)azetidin-3-yl)methanol | $^1$H NMR (500 MHz, MeOD-$d_4$) δ 8.59 (d, J = 7.7 Hz, 1H), 7.61 (s, 1H), 6.90 (d, J = 7.7 Hz, 1H), 4.17 (d, J = 8.1 Hz, 2H), 4.07 (s, 3H), 3.95 (d, J = 8.1 Hz, 2H), 3.69 (s, 2H), 3.00 (m, J = 6.8 Hz, 1H), 1.32 (d, J = 7.0 Hz, 6H). | MS m/z calcd for $C_{17}H_{22}N_6O_2S$ 374.2, found 375.4 [M + H]$^+$ |
| 7-3 | 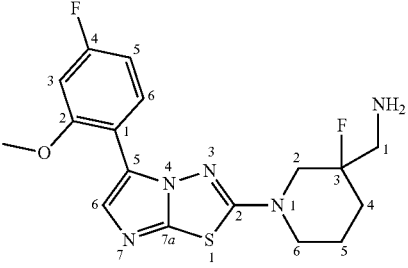<br>(3-fluoro-1-(5-(4-fluoro-2-methoxyphenyl)imidazo[2,1-b][1,3,4]thiadiazol-2-yl)piperidin-3-yl)methanamine | $^1$H NMR (500 MHz, DMSO-$d_6$) δ 8.25-8.14 (m, 4H), 7.51 (s, 1H), 7.07 (dd, J = 11.4, 2.6 Hz, 1H), 6.89 (td, J = 8.4, 2.6 Hz, 1H), 4.08-4.00 (m, 1H), 3.88 (m, 1H), 3.48 (dd, J = 33.3, 14.2 Hz, 1H), 3.36-3.15 (m, 3H), 2.05 (d, J = 12.3 Hz, 1H), 1.89-1.67 (m, 3H). | MS m/z calcd for $C_{17}H_{19}F_2N_5OS$ 379.1, found 380.1 [M + H]$^+$ |
| 7-4 | 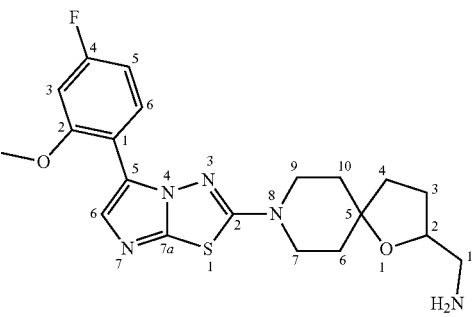<br>(8-(5-(4-fluoro-2-methoxyphenyl)imidazo[1,2-b][1,3,4]thiadiazol-2-yl)-1-oxa-8-azaspiro[4.5]decan-2-yl)methanamine | $^1$H NMR (400 MHz, DMSO-$d_6$) δ 8.19 (dd, J = 8.7, 6.9 Hz, 1H), 7.80 (s, 3H), 7.54 (s, 1H), 7.08 (dd, J = 11.3, 2.5 Hz, 1H), 6.91 (td, J = 8.5, 2.5 Hz, 1H), 4.16-4.09 (m, 1H), 3.91 (s, 3H), 3.63-3.48 (m, 4H), 3.07-2.97 (m, 1H), 2.88-2.74 (m, 1H), 1.88-1.79 (m, 2H), 1.79-1.69 (m, 5H). | MS m/z calcd for $C_{20}H_{24}FN_5O_2S$ 417.2 found 418.2 [M + H]$^+$ |

| Example/Compound Number | Structure | NMR | LC-MS |
|---|---|---|---|
| 7-5 | 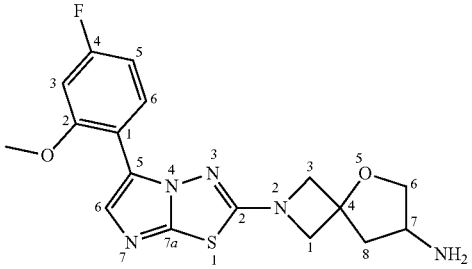<br>2-(5-(4-fluoro-2-methoxyphenyl)imidazo[2,1-b][1,3,4]thiadiazol-2-yl)-5-oxa-2-azaspiro[3.4]octan-7-amine | $^1$H NMR (500 MHz, DMSO-$d_6$) δ 8.20 (s, 2H), 8.13 (dd, J = 8.7, 6.8 Hz, 1H), 7.58 (s, 1H), 7.07 (dd, J = 11.4, 2.6 Hz, 1H), 6.89 (td, J = 8.4, 2.5 Hz, 1H), 4.36 (d, J = 9.2 Hz, 1H), 4.24 (dd, J = 8.9, 4.0 Hz, 2H), 4.14 (d, J = 8.8 Hz, 1H), 3.95 (dd, J = 9.7, 5.7 Hz, 1H), 3.90 (s, 3H), 3.87 (s, 1H), 3.83 (dd, J = 9.7, 3.4 Hz, 1H), 2.64 (dd, J = 14.5, 7.9 Hz, 1H), 2.24 (dd, J = 14.4, 3.9 Hz, 1H). | MS m/z calcd for $C_{17}H_{18}FN_5O_2S$ 375.1 found 376.1 [M + H]$^+$ |
| 7-6 | 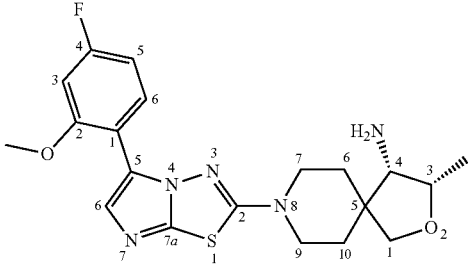<br>(3S,4S)-8-(5-(4-fluoro-2-methoxyphenyl)imidazo[2,1-b][1,3,4]thiadiazol-2-yl)-3-methyl-2-oxa-8-azaspiro[4.5]decan-4-amine | $^1$H NMR (500 MHz, DMSO-$d_6$) δ 8.20 (dd, J = 8.7, 6.9 Hz, 1H), 7.99 (d, J = 5.4 Hz, 3H), 7.59 (s, 1H), 7.10 (dd, J = 11.4, 2.5 Hz, 1H), 6.93 (td, J = 8.4, 2.5 Hz, 1H), 4.30-4.17 (m, 1H), 3.93 (s, 3H), 3.90 (d, J = 9.2 Hz, 1H), 3.86-3.79 (m, 1H), 3.79-3.71 (m, 1H), 3.69 (d, J = 9.2 Hz, 1H), 3.46 (t, J = 5.4 Hz, 1H), 3.31 (ddt, J = 14.1, 11.1, 3.7 Hz, 2H), 1.95-1.77 (m, 3H), 1.65 (d, J = 13.1 Hz, 1H), 1.23 (d, J = 6.6 Hz, 3H). | MS m/z calcd for $C_{20}H_{24}FN_5O_2S$ 417.2 found 418.2 [M + H]$^+$ |

Example 8-0: 4-(aminomethyl)-1-(5-(2-(dimethylamino)-6-methylpyridin-3-yl)imidazo[2,1-b][1,3,4]thiadiazol-2-yl)piperidin-4-ol

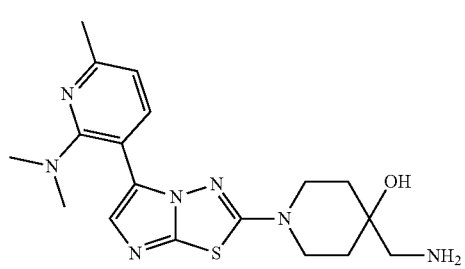 [SMILES: Cc1ccc(-c2cnc3sc(N4CCC(O)(CN)CC4)nn23)c(N(C)C)n1]

The Compound 8-0 was prepared in the following way:

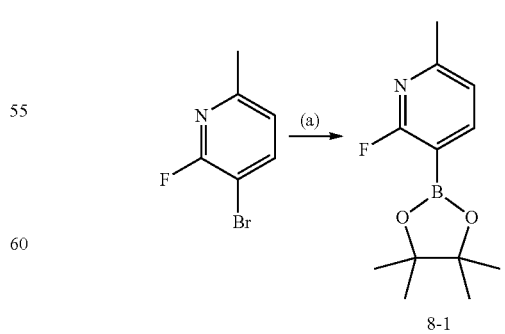

To a solution of 3-bromo-2-fluoro-6-methylpyridine (100 mg, 0.526 mmol) in dioxane (2.6 mL) were added B$_2$Pin$_2$ (200 mg, 0.789 mmol), KOAc (129 mg, 1.316 mmol) and PdCl₂(dppf)-DCM complex (38.5 mg, 0.053 mmol) under argon. The reaction was heated to 90° C. for 2 hours. The reaction mixture was quenched with a sat. solution of NaHCO₃ and then diluted with EtOAc. The organic layer was separated and the aqueous layer was extracted twice with EtOAc. The combined organic layers were dried over MgSO₄, filtered and concentrated in vacuo. The crude product was purified by normal phase chromatography (4 g column) with a running gradient of 0-10% MeOH/DCM to afford 86 mg of Compound 8-1 as an oil. LC-MS=238.4 [M+H]⁺.

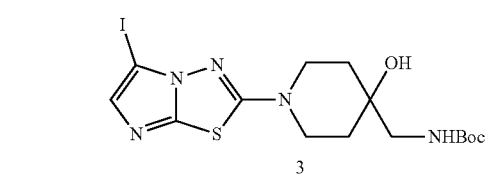

3

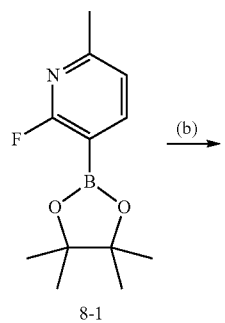

8-1

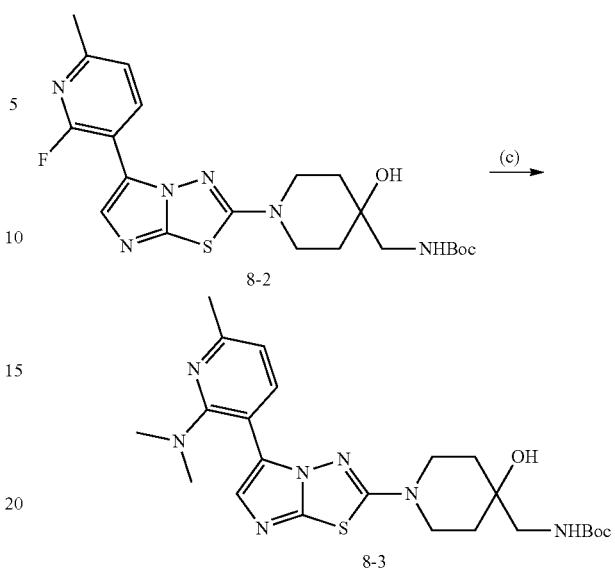

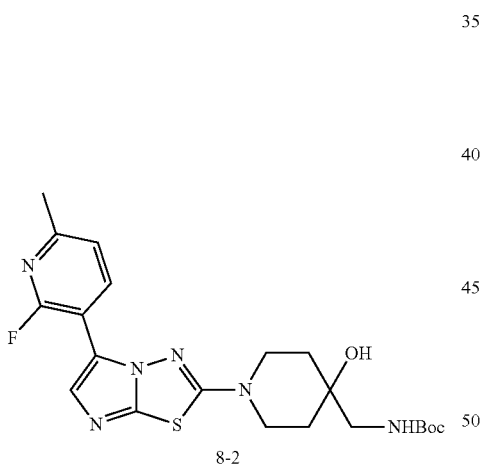

8-2

To a solution of Compound 3 (50 mg, 0.104 mmol) and Compound 8-1 (32.1 mg, 0.136 mmol) in dioxane (1 mL) were added Na₂CO₃ (0.365 mL, 0.730 mmol) and PdCl₂(Ph₃P)₂ (3.66 mg, 5.22 µmol) under argon. The reaction was heated to 100° C. for 2 hours. The mixture was quenched with a sat. solution of NaHCO₃ and then diluted with EtOAc. The organic layer was separated and the aqueous layer was extracted twice with EtOAc. The combined organic layers were dried over MgSO₄, filtered and concentrated in vacuo. The crude product was purified by normal phase chromatography (4 g column) with a running gradient of 0-20% MeOH/DCM to afford 36 mg of Compound 8-2 as a solid. LC-MS=463.2 [M+H]⁺.

A solution of Compound 8-2 (40 mg, 0.065 mmol) in dimethylamine 2 M in THF (1 mL, 2.000 mmol) was heated to 140° C. for 6 hours under MW. Additional dimethylamine 2 M (500 µL) was added and the reaction was stirred for 2 hours at 140° C. The resulting solution was concentrated in vacuo and purified by normal phase chromatography (4 g column) with a running gradient of 0-20% MeOH/DCM to afford 30 mg of Compound 8-3. LC-MS=488.0 [M+H]⁺.

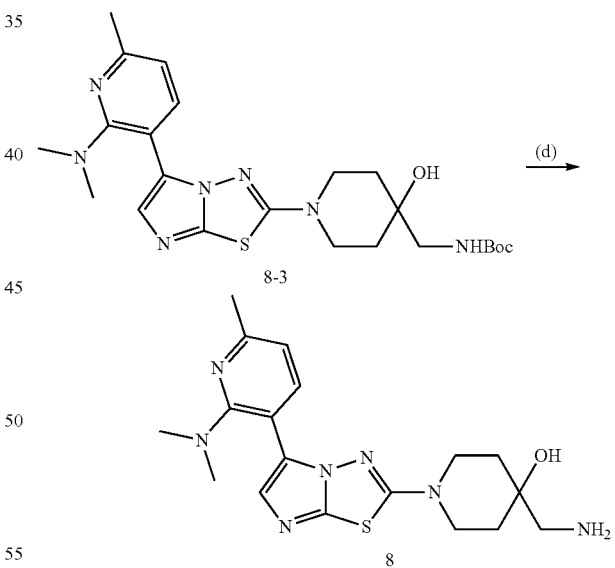

To a solution of Compound 8-3 (30 mg, 0.062 mmol) in MeOH (2 mL), HCl 4 M in THF (200 µL, 0.800 mmol) was added. The reaction was stirred for 1 hour at room temperature and then concentrated in vacuo. The resulting product was purified by prep-HPLC to afford 26 mg of Compound 8 as a solid. 1H NMR (400 MHz, DMSO-d6) δ 7.79 (d, J=7.9 Hz, 4H), 7.35 (s, 1H), 6.80 (d, J=7.6 Hz, 1H), 3.63 (dt, J=13.2, 4.2 Hz, 2H), 3.44 (dt, J=13.7, 7.1 Hz, 2H), 2.84 (d, J=5.9 Hz, 2H), 2.74 (s, 6H), 2.42 (s, 3H), 1.68 (t, J=6.0 Hz, 4H). LC-MS=388.0 [M+H]+.

Example 9-0: 4-(aminomethyl)-1-(5-(6-methyl-2-(methylthio)pyridin-3-yl)imidazo[2,1-b][1,3,4]thiadiazol-2-yl)piperidin-4-ol

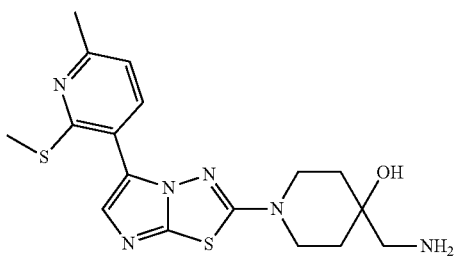 [SMILES: CSc1nc(C)ccc1-c1cnc2sc(N3CCC(O)(CN)CC3)nn12]

The Compound 9-0 was prepared in the following way:

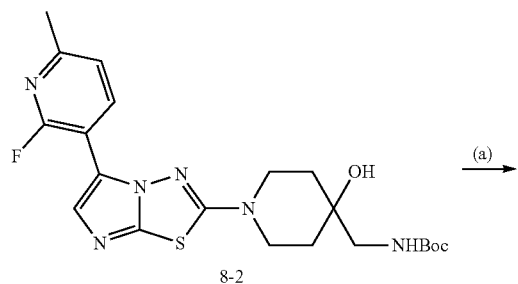

A solution of Compound 8-2 (50 mg, 0.108 mmol) and methanethiol, sodium salt (37.9 mg, 0.540 mmol) in THF (2 mL) was heated to 120° C. for 1 hour. Additional methanethiol sodium salt (20 mg) was added and the reaction was heated for 1 hour at 120° C. The mixture was quenched with a sat. solution of NaHCO₃ and diluted with EtOAc. The organic layer was separated and the aqueous layer was extracted twice with EtOAc. The combined organic layers were dried over MgSO₄, filtered and concentrated in vacuo. The crude product was purified by normal phase chromatography (4 g column) with a running gradient of 0-100% EtOAc/Cyclohexane to afford 10 mg of Compound 9-1 as an oil. LC-MS=491.2 [M+H]⁺.

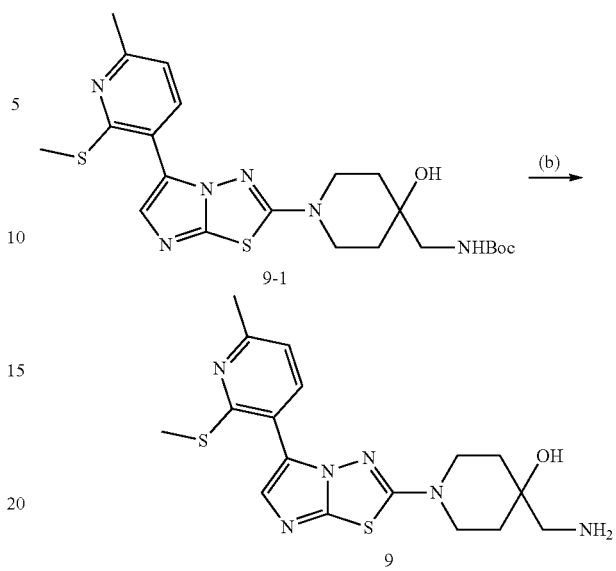

A solution of Compound 9-1 (10 mg, 0.020 mmol) and HCl 4 M in THF (500 µL, 2.000 mmol) in MeOH (1 mL) was stirred for 1 hour at room temperature. The resulting solution was concentrated in vacuo. The crude product was purified by prep-HPLC to afford 3.7 mg of Compound 9-0. ¹H NMR (500 MHz, DMSO-d₆) δ 7.85 (d, J=7.8 Hz, 1H), 7.75 (s, 3H), 7.39 (s, 1H), 7.10 (d, J=7.8 Hz, 1H), 3.61 (d, J=13.4 Hz, 2H), 3.49-3.37 (m, 2H), 2.82 (d, J=5.9 Hz, 2H), 1.66 (d, J=12.4 Hz, 4H). LC-MS=391.1 [M+H]⁺.

Example 10-0: 3-(aminomethyl)-1-(5-(4-fluoro-2-methoxyphenyl)imidazo[2,1-b][1,3,4]thiadiazol-2-yl)piperidin-3-ol

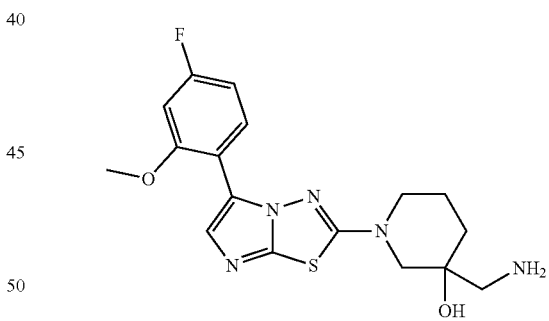

The Compound 10-0 was prepared in the following way:

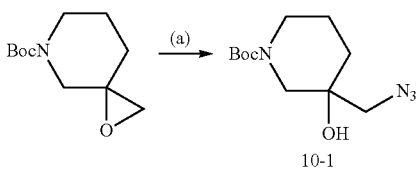

A mixture of tert-butyl 1-oxa-5-azaspiro[2.5]octane-5-carboxylate (500 mg, 2.344 mmol) in MeOH (10 mL) and H₂O (2 mL) was treated with NaN₃ (762 mg, 11.72 mmol) and NH₄Cl (251 mg, 4.69 mmol). The reaction was warmed

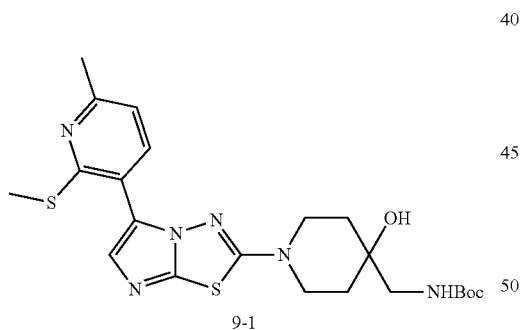

to 65° C. for 18 hours. The reaction was cooled to room temperature, concentrated in vacuo to remove MeOH and extracted with DCM. The organic layer was passed through a phase separator and concentrated in vacuo to afford 616.6 mg of Compound 10-1 as an oil. LC-MS=257.4 [M+H]⁺.

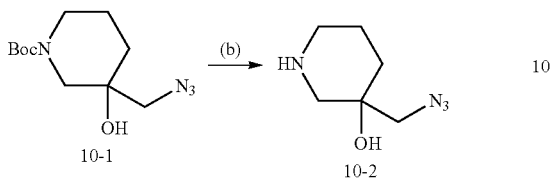

A mixture of Compound 10-1 (616 mg, 2.403 mmol) in HCl in dioxane (4 mL, 16.00 mmol) was stirred at room temperature for 1 hour. The reaction mixture was dried under N₂ stream to afford 570.9 mg of Compound 10-2. LC-MS=157.3 [M+H]⁺.

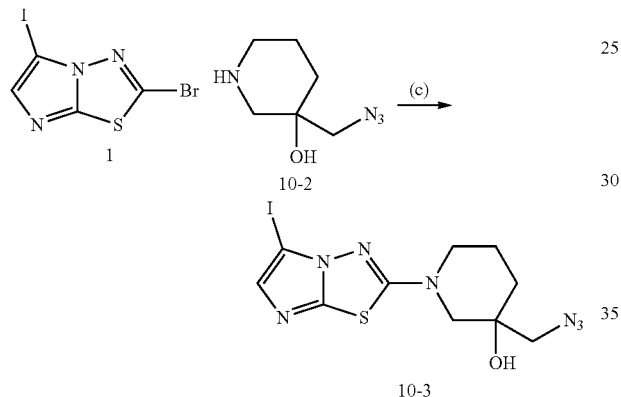

To a mixture of Compound 1 (793 mg, 2.403 mmol) and Compound 10-2 (463 mg, 2.403 mmol) in MeCN (10 mL), DIPEA (1.287 mL, 7.21 mmol) was added. The reaction was heated at 100° C. for 18 hours. The reaction was cooled to room temperature and was purified by normal phase chromatography with a running gradient of 0-100% EtOAc/heptane to afford 789.7 mg of Compound 10-3. LC-MS=406.1 [M+H]⁺.

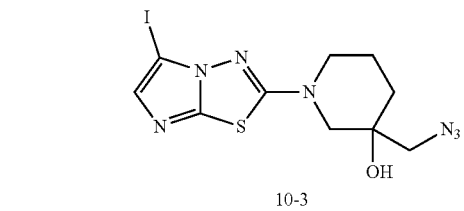

-continued

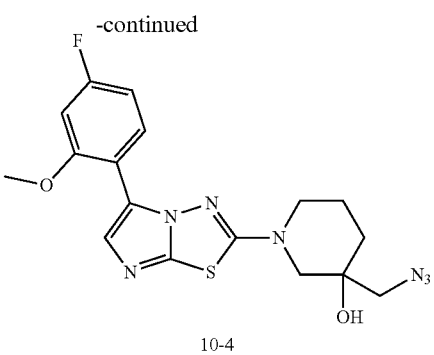

A mixture of Compound 10-3 (180 mg, 0.444 mmol), (4-fluoro-2-methoxyphenyl)boronic acid (113 mg, 0.666 mmol), and PdCl₂(dppf)-DCM complex (16.25 mg, 0.022 mmol) was put under an N₂ atmosphere. Then dioxane (2 mL) and 2 M K₃PO₄ (0.755 mL, 1.510 mmol) were added. The reaction mixture was heated at 90° C. from 18 hours. Then 1.5 equiv. of (4-fluoro-2-methoxyphenyl)boronic acid (113 mg, 0.666 mmol) and 0.05 equiv. PdCl₂(dppf)-DCM complex (16.25 mg, 0.022 mmol) were added and the resulting mixture was heated at 90° C. for 5 hours. The solution was diluted in MeOH/DCM, filtered over a CELITE pad and concentrated in vacuo. The crude material was purified by normal phase chromatography with a running gradient of 0-100% EtOAc/heptane to afford 20.6 mg of Compound 10-4. LC-MS=404.3 [M+H]⁺.

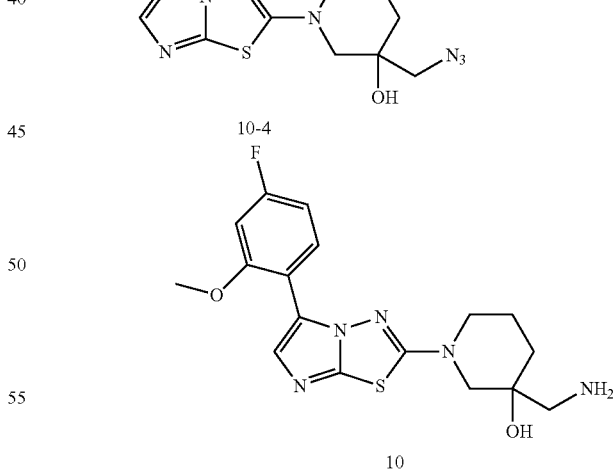

To a solution of Compound 10-4 (20.6 mg, 0.051 mmol) in THF (2 mL) and H₂O (0.050 mL), triphenylphosphane, polymer-bound (20.09 mg, 0.077 mmol) (~3 mmol/g loading so added 26 mg for 0.077 mmol) was added. The reaction was placed on shaker for 18 hours. Then 75 mg of triphenylphosphane, polymer-bound (20.09 mg, 0.077 mmol) was added and placed on shaker for an additional 18 hours. The reaction was filtered and concentrated under N₂.

The resulting crude material was purified by prep-HPLC to afford 1.9 mg of Compound 10. ¹H NMR (500 MHz, MeOD-d₄) δ 8.26 (t, J=7.7 Hz, 1H), 7.69 (s, 1H), 6.99 (d, J=10.9 Hz, 1H), 6.86 (t, J=8.5 Hz, 1H), 3.97 (s, 3H), 3.84 (d, J=12.1 Hz, 1H), 3.69 (d, J=13.5 Hz, 1H), 3.49 (d, J=13.3 Hz, 1H), 3.41 (t, J=11.6 Hz, 1H), 3.12-2.97 (m, 2H), 2.15-2.03 (m, 1H), 1.82 (dd, J=2.4, 8.2 Hz, 3H). LC-MS=378.4 [M+H]⁺.

Example 11-0: 8-(5-(4-fluoro-2-methoxyphenyl) imidazo[2,1-b][1,3,4]thiadiazol-2-yl)-2-oxa-8-azaspiro[4.5]decan-4-amine

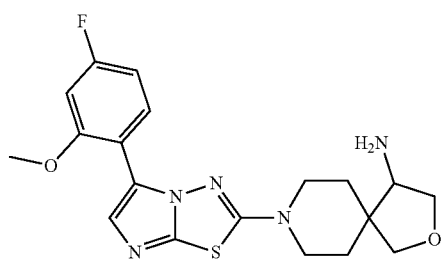 [SMILES: COc1cc(F)ccc1-c1cnc2sc(N3CCC4(CC3)COCC4N)nn12]

Compound 11-0 was prepared in the following way:

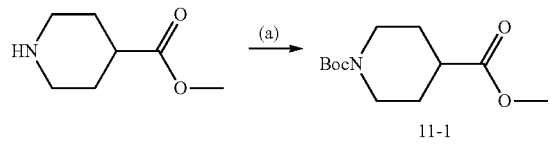

To a solution of methyl piperidine-4-carboxylate (10.0 g, 69.84 mmol) in DCM (200 mL), (Boc)₂O (24.07 mL, 104.76 mmol) and Et₃N (19.63 mL, 139.68 mmol) were added at room temperature. The reaction mixture was stirred at room temperature for 16 hours. The reaction was diluted with DCM (100 mL), washed with H₂O (50 mL) and brine (50 mL). The organic layer was dried over Na₂SO₄ and concentrated in vacuo to afford 16.5 g of Compound 11-1 as a pale brown liquid, which was used in next step without further purification. ¹H NMR (400 MHz, DMSO-d₆) δ 3.83 (dt, J=13.2, 3.9 Hz, 2H), 3.61 (s, 3H), 2.81 (d, J=14.0 Hz, 2H), 2.54 (dt, J=11.1, 3.9 Hz, 1H), 1.84-1.73 (m, 2H), 1.44-1.32 (m, 11H). LC-MS=144.2 [M+H-Boc]⁺, retention time=1.24 minutes (Method N).

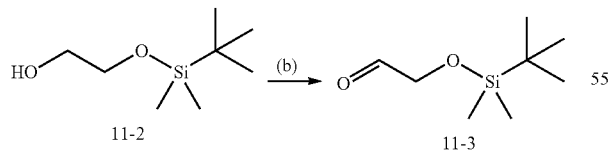

To a solution of oxalyl dichloride (13.37 mL, 155.96 mmol) in DCM (500 mL), anhydrous DMSO (24.17 mL, 340.27 mmol) was added dropwise at −78° C. and the mixture was stirred at −78° C. for 30 minutes. A solution of 2-((tert-butyldimethylsilyl)oxy)ethan-1-ol Compound 11-2 (25.0 g, 141.78 mmol) in DCM (100 mL) was added to the mixture at −78° C. and stirred for 30 minutes. Et₃N (98.81 mL, 708.89 mmol) was added and the reaction was stirred at −78° C. another 1 hour. The reaction mixture was acidified with 2 N aq. HCl solution to pH=4 and then extracted with DCM (3×300 mL). The combined organic layer were washed brine (100 mL), dried over Na₂SO₄ and concentrated in vacuo to afford 24.5 g of Compound 11-3 as an oil. This was used in the next step without further purification. ¹H NMR (400 MHz, CDCl₃) δ 9.69 (d, J=1.0 Hz, 1H), 4.20 (d, J=0.9 Hz, 2H), 0.91 (s, 9H), 0.09 (s, 6H).

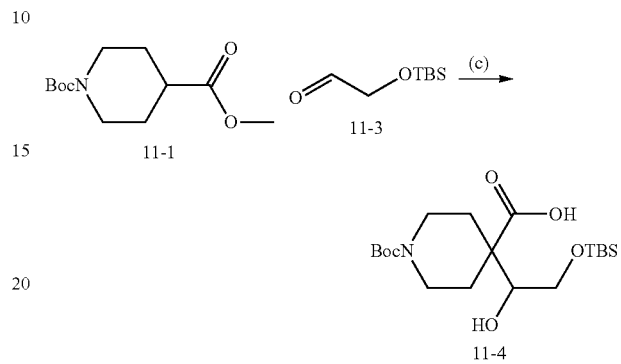

To a solution of Compound 11-1 (6.3 g, 25.89 mmol) in anhydrous THF (70 mL), 1.0 M LiHMDS (31.07 mL, 31.07 mmol) was added dropwise at −78° C. and the mixture was stirred at 0° C. for 1 hour. The resulting orange solution was re-cooled to −78° C. and a solution of Compound 11-3 (7.49 g, 42.98 mmol) in anhydrous THF (30 mL) was added. The mixture was stirred at the same temperature for 1 hour. The reaction mixture was quenched with sat. NH₄Cl solution and extracted with Et₂O (3×100 mL). The combined organic layers were washed with H₂O (50 mL) and brine (50 mL), dried over Na₂SO₄ and concentrated in vacuo to afford 6.3 g of Compound 11-4 as a colourless liquid. ¹H NMR (400 MHz, DMSO-d₆) δ 5.11-4.99 (m, 1H), 3.90-3.78 (m, 2H), 3.62 (s, 3H), 3.56-3.39 (m, 3H), 1.90-1.75 (m, 2H), 1.68-1.42 (m, 2H), 1.38 (s, 9H), 0.85 (s, 9H), 0.01 (s, 6H). LC-MS=318.2 [M+H-Boc]⁺, retention time=1.539 minutes.

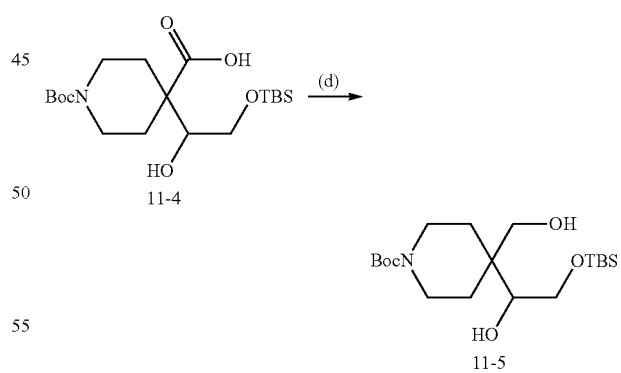

To a solution of Compound 11-4 (21.5 g, 51.48 mmol) in anhydrous THF (150 mL), LiBH₄ (4.49 g, 205.93 mmol) was added portionwise at room temperature and the reaction mixture stirred for 16 hours. The reaction mixture was cooled to 0° C., sat. aqueous NaHCO₃:H₂O (1:2, 50 mL) was added and the resulting mixture was stirred until bubbling subsided. The mixture was diluted with EtOAc (200 mL) and the mixture was filtered. The organic layer was separated, and the aqueous layer was extracted with EtOAc (3×75 mL). The combined organic layers were washed with brine (50 mL), dried over Na$_2$SO$_4$ and concentrated in vacuo to afford 20.0 g of Compound 11-5 as a solid. $^1$H NMR (400 MHz, DMSO-d$_6$) δ 4.63-4.51 (m, 1H), 4.48-4.36 (m, 2H), 4.15-3.93 (m, 1H), 3.82-3.36 (m, 6H), 1.54-1.30 (m, 12H), 0.86 (s, 9H), 0.05--0.00 (m, 6H). LC-MS=290.2 [M+H-Boc]$^+$, retention time=1.412 minutes.

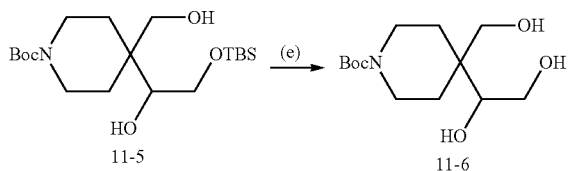 [SMILES: CC(C)(C)OC(=O)N1CCC(CO)(C(O)CO[Si](C)(C)C(C)(C)C)CC1 ; CC(C)(C)OC(=O)N1CCC(CO)(C(O)CO)CC1]

To a solution of Compound 11-5 (20.0 g, 51.33 mmol) in anhydrous THF (200 mL), 1.0 M TBAF in THF (77 mL, 77.0 mmol) was added dropwise at room temperature and the reaction mixture stirred for 1 hour. The reaction mixture was treated with sat. aqueous NaHCO$_3$:H$_2$O (1:2, 60 mL) and the layers were separated. The aqueous layer was extracted with EtOAc (3×150 mL). The combined organic layers were washed with brine (50 mL), dried over Na$_2$SO$_4$ and concentrated in vacuo to afford 9.6 g of Compound 11-6 as a solid. $^1$H NMR (400 MHz, DMSO-d$_6$) δ 4.56 (t, J=5.1, 5.1 Hz, 1H), 4.46 (t, J=4.8, 4.8 Hz, 2H), 4.12-4.03 (m, 1H), 3.59-3.45 (m, 2H), 3.42 (d, J=5.2 Hz, 2H), 3.40-3.32 (m, 2H), 3.17 (d, J=5.3 Hz, 2H), 1.52-1.25 (m, 13H). LC-MS=176.2 [M+H-Boc]$^+$, retention time=1.04 minutes.

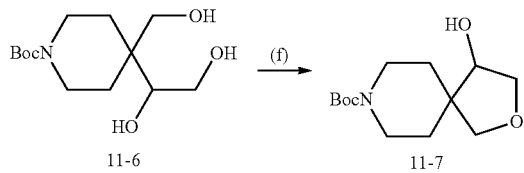 [SMILES: CC(C)(C)OC(=O)N1CCC(CO)(C(O)CO)CC1 ; CC(C)(C)OC(=O)N1CCC2(CC1)COCC2O]

To a suspension of 60% NaH (4.88 g, 122.03 mmol) in anhydrous THF (100 mL), a solution of Compound 11-6 (9.6 g, 34.87 mmol) in anhydrous THF (60 mL) was added dropwise at 0° C., followed by a solution of TsCl (6.65 g, 34.87 mmol) in anhydrous THF (40 mL). The reaction mixture was stirred at 0° C. for 2 hours. The reaction mixture was quenched with sat. NH$_4$Cl solution at −20° C. and stirred until bubbling ceased. Then the aqueous layer was extracted with EtOAc (3×150 mL). The combined organic layers were washed with brine (50 mL), dried over Na$_2$SO$_4$ and concentrated in vacuo to afford 5.0 g, of Compound 11-7 as a solid. $^1$H NMR (400 MHz, DMSO-d$_6$) δ 4.93 (d, J=4.8 Hz, 1H), 4.67 (t, J=5.3 Hz, 1H), 3.51-3.41 (m, 4H), 3.39-3.34 (m, 2H), 2.90-2.63 (m, 3H), 1.54-1.20 (m, 13H). LC-MS=158.2 [M+H-Boc]$^+$, retention time=1.11 minutes.

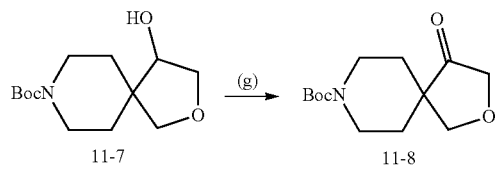 [SMILES: CC(C)(C)OC(=O)N1CCC2(CC1)COCC2O ; CC(C)(C)OC(=O)N1CCC2(CC1)COCC2=O]

To a solution of Compound 11-7 (5.0 g, 19.43 mmol) in DCM (100 mL), DMP (12.36 g, 29.15 mmol) was added at 0° C. The reaction mixture was stirred at 0° C. for 2 hours. The reaction mixture was quenched with sat. Na$_2$S$_2$O$_3$ (100 mL) at 0° C., then the organic layer was separated. The aqueous layer was extracted with DCM (3×100 mL). The combined organic layer was washed with sat. NaHCO$_3$ solution (50 mL), H$_2$O (50 mL) and brine (50 mL), dried over Na$_2$SO$_4$ and concentrated in vacuo and purified by normal phase chromatography with a running gradient of 10% EtOAc/hexane to afford 3.8 g of Compound 11-8 as a solid. LC-MS=156.15 [M+H-Boc]$^+$, retention time=1.20 minutes (Method 0).

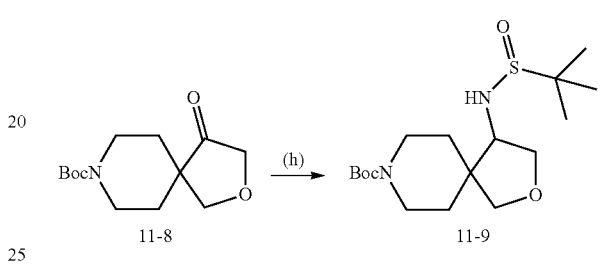

To a solution of Compound 11-8 (3.8 g, 14.88 mmol) in THF (80 mL), Ti(OEt)$_4$ (12.57 mL, 59.53 mmol) and 2-methylpropane-2-sulfinamide (2.71 g, 22.33 mmol) were added at room temperature. The reaction mixture was heated at 90° C. for 1 hour. The reaction mixture was cooled to 0° C. and LiBH$_4$ (0.402 g, 18.46 mmol) was added. The reaction mixture was stirred at 0° C. for 30 minutes. The reaction mixture was quenched with MeOH and then was concentrated in vacuo. The resulting residue was diluted with brine and extracted with EtOAc (4×100 mL). The combined organic layers were dried over Na$_2$SO$_4$ and concentrated in vacuo and purified by normal phase chromatography with a running gradient of 2% MeOH/DCM to afford 1.5 g of Compound 11-9 as a solid. $^1$H NMR (400 MHz, DMSO-d$_6$) δ 5.32-5.27 (m, 1H), 3.99-3.91 (m, 1H), 3.88-3.69 (m, 3H), 3.60 (d, J=8.8 Hz, 1H), 3.50-3.42 (m, 2H), 2.91-2.64 (m, 2H), 1.71-1.51 (m, 2H), 1.40 (d, J=3.2 Hz, 11H), 1.14-1.08 (m, 9H). LC-MS=261.2 [M+H-Boc]$^+$, retention time=1.175 minutes.

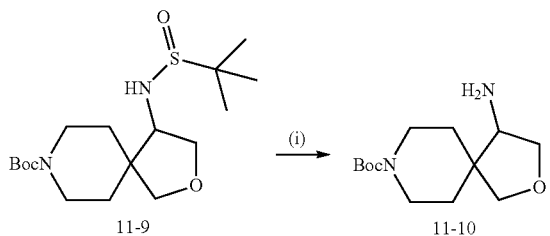 [SMILES: CC(C)(C)OC(=O)N1CCC2(CC1)COCC2NS(=O)C(C)(C)C ; CC(C)(C)OC(=O)N1CCC2(CC1)COCC2N]

To a solution of Compound 11-9 (1.5 g, 4.16 mmol) in MeOH (10 mL), 4 M HCl in dioxane (10.4 mmol) was added at room temperature. The reaction mixture was stirred at room temperature for 2 hours. The reaction mixture was concentrated in vacuo. The crude material was triturated with Et$_2$O (2×20 mL), filtered off and dried to afford 1.0 g of Compound 11-10 as a solid. LC-MS=157.2 [M+H]$^+$, retention time=0.295 minutes.

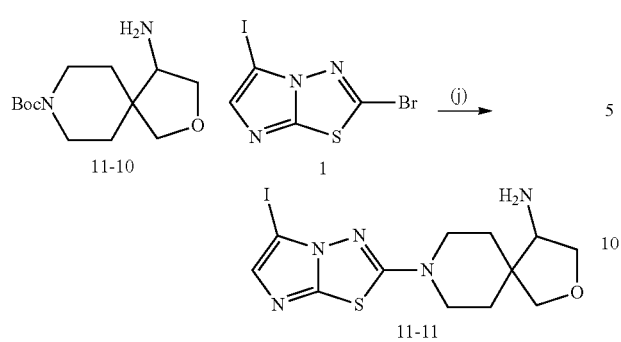

To a solution of Compound 11-10 (1.0 g, 4.36 mmol) in MeCN (10 mL), Compound 1 (1.44 g, 4.36 mmol) and DIPEA (6.08 mL, 34.91 mmol) were added at room temperature. The reaction mixture was heated at 100° C. for 6 hours. The reaction mixture was concentrated in vacuo, purified by normal phase chromatography with a running gradient of 1-2% MeOH/DCM to afford 0.80 g of Compound 11-11 as a solid. LC-MS=405.9 [M+H]$^+$, retention time=1.039 minutes.

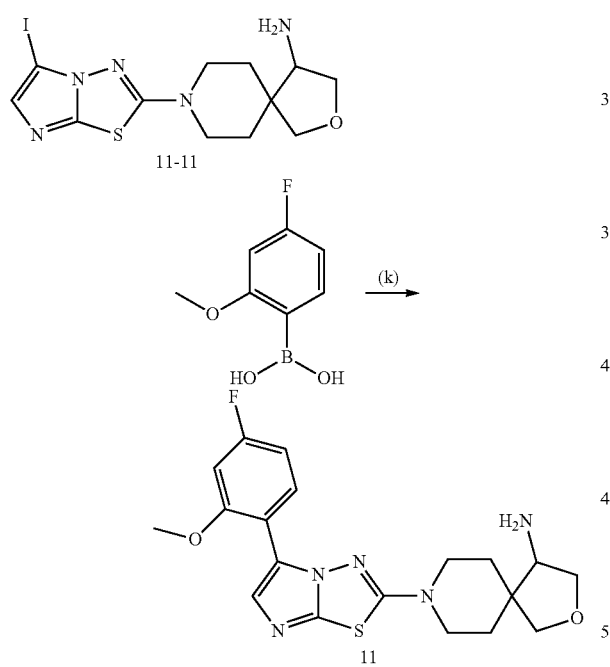

To a suspension of K$_3$PO$_4$ (0.628 g, 2.96 mmol) in dioxane: H$_2$O (1:1) (10 mL, Compound 11-11 (0.8 g, 0.98 mmol), (4-fluoro-2-methoxyphenyl)boronic acid (0.251 g, 1.48 mmol) and PdCl$_2$(dppf)-DCM complex (0.080 g, 0.098 mmol) were added at room temperature. The reaction mixture was heated at 80° C. for 1 hour. The reaction mixture was diluted with EtOAc (100 mL) washed with H$_2$O (10 mL). The aqueous layer was extracted with EtOAc (2×20 mL). The combined organic layers were washed with brine (10 mL). The organic layer was dried over Na$_2$SO$_4$ and concentrated in vacuo, purified by normal phase chromatography with a running gradient of 1-2% MeOH/DCM to afford 0.24 g of Compound 11 as a solid. $^1$H NMR (400 MHz, DMSO-d$_6$) δ 8.19 (dd, J=8.7, 6.8 Hz, 1H), 7.48 (s, 1H), 7.05 (dd, J=11.4, 2.6 Hz, 1H), 6.91 (td, J=8.4, 2.5 Hz, 1H), 3.98 (dd, J=8.9, 6.5 Hz, 1H), 3.90 (s, 2H), 3.78-3.60 (m, 4H), 3.39-3.33 (m, 3H), 3.20-3.11 (m, 1H), 1.88-1.62 (m, 2H), 1.58-1.43 (m, 2H). HPLC: 76.50%, retention time=5.249 minutes (Method W). LC-MS=404.0 [M+H]$^+$, retention time=1.06 minutes.

Compound 12-0: 3-amino-1-(9-(5-(4-fluoro-2-methoxyphenyl)imidazo[2,1-b][1,3,4]thiadiazol-2-yl)-1,4,9-triazaspiro[5.5]undecan-4-yl)-3-methylbutan-1-one

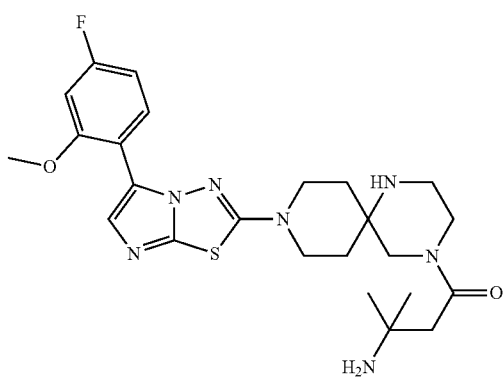 [SMILES: COc1cc(F)ccc1-c1cnc2sc(N3CCC4(CC3)CN(C(=O)CC(C)(C)N)CCN4)nn12]

The Compound 12-0 was prepared in the following way:

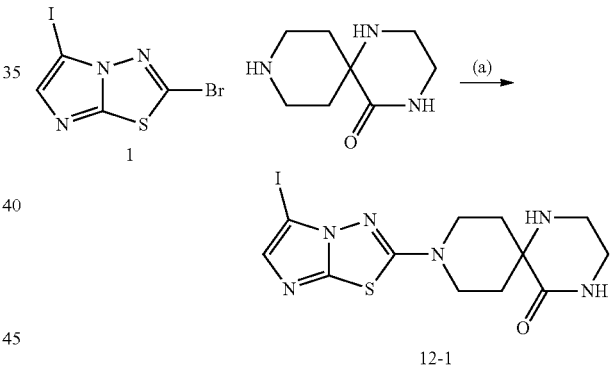

A mixture of Compound 1 (194 mg, 0.588 mmol) and 1,4,9-triazaspiro[5.5]undecan-3-one (150 mg, 0.619 mmol) in EtOH (3 mL) was stirred at 100° C. for 18 hours. The reaction was concentrated in vacuo and was purified by normal phase chromatography (4 g column) with a running gradient of 0-20% MeOH/DCM to give the expected product which was precipitated by adding MeCN, the solid was washed with MeCN to afford 242 mg of Compound 12-1 as a solid. LC-MS=419.2 [M+H]$^+$.

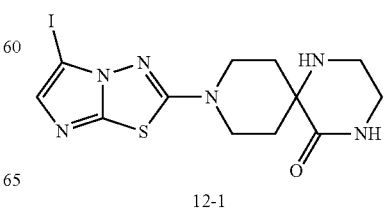

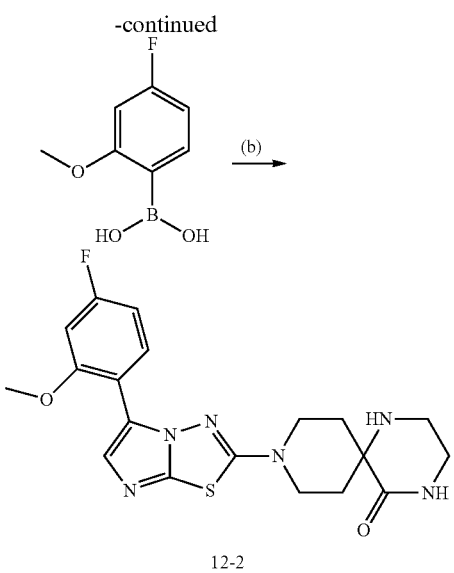

A mixture of Compound 12-1 (70 mg, 0.167 mmol), (4-fluoro-2-methoxyphenyl)boronic acid (37.0 mg, 0.218 mmol) and $Na_2CO_3$ (2 M, 586 μL, 1.172 mmol) was suspended in dioxane (837 μL). The mixture was flushed with $N_2$ and $PdCl_2(Ph_3P)_2$ (5.87 mg, 8.37 μmol) was added. The reaction was heated to 100° C. for 1 hour. The mixture was quenched with $H_2O$ then EtOAc was added. The product was precipitated in the organic layer, therefore it was filtrated and washed with $H_2O$. The resulting solid was dried, then triturated in MeCN, filtrated off to afford 39 mg of Compound 12-2 as a solid. LC-MS=417.4 $[M+H]^+$.

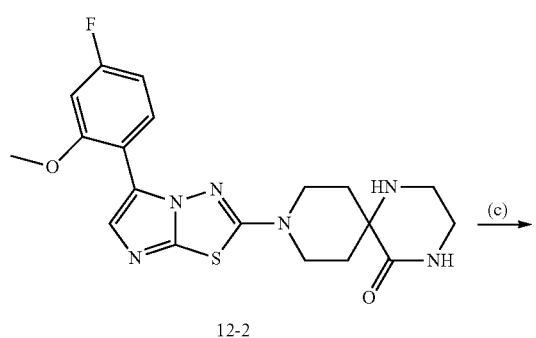

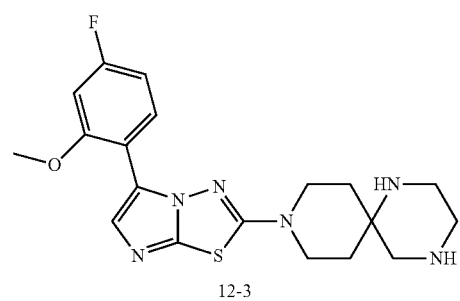

To suspension of Compound 12-2 (39 mg, 0.094 mmol) in anhydrous THF (468 μL), borane tetrahydrofuran complex (281 μL, 0.281 mmol) was added dropwise at 0° C. The reaction was warmed up to room temperature to form a clear solution. After 2 hours, more borane tetrahydrofuran complex (281 μL, 0.281 mmol) was added at 0° C. The reaction was warmed up to room temperature and was stirred for 18 hours. The resulting solution was quenched with 1 M HCl at 0° C. Then a sat. solution of $NaHCO_3$ was added to adjust the pH to neutral. Then EtOAc was added. Then organic layer was separated, was washed with brine, dried over $MgSO_4$, filtered and evaporated. The resulting crude material was purified by prep-HPLC to afford 8.4 mg of Compound 12-3. LC-MS=403.4 $[M+H]^+$.

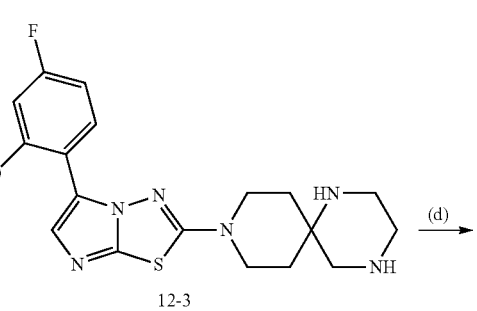

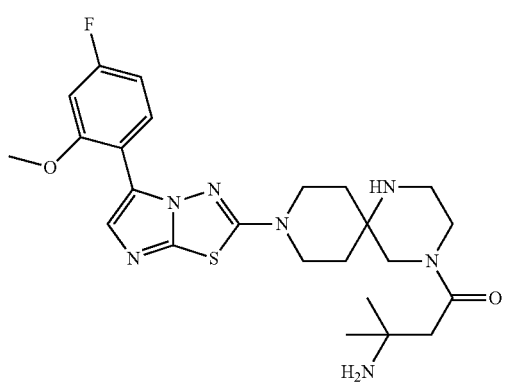

To a solution of Compound 12-3 (8.4 mg, 0.021 mmol) in DMF (1 mL), 3-((tert-butoxycarbonyl)amino)-3-methylbutanoic acid (5.44 mg, 0.025 mmol), HATU (11.90 mg, 0.031 mmol) and $Et_3N$ (8.68 μL, 0.063 mmol) were added. The reaction mixture was stirred for 3 hours. The mixture was quenched with a sat. solution of $NH_4Cl$, dried over $MgSO_4$, filtered and concentrated in vacuo to give a solid. Then the resulting product was dissolved in MeOH (1 mL) and followed by the addition of 4 M HCl (300 μL, 1.200 mmol). The reaction was stirred for 2 days. The resulting solution was concentrated in vacuo and was purified by prep-HPLC to afford 3.7 mg of Compound 12. $^1$H NMR (500 MHz, MeOD-$d_4$) δ 8.23 (dd, J=8.8, 6.5 Hz, 1H), 7.81 (s, 1H), 6.98 (dd, J=11.0, 2.5 Hz, 1H), 6.83 (td, J=8.4, 2.5 Hz, 1H), 4.03 (s, 2H), 3.95 (s, 5H), 3.89-3.84 (m, 2H), 3.62-3.53 (m, 2H), 3.40 (t, J=5.5 Hz, 2H), 2.90 (s, 2H), 2.16 (d, J=13.8 Hz, 2H), 2.07-1.98 (m, 2H), 1.43 (d, J=8.1 Hz, 6H). LC-MS=502.2 $[M+H]^+$.

The following compounds were prepared by the same route used to prepare Compound 12-0, using appropriate starting materials.

| Example/Compound Number | Structure | NMR | LC-MS |
|---|---|---|---|
| 12-4 | 5-(6-isopropyl-2-methoxypyridin-3-yl)-2-(1,4,9-triazaspiro[5.5]undecan-9-yl)imidazo[2,1-b][1,3,4]thiadiazole | $^1$H NMR (500 MHz, MeOD-$d_4$) δ 8.61 (d, J = 7.8 Hz, 1H), 7.84 (s, 1H), 6.96 (d, J = 7.8 Hz, 1H), 4.08 (s, 3H), 3.85 (d, J = 13.9 Hz, 2H), 3.65 (ddd, J = 12.9, 7.7, 3.9 Hz, 2H), 3.44 (m, 2H), 3.41 (d, J = 7.4 Hz, 2H), 3.35 (d, J = 5.9 Hz, 2H), 3.01 (p, J = 6.9 Hz, 1H), 2.20-2.01 (m, 4H), 1.31 (d, J = 6.9 Hz, 6H). | MS m/z calcd for $C_{21}H_{29}N_7OS$ 427.2 found 428.2 $[M + H]^+$ |
| 12-3 | 5-(4-fluoro-2-methoxyphenyl)-2-(1,4,9-triazaspiro[5.5]undecan-9-yl)imidazo[2,1-b][1,3,4]thiadiazole | $^1$H NMR (500 MHz, DMSO-$d_6$) δ 8.18 (dd, J = 8.7, 6.9 Hz, 1H), 7.50 (s, 1H), 7.08 (dd, J = 11.4, 2.6 Hz, 1H), 6.90 (td, J = 8.5, 2.5 Hz, 1H), 3.91 (s, 3H), 3.44 (m, 12H), 1.92 (d, J = 7.4 Hz, 2H). | MS m/z calcd for $C_{19}H_{23}FN_6OS$ 402.2 found 403.4 $[M + H]^+$ |

Example 13-0: 1-(5-(4-fluoro-2-methoxyphenyl)imidazo[2,1-b][1,3,4]thiadiazol-2-yl)-4-(morpholinomethyl)piperidin-4-amine

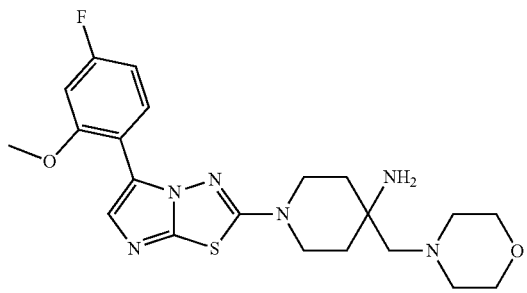 [SMILES: COc1cc(F)ccc1-c1cnc2sc(N3CCC(N)(CN4CCOCC4)CC3)nn12]

The Compound 13-0 was prepared in the following way:

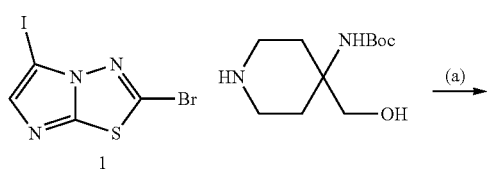

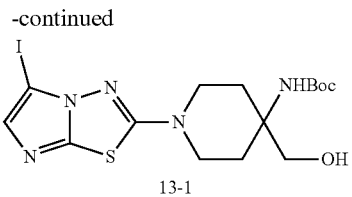

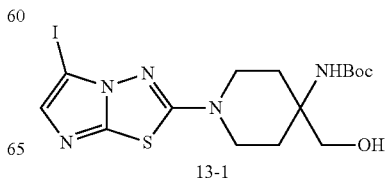

A mixture of Compound 1 (480 mg, 1.455 mmol), tert-butyl (4-(hydroxymethyl)piperidin-4-yl)carbamate acetate salt (507 mg, 1.746 mmol) Compound 2b, Et$_3$N (0.6 mL, 4.3 mmol) in dioxane (10 mL) was heated to 80° C. for 8 hours. The mixture was concentrated in vacuo, then redissolved in DCM, washed with 0.1 M HCl. The aqueous layer was extracted twice with DCM. The combined organic layers were washed with sat. aqueous NaHCO$_3$, dried over Na$_2$SO$_4$, and concentrated in vacuo to afford 511 mg of Compound 13-1 as a solid. LC-MS=480.1 [M+H]$^+$.

-continued

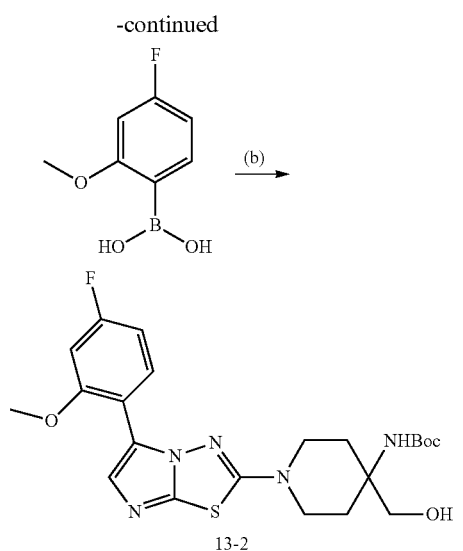

13-2

Compound 13-1 (400 mg, 0.834 mmol), (4-fluoro-2-methoxyphenyl)boronic acid (184 mg, 1.085 mmol) and Na$_2$CO$_3$ (2 M, 2921 μL, 5.84 mmol) were suspended in dioxane (4172 μL). Then the mixture was flushed with N$_2$ and PdCl$_2$(Ph$_3$P)$_2$ (29.3 mg, 0.042 mmol) was added. The reaction was heated to 100° C. for 2 hours. The mixture was diluted with EtOAc and H$_2$O. The organic layer was separated, washed with H$_2$O, was dried over MgSO$_4$, filtered and concentrated in vacuo. The resulting solid was triturated in MeCN, filtered off and washed with MeCN to afford 310 mg of Compound 13-2 as a solid. $^1$H NMR (500 MHz, DMSO-d$_6$) δ 8.22 (dd, J=8.7, 6.8 Hz, 1H), 7.48 (s, 1H), 7.06 (dd, J=11.4, 2.6 Hz, 1H), 6.92 (td, J=8.5, 2.6 Hz, 1H), 6.55 (d, J=25.3 Hz, 1H), 4.78 (t, J=5.7 Hz, 1H), 3.91 (s, 3H), 3.64 (d, J=13.0 Hz, 2H), 3.44 (d, J=5.7 Hz, 2H), 3.31-3.25 (m, 2H), 2.14 (d, J=14.0 Hz, 1H), 2.08 (s, 10H), 1.63 (td, J=13.0, 4.6 Hz, 2H), 1.39 (s, 8H). LC-MS=478.1 [M+H]$^+$.

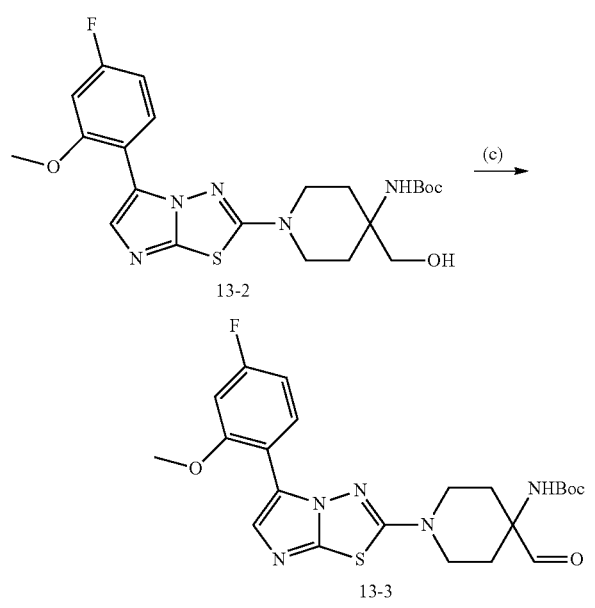

To a mixture of Compound 13-2 (150 mg, 0.314 mmol) in DCM (4986 μL), DMP (266 mg, 0.628 mmol) was added, the resulting mixture was stirred at room temperature for 2 hours. The reaction mixture was poured onto H$_2$O, and extracted twice with EtOAc. The combined organic layers were dried over MgSO$_4$ and concentrated in vacuo to afford 123 mg of Compound 13-3. LC-MS=476.3 [M+H]$^+$.

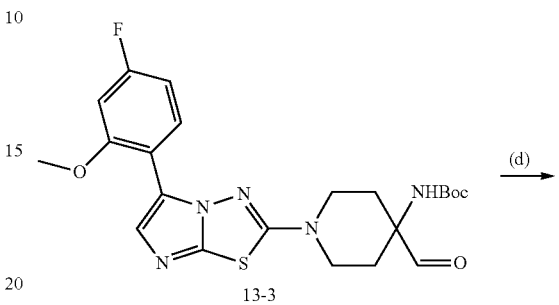

13-3

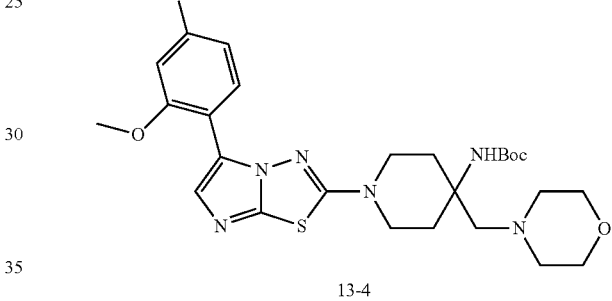

13-4

To a solution of Compound 13-3 (70 mg, 0.074 mmol), morpholine (19.2 mg, 0.221 mmol), sodium acetate (36.2 mg, 0.442 mmol) and AcOH (25.3 μL, 0.442 mmol) in DCM, NaBH(OAc)$_3$ (94 mg, 0.442 mmol) was added. The resulting cloudy mixture was stirred at room temperature for 2 hours. A sat. solution of NaHCO$_3$ was added to the reaction mixture at 0° C. and stirred for 5 minutes. The mixture was extracted twice with DCM. The combined organic layers were washed once with brine, dried over MgSO$_4$, filtered and concentrated in vacuo. The crude material was purified by normal phase chromatography (4 g column) with a running gradient of 0-100% EtOAc/Cyclohexane, followed by 0-10% MeOH/DCM to afford Compound 13-4. LC-MS=547.4 [M+H]$^+$.

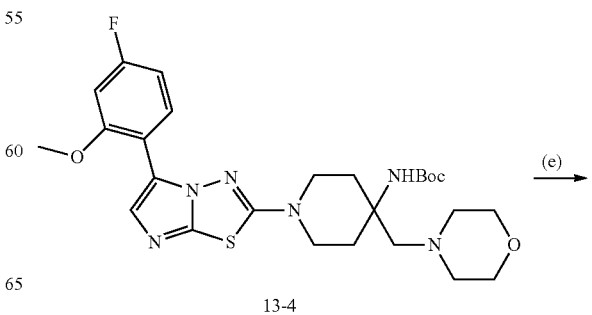

13-4

-continued

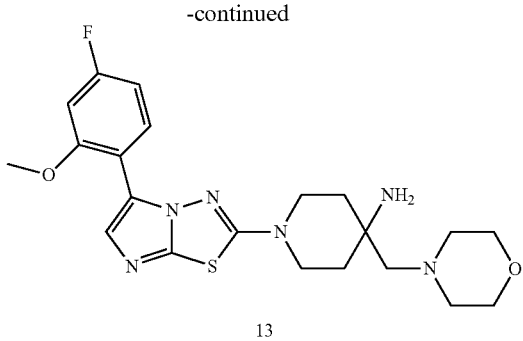

13

Compound 13-4 (30 mg, 0.055 mmol) was dissolved in MeOH (274 μL) and then 4 M HCl (233 μL, 0.933 mmol) was added. The reaction was stirred at room temperature for 2 hours. The resulting solution was concentrated in vacuo, and purified by prep-HPLC to afford 5.1 mg of Compound 13 as a solid. $^1$H NMR (400 MHz, DMSO-$d_6$) δ 8.18 (dd, J=8.7, 6.8 Hz, 1H), 7.88 (s, 3H), 7.52 (s, 1H), 7.08 (dd, J=11.4, 2.5 Hz, 1H), 6.90 (td, J=8.5, 2.5 Hz, 1H), 3.91 (s, 4H), 3.69 (dd, J=14.1, 5.3 Hz, 3H), 3.62 (t, J=4.4 Hz, 4H), 3.59-3.45 (m, 3H), 2.65 (s, 2H), 2.59-2.54 (m, 3H), 1.97-1.77 (m, 4H). LC-MS=447.4 [M+H]$^+$.

Example 14-0: 7-(5-(4-fluoro-2-methoxyphenyl)imidazo[2,1-b][1,3,4]thiadiazol-2-yl)-5,6,7,8-tetrahydroimidazo[1,5-a]pyrazin-3-amine

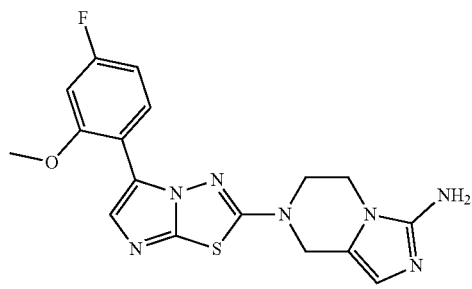 [SMILES: COc1cc(F)ccc1-c1cnc2sc(N3CCn4c(cnc4N)C3)nn12]

The Compound 14-0 was prepared in the following way:

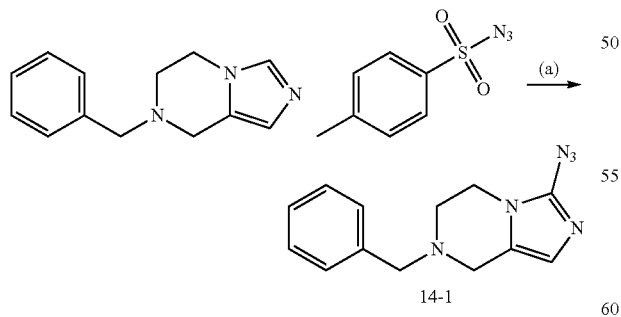

To a solution of 7-benzyl-5,6,7,8-tetrahydroimidazo[1,5-a]pyrazine in THF at −78° C., n-BuLi (2.5 M, 0.7 mL) was added. After 0.5 hour, a solution of 4-methylbenzenesulfonyl azide (30 w/w PhMe) in THF (0.5 mL) was added. The reaction mixture was stirred at −78° C. for 10 minutes, then was allowed to room temperature for 20 minutes. The reaction was quenched with sat. aqueous NaHCO$_3$. The mixture was extracted with EtOAc and the organic layer was washed with brine, dried over Na$_2$SO$_4$, filtered, and concentrated in vacuo. The residue was purified by normal phase chromatography with a running gradient of 0-50% EtOAc/cyclohexane to afford 289 mg of Compound 14-1. LC-MS=255.4 [M+H]$^+$.

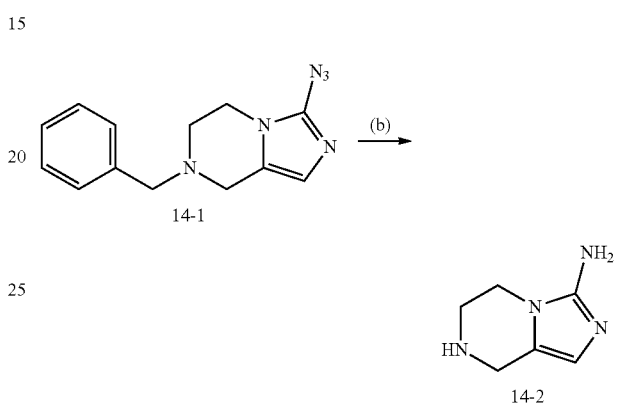

A mixture of Compound 14-1 and Pd(OH)$_2$ on carbon in EtOH was stirred at room temperature under H$_2$ for 13 hours. Then 3 M HCl (0.1 mL) was added. The reaction mixture was stirred at room temperature under H$_2$ for 2 hours. The mixture was filtered through HPLC filter, washed with MeOH. The filtrate was concentrated in vacuo to afford 57.8 mg of Compound 14-2. $^1$H NMR (500 MHz, MeOD-$d_4$) δ 6.63 (d, J=1.7 Hz, 1H), 3.94 (d, J=1.6 Hz, 2H), 3.76 (t, J=5.8 Hz, 2H), 3.33 (m, J=1.6 Hz, 2H), 3.26 (t, J=5.8 Hz, 2H), 1.20 (t, J=7.1 Hz, 1H). LC-MS=139.4 [M+H]$^+$.

The following compound 14-0 was prepared by the same route used to prepare Compound 4-0.

| Example/Compound Number | Structure | NMR | LC-MS |
|---|---|---|---|
| 14-0 | 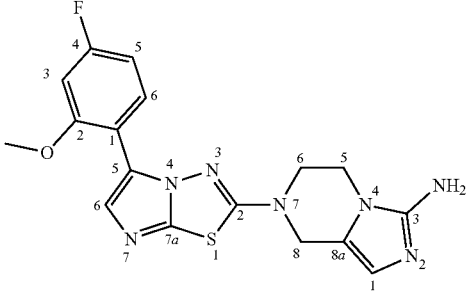<br>7-(5-(4-fluoro-2-methoxyphenyl)imidazo[2,1-b][1,3,4]thiadiazol-2-yl)-5,6,7,8-tetrahydroimidazo[1,5-a]pyrazin-3-amine | $^1$H NMR (500 MHz, DMSO-d$_6$) δ 12.03 (s, 1H), 8.16 (dd, J = 8.7, 6.9 Hz, 1H), 7.72 (s, 2H), 7.50 (s, 1H), 7.08 (dd, J = 11.4, 2.6 Hz, 1H), 6.94-6.83 (m, 2H), 4.70 (d, J = 1.5 Hz, 2H), 3.98 (q, J = 3.1 Hz, 4H), 3.90 (s, 3H). | MS m/z calcd for C$_{17}$H$_{16}$FN$_7$OS 385.1 found 386.3 [M + H]$^+$ |

Example 15-0: (1-(5-(4-fluoro-2-methoxyphenyl)imidazo[2,1-b][1,3,4]thiadiazol-2-yl)-4-((oxetan-3-ylmethyl)amino)piperidin-4-yl)methanol

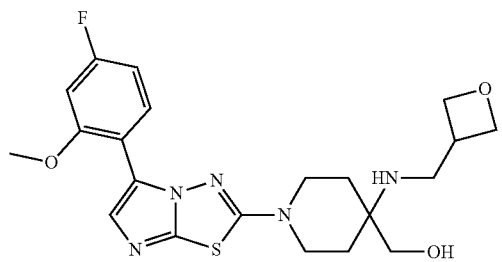 [SMILES: COc1cc(F)ccc1-c1cnc2sc(N3CCC(CO)(NCC4COC4)CC3)nn12]

The Compound 15-0 was prepared from Compound 4-98, followed by a reductive amination.

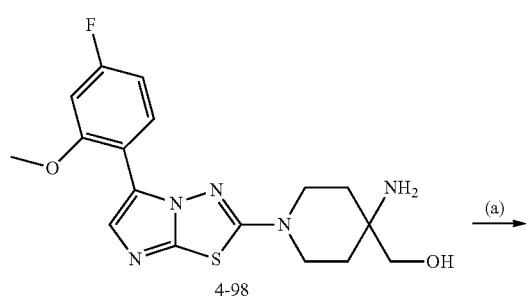

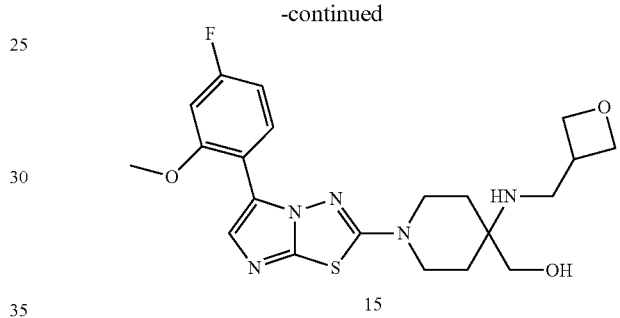

To a solution of Compound 4-98 (50 mg, 0.121 mmol) in anhydrous DCM (604 μL), sodium acetate (59.5 mg, 0.725 mmol), AcOH (41.5 μL, 0.725 mmol), oxetane-3-carbaldehyde (24.76 μL, 0.362 mmol) and NaBH(OAc)$_3$ (154 mg, 0.725 mmol) were added. The reaction was stirred at room temperature for 1 hour. A sat. solution of NaHCO$_3$ was added to the reaction mixture at 0° C. and stirred for 5 minutes. The aqueous layer was extracted twice with DCM. The combined organic layers were washed with brine, dried over MgSO$_4$, filtered and concentrated in vacuo. The crude material was purified by normal phase chromatography (4 g) with a running gradient of 0-10% MeOH/DCM to afford 29 mg of Compound 15-0 as a white foam. $^1$H NMR (500 MHz, DMSO-d$_6$) δ 8.20 (dd, J=8.7, 6.8 Hz, 1H), 7.47 (s, 1H), 7.06 (dd, J=11.4, 2.5 Hz, 1H), 6.91 (td, J=8.5, 2.6 Hz, 1H), 4.64 (dd, J=7.7, 5.8 Hz, 3H), 4.28 (t, J=5.9 Hz, 2H), 3.91 (s, 3H), 3.59-3.42 (m, 4H), 3.30 (s, 2H), 3.02-2.88 (m, 1H), 2.74 (m, 2H), 1.59 (dd, J=35.0, 13.1 Hz, 4H). LC-MS=448.3 [M+H]$^+$.

The following compound was prepared by the same route used to prepare Compound 15-0, using appropriate starting materials.

| Example/Compound Number | Structure | NMR | LC-MS |
|---|---|---|---|
| 15-2 | 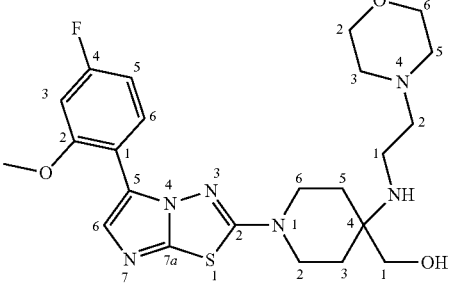<br>(1-(5-(4-fluoro-2-methoxyphenyl)imidazo[2,1-b][1,3,4]thiadiazol-2-yl)-4-((2-morpholinoethyl)amino)piperidin-4-yl)methanol | $^1$H NMR (400 MHz, DMSO-$d_6$) δ 8.17 (dd, J = 8.7, 6.8 Hz, 1H), 7.54 (s, 1H), 7.08 (dd, J = 11.4, 2.6 Hz, 1H), 6.90 (td, J = 8.4, 2.5 Hz, 1H), 3.91 (s, 3H), 3.82 (d, J = 11.1 Hz, 8H), 3.41 (t, J = 12.2 Hz, 2H), 3.29 (s, 2H), 3.16 (s, 6H), 2.01 (d, J = 13.2 Hz, 2H), 1.87 (ddd, J = 15.8, 12.5, 4.9 Hz, 2H). | MS m/z calcd for $C_{23}H_{31}FN_6O_3S$ 490.2 found 491.2 [M + H]$^+$ |

Example 16-0: (4-((3-aminopropyl)amino)-1-(5-(4-fluoro-2-methoxyphenyl)imidazo[2,1-b][1,3,4]thiadiazol-2-yl)piperidin-4-yl)methanol

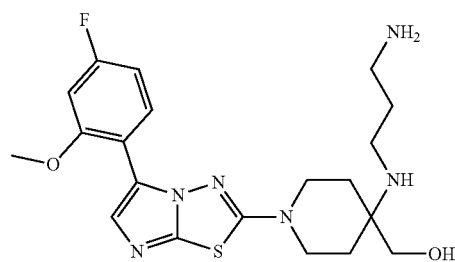 [SMILES: COc1cc(F)ccc1-c1cnc2sc(N3CCC(CO)(NCCCN)CC3)nn12]

The Compound 16-0 was prepared from Compound 4-98, followed by reductive amination and Boc deprotection.

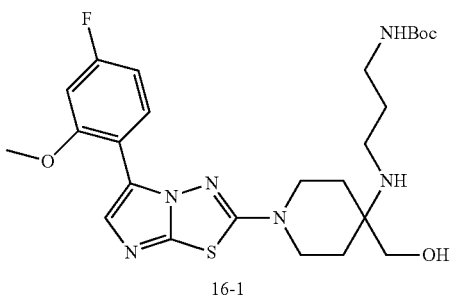

16-1

To a solution of Compound 4-98 (50 mg, 0.121 mmol) in anhydrous DCM (1.5 mL), sodium acetate (59.5 mg, 0.725 mmol), AcOH (0.041 mL, 0.725 mmol), tert-butyl (3-oxopropyl)carbamate (0.062 mL, 0.362 mmol) and NaBH(OAc)$_3$ (154 mg, 0.725 mmol) were added. The reaction mixture was stirred at room temperature for 1 hour. A sat. solution of NaHCO$_3$ was added to the reaction mixture at 0° C. and stirred for 5 minutes. The aqueous layer was extracted twice with DCM. The combined organic layers were washed with brine, dried over MgSO$_4$, filtered and concentrated in vacuo. The crude material was purified by normal phase chromatography (4 g) using a running gradient of DCM/MeOH 0-10% to afford 28 mg of Compound 16-1 as white foam. LC-MS=535.4 [M+H]$^+$.

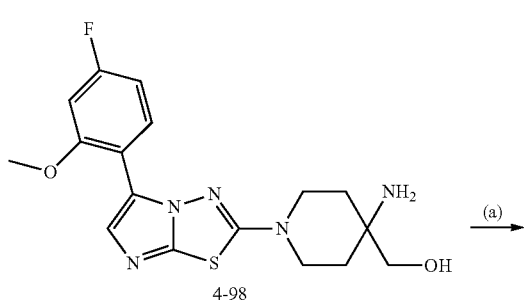

4-98

(a)

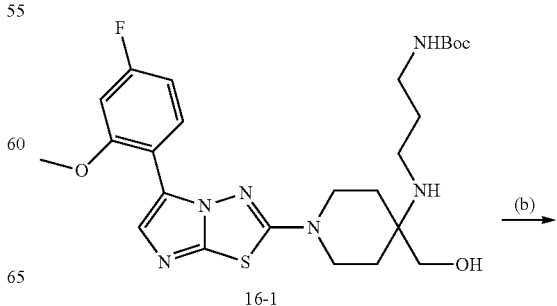

16-1

(b)

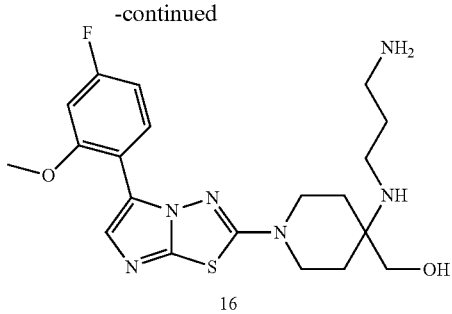

16

To a solution of Compound 16-1 (27 mg, 0.051 mmol) in anhydrous dioxane (300 μL) was added 4 M HCl in dioxane (101 μL, 0.404 mmol). The resulting white suspension was stirred at room temperature for 40 minutes. The resulting white suspension was concentrated in vacuo and then triturated in MeCN. The white suspension was filtered off and dried to afford a white powder Compound 16. $^1$H NMR (500 MHz, MeOD-d$_4$) δ 8.28 (dd, J=8.7, 6.5 Hz, 1H), 7.89 (s, 1H), 7.05 (dd, J=11.0, 2.5 Hz, 1H), 6.89 (td, J=8.4, 2.5 Hz, 1H), 4.04 (d, J=13.8 Hz, 1H), 3.99 (s, 3H), 3.96 (s, 2H), 3.61-3.48 (m, 2H), 3.26-3.19 (m, 2H), 3.11 (t, J=7.7 Hz, 2H), 2.23 (d, J=13.5 Hz, 3H), 2.20-2.09 (m, 3H). LC-MS=435.4 [M+H]$^+$.

Compound 17-0: 6-(aminomethyl)-2-(5-(4-fluoro-2-methoxyphenyl)imidazo[2,1-b][1,3,4]thiadiazol-2-yl)-2-azaspiro[3.3]heptan-6-ol The Compound 17-0 was prepared in the following way:

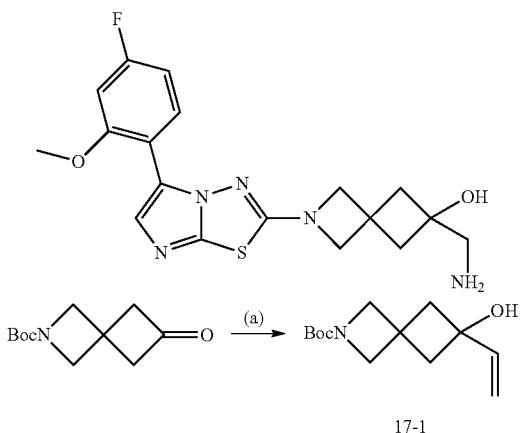

To a stirred solution of tert-butyl 6-oxo-2-azaspiro [3.3] heptane-2-carboxylate (3 g, 14.198 mmol) in THF (30 mL) at −78° C., vinyl magnesium bromide (1.0 M in THF, 17 mL, 17.037 mmol) was added dropwise and stirred for 30 minutes at −78° C. The reaction mixture was quenched by sat. NH$_4$Cl. The layers were separated and aqueous layer was extracted with DCM and the combined organic layers were dried over Na$_2$SO$_4$ and concentrated in vacuo. The crude material was purified by normal phase chromatography with a running gradient of 50-60% EtOAc/hexane to afford 1.15 g of Compound 17-1 as a solid. $^1$H NMR (600 MHz, CDCl$_3$) δ 5.99 (dd, J=17.3, 10.6 Hz, 1H), 5.24 (d, J=17.2 Hz, 1H), 5.10 (d, J=10.6 Hz, 1H), 3.94 (s, 2H), 3.87 (s, 2H), 2.51-2.40 (m, 2H), 2.37-2.27 (m, 2H), 1.80 (s, 1H), 1.42 (s, 9H). LC-MS=240.25 [M+H]$^+$, retention time=1.46 minutes.

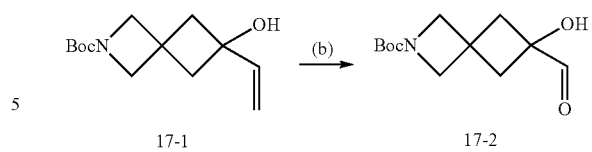

To a stirred solution of Compound 17-1 (700 mg, 2.924 mmol) in 10% MeOH in DCM (20 mL) at −78° C., ozone was purged for 40 minutes, then excess ozone was removed by purging N$_2$. After 10 minutes of N$_2$ purging, dimethyl sulfide (1.81 g, 29.249 mmol) was added at −78° C. dropwise, allowed to warm up to room temperature for 30 minutes. The reaction mixture was quenched by sat. NH$_4$Cl. The layers were separated and the aqueous layer was extracted with DCM. The combined organic layers were dried over Na$_2$SO$_4$ and concentrated in vacuo at 30° C. to afford 700 mg of Compound 17-2 as a colourless liquid. $^1$H NMR (300 MHz, CDCl$_3$) δ 4.05-3.83 (m, 4H), 2.78-2.65 (m, 1H), 2.60-2.44 (m, 2H), 2.31-2.12 (m, 1H), 1.43 (s, 9H).

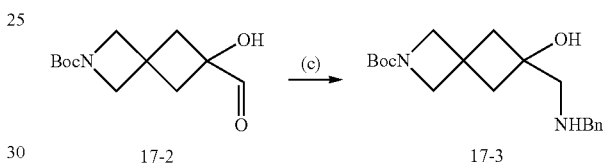

To a solution of Compound 17-2 (300 mg, 1.243 mmol) in dichloroethane (4 mL), benzyl amine (133 mg, 1.243 mmol) was added at 0° C. Then NaBH(OAc)$_3$ (395 mg, 1.865 mmol) was added portionwise at 0° C. The reaction was stirred at room temperature for 1 hour. The reaction mixture was quenched by sat. NH$_4$Cl. Both layers were separated and the aqueous layer was extracted with DCM. The combined organic layers were dried over Na$_2$SO$_4$ and concentrated in vacuo at 30° C. The crude material was purified by normal phase chromatography with a running gradient of 8-10% MeOH/DCM to afford 150 mg of Compound 17-3 as a yellow sticky mass. LC-MS=333.20 [M+H]$^+$, retention time=1.32 minutes

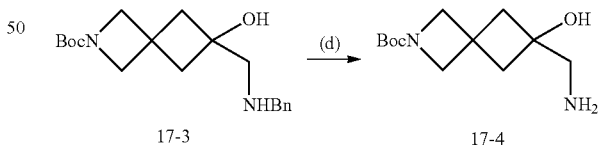

To a solution of Compound 17-3 (150 mg, 0.451 mmol) in MeOH (4 mL), 10% Pd/C (100 mg) was added at room temperature under H$_2$, stirred for 5 hours at room temperature maintaining H$_2$ pressure. The reaction mixture was filtered through CELITE pad, the CELITE pad was washed with MeOH, the filtrate was concentrated in vacuo to get 100 mg of Compound 17-4 as a colourless sticky mass. $^1$H NMR (600 MHz, CDCl$_3$) δ 3.91 (s, 2H), 3.88 (s, 2H) 2.69 (s, 2H), 2.33-2.13 (m, 4H) 1.42 (s, 9H). LC-MS=284.15 [M+42]$^+$ (MeCN adduct), retention time=1.23 minutes.

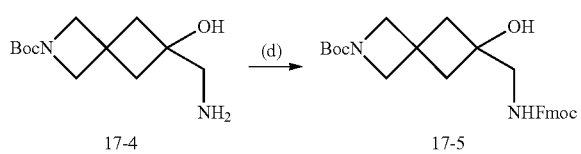

To a solution of Compound 17-4 (170 mg, 0.702 mmol) in DCM (10 mL), DIPEA (109 mg, 0.842 mmol) was added at 0° C. After 15 minutes, Fmoc chloride (199 mg, 0.772 mmol) was added dropwise at 0° C. Then the reaction was allowed to reach the room temperature and stirred for 1 hour. The reaction mixture was quenched with sat. NH₄Cl and extracted with DCM and the combined organic layers were washed with brine and dried over Na₂SO₄, concentrated in vacuo. The crude material was purified by normal phase chromatography with a running gradient of 6-8% MeOH/DCM to afford 280 mg of Compound 17-5 as a solid. ¹H NMR (300 MHz, CDCl₃) δ 7.77 (d, J=7.5 Hz, 2H), 7.59 (d, J=7.3 Hz, 2H), 7.46-7.37 (m, 2H), 7.35-7.28 (m, 2H), 4.45 (d, J=6.7 Hz, 2H), 4.21 (t, 6.6 Hz, 1H), 3.92 (d, J=7.8 Hz, 4H), 3.22 (d, J=6.1 Hz, 2H), 2.40-2.06 (m, 4H), 1.42 (s, 9H). LC-MS=465.25 [M+H]⁺ retention time=1.57 minutes.

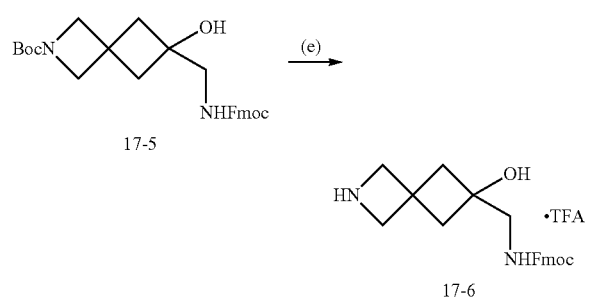

To a solution of Compound 17-5 (280 mg, 0.603 mmol) in DCM (3 mL), TFA (1 mL) was added dropwise at 0° C., then reaction mixture was allowed to reach the room temperature for 1 hour. The reaction mixture was concentrated in vacuo at 30° C. The crude material was triturated with pentane to afford 300 mg of Compound 17-6 as a colourless sticky mass. ¹H NMR (300 MHz, CDCl₃) δ 8.41 (s, 1H), 7.77 (d, J=7.5 Hz, 2H), 7.56 (d, J=7.5 Hz, 2H), 7.41 (t, J=7.4 Hz, 2H), 7.37-7.27 (m, 2H), 4.46 (d, J=6.5 Hz, 2H), 4.19 (s, 5H), 3.18 (s, 1H), 2.52-2.21 (m, 4H). LC-MS=365.20 [M+H]⁺, retention time=1.31 minutes.

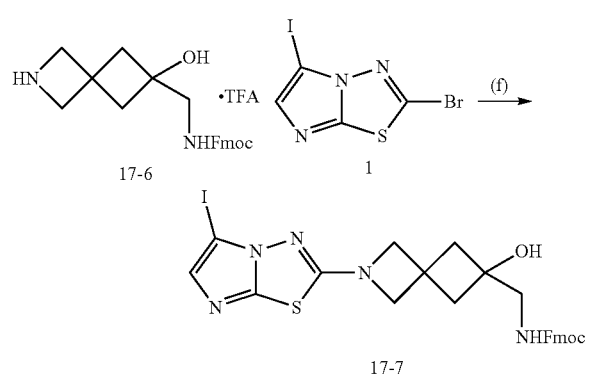

A mixture of Compound 17-6 (300 mg, 0.627 mmol), Compound 1 (207 mg, 0.627 mmol), DIPEA (86 mg, 3.762 mmol) in MeCN (4 mL) was heated at 100° C. for 90 minutes in MW. The reaction mixture was allowed to reach the room temperature for 1 hour until precipitate was formed. The solid was filtered and washed with MeCN and pentane. The solid was dried to afford Compound 17-7, which was used directly in next step. LC-MS=614.10 [M+H]⁺, retention time=1.55 minutes.

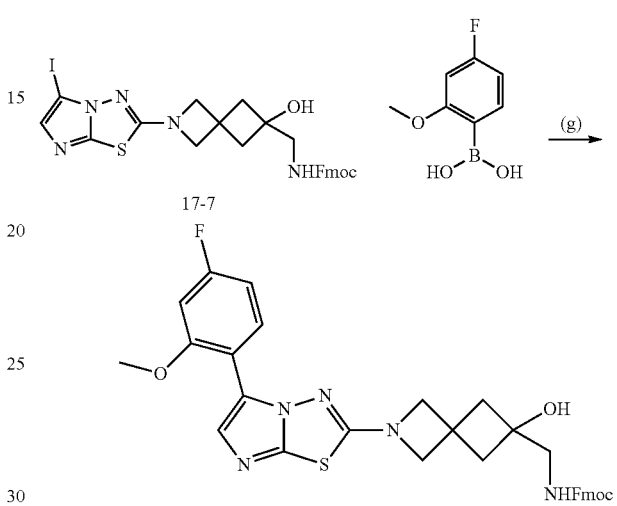

A solution of Compound 17-7 (120 mg, 0.196 mmol) in 4:1 dioxane/H₂O (4 mL/1 mL) was added K₃PO₄ (104 mg, 0.489 mmol), (4-fluoro-2-methoxyphenyl) boronic acid (67 mg, 0.391 mmol) and PdCl₂(dppf)-DCM complex (16 mg, 0.019 mmol). The reaction mixture was heated at 100° C. for 6 hours before it was diluted with H₂O and extracted with EtOAc (twice). The combined organic layers were washed with H₂O, brine, dried over Na₂SO₄, filtered and concentrated in vacuo to give crude material which was purified by normal phase chromatography with a running gradient of 8-10% MeOH/DCM to afford Compound 17-8 as a solid. ¹H NMR (600 MHz, CDCl₃) δ 8.17 (dd, J=8.6, 6.7 Hz, 1H), 7.77 (d, J=7.6 Hz, 2H), 7.59 (d, J=7.6 Hz, 3H), 7.41 (t, J=7.5, 7.5 Hz, 2H), 7.32 (t, J=7.5, 7.5 Hz, 2H), 6.79-6.68 (m, 2H), 5.19 (d, J=6.3 Hz, 1H), 4.48 (d, J=6.7 Hz, 2H), 4.27-4.11 (m, 4H), 3.90 (s, 3H), 3.27 (d, J=6.2 Hz, 2H), 2.28 (d, J=12.8 Hz, 2H), 2.44 (d, J=12.8 Hz, 2H). LC-MS=612.10 [M+H]⁺, retention time=1.59 minutes.

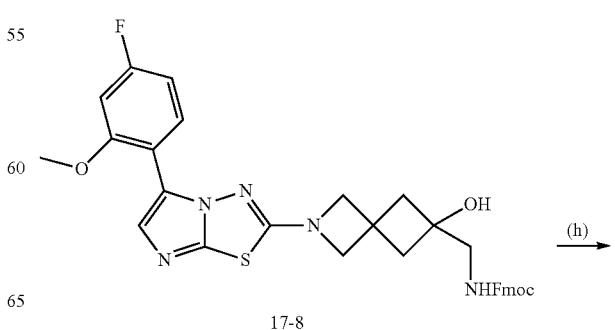

-continued

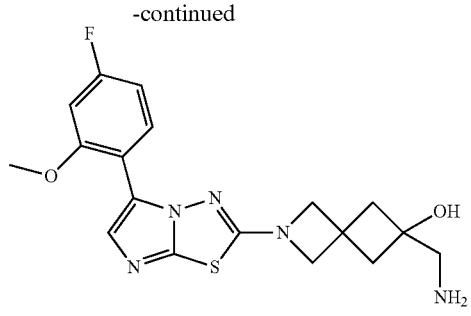

17

To a solution of Compound 17-8 (90 mg, 0.147 mmol) in DCM (2.0 mL), piperidine (0.1 mL) was added at 0° C. Then reaction stirred for 16 hours at room temperature. The reaction mixture was concentrated in vacuo. The crude material was triturated with Et$_2$O. This resulting mixture was purified by prep-HPLC (Method M) to afford 23 mg of Compound 17 as a solid. $^1$H NMR (400 MHz, MeOD-d$_4$) δ 8.26 (dd, J=8.8, 6.5 Hz, 1H), 7.90 (d, J=17.3 Hz, 1H), 7.03 (dd, J=11.0, 2.5 Hz, 1H), 6.86 (td, J=8.5, 2.5 Hz, 1H), 4.33 (s, 4H), 3.97 (s, 3H), 3.00 (s, 2H), 2.64-2.41 (m, 4H). LC-MS=390.05 [M+H]$^+$, retention time=1.29 min.

Example 18-0 (single enantiomer): 3-(aminomethyl)-1-(5-(6-isopropyl-2-methoxypyridin-3-yl)imidazo[2,1-b][1,3,4]thiadiazol-2-yl)pyrrolidin-3-ol

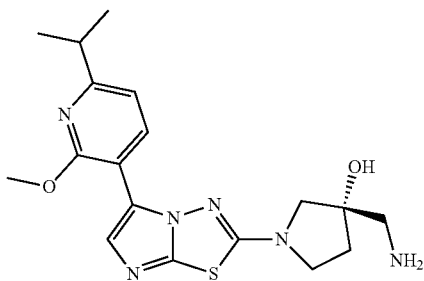 [SMILES: COc1nc(C(C)C)ccc1-c1cnc2sc(N3CC[C@](O)(CN)C3)nn12]

Compound 18-0 was prepared in the following way:

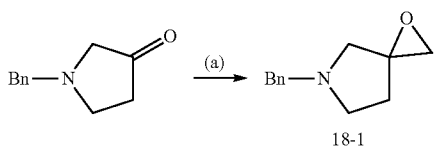 [SMILES: O=C1CCN(Cc2ccccc2)C1 ; c1ccc(CN2CCC3(CO3)C2)cc1]

18-1

To a suspension of NaH (60% in mineral oil, 1.78 g, 44.51 mmol) in DMSO (40 mL) at 10° C., trimethylsulfoxonium iodide (8.31 g, 37.66 mmol) was added in portion and the reaction was stirred at room temperature for 1 hour. A solution of 1-benzylpyrrolidin-3-one (6 g, 34.24 mmol) in DMSO (30 mL) was added and the reaction was stirred at room temperature for 2 hours. The reaction mixture was quenched with sat. NH$_4$Cl solution and extracted with EtOAc. The organic layer was washed with brine, dried over Na$_2$SO$_4$ and concentrated in vacuo. The crude compound was purified by normal phase chromatography with a running gradient of 50-100% EtOAc/hexane to afford 3.0 g of Compound 18-1 as a colourless liquid. $^1$H NMR (400 MHz, CDCl$_3$) δ 7.38-7.21 (m, 5H), 3.72-3.58 (m, 2H), 2.85 (d, J=0.8 Hz, 2H), 2.82-2.77 (m, 2H), 2.69 (ddd, J=9.1, 7.6, 5.5 Hz, 1H), 2.59 (d, J=10.7 Hz, 1H), 2.20 (dt, J=14.2, 7.2 Hz, 1H), 1.92 (ddd, J=13.6, 7.6, 5.5 Hz, 1H). LC-MS=190.1 [M+H]$^+$, retention time=0.13 and 0.28 minutes (Method 12).

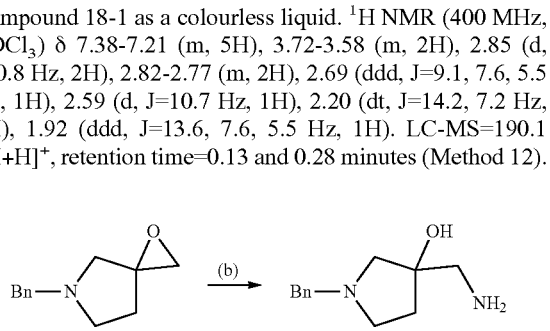

To a solution of Compound 18-1 (3.0 g, 15.85 mmol) in MeOH (18 mL) at 0° C., 28% aq. NH$_3$ (36 mL) was added dropwise and stirred at room temperature for 16 hours. The reaction mixture was diluted with DCM, washed with 1 N NaOH solution, H$_2$O, brine, dried over Na$_2$SO$_4$ and concentrated in vacuo to afford Compound 18-2. $^1$H NMR (600 MHz, CDCl$_3$) δ 7.37-7.20 (m, 5H), 3.62 (d, J=2.7 Hz, 2H), 2.83 (q, J=7.7 Hz, 1H), 2.77 (s, 2H), 2.60 (d, J=9.8 Hz, 1H), 2.47 (q, J=7.9 Hz, 1H), 2.41 (d, J=9.6 Hz, 1H), 1.83 (t, J=7.3 Hz, 2H). LC-MS=206.9 [M+H]$^+$, retention time=0.27 minutes (Method Q).

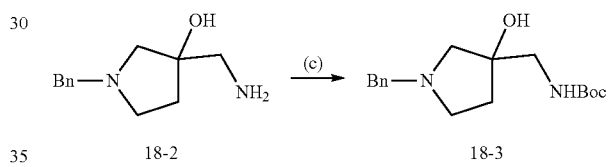

To a solution of Compound 18-2 (2.60 g, 12.60 mmol) in DCM (25 mL) at 0° C., (Boc)$_2$O (3.30 g, 15.12 mmol) was added dropwise and stirred at room temperature for 2 hours. The reaction mixture was concentrated in vacuo. The crude material was purified by normal phase chromatography with a running gradient of 5-10% MeOH/DCM to afford 1.75 g of Compound 18-3 as a solid. $^1$H NMR (300 MHz, CDCl$_3$) δ 7.40-7.13 (m, 5H), 3.61 (d, J=1.8 Hz, 2H), 3.27 (d, J=5.9 Hz, 2H), 3.03-2.74 (m, 1H), 2.62 (d, J=9.7 Hz, 1H), 2.43 (td, J=9.5, 6.0 Hz, 2H), 2.09-1.71 (m, 2H), 1.43 (s, 9H). LC-MS=307.1 [M+H]$^+$, retention time=1.29 minutes (Method 12).

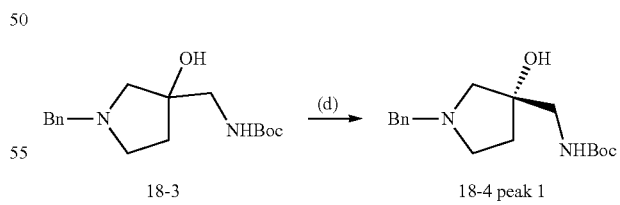

A chiral separation of racemic Compound 18-3 (700 mg) using chiral purification method (Method 14) afforded Compound 1-4 peak 1 (300 mg) as a solid, LC-MS=307.5 [M+H]$^+$, retention time=0.11 minutes. HPLC: 97.55%, retention time=5.17 minutes (Method 14). Chiral HPLC 98.26%, retention time=7.97 minutes and Compound 1-4 Peak-2 (240 mg) as a solid. LC-MS=307.5 [M+H]$^+$, retention time=0.12 minutes. Chiral HPLC 98.23%, retention time=9.47 minutes.

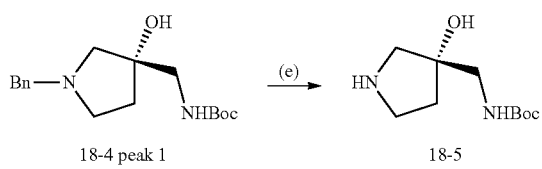 [SMILES: CC(C)(C)OC(=O)NC[C@@]1(O)CCN(Cc2ccccc2)C1 ; CC(C)(C)OC(=O)NC[C@@]1(O)CCNC1]

18-4 peak 1 → 18-5

To a solution of Compound 18-4 Peak 1 (300 mg, 0.979 mmol) in MeOH (10 mL), 10% Pd/C (100 mg) and HCOONH$_4$ (374 mg, 5.874) were added. The reaction was heated to 70° C. for 3 hours. The reaction mixture was cooled to room temperature, filtered through CELITE pad, the CELITE pad was washed with MeOH. The resulting filtrate was concentrated in vacuo to afford 210 mg of compound 18-5 as a colourless sticky mass. $^1$H NMR (400 MHz, DMSO-d$_6$) δ 6.64 (t, J=6.1 Hz, 1H), 4.56 (s, 1H), 3.17 (d, J=1.8 Hz, 2H), 3.05 (d, J=6.0 Hz, 2H), 2.86 (dt, J=10.6, 7.7 Hz, 1H), 2.69 (ddd, J=10.3, 8.2, 4.4 Hz, 1H), 2.61 (d, J=11.5 Hz, 1H), 1.69-1.42 (m, 2H), 1.38 (s, 9H). LC-MS=217.0 [M+H]$^+$, retention time=0.33 minutes (Method 12).

The following compounds were prepared by the same route used to prepare Compound 4-0, using appropriate starting materials.

| Example/Compound Number | Structure | NMR | LC-MS |
|---|---|---|---|
| 18-0 | (S)-3-(aminomethyl)-1-(5-(6-isopropyl-2-methoxypyridin-3-yl)imidazo[2,1-b][1,3,4]thiadiazol-2-yl)pyrrolidin-3-ol | $^1$H NMR (300 MHz, MeOD-d$_4$) δ 8.66 (d, J = 7.8 Hz, 1H), 7.60 (s, 1H), 6.88 (d, J = 7.8 Hz, 1H), 4.06 (s, 3H), 3.80-3.62 (m, 2H), 3.61-3.43 (m, 2H), 3.04-2.90 (m, 1H), 2.86 (s, 2H), 2.22-1.97 (m, 2H), 1.31 (s, 3H), 1.29 (s, 3H). | MS m/z calcd for C$_{18}$H$_{24}$N$_6$O$_2$S 388.2, found 389.0 [M + H]$^+$ |
| 18-6 | (R)-3-(aminomethyl)-1-(5-(6-isopropyl-2-methoxypyridin-3-yl)imidazo[2,1-b][1,3,4]thiadizol-2-yl)pyrrolidin-3-ol | $^1$H NMR (400 MHz, MeOD-d$_4$) δ 8.69 (d, J = 7.7 Hz, 1H), 7.62 (s, 1H), 6.91 (d, J = 7.8 Hz, 1H), 4.08 (s, 3H), 3.85-3.65 (m, 2H), 3.65-3.46 (m, 2H), 3.07-2.94 (m, 1H), 2.90 (s, 2H), 2.24-2.06 (m, 2H), 1.33 (s, 3H), 1.32 (s, 3H). | MS m/z calcd for C$_{18}$H$_{24}$N$_6$O$_2$S 388.2, found 389.2 [M + H]$^+$ |

-continued

| Example/Compound Number | Structure | NMR | LC-MS |
|---|---|---|---|
| 18-7 | (S)-3-(aminomethyl)-1-(5-(2-methoxy-6-methylpyridin-3-yl)imidazo[2,1-b][1,3,4]thiadiazol-2-yl)pyrrolidin-3-ol | $^1$H NMR (400 MHz, MeOD-d$_4$) δ 8.67 (d, J = 7.7 Hz, 1H), 7.61 (s, 1H), 6.89 (d, J = 7.7 Hz, 1H), 4.06 (s, 3H), 3.81-3.64 (m, 2H), 3.64-3.48 (m, 2H), 2.88 (s, 2H), 2.47 (s, 3H), 2.25-2.02 (m, 2H). | MS m/z calcd for $C_{16}H_{20}N_6O_2S$ 360.1, found 361.0 $[M + H]^+$ |
| 18-8 | (R)-3-(aminomethyl)-1-(5-(2-methoxy-6-methylpyridin-3-yl)imidazo[2,1-b][1,3,4]thiadiazol-2-yl)pyrrolidin-3-ol | $^1$H NMR (400 MHz, MeOD-d$_4$) δ 8.68 (d, J = 7.7 Hz, 1H), 7.62 (s, 1H), 6.90 (d, J = 7.7 Hz, 1H), 4.06 (s, 3H), 3.85-3.65 (m, 2H), 3.63-3.44 (m, 2H), 2.87 (s, 2H), 2.47 (s, 3H), 2.24-2.04 (m, 2H). | MS m/z calcd for $C_{16}H_{20}N_6O_2S$ 360.1, found 361.0 $[M + H]^+$ |

Example 19-0: 4-amino-1-(5-(2-methoxy-4-methylphenyl)imidazo[2,1-b][1,3,4]thiadiazol-2-yl)-4-methylpiperidin-3-ol

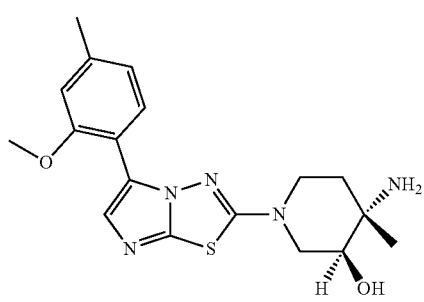

Compound 19-0 was prepared in the following way:

To a solution of 4-methylpyridine (1-1, 20 g, 214.7 mmol) in MeCN (200 mL), BnBr (28 mL, 236.2 mmol) was added at 0° C. The resulting solution was stirred at 70° C. for 3 hours. The reaction was cooled to room temperature and concentrated in vacuo to afford 55 g of Compound 19-2 as a solid, which was used in next step without further purification. $^1$H NMR (300 MHz, DMSO-d$_6$) δ 9.08 (d, J=6.3 Hz, 2H), 8.03 (d, J=6.3 Hz, 2H), 7.57-7.42 (m, 5H), 5.81 (s, 2H), 2.63 (s, 3H).

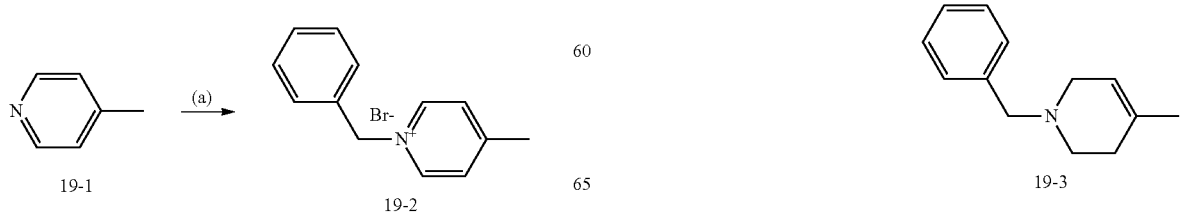

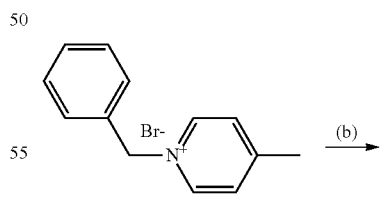

A solution of Compound 19-2 (55 g, 208.2 mmol) in MeOH (100 mL) was cooled to 0° C., NaBH₄ (16 g, 416.4 mmol) was added portionwise at 0° C. The reaction was stirred at room temperature for 1 hour. The reaction was concentrated in vacuo, ice H₂O was added and then extracted with EtOAc (3×100 mL). The combined organic layers were washed with H₂O, brine then dried over Na₂SO₄, filtered and concentrated in vacuo. The crude compound was purified by normal phase chromatography (40.0 g neutral alumina column) with a running gradient of 0-20% EtOAc/hexane to afford 27 g of Compound 19-3 as an oil. ¹H NMR (300 MHz, CDCl₃) δ 7.44-7.17 (m, 5H), 5.37 (bs, 1H), 3.57 (s, 2H), 2.98-2.90 (m, 2H), 2.56 (t, J=5.8 Hz, 2H), 2.14-2.03 (m, 2H), 1.68 (s, 3H). LC-MS=188.2 [M+H]⁺, retention time=0.146 minutes.

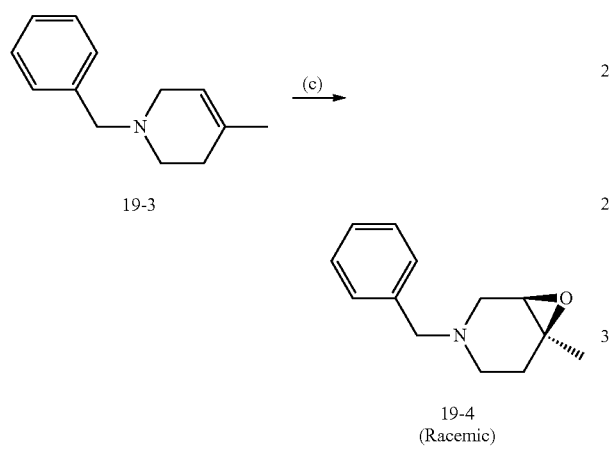

19-3

19-4
(Racemic)

To a solution of Compound 19-3 (27 g, 72.14 mmol) in IPA: H₂O (204.5 mL, 1:2), TFA (5.5 mL, 72.14 mmol) was added dropwise over period of 5 minutes at 0° C., followed by addition of NBS (16.7 g, 93.8 mmol) in portionwise at same temperature. The reaction was stirred at room temperature and then heated to 50° C. for 16 hours. The reaction was cooled down to room temperature and 20% aq. NaOH (120 mL) was added. The resulting mixture was stirred at room temperature for 6 hours and then concentrated in vacuo, diluted with H₂O and extracted twice with Et₂O (100 mL). The combined organic layers were washed with H₂O, brine then dried over Na₂SO₄, filtered off and concentrated in vacuo. The crude compound was purified by normal phase chromatography (80 g column) with a running gradient of 0-50% EtOAc/n-hexane to afford 18 g of Compound 19-4 as an oil. ¹H NMR (600 MHz, CDCl₃) δ 7.38-7.14 (m, 5H), 3.52-3.34 (m, 2H), 3.14-2.97 (m, 2H), 2.57 (d, J=13.3 Hz, 1H), 2.43-2.27 (m, 1H), 2.15-2.10 (m, 1H), 1.92-1.86 (m, 2H), 1.34 (s, 3H). LC-MS=204.1 [M+H]⁺, retention time=0.134 minutes.

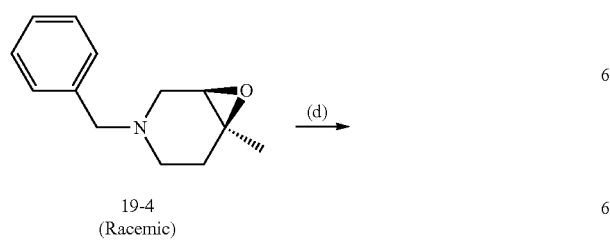

19-4
(Racemic)

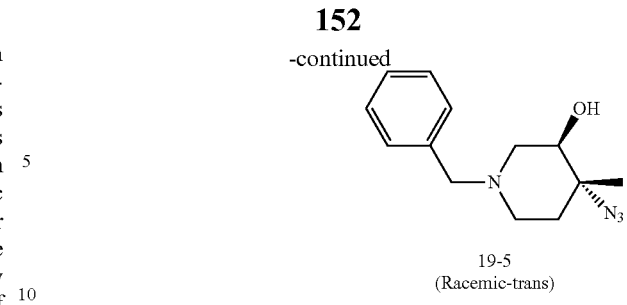

19-5
(Racemic-trans)

To a solution of Compound 19-4 (9 g, 44.27 mmol) in H₂O (119 mL), AcOH (58 mL) was added at 0° C., followed by portionwise addition of NaN₃ (14.4 g, 221.4 mmol) at same temperature. The reaction was stirred at room temperature for 24 hours, quenched reaction with sat. NaHCO₃ solution and extracted twice with EtOAc (100 mL). The combined organic layers were washed with H₂O and brine, dried over Na₂SO₄, filtered and concentrated in vacuo. Repeated one more 9 g batch, the resulting crude materials were combined and were purified by normal phase chromatography (80 g column) with a running gradient of 20-30% EtOAc/n-hexane to afford 11.7 g of Compound 19-5 as an oil. ¹H NMR (300 MHz, CDCl₃) δ 7.41-7.18 (m, 5H), 3.53 (s, 2H), 3.36 (s, 1H), 3.00 (d, J=9.2 Hz, 1H), 2.73-2.47 (m, 3H), 2.30 (td, J=11.4, 3.2 Hz, 1H), 1.90-1.78 (m, 1H), 1.63-1.55 (m, 1H), 1.39 (s, 3H). LC-MS=247.1 [M+H]⁺, retention time=0.27 minutes.

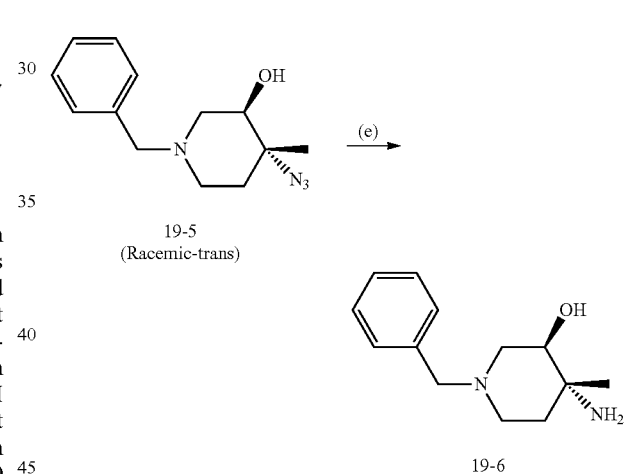

19-5
(Racemic-trans)

19-6

To a solution of Compound 19-5 (6 g, 24.35 mmol) in MeOH (100 mL), HCOONH₄ (3.07 g, 48.7 mmol) was added, followed by addition of Zn dust (4.77 g, 73.1 mmol) at room temperature. The reaction was stirred for 30 minutes at room temperature. The reaction filtered over CELITE pad, washed with MeOH (2×30 mL) and the resulting filtrate was concentrated in vacuo. A repeated batch with same scale was done and combined together to afford 10.3 g of crude Compound 19-6 which was used in next step without further purification. LC-MS=221.1 [M+H]⁺, retention time=0.131 minutes.

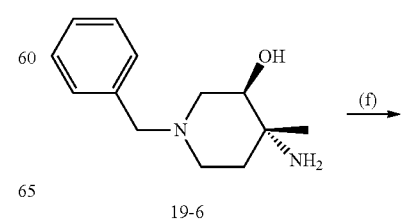

19-6

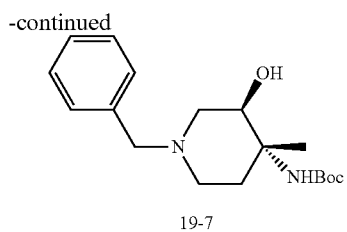

19-7

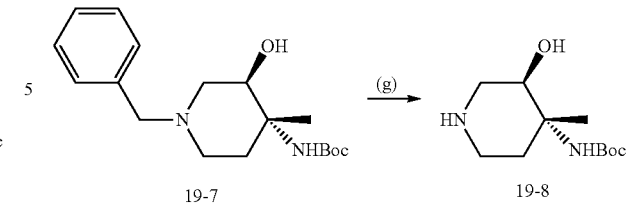

19-7   19-8

To a solution of Compound 19-6 (10.3 g, 46.75 mmol) in dioxane (60 mL), Na₂CO₃ (19.8 g, 187.2 mmol) was added at 0° C., followed by addition of (Boc)₂O (21.5 mL, 93.5 mmol). The reaction mixture was stirred at room temperature for 16 hours, concentrated in vacuo, diluted with EtOAc (200 mL) and then washed with H₂O. The combined organic layers were washed with H₂O, brine then dried over Na₂SO₄, filtered and concentrated in vacuo to get crude compound. The crude compound was purified by normal phase chromatography (40.0 g column) with a running gradient of 5-10% EtOAc/n-hexane to afford 11.8 g of Compound 19-7 as a solid. $^1$H NMR (400 MHz, DMSO-d₆) δ 7.39-7.16 (m, 5H), 6.28 (s, 1H), 4.76 (s, 1H), 3.70 (s, 2H), 3.45 (q, J=13.2 Hz, 2H), 2.10 (t, J=10.5 Hz, 1H), 2.04-1.92 (m, 1H), 1.92-1.69 (m, 2H), 1.37 (s, 9H), 1.13 (s, 3H). LC-MS=321.2 [M+H]⁺, retention time=1.33 minutes.

10% Pd/C (6.0 g) was added to a N₂ degassed solution of Compound 19-7 (13 g, 40.57 mmol) in MeOH (200 mL) and stirred at room temperature for 4 hours under H₂. The reaction was filtered over CELITE pad, washed with MeOH (2×30 mL) and the resulting filtrate was concentrated in vacuo to afford 10 g of compound 19-8 as a solid which was used in next step without further purification. $^1$H NMR (600 MHz, CDCl₃) δ 4.61 (s, 1H), 3.75 (dd, J=9.1, 4.4 Hz, 1H), 3.07 (dd, J=12.5, 4.4 Hz, 1H), 2.85 (dt, J=12.9, 4.5 Hz, 1H), 2.69 (ddd, J=13.2, 10.4, 3.1 Hz, 1H), 2.59-2.46 (m, 1H), 1.70-1.64 (m, 1H), 1.56-1.49 (m, 1H), 1.44 (s, 9H), 1.36 (s, 3H).

The following Compounds below were prepared by the same route used to prepare Compound 4-0.

| Example/Compound Number | Structure | NMR | LC-MS | Chiral HPLC Prep Method |
|---|---|---|---|---|
| 19-0 | (3S,4S)-4-amino-1-(5-(2-methoxy-4-methylphenyl)imidazo[2,1-b][1,3,4]thiadiazol-2-yl)-4-methylpiperidin-3-ol | $^1$H NMR (400 MHz, MeOD-d₄) δ 8.12 (d, J = 8.0 Hz, 1H), 7.84 (s, 1H), 7.04-6.99 (m, 1H), 6.93 (dd, J = 8.0, 1.6 Hz, 1H), 4.00 (dd, J = 12.8, 5.2 Hz, 1H), 3.95 (s, 3H), 3.93-3.90 (m, 1H), 3.86 (dd, J = 10.6, 5.3 Hz, 1H), 3.57-3.44 (m, 1H), 3.28-3.22 (m, 1H), 2.42 (s, 3H), 2.08-1.97 (m, 2H), 1.46 (s, 3H). | MS m/z calcd for C₁₈H₂₃N₅O₂S 373.2 found 374.15 [M + H]⁺ | 12 |
| 19-9 | (3R,4R)-4-amino-1-(5-(2-methoxy-4-methyphenyl)imidazo[2,1-b][1,3,4]thiadiazol-2-yl)-4-methylpiperidin-3-ol | $^1$H NMR (400 MHz, MeOD-d₄) δ 8.13 (d, J = 8.0 Hz, 1H), 7.85 (s, 1H), 7.07-6.98 (m, 1H), 6.93 (ddd, J = 7.9, 1.7, 0.8 Hz, 1H), 4.00 (dd, J = 12.4, 4.8 Hz, 1H). 3.95 (s, 3H), 3.93-3.90 (m, 1H), 3.86 (dd, J = 10.6, 5.2 Hz, 1H), 3.56-3.44 (m, 1H), 3.29-3.23 (m, 1H), 2.42 (s, 3H), 2.11-1.92 (m, 2H), 1.46 (s, 3H). | MS m/z calcd for C₁₈H₂₃N₅O₂S 373.2 found 374.15 [M + H]⁺ | 12 |

| Example/ Compound Number | Structure | NMR | LC-MS | Chiral HPLC Prep Method |
|---|---|---|---|---|
| 19-10 | (3R,4R)-4-amino-1-(5-(6-isopropyl-2-methoxypyridin-3-yl)imidazo[2,1-b][1,3,4]thiadiazol-2-yl)-4-methylpiperidin-3-ol | $^1$H NMR (300 MHz, MeOD-$d_4$) δ 8.61 (d, J = 7.8 Hz, 1H), 7.60 (s, 1H), 6.90 (d, J = 7.8 Hz, 1H), 4.06 (s, 3H), 3.89-3.79 (m, 1H), 3.74-3.59 (m, 1H), 3.60-3.42 (m, 2H), 3.28-3.23 (m, 1H), 3.05-2.95 (m, 1H), 1.87 (ddd, J = 13.3, 5.7, 3.6 Hz, 1H), 1.64 (ddd, J = 13.7, 9.3, 4.4 Hz, 1H), 1.36-1.25 (m, 6H), 1.19 (s, 3H). | MS m/z calcd for $C_{19}H_{26}N_6O_2S$ 402.2 found 403.5 [M + H]$^+$ | 12 |
| 19-11 | (3S,4S)-4-amino-1-(5-(6-isopropyl-2-methoxypyridin-3-yl)imidazo[2,1-b][1,3,4]thiadiazol-2-yl)-4-methylpiperidin-3-ol | $^1$H NMR (300 MHz, MeOD-$d_4$) δ 8.61 (d, J = 7.8 Hz, 1H), 7.60 (s, 1H), 6.90 (d, J = 7.8 Hz, 1H), 4.06 (s, 3H), 3.90-3.78 (m, 1H), 3.68 (dt, J = 13.5, 5.1 Hz, 1H), 3.59-3.42 (m, 2H), 3.28-3.22 (m, 1H), 3.05-2.95 (m, 1H), 1.87 (ddd, J = 13.6, 5.8, 3.7 Hz, 1H), 1.63 (ddd, J = 13.7, 9.4, 4.4 Hz, 1H), 1.30 (d, J = 6.9 Hz, 6H), 1.19 (s, 3H). | MS m/z calcd for $C_{19}H_{26}N_6O_2S$ 402.2 found 403.5 [M + H]$^+$ | 12 |
| 19-12 | (3R,4R)-4-amino-1-(5-(4-fluoro-2-methoxyphenyl)imidazo[2,1-b][1,3,4]thiadiazol-2-yl)-4-methylpiperidin-3-ol | $^1$H NMR (400 MHz, MeOD-$d_4$) δ 8.26 (dd, J = 8.7, 6.5 Hz, 1H), 7.89 (s, 1H), 7.03 (dd, J = 11.0, 2.5 Hz, 1H), 6.87 (ddd, J = 8.7, 8.0, 2.5 Hz, 1H), 4.04-3.85 (m, 7H), 3.37-3.31 (m, 1H), 2.12-1.91 (m, 2H), 1.46 (s, 3H). | MS m/z calcd for $C_{17}H_{20}FN_5O_2S$ 377.1 found 378.3 [M + H]$^+$ | 13 |

-continued

| Example/ Compound Number | Structure | NMR | LC-MS | Chiral HPLC Prep Method |
|---|---|---|---|---|
| 19-13 | (3S,4S)-4-amino-1-(5-(4-fluoro-2-methoxyphenyl)imidazo[2,1-b][1,3,4]thiadiazol-2-yl)-4-methylpiperidin-3-ol | $^1$H NMR (300 MHz, MeOD-$d_4$) δ 8.26 (dd, J = 8.8, 6.5 Hz, 1H), 7.90 (s, 1H), 7.03 (dd, J = 11.0, 2.4 Hz, 1H), 6.94-6.79 (m, 1H), 4.04-3.85 (m, 7H), 3.64-3.40 (m, 1H), 2.10-1.94 (m, 2H), 1.46 (s, 3H). | MS m/z calcd for $C_{17}H_{20}FN_5O_2S$ 377.1 found 378.3 [M + H]$^+$ | 13 |
| 19-14 | (3R,4R)-4-amino-1-(5-(2-methoxy-2-methylpyridin-3-yl)imidazo[2,1-b][1,3,4]thiadiazol-2-yl)-4-methylpiperidin-3-ol | $^1$H NMR (400 MHz, Methanol-$d_4$) δ 8.59 (d, J = 7.7 Hz, 1H), 7.59 (s, 1H), 6.89 (d, J = 7.6 Hz 1H), 4.04 (s, 3H), 3.87-3.79 (m, 1H), 3.70-3.63 (m, 1H), 3.55-3.44 (m, 2H), 3.28-3.22 (m, 1H), 2.45 (s, 3H), 1.90-1.82 (m, 1H), 1.68-1.58 (m, 1H), 1.19 (s, 3H). | MS m/z calcd for $C_{17}H_{22}N_6O_2S$ 374.2 found 375.1 [M + H]$^+$ | 12 |
| 19-15 | (3S,4S)-4-amino-1-(5-(2-methoxy-6-methylpyridin-3-yl)imidazo[2,1-b][1,3,4]thiadiazol-2-yl)-4-methylpiperidin-3-ol | $^1$H NMR (400 MHz, Methanol-$d_4$) δ 8.59 (d, J = 7.7 Hz, 1H), 7.59 (s, 1H), 6.89 (d, J = 7.8 Hz, 1H), 4.04 (s, 3H), 3.83 (dd, J = 13.1, 4.2 Hz, 1H), 3.67 (dt, J = 13.4, 5.2 Hz, 1H), 3.50 (ddt, J = 22.8, 9.5, 4.9 Hz, 2H), 3.28-3.21 (m, 1H), 2.45 (s, 3H), 1.92-1.81 (m, 1H), 1.67-1.57 (m, 1H), 1.18 (s, 3H). | MS m/z calcd for $C_{17}H_{22}N_6O_2S$ 374.2 found 375.1 [M + H]$^+$ | 12 |

Example 20-0: (3S,4S)-3-amino-1-(5-(4-fluoro-2-methoxyphenyl)imidazo[2,1-b][1,3,4]thiadiazol-2-yl)-4-methylpiperidin-4-ol

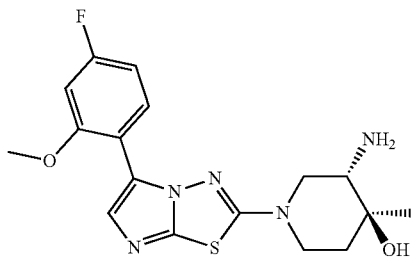

Compound 20-0 was prepared in the following way:

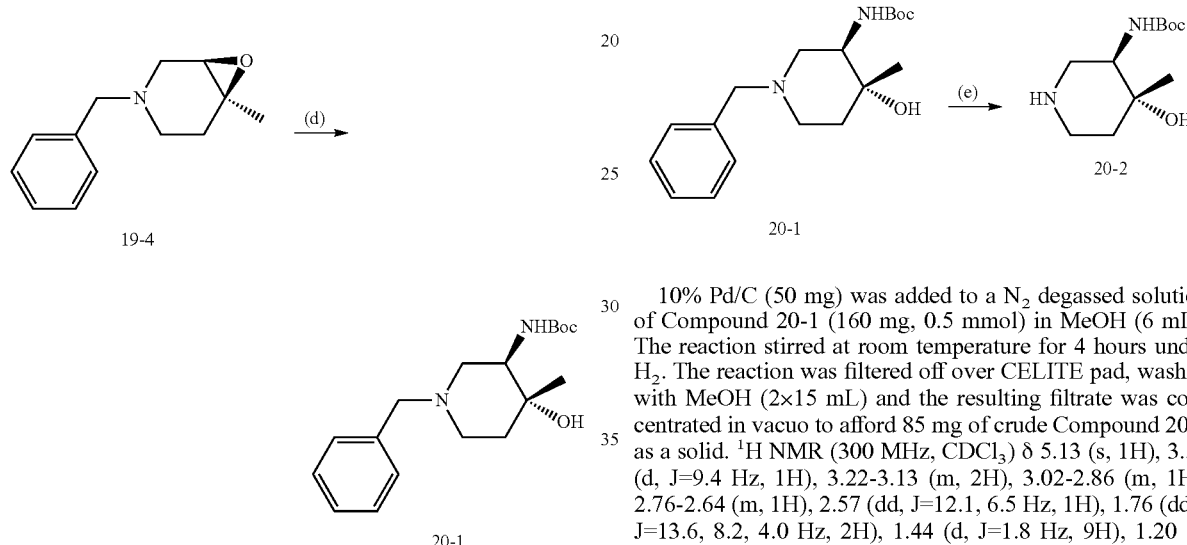

Compound 19-4 (500 mg, 2.46 mmol) was diluted in 30% aqueous ammonia solution (2 mL) and the reaction was stirred at 60° C. for 20 hours. The intermediate was formed. Then dioxane (10 mL) was added and the mixture was cooled to 0° C. before Na$_2$CO$_3$ (919 mg, 9.35 mmol) was added, followed by dropwise addition of (Boc)$_2$O (1.02 g, 4.67 mmol). The reaction was stirred at room temperature for 16 hours. The reaction mixture was quenched by sat. NH$_4$Cl and extracted twice with DCM (50 mL) and the combined organic layers were dried over Na$_2$SO$_4$ and concentrated in vacuo. The crude compound was purified by normal phase chromatography (12 g column) with a running gradient of 25-30% EtOAc/n-hexane to afford 230 mg of Compound 20-1 as a solid. $^1$H NMR (400 MHz, CDCl$_3$) δ 7.37-7.17 (m, 5H), 5.24 (s, 1H), 3.66-3.55 (m, 1H), 3.55-3.37 (m, 2H), 2.72 (dd, J=11.2, 2.9 Hz, 1H), 2.55-2.34 (m, 3H), 1.80 (bs, 1H), 1.78-1.69 (m, 1H), 1.62-1.48 (m, 1H), 1.44 (s, 9H), 1.20 (s, 3H). LC-MS=320.9 [M+H]$^+$, retention time=1.294 minutes.

10% Pd/C (50 mg) was added to a N$_2$ degassed solution of Compound 20-1 (160 mg, 0.5 mmol) in MeOH (6 mL). The reaction stirred at room temperature for 4 hours under H$_2$. The reaction was filtered off over CELITE pad, washed with MeOH (2×15 mL) and the resulting filtrate was concentrated in vacuo to afford 85 mg of crude Compound 20-2 as a solid. $^1$H NMR (300 MHz, CDCl$_3$) δ 5.13 (s, 1H), 3.50 (d, J=9.4 Hz, 1H), 3.22-3.13 (m, 2H), 3.02-2.86 (m, 1H), 2.76-2.64 (m, 1H), 2.57 (dd, J=12.1, 6.5 Hz, 1H), 1.76 (ddd, J=13.6, 8.2, 4.0 Hz, 2H), 1.44 (d, J=1.8 Hz, 9H), 1.20 (s, 3H). LC-MS=230.95 [M+H]$^+$, retention time=0.469 minutes.

The following Compounds were prepared by the same route used to prepare Compound 4-0.

| Example/Compound Number | Structure | NMR | LC-MS | Chiral Prep HPLC Method |
|---|---|---|---|---|
| 20-0 | (3S,4S)-3-amino-1-(5-(4-fluoro-2-methoxyphenyl)imidazo[2,1-b][1,3,4]thiadiazol-2-yl)-4-methylpiperidin-4-ol | $^1$H NMR (400 MHz, MeOD-d$_4$) δ 8.29 (dd, J = 8.7, 6.5 Hz, 1H), 7.91 (s, 1H), 7.05 (dd, J = 10.9, 2.4 Hz, 1H), 6.89 (td, J = 8.5, 2.4 Hz, 1H), 4.17 (dd, J = 13.5, 3.8 Hz, 1H), 3.99 (s, 3H), 3.80-3.72 (m, 2H), 3.63-3.49 (m, 1H), 3.36 (dd, J = 7.3, 3.8 Hz, 1H), 2.09-2.03 (m, 1H), 1.96-1.87 (m, 1H), 1.40 (s, 3H). | MS m/z calcd for C$_{17}$H$_{20}$FN$_5$O$_2$S 377.1 found 378.3 [M + H]$^+$ | 13 |

| Example/ Compound Number | Structure | NMR | LC-MS | Chiral Prep HPLC Method |
|---|---|---|---|---|
| 20-3 (3R,4R)-3-amino-1-(5-(4-fluoro-2-methoxyphenyl)imidazo[2,1-b][1,3,4]thiadiazol-2-yl)-4-methylpyridin-4-ol | | $^1$H NMR (400 MHz, MeOD-d$_4$) δ 8.30 (dd, J = 8.7, 6.5 Hz, 1H), 7.92 (s, 1H), 7.05 (dd, J = 11.0, 2.4 Hz, 1H), 6.90 (td, J = 8.5, 2.4 Hz, 1H), 4.17 (dd, J = 13.5, 3.7 Hz, 1H), 3.99 (s, 3H), 3.82-3.72 (m, 2H), 3.63-3.49 (m, 1H), 3.36 (dd, J = 7.3, 3.8 Hz, 1H), 2.10-2.02 (m, 1H), 1.96-1.87 (m, 1H), 1.40 (s, 3H). | MS m/z calcd for C$_{17}$H$_{20}$FN$_5$O$_2$S 377.1 found 378.3 [M + H]$^+$ | 13 |

Example 21-0: (3R,4R)-4-amino-1-(5-(4-fluoro-2-methoxyphenyl)imidazo[2,1-b][1,3,4]thiadiazol-2-yl)-4-methylpiperidin-3-ol Compound 21-0 was prepared in the following way:

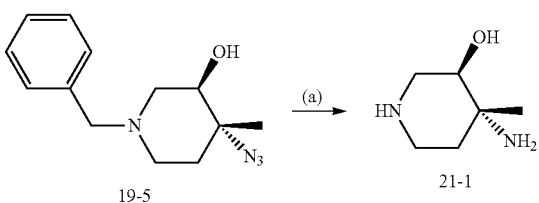

10% Pd/C (100 mg) was added to N$_2$ degassed solution of Compound 19-5 (800 mg, 3.25 mmol) in MeOH (5 mL) and stirred at room temperature for 16 hours under H$_2$. The suspension was filtered off over CELITE pad, was washed twice with MeOH (30 mL). The filtrate was evaporated to afford 400 mg of Compound 21-1 as a solid. $^1$H NMR (400 MHz, DMSO-d$_6$) δ 4.44 (bs, 1H), 3.32 (bs, 1H), 3.04 (dd, J=8.4, 4.0 Hz, 1H), 2.77 (dd, J=12.5, 4.0 Hz, 1H), 2.64 (dt, J=12.8, 4.7 Hz, 1H), 2.48-2.43 (m, 1H), 2.28 (dd, J=12.5, 8.3 Hz, 1H), 1.81-1.50 (m, 2H), 1.46-1.37 (m, 1H), 1.23-1.13 (m, 1H), 0.92 (s, 3H). LC-MS=131.2 [M+H]$^+$, retention time=0.255 minutes.

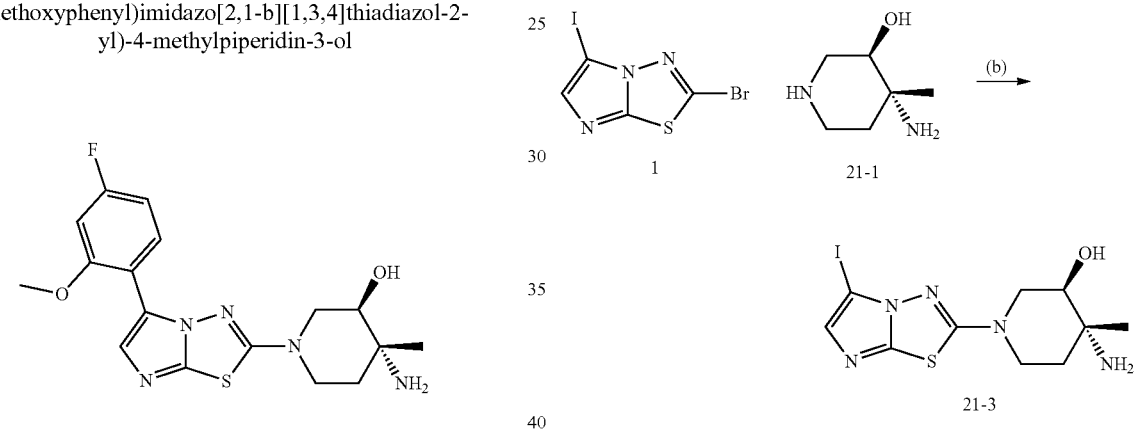

Compound 1 (400 mg, 1.21 mmol), Compound 21-1 (190 mg, 1.5 mmol), DIPEA (457 mg, 3.63 mmol) and MeCN (5 mL) was heated to 120° C. for 16 hours. The reaction was diluted with H$_2$O and extracted twice with EtOAc (50 mL) The combined organic layers were washed with brine (50 mL), dried over Na$_2$SO$_4$ and evaporated in vacuo. The crude compound was purified by normal phase chromatography with a running gradient of 0-17% MeOH/DCM to afford compound 21-3 350 mg as a solid. $^1$H NMR (400 MHz, DMSO-d$_6$) δ 7.60 (bs, 2H), 7.10 (s, 1H), 5.87 (d, J=4.4 Hz, 1H), 3.80-3.60 (m, 3H), 3.40-3.35 (m, 1H), 3.13 (d, J=10.0 Hz, 1H), 1.91-1.75 (m, 2H), 1.27 (s, 3H). LC-MS=380.0 [M+H]$^+$, retention time=0.97 minutes.

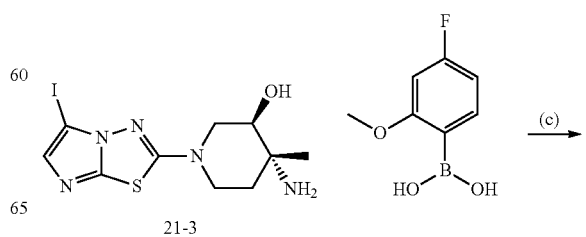

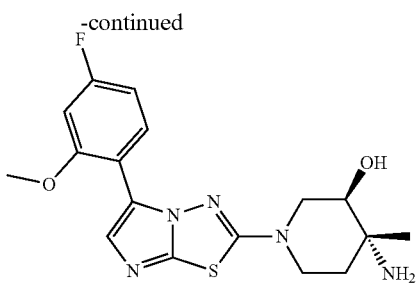

21

A solution of Compound 21-3 (1.0 equiv.), Na₂CO₃ (3.0 equiv.) and (4-fluoro-2-methoxyphenyl)boronic acid (1.2 equiv.) in 2:1:1 DMF/EtOH/H₂O, was degassed with argon for 15 minutes and then Pd(PPh₃)₄ (10 mol %) was added. The reaction mixture was heated at 80° C. for 2 hours. Then it was diluted with H₂O and extracted twice with EtOAc. The combined organic layers were washed with H₂O, then brine, dried over Na₂SO₄, filtered and concentrated in vacuo. The crude material was purified by normal phase chromatography with a running gradient of 0-30% MeOH/DCM to give 12 mg of Compound 21 as a solid. ¹H NMR (400 MHz, DMSO-d₆) δ 8.19 (dd, J=8.8, 7.6 Hz, 1H), 7.45 (s, 1H), 7.05 (dd, J=11.2, 2.4 Hz, 1H), 6.91 (dt, J=8.0, 2.4 Hz, 1H), 5.12 (d, J=4.4 Hz, 1H), 3.90 (s, 3H), 3.72 (dd, J=12.8, 3.6 Hz, 1H), 3.59-3.51 (m, 1H), 3.49-3.35 (m, 2H), 3.21 (dd, J=12.8, 6.8 Hz, 1H), 1.80-1.73 (m, 1H), 1.47-1.39 (m, 1H), 1.09 (s, 3H). LC-MS=378.1 [M+H]⁺, retention time=1.09 minutes.

Example 22-0: 4-(aminomethyl)-1-(5-(4-fluoro-2-methoxyphenyl)imidazo[2,1-b][1,3,4]thiadiazol-2-yl)piperidine-4-carboxamide

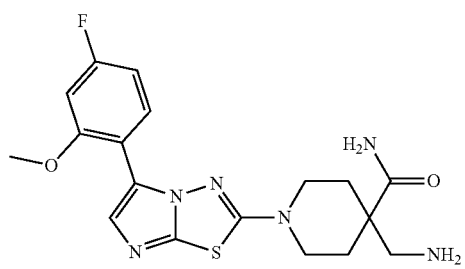 [SMILES: COc1cc(F)ccc1-c1cnc2sc(N3CCC(CN)(C(N)=O)CC3)nn12]

Compound 22-0 was prepared in the following way:

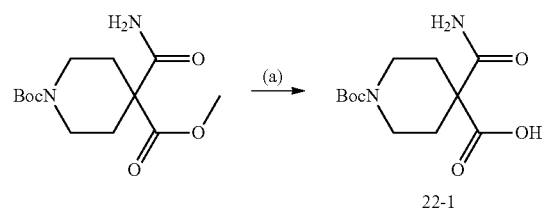 [SMILES: COC(=O)C1(C(N)=O)CCN(C(=O)OC(C)(C)C)CC1 ; CC(C)(C)OC(=O)N1CCC(C(N)=O)(C(=O)O)CC1]

To a suspension of 1-(tert-butoxycarbonyl)-4-(methoxycarbonyl)piperidine-4-carboxylic acid (500 mg, 1.740 mmol), NH₄Cl (186 mg, 3.48 mmol), HATU (794 mg, 2.088 mmol) in dry THF (10 mL) was added DIPEA (760 μL, 4.35 mmol). The resulting mixture was heated to 60° C. for 2.5 hours. The resulting mixture was quenched with sat. solution of NaHCO₃, extracted twice with EtOAc. The combined organic layers were dried over MgSO₄, filtered and concentrated in vacuo. The crude material was purified by normal phase chromatography (12 g column) with a running gradient of 0-20%. DCM/MeOH to afford 250 mg of Compound 22-1 as an oil. ¹H NMR (500 MHz, DMSO-d₆) δ 7.29 (s, 1H), 7.24 (s, 1H), 3.66 (s, 3H), 3.45-3.38 (m, 2H), 3.19-3.04 (m, 2H), 2.01-1.78 (m, 4H), 1.39 (s, 9H).

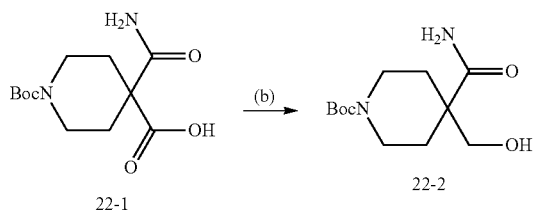 [SMILES: CC(C)(C)OC(=O)N1CCC(C(N)=O)(C(=O)O)CC1 ; CC(C)(C)OC(=O)N1CCC(CO)(C(N)=O)CC1]

To a solution of Compound 22-1 (250 mg, 0.611 mmol) in EtOH (3 mL) were added NaBH₄ (69.4 mg, 1.834 mmol). The reaction was stirred for 18 hours at room temperature. The mixture was quenched with H₂O at 0° C. The resulting cloudy mixture was concentrated in vacuo. The crude material was purified by normal phase chromatography (4 g column) with a running gradient of 0-100% to afford 90 mg of Compound 22-2 was a white foam. ¹H NMR (500 MHz, DMSO-d₆) δ 7.30 (s, 1H), 7.24 (s, 1H), 4.81 (t, J=5.5 Hz, 1H), 3.63 (d, J=13.1 Hz, 2H), 3.37 (d, J=5.4 Hz, 2H), 2.90 (s, 2H), 1.87 (d, J=13.7 Hz, 2H), 1.39 (s, 9H), 1.30 (ddd, J=14.2, 10.8, 4.2 Hz, 2H).

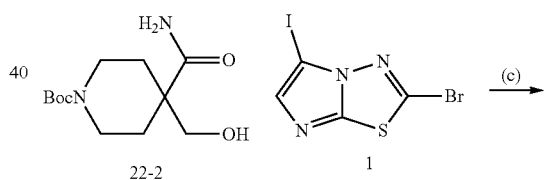

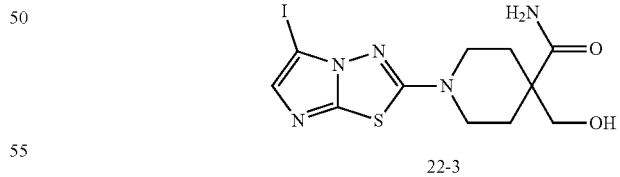

To a solution of Compound 22-2 (80 mg, 0.310 mmol) in MeOH (666 μL), 4 M HCl in dioxane (1316 μL, 5.26 mmol) was added. The reaction mixture was stirred at room temperature for 1.5 hours. The resulting white suspension was then concentrated in vacuo and mixed with Compound 1 (92 mg, 0.279 mmol) and DIPEA (162 μL, 0.929 mmol) in EtOH (1.3 mL). The reaction mixture was stirred at 90° C. for 3.5 hours. The reaction was concentrated in vacuo to afford Compound 22-3. LC-MS=408.1 [M+H]⁺.

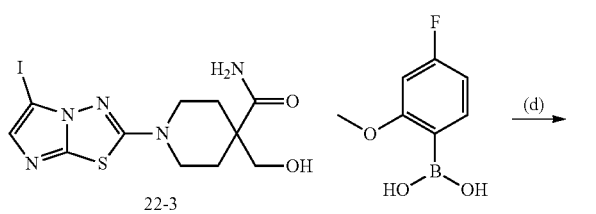
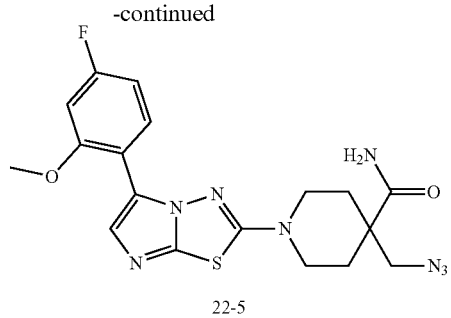

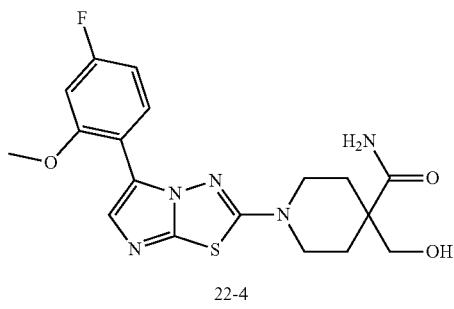

To a solution of Compound 22-3 (126 mg, 0.309 mmol) and (4-fluoro-2-methoxyphenyl)boronic acid (68.4 mg, 0.402 mmol) in dioxane (1.5 mL), Na$_2$CO$_3$ 2 M (1083 μL, 2.166 mmol), PdCl$_2$(Ph$_3$P)$_2$ (10.86 mg, 0.015 mmol) were added under argon. The reaction mixture was heated to 100° C. for 1 hour. The resulting solution was diluted in EtOAc and H$_2$O. The aqueous layer was separated and the organic layer was washed with H$_2$O. The resulting organic layer was dried over MgSO$_4$, filtered and concentrated in vacuo. The crude material was purified by normal phase chromatography (4 g column) with a running gradient of 0-100% DCM/MeOH to afford 73 mg of Compound 22-4 as a light orange foam. $^1$H NMR (500 MHz, DMSO-d$_6$) δ 8.20 (ddd, J=8.5, 6.8, 1.4 Hz, 1H), 7.47 (d, J=1.3 Hz, 1H), 7.25 (s, 1H), 7.10-7.01 (m, 2H), 6.92 (tt, J=8.5, 1.9 Hz, 1H), 4.93-4.88 (m, 1H), 4.10 (tt, J=6.3, 3.1 Hz, 1H), 3.91 (d, J=1.3 Hz, 3H), 3.68 (dt, J=13.1, 4.4 Hz, 2H), 3.44 (d, J=5.7 Hz, 2H), 3.32 (d, J=1.5 Hz, 2H), 3.32-3.21 (m, 2H), 3.18 (dd, J=5.2, 1.4 Hz, 2H), 2.06 (d, J=13.9 Hz, 2H), 1.58 (ddd, J=14.6, 11.3, 4.4 Hz, 2H). LC-MS=406.1 [M+H]$^+$.

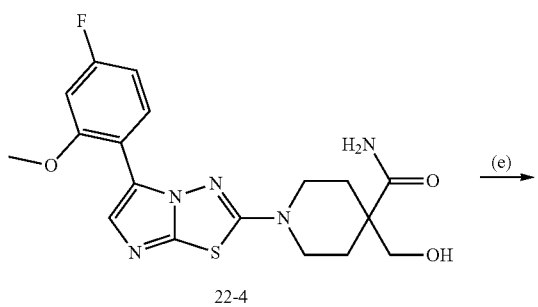

To a solution of Compound 22-4 (32 mg, 0.079 mmol) in DCM (1 mL), Et$_3$N (0.055 ml, 0.395 mmol), MsCl (0.08 mmol), and DMAP (9.64 mg, 0.079 mmol) were added at 0° C. The reaction mixture was stirred at room temperature for 2 hours. After dilution with EtOAc, the organic layer was washed with H$_2$O and brine, dried over Na$_2$SO$_4$, filtered and concentrated in vacuo to give a solid. Then DMF (1 mL), 15-crown-5 (0.126 ml, 0.631 mmol) and NaN$_3$ (41.0 mg, 0.631 mmol) were added. The resulting solution was heated to 100° C. for 18 hours. After dilution with EtOAc, the organic layer was washed with H$_2$O and brine, dried over Na$_2$SO$_4$, filtered, and concentrated in vacuo to give 15 mg of Compound 22-5. LC-MS=431.3 [M+H]$^+$.

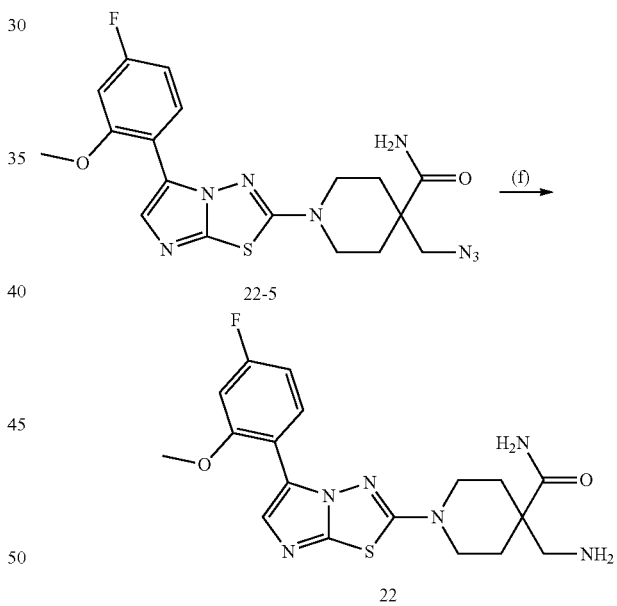

A solution of Compound 22-5 (23 mg, 0.053 mmol) and Ph$_3$P (28.0 mg, 0.107 mmol) in THF (427 μL) was heated at 60° C. for 4 hours. The resulting solution was quenched with aqueous HCl. The resulting mixture was concentrated in vacuo and diluted in THF (1 mL). The reaction was heated again to 60° C. for 18 hours and then 100° C. for 2 days. The resulting mixture was concentrated in vacuo and purified by prep-HPLC to afford 5.8 mg of Compound 22. $^1$H NMR (500 MHz, DMSO-d$_6$) δ 8.20 (dd, J=8.7, 6.9 Hz, 1H), 7.80 (s, 2H), 7.67 (s, 1H), 7.51 (s, 1H), 7.48 (s, 1H), 7.07 (dd, J=11.4, 2.6 Hz, 1H), 6.91 (td, J=8.4, 2.5 Hz, 1H), 3.91 (s, 3H), 3.66-3.60 (m, 2H), 3.40 (t, J=9.1 Hz, 2H), 3.07 (d, J=6.1 Hz, 2H), 2.19-2.12 (m, 2H), 1.73-1.65 (m, 2H). LC-MS=405.3 [M+H]$^+$.

167

Example 23-0: N-((1-aminocyclopropyl)methyl)-4-(aminomethyl)-1-(5-(4-fluoro-2-methoxyphenyl)imidazo[2,1-b][1,3,4]thiadiazol-2-yl)piperidine-4-carboxamide

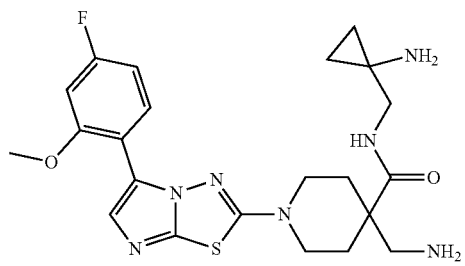 [SMILES: COc1cc(F)ccc1-c1cnc2sc(N3CCC(CN)(C(=O)NCC4(N)CC4)CC3)nn12]

Compound 23-0 was prepared in the following way:

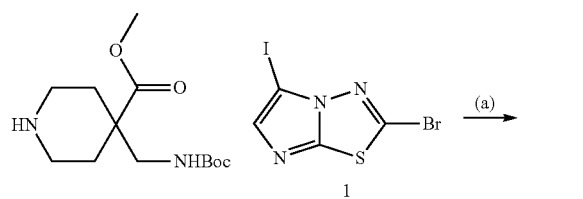

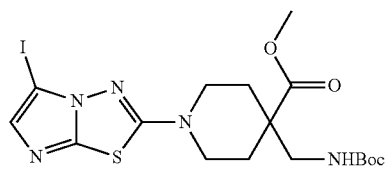

To a suspension of Compound 1 (363 mg, 1.102 mmol) in EtOH (5 mL), DIPEA (0.385 mL, 2.203 mmol) and methyl 4-(((tert-butoxycarbonyl)amino)methyl)piperidine-4-carboxylate (300 mg, 1.102 mmol) were added. The resulting suspension was heated at 80° C. for 8 hours. The mixture was quenched with a sat. solution of NaHCO₃ and diluted with EtOAc. The organic layer was separated and the aqueous layer was extracted twice with EtOAc. The combined organic layers were dried over MgSO₄, filtered and concentrated in vacuo to afford 460 mg of Compound 23-1. LC-MS=522.1 [M+H]⁺.

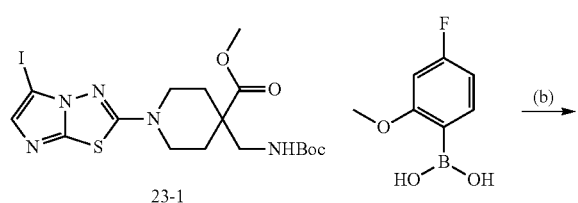

168

-continued

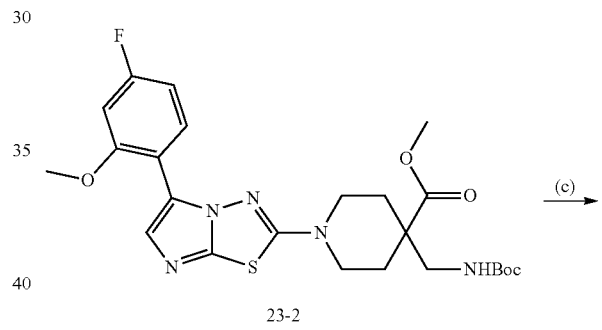

To a solution of Compound 23-1 (100 mg, 0.192 mmol), (4-fluoro-2-methoxyphenyl)boronic acid (42.4 mg, 0.249 mmol) and Na₂CO₃ 2 M (0.671 mL, 1.343 mmol) in dioxane (2 mL) was added PdCl₂(Ph₃P)₂ (9.59 μmol). The resulting mixture was heated to 100° C. for 2 hours. The mixture was quenched with a sat. solution of NaHCO₃ and then diluted with EtOAc. The organic layer was separated and the aqueous layer was extracted twice with EtOAc. The combined organic layers were dried over MgSO₄, filtered and concentrated in vacuo. The crude product was purified by normal phase chromatography (4 g column) with a running gradient of 0-100% EtOAc/Cyclohexane to afford 83 mg of Compound 23-2 as a solid. LC-MS=520.0 [M+H]⁺.

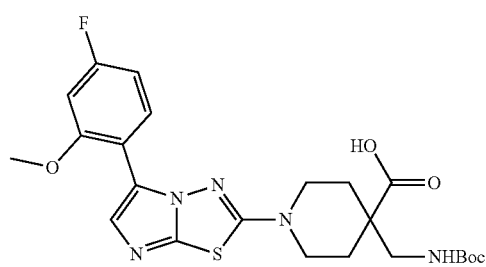

To a solution of Compound 23-2 (30 mg, 0.058 mmol) in MeOH (462 μL) and H₂O (115 μL), LiOH (2.77 mg, 0.115 mmol) was added at room temperature. The reaction mixture was stirred for 18 hours at room temperature and then concentrated in vacuo to afford Compound 23-3. LC-MS=506.2 [M+H]⁺.

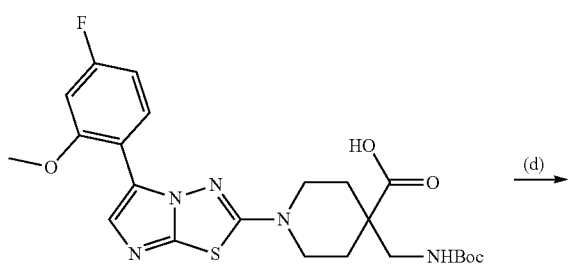

23-3

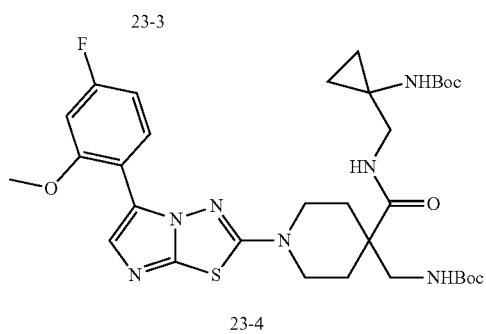

23-4

A solution of Compound 23-3 (29 mg, 0.057 mmol), tert-butyl (1-(aminomethyl)cyclopropyl)carbamate (14.75 mg, 0.079 mmol), HATU (34.4 mg, 0.091 mmol) and DIPEA (0.025 mL, 0.141 mmol) was dissolved in DMF (1 mL). The reaction was stirred for 48 hours. The mixture was quenched with a sat. solution of NaHCO$_3$ and then EtOAc was added. The organic layer was separated and the aqueous layer was extracted twice with EtOAc. The combined organic layers were dried over MgSO$_4$, filtered and concentrated in vacuo. The crude product was purified by normal phase chromatography (4 g column) with a running gradient of 0-20% MeOH/DCM to afford 22 mg of Compound 23-4 as an oil. LCMS=674.6 [M+H]$^+$.

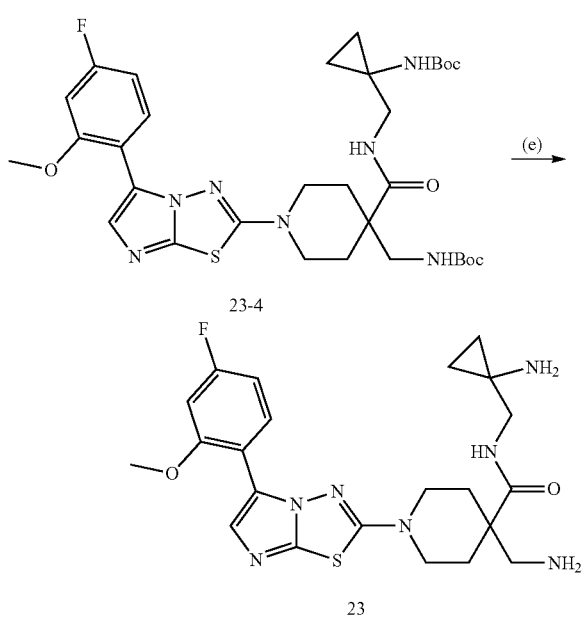

23-4

23

A solution of Compound 23-4 (22 mg, 0.033 mmol) and TFA (200 μL, 2.60 mmol) in DCM (600 μL) was stirred at room temperature for 2 hours. The reaction was concentrated in vacuo and purified by prep-HPLC to afford 10.5 mg of Compound 23. $^1$H NMR (500 MHz, DMSO-d$_6$) δ 8.33 (d, J=6.2 Hz, 1H), 8.22 (dd, J=8.7, 6.8 Hz, 1H), 8.15 (s, 3H), 7.86 (s, 3H), 7.54 (s, 1H), 7.10 (dd, J=11.4, 2.6 Hz, 1H), 6.92 (td, J=8.4, 2.6 Hz, 1H), 3.93 (s, 3H), 3.66 (d, J=11.4 Hz, 2H), 3.51-3.34 (m, 4H), 3.15 (d, J=5.9 Hz, 2H), 2.19 (d, J=13.4 Hz, 2H), 1.83-1.67 (m, 2H), 0.92-0.79 (m, 4H). LC-MS=474.2 [M+H]$^+$.

Example 24-0: N-(2-amino-2-methylpropyl)-8-(5-(4-fluoro-2-methoxyphenyl)imidazo[2,1-b][1,3,4]thiadiazol-2-yl)-1-thia-8-azaspiro[4.5]decane-4-carboxamide 1,1-dioxide

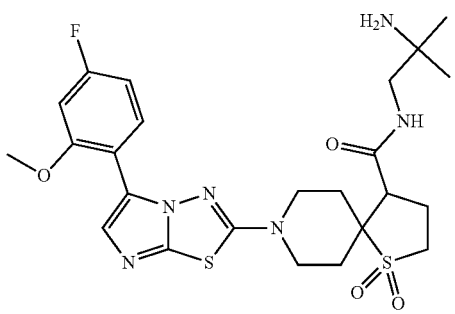 [SMILES: COc1cc(F)ccc1-c1cnc2sc(N3CCC4(CC3)C(C(=O)NCC(C)(C)N)CCS4(=O)=O)nn12]

Compound 24-0 was prepared in the following way:

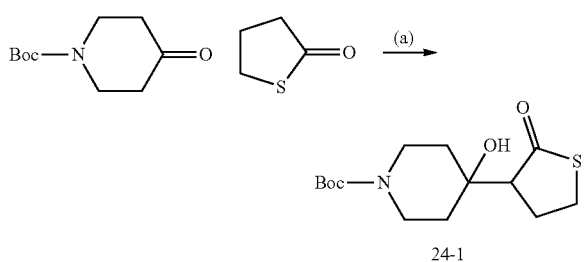

24-1

To the stirred solution of dihydrothiophen-2(3H)-one (3.07 g, 30.11 mmol) in THF (50 mL) was added LiHMDS (30 mL, 30.11 mmol) at −78° C. and stirred for 1 hour. The tert-butyl 4-oxopiperidine-1-carboxylate (5 g, 25.09 mmol) in THF (30 mL) was added to the reaction mixture at −78° C. and stirred at same temperature for 2 hours. The reaction mixture was quenched with sat. NH$_4$Cl solution and extracted with EtOAc (3×50 mL). The organic layer was washed with brine and dried over Na$_2$SO$_4$ and concentrated in vacuo. The crude product was purified normal phase chromatography with a running gradient of 30-40% EtOAc/n-hexane to afford 6.12 g of Compound 24-1 as a solid. $^1$H NMR (600 MHz, CDCl$_3$) δ 3.94 (br s, 2H), 3.68 (br s, 1H), 3.28-3.25 (m, 2H), 3.13 (br s, 2H), 2.66 (dd, J=13.2, 7.0 Hz, 1H), 2.43 (dtd, J=12.0, 7.0, 2.9 Hz, 1H), 2.06-2.03 (m, 1H), 1.67 (dd, J=13.2, 2.4 Hz, 1H) 1.59-1.48 (m, 3H), 1.45 (s, 9H). LC-MS=202.10 [M-100]$^+$ (De-Boc), retention time=1.47 minutes.

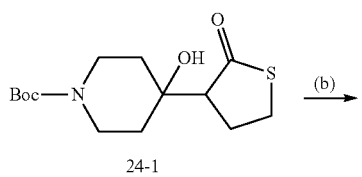

To a stirred solution of Compound 24-1 (6.0 g, 19.9 mmol) in DCM (60 mL) at 0° C. was added Et₃N (27.7 mL, 199 mmol) and MsCl (3.08 mL, 39.81 mmol). The reaction allowed to warm at room temperature and stirred for 18 hours. The reaction mixture was quenched with sat. NaHCO₃ solution and extracted with DCM (3×50 mL). The organic layer was washed with brine and dried over Na₂SO₄ and concentrated in vacuo. The crude product was purified by normal phase chromatography with a running gradient of 30-40% EtOAc/hexane to afford 1.2 g of Compound 24-2 as a colourless liquid. ¹H NMR (400 MHz, CDCl₃) δ 3.53 (t, J=6.0 Hz, 2H), 3.43 (t, J=5.8 Hz, 2H), 3.26 (t, J=6.8 Hz, 2H), 3.07-2.94 (m, 4H), 2.34 (t, J=6.0 Hz, 2H), 1.46 (s, 9H). LC-MS=184.10 [M-100]⁺ (De-Boc), retention time=1.54 minutes.

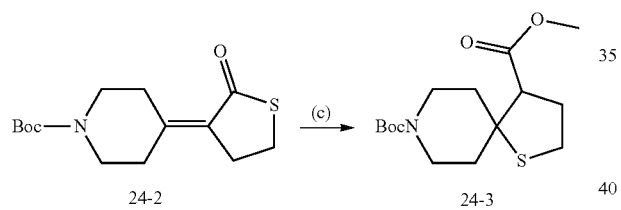

To a stirred solution of Compound 24-2 (3.3 g, 2.82 mmol) in MeOH (330 mL) was added Et₃N (0.79 mL, 5.64 mmol). The reaction mixture was heated at 70° C. and stirred for 32 hours. The reaction was concentrated in vacuo. The crude product was purified by normal phase chromatography with a running gradient of 5-10% EtOAc/n-hexane to afford 1.2 g of Compound 24-3 as a colourless liquid. ¹H NMR (300 MHz, CDCl₃) δ 4.09 (br s, 2H), 3.71 (s, 3H), 3.06-2.68 (m, 5H), 2.50-2.27 (m, 2H), 2.14 (td, J=13.0, 4.6 Hz, 1H), 1.67 (ddd, J=13.1, 10.1, 2.6 Hz, 2H), 1.45 (s, 9H) 1.42-1.48 (m, 1H). LC-MS=216.15 [M-100]⁺ (De-Boc), retention time=1.61 minutes.

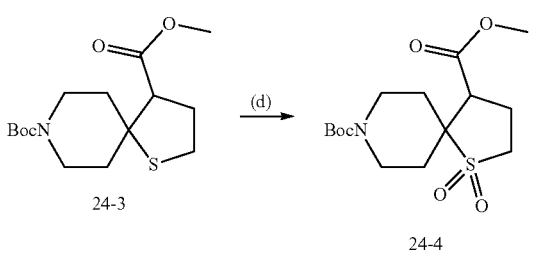 [SMILES: COC(=O)C1CCSC12CCN(C(=O)OC(C)(C)C)CC2 ; COC(=O)C1CCS(=O)(=O)C12CCN(C(=O)OC(C)(C)C)CC2]

To a stirred solution of Compound 24-3 (1.1 g, 2.85 mmol) in DCM (30 mL) was added mCPBA (1.4 g, 5.17 mmol) portionwise at 0° C. and the reaction mixture was stirred at room temperature for 4 hours. The reaction mixture filtered over CELITE pad and filtrate washed with sat. NaHCO₃, extracted aqueous layer with DCM (50 mL×2). The combined organic layers were washed with brine, dried over Na₂SO₄ and concentrated in vacuo to get 1.1 g of Compound 24-4 as a colourless liquid, which was used in next step without further purification. ¹H NMR (400 MHz, CDCl₃) δ 3.94 (bs, 2H), 3.76 (s, 3H), 3.50-3.32 (m, 2H), 3.30-3.18 (m, 1H), 3.15-3.06 (m, 1H), 2.99 (dd, J=11.1, 6.3 Hz, 1H), 2.51-2.40 (m, 1H), 2.29-2.20 (m, 2H), 2.16-2.02 (m, 2H), 1.65-1.52 (m, 1H), 1.45 (s, 9H).

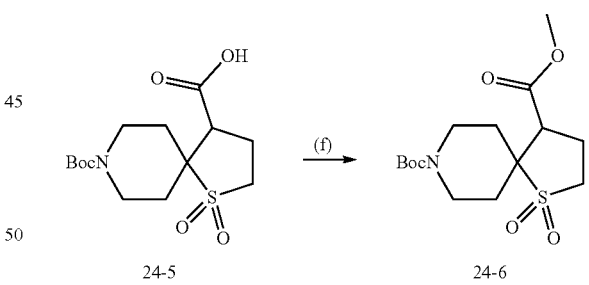

To the stirred solution of Compound 24-4 (1.1 g, 3.16 mmol) in THF:H₂O (10 mL, 1:1) was added LiOH H₂O (0.19 g, 4.74 mmol) at 0° C. and the reaction mixture was stirred at room temperature for 3 hours. The reaction mixture was acidified with sat. citric acid to pH=4 and extracted with DCM (50 mL×2). The organic layer was washed with brine and dried over Na₂SO₄ and concentrated in vacuo to afford 0.9 g of Compound 24-5 as a solid. ¹H NMR (300 MHz, DMSO-d₆) δ 3.85-3.70 (m, 2H), 3.46-3.35 (m, 2H), 3.15 (dt, J=13.3, 9.0 Hz, 2H), 2.94 (dd, J=10.4, 7.1 Hz, 1H), 2.31-2.11 (m, 2H), 2.04 (td, J=9.9, 4.0 Hz, 3H), 1.57 (ddd, J=15.0, 11.2, 4.9 Hz, 1H), 1.39 (s, 9H).

To the stirred solution of Compound 24-5 (350 mg, 1.05 mmol) in DMF (5 mL) was added K₂CO₃ (290 mg, 2.1 mmol) at 0° C., after stirring for 10 minutes added MeI (296 mg, 2.1 mmol) dropwise and the reaction mixture was stirred at room temperature for 7 hours. Then H₂O was added to the reaction mixture and the aqueous layer was extracted with EtOAc (2×30 mL), the organic layer was washed with brine, dried over Na₂SO₄ and concentrated in vacuo to afford 350 mg of Compound 24-6 as an oil. ¹H NMR (400 MHz, CDCl₃) δ 3.95 (bs, 2H), 3.75 (s, 3H), 3.44 (bs, 1H), 3.35 (ddd, J=13.4, 9.5, 3.9 Hz, 1H), 3.30-3.18 (m, 1H), 3.15-3.06 (m, 1H), 2.98 (dd, J=11.2, 6.5 Hz, 1H), 2.45 (ddt, J=14.1, 11.2, 9.3 Hz, 1H), 2.30-2.17 (m, 2H), 2.15-2.01 (m, 3H), 1.65-1.52 (m, 1H), 1.45 (s, 9H).

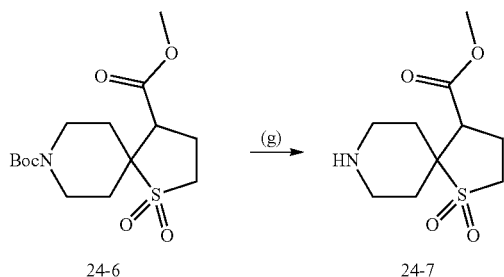 [SMILES: COC(=O)C1CCS(=O)(=O)C12CCN(C(=O)OC(C)(C)C)CC2 ; COC(=O)C1CCS(=O)(=O)C12CCNCC2]

To a solution of Compound 24-6 (350 mg, 1.0 mmol) in dioxane (3 mL) was added 4 M HCl in dioxane (3 mL) at 0° C., then stirred at 0° C. to room temperature for 2 hours. The reaction was concentrated in vacuo to get 350 mg of Compound 24-7 which was used in next step without purification. LC-MS=248.0 [M+H]$^+$, retention time=0.15 minutes.

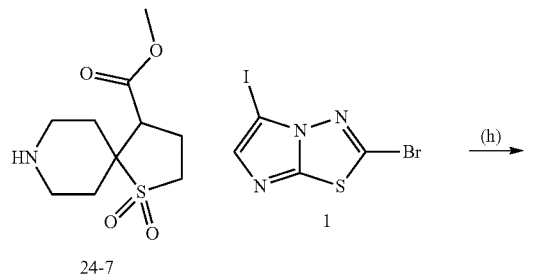

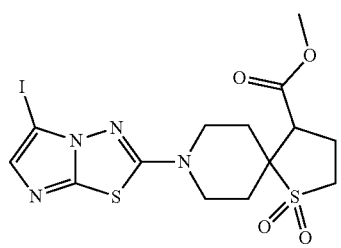

Compound 24-7 (1 equiv), Compound 1 (1 equiv), DIPEA (2 equiv) and MeCN (15-20 volume) was heated to 100° C. for 90 minutes in MW. The reaction mixture was cooled to room temperature, stirred for 1 hour at room temperature until precipitate was formed. The solid was filtered and washed with MeCN and pentane. The crude material was purified by normal phase chromatography with a running gradient of 5/95 MeOH/DCM to get Compound 24-8 as an oil. $^1$H NMR (300 MHz, CDCl$_3$) δ 7.11 (s, 1H), 3.82-3.77 (m, 2H), 3.75 (s, 3H), 3.67-3.34 (m, 3H), 3.23-2.98 (m, 2H), 2.59-2.18 (m, 4H), 1.94-1.76 (m, 2H).

To a sealed tube containing Compound 24-8 (1.0 equiv.) in dioxane:H$_2$O (4:1) was added K$_2$CO$_3$ (3 equiv.), (4-fluoro-2-methoxyphenyl)boronic acid (1.5 equiv.) and PdCl$_2$(dppf)-DCM complex (5 mol %). The reaction mixture was heated at 100° C. for 6 hours before it was diluted with H$_2$O and extracted twice with EtOAc. The combined organic layers were washed with H$_2$O, then brine, dried over Na$_2$SO$_4$, filtered and concentrated in vacuo to give crude material confirmed by LC-MS=495.05 [M+H]$^+$, retention time=1.48 minutes=481.15 [M+H]$^+$, retention time=1.40 minutes for acid (Method 12). The crude compound was taken THF:H$_2$O (5 mL, 4:1) cooled to 0° C. and LiOH (22 mg, 0.52 mmol) was added. The reaction mixture was stirred at room temperature for 5 hours. The reaction was concentrated in vacuo, was dissolved in H$_2$O, washed with DCM (10 mL×3) and then aqueous layer was acidified with KHSO$_4$ to acidic pH. The aqueous layer was extracted with DCM (20 mL×3), the combined organic layers were washed with brine, dried over Na$_2$SO$_4$ and concentrated in vacuo to get Compound 24-9 as a solid. LC-MS=481.15 [M+H]$^+$, retention time=1.39 minutes.

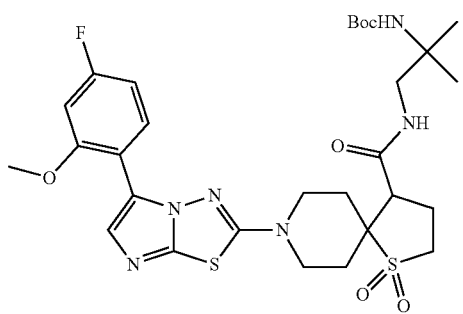

24-10

To a solution of Compound 24-9 (100 mg, 0.21 mmol) in DCM (8 mL) was added DIPEA (0.072 mL, 0.42 mmol) followed by addition of tert-butyl (1-amino-2-methylpropan-2-yl)carbamate (31 mg, 0.17 mmol) at 0° C. stirred over 5 minutes. T₃P-50% in EtOAc (159 mg, 0.25 mmol) was added at 0° C. and the reaction mixture was stirred at room temperature for 2 hours. The aqueous layer was extracted with DCM (50 mL×2). The combined organic layers were washed with brine, dried over Na₂SO₄ and concentrated in vacuo. The crude product was purified by normal phase chromatography with a running gradient of 2-3% MeOH in DCM to get 50 mg of Compound 24-10 as a solid. ¹H NMR (300 MHz, CDCl₃) δ 8.11 (dd, J=8.5, 6.8 Hz, 1H), 7.56 (s, 1H), 6.82-6.67 (m, 2H), 4.56 (s, 1H), 3.91 (s, 3H), 3.87-3.72 (m, 3H), 3.69-3.52 (m, 1H), 3.49-3.28 (m, 3H), 3.24-3.09 (m, 1H), 2.80 (dd, J=11.6, 6.3 Hz, 1H), 2.69-2.51 (m, 1H), 2.41 (d, J=13.9 Hz, 1H), 2.30-2.15 (m, 3H), 2.12-1.97 (m, 2H), 1.59 (s, 9H), 1.41 (s, 6H). LC-MS=651.35 [M+H]⁺ retention time=1.49 minutes.

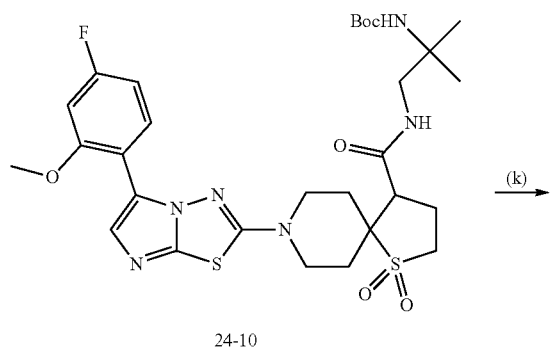

24-10

24

To a solution of Compound 24-10 in dioxane (10 mL) was added 4 M HCl in dioxane (10 mL) at 0° C., then stirred at 0° C. to room temperature for 2 hours. The solvent was evaporated in vacuo. The crude compound was purified by triturating in MeCN and pentane, filtered and dried resultant solid to get Compound 24 as HCl salt. ¹H NMR (300 MHz, MeOD-d₄) δ 8.55 (t, J=5.7 Hz, 1H), 8.28 (dd, J=8.8, 6.5 Hz, 1H), 7.89 (s, 1H), 7.02 (dd, J=11.0, 2.5 Hz, 1H), 6.88 (ddd, J=8.8, 8.1, 2.5 Hz, 1H), 3.97 (s, 3H), 3.94-3.83 (m, 2H), 3.77-3.64 (m, 1H), 3.60-3.47 (m, 2H), 3.27-3.21 (m, 1H), 3.20-3.05 (m, 2H), 2.57-2.40 (m, 2H), 2.40-2.05 (m, 4H), 1.28 (d, J=4.0 Hz, 6H). LC-MS=551.6 [M+H]⁺, retention time=1.32 minutes.

Compound 25-0: 2-(4-amino-1-(5-(4-fluoro-2-methoxyphenyl)imidazo[2,1-b][1,3,4]thiadiazol-2-yl)piperidin-4-yl)propan-2-ol

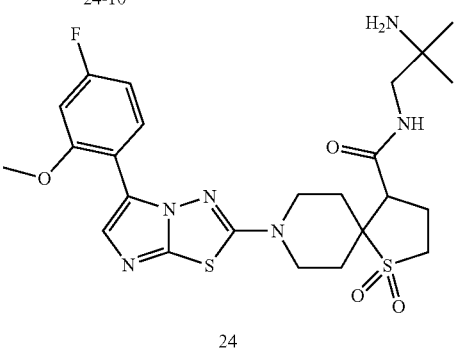

The Compound 25-0 was prepared in the following way:

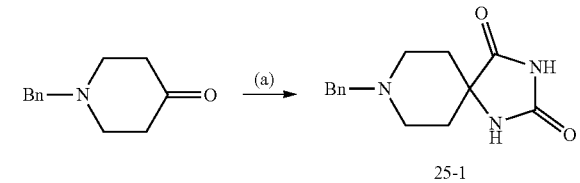 [SMILES: O=C1CCN(Cc2ccccc2)CC1 ; O=C1NC(=O)C2(CCN(Cc3ccccc3)CC2)N1]

25-1

A mixture of 1-benzylpiperidin-4-one (30 g, 159 mmol), (NH₄)₂CO₃ (107 g, 1113 mmol) and NaCN (23.4 g, 477 mmol) in H₂O (210 mL) and EtOH (210 mL) was stirred at 60° C. for 12 hours. The reaction mixture was filtered and the resulting solid was washed with H₂O (150 mL), dried to afford 37 g of Compound 25-1 as a solid. ¹H NMR (DMSO-d₆, 400 MHz) δ 1.51 (br, d, J=13.0 Hz, 2H), 1.73-1.90 (m, 2H), 2.15-2.35 (m, 2H), 2.60-2.77 (m, 2H), 3.48 (s, 2H), 7.18-7.39 (m, 5H).

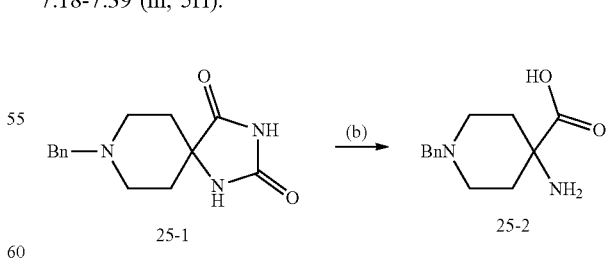

25-1
25-2

A mixture of Compound 25-1 (37 g, 143 mmol) and KOH (80 g, 1430 mmol) in H₂O (400 mL) was stirred at 100° C. for 24 hours. The mixture was cooled to 15° C. The pH of the reaction was adjusted to 6 with aqueous HCl (6 M) at 0° C. The reaction mixture was filtered, washed with H₂O and MTBE, and concentrated in vacuo to afford 31 g of Compound 25-2 as a solid. ¹H NMR (400 MHz, DMSO-d₆) δ

1.86 (br, s, 2H), 2.11 (br, d, J=6.1 Hz, 2H), 2.80-3.06 (m, 4H), 3.92 (br, s, 2H), 7.29-7.49 (m, 5H).

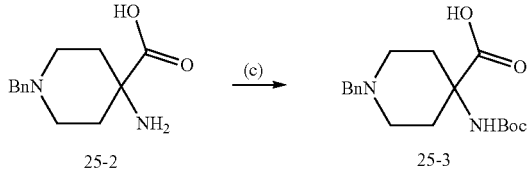 [SMILES: NC1(C(=O)O)CCN(Cc2ccccc2)CC1 ; CC(C)(C)OC(=O)NC1(C(=O)O)CCN(Cc2ccccc2)CC1]

25-2    25-3

To a solution of Compound 25-2 (15 g, 64 mmol) and NaOH (10.2 g, 256 mmol) in H₂O (50 mL) and dioxane (50 mL), (Boc)₂O (41.9 g, 192 mmol) was added. The resulting mixture was stirred at 15° C. for 3 hours. The mixture was filtered and the resulting solid was washed with H₂O (50 mL) and dried to afford 17 g of Compound 25-3 as a white solid. $^1$H NMR (400 MHz, MeOD-d$_4$) δ 1.43 (s, 9H), 2.35-2.11 (m, 4H), 2.99-2.77 (m, 2H), 3.16 (br, s, 2H), 4.07 (br, s, 2H), 7.54-7.20 (m, 5H). LC-MS=335.3 [M+H]⁺.

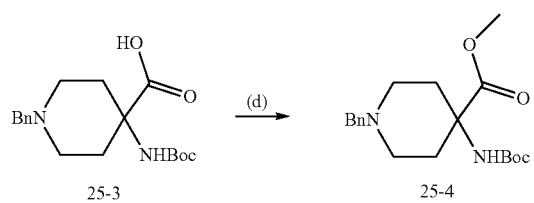 [SMILES: CC(C)(C)OC(=O)NC1(C(=O)O)CCN(Cc2ccccc2)CC1 ; COC(=O)C1(NC(=O)OC(C)(C)C)CCN(Cc2ccccc2)CC1]

25-3    25-4

To a solution of Compound 25-3 (8 g, 20 mmol) in DCM (50 mL) and MeOH (5 mL), TMSCHN₂ (2 M, 4.6 g, 40 mmol) was added. The resulting mixture was stirred at 15° C. for 3 hours. The mixture was concentrated in vacuo. The reaction was purified by normal phase chromatography with a running gradient of 1:0 to 1:2 petroleum ether:EtOAc to afford 4.5 g of Compound 25-4 as a solid. $^1$H NMR (400 MHz, DMSO-d$_6$) δ 1.36 (br, s, 9H), 1.81-1.88 (m, 2H), 2.12-2.29 (m, 2H), 3.32 (br, s, 4H), 3.43 (s, 2H), 3.58 (s, 3H), 7.20-7.37 (m, 5H). LC-MS=349.3 [M+H]⁺.

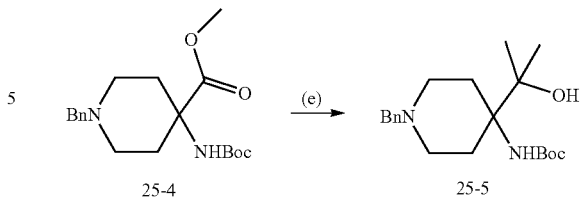

25-4    25-5

To a solution of Compound 25-5 (4.5 g, 12 mmol) in anhydrous THF (50 mL), MeMgBr (3 M in Et₂O, 12.6 mL, 37.8 mol) was slowly added at −15° C. The mixture was stirred for 0.5 hour and then warmed up to 15° C. for 15.5 hours. The mixture was poured into sat. NH₄Cl (30 mL) solution and extracted with EtOAc (3×50 mL). The combined organic layers were washed with brine, dried over MgSO₄ and concentrate in vacuo. The crude product was purified by prep-HPLC to afford 1.6 g of Compound 25-5 as a solid. $^1$H NMR (400 MHz, DMSO-d$_6$) δ 1.03 (s, 6H), 1.37 (s, 9H), 1.51-1.69 (m, 2H), 1.89-2.11 (m, 4H), 2.58 (br, d, J=11.0 Hz, 2H), 3.39 (s, 2H), 4.49 (s, 1H), 6.20 (s, 1H), 7.17-7.35 (m, 5H). LC-MS=349.4 [M+H]⁺.

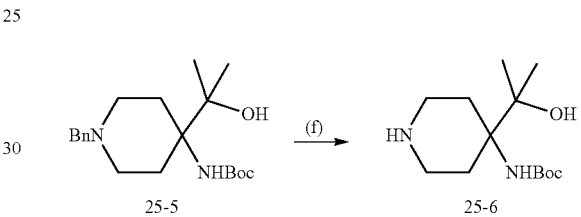

25-5    25-6

A suspension of Compound 25-5 (1.6 g, 4.6 mmol) and Pd/C (2 g, 10% content) in MeOH (1 mL) was stirred under H₂ (15 psi) at room temperature for 1 hour. The reaction mixture was filtered and the filtrate was concentrated in vacuo to afford 968.5 mg of Compound 25-6 as a solid. $^1$H NMR (400 MHz, MeOD-d$_4$) δ 1.17 (s, 6H), 1.45 (s, 9H), 1.62 (dt, J=4.3, 13.2 Hz, 2H), 2.00-2.15 (m, 2H), 2.64-2.79 (m, 2H), 2.80-2.92 (m, 2H). LC-MS=259.2 [M+H]⁺.

The following compound 25-0 was prepared by the same route used to prepare Compound 4-0.

| Example/ Compound Number | Structure | NMR | LC-MS |
| --- | --- | --- | --- |
| 25-0 | 2-(4-amino-1-(5-(4-fluoro-2-methoxyphenyl)imidazo[2,1-b][1,3,4]thiadiazol-2-yl)piperidin-4-yl)propan-2-ol | $^1$H NMR (500 MHz, MeOD-d$_4$) δ 8.27 (t, J = 7.7 Hz, 1H), 7.83 (s, 1H), 7.02 (d, J = 10.9 Hz, 1H), 6.92-6.84 (m, 1H), 4.11-4.03 (m, 2H), 3.98 (s, 3H), 3.53 (t, J = 13.0 Hz, 2H), 2.20 (td, J = 13.2, 5.2 Hz, 2H), 2.06 (d, J = 14.7 Hz, 2H), 1.34 (s, 6H). | MS m/z calcd for C$_{19}$H$_{24}$FN$_5$O$_2$S 405.2 found 406.3 [M + H]⁺ |

Example 26-0: 4-(aminomethyl)-1-(5-(4-(1-hydroxycyclobutyl)-2-methoxyphenyl)imidazo[2,1-b][1,3,4]thiadiazol-2-yl)piperidin-4-ol

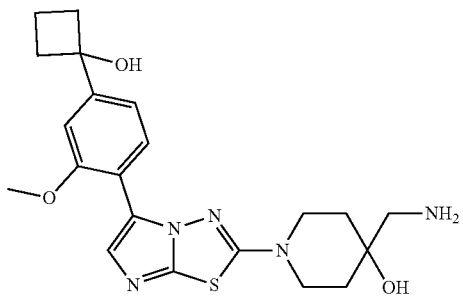 [SMILES: COc1cc(C2(O)CCC2)ccc1-c1cnc2sc(N3CCC(O)(CN)CC3)nn12]

The Compound 26-0 was prepared in the following way:

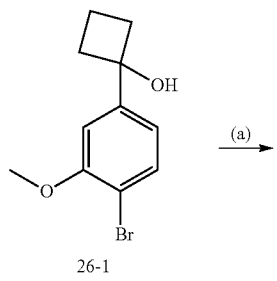

To a solution of Compound 26-1 (500 mg, 2.06 mmol) in DCM (25 mL) at 0° C., imidazole (420 mg, 6.17 mmol), TBDMS-Cl (620 mg, 4.11 mmol) and DMAP (5 mg) were added. The resulting solution was stirred at room temperature for 18 hours. The reaction was diluted with H$_2$O and extracted twice with EtOAc (100 mL). The combined organic layers were washed with brine, dried over Na$_2$SO$_4$ and concentrated in vacuo. The crude material was purified by normal phase chromatography with a running gradient of 0-2% EtOAc/n-hexane to afford 410 mg of Compound 26-2 as an oil. $^1$H NMR (300 MHz, CDCl$_3$) δ 7.41 (d, J=8.1 Hz, 1H), 7.06 (d, J=2.0 Hz, 1H), 6.59 (dd, J=8.3, 2.1 Hz, 1H), 3.90 (s, 3H), 1.70-1.60 (m, 1H), 1.26-1.14 (m, 3H), 1.02-0.95 (m, 3H), 0.89 (s, 9H), 0.02 (s, 6H).

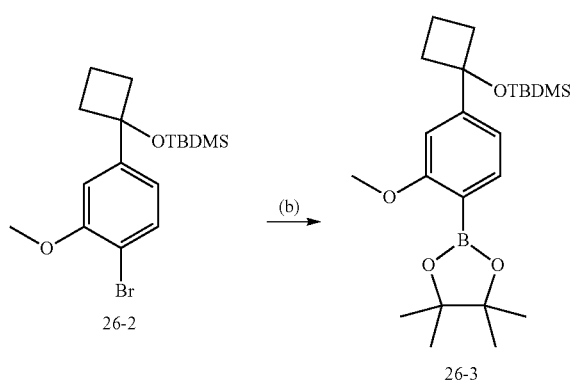

A solution of Compound 26-2 (0.15 mmol), B(O$^i$Pr)$_3$ (1.0 equiv.), Pd(dppf)Cl$_2$-DCM complex (5 mol %), 1 M aq. Na$_2$CO$_3$ solution (2.0 equiv.) in DMF (1.7 mL) was allowed to purge under Argon for a few minutes before the reaction tube was subjected to microwave heating at 120° C. for 30 minutes. The reaction mixture was diluted with H$_2$O and extracted twice with EtOAc. The combined organic layers were washed with brine, dried over Na$_2$SO$_4$, filtered and concentrated in vacuo to afford 365 mg of Compound 26-3 as a brown liquid.

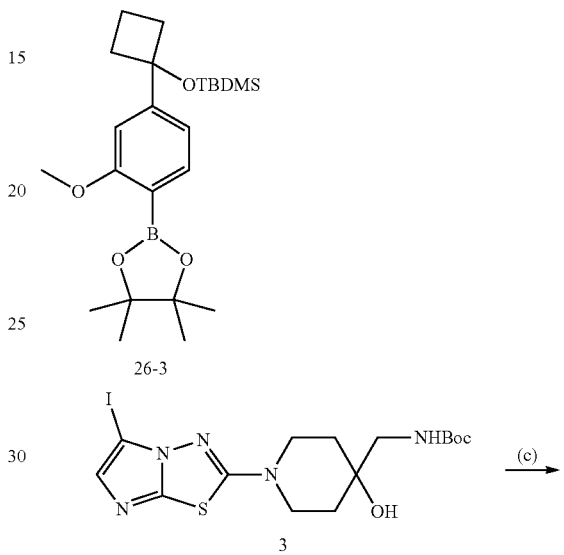

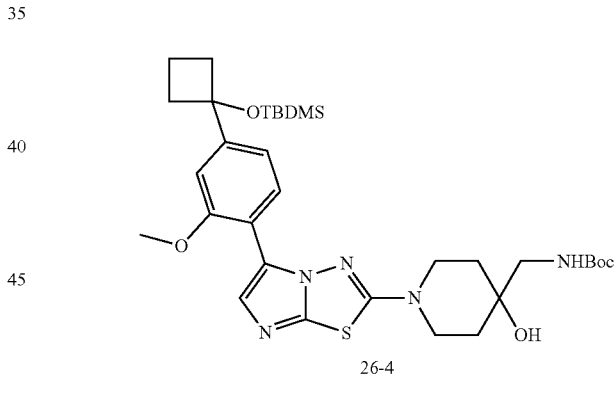

A solution of Compound 3 (1.0 equiv.) in dioxane/H$_2$O (4:1), K$_2$CO$_3$ (3.0 equiv.), Compound 26-3 (1.5 equiv.) and Pd(dppf)Cl$_2$-DCM complex (5 mol %) were added. The reaction mixture was heated at 100° C. for 6 hours. The reaction mixture was diluted with H$_2$O and extracted twice with EtOAc. The combined organic layers were washed with H$_2$O, then brine, dried over Na$_2$SO$_4$, filtered and concentrated in vacuo. The crude product was purified by prep-HPLC to provide 70 mg of Compound 26-4 as a solid. $^1$H NMR (300 MHz, CDCl$_3$) δ 8.18 (d, J=8.2 Hz, 2H), 7.67 (s, 1H), 7.17 (d, J=1.7 Hz, 1H), 6.77 (dd, J=8.2, 1.8 Hz, 1H), 5.04-4.85 (m, 1H), 3.94 (s, 3H), 3.78-3.64 (m, 2H), 3.62-3.45 (m, 2H), 3.18 (d, J=6.2 Hz, 2H), 1.75-1.70 (m, 3H), 1.70-1.55 (m, 4H), 1.46 (s, 9H), 1.35-1.15 (m, 3H), 1.08-0.99 (m, 1H), 0.91 (s, 6H), 0.13--0.20 (m, 9H); LC-MS m/z 631.0 [M+H]$^+$, retention time=1.76 minutes.

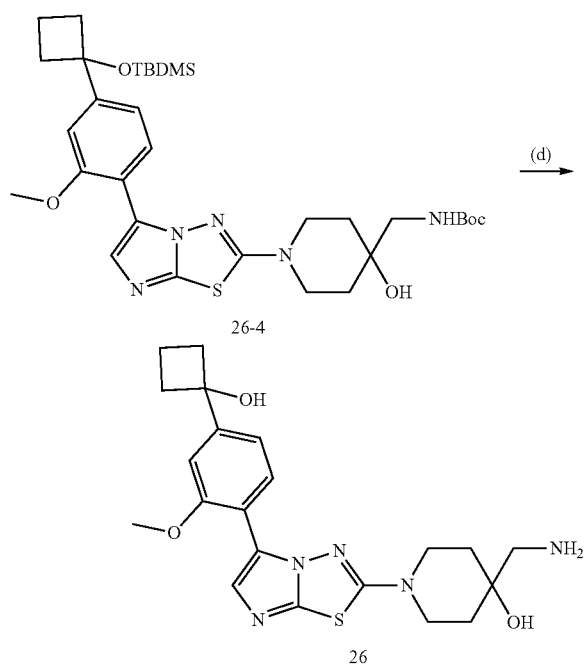 [SMILES: COc1cc(C2(O[Si](C)(C)C(C)(C)C)CCC2)ccc1-c1cnc2sc(N3CCC(O)(CNC(=O)OC(C)(C)C)CC3)nn12 ; "(d)" ; COc1cc(C2(O)CCC2)ccc1-c1cnc2sc(N3CCC(O)(CN)CC3)nn12]

26-4

26

Compound 26 was prepared from Compound 26-4 (40 mg) using Boc-deprotection procedure B. The crude material was purified by triturating in 5% MeOH in MeCN, followed by triturating in pentane to give 26 mg of Compound 26 as a solid. $^1$H NMR (300 MHz, MeOD-d$_4$) δ 8.53 (dd, J=8.1, 3.4 Hz, 1H), 8.09 (s, 1H), 7.84-7.64 (m, 2H), 4.06 (s, 3H), 3.94-3.76 (m, 2H), 3.76-3.55 (m, 2H), 3.26-3.16 (m, 3H), 3.19-3.02 (m, 2H), 2.99 (s, 2H), 1.92-1.74 (m, 3H), 1.26-1.13 (m, 2H); LC-MS=415.85 [M+H]$^+$, retention time=1.30 minutes.

Example 27-0: ((1-(5-(4-fluoro-2-methoxyphenyl)imidazo[2,1-b][1,3,4]thiadiazol-2-yl)-4-((methylsulfonyl)methyl)piperidin-4-yl)methanamine

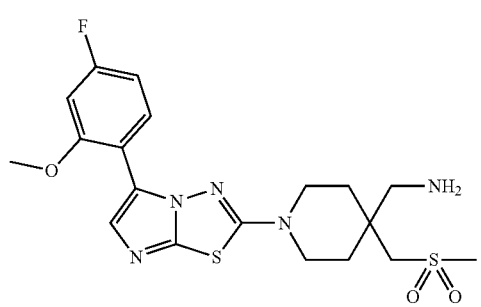

The Compound 27-0 was prepared in the following way:

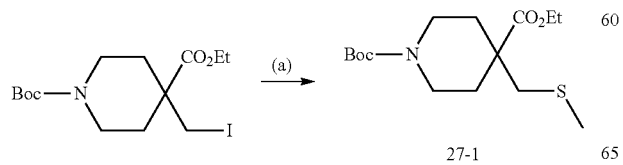

27-1

To a solution of 1-(tert-butyl) 4-ethyl 4-(iodomethyl)piperidine-1,4-dicarboxylate in DMF (2 mL), NaSMe (48.5 mg) was added. The reaction mixture was stirred at room temperature for 14 hours. After dilution with EtOAc, the mixture was washed twice with H$_2$O and brine, dried over Na$_2$SO$_4$, filtered, and concentrated in vacuo. The residue was purified by normal phase chromatography with a running gradient of 0-10% EtOAc/heptane to afford 180 mg of Compound 27-1 as an oil.

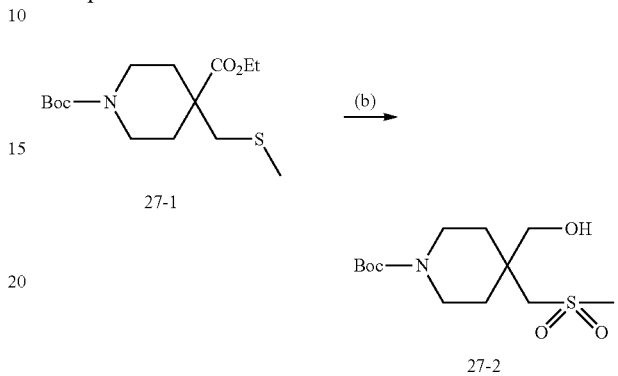

27-1

27-2

To a solution of Compound 27-1 in DCM (1.8 mL), mCPBA was added at −5° C. The reaction mixture was stirred at −5° C. for 15 minutes, then at room temperature for 30 minutes. The reaction was quenched with sat. aqueous NaHCO$_3$. The mixture was extracted with EtOAc, the organic layer was washed with sat. aqueous NaHCO$_3$, H$_2$O and brine, dried over Na$_2$SO$_4$, filtered, and concentrated in vacuo. The crude material was dissolved in THF (1.2 mL) and LiAlH$_4$ (2 M in THF) was added at 0° C. The reaction mixture was stirred at 0° C. to room temperature for 4 hours. The reaction was quenched with 2 M NaOH and water, then diluted with EtOAc and Na$_2$SO$_4$ was added. The mixture was filtered and concentrated in vacuo. The residue was dissolved in EtOAc-DCM, then filtered and concentrated in vacuo to afford 177 mg of Compound 27-2 as an oil.

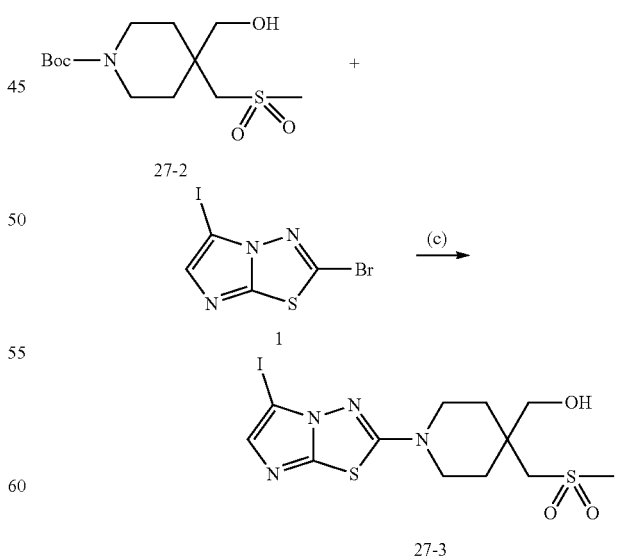

27-2

1

27-3

To a solution of Compound 27-2 in MeOH (0.5 mL) was added 4 M HCl in dioxane (0.8 mL). The reaction mixture was stirred at room temperature for 30 minutes. Then the mixture was concentrated in vacuo. This residue was dissolved in EtOH (1.5 mL). To this solution DIPEA (0.380 mL, 2.30 mmol) and Compound 1 (140 mg, 0.424 mmol) were added. The reaction mixture was stirred at 100° C. for 3 hours. The resulting precipitate was triturated with MeCN, filtered, washed with MeCN, and dried to afford 108 mg of Compound 27-3 as a solid. LC-MS=457.1 [M+H]$^+$.

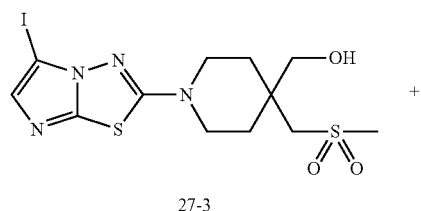

27-3

+

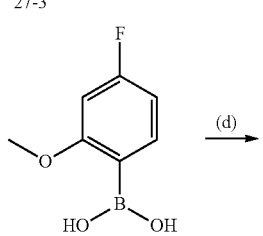 (d)

A mixture of Compound 27-3 (66.9 mg, 0.147 mmol), (4-fluoro-2-methoxyphenyl)boronic acid (32.4 mg, 0.191 mmol) and PdCl$_2$(Ph$_3$P)$_2$ (5.15 mg, 7.33 μmol) in 2 M Na$_2$CO$_3$ and dioxane (0.5 mL) was stirred at 100° C. for 1 hour. This mixture was purified by normal phase chromatography with running gradient 0-100% EtOAc/Heptane then to 95/5 MeOH/DCM to afford 67.5 mg of Compound 27-4. LC-MS=455.3 [M+H]$^+$.

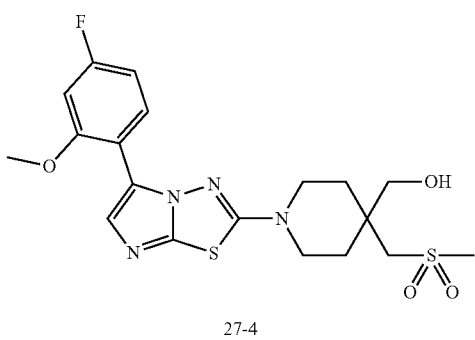

27-4

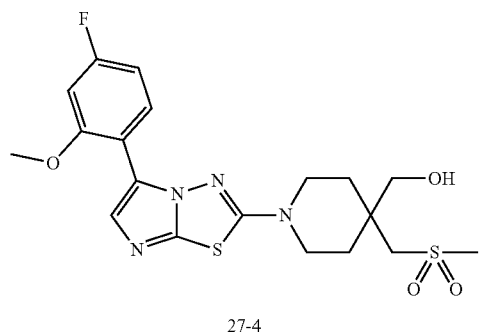 (e)

27-4

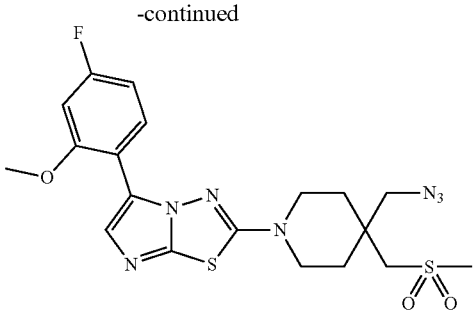

27-5

To a solution of Compound 27-4 (67 mg, 0.147 mmol) in DCM (1.8 mL), Et$_3$N (0.103 mL, 0.737 mmol), DMAP (1 mg, 8.19 μmol) and MsCl (0.029 mL, 0.369 mmol) were added at 0° C. The reaction mixture was stirred at room temperature for 1 hour. More MsCl (0.02 mL) was added. The reaction mixture was stirred at room temperature for 30 minutes. After dilution with EtOAc, the mixture was washed with H$_2$O and brine, dried over Na$_2$SO$_4$, filtered and concentrated in vacuo. The resulting residue was dissolved in DMF (0.5 mL) and NaN$_3$ (90 mg, 1.38 mmol) and 15-crown-5 (0.233 mL, 1.18 mmol) were added. The reaction mixture was stirred at 60° C. for 17 hours. After dilution with EtOAc, the mixture was washed with H$_2$O and brine, dried over Na$_2$SO$_4$, filtered, and concentrated in vacuo to afford 60 mg of Compound 27-5. LC-MS=480.2 [M+H]$^+$.

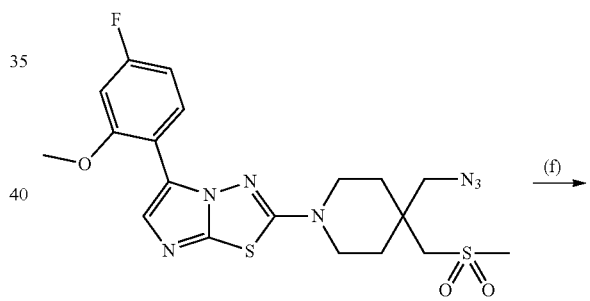 (f)

27-5

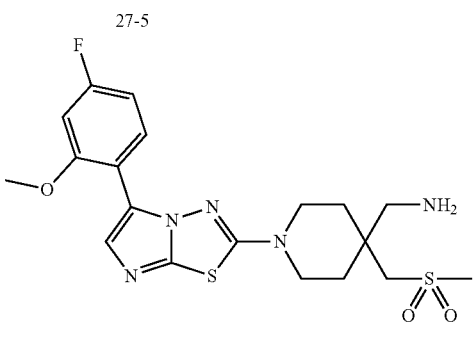

27

To a solution of Compound 27-5 (60 mg, 0.125 mmol) in THF (0.8 mL) and H$_2$O (0.2 mL), Ph$_3$P (65.6 mg, 0.250 mmol) was added. The reaction mixture was stirred at 60° C. for 6.5 hours. After dilution with EtOAc, the mixture was extracted with aqueous HCl and water. The combined aqueous layers were washed with EtOAc and then was basified with aqueous NaOH, and extracted with EtOAc. The organic layer was dried over Na$_2$SO$_4$, filtered, and concentrated in vacuo. The residue was purified by prep-HPLC to afford 31.4 mg of Compound 27. $^1$H NMR (400 MHz, DMSO-d$_6$) δ 8.22 (dd, J=8.7, 6.8 Hz, 1H), 7.94 (s, 3H), 7.59 (s, 1H), 7.09 (dd, J=11.4, 2.6 Hz, 1H), 6.93 (td, J=8.4, 2.5 Hz, 1H), 3.92 (s, 3H), 3.69 (d, J=16.0 Hz, 4H), 3.54 (ddd, J=13.4, 9.6, 3.4 Hz, 2H), 3.26 (d, J=6.0 Hz, 2H), 3.07 (s, 3H), 2.18-1.83 (m, 2H), 1.77 (ddd, J=13.9, 10.1, 4.3 Hz, 2H). LC-MS=454.1 [M+H]$^+$.

Example 28-0: 1-(4-(aminomethyl)-1-(5-(4-fluoro-2-methoxyphenyl)imidazo[2,1-b][1,3,4]thiadiazol-2-yl)piperidin-4-yl)-N,N-dimethylmethanesulfonamide

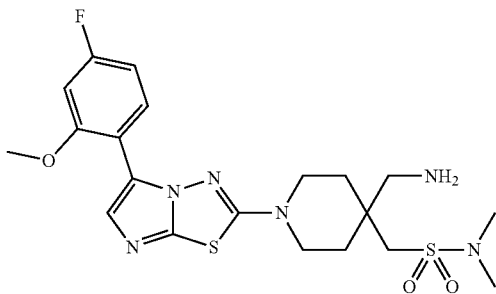

The Compound 28-0 was prepared in the following way:

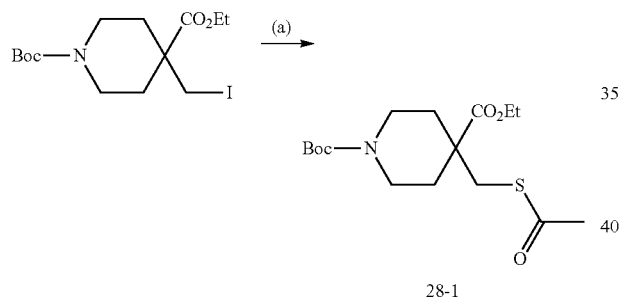

To a solution of 1-(tert-butyl) 4-ethyl 4-(iodomethyl)piperidine-1,4-dicarboxylate (250 mg, 0.629 mmol) in DMF (2 mL), potassium ethanethioate (144 mg, 1.259 mmol) was added. The reaction mixture was stirred at room temperature for 15 hours. More potassium ethanethioate (60 mg) was added, then the reaction mixture was stirred at room temperature for 13 hours. After dilution with EtOAc, the mixture was washed with H$_2$O and brine, dried over Na$_2$SO$_4$, filtered, and concentrated in vacuo. The residue was purified by normal phase chromatography with a running gradient 0-10% EtOAc/heptane to afford 165 mg of Compound 28-1 as an oil.

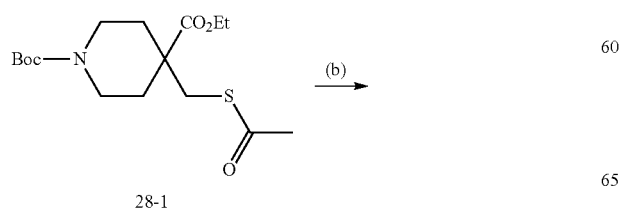

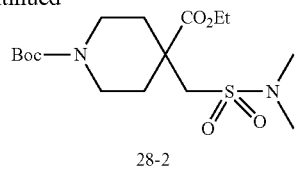

NCS (255 mg, 1.911 mmol) was added a solution of 3 M HC (0.167 mL), H$_2$O (0.06 mL) and MeCN (1 mL). To this mixture was added a solution of Compound 28-1 in MeCN (1 mL) at 0° C. The reaction mixture was stirred at room temperature for 50 minutes. After dilution with EtOAc, the mixture was washed with H$_2$O and brine, dried over Na$_2$SO$_4$, filtered, and concentrated in vacuo. The resulting residue was dissolved in MeCN (1.5 mL) and aqueous Me$_2$NH (0.3 mL) was added. The reaction mixture was stirred at room temperature for 3 hours. After dilution with EtOAc, the mixture was washed with H$_2$O and brine, dried over Na$_2$SO$_4$, filtered, and concentrated in vacuo to give Compound 28-2.

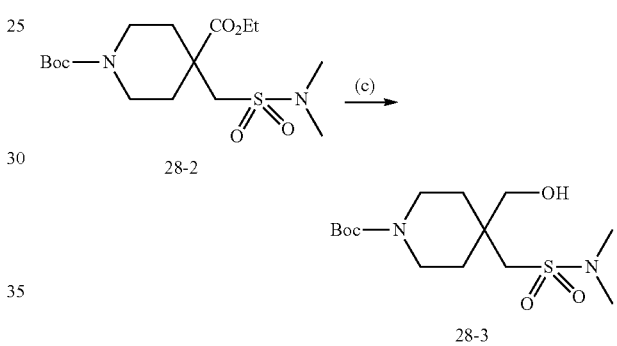

To a solution of Compound 28-2 (130 mg, 0.343 mmol) in THF (1.2 mL), LiAlH$_4$ (2 M, 0.24 mL) was added at 0° C. The reaction mixture was stirred at room temperature for 1 hour. The reaction was quenched by addition of 2 M NaOH and water. The mixture was diluted with EtOAc, and dried over Na$_2$SO$_4$, filtered, and concentrated in vacuo to afford 88 mg of Compound 28-3.

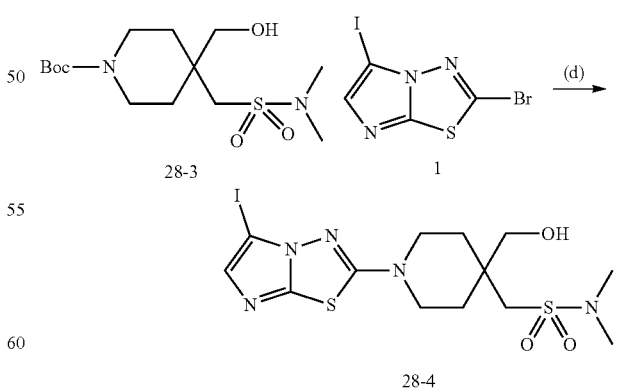

To a solution of Compound 28-3 (88 mg, 0.262 mmoL) in MeOH (0.5 mL), HCl in dioxane (0.8 mL) was added. The reaction mixture was stirred at room temperature for 1.5 hours. Then the mixture was concentrated in vacuo. The residue was dissolved in EtOH (1.5 mL) and then Compound 1 (78 mg, 0.235 mmol) and DIPEA (0.8 mL, 3.20 mmol) were added. The reaction mixture was stirred at 100° C. for 3 hours. The mixture was concentrated in vacuo. The residue was purified by normal phase chromatography with a running gradient 0-100% EtOAc/heptane to afford 76 mg of Compound 28-4. LC-MS=486.1 [M+H]+.

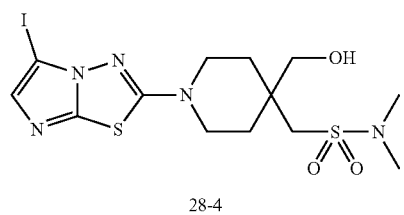

28-4

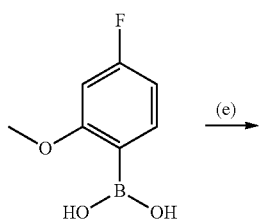

A mixture of Compound 28-4 (76 mg, 0.157 mmol), (4-fluoro-2-methoxyphenyl)boronic acid (334.6 mg, 0.204 mmol), and PdCl$_2$(Ph$_3$P)$_2$ (5.5 mg, 7.83 μmol) in aqueous Na$_2$CO$_3$ (2 M, 0.391 mL, 0.783 mmol) and dioxane (0.5 mL) was stirred at 100° C. for 1 hour. The mixture was purified by normal phase chromatography with a running gradient 0-100% EtOAc/heptane then 100% (10:90 MeOH:DCM) to afford 55.9 mg of Compound 28-5. LC-MS=484.2 [M+H]+.

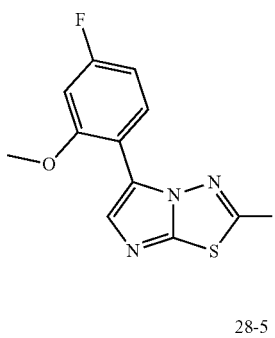

28-5

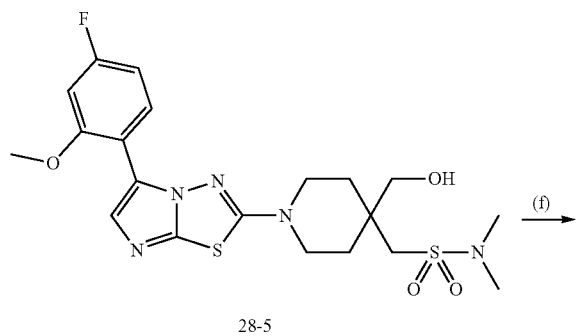

28-5

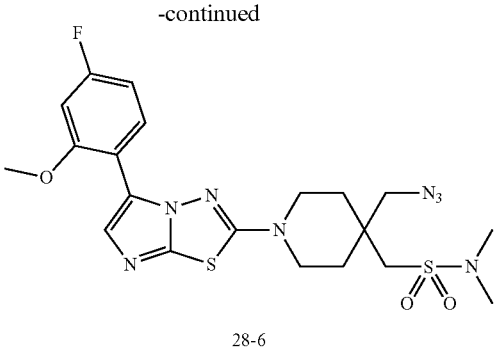

28-6

To a solution of Compound 28-5 (55 mg, 0.114 mmol) in DCM (0.8 mL), Et$_3$N (0.079 mL, 0.569 mmol), DMAP (13.90 mg, 0.114 mmol) and MsCl (0.022 mL, 0.284 mmol) were added at 0° C. The reaction mixture was stirred at room temperature for 30 minutes. After dilution with EtOAc, the mixture was washed with H$_2$O and brine, dried over Na$_2$SO$_4$, filtered and concentrated in vacuo. The residue was dissolved in DMF (0.5 mL) and then NaN$_3$ (59.2 mg, 0.910 mmol) and 15-crown-5 (0.180 mL, 0.910 mmol) were added. The reaction mixture was stirred at 60° C. for 1 hour, then at 100° C. for 7 hours. More NaN$_3$ (26 mg) was added. The reaction mixture was stirred at 100° C. for 13 hours. After dilution with EtOAc, the mixture was washed with H$_2$O and brine, dried over Na$_2$SO$_4$, filtered, and concentrated in vacuo to afford 44 mg of Compound 28-6. LC-MS=509.2 [M+H]+.

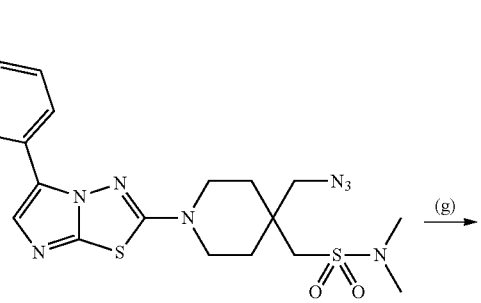

28-6

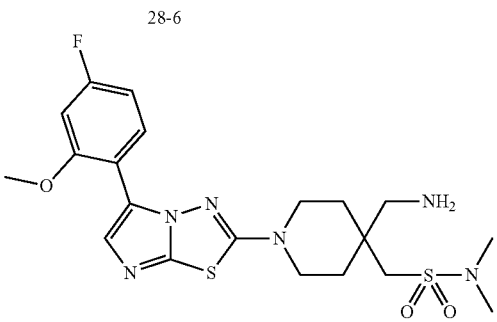

28

To a solution of Compound 28-6 (44 mg, 0.087 mmol) in THF (0.7 mL) and H$_2$O (0.16 mL), Ph$_3$P (45.4 mg, 0.173 mmol) was added. The reaction mixture was stirred at 60° C. for 9 hours. After dilution with EtOAc, the mixture was extracted with aqueous HCl and water. The combined aqueous layers were washed with EtOAc, were basified with aqueous NaOH, and extracted with EtOAc. The organic layer was dried over Na$_2$SO$_4$, filtered, and concentrated in vacuo. The residue was dissolved in MeOH and treated with HCl in dioxane, then concentrated in vacuo. The residue was purified by prep-HPLC to afford 23.6 mg of Compound 28. $^1$H NMR (400 MHz, DMSO-d$_6$) δ 8.23 (dd, J=8.7, 6.9 Hz, 1H), 7.88 (s, 3H), 7.53 (s, 1H), 7.08 (dd, J=11.4, 2.5 Hz, 1H), 6.92 (td, J=8.5, 2.6 Hz, 1H), 3.92 (s, 3H), 3.58 (m, 4H), 3.38 (s, 2H), 3.22 (d, J=5.9 Hz, 2H), 1.94-1.84 (m, 2H), 1.77 (ddd, J=13.6, 8.4, 4.6 Hz, 2H). LC-MS=483.2 [M+H]$^+$.

Compound 29-0: ((3R,5S)-5-amino-1-(5-(4-fluoro-2-methoxyphenyl)imidazo[2,1-b][1,3,4]thiadiazol-2-yl)piperidin-3-ol

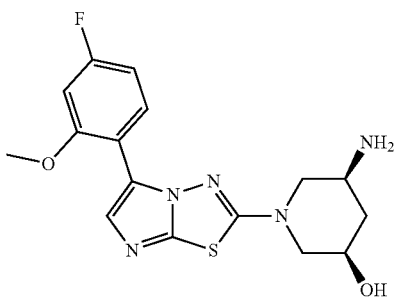 [SMILES: COc1cc(F)ccc1-c1cnc2sc(N3C[C@@H](N)C[C@@H](O)C3)nn12]

The Compound 29-0 was prepared by the same route used to prepare Compound 4-0, using appropriate starting materials:

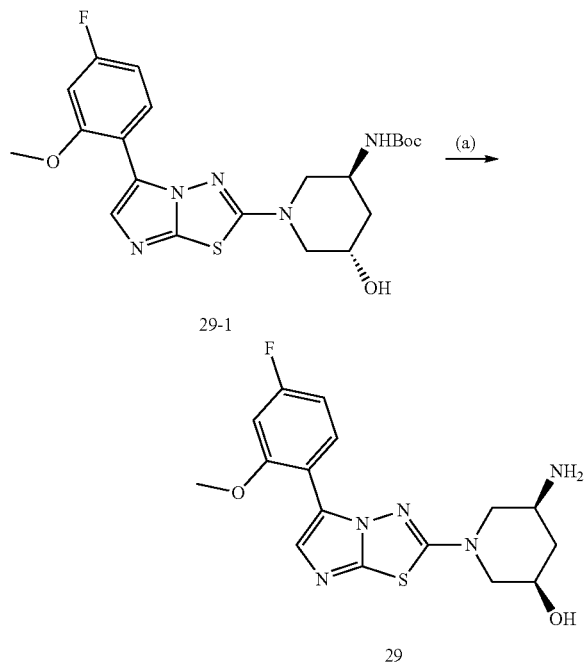

To a mixture of Compound 29-1 (18.3 mg, 0.039 mmol), 4-nitrobenzoic acid, (7.92 mg, 0.047 mmol) and Ph$_3$P (12.43 mg, 0.047 mmol) in THF (0.8 mL), disopropyl azodicarboxylate (9.33 µL, 0.047 mmol) was added. The reaction mixture was stirred at room temperature for 14 hours and then concentrated in vacuo. The crude was purified by normal phase chromatography with a running gradient of 0-100% EtOAc/heptane to afford the intermediate compound which was treated with MeOH/4 M HCl in dioxane at room temperature for 1 hour. The reaction mixture was concentrated in vacuo. The residue was then triturated with MeOH/MeCN and filtrated off. The resulting solid was washed with CH$_3$CN and dried before it was treated with 2 M aq. NaOH in MeOH at room temperature for 1 hour. After dilution with water, the mixture was extracted with EtOAc. The combined organic layers were washed with aq. NaOH, dried over Na$_2$SO$_4$, filtered, and concentrated in vacuo. The residue was then treated with 4 M HCl in dioxane, and concentrated in vacuo, then diluted with water, and freeze-dried to afford 2.7 mg of Compound 29 as a solid. $^1$H NMR suggested the stereochemistry of the —OH was inverted. $^1$H NMR (500 MHz, MeOD-d$_4$) δ 8.27 (dd, J=8.7, 6.5 Hz, 1H), 7.90 (s, 1H), 7.03 (dd, J=11.0, 2.4 Hz, 1H), 6.88 (td, J=8.4, 2.4 Hz, 1H), 4.20-4.09 (m, 2H), 3.96 (s, 3H), 3.83 (dd, J=14.1, 3.0 Hz, 1H), 3.73-3.66 (m, 3H), 2.21 (dt, J=14.4, 3.6 Hz, 1H), 2.09-2.01 (m, 1H). LCMS=364.2 [M+H]$^+$.

Example 30-0: (4S,4aR,7aS)-6-(5-(2-ethoxy-6-isopropylpyridin-3-yl)imidazo[2,1-b][1,3,4]thiadiazol-2-yl)octahydropyrano[2,3-c]pyrrol-4-amine

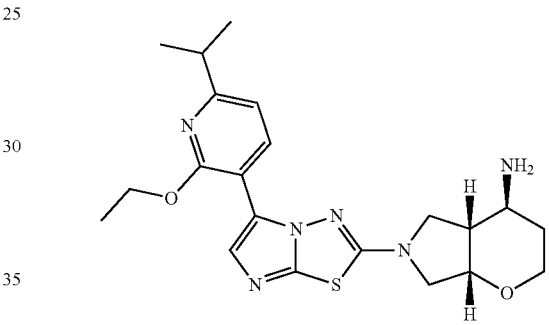

The Compound 30-0 was prepared in the following way:

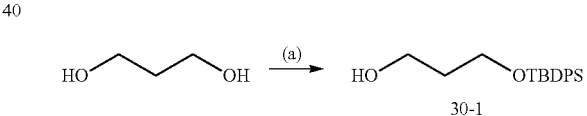

NaH (60% moistened with paraffin) (21.0 g, 526.3 mmol,) was suspended in THF (300 mL) under N$_2$ and cooled to 0° C. 1,3-dihydroxy propane (40 g, 526.3 mmol) dissolved in THF (200 mL) was added dropwise via addition funnel and stirred at 0° C. for 1 hour. TBDPS-Cl (144.6 g, 526.3 mmol) dissolved in THF (100 mL) was added into the reaction mixture via addition funnel at 0° C. and stirred for 2 hours. The reaction mixture was quenched with ice cold H$_2$O and extracted with Et$_2$O. The combined organic layers were washed brine, dried over Na$_2$SO$_4$ and concentrated in vacuo. The crude compound was purified by normal phase chromatography with a running gradient of 30/70 EtOAc/n-hexane to afford 90 g of Compound 30-1 as a solid. $^1$H NMR (300 MHz, CDCl$_3$) δ 7.75-7.57 (m, 4H), 7.51-7.31 (m, 6H), 3.91-3.79 (m, 4H), 2.38 (t, J=5.6 Hz, 1H), 1.81 (p, J=5.6 Hz, 2H), 1.05 (s, 9H).

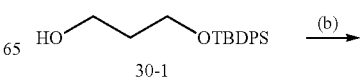

-continued

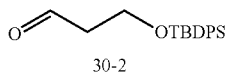
30-2

Oxalyl chloride (19.0 mL, 214.96 mmol) was dissolved in DCM (200 mL) under $N_2$ and cooled to −78° C. DMSO (34.0 mL, 429.93 mmol) dissolved in DCM (200 mL) was added dropwise via addition funnel at −78° C. and stirred at the same temperature for 1 hour. Compound 30-1 (45.0 g, 143.31 mmol) dissolved in DCM (200 mL) was added into the reaction mixture at −78° C. and allowed to stir for another 2 hours. The reaction mixture was quenched with $Et_3N$ (125 mL) at −78° C. and allowed to warm to room temperature for 15 minutes followed by addition of $H_2O$ (200 mL). The aqueous layer was extracted with DCM. The combined organic layers were washed brine, dried over $Na_2SO_4$ and concentrated in vacuo to afford 45 g, of Compound 30-2. $^1$H NMR (300 MHz, $CDCl_3$) δ 9.82 (t, J=2.2 Hz, 1H), 7.71-7.62 (m, 4H), 7.48-7.31 (m, 6H), 4.02 (t, J=6.0 Hz, 2H), 2.68-2.48 (m, 2H), 1.04 (s, 9H).

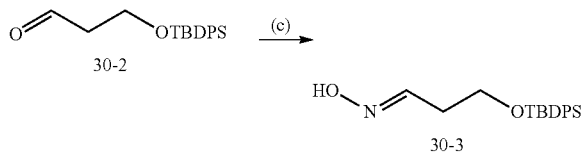

Compound 30-2 (82.1 g, 263 mmol was dissolved in MeOH (1.60 L) under $N_2$ and cooled to 0° C. Pyridine (80.5 g, 1.012 mol) was added dropwise followed by portionwise addition of hydroxyl amine hydrochloride (27.4 g, 395 mmol) at 0° C. The reaction mixture was stirred at room temperature for 16 hours. The reaction mixture was concentrated in vacuo to afford a crude residue which was dissolved into $H_2O$ and extracted with EtOAc. The combined organic layers were washed brine, dried over $Na_2SO_4$ and concentrated in vacuo to afford 86 g of Compound 30-3. $^1$H NMR (400 MHz, $CDCl_3$) δ 7.79-7.69 (m, 4H), 7.56-7.30 (m, 7H), 4.19-4.14 (m, 1H), 3.87-3.84 (m, 2H), 2.69-2.65 (m, 1H), 2.51-2.46 (m, 1H), 1.16 (s, 9H).

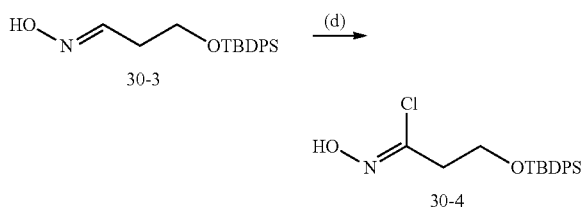

Compound 30-3 (86.0 g, 263 mmol) was dissolved in DMF (860 mL) under $N_2$ and cooled to 0° C. NCS (38.6 g, 289 mmol) was added portionwise into the reaction mixture at 0° C. The reaction mixture was stirred at room temperature for 2 hours. The reaction mixture was quenched with ice cold $H_2O$ and extracted with EtOAc. The combined organic layers were washed with cold $H_2O$ (150 mL×3), brine, dried over $Na_2SO_4$ and concentrated in vacuo to afford 95 g of Compound 30-4. $^1$H NMR (400 MHz, $CDCl_3$) δ 7.79-7.69 (m, 4H), 7.56-7.30 (m, 7H), 4.19-4.14 (m, 1H), 3.87-3.84 (m, 2H), 2.69-2.65 (m, 1H), 2.51-2.46 (m, 1H), 1.16 (s, 9H).

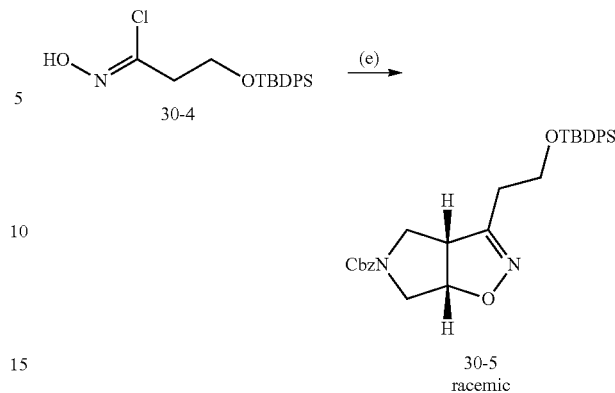

Compound 30-4 (47.0 g, 130 mmol) and benzyl 2,5-dihydro-H-pyrrole-1-carboxylate (24.0 g, 118 mmol) were dissolved in IPA (500 mL) at room temperature. $NaHCO_3$ (56.0 g, 667 mmol) was added into the reaction mixture and heated to 50° C. and allowed to stir for 16 hours. The reaction mixture was quenched with ice cold $H_2O$ and extracted with EtOAc. The combined organic layers were washed with cold water, brine, dried over $Na_2SO_4$ and concentrated in vacuo. The crude residue was purified by normal phase chromatography with a running gradient (80 g column) with a running gradient of 35-45% EtOAc/n-hexane to afford 11.5 g of Compound 30-5. $^1$H NMR (400 MHz, $CDCl_3$) δ 7.68-7.67 (m, 4H), 7.47-7.30 (m, 11H), 5.16-5.12 (m, 2H), 3.96-3.86 (m, 5H), 3.60-3.50 (m, 2H), 2.76-2.73 (m, 2H), 2.10-2.08 (m, 1H), 1.10 (s, 9H). LC-MS=546.6 $[M+H_2O]^+$.

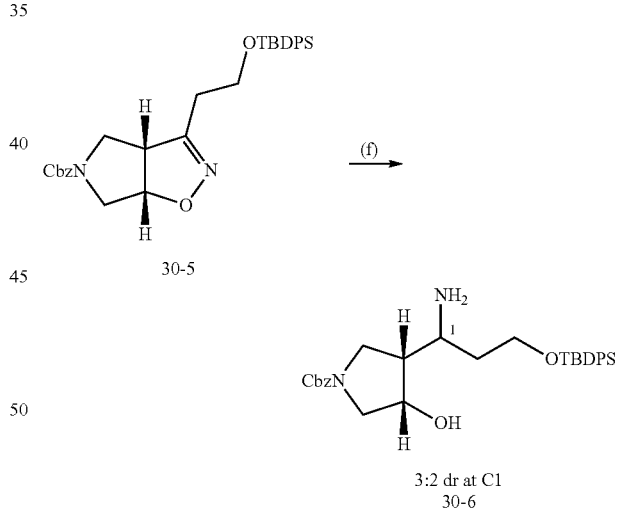

Compound 30-5 (11.5 g, 21.8 mmol) was dissolved in MeOH:THF (3:1) (560 mL) under $N_2$ and cooled to −30° C. $NiCl_2.6H_2O$ (15.5 g, 65.3 mmol) was added. $NaBH_4$ (8.27 g, 218 mmol) was added portionwise to the reaction mixture at −30° C. and allowed to stir for 2 hours. $Et_3N$ (7 mL) was added to the reaction mixture and stirred for 15 minutes at −30° C. The reaction mixture was filtered through CELITE pad and washed with excess of MeOH. The filtrate was concentrated in vacuo to afford a crude residue which was dissolved into EtOAc washed with brine, dried over $Na_2SO_4$ and concentrated in vacuo to afford 10.4 g of Compound 30-6 as a solid. LC-MS=533.20 $[M+H]^+$.

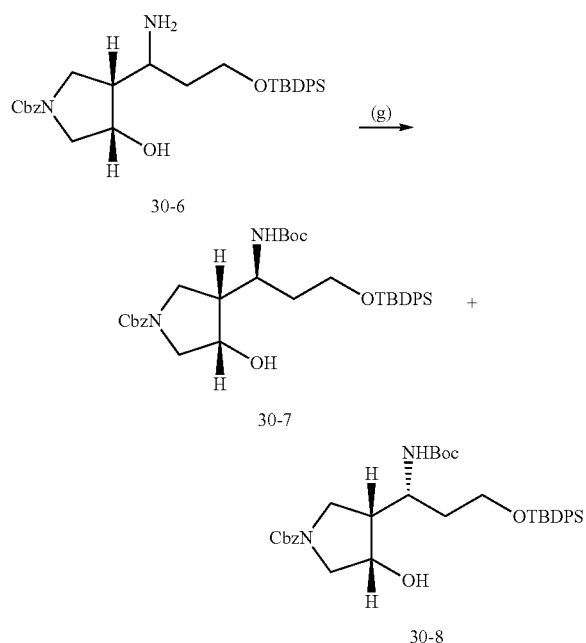

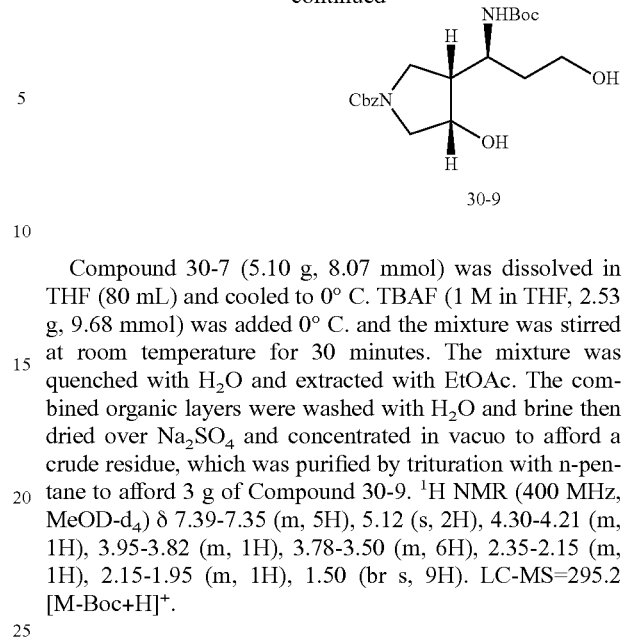

Compound 30-6 (10.4 g, 19.6 mmol) was dissolved in DCM (160 mL) and cooled to 0° C. Et₃N (5.94 g, 58.8 mmol) and (Boc)₂O (6.41 g, 29.4 mmol) were added and the reaction mixture was stirred at room temperature for 16 hours. The reaction mixture was quenched with H₂O and extracted with DCM. The combined organic layers were washed with water, brine, dried over Na₂SO₄ and concentrated in vacuo. The crude residue was purified by normal phase chromatography (80 g column) with a running gradient of 30-65% EtOAc/n-hexane to give two diastereomeric products Compound 30-7 and 30-8.

Major peak Compound 30-7: rac-Benzyl (3S,4R)-3-hydroxy-4-((S)-2,2,11,11-tetramethyl-9-oxo-3,3-diphenyl-4,10-dioxa-8-aza-3-siladodecan-7-yl)pyrrolidine-1-carboxylate (5.10 g): $^1$H NMR (400 MHz, MeOD-d₄) δ 7.69-7.66 (m, 4H), 7.47-7.30 (m, 11H), 5.17 (s, 2H), 4.20 (s, 1H), 4.00-3.70 (m, 3H), 3.60-3.45 (m, 2H), 3.31-3.29 (m, 2H), 2.21-2.19 (m, 1H), 2.11-2.09 (m, 1H), 1.77-1.75 (m, 1H), 1.47 (s, 9H), 1.08 (s, 9H). LCMS=533.58 [M-Boc+H]⁺.

Minor peak Compound 30-8: rac-Benzyl (3S,4R)-3-hydroxy-4-((R)-2,2,11,11-tetramethyl-9-oxo-3,3-diphenyl-4,10-dioxa-8-aza-3-siladodecan-7-yl)pyrrolidine-1-carboxylate (3.60 g): $^1$H NMR (400 MHz, CDCl₃) δ 7.68-7.67 (m, 4H), 7.47-7.30 (m, 11H), 6.20-6.10 (m, 1H), 5.16-5.12 (m, 2H), 4.20 (s, 1H), 4.05-3.75 (m, 3H), 3.70-3.60 (m, 1H), 3.36-3.34 (m, 1H), 3.21-3.19 (m, 1H), 2.10-2.08 (m, 2H), 1.45 (s, 9H), 1.10 (s, 9H). LCMS=533.63 [M-Boc+H]⁺.

Compound 30-7 (5.10 g, 8.07 mmol) was dissolved in THF (80 mL) and cooled to 0° C. TBAF (1 M in THF, 2.53 g, 9.68 mmol) was added 0° C. and the mixture was stirred at room temperature for 30 minutes. The mixture was quenched with H₂O and extracted with EtOAc. The combined organic layers were washed with H₂O and brine then dried over Na₂SO₄ and concentrated in vacuo to afford a crude residue, which was purified by trituration with n-pentane to afford 3 g of Compound 30-9. $^1$H NMR (400 MHz, MeOD-d₄) δ 7.39-7.35 (m, 5H), 5.12 (s, 2H), 4.30-4.21 (m, 1H), 3.95-3.82 (m, 1H), 3.78-3.50 (m, 6H), 2.35-2.15 (m, 1H), 2.15-1.95 (m, 1H), 1.50 (br s, 9H). LC-MS=295.2 [M-Boc+H]⁺.

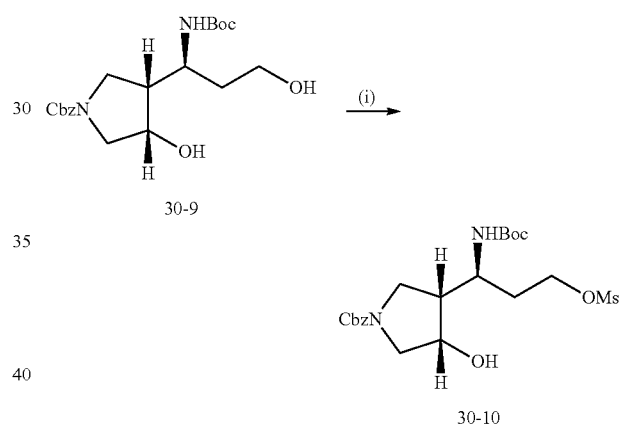

To a solution of Compound 30-9 (3.00 g, 7.61 mmol) in DCM (60 mL) and Et₃N (0.770 g, 7.61 mmol), a solution of MsCl (0.870 g, 7.61 mmol) in DCM (5 mL) was added at 0° C. and the resulting mixture was stirred at 0° C. for 2 hours. The mixture was concentrated in vacuo to afford 3.60 g of Compound 30-10 which was used in the next step without any further purification. $^1$H NMR (400 MHz, CDCl₃) δ 7.75-7.46 (m, 5H), 5.30-5.10 (m, 2H), 4.73-4.71 (m, 1H), 4.35-4.34 (m, 1H), 4.05-3.99 (m, 1H), 3.84-3.45 (m, 3H), 3.44-3.14 (m, 1H), 3.14 (s, 3H), 2.95-2.71 (m, 1H), 2.35-2.15 (m, 1H), 2.15-1.95 (m, 1H), 1.35 (br s, 9H). LC-MS=373.1 [M-Boc+H]⁺.

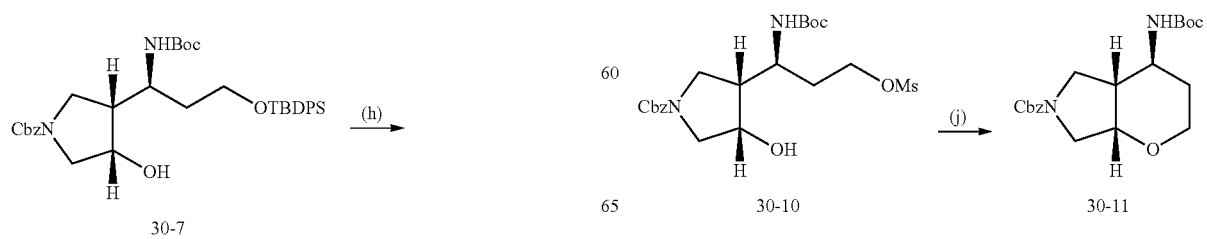

Compound 30-10 (3.60 g, 7.63 mmol) was dissolved in THF (80.0 mL) and Cs$_2$CO$_3$ (7.46 g, 22.9 mmol) was added at 0° C. The mixture was heated to reflux for 16 hours. The mixture was filtered through a CELITE pad and the pad was washed with THF. The filtrate was concentrated in vacuo, which was purified by normal phase chromatography (basic alumina column) with a running gradient of 30-45% EtOAc/n-hexane to afford 1.40 g of Compound 30-11. $^1$H NMR (400 MHz, CDCl$_3$) δ 7.41-7.30 (m, 5H), 5.21-5.12 (m, 2H), 4.83-4.81 (m, 1H), 4.15-4.13 (m, 1H), 3.86-3.73 (m, 2H), 3.70-3.48 (m, 3H), 3.47-3.39 (m, 2H), 2.27-2.25 (m, 1H), 2.06-2.08 (m, 1H), 1.52 (s, 9H). LC-MS=377.3 [M+H]$^+$.

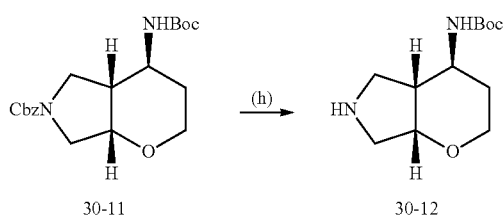 [SMILES: CC(C)(C)OC(=O)N[C@H]1CCO[C@@H]2CN(C(=O)OCc3ccccc3)C[C@H]12 ; CC(C)(C)OC(=O)N[C@H]1CCO[C@@H]2CNC[C@H]12]

30-11  30-12

Compound 30-11 (0.400 g, 1.06 mmol) was dissolved in t-BuOH (60 mL) and then Pd/C (10% anhydrous wt, 0.2 g) and Pd(OH)$_2$ (20% dry wt, 0.2 g) were added and the mixture was stirred under 10 kg/cm$^2$ H$_2$ pressure at room temperature for 45 minutes. The mixture was filtered over CELITE pad and the pad was washed with DCM. The filtrate was concentrated in vacuo to afford 0.253 g of Compound 30-12. $^1$H NMR (400 MHz, CDCl$_3$) δ 4.85-4.83 (m, 1H), 4.10-4.08 (m, 1H), 3.91-3.82 (m, 2H), 3.25-3.03 (m, 4H), 2.70-2.40 (m, 3H), 2.20-2.00 (m, 2H), 1.62-1.59 (m, 1H), 1.44 (s, 9H). LC-MS=243.2 [M+H]$^+$.

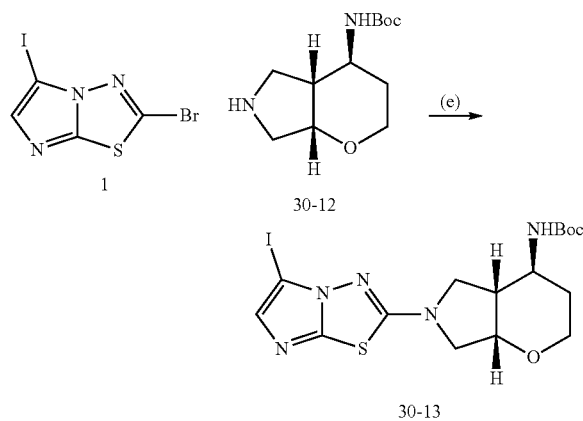

A solution of Compound 1 (300 mg, 0.909 mmol), Compound 30-12 (264 mg, 1.091 mmol) and Et$_3$N (0.26 mL, 1.865 mmol) in dioxane (10 mL) was heated to 80° C. for 8 hours, then was heated at 100° C. for 4 hours. The reaction was cooled to room temperature, concentrated down. The crude material redissolved in DCM and was washed with 0.1 M HCl (20 mL). The aqueous layer was extracted with DCM. The combined organic layers were washed with sat. aqueous NaHCO$_3$, dried over Na$_2$SO$_4$, and concentrated in vacuo to afford 421 mg of Compound 30-13 as a solid. LC-MS=492.2 [M+H]$^+$.

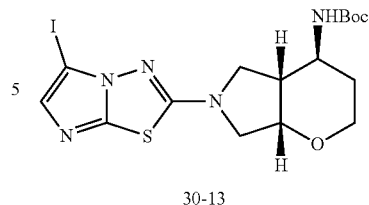

30-13

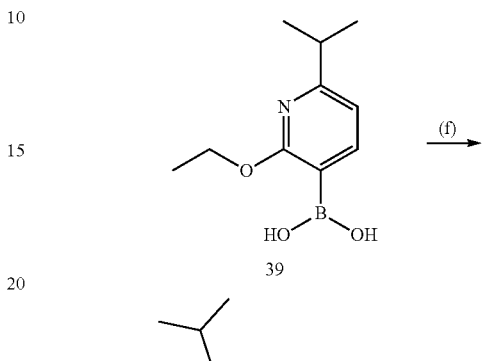

39

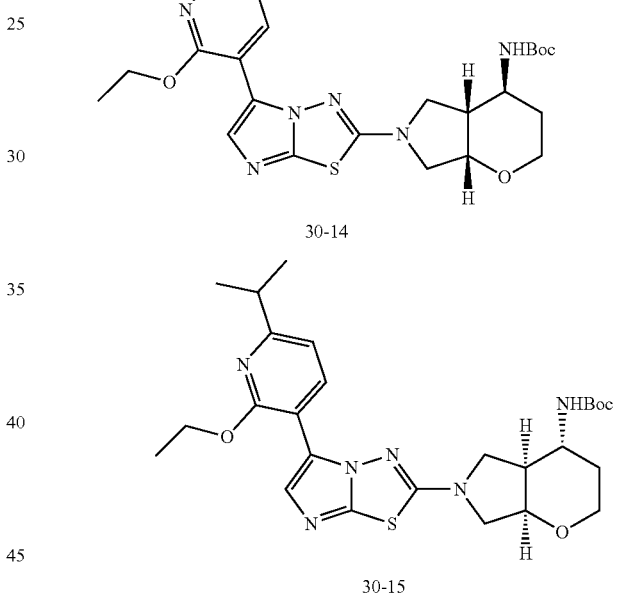

30-14

30-15

A mixture of Compound 30-13 (190 mg, 0.387 mmol), Compound 39 (162 mg, 0.773 mmol), PdCl$_2$(dppf)-DCM complex (31.6 mg, 0.039 mmol) and K$_3$PO$_4$ (246 mg, 1.160 mmol) was put under N$_2$ for a few minutes, then dioxane (2.5 mL) and H$_2$O (0.5 mL) were added. The vial was put under N$_2$ for an additional minute and then the reaction was heated to 90° C. for 1 hour. The reaction was concentrated in vacuo and purified by normal phase chromatography (40 g column) with a running gradient of 0-40% (3:1 EtOAc:EtOH)/heptane to afford a racemic mixture. A chiral purification was done using SFC (Method 3) to afford 38 mg of the first eluting peak Compound 30-14 (97.78% retention=4.12 minutes) and 59 mg of the second elution peak Compound 30-15 (87.3% retention=5.02 minutes). The second peak was purified again using the same SFC method to recover 6 mg of the first eluting compound and 31 mg of the second eluting peak which showed 96.8% retention=5.38 minutes.

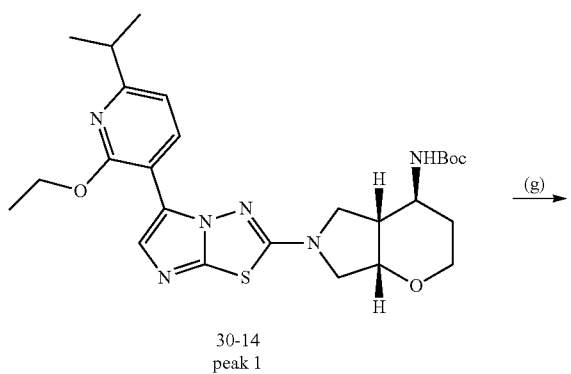

30-14
peak 1

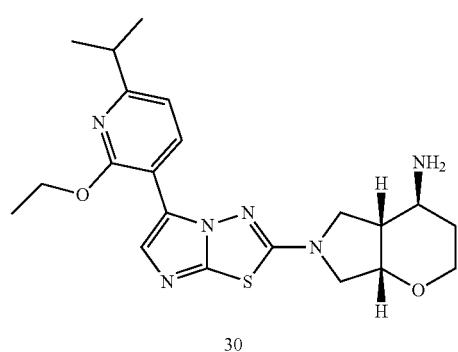

30

Compound 30-14 (44 mg, 0.084 mmol) underwent a Boc-deprotection following treatment with formic acid (0.5 mL, 13.04 mmol). The reaction was stirred at room temperature for 24 hours. The reaction was concentrated in vacuo and purified by prep-HPLC to afford 21.3 mg of one the enantiomer Compound 30 assigned as single compound with absolute stereochemistry unknown. $^1$H NMR (400 MHz, DMSO-$d_6$) δ 8.59 (d, J=7.7 Hz, 1H), 7.59 (s, 1H), 6.97 (d, J=7.8 Hz, 1H), 4.47 (q, J=7.0 Hz, 2H), 4.40 (t, J=3.7 Hz, 1H), 3.81 (t, J=11.3 Hz, 1H), 3.66 (dd, J=11.1, 4.1 Hz, 1H), 3.60 (d, J=9.2 Hz, 2H), 3.47 (dt, J=9.9, 4.3 Hz, 2H), 3.25 (s, 1H), 2.95 (p, J=6.8 Hz, 1H), 2.26 (d, J=9.7 Hz, 1H), 1.94 (s, 1H), 1.42 (t, J=7.0 Hz, 3H), 1.33 (d, J=13.9 Hz, 1H), 1.26 (d, J=6.9 Hz, 6H). MS m/z calcd for $C_{21}H_{28}N_6O_2S$ 428.6. found 429.5 [M+H]$^+$. Chiral analytic (Method 4): 100% retention=5.46 minutes.

The same N-Boc de-protection procedure was done for the second eluting peak, Compound 30-15. The resulting compound was assigned as single compound with absolute stereochemistry unknown Compound 30-16. $^1$H NMR (400 MHz, DMSO-$d_6$) δ 8.59 (d, J=7.7 Hz, 1H), 7.59 (s, 1H), 6.97 (d, J=7.8 Hz, 1H), 4.47 (q, J=7.0 Hz, 2H), 4.40 (t, J=3.7 Hz, 1H), 3.81 (t, J=11.3 Hz, 1H), 3.66 (dd, J=11.1, 4.1 Hz, 1H), 3.60 (d, J=9.2 Hz, 2H), 3.47 (dt, J=9.9, 4.3 Hz, 2H), 3.25 (s, 1H), 2.95 (p, J=6.8 Hz, 1H), 2.26 (d, J=9.7 Hz, 1H), 1.94 (s, 1H), 1.42 (t, J=7.0 Hz, 3H), 1.33 (d, J=13.9 Hz, 1H), 1.26 (d, J=6.9 Hz, 6H). MS m/z calcd for $C_{21}H_{28}N_6O_2S$ 428.6. found 429.5 [M+H]$^+$. Chiral analytic (Method 4): 100% retention=4.60 minutes.

The following compounds were prepared by the same route used to prepare Compound 30-0, using appropriate starting materials:

| Example/Compound Number | Structure | NMR | LC-MS | Chiral Prep Method |
|---|---|---|---|---|
| 30-17 | (4S,4aR,7aS)-6-(5-(2-methoxy-4-(trifluoromethyl)phenyl)imidazo[2,1-b][1,3,4]thiadiazol-2-yl)octahydropyrano[2,3-c]pyrrol-4-amine | $^1$H NMR (500 MHz, DMSO-$d_6$) δ 8.57-8.49 (m, 1H), 8.24 (d, J = 5.7 Hz, 3H), 7.76 (s, 1H), 7.46-7.35 (m, 2H), 4.50 (td, J = 4.1, 1.5 Hz, 1H), 4.02 (s, 3H), 3.82-3.68 (m, 4H), 3.68-3.54 (m, 3H), 2.55 (dq, J = 6.5, 3.3 Hz, 1H), 2.13 (dtd, J = 15.0, 8.2, 4.5 Hz, 1H), 1.62 (dd, J = 15.1, 3.2 Hz, 1H). | MS m/z calcd for $C_{19}H_{20}F_3N_5O_2$ 439.1 found 440.1 [M + H]$^+$ | 1 |

-continued

| Example/ Compound Number | Structure | NMR | LC-MS | Chiral Prep Method |
|---|---|---|---|---|
| 30-18 | 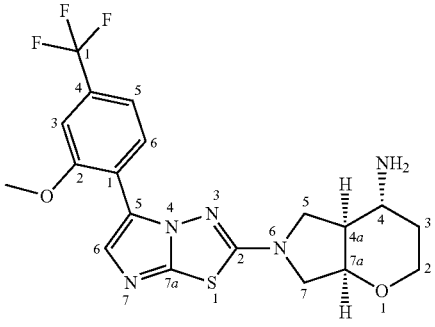<br>(4R,4aS,7aR)-6-(5-(2-methoxy-4-(trifluoromethyl)phenyl)imidazo[2,1-b][1,3,4]thiadiazol-2-yl)octahydropyrano[2,3-c]pyrrol-4-amine | $^1$H NMR (500 MHz, DMSO-d$_6$) δ 8.57-8.51 (m, 1H), 8.24 (d, J = 5.7 Hz, 3H), 7.76 (s, 1H), 7.42 (d, J = 7.3 Hz, 2H), 4.53-4.48 (m, 1H), 4.02 (s, 3H), 3.81-3.68 (m, 4H), 3.68-3.53 (m, 3H), 2.55 (dq, J = 5.9, 3.1 Hz, 1H), 2.13 (dtd, J = 15.6, 7.5, 3.4 Hz, 1H), 1.62 (dd, J = 15.1, 3.2 Hz, 1H). | MS m/z calcd for C$_{19}$H$_{20}$F$_3$N$_5$O$_2$ 439.1 found 440.1 [M + H]$^+$ | 1 |
| 30-19 | 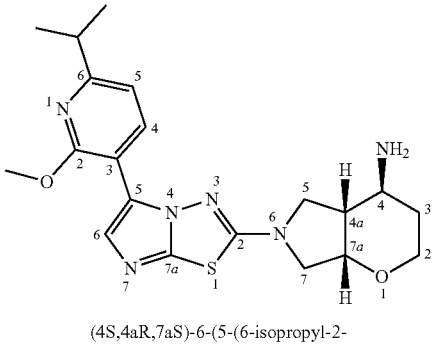<br>(4S,4aR,7aS)-6-(5-(6-isopropyl-2-methoxypyridin-3-yl)imidazo[2,1-b][1,3,4]thiadiazol-2-yl)octahydropyran[2,3-b]pyrrol-4-amine | $^1$H NMR (400 MHz, DMSO-d$_6$) δ 8.56 (d, J = 7.7 Hz, 1H), 8.20 (d, J = 5.7 Hz, 3H), 7.61 (s, 1H), 6.98 (d, J = 7.8 Hz, 1H), 4.49 (d, J = 4.1 Hz, 1H), 4.01 (s, 3H), 3.77-3.52 (m, 8H), 2.98 (p, J = 6.9 Hz, 1H), 2.22-2.00 (m, 1H), 1.66-1.54 (m, 1H), 1.27 (d, J = 6.8 Hz, 6H). | MS m/z calcd for C$_{20}$H$_{26}$N$_6$O$_2$S 414.2 found 415.2 [M + H]$^+$ | 1 |
| 30-20 | 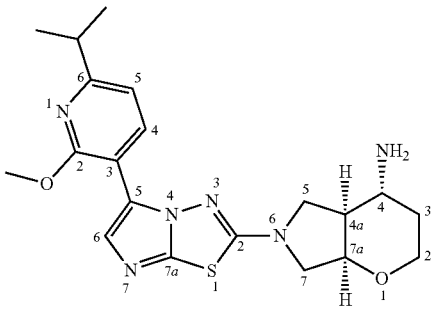<br>(4R,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine | $^1$H NMR (400 MHz, DMSO-d$_6$) δ 8.56 (d, J = 7.7 Hz, 1H), 8.20 (d, J = 5.7 Hz, 3H), 7.59 (s, 1H), 6.98 (d, J = 7.7 Hz, 1H), 4.57-4.37 (m, 1H), 4.01 (s, 3H), 3.78-3.68 (m, 8H), 2.98 (p, J = 6.9 Hz, 1H), 2.12 (d, J = 8.5 Hz, 1H), 1.61 (d, J = 14.8 Hz, 1H), 1.27 (d, J = 6.9 Hz, 6H). | MS m/z calcd for C$_{20}$H$_{26}$N$_6$O$_2$S 414.2 found 415.2 [M + H]$^+$ | 1 |

| Example/ Compound Number | Structure | NMR | LC-MS | Chiral Prep Method |
|---|---|---|---|---|
| 30-21 | (4S,4aR,7aS)-6-(5-(4-fluoro-2-methoxyphenyl)imidazo[2,1-b][1,3,4]thiadiazol-2-yl)octahydropyrano[2,3-c]pyrrol-4-amine | $^1$H NMR (500 MHz, DMSO-d$_6$) δ 8.43-8.39 (m, 3H), 8.21 (dd, J = 8.7, 6.8 Hz, 1H), 7.59 (s, 1H), 7.10 (dd, J = 11.4, 2.5 Hz, 1H), 6.92 (td, J = 8.4, 2.6 Hz, 1H), 4.54 (t, J = 4.0 Hz, 1H), 3.92 (s, 3H), 3.82 (t, J = 11.7 Hz, 1H), 3.73 (m, 2H), 3.68 (d, J = 8.8 Hz, 1H), 3.58 (m, 2H), 3.52 (d, J = 11.1 Hz, 1H), 2.56 (s, 1H), 2.47 (d, J = 3.1 Hz, 1H), 2.10 (s, 1H), 1.63 (d, J = 14.8 Hz, 1H). | MS m/z calcd for C$_{18}$H$_{20}$FN$_5$O$_2$S 389.1 found 390.3 [M + H]$^+$ | 2 |
| 30-22 | (4R,4aS,7aR)-6-(5-(4-fluoro-2-methoxyphenyl)imidazo[2,1-b][1,3,4]thiadiazol-2-yl)octahydropyran[2,3-c]pyrrol-4-amine | $^1$H NMR (500 MHz, DMSO-d$_6$) δ 8.43-8.39 (m, 3H), 8.21 (dd, J = 8.7, 6.8 Hz, 1H), 7.59 (s, 1H), 7.10 (dd, J = 11.4, 2.5 Hz, 1H), 6.92 (td, J = 8.4, 2.6 Hz, 1H), 4.54 (t, J = 4.0 Hz, 1H), 3.92 (s, 3H), 3.82 (t, J = 11.7 Hz, 1H), 3.73 (m, 2H), 3.68 (d, J = 8.8 Hz, 1H), 3.58 (m, 2H), 3.52 (d, J = 11.1 Hz, 1H), 2.56 (s, 1H), 2.47 (d, J = 3.1 Hz, 1H), 2.10 (s, 1H), 1.63 (d, J = 14.8 Hz, 1H). | MS m/z calcd for C$_{18}$H$_{20}$FN$_5$O$_2$S 389.1 found 390.3 [M + H]$^+$ | 2 |

Example 31-0: ((4S,4aS,7aR)-6-(5-(4-fluoro-2-methoxyphenyl)imidazo[2,1-b][1,3,4]thiadiazol-2-yl)octahydropyrano[2,3-c]pyrrol-4-amine

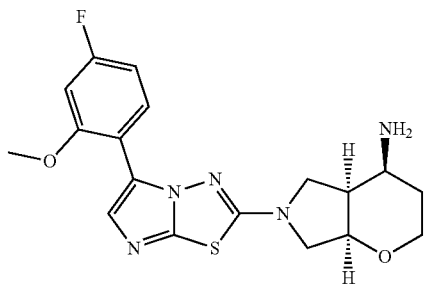 [SMILES: COc1cc(F)ccc1-c1cnc2sc(N3C[C@@H]4[C@H](C3)OCC[C@@H]4N)nn12]

The Compound 31-0 was prepared in the following way:

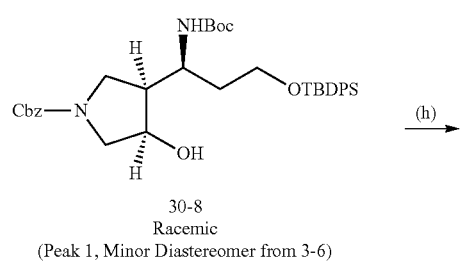

30-8
Racemic
(Peak 1, Minor Diastereomer from 3-6)

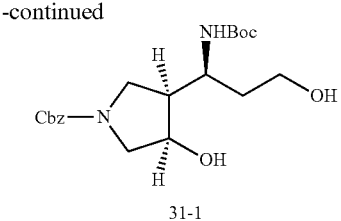

31-1

Compound 30-8 (0.86 g, 1.358 mmol) was dissolved in THF (10 mL) and cooled to 0° C. TBAF (1 M in THF) (1.6 mL, 1.630 mmol) was added at 0° C. and the reaction mixture was stirred at room temperature for 30 minutes. The reaction mixture was quenched with H$_2$O and extracted with EtOAc. The combined organic layers were washed with water, brine, dried over Na$_2$SO$_4$ and concentrated in vacuo at 35° C. The crude residue was purified by trituration with n-pentane to obtain 800 mg of Compound 31-1 as a solid. LC-MS=295.15 [M-100]$^+$, retention time=1.44 minutes.

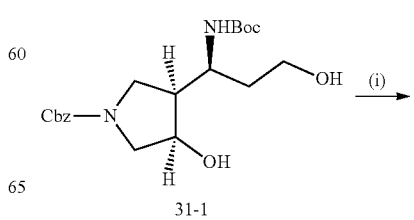

31-1

-continued

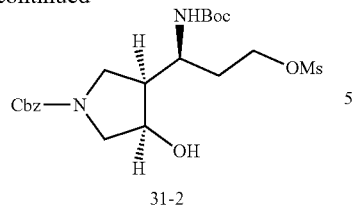
31-2

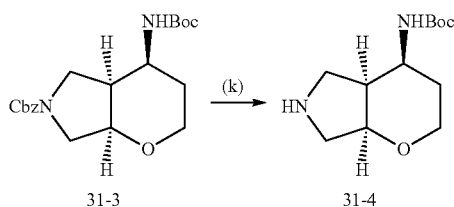 [SMILES: CC(C)(C)OC(=O)N[C@H]1CCO[C@H]2CN(C(=O)OCc3ccccc3)C[C@@H]12 ; CC(C)(C)OC(=O)N[C@H]1CCO[C@H]2CNC[C@@H]12]
31-3      31-4

To a solution of Compound 31-1 (800 mg, 2.21 mmol) in THF (60 mL) Et₃N (402 mg, 3.98 mmol) was added at 0° C. Then MsCl (378 mg, 3.32 mmol) was added dropwise at 0° C. and the resulting reaction mixture was allowed to stir for 2 hours. The reaction mixture was diluted with H₂O and extracted with DCM. The organic layers were dried over Na₂SO₄ and was concentrated in vacuo to afford 750 mg of Compound 31-2. LC-MS=373.0 [M-100]⁺, retention time=1.52 minutes.

To a solution of Compound 31-3 (350 mg, 0.13 mmol) in t-BuOH (50 mL), Pd/C (10% dry basis) (0.2 g) and Pd(OH)₂ (20% dry basis) (50 mg) were added and the reaction mixture was stirred at room temperature for 7 hours under H₂. The reaction mixture was filtered through CELITE pad and washed with excess of DCM. The filtrate was concentrated in vacuo to afford 300 mg of Compound 31-4. LC-MS=243.0 [M+H]⁺, retention time=0.83 minutes.

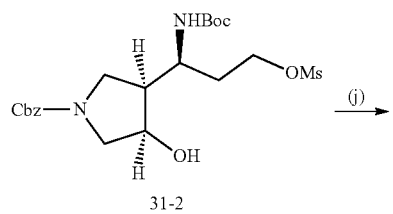
31-2

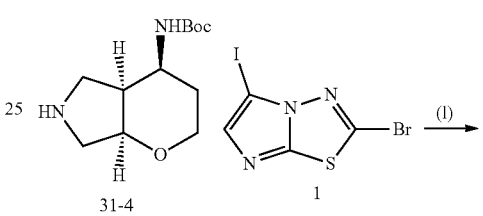
31-4     1

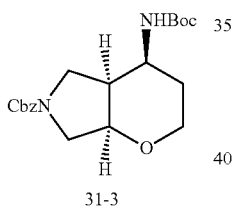
31-3

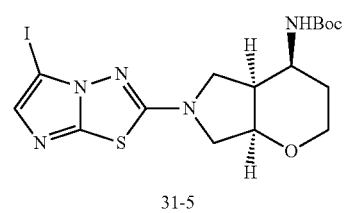
31-5

To a solution of Compound 31-2 (750 mg, 1.58 mmol) in THF (15 mL) Cs₂CO₃ (1.54 g, 4.76 mmol) was added at 0° C. and the reaction mixture was then heated to 75° C. and stirred for 16 hours. The reaction was diluted in EtOAc and the combined organic layers were washed with water, dried over Na₂SO₄ and concentrated in vacuo. The crude residue was purified by normal phase chromatography with a running gradient of 5/95 MeOH/DCM. The product was taken in ethyl acetate, MTBE was added and stirred for 10 hours, the resulting suspension was filtered and dried to afford 400 mg of Compound 31-3 as a solid. LC-MS=277.2 [M-100]⁺ (De-Boc), retention time=1.52 minutes.

A suspension of Compound 31-4 (1 equiv.), Compound 1 (1 equiv), DIPEA (2 equiv) in MeCN (20 volume) was heated at 100° C. for 90 minutes in MW. The reaction mixture was cooled to room temperature. The solid was filtered and washed with an excess of cold MeCN to get 250 mg of Compound 31-5 as a solid. ¹H NMR (300 MHz, DMSO-d₆) δ 7.08 (s, 1H), 7.06-6.99 (m, 1H), 4.13 (t, J=3.3 Hz, 1H), 3.97-3.80 (m, 2H), 3.73-3.61 (m, 1H), 3.58-3.43 (m, 1H), 3.43-3.35 (m, 2H), 2.84-2.70 (m, 1H), 1.76-1.59 (m, 1H), 1.56-1.46 (m, 2H), 1.40 (s, 9H). LC-MS=492.0 [M+H]⁺, retention time=1.51 minutes.

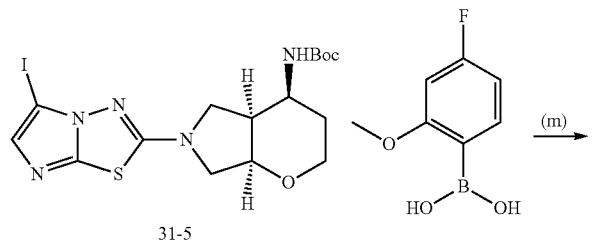
31-5

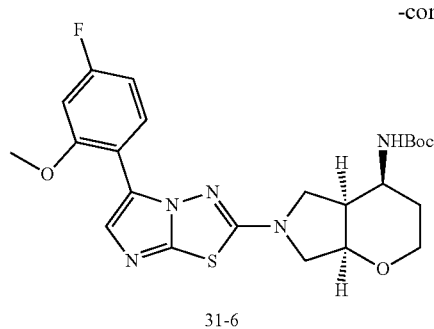

31-6

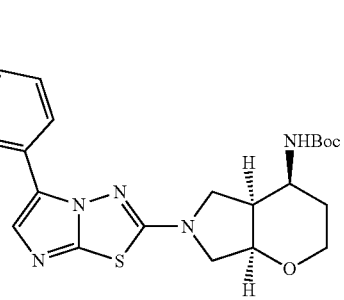

31-7

A solution of Compound 31-5 (1.0 equiv.) in dioxane/H$_2$O (4:1) was added K$_2$CO$_3$ (3.0 equiv.), (4-fluoro-2-methoxyphenyl)boronic acid (1.5 equiv.) and PdCl$_2$(dppf)-DCM complex (5 mol %) was heated at 100° C. for 6 hours. The reaction mixture was diluted with H$_2$O and extracted twice with EtOAc. The combined organic layers were washed with H$_2$O, then brine, dried over Na$_2$SO$_4$, filtered and concentrated in vacuo. The crude was triturated in 5% MeOH in MeCN, filtered and dried. The resulting product was separated by chiral HPLC purification (Method 2) to afford:

Compound 31-6 (50 mg) as a solid. LC-MS=490.5 [M+H]$^+$, retention time=1.50 minutes. Chiral HPLC: 99.0%, retention time=9.80 (Method 2).

Compound 31-7 (50 mg) as a solid. LC-MS=490.5 [M+H]$^+$, retention time=1.50 minutes. Chiral HPLC: 97.11%, retention time=16.01 (Method 2).

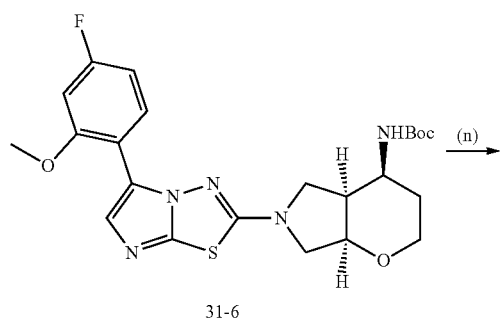

31-6

-continued

[structure]

31

Compound 31 was prepared from Compound 31-6 using Boc-deprotection procedure B. The reaction mixture was concentrated in vacuo and washed with 5% MeOH in MeCN and dried to afford 40 mg of Compound 31 as a solid. $^1$H NMR (400 MHz, MeOD-d$_4$) δ 8.31 (dd, J=8.7, 6.5 Hz, 1H), 7.88 (s, 1H), 7.03 (dd, J=11.0, 2.5 Hz, 1H), 6.84 (td, J=8.6, 2.5 Hz, 1H), 4.34 (t, J=3.2 Hz, 1H), 4.12-4.02 (m, 1H), 3.96 (s, 2H), 3.93-3.71 (m, 4H), 3.69-3.51 (m, 3H), 2.02-1.77 (m, 3H); LC-MS=390.1 [M+H]$^+$, retention time=1.26 minutes. Chiral HPLC: 94.36%, retention time=6.43.

The same procedure is done for the second eluting peak Compound 31-7 using Boc-deprotection procedure B. The reaction mixture was concentrated in vacuo and washed with 5% MeOH in MeCN and dried to afford 40 mg of Compound 31-8 as a solid. $^1$H NMR (400 MHz, MeOD-d$_4$) δ 8.30 (dd, J=8.8, 6.5 Hz, 1H), 7.85 (s, 1H), 7.02 (dd, J=11.0, 2.4 Hz, 1H), 6.83 (td, J=8.5, 2.5 Hz, 1H), 4.34 (t, J=3.2 Hz, 1H), 4.11-4.02 (m, 1H), 3.96 (s, 3H), 3.93-3.69 (m, 3H), 3.68-3.53 (m, 2H), 2.93 (s, 1H), 2.08-1.71 (m, 3H); $^{19}$F NMR (376 MHz, MeOD-d$_4$) δ −110.24. LC-MS=390.1 [M+H]$^+$, retention time=1.26 minutes. Chiral HPLC: 98.85%, retention time=8.16.

The following Compounds were prepared by the same route used to prepare Compound 31-0, using appropriate starting materials:

| Example/Compound Number | Structure | NMR | LC-MS | Chiral HPLC method |
|---|---|---|---|---|
| 31-9 | (4S,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine | $^1$H NMR (400 MHz, MeOD-$d_4$) δ 8.66 (d, J = 7.8 Hz, 1H), 7.59 (s, 1H), 6.88 (d, J = 7.7 Hz, 1H), 4.17 (t, J = 3.3 Hz, 1H), 4.06 (s, 3H), 4.00-3.91 (m, 1H), 3.74 (dd, J = 11.2, 3.7 Hz, 1H), 3.68-3.55 (m, 3H), 3.53-3.43 (m, 1H), 3.06-2.90 (m, 1H), 2.76-2.63 (m, 1H), 1.80-1.59 (m, 3H), 1.30 (d, J = 6.8 Hz, 6H). | MS m/z calcd for $C_{20}H_{26}N_6O_2S$ 414.2 found 415.2 [M + H]$^+$ | 1 |
| 31-10 | (4R,4aR,7aS)-6-(5-(6-isopropyl-2-methoxypyridin-3-yl)imidazo[2,1-b][1,3,4]thiadiazol-2-yl)octahydropyrano[2,3-c]pyrrol-4-amine | $^1$H NMR (400 MHz, MeOD-$d_4$) δ 8.66 (d, J = 7.8 Hz, 1H), 7.59 (s, 1H), 6.87 (d, J = 7.8 Hz, 1H), 4.16 (t, J = 3.3 Hz, 1H), 4.05 (s, 3H), 3.99-3.91 (m, 1H), 3.74 (dd, J = 11.3, 3.7 Hz, 1H), 3.68-3.54 (m, 3H), 3.48 (ddd, J = 11.7, 10.1, 3.6 Hz, 1H), 2.97 (p, J = 6.9 Hz, 1H), 2.76-2.63 (m, 1H), 1.77-1.59 (m, 3H), 1.30 (d, J = 6.8 Hz, 6H). | MS m/z calcd for $C_{20}H_{26}N_6O_2S$ 414.2 found 415.2 [M + H]$^+$ | 1 |

Example 32-0: (4S,4aR,7aR)-6-(5-(6-isopropyl-2-methoxypyridin-3-yl)imidazo[2,1-b][1,3,4]thiadiazol-2-yl)octahydropyrano[2,3-c]pyrrol-4-amine

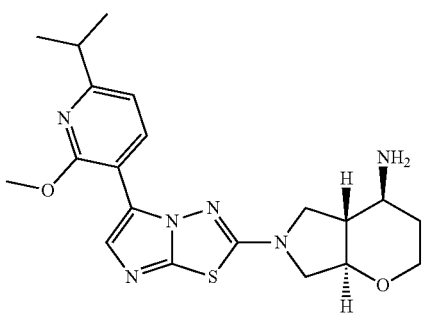 [SMILES: COc1nc(C(C)C)ccc1-c1cnc2sc(N3C[C@H]4[C@H](C3)OCC[C@@H]4N)nn12]

The Compound 32-0 was prepared in the following way:

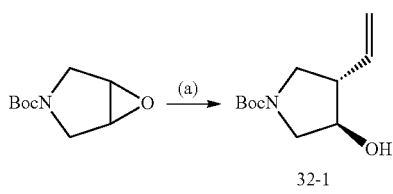

tert-Butyl 6-oxa-3-azabicyclo[3.1.0]hexane-3-carboxylate (6.00 g, 32.4 mmol) was combined with copper(I) bromide-dimethyl sulfide complex (6.66 g, 32.4 mmol) in anhydrous THF (162 mL). The mixture was cooled to −40° C. Vinylmagnesium chloride (1.6 M in THF, 81.0 mL, 130 mmol, 4.01 mmol) was added dropwise over 15 minutes. The mixture was allowed to warm to −10° C. over 4.5 hours, then quenched by the addition of sat. aqueous NH$_4$Cl. The reaction mixture was diluted with 400 mL of sat. aqueous NH$_4$Cl and 200 mL H$_2$O and the mixture was stirred vigorously. The mixture was then extracted with EtOAc (3×100 mL) and the combined organic layers were washed with sat. aqueous NH$_4$Cl and brine, dried over MgSO$_4$, filtered and concentrated in vacuo. The crude material was combined with crude compounds from a previous 1 g scale reaction. The crude material was purified by normal phase chromatography (120 g column) with a running gradient of 0-100% EtOAc/heptane to afford 7.59 g of Compound 32-1 as an oil. $^1$H NMR (500 MHz, CDCl$_3$) δ 5.70 (ddd, J=17.7, 10.3, 7.9 Hz, 1H), 5.23-5.12 (m, 2H), 4.09 (q, J=5.9 Hz, 1H), 3.73-3.60 (m, 2H), 3.28-3.16 (m, 2H), 2.73-2.63 (m, 1H), 1.46 (s, 9H). LC-MS=158.1 [M-$^t$Bu+H]$^+$.

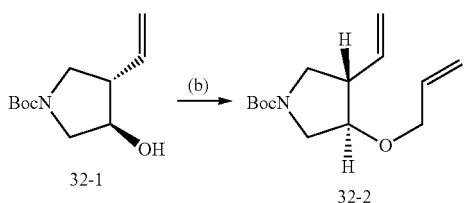 [SMILES: C=C[C@H]1CN(C(=O)OC(C)(C)C)C[C@@H]1O ; C=CCO[C@H]1CN(C(=O)OC(C)(C)C)C[C@@H]1C=C]

32-1 → 32-2

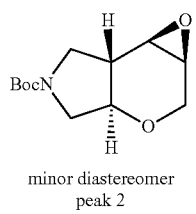

minor diastereomer
peak 2

32-5

NaH (60% in mineral oil, 0.844 g, 21.1 mmol) was added to a mixture of Compound 32-1 (3.00 g, 14.1 mmol) in DMF (56.3 mL) at 0° C. After 20 minutes, allyl bromide (2.43 mL, 28.1 mmol) was added dropwise. The reaction mixture was stirred for 3.5 hours, during which time the temperature increased to 6° C. The reaction was quenched by the addition of sat. aqueous NH$_4$Cl (100 mL). The mixture was diluted with H$_2$O (200 mL) and extracted with EtOAc (3×50 mL). The combined organic layers were washed with brine, dried over MgSO$_4$ and concentrated in vacuo. The crude material was purified by normal phase chromatography (80 g column) with a running gradient of 0-50% EtOAc/heptane to afford 3.25 g of Compound 32-2 as an oil. $^1$H NMR (400 MHz, CDCl$_3$) δ 5.89 (ddt, J=17.2, 10.3, 5.6 Hz, 1H), 5.73 (ddd, J=17.6, 10.4, 7.5 Hz, 1H), 5.28 (dq, J=17.2, 1.7 Hz, 1H), 5.21-5.07 (m, 3H), 4.07-3.96 (m, 2H), 3.80 (q, J=5.1 Hz, 1H), 3.65-3.52 (m, 2H), 3.36-3.16 (m, 2H), 2.86-2.78 (m, 1H), 1.45 (s, 9H). LC-MS=198.2 [M-$^t$Bu+H]$^+$.

A mixture of Compound 32-3 (2.75 g, 12.2 mmol) in DCM (122 mL) was treated with mCPBA (6.32 g, 36.6 mmol) at 0° C. which was added in four separate, equal portions. The mixture was allowed to warm to room temperature slowly and stirred overnight. The mixture was then cooled to 0° C., poured into sat. aqueous sodium thiosulfate (150 mL) that was also cooled to 0° C. The mixture was stirred at this temperature for 1.5 hours. The mixture was then further diluted with DCM and water. The aqueous layer was extracted once with DCM (100 mL) and the organic layer was washed with sat. aqueous NaHCO$_3$ and brine, dried over MgSO$_4$, filtered and concentrated in vacuo. The crude material was purified by normal phase chromatography (120 g column) with a running gradient of 0-100% EtOAc/heptane to afford two fractions:

Fraction 1 Compound 32-4: rac-tert-Butyl (1aR,3aR,6aS,6bS)-hexahydrooxireno[2',3':4,5]pyrano[2,3-c]pyrrole-5(2H)-carboxylate, 911 mg. $^1$H NMR (400 MHz, CDCl$_3$) δ 4.26 (dt, J=13.6, 3.0 Hz, 1H), 4.11 (ddd, J=13.6, 3.3, 1.1 Hz, 1H), 3.75-3.54 (m, 3H), 3.49 (dd, J=15.4, 4.5 Hz, 1H), 3.23 (dd, J=4.5, 3.5 Hz, 1H), 3.11 (ddd, J=11.9, 10.2, 8.2 Hz, 1H), 3.03-2.90 (m, 1H), 2.35-2.19 (m, 1H), 1.45 (d, J=2.3 Hz, 9H). LC-MS=186.1 [M-tBu+H]$^+$.

Fraction 2 Compound 32-5: rac-tert-Butyl (1aS,3aR,6aS,6bR)-hexahydrooxireno[2',3':4,5]pyrano[2,3-c]pyrrole-5(2H)-carboxylate, 475 mg. $^1$H NMR (400 MHz, CDCl$_3$) δ 4.34 (dd, J=13.8, 1.9 Hz, 1H), 3.99 (ddd, J=13.8, 5.1, 1.7 Hz, 1H), 3.78 (ddd, J=26.2, 10.2, 8.3 Hz, 1H), 3.67 (dd, J=9.9, 7.0 Hz, 1H), 3.58 (dd, J=9.7, 6.9 Hz, 1H), 3.42 (dd, J=15.9, 4.0 Hz, 1H), 3.26 (td, J=10.5, 6.9 Hz, 1H), 3.14-3.05 (m, 2H), 3.01 (q, J=10.1 Hz, 1H), 2.05-1.89 (m, 1H), 1.48-1.42 (m, 12H). LC-MS=186.1 [M-$^t$Bu+H]$^+$.

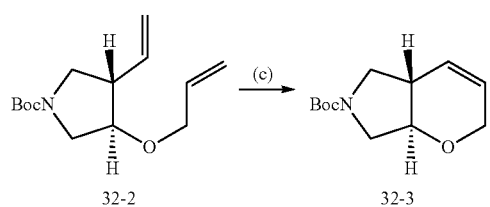 [SMILES: C=CCO[C@H]1CN(C(=O)OC(C)(C)C)C[C@@H]1C=C ; CC(C)(C)OC(=O)N1C[C@@H]2OCC=C[C@H]2C1]

32-2 → 32-3

Compound 32-2 (1.93 g, 7.62 mmol) was dissolved in DCM (152 mL) under N$_2$, copper(I) iodide (0.073 g, 0.381 mmol) and Grubbs II (0.485 g, 0.571 mmol) were added. The reaction was stirred overnight. The mixture was concentrated in vacuo. The crude material was purified by normal phase chromatography (80 g column) with a running gradient of 0-50% EtOAc/heptane to afford 934 mg of Compound 32-3 as an oil. $^1$H NMR (400 MHz, CDCl$_3$) δ 6.01-5.89 (m, 1H), 5.69 (dq, J=10.1, 2.6 Hz, 1H), 4.44-4.35 (m, 2H), 3.77-3.68 (m, 1H), 3.68-3.58 (m, 2H), 3.16-3.07 (m, 1H), 2.93-2.83 (m, 1H), 2.61-2.42 (m, 1H), 1.46 (s, 9H). LC-MS=170.1 [M-$^t$Bu+H]$^+$.

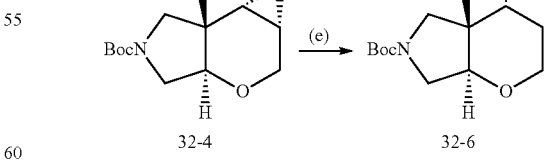

32-4 → 32-6

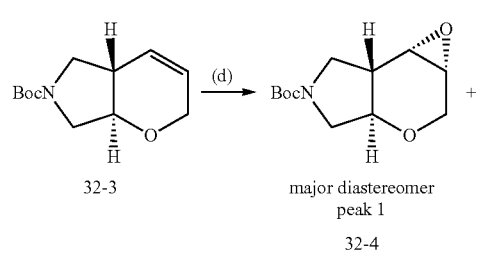

32-3 → major diastereomer peak 1

32-4

DIBAL (1 M in PhMe, 2.22 mL, 2.22 mmol) was added dropwise to a mixture of Compound 32-4 (268 mg, 1.11 mmol) in DCM (11.1 mL) at −78° C. The mixture was allowed to warm slowly to 0° C. over 4 hours. The reaction was quenched with MeOH (1 mL), then 1:1 water/Rochelle salt was added (15 mL). The mixture was stirred for 1 hour before being diluted with H₂O and DCM. The layers were separated and the aqueous layer was extracted twice with DCM (25 mL). The combined organic layers were washed with brine, dried over MgSO₄ and concentrated in vacuo. The crude material was purified by normal phase chromatography (12 g column) with a running gradient of 0-100% EtOAc/heptane to afford 150 mg of Compound 32-6 as a colorless foam. ¹H NMR (400 MHz, CDCl₃-d) δ 4.39-4.21 (m, 1H), 4.02-3.81 (m, 3H), 3.81-3.58 (m, 1H), 3.53-3.33 (m, 1H), 3.16 (dd, J=11.7, 10.3 Hz, 1H), 3.02 (dt, J=12.7, 9.8 Hz, 1H), 2.02-1.83 (m, 2H), 1.82-1.57 (m, 2H), 1.45 (s, 9H). LC-MS=188.1 [M-ᵗBu+H]⁺. Structure and stereochemistry confirmed by removal of the Boc group (TFA/DCM) with 2D NMR analysis.

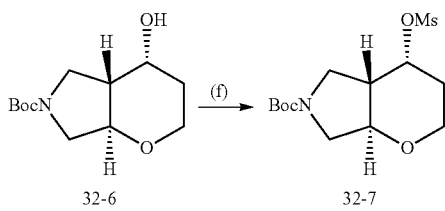 [SMILES: CC(C)(C)OC(=O)N1C[C@@H]2[C@H](O)CCO[C@H]2C1 ; CC(C)(C)OC(=O)N1C[C@H]2[C@H](C1)OCC[C@H]2OS(C)(=O)=O]

MsCl (0.072 mL, 0.925 mmol) was added to a mixture of Compound 32-6 (150 mg, 0.617 mmol) and Et₃N (0.258 mL, 1.85 mmol) in DCM (6.17 mL) at 0° C. The mixture was allowed to warm to room temperature and was stirred overnight. More Et₃N (0.086 mL) and MsCl (0.024 mL) were added. The reaction was stirred for 45 minutes. The reaction mixture was poured into sat. aqueous NH₄Cl and then extracted with DCM. The combined organic layers were washed with sat. aqueous NaHCO₃ and brine, then dried over Na₂SO₄ and concentrated in vacuo. The crude material was purified by normal phase chromatography (12 g column) with a running gradient of 0-100% EtOAc/ heptane to provide 96 mg of Compound 32-7 as a colorless foam. ¹H NMR (400 MHz, CDCl₃) δ 5.24-5.14 (m, 1H), 4.04-3.80 (m, 3H), 3.81-3.65 (m, 1H), 3.62-3.47 (m, 1H), 3.15-2.99 (m, 5H), 2.16-1.92 (m, 3H), 1.45 (s, 9H). LC-MS=266.1 [M-ᵗBu+H]⁺.

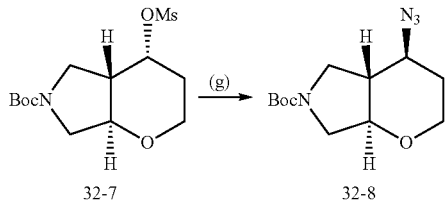 [SMILES: CC(C)(C)OC(=O)N1C[C@H]2[C@H](C1)OCC[C@H]2OS(C)(=O)=O ; CC(C)(C)OC(=O)N1C[C@@H]2[C@@H](N=[N+]=[N-])CCO[C@H]2C1]

NaN₃ (199 mg, 3.07 mmol) was added to a mixture Compound 32-7 (493 mg, 1.53 mmol) in DMF (15.3 mL) and the resulting mixture was heated to 85° C. for 1.5 hours. The mixture was diluted with H₂O (50.0 mL) and extracted with EtOAc (3×25 mL). The combined organic layers were washed with sat. aqueous NaHCO₃ and brine, then dried over MgSO₄ and concentrated in vacuo. The crude material was purified by normal phase chromatography (24 g column) with a running gradient of 0-100% EtOAc/heptane to afford 284 mg of Compound 32-8 as an oil. ¹H NMR (400 MHz, CDCl₃) δ 4.16 (dt, J=11.6, 5.6 Hz, 1H), 3.88-3.66 (m, 2H), 3.65-3.55 (m, 1H), 3.45-3.34 (m, 2H), 3.12 (q, J=10.2 Hz, 1H), 3.01 (t, J=11.0 Hz, 1H), 2.05-1.95 (m, 1H), 1.93-1.66 (m, 2H), 1.46 (s, 9H). LC-MS=213.2 [M-ᵗBu+ H]⁺.

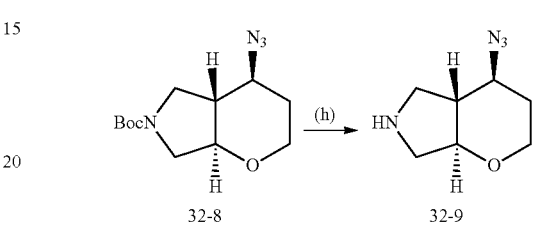

A solution of Compound 32-8 (300 mg, 1.118 mmol) in anhydrous DCM (5.6 mL) was treated with 4 M HCl in dioxane (3 mL, 12.00 mmol) at room temperature for 1 hour. The mixture was concentrated in vacuo, dried under high vacuum to give Compound 32-9 as a brown residue which was used in the next step without further purification.

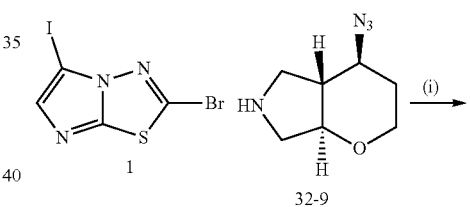

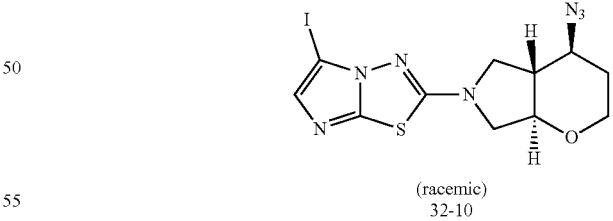

To a suspension of Compound 32-9 (229 mg, 1.119 mmol) and Compound 1 (351 mg, 1.063 mmol) in anhydrous MeCN (5.6 mL), DIPEA (1.173 mL, 6.71 mmol) was added. The reaction was heated to 80° C. for 3 hours. The reaction was concentrated in vacuo. The crude was purified by normal phase chromatography (12 g column) with a running gradient of 0-40% (5:95 MeOH:EtOAc)/heptane to afford 338 mg of Compound 32-10 as a solid.

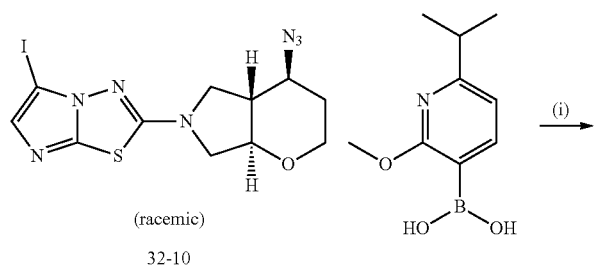

32-10

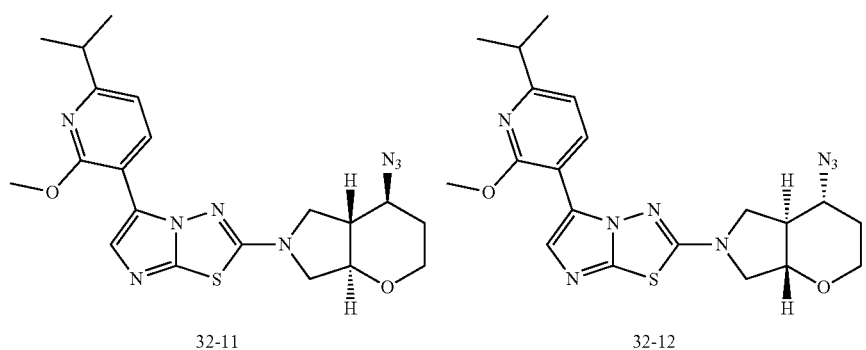

32-11        32-12

Compound 32-10 (338 mg, 0.810 mmol), PdCl$_2$(dppf)-DCM complex (99 mg, 0.122 mmol), (2-methoxy-6-methylpyridin-3-yl)boronic acid (316 mg, 1.620 mmol), K$_3$PO$_4$ (516 mg, 2.430 mmol) were suspended in dioxane (6751 µL) and H$_2$O (1350 µL). The resulting suspension was sparged under argon for 15 minutes and the reaction was heated to 80° C. overnight. The reaction mixture was diluted with EtOAc and H$_2$O and the aqueous layer was extracted twice with EtOAc. The combined organic layers were dried over MgSO$_4$, filtered, and concentrated. The crude material was purified by normal phase chromatography (12 g column) with a running gradient of 0-40% (5:95 MeOH:EtOAc)/heptane to afford 206 mg of a mixture of Compound 32-11 and Compound 32-12 as a solid. A chiral separation was done using (Method 7) to afford 77.4 mg of the first elution peak Compound 32-11 (100%; retention time 1.89 minutes) and 79.8 mg of the second elution peak Compound 32-12 (99.23%; 3.03 minutes). Relative stereochemistry known, absolute stereochemistry unknown. LC-MS=441.1 [M+H]$^+$.

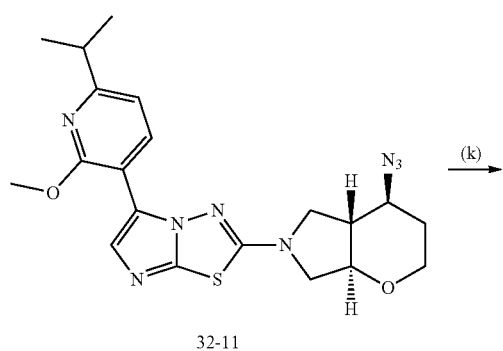

32-11

-continued

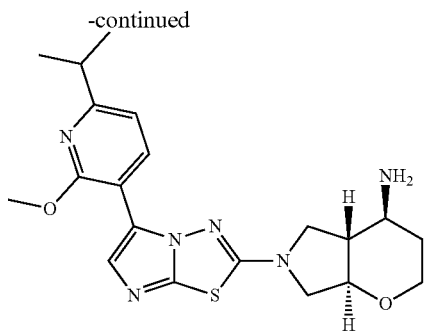

32

A suspension of the first eluting Compound 32-11, (77.4 mg, 0.176 mmol) and Ph$_3$P (92 mg, 0.351 mmol) in 10:1 THF/H$_2$O (1500 µL) was stirred at room temperature overnight. The crude material was purified by prep-HPLC to afford 35.2 mg of Compound 32. $^1$H NMR (400 MHz, DMSO-d$_6$) δ 8.53 (d, J=7.7 Hz, 1H), 8.09 (s, 3H), 7.60 (s, 1H), 6.97 (d, J=7.8 Hz, 1H), 4.10 (dd, J=11.7, 5.0 Hz, 1H), 4.01 (s, 3H), 3.83 (ddd, J=11.2, 7.5, 2.8 Hz, 2H), 3.76 (dd, J=9.7, 7.4 Hz, 1H), 3.66-3.56 (m, 1H), 3.51-3.39 (m, 1H), 3.40-3.31 (m, 2H), 2.98 (p, J=6.9 Hz, 1H), 2.14-2.02 (m, 1H), 1.97 (d, J=13.0 Hz, 1H), 1.63 (qd, J=12.6, 5.4 Hz, 1H), 1.27 (d, J=6.9 Hz, 6H). LC-MS=415.2 [M+H]$^+$.

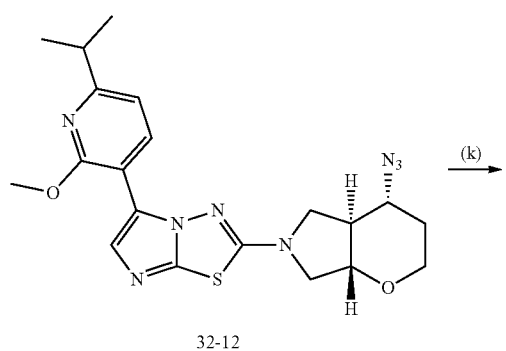

32-12

(k)

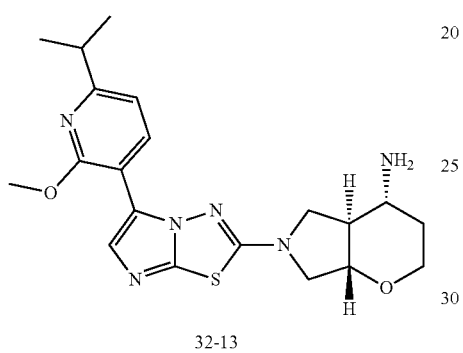

32-13

The same procedure as for Compound 32 is done for the second eluting peak Compound 32-12 to give Compound 32-13 as single compound with absolute stereochemistry unknown. ¹H NMR (400 MHz, DMSO-d₆) δ 8.53 (d, J=7.7 Hz, 1H), 8.08 (s, 3H), 7.60 (s, 1H), 6.97 (d, J=7.8 Hz, 1H), 4.11 (dd, J=11.7, 5.0 Hz, 1H), 4.01 (s, 3H), 3.87-3.82 (m, 2H), 3.76 (dd, J=9.7, 7.4 Hz, 1H), 3.65-3.57 (m, 1H), 3.51-3.40 (m, 1H), 3.40-3.29 (m, 2H), 2.98 (p, J=6.9 Hz, 1H), 2.14-2.02 (m, 1H), 1.97 (d, J=12.8 Hz, 1H), 1.63 (qd, J=12.6, 5.3 Hz, 1H), 1.27 (d, J=6.9 Hz, 6H). LC-MS=415.2 [M+H]⁺.

Example 33-0: (3aS,5R,7R,7aR)-7-amino-2-(5-(6-isopropyl-2-methoxypyridin-3-yl)imidazo[2,1-b][1,3,4]thiadiazol-2-yl)octahydro-1H-isoindol-5-ol

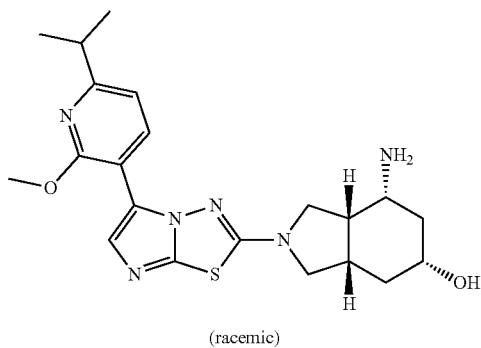 [SMILES: COc1nc(C(C)C)ccc1-c1cnc2sc(N3C[C@H]4C[C@@H](O)C[C@@H](N)[C@H]4C3)nn12]
(racemic)

The Compound 33-0 was prepared in the following way:

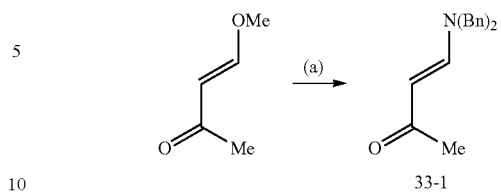

(Z)-4-Methoxybut-3-en-2-one (5. g, 50 mmol) was dissolved in anhydrous THF (25 mL). Dibenzylamine (19.7 g, 100 mmol) in anhydrous THF (40 mL) was added dropwise and the reaction mixture was allowed to stir at room temperature for 16 hours. The mixture was quenched with H₂O and extracted with EtOAc. The combined organic layers were dried over Na₂SO₄ and concentrated in vacuo. The crude material was purified by normal phase chromatography with a running gradient of 20-45% EtOAc/n-hexane to afford 10 g of Compound 33-1 as a pale orange gum. ¹H NMR (400 MHz, CDCl₃) δ 7.89 (d, J=12.8 Hz, 1H), 7.41-7.20 (m, 10H), 5.37 (d, J=12.8 Hz, 1H), 4.37 (br s, 4H), 2.15 (s, 3H). LC-MS=266.42 [M+H]⁺.

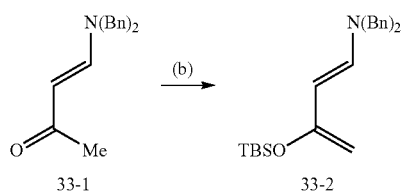

KHMDS (0.5 M in PhMe, 9.01 g, 45.3 mmol) was added to anhydrous THF (95 mL) at −78° C. under a N₂ atmosphere. A solution of Compound 33-1 (10.0 g, 37.73 mmol) in anhydrous THF (100 mL) was added over a period of 15 minutes. The reaction was allowed to slowly warm to −50° C. and stirred for 2 hours. The reaction was cooled to −78° C. and a solution of TBSCl (7.40 g, 49.1 mmol) in anhydrous THF (75 mL) was added dropwise over a period of 10 minutes. The resulting mixture was allowed to warm to 0° C. over 2.5 hours, then poured onto Et₂O and filtered through a CELITE pad. The filtrate was concentrated in vacuo to afford 11.8 g of Compound 33-2, which was immediately used in the next step without any further purification.

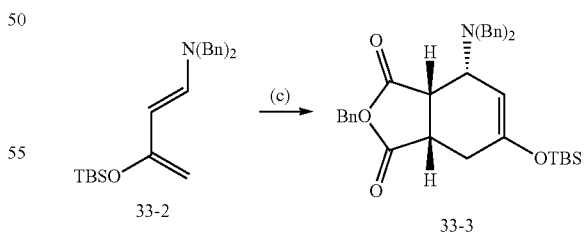

Compound 33-2 (11.8 g, 31.1 mmol) was dissolved in anhydrous PhMe (100 mL) and cooled to −78° C. under N₂. A solution of N-benzyl maleimide (5.24 g, 28.0 mmol) in anhydrous PhMe (75 mL) was added dropwise and the reaction was allowed to cool to room temperature slowly and stirred for 16 hours. The mixture was quenched with H₂O and extracted with EtOAc. The combined organic layers were dried over Na₂SO₄ and concentrated in vacuo to afford a crude residue, which was purified by normal phase chromatography (basic alumina) with a running gradient of 3-12% EtOAc/n-hexane to afford 5 g of Compound 33-3. $^1$H NMR (400 MHz, CDCl$_3$) δ 7.43-7.25 (m, 15H), 4.92-4.91 (m, 1H), 4.72-4.63 (m, 1H), 4.48-4.44 (m, 1H), 3.95-3.92 (m, 1H), 3.86-3.76 (m, 2H), 3.67-3.61 (m, 2H), 3.30-3.25 (m, 1H), 3.15-3.10 (m, 1H), 2.72-2.67 (m, 1H), 2.32-2.25 (m, 1H), 0.89 (s, 9H), 0.14-0.10 (m, 6H). LC-MS=567.45 [M+H]$^+$.

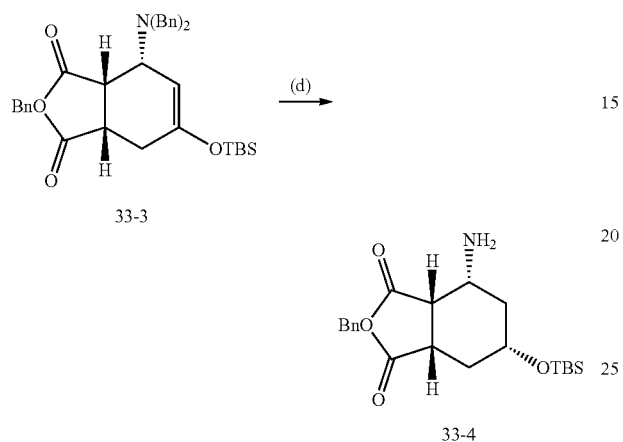

Compound 33-3 (5 g, 8.84 mmol) was dissolved in i-PrOH (50 mL) and then 10% Pd/C (2.50 g) was added. The reaction was stirred at room temperature under 1 atm of H$_2$ for 30 hours. The mixture was filtered through a CELITE pad and the pad was washed with EtOAc. The filtrate was concentrated in vacuo to afford 3.03 g of Compound 33-4, which was used in the next step without any further purification. LC-MS=389.25 [M+H]$^+$.

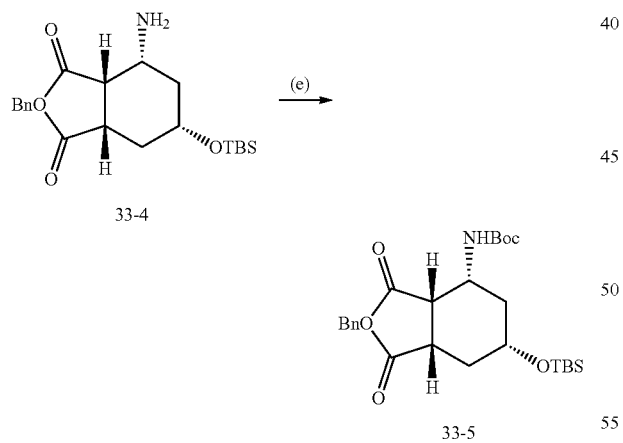

Compound 33-4 (3.03 g, 7.73 mmol) was dissolved in DCM (30 mL) and then Et$_3$N (2.34 g, 23.2 mmol) was added. The reaction was stirred at room temperature for 15 minutes. A solution of (Boc)$_2$O (1.87 g, 8.59 mmol) in DCM (5 mL) was then added dropwise at 0° C. The mixture was concentrated in vacuo, then was diluted with EtOAc and washed successively with water, 5% citric acid solution and sat. NaHCO$_3$. The organic layer was dried over Na$_2$SO$_4$ and concentrated in vacuo. The crude material was purified by normal phase chromatography (basic alumina) with a running gradient of 8-22% EtOAc/n-hexane to afford 1.20 g of Compound 33-5. $^1$H NMR (400 MHz, CDCl$_3$) δ 7.41-7.32 (m, 5H), 6.19 (d, J=9.2 Hz, 1H), 4.70-4.59 (m, 1H), 4.08-4.03 (m, 1H), 3.10-3.01 (m, 1H), 2.33-2.26 (m, 1H), 2.09-1.99 (m, 1H), 1.83-1.77 (m, 1H), 1.43 (s, 9H), 1.30-1.26 (m, 1H), 0.89 (s, 9H), 0.14-0.10 (m, 6H). LC-MS=487.35 [M−H]$^−$.

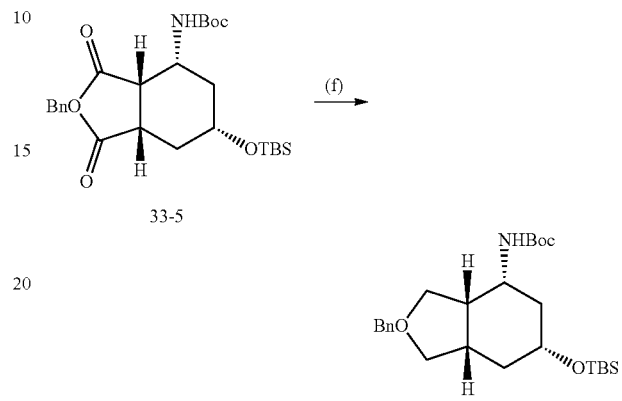

Compound 33-5 (0.690 g, 1.41 mmol) was dissolved in anhydrous PhMe (15 mL) and cooled to −78° C. Red-Al (5.71 g, 28.5 mmol, 70% in PhMe) was added and the reaction mixture was stirred at room temperature for 1 hour. The mixture was cooled to 0° C. and H$_2$O (2.75 mL) was added followed by a mixture of 1 N NaOH (3 mL) and H$_2$O (3 mL). The mixture was then diluted with EtOAc (25 mL) and filtered through a CELITE pad. The filtrate was dried over Na$_2$SO$_4$ and concentrated in vacuo to afford 0.730 g of Compound 33-6, which was used in the next step without any further purification. LC-MS=461.61 [M+H]$^+$.

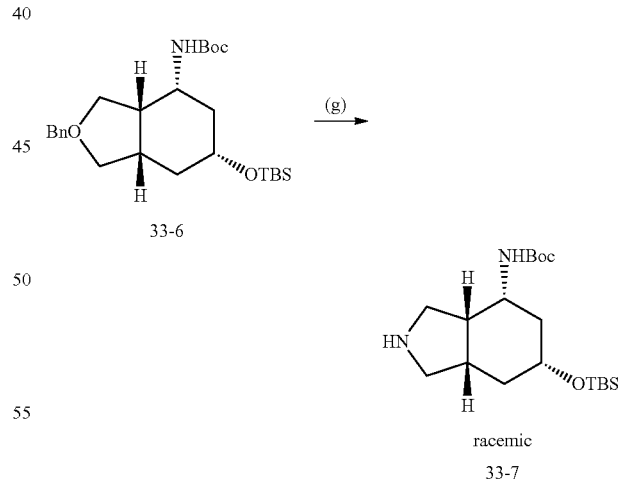

Compound 33-6 (0.730 g, 1.58 mmol) was dissolved in i-PrOH (15 mL) and then 10% Pd/C (0.350 g) was added. The reaction mixture was stirred at room temperature under 1 atmosphere of H$_2$ for 16 hours. The mixture was filtered through a CELITE pad and concentrated under vacuum to afford 0.550 g of Compound 33-7 as a racemic mixture which was used in the next step without any further purification. LC-MS=371.49 [M+H]$^+$.

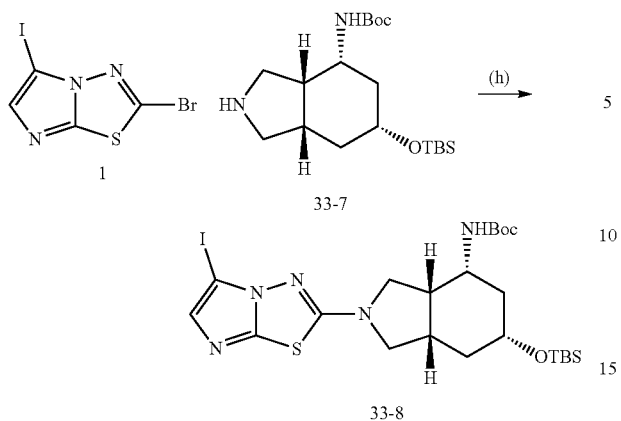

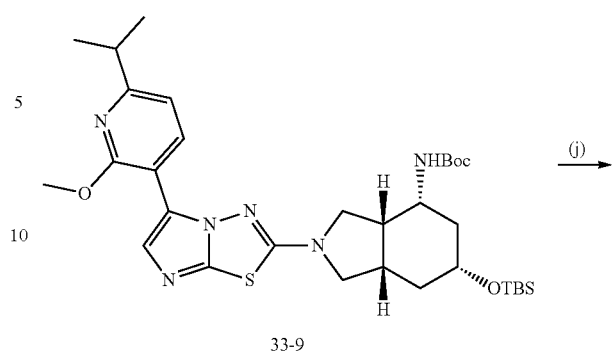

To a suspension of Compound 1 and Compound 33-7 in anhydrous MeCN (3 mL), DIPEA (0.635 mL, 3.64 mmol) was added. The reaction was heated to 100° C. for 10 hours. The reaction mixture was washed with DCM, and concentrated in vacuo. The crude material was purified by normal phase chromatography (40 g column) with a running gradient of 0-30% (3:1 EtOAc:EtOH)/heptane to afford 150 mg of Compound 33-8 as a solid. LC-MS=620.5 [M+H]$^+$.

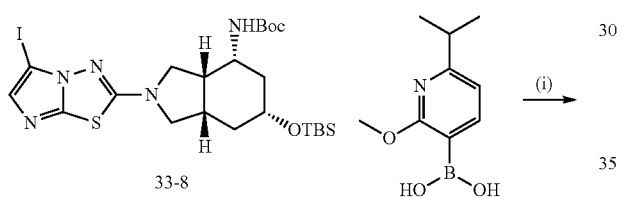

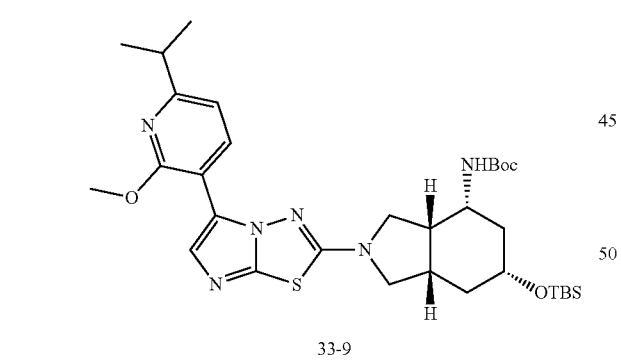

A mixture of PdCl$_2$(dppf)-DCM complex (9.88 mg, 0.012 mmol), Compound 33-8 (75 mg, 0.121 mmol), K$_3$PO$_4$ (0.182 mL, 0.363 mmol) in dioxane (3 mL) and H$_2$O (0.6 mL) was sparged with N$_2$ gas for 5 minutes. After degassing, the suspension was stirred at 80° C. for 3 hours. The reaction mixture was diluted with DCM and extracted twice from water. The combined organic layers were dried over MgSO$_4$, filtered, and concentrated in vacuo. The crude reaction mixture was purified by normal phase chromatography (12 g column) with a running gradient of 0-70% EtOAc/DCM to afford 40 mg of Compound 33-9. LC-MS=643.7 [M+H]$^+$.

To a solution of Compound 33-9 (40 mg, 0.062 mmol) in DCM (4 mL), 4 M HCl (0.016 mL, 0.062 mmol) was added and the resulting suspension was stirred at room temperature for 1 hour. The crude product was concentrated in vacuo and purified by prep-HPLC to afford 9.5 mg of Compound 33. $^1$H NMR (400 MHz, DMSO-d$_6$) δ 8.54 (d, J=7.7 Hz, 1H), 8.00 (s, 3H), 7.61 (s, 1H), 6.96 (d, J=7.7 Hz, 1H), 4.01 (s, 3H), 3.68 (dd, J=9.7, 5.3 Hz, 1H), 3.52 (dq, J=18.0, 10.1 Hz, 4H), 3.35 (d, J=9.8 Hz, 1H), 2.98 (p, J=6.8 Hz, 1H), 2.77 (s, 1H), 1.97 (d, J=11.9 Hz, 1H), 1.85 (d, J=12.6 Hz, 1H), 1.45 (q, J=12.1 Hz, 1H), 1.27 (d, J=6.8 Hz, 7H), 1.08 (q, J=12.2 Hz, 1H). LC-MS=429.4 [M+H]$^+$.

Example 34-0: (3aR,4S,5S,7aS)-4-amino-2-(5-(6-isopropyl-2-methoxypyridin-3-yl)imidazo[2,1-b][1,3,4]thiadiazol-2-yl)octahydro-1H-isoindol-5-ol

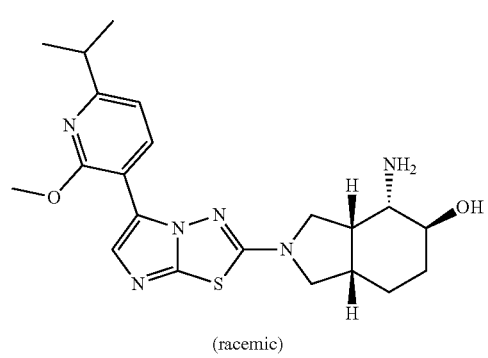 [SMILES: COc1nc(C(C)C)ccc1-c1cnc2sc(N3C[C@H]4CC[C@H](O)[C@@H](N)[C@H]4C3)nn12]

(racemic)

The Compound 34-0 was prepared in the following way:

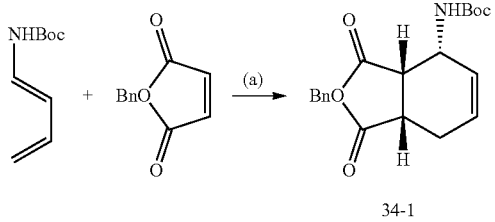

34-1

A mixture of N-benzylmaleimide (5.53 g, 29.5 mmol) and to tert-butyl (E)-buta-1,3-dien-1-ylcarbamate (5 g, 29.5 mmol) in anhydrous dioxane (148 mL) was heated to reflux for 16 hours. The reaction mixture was then cooled to room temperature and concentrated in vacuo. The crude residue was dissolved in a minimal amount of DCM, applied to the top of a solid loading cartridge, and purified by normal phase chromatography (120 g column) with a running gradient of 0-30% EtOAc/heptane to afford 10 g of Compound 34-1 as a white foam. $^1$H NMR (500 MHz, CDCl$_3$) δ 7.42-7.14 (m, 5H), 6.25 (d, J=9.4 Hz, 1H), 5.89-5.75 (m, 2H), 4.59 (s, 2H), 4.50-4.35 (m, 1H), 3.23 (dd, J=9.0, 6.1 Hz, 1H), 3.20-3.09 (m, 1H), 2.76-2.59 (m, 1H), 2.26-2.14 (m, 1H), 1.46 (s, 9H). LC-MS=257.2 [M-Boc+H]$^+$.

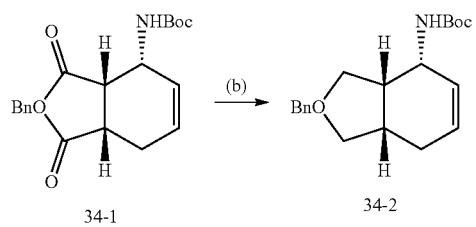

34-1       34-2

Compound 34-1 (2.91 g, 8.16 mmol) was sparged with N$_2$ and then anhydrous PhMe (100 mL) was added to give a homogenous solution. Then Red-Al (60% in PhMe, 13.3 mL, 40.8 mmol) was added dropwise at −78° C. The reaction became extremely viscous, precluding adequate stirring in the thick gel. The reaction was allowed to warm to room temperature, at which point stirring resumes. After 1.5 hours, the reaction was cooled to −78° C. and carefully quenched with dropwise addition of MeOH (5 mL). When all bubbling ceased, the reaction was warmed to room temperature and an aqueous solution of Rochelle salt was added. The resulting layers were separated and the aqueous layer was extracted 3× with EtOAc. The combined organic layers were dried over MgSO$_4$, filtered, and concentrated in vacuo. The crude residue was purified by normal phase chromatography (40 g column) with a running gradient of 0-40% EtOAc/heptane to afford 1.73 g of Compound 34-2 as a solid. $^1$H NMR (400 MHz, CDCl$_3$) δ 7.36-7.20 (m, 5H), 5.85 (dddd, J=9.4, 5.7, 3.9, 2.0 Hz, 1H), 5.74 (d, J=9.9 Hz, 1H), 5.31 (d, J=7.3 Hz, 1H), 4.23 (s, 1H), 3.60 (d, J=3.3 Hz, 2H), 2.85 (dd, J=9.0, 7.6 Hz, 1H), 2.74 (ddt, J=19.8, 15.7, 7.4 Hz, 2H), 2.56 (dtd, J=11.7, 8.7, 5.8 Hz, 1H), 2.36 (t, J=7.8 Hz, 1H), 2.24 (t, J=7.8 Hz, 1H), 2.18-2.06 (m, 1H), 2.02-1.90 (m, 1H), 1.44 (s, 9H). LC-MS=329.4 [M+H]$^+$.

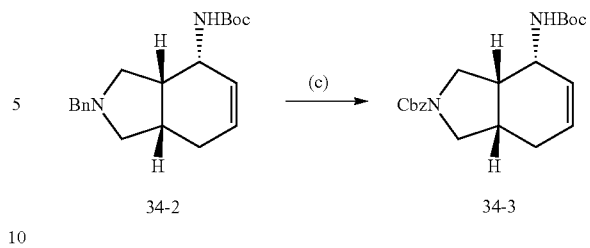

34-2       34-3

Compound 34-2 (2.07 g, 6.30 mmol) was sparged with N$_2$ and then dissolved in anhydrous DCM (63.0 mL). Cbz-Cl (1.80 mL, 12.6 mmol) was added dropwise at room temperature and the reaction was stirred for 6 hours, then quenched with NaHCO$_3$ and stirred for 15 minutes. The layers were separated and the aqueous layer extracted twice with DCM. The combined organics were dried over MgSO$_4$, filtered, and concentrated. The crude residue was purified by normal phase chromatography (40 g column) with a running gradient of 0-100% EtOAc/heptane to afford 1.54 g of Compound 34-3 as a solid. $^1$H NMR (400 MHz, CDCl$_3$) δ 7.45-7.27 (m, 4H), 5.74 (ddt, J=10.0, 5.0, 2.5 Hz, 1H), 5.44 (dt, J=10.2, 2.6 Hz, 1H), 5.23-5.02 (m, 2H), 4.53 (s, 1H), 4.43 (dd, J=18.7, 8.6 Hz, 1H), 3.61-3.26 (m, 3H), 3.15 (dt, J=10.6, 9.3 Hz, 1H), 2.84 (s, 1H), 2.42 (ddt, J=13.5, 9.2, 5.0 Hz, 1H), 2.31-2.10 (m, 1H), 1.83 (ddq, J=18.8, 9.4, 3.2 Hz, 1H), 1.44 (s, 9H). LC-MS=273.3 [M-Boc+H]$^+$.

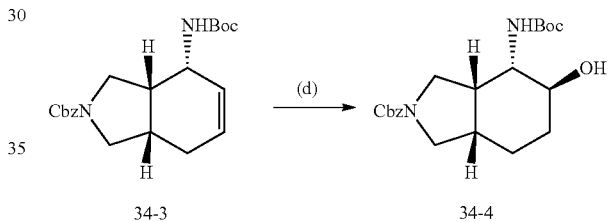

34-3       34-4

Compound 34-3 (117 mg, 0.314 mmol) was sparged with N$_2$ and then dissolved in anhydrous THF (10 ml). The solution was cooled to 0° C. and borane tetrahydrofuran complex (0.628 ml, 0.628 mmol) was added dropwise for 1 hour. More borane tetrahydrofuran complex was added (0.628 ml, 0.628 mmol). After 5 hours, the reaction was cooled to 0° C. and the excess borane was carefully quenched with H$_2$O (10 mL), followed by sodium perborate monohydrate (267 mg, 2.67 mmol) and the reaction stirred at room temperature overnight. The reaction was diluted with H$_2$O and EtOAc, then filtered off. The resulting filtrate was extracted 3× with EtOAc, the combined organic layers were dried over MgSO$_4$, filtered, and concentrated. The crude residue was purified by normal phase chromatography (12 g) with a running gradient of 0-60% EtOAc/heptane to afford 99.7 mg of Compound 34-4 as an oil. LC-MS=291.3 [M+H]$^+$.

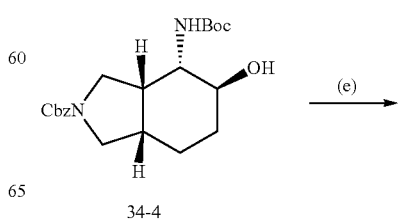

34-4

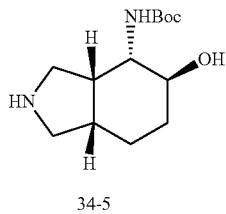

34-5

A mixture of Compound 34-4 (95 mg, 0.243 mmol) and 10% Pd/C (78 mg, 0.073 mmol) was sparged with $N_2$. EtOAc (4.8 ml) and AcOH (20 µL, 0.349 mmol) were added. Then the reaction was put under $H_2$ and was stirred at room temperature for 4.5 hours. The reaction was purged with argon, diluted with MeOH, and filtered over a CELITE pad. The CELITE was washed thoroughly with MeOH and EtOAc and the filtrate was concentrated in vacuo. The crude residue Compound 34-5 was taken forward to the next step without any further characterization or purification.

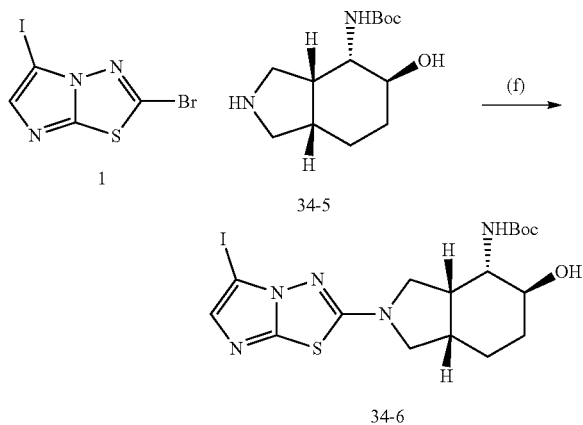

To a suspension of Compound 34-5 (84.5 mg, 0.330 mmol) and Compound 1 (103 mg, 0.313 mmol) in anhydrous MeCN (3.3 ml), DIPEA (173 µL, 0.989 mmol) was added. The reaction mixture was heated to 100° C. for 2 hours. The reaction mixture was concentrated in vacuo. The crude residue was purified by normal phase chromatography (12 g column) with a running gradient of 0-60% (5% MeOH:EtOAc)/heptane to afford 86.8 mg of Compound 34-6 as a solid. $^1$H NMR (500 MHz, CDCl$_3$) δ 7.13 (t, J=1.3 Hz, 1H), 4.83 (d, J=6.8 Hz, 1H), 3.74 (d, J=10.5 Hz, 1H), 3.69-3.58 (m, 3H), 3.44 (t, J=10.6 Hz, 1H), 3.32 (d, J=9.8 Hz, 1H), 3.18 (d, J=10.3 Hz, 1H), 2.61 (s, 1H), 2.43 (dq, J=11.3, 5.6 Hz, 1H), 2.16-2.08 (m, 1H), 1.80 (dd, J=14.8, 4.7 Hz, 1H), 1.71 (s, 1H), 1.49 (s, 9H), 1.42-1.33 (m, 1H). LC-MS=506.4 [M+H]$^+$.

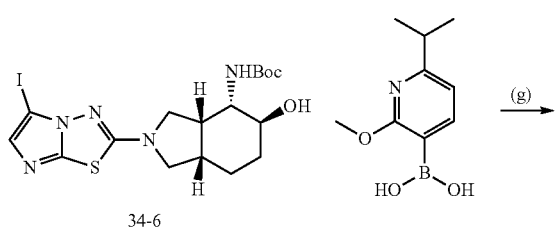

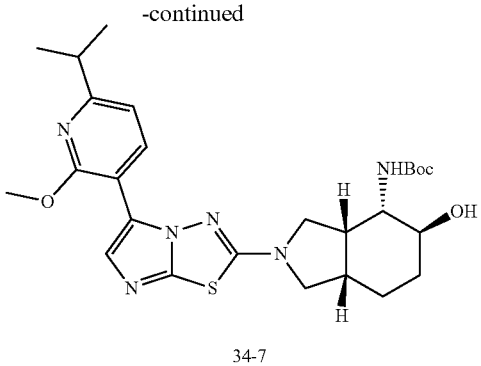

34-7

Compound 34-6 (84 mg, 0.166 mmol), PdCl$_2$(dppf)-DCM complex (20.36 mg, 0.025 mmol), (2-methoxy-6-methylpyridin-3-yl)boronic acid (64.8 mg, 0.332 mmol), K$_3$PO$_4$ (106 mg, 0.499 mmol) were suspended in dioxane (1.4 mL) and H$_2$O (0.3 mL). After degassing with argon for 15 minutes, the reaction mixture was heated to 80° C. for 2.5 hours. The reaction mixture was diluted with DCM and extracted twice from the aqueous layer. The combined organic layers were dried over MgSO$_4$, filtered, and concentrated in vacuo. The crude residue was purified by normal phase chromatography (12 g column) with a running gradient of 0-50% (5% MeOH:EtOAc)/heptane to afford 49.3 mg of Compound 34-7. LC-MS=529.6 [M+H]$^+$.

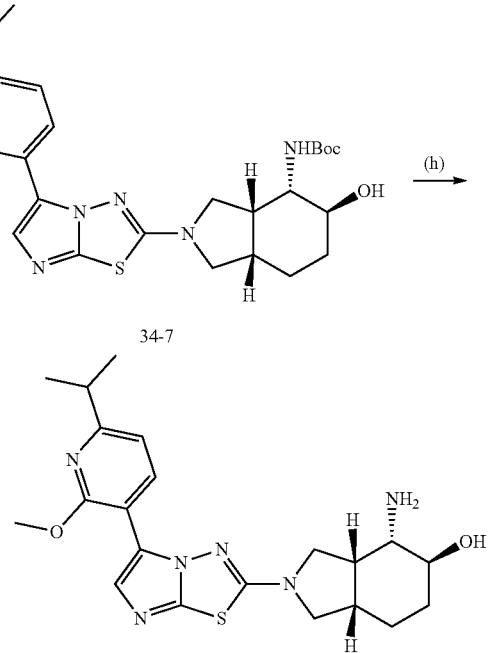

Compound 34-7 (48.3 mg, 0.091 mmol) was dissolved in anhydrous DCM (2 ml) and TFA (352 µL, 4.57 mmol) was added. The reaction was stirred at room temperature for 1 hour. The reaction mixture concentrated in vacuo and purified by prep-HPLC to afford 40.8 mg of Compound 34. $^1$H NMR (400 MHz, DMSO-d$_6$) δ 8.54 (d, J=7.7 Hz, 1H), 8.16-7.92 (m, 3H), 7.62 (s, 1H), 6.96 (d, J=7.7 Hz, 1H), 4.01 (s, 3H), 3.66 (ddd, J=15.6, 9.8, 5.0 Hz, 2H), 3.54 (d, J=10.1

Hz, 2H), 3.30 (d, J=9.8 Hz, 1H), 3.27-3.16 (m, 1H), 2.94 (ddt, J=26.4, 10.0, 5.8 Hz, 2H), 2.46 (q, J=5.6 Hz, 1H), 1.88 (d, J=8.5 Hz, 1H), 1.71 (d, J=11.2 Hz, 1H), 1.36 (t, J=10.8 Hz, 2H), 1.27 (d, J=7.6 Hz, 6H). LC-MS=429.2 [M+H]+.

Example 35-0: (3aR,4S,5R,7aS)-4-amino-2-(5-(2-methoxy-6-methylpyridin-3-yl)imidazo[2,1-b][1,3,4]thiadiazol-2-yl)octahydro-1H-isoindol-5-ol

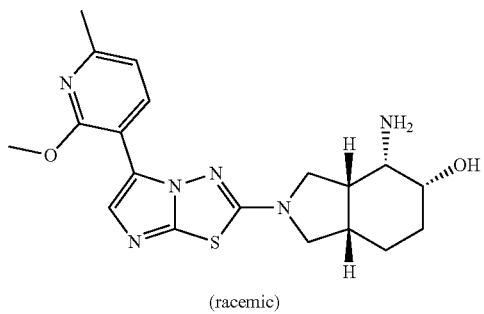 [SMILES: COc1nc(C)ccc1-c1cnc2sc(N3C[C@H]4CC[C@@H](O)[C@@H](N)[C@H]4C3)nn12]

(racemic)

The Compound 35-0 was prepared in the following way, starting with Compound 34-4:

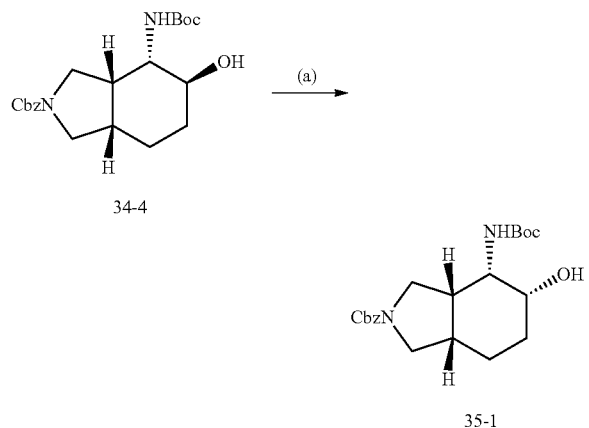

A mixture of Compound 34-4 (1.14 g, 2.92 mmol), 4-nitrobenzoic acid (0.732 g, 4.38 mmol), and Ph₃P (1.149 g, 4.38 mmol) was suspended in anhydrous THF (60.0 mL) under N₂. Then DEAD (0.690 ml, 4.38 mmol) was added at 0° C. The reaction was stirred at 0° C. for 5 minutes, then warmed to room temperature over 15 minutes, before the reaction was heated to 70° C. 16 hours. The reaction mixture was concentrated in vacuo and was purified by normal phase chromatography (80 g column) with a running gradient of 0-30% EtOAc/heptane to afford 1.65 g of the desired intermediate as a solid. ¹H NMR showed an inseparable 3:1 mixture of desired product and diethyl hydrazine-1,2-dicarboxylate, respectively. ¹H NMR (500 MHz, CDCl₃) δ 8.32 (d, J=8.5 Hz, 1H), 8.16 (d, J=8.5 Hz, 1H), 8.14-8.01 (m, 2H), 7.45-7.28 (m, 5H), 5.42 (s, 1H), 5.31-5.10 (m, 1H), 5.16 (d, J=2.1 Hz, 1H), 4.80-4.68 (m, 1H), 4.13 (s, 1H), 3.79 (t, J=11.2 Hz, 1H), 3.72-3.57 (m, 1H), 3.55-3.33 (m, 2H), 2.85 (s, 1H), 2.37-2.30 (m, 1H), 2.25-2.16 (m, 1H), 1.77-1.64 (m, 1H), 1.55-1.49 (m, 2H), 1.42 (s, 9H). LC-MS=440.4 [M-Boc+H]+. The resulting intermediate (820 mg, 1.52 mmol) and K₂CO₃ (6.15 g, 44.5 mmol) were suspended in MeOH (15.2 mL) and the reaction mixture was stirred at room temperature for 2 hours. The reaction was quenched with NH₄Cl, diluted with EtOAc, and the layers separated. The aqueous layer was extracted, the combined organic layers were dried over MgSO₄, filtered, and concentrated in vacuo. The crude residue was purified by normal phase chromatography (24 g column) with a running gradient of 0-40% EtOAc/heptane to afford 748 mg of Compound 35-1. ¹H NMR showed an inseparable mixture of desired product and dimethyl/diethyl hydrazine-1,2-dicarboxylates. ¹H NMR (500 MHz, CDCl₃) δ 7.40-7.31 (m, 4H), 7.29 (t, J=5.1 Hz, 1H), 5.31-5.20 (m, 1H), 5.18-5.02 (m, 2H), 4.00 (s, 1H), 3.90-3.71 (m, 2H), 3.55-3.26 (m, 3H), 2.78-2.62 (m, 1H), 2.20-2.09 (m, 1H), 1.91-1.77 (m, 1H), 1.63 (q, J=12.8 Hz, 1H), 1.54 (q, J=12.8 Hz, 1H), 1.42 (s, 9H), 1.38-1.32 (m, 1H). LC-MS=291.3 [M-Boc+H]+.

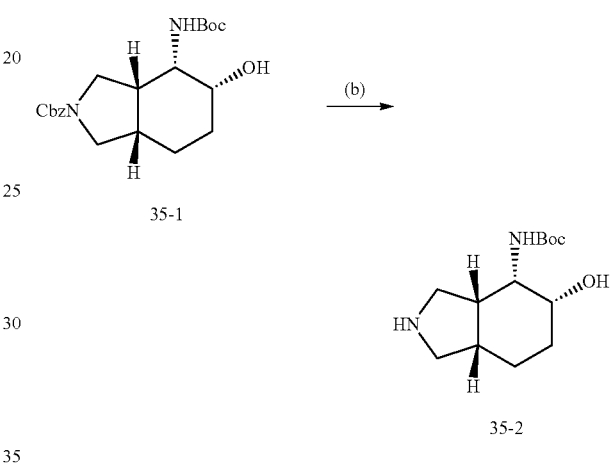

Compound 35-1 (347 mg, 0.889 mmol) and 10% Pd/C (284 mg, 0.267 mmol) were put under N₂. Then EtOAc (15.4 mL) and AcOH (0.051 mL, 0.889 mmol) were added. The reaction was stirred at room temperature under H₂ for 1 hour. The reaction was diluted with MeOH, and filtered over CELITE pad. The CELITE pad was washed thoroughly with MeOH and EtOAc and the filtrate was concentrated in vacuo to afford Compound 35-2.

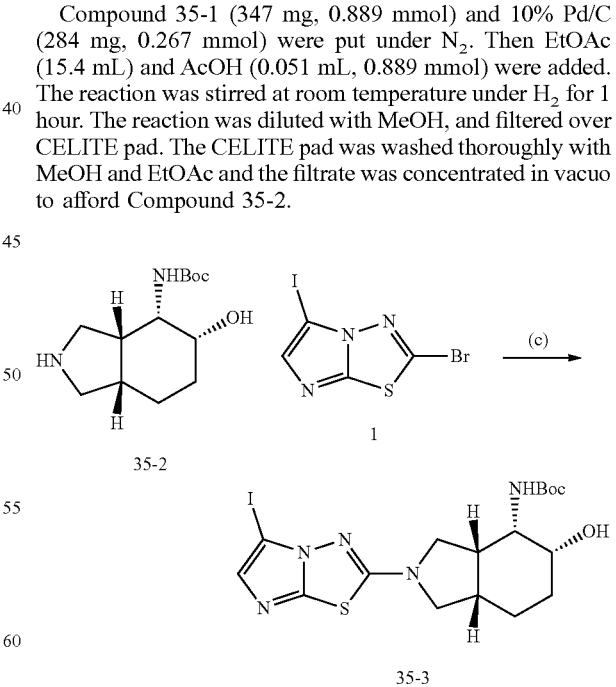

Compound 35-2 (223 mg, 0.870 mmol) and Compound 1 (273 mg, 0.826 mmol) were suspended in anhydrous MeCN (5 mL), then DIPEA (0.456 mL, 2.61 mmol) was added. The reaction was heated to 100° C. for 2 hours. The reaction was concentrated in vacuo. The crude material was purified by normal phase chromatography (40 g column) with a running gradient of 0-30% (3:1 EtOAc/EtOH)/heptane to afford 326 mg of Compound 35-3 as a solid. $^1$H NMR (500 MHz, CDCl$_3$) δ 7.09 (s, 1H), 5.26 (d, J=7.1 Hz, 1H), 4.12 (s, 1H), 4.00 (t, J=10.3 Hz, 1H), 3.94-3.81 (m, 1H), 3.60 (dd, J=9.6, 5.5 Hz, 1H), 3.49 (t, J=9.1 Hz, 1H), 3.37 (d, J=10.1 Hz, 1H), 2.99-2.82 (m, 1H), 2.35 (d, J=10.5 Hz, 1H), 2.01-1.83 (m, 2H), 1.75-1.60 (m, 2H), 1.50 (d, J=14.2 Hz, 1H), 1.47 (s, 9H).

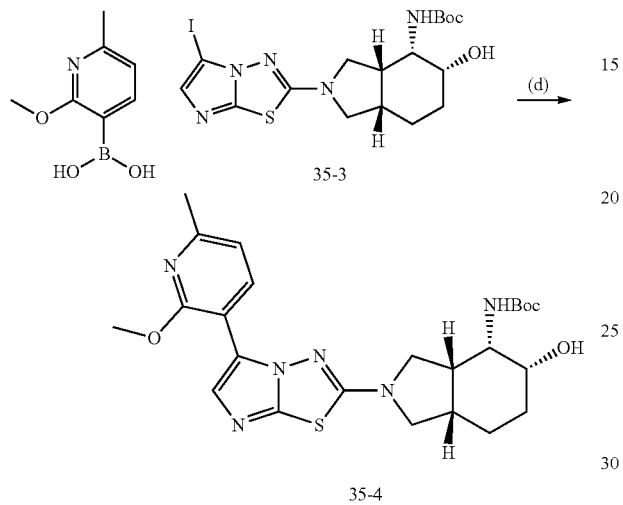

To a mixture PdCl$_2$(dppf)-DCM complex (24.97 mg, 0.031 mmol), (2-methoxy-6-methylpyridin-3-yl)boronic acid (68.1 mg, 0.408 mmol), K$_3$PO$_4$ (130 mg, 0.611 mmol) was added a solution of Compound 35-3 (103 mg, 0.204 mmol) in dioxane (1.7 mL) and H$_2$O (0.34 mL). The reaction was heated to 80° C. for 2.5 hours. The reaction mixture was diluted with DCM and extracted twice from water. The combined organic layers were dried over MgSO$_4$, filtered, and concentrated in vacuo. The crude mixture was purified by normal phase chromatography (12 g column) with a running gradient of 0-50% (2% MeOH/EtOAc)/DCM to afford 77 mg of Compound 35-4. LC-MS=501.5 [M-Boc+H]$^+$.

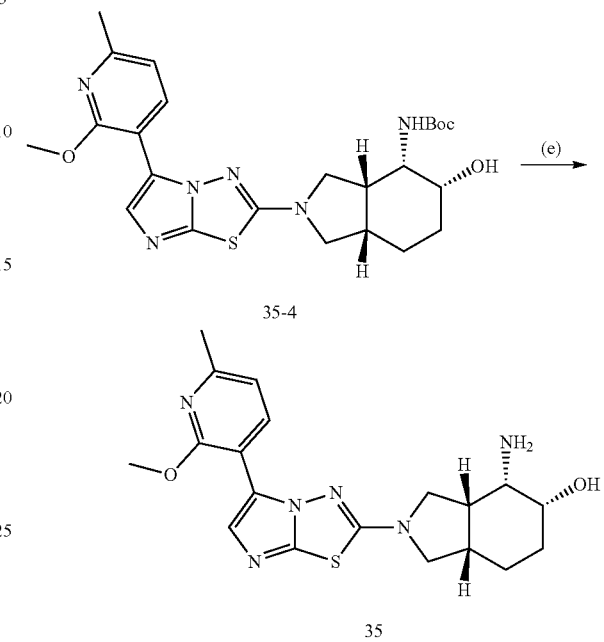

A solution of Compound 35-4 (76.7 mg, 0.153 mmol) in DCM (3 mL) was treated with TFA (590 μL, 7.66 mmol). The reaction was stirred at room temperature for 1 hour. The reaction mixture concentrated in vacuo and purified twice by prep-HPLC to afford 9.9 mg of Compound 35. $^1$H NMR (500 MHz, DMSO-d$_6$) δ 8.59 (d, J=7.7 Hz, 1H), 7.57 (s, 1H), 6.99 (d, J=7.7 Hz, 1H), 4.89 (s, 1H), 4.00 (s, 3H), 3.95 (t, J=10.0 Hz, 1H), 3.80 (s, 1H), 3.61 (dd, J=9.7, 5.8 Hz, 1H), 3.51 (t, J=8.6 Hz, 1H), 3.02 (s, 1H), 2.62 (s, 1H), 2.45 (s, 3H), 2.34 (s, 1H), 1.78 (s, 1H), 1.61-1.39 (m, 3H). LC-MS=401.2 [M+H]$^+$.

The following compounds were prepared by the same route used to prepare compound 35-0.

| Example/Compound Number | Structure | NMR | LC-MS |
|---|---|---|---|
| 35-5 | ![structure] (3aR,4S,5R,7aS)-4-amino-2-(5-(6-isopropyl-2-methoxypyridin-3-yl)imidazo[2,1-b][1,3,4]thiadiazol-2-yl)octahydro-1H-isoindol-5-ol | $^1$H NMR (500 MHz, DMSO-d$_6$) δ 8.56 (d, J = 7.8 Hz, 1H), 8.11-7.95 (m, 3H), 7.63 (s, 1H), 6.99 (d, J = 7.8 Hz, 1H), 5.51 (s, 1H), 4.02 (s, 5H), 3.66 (dd, J = 9.9, 5.5 Hz, 1H), 3.59-3.46 (m, 2H), 3.35 (d, J = 9.9 Hz, 1H), 2.98 (h, J = 6.8 Hz, 1H), 2.82-2.71 (m, 1H), 2.49-2.40 (m, 1H), 1.88-1.80 (m, 1H), 1.58 (t, J = 10.5 Hz, 2H), 1.49 (s, 1H), 1.28 (d, J = 6.9 Hz, 6H). | MS m/z calcd for C$_{21}$H$_{28}$N$_6$O$_2$S 428.2 found 429.2 [M + H]$^+$ |

-continued

| Example/Compound Number | Structure | NMR | LC-MS |
|---|---|---|---|
| 35-6 | 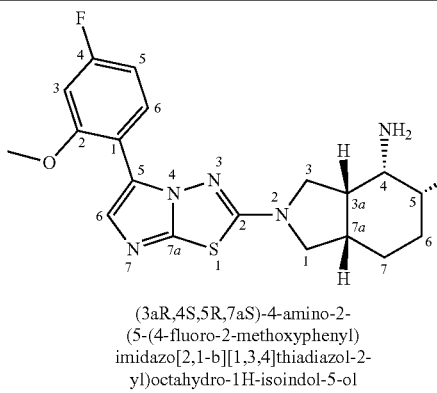<br>(3aR,4S,5R,7aS)-4-amino-2-(5-(4-fluoro-2-methoxyphenyl)imidazo[2,1-b][1,3,4]thiadiazol-2-yl)octahydro-1H-isoindol-5-ol | $^1$H NMR (500 MHz, DMSO-d$_6$) δ 8.20 (dd, J = 8.7, 6.9 Hz, 1H), 8.10-7.98 (m, 3H), 7.51 (s, 1H), 7.10 (dd, J = 11.4, 2.5 Hz, 1H), 6.89 (td, J = 8.4, 2.5 Hz, 1H), 5.50 (s, 1H), 3.99 (d, J = 9.8 Hz, 2H), 3.92 (s, 3H), 3.65 (dd, J = 9.9, 5.6 Hz, 1H), 3.55-3.45 (m, 2H), 3.33 (d, J = 9.8 Hz, 1H), 2.74 (q, J = 11.1, 9.6 Hz, 1H), 2.46-2.40 (m, 1H), 1.86-1.79 (m, 1H), 1.65-1.46 (m, 3H). | MS m/z calcd for C$_{19}$H$_{22}$FN$_5$O$_2$S 403.2 found 404.1 [M + H]$^+$ |

Example 36-0: (3aR,4R,7aS)-2-(5-(6-isopropyl-2-methoxypyridin-3-yl)imidazo[2,1-b][1,3,4]thiadiazol-2-yl)-2,3,3a,4,7,7a-hexahydro-1H-isoindol-4-amine

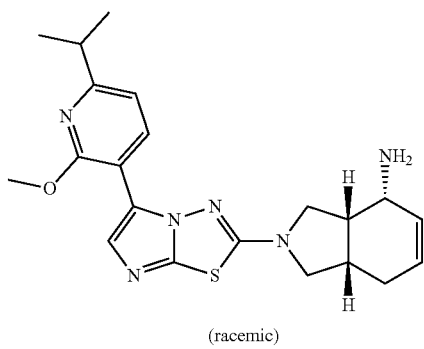 [SMILES: COc1nc(C(C)C)ccc1-c1cnc2sc(N3C[C@H]4CC=C[C@@H](N)[C@H]4C3)nn12]

(racemic)

The Compound 36-0 was prepared in the following way:

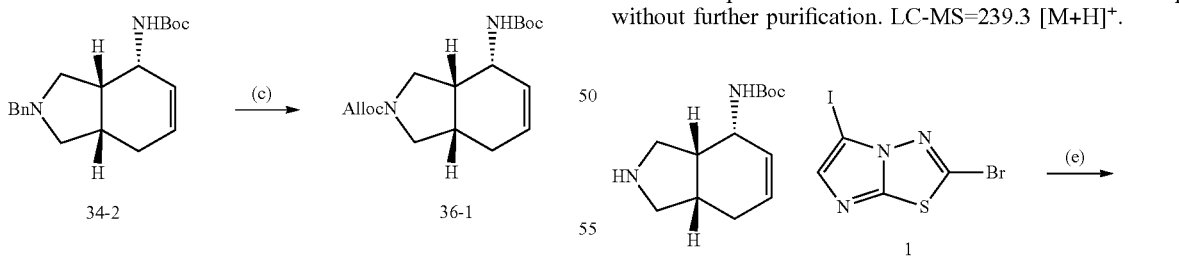

Compound 34-2 (1.04 g, 3.17 mmol) was dissolved in anhydrous DCM (30 mL) then Alloc-Cl (0.650 mL, 6.12 mmol) was added dropwise. The reaction was stirred at room temperature for 6 hours, then quenched with aq. NaHCO$_3$ and was stirred overnight. The layers were then separated and the aqueous layer extracted with DCM. The combined organic layers were dried over MgSO$_4$, filtered, and concentrated in vacuo. The crude material was purified by normal phase chromatography (24 g column) with a running gradient of 10-30% EtOAc/heptane to afford 0.732 g of Compound 36-1 as a solid. $^1$H NMR (500 MHz, CDCl$_3$) δ 5.92 (ddq, J=16.7, 11.2, 5.8 Hz, 1H), 5.73 (ddp, J=10.4, 5.1, 2.5 Hz, 1H), 5.43 (d, J=10.3 Hz, 1H), 5.28 (dd, J=17.4, 5.3 Hz, 1H), 5.18 (dd, J=10.4, 6.8 Hz, 1H), 4.57 (br s, 2H), 4.52 (br s, 2H), 3.56-3.42 (m, 1H), 3.42-3.25 (m, 2H), 3.13 (t, J=10.9 Hz, 1H), 2.82 (dt, J=13.1, 6.4 Hz, 1H), 2.40 (tq, J=9.2, 4.6 Hz, 1H), 2.18 (dq, J=18.9, 6.7 Hz, 1H), 1.85-1.74 (m, 1H), 1.42 (s, 9H). LC-MS=223.2 [M-Boc+H]$^+$.

Compound 36-1 (725 mg, 2.25 mmol) was dissolved in anhydrous DCM (22.5 mL) and then phenylsilane (0.832 mL, 6.75 mmol) and Pd(PPh$_3$)$_4$ (260 mg, 0.225 mmol) were added. The reaction was stirred at room temperature for 1.5 hours. The reaction mixture was concentrated in vacuo to afford Compound 36-2 which was used in the next step without further purification. LC-MS=239.3 [M+H]$^+$.

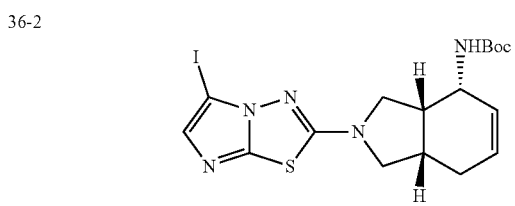

Compound 36-2 (181 mg, 0.759 mmol) and Compound 1 (238 mg, 0.721 mmol) were suspended in anhydrous MeCN (5 mL) and then DIPEA (0.4 mL, 2.278 mmol) was added. The reaction was heated to 100° C. overnight. The reaction mixture was concentrated in vacuo and was purified by normal phase chromatography (12 g column) with a running gradient of 0-30% (5% MeOH/EtOAc)/heptane to afford 74 mg of Compound 36-3 as a solid. LC-MS=488.3 [M+H]$^+$.

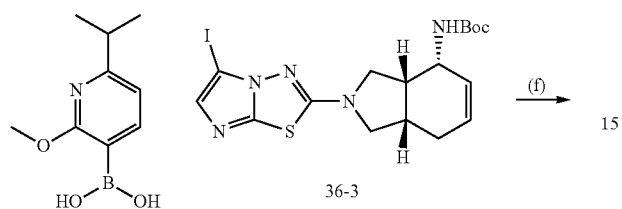

36-3

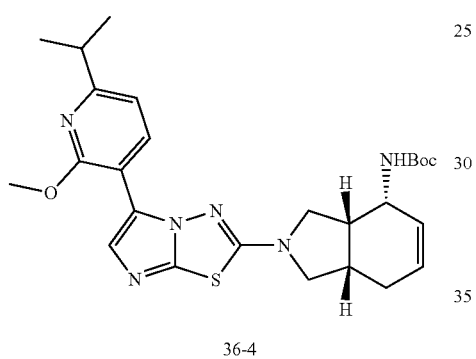

36-4

Compound 36-3 (73 mg, 0.150 mmol), PdCl$_2$(dppf)-DCM complex (18.35 mg, 0.022 mmol), (2-methoxy-6-methylpyridin-3-yl)boronic acid (58.4 mg, 0.300 mmol), K$_3$PO$_4$ (95 mg, 0.449 mmol) were dissolved in dioxane (1.2 mL) and H$_2$O (0.250 mL) The reaction was heated to 80° C. for 2.5 hours. The reaction mixture was diluted with EtOAc and extracted from water. The combined organic layers were filtered over Na$_2$SO$_4$, filtered, and concentrated. The crude residue was purified by normal phase chromatography (4 g column) with a running gradient of 0-40% (5% MeOH/EtOAc)/heptane to afford 60 mg of Compound 36-4 as a solid. LC-MS=511.5 [M+H]$^+$.

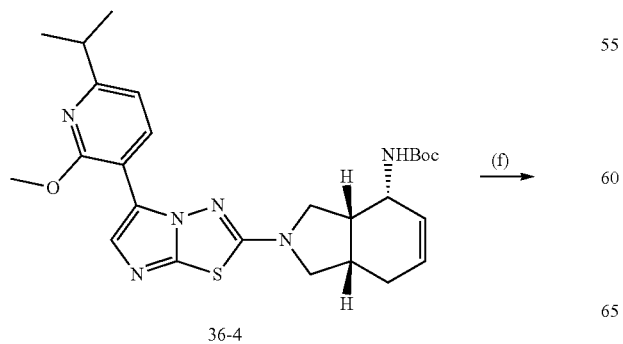

36-4

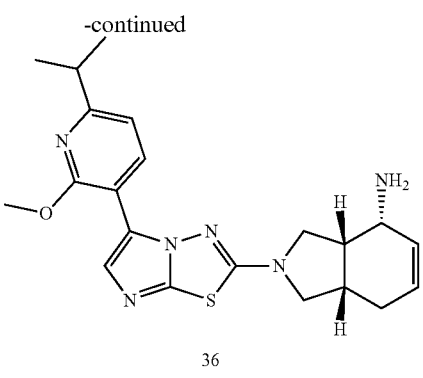

36

A solution of Compound 36-4 (60 mg, 0.117 mmol) in DCM (1.2 mL) was treated with TFA (453 μL, 5.87 mmol). The reaction was stirred at room temperature for 1 hour. The reaction mixture concentrated in vacuo and purified by prep-HPLC to afford 47.6 mg of Compound 36. $^1$H NMR (500 MHz, DMSO-d$_6$) δ 8.56 (d, J=7.7 Hz, 1H), 8.17 (d, J=5.7 Hz, 3H), 7.64 (s, 1H), 6.97 (d, J=7.7 Hz, 1H), 5.94 (ddt, J=10.2, 5.0, 2.6 Hz, 1H), 5.59 (d, J=10.4 Hz, 1H), 4.26 (s, 1H), 4.02 (s, 3H), 3.68 (dd, J=9.6, 4.7 Hz, 1H), 3.60 (t, J=8.8 Hz, 1H), 3.40 (dd, J=11.6, 9.7 Hz, 2H), 2.99 (p, J=6.9 Hz, 1H), 2.91 (dt, J=12.1, 6.0 Hz, 1H), 2.70 (tt, J=9.1, 4.7 Hz, 1H), 2.39-2.31 (m, 1H), 1.92-1.80 (m, 1H), 1.28 (d, J=6.9 Hz, 6H). LC-MS=411.2 [M+H]$^+$.

Example 37-0: 2-(4-chloro-5-fluoro-2-methoxyphenyl)-4,4,5,5-tetramethyl-1,3,2-dioxaborolane

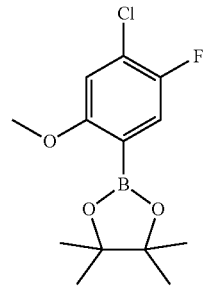 [SMILES: COc1cc(Cl)c(F)cc1B1OC(C)(C)C(C)(C)O1]

The Compound 37-0 was prepared in the following way:

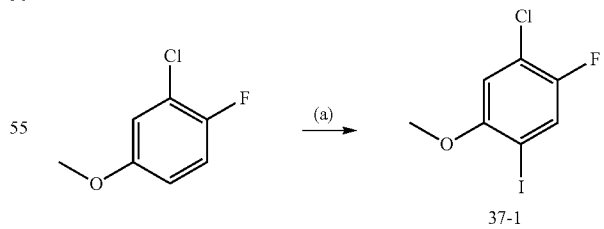

37-1

To a stirred solution of 2-chloro-1-fluoro-4-methoxybenzene (1.8 g, 9.34 mmol) in CHCl$_3$ (70 mL) was added silvertrifluoroacetate (7.42 g, 33.62 mmol, followed by 12 (4.98 g, 19.61 mmol). The resulting solution was stirred at room temperature for 2 hours. The reaction mixture was filtered through CELITE pad, the filtrate was extracted with EtOAc (100 mL×2) and washed H$_2$O with brine. The combined organic layers were dried over Na$_2$SO$_4$, filtered and evaporated in vacuo. The crude compound was purified by normal phase chromatography to afford 2.2 g of Compound 37-1 as a pale pink liquid. $^1$H NMR (400 MHz, DMSO-d$_6$) δ 7.87 (d, J=8.5 Hz, 1H), 7.21 (d, J=6.4 Hz, 1H), 3.83 (s, 3H); HPLC: 97.99%, retention time=7.351 minutes.

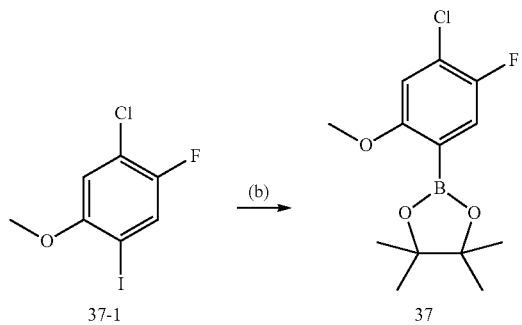 [SMILES: COc1cc(Cl)c(F)cc1I ; COc1cc(Cl)c(F)cc1B1OC(C)(C)C(C)(C)O1]

A solution of Compound 37-1 (1.8 g, 6.28 mmol) in THF (20 mL) under argon atmosphere was cooled to −40° C. Then iPrMgCl.LiCl solution (9.6 mL, 1.3 M in THF, 12.56 mmol) was added. The resulting mixture was stirred at −40° C. for 2 hours. Then 2-methoxy-4,4,5,5-tetramethyl-1,3,2-dioxaborolane (2.5 g, 15.70 mmol) was added at −40° C. The resulting solution was stirred at room temperature for 16 hours. The reaction was concentrated in vacuo and the crude product was purified by normal phase chromatography with a running gradient of 5-10% EtOAc/n-hexane to afford 700 mg of Compound 37 as a colourless liquid. $^1$H NMR (300 MHz, CDCl$_3$) δ 7.43 (dd, J=9.1, 1.1 Hz, 1H), 6.85 (dd, J=5.6, 1.1 Hz, 1H), 3.80 (s, 3H), 1.34 (s, 12H); HPLC: 65.21%, retention time=6.274 minutes.

Example 38-0:
(2-isopropoxy-6-isopropylpyridin-3-yl)boronic Acid

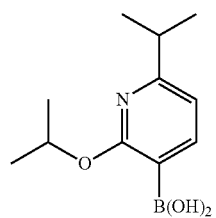

The Compound 38-0 was prepared in the following way:

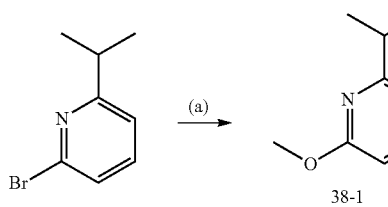

A mixture of allylpalladium chloride dimer (9.09 mg, 0.025 mmol), RockPhos (34.9 mg, 0.075 mmol), and cesium carbonate (2428 mg, 7.45 mmol) was flushed with argon for a few minutes, then anhydrous PhMe (5 mL) was added, followed by IPA (0.76 mL, 9.94 mmol). The reaction was heated to 90° C. for 3 minutes, then 2-bromo-6-isopropylpyridine (0.71 mL, 4.97 mmol) was added and the reaction continued at 90° C. for 1 hour. The mixture was filtered over a CELITE pad and concentrated in vacuo, then purified by normal phase chromatography (80 g column) with a running gradient of 0-10% EtOAc/heptane to afford 519 mg of Compound 38-1 as an oil. LC-MS=180.2 [M+H]$^+$.

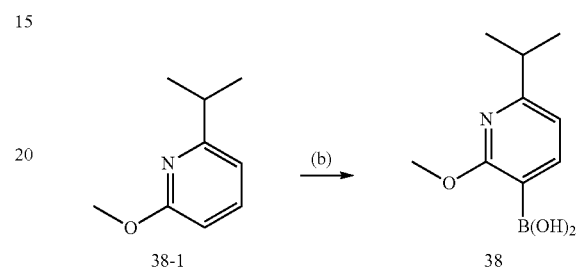

A solution of Compound 38-1 (519 mg, 2.90 mmol), TMEDA (0.52 mL, 3.45 mmol), and anhydrous Et$_2$O (6 mL) was put under N$_2$ atmosphere, and cooled to −78° C. Then n-BuLi (2.7 mL, 4.32 mmol) (1.6 M in hexanes) was added dropwise over a few minutes. The reaction turned a brown color, and was allowed to warm to room temperature over 1 hour, where it slowly became dark red-brown color. The reaction was cooled to −78° C., and B(O$^i$Pr)$_3$ (2 mL, 8.61 mmol) was added dropwise over a few minutes. The reaction was warmed to room temperature over 1 hour. The reaction was quenched with 6 M HCl (2 mL), then the mixture was basified with 2 M NaOH (1 mL) to adjust the pH at 7. Then the reaction was again acidified with 1 M HCl until pH was around 4 and was stirred vigorously at room temperature for 30 min, then extracted with EtOAc. The resulting organic layer was dried over Na$_2$SO$_4$, concentrated in vacuo and purified by normal phase chromatography (80 g column) with a running gradient of 0-20% (3:1 EtOAc:EtOH)/heptane to afford 300.6 mg of Compound 38 as a light yellow gum. $^1$H NMR (500 MHz, DMSO-d$_6$) δ 7.85 (d, J=7.2 Hz, 1H), 7.65 (s, 2H), 6.82 (dd, J=7.3, 0.4 Hz, 1H), 5.33 (p, J=6.2 Hz, 1H), 2.90 (h, J=6.7 Hz, 1H), 1.33 (d, J=6.2 Hz, 6H), 1.20 (d, J=6.8 Hz, 6H).

Example 39-0:
(2-ethoxy-6-isopropylpyridin-3-yl)boronic Acid

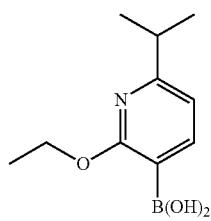

The Compound 39-0 was prepared in the following way:

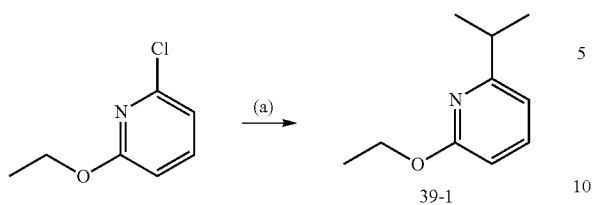

A solution of 2-chloro-6-ethoxypyridine (4.20 mL, 31.7 mmol), anhydrous THF (110 mL), and anhydrous NMP (15 mL) was put under $N_2$ atmosphere, and iron(III) acetylacetonate (0.672 g, 1.904 mmol) was added. The flask was cooled to −40° C., then i-PrMgCl (24 mL, 48.0 mmol) was added over a few minutes. The reaction mixture turned dark brown immediately and was allowed to warm to 0° C. for 1 hour. The reaction was quenched with aqueous $NH_4Cl$ (150 mL), the extracted twice with EtOAc, the combined organic layers were washed with brine, dried over $Na_2SO_4$, and concentrated in vacuo. The crude material was purified by normal phase chromatography (330 g column) with a running a gradient of 0-5% EtOAc/heptane to afford 2.5 g of Compound 39-1 as an oil.

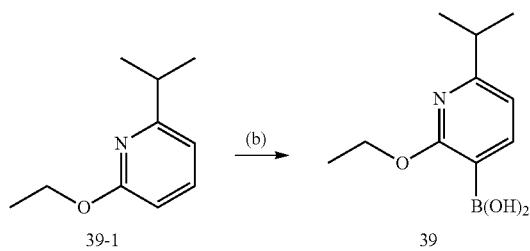

A solution of Compound 39-1 (500 mg, 3.03 mmol), TMEDA (0.46 mL, 3.05 mmol), and anhydrous $Et_2O$ (6 mL) was put under $N_2$ atmosphere, then cooled to −78° C. n-BuLi (2.3 mL, 3.68 mmol) (1.6 M in hexane) was added dropwise over a few minutes. The reaction turned dark orange color, and was allowed to warm to room temperature over 30 minutes. The reaction was cooled to −78° C., and $B(O^iPr)_3$ (1.5 mL, 6.46 mmol) was added dropwise over a few minutes. The reaction mixture was warmed to room temperature over 30 minutes. The orange color did not appear to discharge, so the reaction was cooled to −78° C. again, and an additional $B(O^iPr)_3$ (2 mL, 8.61 mmol) was added. The reaction was warmed to room temperature and stirred for 30 min, although reaction still appeared red-orange at this point. The reaction was cooled again to −78° C., added more $B(O^iPr)_3$ (1 mL, 4.31 mmol), warmed to room temperature and stirred for 17 hours. The reaction was quenched with 6 M HCl, then acidified to around pH 4 with 1 M HCl. The biphasic mixture was vigorously stirred at room temperature for 30 minutes, then extracted with EtOAc, dried over $Na_2SO_4$, and concentrated in vacuo. The crude material was purified by normal phase chromatography (120 g column) with a running gradient of 0-10% (3:1 EtOAc:EtOH)/heptane to afford 497 mg of Compound 39. $^1$H NMR (400 MHz, DMSO-$d_6$) δ 7.84 (d, J=7.2 Hz, 1H), 7.68 (s, 2H), 6.82 (dd, J=7.2, 0.4 Hz, 1H), 4.38 (q, J=7.0 Hz, 2H), 2.89 (p, J=6.8 Hz, 1H), 1.33 (t, J=7.0 Hz, 3H), 1.29-1.12 (m, 6H).

Example 40-0: (6-isopropyl-2-(2-((tetrahydro-2H-pyran-2-yl)oxy)ethoxy)pyridin-3-yl)boronic Acid

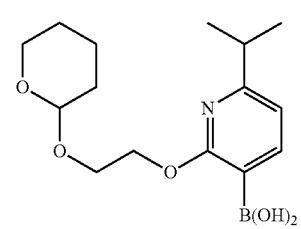 [SMILES: CC(C)c1ccc(B(O)O)c(OCCOC2CCCCO2)n1]

The Compound 40-0 was prepared in the following way:

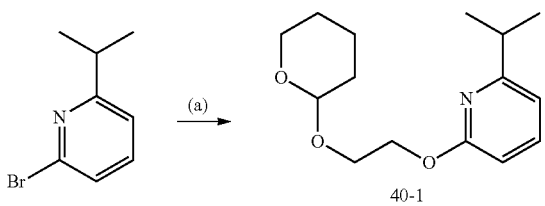

A mixture of allylpalladium chloride dimer (8.96 mg, 0.024 mmol), RockPhos (0.034 g, 0.073 mmol), and cesium carbonate (2.394 g, 7.35 mmol) was flushed with argon for a few minutes, then anhydrous PhMe (5 mL) was added, followed by 2-((tetrahydro-2H-pyran-2-yl)oxy)ethan-1-ol (1.330 mL, 9.80 mmol). The reaction was heated to 90° C. for 3 minutes, then 2-bromo-6-isopropylpyridine (0.7 mL, 4.90 mmol) was added and the reaction continued at 90° C. for 30 minutes. The resulting mixture was filtered over a CELITE pad, concentrated in vacuo and purified by normal phase chromatography (80 g column) with a running gradient of 0-15% EtOAc/heptane to afford 1.018 g of Compound 40-1 as an oil. $^1$H NMR (500 MHz, DMSO-$d_6$) δ 7.60 (dd, J=8.2, 7.3 Hz, 1H), 6.83 (dt, J=7.3, 0.6 Hz, 1H), 6.61 (dd, J=8.2, 0.8 Hz, 1H), 4.64 (t, J=3.7 Hz, 1H), 4.50-4.31 (m, 2H), 3.93 (ddd, J=11.3, 6.0, 3.8 Hz, 1H), 3.83-3.66 (m, 2H), 3.49-3.38 (m, 1H), 2.91 (h, J=6.9 Hz, 1H), 1.78-1.55 (m, 2H), 1.56-1.38 (m, 4H), 1.21 (d, J=6.8 Hz, 6H).

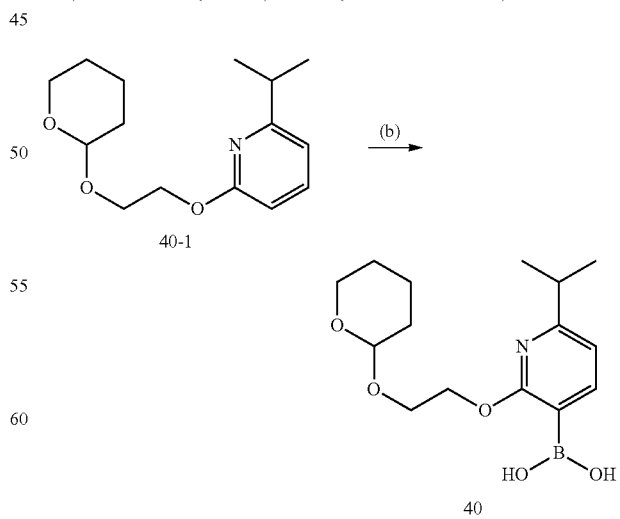

A solution of 2-isopropyl-6-(2-((tetrahydro-2H-pyran-2-yl)oxy)ethoxy)pyridine Compound 40-1 (1018 mg, 3.84 mmol), TMEDA (0.64 mL, 4.24 mmol), and anhydrous Et$_2$O (8 mL) was put under N$_2$ atmosphere, and cooled to −78° C. Then n-BuLi (3.2 mL, 5.12 mmol) (1.6 M in hexane) was added dropwise over a few minutes. The reaction turned an orange color, and was allowed to warm to room temperature over 30 minutes, where it slowly became red-orange. The reaction was recooled to −78° C., and B(O$^i$Pr)$_3$ (2.7 mL, 11.63 mmol) was added dropwise over a few minutes. The reaction was warmed to room temperature over 1 hour. The reaction was quenched with 6 M HCl, then acidified to around pH 4 with 1 M HCl. The resulting biphasic mixture was vigorously stirred at room temperature for 30 minutes, then extracted with EtOAc, the combined organic layer were dried over Na$_2$SO$_4$, concentrated in vacuo and was purified by normal phase chromatography (120 g column) with a running gradient of 0-35% (3:1 EtOAc:EtOH)/heptane to afford 2.245 g of Compound 40 as a clear gum.

Example 41-0: 2-(4-(1,2-difluoroethyl)-2-methoxyphenyl)-4,4,5,5-tetramethyl-1,3,2-dioxaborolane

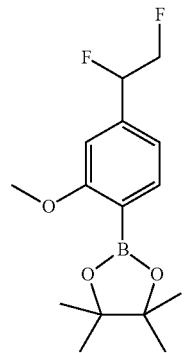

The Compound 41-0 was prepared in the following way:

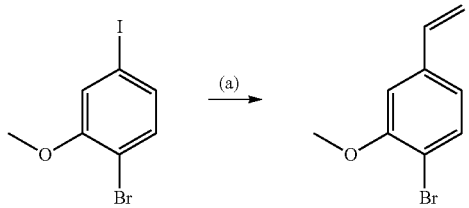

To a solution of K$_2$CO$_3$ (6.62 g, 47.94 mmol) in THF/Water (50 mL, 4:1), 1-bromo-4-iodo-2-methoxybenzene (5.0 g, 15.98 mmol) and potassium vinyltrifluoroborate (3.21 g, 23.97 mmol) were added. The reaction was degassed with argon for 10 minutes. Then Pd(dppf)Cl$_2$-DCM complex (652 mg, 0.80 mmol) was added and the reaction mixture was heated at 70° C. for 6 hours. The reaction mixture was partitioned between EtOAc and water. The organic layer was washed with brine, dried over Na$_2$SO$_4$ and concentrated in vacuo. The crude was purified by normal phase chromatography with a running gradient of 5-10% EtOAc/n-hexane to afford 1.9 g of Compound 41-1 as a colourless liquid. $^1$H NMR (400 MHz, CDCl$_3$) δ 7.48 (d, J=8.1 Hz, 1H), 6.93-6.83 (m, 1H), 6.66 (dd, J=17.6, 10.9 Hz, 1H), 5.75 (d, J=17.6 Hz, 1H), 5.29 (d, J=10.9 Hz, 1H), 3.90 (d, J=15.4 Hz, 3H).

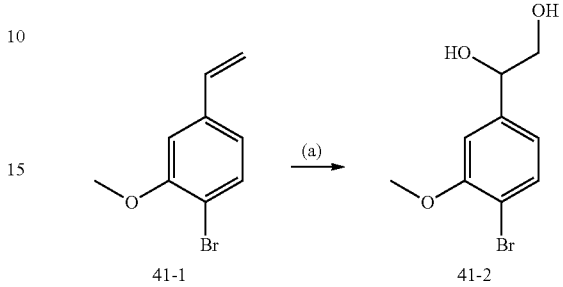

To a solution of Compound 41-1 in THF:H$_2$O (30 mL, 9:1), NMO (3.13 g, 26.73 mmol) and OsO$_4$ (22 mg, 0.089 mmol) were added at 0° C. The reaction mixture was stirred at room temperature for 16 hours. The reaction mixture was partitioned between EtOAc and H$_2$O and separated. The organic layer was dried over Na$_2$SO$_4$ and concentrated in vacuo. The crude compound was purified by normal phase chromatography with a running gradient of 80-100% EtOAc/n-hexane to afford 1.3 g of Compound 41-2 as a solid. $^1$H NMR (300 MHz, CDCl$_3$) δ 7.51 (d, J=8.1 Hz, 1H), 6.97 (d, J=1.9 Hz, 1H), 6.82 (ddd, J=8.1, 1.9, 0.7 Hz, 1H), 4.81 (dt, J=7.9, 3.5 Hz, 1H), 3.91 (s, 3H), 3.78 (ddd, J=10.9, 7.1, 3.6 Hz, 1H), 3.64 (ddd, J=11.3, 8.1, 4.9 Hz, 1H), 2.60 (dd, J=3.4, 0.6 Hz, 1H), 2.01 (dd, J=7.1, 4.9 Hz, 1H).

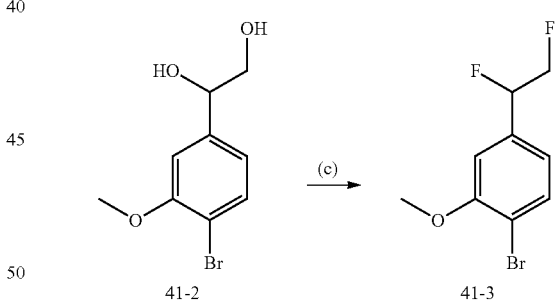

To a solution of Compound 41-2 in THF (20 mL), DAST (3.5 mL, 26.31 mmol) was added dropwise at −78° C. The reaction mixture was stirred at room temperature for 16 hours and then was quenched with ice and extracted with EtOAc. The organic layer was dried over Na$_2$SO$_4$ and concentrated in vacuo. The crude compound was purified by normal phase chromatography with a running gradient of 0-10% EtOAc/n-hexane to afford 150 mg of Compound 41-3 as a colourless liquid. $^1$H NMR (300 MHz, CDCl$_3$) δ 7.56 (dd, J=8.1, 1.0 Hz, 1H), 6.91 (d, J=1.9 Hz, 1H), 6.80 (ddt, J=8.1, 1.8, 0.9 Hz, 1H), 5.82-5.50 (m, 1H), 4.91-4.21 (m, 2H), 3.92 (s, 3H).

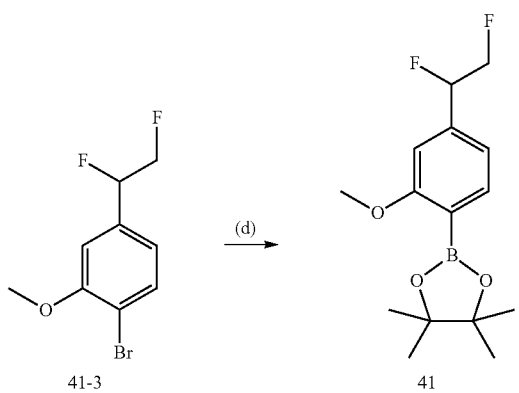

To a solution of KOAc (177 mg, 1.80 mmol) in DMSO (3 mL), Compound 41-3 and B$_2$Pin$_2$ (303 mg, 1.19 mmol) were added. The reaction mixture was degassed with argon for 10 minutes. Then PdCl$_2$(dppf)-DCM complex (24 mg, 0.03 mmol) was added and the reaction mixture was heated at 100° C. for 2 hours. The reaction mixture was partitioned between EtOAc and water. The organic layer was washed with brine, dried over Na$_2$SO$_4$ and concentrated in vacuo to afford 150 mg of Compound 41. The crude compound was taken directly to next step without further purification.

Example 42-0: 2-(4-(difluoromethyl)-2-methoxyphenyl)-4,4,5,5-tetramethyl-1,3,2-dioxaborolane

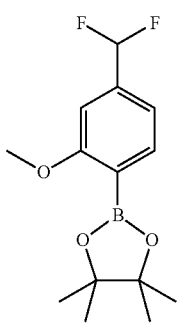

The Compound 42-0 was prepared in the following way:

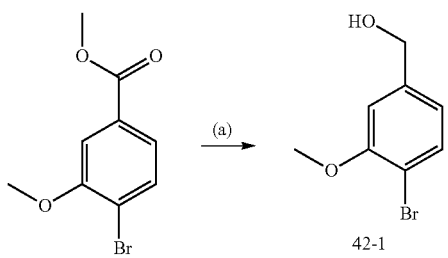

To a solution of methyl 4-bromo-3-methoxybenzoate (2.0 g, 8.16 mmol) in THF (15 mL) at −40° C. was added LiAlH$_4$ (309 mg, 8.16 mmol). The resulting solution was stirred at −40° C. for 45 minutes. The reaction mixture was quenched with sat. NH$_4$Cl (20 mL) at 0° C. and extracted twice with EtOAc (100 mL). The combined organic layers were dried over Na$_2$SO$_4$ and concentrated in vacuo to afford 1.6 g of Compound 42-1 as a colourless liquid. $^1$H NMR (300 MHz, CDCl$_3$) δ 7.50 (dd, J=8.0, 0.6 Hz, 1H), 6.98-6.91 (m, 1H), 6.84-6.76 (m, 1H), 4.67 (d, J=5.5 Hz, 2H), 3.91 (s, 3H).

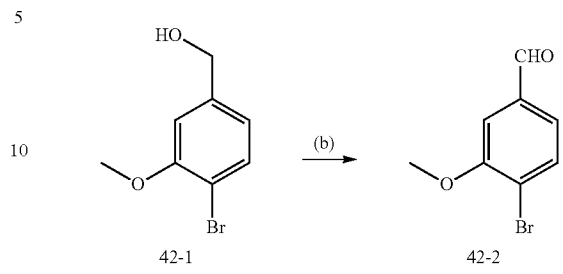

To a solution of Compound 42-1 (800 mg, 3.03 mmol) in DCM (15 mL) at 0° C., DMP (2.56 g, 6.06 mmol) and NaHCO$_3$ (510 mg, 6.06 mmol) were added. The resulting solution was stirred at room temperature for 10 hours. The reaction mixture was filtered on CELITE pad and concentrated in vacuo. The crude compound was purified by normal phase chromatography with a running gradient of 10% EtOAc/n-hexane to afford 600 mg of Compound 42-2 as a solid. $^1$H NMR (600 MHz, CDCl$_3$) δ 9.96 (s, 1H), 7.75 (d, J=7.9 Hz, 1H), 7.41 (d, J=1.8 Hz, 1H), 7.34 (dd, J=7.9, 1.8 Hz, 1H), 3.98 (s, 3H).

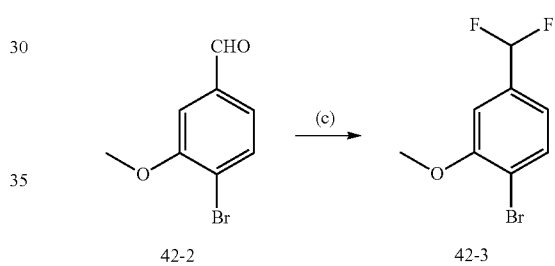

To a solution of Compound 42-2 (500 mg, 2.32 mmol) in DCM (30 mL), DAST (1.53 mL, 11.62 mmol) was added. The resulting solution was stirred at 40° C. for 24 hours. Then H$_2$O (50 mL) was added to the reaction mixture and extracted twice with DCM (50 mL). The combined organic layers were dried over Na$_2$SO$_4$ and concentrated in vacuo to afford 490 mg of Compound 42-3 as a colourless liquid. $^1$H NMR (300 MHz, CDCl$_3$) δ 7.62 (dt, J=8.0, 1.0, 1.0 Hz, 1H), 7.03 (d, J=1.7 Hz, 1H), 6.99-6.93 (m, 1H), 6.61 (t, J=56.4 Hz, 1H), 3.94 (s, 3H).

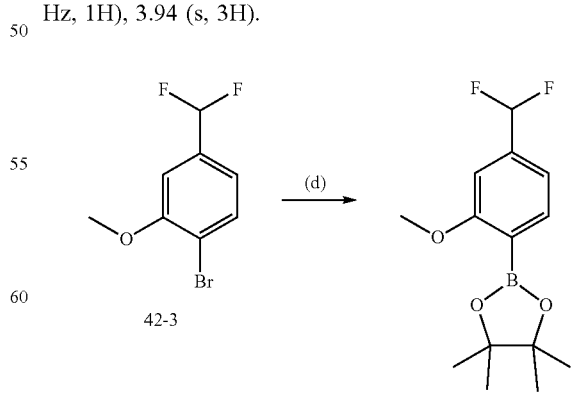

To a solution of Compound 42-3 (1.0 equiv.) and B₂Pin₂ in dioxane/DMSO (10 vol), KOAc (3.0 equiv.) and PdCl₂(dppf)-DCM complex (10 mol %) were added. The reaction mixture was heated at 80° C. for 16 hours. The reaction mixture was diluted with H₂O and extracted twice with EtOAc. The combined organic layers were washed with water, then brine, dried over Na₂SO₄, filtered and concentrated in vacuo to afford Compound 42. ¹H NMR (400 MHz, CDCl₃) δ 7.73-7.67 (m, 1H), 7.06-6.99 (m, 1H), 6.75-6.42 (m, 1H), 6.61 (t, J=56.4 Hz, 1H), 3.84 (s, 2H), 1.23 (s, 11H).

Example 43-0: 2-(4-isopropyl-2-methoxyphenyl)-4,4,5,5-tetramethyl-1,3,2-dioxaborolane

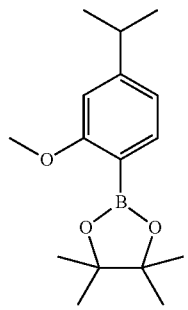

The Compound 43-0 was prepared in the following way:

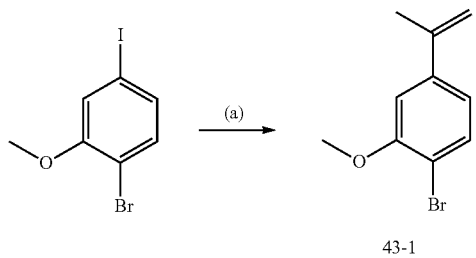

To a solution of 1-bromo-4-iodo-2-methoxybenzene (1.0 equiv.) in dioxane/H₂O (4:1) was added K₂CO₃ (3.0 equiv.), arylboronic ester (1.5 equiv.) and PdCl₂(dppf)-DCM complex (5 mol %). The reaction mixture was heated at 100° C. for 6 hours. The reaction was diluted with H₂O and extracted twice with EtOAc. The combined organic layers were washed with H₂O, then brine, dried over Na₂SO₄, filtered and concentrated in vacuo. The crude material was purified by normal phase chromatography with a running gradient of n-hexane to afford 940 mg of Compound 43-1 as a colourless liquid. ¹H NMR (600 MHz, CDCl₃) δ 7.47 (d, J=8.2 Hz, 1H), 6.98 (d, J=2.1 Hz, 1H), 6.94 (d, J=2.1 Hz, 1H), 5.40-5.05 (m, 2H), 3.92 (s, 3H), 2.14 (s, 3H).

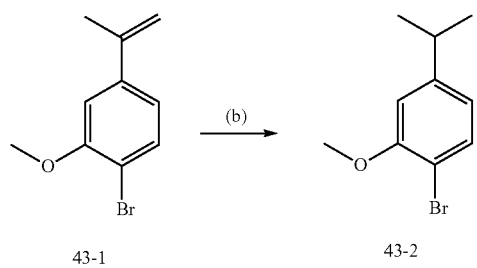

A solution of Compound 43-1 (940 mg, 4.14 mmol) and 10% Pd—C (94 mg) in EtOAc (30 mL) was stirred under H₂ for 1 hour. The reaction mixture was filtered on CELITE pad and concentrated in vacuo to afford 920 mg of Compound 43-2. ¹H NMR (300 MHz, CDCl₃) δ 7.47 (d, J=8.2 Hz, 1H), 6.98 (d, J=2.0 Hz, 1H), 6.76 (d, J=2.0 Hz, 1H), 3.92 (s, 3H), 2.92-2.82 (m, 1H), 1.24 (d, J=6.9 Hz, 6H).

A solution of Compound 43-2 (1.0 equiv.), B₂Pin₂, KOAc (3.0 equiv.) and PdCl₂(dppf)-DCM complex (10 mol %) in dioxane (30.0 mL) was heated at 80° C. for 16 hours. The reaction mixture was diluted with H₂O and extracted twice with EtOAc. The combined organic layers were washed with H₂O, then brine, dried over Na₂SO₄, filtered and concentrated in vacuo. The crude product was purified by normal phase with a running gradient of 10/90 EtOAc/n-hexane to afford 1.3 g of Compound 43 as a solid. ¹H NMR (600 MHz, CDCl₃) δ 7.60 (d, J=7.5 Hz, 1H), 6.81 (dd, J=7.6, 1.4 Hz, 1H), 6.70 (s, 1H), 3.82 (s, 3H), 2.87 (h, J=7.0 Hz, 1H), 1.24 (s, 18H).

Example 44-0: 2 2-(2-ethoxy-4-isopropylphenyl)-4,4,5,5-tetramethyl-1,3,2-dioxaborolane The Compound 44-0 was prepared in the following way.

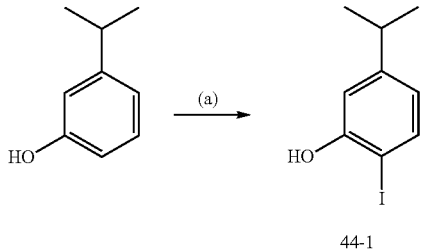

44-1

To a solution of 3-isopropylphenol (2.0 g, 14.68 mmol) in AcOH (16 mL), KIO$_3$ (629 mg, 2.93 mmol) was added. Then iodine (1.5 g, 5.87 mmol) was added portionwise at room temperature. The resulting solution was stirred at room temperature for 16 hours. The reaction mixture was concentrated in vacuo and extracted twice with EtOAc (100 mL) and the combined organic layers were washed with water, saturated NaHCO$_3$ solution and then brine. The combined organic layers were dried over Na$_2$SO$_4$, filtered and concentrated in vacuo. The crude compound was purified by normal phase chromatography with a running gradient of n-hexane to afford 1.6 g of Compound 44-1 as a brown liquid. $^1$H NMR (300 MHz, CDCl$_3$) δ 7.54 (d, J=8.2 Hz, 1H), 6.89 (d, J=2 Hz, 1H), 6.58 (dd, J=8.0, 2.0, 1 Hz), 2.84 (m, 1H), 1.22 (d, J=6.9 Hz, 6H).

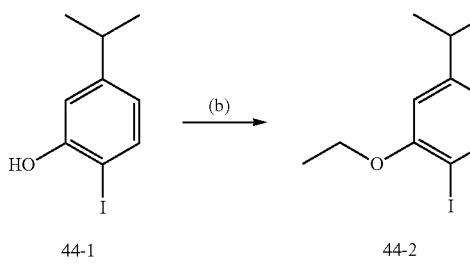

44-1          44-2

To a solution of Compound 44-1 (600 mg, 2.48 mmol) in EtOH (15 mL), K$_2$CO$_3$ (1.03 g, 7.44 mmol) was added at room temperature. After 10 minutes, ethyl iodide (0.6 mL, 7.44 mmol) was added dropwise and the reaction mixture was stirred at 70° C. for 16 hours. The reaction mixture was diluted with H$_2$O and extracted twice with EtOAc (50 mL), the combined organic layers were washed with brine, dried over Na$_2$SO$_4$ and concentrated in vacuo. The crude compound was purified by normal phase chromatography with a running gradient of 0-10% EtOAc/n-hexane to afford 550 mg of Compound 44-2 as a colourless liquid. $^1$H NMR (600 MHz, CDCl$_3$) δ 7.65 (d, J=8.0, 1H), 6.68 (d, J=2.0 Hz, 1H), 6.60 (dd, J=8.0, 2.0 Hz, 1H), 4.09 (q, J=6.9 Hz, 2H), 2.85 (m, 1H), 1.48 (t, J=6.9 Hz, 3H), 1.24 (s, 3H), 1.23 (s, 3H).

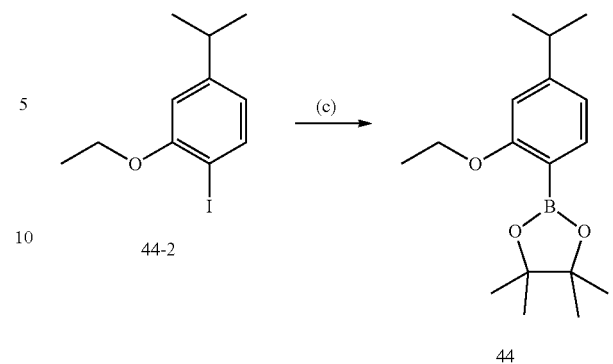

44-2

44

A solution of Compound 44-2 (1.0 equiv.), B$_2$Pin$_2$ in dioxane (10 vol), KOAc (3.0 equiv.) and PdCl$_2$(dppf)-DCM complex (10 mol %) was heated at 80° C. for 16 hours. The reaction mixture was diluted with H$_2$O and extracted twice with EtOAc. The combined organic layers were washed with H$_2$O, then brine, dried over Na$_2$SO$_4$, filtered and concentrated in vacuo to afford 400 mg of Compound 44-0 as a brown liquid. LC-MS=291.30 [M+H]$^+$, retention time=1.97 minutes.

Example 45-0: 2-(2-methoxy-4-(tetrahydrofuran-3-yl)phenyl)-4,4,5,5-tetramethyl-1,3,2-dioxaborolane

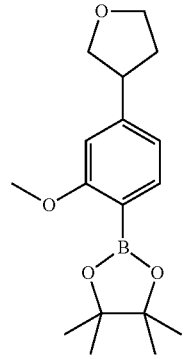

The Compound 45-0 was prepared in the following way:

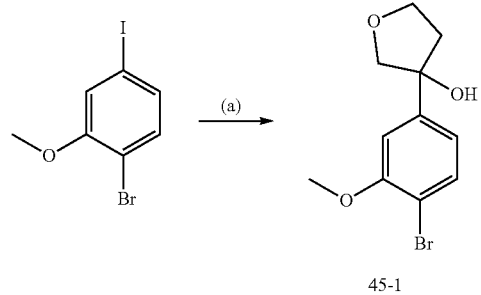

45-1

To the solution of 1-bromo-4-iodo-2-methoxybenzene (1.5 g, 0.003 mmol) in THF (12 mL) at −20° C., was added i-PrMgCl—LiCl (5.3 mL, 0.012 mmol) dropwise and stirred for 30 minutes. A solution of dihydrofuran-3(2H)-one (0.824 g, 0.003 mmol) in THF (12 mL) was added dropwise. It was stirred under room temperature for 2 hours. The reaction mixture was quenched with NH$_4$Cl solution at 0° C. and extracted with EtOAc and the organic layer was concentrated in vacuo. The crude product was purified by normal phase chromatography with a running gradient of 30:70=EtOAc:n-hexane to afford 450 mg of Compound 45-1 as a colourless liquid. $^1$H NMR (400 MHz, CDCl$_3$) δ 7.51 (dd, J=8.2, 1.8 Hz, 1H), 7.12 (s, 1H), 6.90 (dd, J=8.0, 2.0, Hz, 1H), 4.24-3.99 (m, 4H), 3.92 (s, 3H), 2.30-2.15 (m, 2H).

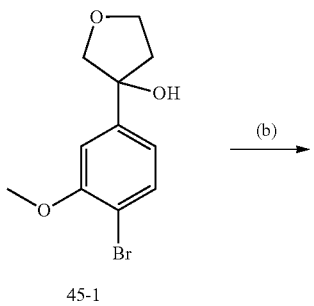
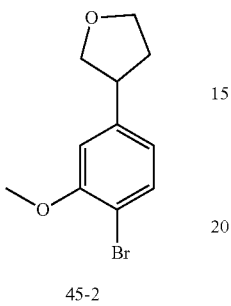

To the solution of Compound 45-1 (0.540 g, 1.98 mmol) in DCM (10 mL) at −78° C., BF$_3$.OEt$_2$ (1.40 g, 9.9 mmol) was added then Et$_3$SiH (1.38 mL, 11.9 mmol) added dropwise and the reaction allowed to come at room temperature and stirred for 2 hours. The reaction mixture was quenched with NH$_4$Cl solution and extracted with EtOAc. The organic layer was concentrated in vacuo to afford compound 200 mg of a mixture of Compound 45-2 and 3-(4-bromo-3-methoxyphenyl)-2,5-dihydrofuran. This mixture underwent a hydrogenation step using 20% Pd/C (60 mg) in EtOAc (10 mL) for 12 hours. The reaction mixture was filtered on CELITE pad, the organic layer was concentrated in vacuo to afford 250 mg of Compound 45-2 as a colorless liquid. $^1$H NMR (300 MHz, CDCl$_3$) δ 7.45 (d, J=8.2 Hz, 1H), 6.79 (d, J=2.0 Hz, 1H), 6.74 (dt, J=8.1, 1.3 Hz, 1H), 4.16-4.01 (m, 2H), 3.96-3.90 (m, 1H), 3.90 (s, 3H), 3.78-3.69 (m, 1H), 3.43-3.30 (m, 1H), 2.47-2.28 (m, 1H), 2.05-1.90 (m, 1H). LC-MS=258.90 [M+H]$^+$, retention time=1.56 minutes.

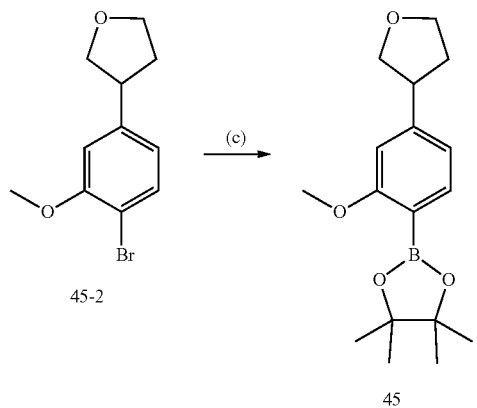

To a sealed tube containing aryl bromide Compound 45-2 (1.0 equiv.) and B$_2$Pin$_2$ in dioxane (12 mL) was added KOAc (3.0 equiv.) and PdCl$_2$(dppf)-DCM complex (10 mol %). The reaction mixture was heated at 80° C. for 16 hours. The reaction mixture was diluted with H$_2$O and extracted twice with EtOAc. The combined organic layers were washed with H$_2$O, then brine, dried over Na$_2$SO$_4$, filtered and concentrated in vacuo to afford 310 mg of Compound 45 as a crude material. LC-MS=305.05 [M+H]$^+$, retention time=1.57 minutes.

Example 46-0: 2-(2-methoxy-4-(1-methoxycyclopropyl)phenyl)-4,4,5,5-tetramethyl-1,3,2-dioxaborolane

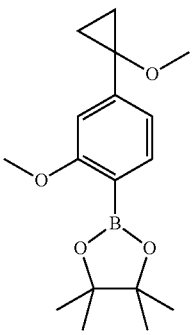

The Compound 46-0 was prepared in the following way:

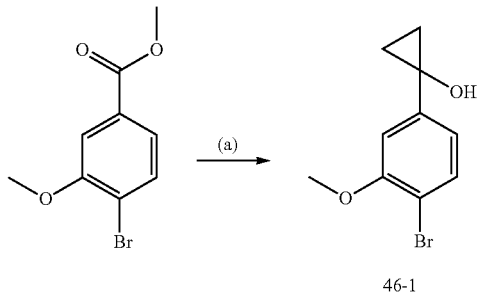

To a solution of methyl 4-bromo-3-methoxybenzoate (4.0 g, 16.32 mmol) in THF (80 mL) at −78° C., Ti(iPrO)$_4$ (4.6 g, 16.32 mmol) was added dropwise and the resulting solution was stirred at −78° C. for 10 minutes. Then ethylmagnesium bromide (21.76 mL, 65.28 mmol) was added dropwise and the reaction mixture was stirred at room temperature for 18 hours. The reaction mixture was quenched with sat. NH$_4$Cl and extracted twice with EtOAc (200 mL). The combined organic layers were washed with water, brine and then dried over Na$_2$SO$_4$, filtered and evaporated in vacuo. The crude Compound 46-1 was directly used in the next step.

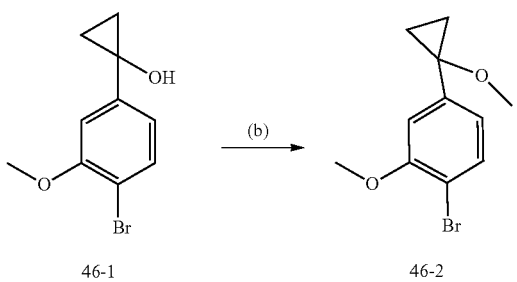

To a solution of Compound 46-1 (1.0 g, 4.11 mmol) in dioxane (10 mL), TBAB (1.32 g, 4.11 mmol), KOH (920 mg, 16.44 mmol) and MeI (0.76 mL, 12.23 mmol) were added at room temperature. The resulting solution was stirred at 80° C. for 4 hours. The reaction mixture was cooled to room temperature, H$_2$O was added and extracted twice with EtOAc (100 mL). The combined organic layers were washed with brine. dried over Na$_2$SO$_4$, filtered and concentrated in vacuo. The crude compound was purified by normal phase chromatography with a running gradient of 2-3% EtOAc/n-hexane to afford 1.2 g of Compound 46-2 as a colourless liquid. $^1$H NMR (300 MHz, CDCl$_3$) δ 7.47-7.42 (m, 1H), 6.97 (d, J=2.0 Hz, 1H), 6.68 (dd, J=8.2, 2.0 Hz, 1H), 3.91 (s, 3H), 3.22 (s, 3H), 1.23-1.14 (m, 2H), 0.99-0.90 (m, 2H); LC-MS=256.75 [M+H]$^+$, retention time=1.60 minutes.

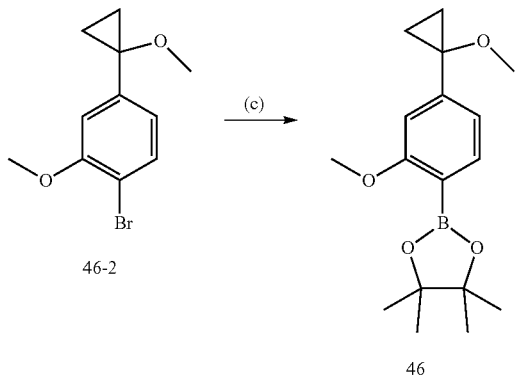

To a solution of Compound 46-2 (500 mg, 1.95 mmol) and B$_2$Pin$_2$ (545.5 mg, 2.15 mmol) in dioxane (5 mL), KOAc (575 mg, 5.6 mmol) and PdCl$_2$(dppf)-DCM complex (220 mg, 0.273 mmol) were added. The reaction mixture was heated at 80° C. for 16 hours. The reaction mixture was diluted with H$_2$O and extracted twice with EtOAc. The combined organic layers were washed with water, then brine, dried over Na$_2$SO$_4$, filtered and concentrated in vacuo to give the crude material which was purified by normal phase chromatography with a running gradient of 5-8% EtOAc/n-hexane to afford Compound 46 as a colorless liquid.

Example 47-0: 2-(2-methoxy-4-(1-methoxycyclobutyl)phenyl)-4,4,5,5-tetramethyl-1,3,2-dioxaborolane

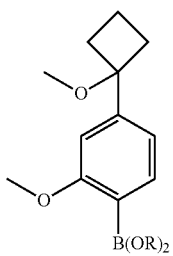

The Compound 47-0 was prepared in the following way:

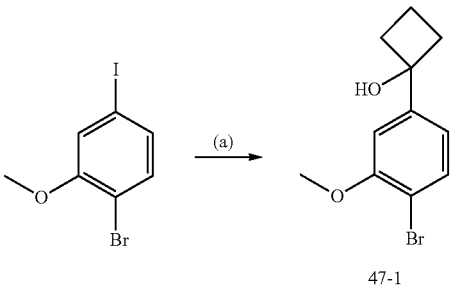

A solution of 1-bromo-4-iodo-2-methoxybenzene (2.0 g, 6.39 mmol) and cyclobutanone (1.34 g, 19.17 mmol) in THF (20 mL) under N$_2$ atmosphere was cooled to −78° C. Then n-BuLi in n-hexane solution (2.8 mL, 2.5 M, 7.02 mmol) was added over 10 minutes, the resulting mixture was stirred at −78° C. for 2 hours. The reaction mixture was quenched with sat. NH$_4$Cl solution (50 mL) and extracted twice with EtOAc (100 mL). The combined organic layers were washed with H$_2$O (50 mL), brine (50 mL) and dried over Na$_2$SO$_4$ and concentrated in vacuo. The crude compound was purified by normal phase chromatography with a running gradient of 10-30% EtOAc/n-hexane to afford 500 mg of Compound 47-1 as a colourless viscous liquid. $^1$H NMR (400 MHz, CDCl$_3$) δ 7.51 (d, J=8.2 Hz, 1H), 7.07 (d, J=2.0 Hz, 1H), 6.96 (dd, J=8.1, 2.0 Hz, 1H), 3.92 (s, 3H), 2.59-2.47 (m, 2H), 2.42-2.30 (m, 2H), 2.09-1.97 (m, 2H), 1.77-1.64 (m, 1H).

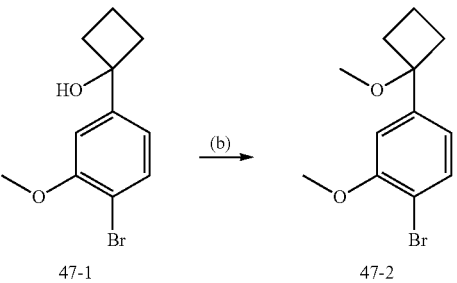

To a suspension of NaH (47 mg, 1.16 mmol) in DMF (1 mL) at 0° C., Compound 47-1 (250 mg, 0.97 mmol) in DMF (1 mL) was added under N$_2$ atmosphere. The reaction was stirred at room temperature for 10 minutes. Then MeI (206 mg, 1.45 mmol) was added at 0° C., the resulting mixture was stirred at room temperature for 2 hours. The reaction mixture was quenched with sat. NH$_4$Cl (50 mL) and extracted twice with EtOAc (100 mL). The combined organic layers were washed with H$_2$O (50 mL), brine (50 mL) and dried over Na$_2$SO$_4$ and concentrated in vacuo. The crude compound was purified by normal phase chromatography with a running gradient of 10-30% EtOAc/n-hexane to afford 220 mg of Compound 47-2 as a colourless liquid. $^1$H NMR (400 MHz, CDCl$_3$) δ 7.51 (d, J=8.2 Hz, 1H), 6.96 (d, J=2.0 Hz, 1H), 6.90 (dd, J=8.1, 2.0 Hz, 1H), 3.91 (s, 3H), 2.94 (s, 3H), 2.40-2.30 (m, 4H), 2.00-1.87 (m, 1H), 1.75-1.62 (m, 1H).

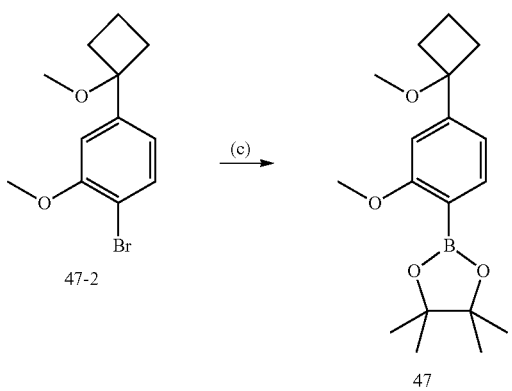

To a solution of Compound 47-2 (200 mg, 0.74 mmol) and B₂Pin₂ (225 mg, 0.88 mmol) in dioxane (3 mL), KOAc (218 mg, 2.22 mmol) and PdCl₂(dppf)-DCM complex (30 mg, 0.04 mmol) were added. The reaction mixture was heated at 80° C. for 16 hours. The reaction mixture was diluted with H₂O and extracted twice with EtOAc. The combined organic layers were washed with water, then brine, dried over Na₂SO₄, filtered and concentrated in vacuo to give Compound 47. $^1$H NMR (300 MHz, CDCl₃) δ 7.67 (d, J=7.5 Hz, 1H), 7.06-6.96 (m, 2H), 3.85 (s, 3H), 2.93 (s, 3H), 2.40-2.30 (m, 4H), 2.00-1.87 (m, 1H), 1.75-1.62 (m, 1H), 1.35 (s, 12H).

Example 48-0: 2-(2-(2-fluoroethoxy)phenyl)-4,4,5,5-tetramethyl-1,3,2-dioxaborolane

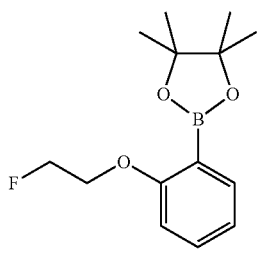 [SMILES: CC1(C)OB(c2ccccc2OCCF)OC1(C)C]

The Compound 48-0 was prepared in the following way:

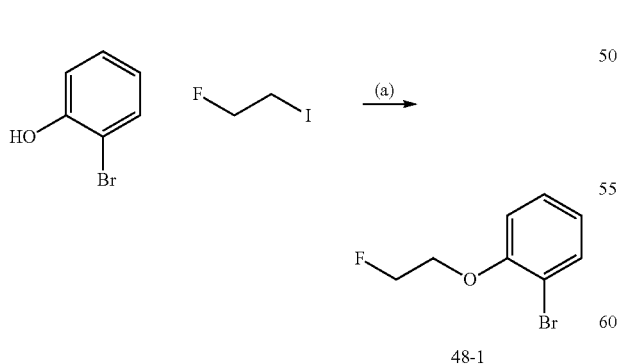

To a solution of 2-bromophenol (1.6 g, 9.248 mmol) and K₂CO₃ (3.82 g, 27.74 mmol) in DMF (10 mL), 1-fluoro-2-iodoethane (1.93 g, 11.098 mmol) was added and stirred at 70° C. for 3 hours. The reaction mixture was quenched with H₂O and extracted with EtOAc. The organic layer was washed with brine, dried over Na₂SO₄ and concentrated in vacuo. The crude material was purified by normal phase chromatography with a running gradient of 0-10% EtOAc/n-hexane to afford 1.0 g, of Compound 48-1 as a colourless liquid.

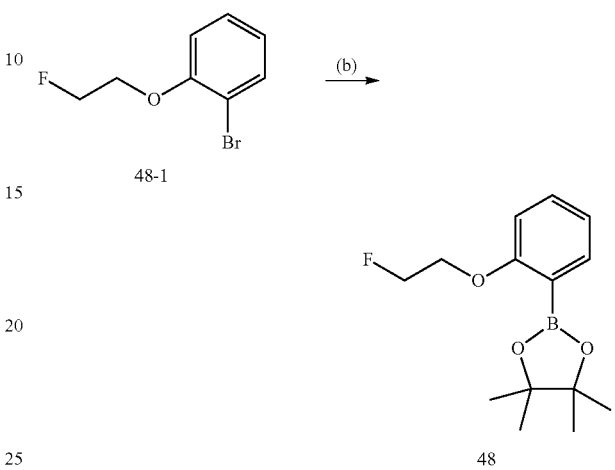

Argon was bubbled through dioxane (10.0 mL) for 15 minutes, then Compound 48-1 (1.0 g, 4.56 mmol), B₂Pin₂ (2.31 g, 9.129 mmol), KOAc (1.34 g, 13.69 mmol), and PdCl₂(dppf)-DCM complex (372.38 g, 0.456 mmol) were added. The reaction mixture was bubbled with argon for an additional 10 minutes, then the reaction was heated at 100° C. for 4 hours. The reaction mixture was diluted with MTBE, and filtered through CELITE pad. The filtrate was dried over Na₂SO₄ and concentrated in vacuo to afford 560 mg of Compound 48 as a solid. The crude compound was used for next reaction without further purification. $^1$H NMR (300 MHz, CDCl₃) δ 7.63 (dd, J=7.3, 1.9 Hz, 1H), 7.45-7.30 (m, 1H), 7.06-6.93 (m, 1H), 6.85 (dd, J=8.3, 0.8 Hz, 1H), 4.88-4.78 (m, 1H), 4.67 (ddd, J=4.4, 3.7, 1.0 Hz, 1H), 4.29-4.22 (m, 1H), 4.21-4.10 (m, 1H), 1.35 (s, 6H), 1.26 (s, 6H).

Example 49-0: 2-(2-(2,2-difluoroethoxy)phenyl)-4,4,5,5-tetramethyl-1,3,2-dioxaborolane

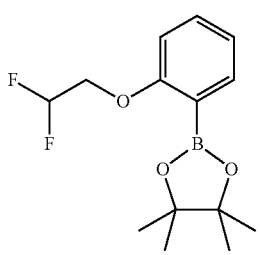 [SMILES: CC1(C)OB(c2ccccc2OCC(F)F)OC1(C)C]

The Compound 49-0 was prepared in the following way:

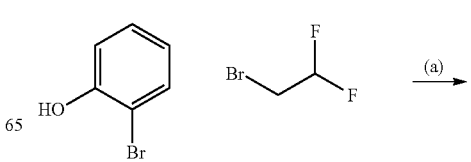

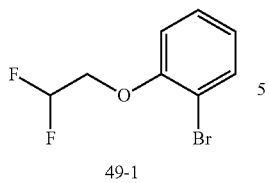

49-1

To a suspension of 2-bromophenol (1 g, 5.78 mmol) in DMF (10 mL), K₂CO₃ (1.59 g, 11.5 mmol), KI (1.59 g, 9.57 mmol) and 2-bromo-1,1-difluoroethane (1.67 g, 11.5 mmol) were added. The reaction mixture was heated at 70° C. 3 hours. The reaction mixture was quenched with H₂O and extracted with EtOAc. The organic layer was washed with brine dried over Na₂SO₄ and the filtrate was concentrated in vacuo. The crude compound was purified by normal phase chromatography with a running gradient 1% EtOAc/n-hexane to afford 0.955 g of Compound 49-1 as an oil. $^1$H NMR (300 MHz, CDCl₃) δ 7.65-7.51 (m, 1H), 7.35-7.20 (m, 1H), 6.97-6.83 (m, 2H), 6.16 (tt, J=55.1, 4.2 Hz, 1H), 4.24 (td, J=12.9, 4.2 Hz, 2H).

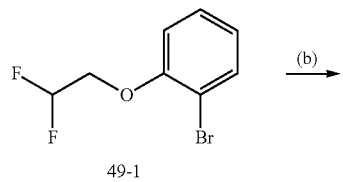

49-1

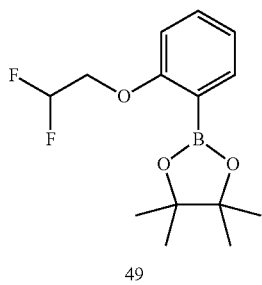

49

To a stirred suspension of Compound 49-1 (0.9 g, 3.79 mmol) in dioxane (15 mL) was purged with argon and then KOAc (0.745 g, 7.59 mmol), 4,4,4',4',5,5,5',5'-octamethyl-2,2'-bi(1,3,2-dioxaborolane) (1.44 g, 5.68 mmol) and PdCl₂ (dppf)-DCM complex (0.154 g, 0.189 mmol) were added. The reaction was purged further for an additional 15 minutes and then was heated at 100° C. for 3 hours. The reaction mixture was filtered on CELITE pad and washed with EtOAc (20 mL). The organic layer was washed with H₂O and brine, dried over Na₂SO₄ and concentrated in vacuo to afford 1.1 g of Compound 49 as a solid. $^1$H NMR (300 MHz, CDCl₃) δ 7.67 (dd, J=7.3, 1.8 Hz, 1H), 7.40 (ddd, J=8.3, 7.4, 1.9 Hz, 1H), 7.03 (td, J=7.3, 0.9 Hz, 1H), 6.85 (d, J=8.3 Hz, 1H), 6.41-5.81 (m, 1H), 4.35-4.05 (m, 2H), 1.35 (s, 6H), 1.26 (s, 6H).

Example 50-0: 2-(2-(2,3-difluoropropoxy)phenyl)-4,4,5,5-tetramethyl-1,3,2-dioxaborolane

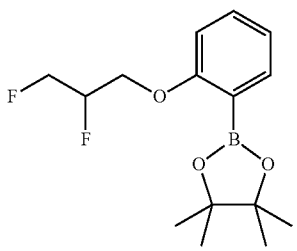 [SMILES: CC1(C)OB(c2ccccc2OCC(F)CF)OC1(C)C]

The Compound 50-0 was prepared in the following way:

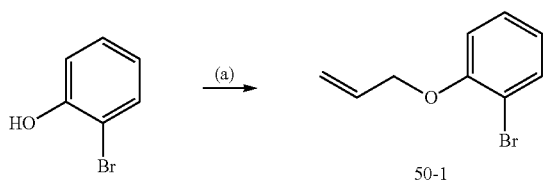

50-1

Allyl bromide (1.54 g, 12.70 mmol) was added to the solution of 2-bromo phenol (2 g, 11.56 mmol), K₂CO₃ (4.8 g, 34.68 mmol) and KI (574 mg, 3.46 mmol) in Acetone (30 mL). The reaction was heated at 60° C. for 3 hours. The reaction mixture was partitioned between EtOAc and water. The organic layer was dried over Na₂SO₄ and concentrated in vacuo. The crude compound was purified by normal phase chromatography with a running gradient of 0-10% EtOAc/n-hexane to afford 2.4 g of Compound 50-1 as a colourless liquid. $^1$H NMR (600 MHz, Chloroform-d) δ 7.59-7.49 (m, 1H), 7.31-7.16 (m, 1H), 6.90 (d, J=8.3 Hz, 1H), 6.84 (t, J=7.6, 1H), 6.15-5.97 (m, 1H), 5.49 (dt, J=16.9, 1.9 Hz, 1H), 5.31 (m 1H), 4.62 (dd, J=4.9, 1.9 Hz, 2H).

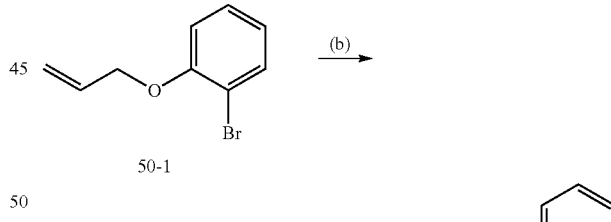

50-2

To a solution of Compound 50-1 (2.4 g, 11.26 mmol) in THF:H₂O (35 mL, 9:1), NMO (4.0 g, 33.78 mmol) and OSO₄ (29 mg, 0.11 mmol) were added at 0° C. The reaction was stirred at room temperature for 16 hours. The reaction mixture was partitioned between EtOAc and water. The organic layer was dried over Na₂SO₄ and concentrated in vacuo. The crude compound was purified by normal phase chromatography with a running gradient of 80-100% EtOAc/n-hexane to afford 2.5 g of Compound 50-2 as a solid. $^1$H NMR (600 MHz, CDCl₃) δ 7.54 (dd, J=7.9, 1.7 Hz, 1H), 7.30-7.23 (m, 1H), 6.94-6.85 (m, 2H), 4.19-4.08 (m, 3H), 3.92-3.81 (m, 2H), 2.87 (d, J=5.1 Hz, 1H), 2.26 (t, J=6.1 Hz, 1H).

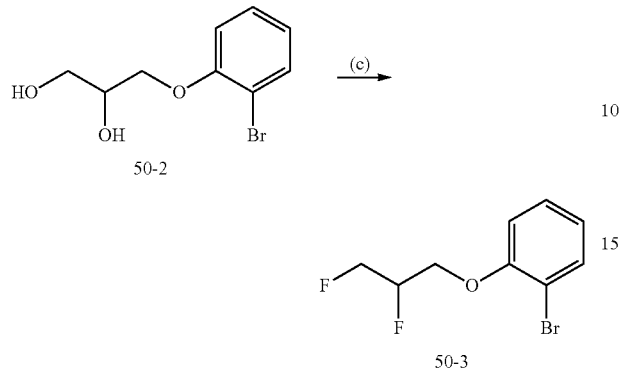

To a solution of Compound 50-2 (2.8 g, 11.33 mmol) in THF (40 mL), DAST (6 mL, 1.22 mmol) was added dropwise at −78° C. The reaction was then stirred at room temperature for 16 hours. The reaction mixture was quenched with ice and extracted with EtOAc. The organic layer was dried over Na$_2$SO$_4$ and concentrated in vacuo. The crude compound was purified by normal phase chromatography with a running gradient of 0-10% EtOAc/n-hexane to afford 1.3 g of Compound 50-3 as a colourless liquid. $^1$H NMR (600 MHz, CDCl$_3$) δ 7.55 (dd, J=7.8, 1.6 Hz, 1H), 7.36-7.15 (m, 1H), 7.05-6.70 (m, 2H), 5.24-4.92 (m, 1H), 4.90-4.72 (m, 2H), 4.39-4.22 (m, 2H).

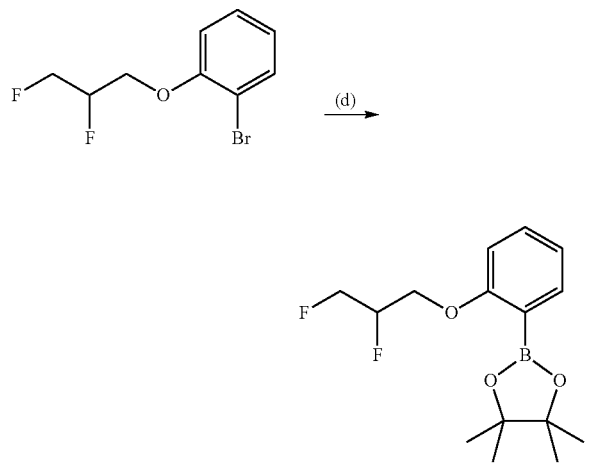

To a solution of KOAc (468 mg, 4.77 mmol) in DMSO (6 mL), Compound 50-3 (400 mg, 1.59 mmol) and B$_2$Pin$_2$ (809 mg, 3.18 mmol) were added. The reaction was degassed with argon gas for 10 minutes. Then PdCl$_2$(dppf)-DCM complex (65 mg, 0.08 mmol) was added and the resulting mixture was heated at 80° C. for 2 hours. The reaction mixture was partitioned between EtOAc and water. The organic layer was washed with brine, dried over Na$_2$SO$_4$ and concentrated in vacuo to afford 350 mg of Compound 50. The crude compound was taken directly to the next step without further purification.

Example 51-0:
(4-chloro-5-isopropyl-2-methoxyphenyl)boronic Acid

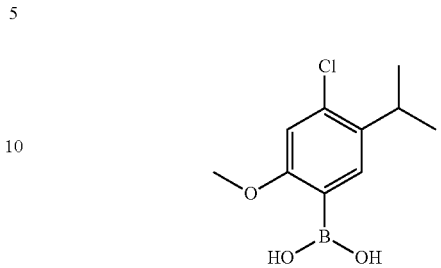

The Compound 51-0 was prepared in the following way:

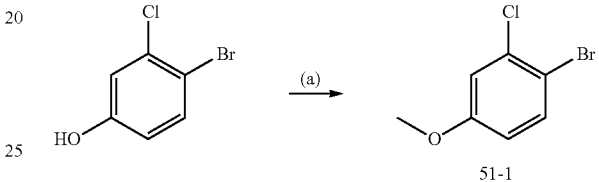

To the solution of 4-bromo-3-chlorophenol (3 g, 1.05 mmol) in DMF (30 mL) K$_2$CO$_3$ (4 g, 28.98 mmol) was added at 0° C. After 10 minutes, methyl iodide (3.06 g, 21.73 mmol) was added dropwise and the reaction mixture was stirred at room temperature for 7 hours. Then reaction mixture was diluted in H$_2$O and extracted twice with EtOAc (100 mL). The combined organic layers were washed with brine, dried over Na$_2$SO$_4$ and concentrated in vacuo to afford 2.1 g of Compound 51-1 as a light brown liquid. $^1$H NMR (600 MHz, CDCl$_3$) δ 7.47 (d, J=8.9 Hz, 1H), 7.01 (d, J=3.0 Hz, 1H), 6.70 (dd, J=8.8, 3.0 Hz, 1H), 3.79 (s, 3H).

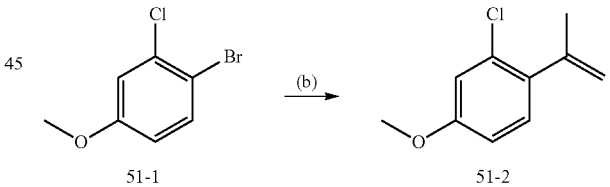

To a solution of Compound 51-1 (1.0 equiv.) in dioxane/H$_2$O (4:1), K$_2$CO$_3$ (3.0 equiv.), allylboronic ester (1.5 equiv.) and PdCl$_2$(dppf)-DCM complex (5 mol %) were added. The reaction mixture was heated at 100° C. for 6 hours. The reaction mixture was diluted with H$_2$O and extracted twice with EtOAc. The combined organic layers were washed with H$_2$O, then brine, dried over Na$_2$SO$_4$, filtered and concentrated in vacuo. The crude material was purified by normal phase chromatography with a running gradient of 5/95 EtOAc/n-hexane to afford 1.6 g of Compound 51-2 as a colourless liquid. $^1$H NMR (300 MHz, CDCl$_3$) δ 7.26 (s, 1H), 7.12 (d, J=8.5 Hz, 1H), 6.91 (d, J=2.6 Hz, 1H), 5.22-5.17 (m, 1H), 4.94 (dq, J=1.9, 0.9 Hz, 1H), 3.79 (s, 3H), 2.08 (dd, J=1.6, 0.9 Hz, 3H).

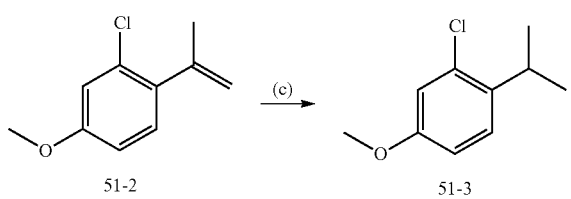

A solution of Compound 51-2 (1.8 g, 9.85 mmol) and 10% Pd—C (100 mg) in EtOAc (30 mL) was stirred under $H_2$ for 7 hours. The reaction mixture was filtered on CELITE pad and concentrated in vacuo to afford 1.6 g of Compound 51-3. $^1$H NMR (300 MHz, CDCl$_3$) δ 7.26 (s, 1H), 7.19 (d, J=8.6 Hz, 1H), 6.90 (d, J=2.7 Hz, 1H), 3.78-3.77 (m, 3H), 3.33 (m, 1H), 1.23 (d, J=0.6 Hz, 3H), 1.20 (d, J=0.7 Hz, 3H).

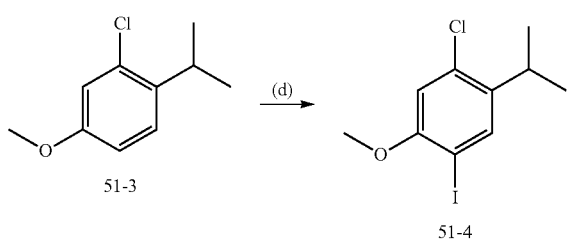

a solution of Compound 51-3 (1.6 g, 8.66 mmol) in chloroform (70 mL), Ag$_2$SO$_4$ (3.24 g, 13.05 mmol) was added at room temperature. Then iodine (2.64 g, 13.03 mmol) was added portionwise at room temperature. The resulting solution was stirred at room temperature for 12 hours. The reaction mixture was filtered through CELITE pad. The filtrate was extracted twice with EtOAc (100 mL) and the combined organic layers were washed H$_2$O and brine, dried over Na$_2$SO$_4$, filtered and evaporated in vacuo. The crude compound was purified by normal phase chromatography with a running gradient of 10/90 EtOAc/n-hexane to afford 1.03 g of Compound 51-4 as a light yellow liquid. $^1$H NMR (300 MHz, CDCl$_3$) δ 7.62 (s, 1H), 6.79 (s, 1H), 3.85 (s, 3H), 3.26 (m, 1H), 1.22 (d, J=7.6 Hz, 3H), 1.19 (d, J=7.6 Hz, 3H).

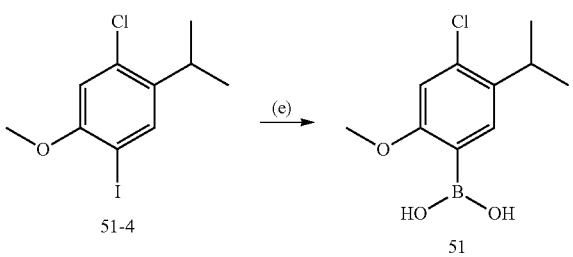

To a solution of Compound 51-4 (1.03 g, 3.34 mmol) in dry THF (15 mL) at −78° C., n-BuLi (1.67 mL, 2.5 M in hexane, 3.34 mmol) was added dropwise. Then B($^i$PrO)$_3$ (0.93 mL, 8.35 mmol) in THF (5 mL) was added dropwise at −78° C. and slowly brought to room temperature and the reaction mixture was stirred for 3 hours. The reaction mixture was quenched with H$_2$O and extracted twice with EtOAc (50 mL). The combined organic layers were washed with brine, dried over Na$_2$SO$_4$ and concentrated in vacuo to afford 350 mg of Compound 51 as a solid. $^1$H NMR (300 MHz, CDCl$_3$) δ 7.74 (s, 1H), 6.90 (s, 1H), 3.89 (s, 3H), 3.39-3.26 (m, 1H), 1.23-1.19 (m, 6H).

Example 52-0: 6-isopropyl-2-(2-methoxyethoxy) pyridin-3-yl)boronic Acid

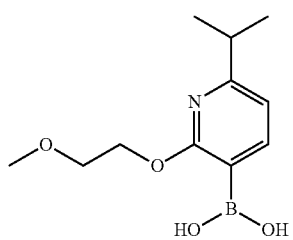 [SMILES: COCCOc1nc(C(C)C)ccc1B(O)O]

The Compound 52-0 was prepared in the following way:

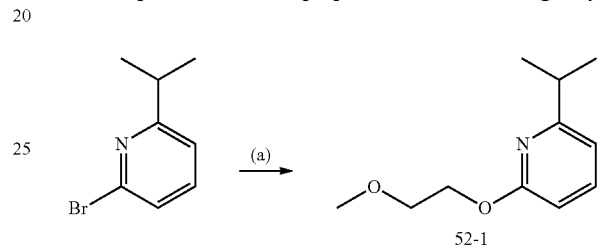

A mixture of allylpalladium chloride dimer (9.09 mg, 0.025 mmol), RockPhos (34.9 mg, 0.075 mmol), and cesium carbonate (2428 mg, 7.45 mmol) was flushed with argon for a few minutes, then anhydrous PhMe (5 mL) was added, followed by 2-methoxyethanol (0.8 mL, 10.15 mmol). The reaction was heated to 90° C. for 3 minutes, then 2-bromo-6-isopropylpyridine (0.71 mL, 4.97 mmol) was added and the reaction continued at 90° C. for 1 hour. The resulting reaction was filtered over a CELITE pad and concentrated in vacuo. The crude material was purified by normal phase chromatography (40 g) with a running gradient of 0 to 25% EtOAc/heptane to afford 848 mg of Compound 52-1 as an oil.

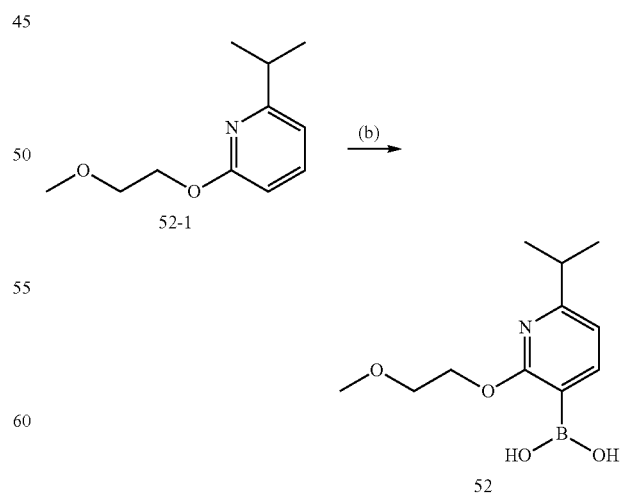

A solution of Compound 52-1 (848 mg, 4.34 mmol) and TMEDA (0.8 mL, 5.30 mmol) in anhydrous Et$_2$O (9 mL) was put under an N$_2$ atmosphere, and cooled to −78° C. Then n-BuLi (4 mL, 6.40 mmol) (1.6 M in hexane) was added dropwise over a few minutes. The reaction turned an orange color, and was allowed to warm to room temperature over 30 minutes, where it slowly became red-orange. The reaction was recooled to −78° C., and B(O$^i$Pr)$_3$ (3 mL, 12.92 mmol) was added dropwise over a few minutes. The reaction was warmed to room temperature over 30 minutes. The reaction was quenched with 6 M HCl, then acidified to around pH 4 with 1 M HCl. The resulting biphasic mixture was vigorously stirred at room temperature for 30 minutes, then extracted with EtOAc, the combined organic layers were dried over Na$_2$SO$_4$, concentrated in vacuo. The crude material was purified by normal phase chromatography (80 g column) with a running gradient of 0 to 25% (3:1 EtOAc/EtOH)/heptane to afford 813 mg of Compound 52 as a yellow gum. $^1$H NMR (500 MHz, DMSO-d$_6$) δ 7.88 (d, J=7.3 Hz, 1H), 7.69 (s, 2H), 6.87 (d, J=7.2 Hz, 1H), 4.48-4.41 (m, 2H), 3.68 (ddd, J=6.4, 4.2, 1.5 Hz, 2H), 3.31 (s, 3H), 2.95-2.87 (m, 1H), 1.21 (dd, J=6.9, 2.1 Hz, 6H). LC-MS=240.3 [M+H].

The following compounds were prepared by the same route used for Compound 4-0.

| Example/Compound Number | Structure | NMR | LC-MS |
|---|---|---|---|
| 37-2 | 4-(aminomethyl)-1-(5-(4-chloro-5-fluoro-2-methoxyphenyl)imidazo[2,1-b][1,3,4]thiadiazol-2-yl)piperidin-4-ol | $^1$H NMR (300 MHz, MeOD-d$_4$) δ 8.35 (d, J = 10.5 Hz, 1H), 8.04 (s, 1H), 7.34 (d, J = 6.3 Hz, 1H), 3.99 (s, 3H), 3.87 (d, J = 13.1 Hz, 2H), 3.75-3.61 (m, 2H), 3.05-3.00 (m, 2H), 1.95-1.90 (m, 4H). | MS m/z calcd for C$_{17}$H$_{19}$ClFN$_5$O$_2$S 411.1 found 412.1 [M + H]$^+$ |
| 38-2 | 4-(aminomethyl)-1-(5-(2-isopropoxy-6-isopropylpyridin-3-yl)imidazo[2,1-b][1,3,4]thiadiazol-2-yl)piperidin-4-ol | $^1$H NMR (400 MHz, DMSO-d$_6$) δ 8.54 (d, J = 7.7 Hz, 1H), 7.82 (s, 3H), 7.64 (s, 1H), 6.96 (d, J = 7.8 Hz, 1H), 5.43 (p, J = 6.2 Hz, 1H), 3.76-3.65 (m, 2H), 3.49 (ddd, J = 13.6, 9.0, 5.4 Hz, 2H), 2.95 (h, J = 6.8 Hz, 1H), 2.85 (d, J = 5.8 Hz, 2H), 1.72 (q, J = 4.4 Hz, 4H), 1.40 (d, J = 6.2 Hz, 6H), 1.25 (d, J = 6.8 Hz, 6H). | MS m/z calcd for C$_{21}$H$_{30}$N$_6$O$_2$S 430.2 found 431.2 [M + H]$^+$ |
| 39-2 | 4-(aminomethyl)-1-(5-(2-ethoxy-6-isopropylpyridin-3-yl)imidazo[2,1-b][1,3,4]thiadiazol-2-yl)piperidin-4-ol | $^1$H NMR (400 MHz, DMSO-d$_6$) δ 8.55 (d, J = 7.7 Hz, 1H), 7.85 (t, J = 5.8 Hz, 3H), 7.65 (s, 1H), 6.98 (d, J = 7.8 Hz, 1H), 4.48 (q, J = 7.0 Hz, 2H), 3.71 (dt, J = 13.2, 4.1 Hz, 2H), 3.49 (ddd, J = 13.8, 8.9, 5.7 Hz, 2H), 2.95 (h, J = 7.0 Hz, 1H), 2.86 (q, J = 5.8 Hz, 2H), 1.72 (q, J = 4.4 Hz, 4H), 1.42 (t, J = 7.0 Hz, 3H), 1.26 (d, J = 7.0 Hz, 6H). | MS m/z calcd for C$_{20}$H$_{28}$N$_6$O$_2$S 416.2 found 417.2 [M + H]$^+$ |

| Example/ Compound Number | Structure | NMR | LC-MS |
|---|---|---|---|
| 39-3 | 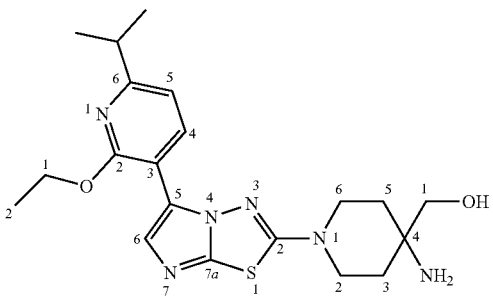<br>(4-amino-1-(5-(2-ethoxy-6-isopropylpyridin-3-yl)imidazo[2,1-b][1,3,4]thiadiazol-2-yl)piperidin-4-yl)methanol | $^1$H NMR (500 MHz, DMSO-$d_6$) δ 8.54 (d, J = 7.7 Hz, 1H), 7.57 (s 1H), 6.97 (d, J = 7.8 Hz, 1H), 4.71 (s, 1H), 4.46 (q, J = 7.0 Hz, 2H), 3.64-3.57 (m, 2H), 3.53 (td, J = 12.2, 3.3 Hz, 2H), 3.18 (d, J = 4.2 Hz, 2H), 2.94 (p, J = 6.9 Hz, 1H), 1.68-1.58 (m, 2H), 1.40 (q, J = 6.1, 5.2 Hz, 5H), 1.25 (d, J = 6.9 Hz, 6H). | MS m/z calcd for $C_{20}H_{28}N_6O_2S$ 416.2 found 417.4 [M + H]$^+$ |
| 39-4 | 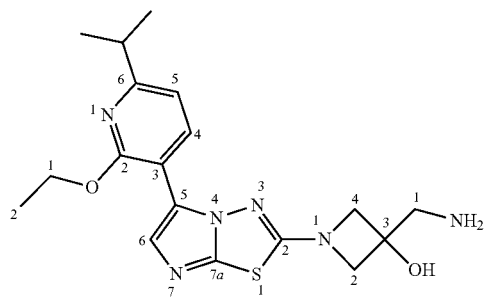<br>3-(aminomethyl)-1-(5-(2-ethoxy-6-isopropylpyridin-3-yl)imidazo[2,1-b][1,3,4]thiadiazol-2-yl)azetidin-3-ol | $^1$H NMR (400 MHz, DMSO-$d_6$) δ 8.49 (d, J = 7.7 Hz, 1H), 7.58 (s, 1H), 6.97 (d, J = 7.7 Hz, 1H), 4.47 (q, J = 7.0 Hz, 2H), 4.18 (d, J = 8.4 Hz, 2H), 3.95 (d, J = 8.3 Hz, 2H), 2.94 (p, J = 6.8 Hz, 1H), 2.89 (s, 2H), 1.41 (t, J = 7.0 Hz, 3H), 1.25 (d, J = 6.9 Hz, 6H). | MS m/z calcd for $C_{18}H_{24}N_6O_2S$ 388.2, found 389.2 [M + H]$^+$ |
| 39-5 | 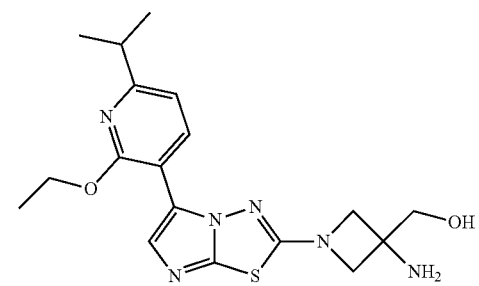<br>(4-amino-1-(5-(4-(1,2-difluoroethyl)-2-methoxyphenyl)imidazo[2,1-b][1,3,4]thiadiazol-2-yl)piperidin-4-yl)methanol | $^1$H NMR (500 MHz, DMSO-$d_6$) δ 8.52 (d, J = 7.7 Hz, 1H), 8.28 (s, 2H), 7.59 (s, 1H), 6.99 (d, J = 7.8 Hz, 1H), 4.48 (q, J = 7.1 Hz, 2H), 4.07 (d, J = 7.8 Hz, 2H), 3.83 (d, J = 7.8 Hz, 2H), 3.45 (s, 2H), 2.95 (h, J = 6.9 Hz, 1H), 1.42 (t, J = 7.0 Hz, 3H), 1.26 (d, J = 6.9 Hz, 6H). | MS m/z calcd for $C_{18}H_{24}N_6O_2S$ 388.2, found 389.2 [M + H]$^+$ |

| Example/Compound Number | Structure | NMR | LC-MS |
|---|---|---|---|
| 40-2 | 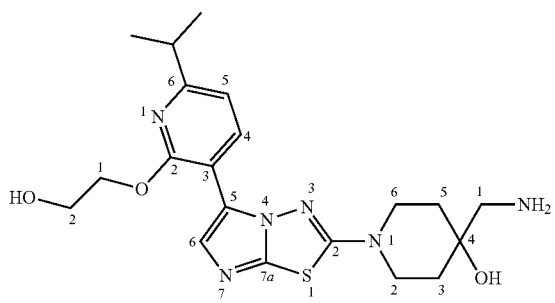<br>4-(aminomethyl)-1-(5-(2-(2-hydroxyethoxy)-6-isopropylpyridin-3-yl)imidazo[2,1-b][1,3,4]thiadiazol-2-yl)piperidin-4-ol | $^1$H NMR (500 MHz, DMSO-$d_6$) δ 8.62 (d, J = 7.8 Hz, 1H), 7.89-7.82 (m, 3H), 7.80 (s, 1H), 7.01 (d, J = 7.9 Hz, 1H), 4.45 (dd, J = 5.9, 4.2 Hz, 2H), 3.86-3.82 (m, 2H), 3.74 (dq, J = 13.0, 4.3 Hz, 2H), 3.51 (m, 2H), 2.97 (m, 1H), 2.87 (q, J = 5.7 Hz, 2H), 1.73 (q, J = 4.7 Hz, 4H), 1.27 (d, J = 6.9 Hz, 6H). | MS m/z calcd for $C_{20}H_{28}N_6O_3S$ 432.2 found 433.2 [M + H]$^+$ |
| 41-3 | 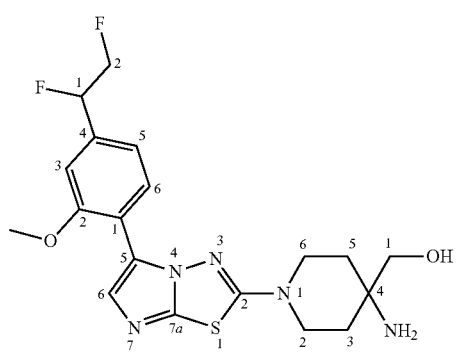<br>(4-amino-1-(5-(4-(1,2-difluoroethyl)-2-methoxyphenyl)imidazo[2,1-b][1,3,4]thiadiazol-2-yl)piperidin-4-yl)methanol | $^1$H NMR (400 MHz, MeOD-$d_4$) δ 8.36 (d, J = 8.0 Hz, 1H), 8.00 (s, 1H), 7.26 (s, 1H), 7.19 (dd, J = 8.3, 1.2 Hz, 1H), 5.89 (dd, J = 18.2, 4.7 Hz, 1H), 5.82-5.71 (m, 1H), 4.83-4.78 (m, 1H), 4.74 (d, J = 4.4 Hz, 1H), 4.70-4.66 (m, 1H), 4.62 (d, J = 4.4 Hz, 1H), 4.02 (s, 3H), 3.94-3.84 (m, 2H), 3.81 (s, 2H), 3.66 (ddd, J = 13.5, 9.5, 3.7 Hz, 2H), 2.15 (dt, J = 13.9, 4.7 Hz, 2H), 2.01 (td, J = 9.4, 4.8 Hz, 2H). | MS m/z calcd for $C_{19}H_{23}F_2N_5O_2S$ 423.2 found 424.0 [M + H]$^+$ |
| 41-4 | 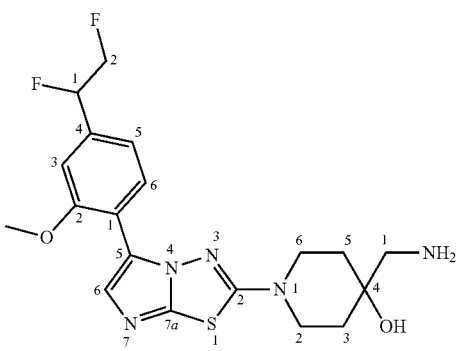<br>4-(aminomethyl)-1-(5-(4-(1,2-difluoroethyl)-2-methoxyphenyl)imidazo[2,1-b][1,3,4]thiadiazol-2-yl)piperidin-4-ol | $^1$H NMR (400 MHz, MeOD-$d_4$) δ 8.37 (d, J = 8.0 Hz, 1H), 7.95 (s, 1H), 7.28-7.21 (m, 1H), 7.18 (d, J = 8.4 Hz, 1H), 5.75-5.55 (m, 1H), 4.71 (ddd, J = 47.5, 25.0, 4.6 Hz, 2H), 4.01 (s, 3H), 3.87 (d, J = 13.5 Hz, 2H), 3.66 (dd, J = 13.4, 7.2 Hz, 2H), 2.99 (s, 2H), 1.86-1.84 (m, 4H). | MS m/z calcd for $C_{19}H_{23}F_2N_5O_2S$ 423.2 found 424.1 [M + H]$^+$ |

| Example/ Compound Number | Structure | NMR | LC-MS |
|---|---|---|---|
| 42-4 | 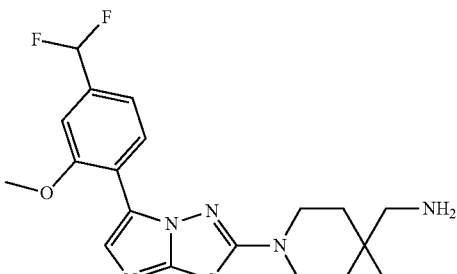<br>4-(aminomethyl)-1-(5-(2-(2,2-difluoroethoxy)phenyl)imidazo[2,1-b][1,3,4]thiadiazol-2-yl)piperidin-4-ol | $^1$H NMR (400 MHz, MeOD-d$_4$) δ 8.48 (d, J = 8.0 Hz, 1H), 8.05 (s, 1H), 7.40-7.36 (m, 1H), 7.33 (dd, J = 8.1, 1.5 Hz, 1H), 6.85 (t, J = 56.0 Hz, 1H), 3.89 (dt, J = 12.9, 3.9, 3.9 Hz, 2H), 3.70-3.68 (m, 2H), 3.67 (s, 3H), 3.00 (s, 2H), 1.86 (dd, J = 7.9, 4.0 Hz, 4H). | MS m/z calcd for C$_{18}$H$_{21}$F$_2$N$_5$O$_2$S 409.1 found 410.0 [M + H]$^+$ |
| 43-3 | 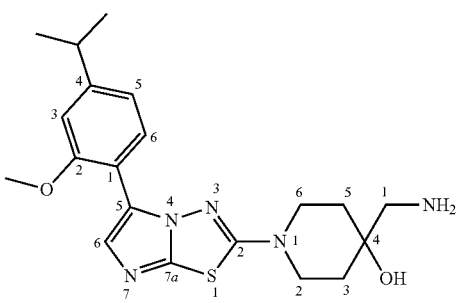<br>4-(aminomethyl)-1-(5-(4-isopropyl-2-methoxyphenyl)imidazo[2,1-b][1,3,4]thiadiazol-2-yl)piperidin-4-ol | $^1$H NMR (400 MHz, MeOD-d$_4$) δ 8.18 (d, J = 8.0 Hz, 1H), 7.87 (s, 1H), 7.04 (d, J = 1.5 Hz, 1H), 7.00 (dd, J = 8.1, 1.6 Hz, 1H), 3.96 (s, 3H), 3.90-3.81 (m, 2H), 3.71-3.58 (m, 2H), 3.03-2.93 (m, 3H), 1.89-1.78 (m, 4H), 1.30 (d, J = 6.9 Hz, 6H); | MS m/z calcd for C$_{20}$H$_{27}$N$_5$O$_2$S 401.2 found 402.1 [M + H]$^+$ |
| 44-3 | 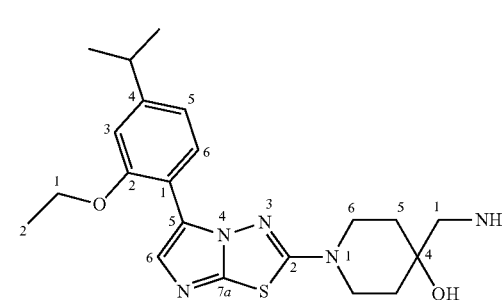<br>4-(aminomethyl)-1-(5-(2-ethoxy-4-isopropylphenyl)imidazo[2,1-b][1,3,4]thiadiazol-2-yl)piperidin-4-ol | $^1$H NMR (400 MHz, MeOD-d$_4$) δ 8.17 (d, J = 8.0 Hz, 1H), 7.62 (s, 1H), 7.00-6.87 (m, 2H), 4.19 (q, J = 6.9 Hz, 2H), 3.82 (d, J = 13.2 Hz, 2H), 3.66-3.54 (m, 2H), 2.98 (s, 2H), 2.97-2.88 (m, 1H), 1.87-1.74 (m, 4H), 1.49 (t, J = 6.9 Hz, 2H), 1.30 (d, J = 6.9 Hz, 6H). | MS m/z calcd for C$_{21}$H$_{29}$N$_5$O$_2$S 415.2 found 416.3 [M + H]$^+$ |

| Example/ Compound Number | Structure | NMR | LC-MS |
|---|---|---|---|
| 45-3 | 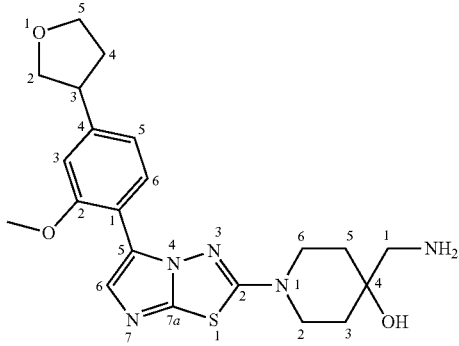<br>4-(aminomethyl)-1-(5-(2-methoxy-4-(tetrahydrofuran-3-yl)phenyl)imidazo[2,1-b][1,3,4]thiadiazol-2-yl)piperidin-4-ol | $^1$H NMR (400 MHz, DMSO-$d_6$) δ 8.11 (dd, J = 8.0, 1.4 Hz, 1H), 7.97 (s, 2H), 7.66 (d, J = 1.4 Hz, 1H), 7.08 (d, J = 1.6 Hz, 1H), 7.02 (dd, J = 8.1, 1.6 Hz, 1H), 4.08-4.01 (m, 1H), 4.00-3.94 (m, 1H), 3.90 (s, 3H), 3.87-3.78 (m, 2H), 3.53-3.36 (m, 4H), 2.88-2.79 (m, 2H), 2.38-2.27 (m, 1H), 1.99 (dq, J = 12.1, 8.1, 1H), 1.80-1.61 (m, 4H). | MS m/z calcd for $C_{21}H_{27}N_5O_3S$ 429.2, found 430.1 [M + H]$^+$ |
| 46-3 | 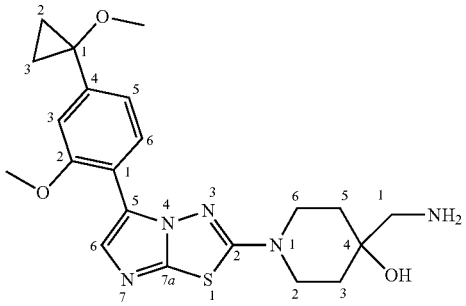<br>4-(aminomethyl)-1-(5-(2-methoxy-4-(1-methoxycyclopropyl)phenyl)imidazo[2,1-b][1,3,4]thiadiazol-2-yl)piperidin-4-ol | $^1$H NMR (400 MHz, DMSO-$d_6$) δ 8.24 (d, J = 8.1 Hz, 1H), 7.44 (s, 1H), 7.10 (br s, 1H), 6.98 (d, J = 8.1 Hz, 1H), 4.50 (br s, 3H), 3.85-3.80 (m, 3H), 3.65-3.50 (m, 3H), 1.85-1.65 (m, 4H), 1.28-1.20 (m, 2H), 1.10-1.05 (m, 2H). | MS m/z calcd for $C_{21}H_{27}N_5O_3S$ 429.2 found 430.4 [M + H]$^+$ |
| 47-3 | 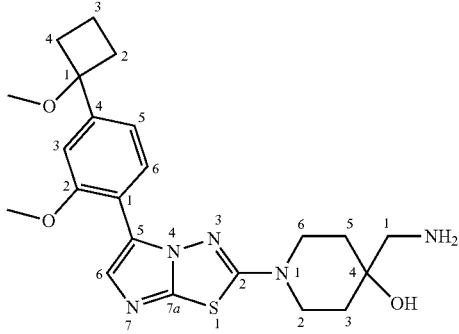<br>4-(aminomethyl)-1-(5-(2-methoxy-4-(1-methoxycyclobutyl)phenyl)imidazo[2,1-b][1,3,4]thiadiazol-2-yl)piperidin-4-ol | $^1$H NMR (400 MHz, DMSO-$d_6$) δ 8.23 (d, J = 8.0 Hz, 1H), 7.52 (s, 1H), 7.13 (dd, J = 8.1, 1.7 Hz, 1H), 7.06 (d, J = 1.7 Hz, 1H), 4.50 (br s, 2H), 3.91 (s, 3H), 3.65 (dt, J = 13.0, 3.8 Hz, 2H), 3.51-3.38 (m, 4H), 2.88 (s, 3H), 2.39 (td, J = 10.9, 4.4 Hz, 2H), 2.30 (dt, J = 12.3, 9.3 Hz, 2H), 1.88 (ddt, J = 15.8, 9.5, 4.6 Hz, 1H), 1.70-1.48 (m, 5H). | MS m/z calcd for $C_{22}H_{29}N_5O_3S$ 443.2 found 444.2 [M + H]$^+$ |

| Example/ Compound Number | Structure | NMR | LC-MS |
|---|---|---|---|
| 48-2 | 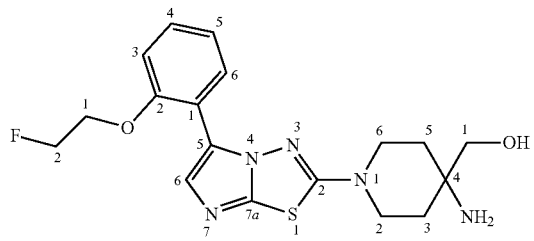<br>(4-amino-1-(5-(2-(2-fluoroethoxy) phenyl)imidazo[2,1-b][1,3,4]thiadiazol-2-yl)piperidin-4-yl)methanol | $^1$H NMR (400 MHz, MeOD-$d_4$) δ 8.32 (dd, J = 7.8, 1.7 Hz, 1H), 8.00 (s, 1H), 7.49 (ddd, J = 8.5, 7.4, 1.7 Hz, 1H), 7.23 (dd, J = 8.4, 1.0 Hz, 1H), 7.17 (td, J = 7.6, 1.1 Hz, 1H), 4.90-4.87 (m, 1H), 4.81-4.72 (m, 1H), 4.49-4.34 (m, 2H), 3.89 (dt, J = 13.8, 5.1 Hz, 2H), 3.81 (s, 2H), 3.66 (ddd, J = 13.7, 9.6, 3.8 Hz, 2H), 2.15 (dt, J = 14.1, 4.6 Hz, 2H), 2.00 (ddd, J = 14.1, 9.6, 4.7 Hz, 2H). | MS m/z calcd for $C_{18}H_{22}FN_5O_2S$ 391.2 found 392.1 [M + H]$^+$ |
| 48-3 | 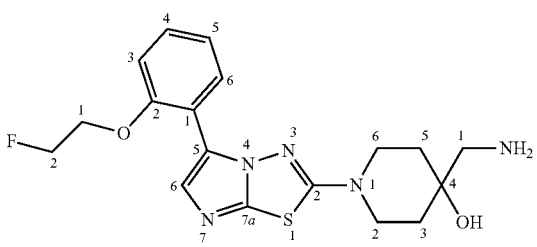<br>4-(aminomethyl)-1-(5-(2-(2-fluoroethoxy)phenyl)imidazo[2,1-b][1,3,4]thiadiazol-2-yl)piperidin-4-ol | $^1$H NMR (400 MHz, MeOD-$d_4$) δ 8.34 (dd, J = 7.9, 1.7 Hz, 1H), 7.54-7.43 (m, 1H), 7.23 (dd, J = 8.5, 1.0 Hz, 1H), 7.20-7.14 (m, 1H), 4.90-4.88 (m, 1H), 4.82-4.74 (m, 1H), 4.48-4.40 (m, 1H), 4.41-4.33 (m, 1H), 3.94-3.81 (m, 2H), 3.73-3.61 (m, 2H), 3.01 (s, 2H), 1.92-1.82 (m, 4H). | MS m/z calcd for $C_{18}H_{22}FN_5O_2S$ 391.2 found 392.1 [M + H]$^+$ |
| 49-2 | 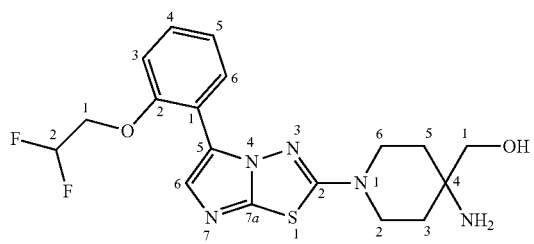<br>(4-amino-1-(5-(2-(2,2-difluoroethoxy) phenyl)imidazo[2,1-b][1,3,4]thiadiazol-2-yl)piperidin-4-yl)methanol | $^1$H NMR (300 MHz, MeOD-$d_4$) δ 8.29 (dd, J = 7.8, 1.7 Hz, 1H), 7.91 (s, 1H), 7.49 (ddd, J = 8.9, 7.4, 1.7 Hz, 1H), 7.30-7.12 (m, 2H), 6.29 (tt, J = 54.5, 3.4 Hz, 2H), 4.43 (td, J = 14.3, 3.3 Hz, 2H), 3.87 (dt, J = 13.8, 5.1 Hz, 2H), 3.79 (s, 2H), 3.64 (ddd, J = 13.8, 9.7, 3.9 Hz, 2H), 2.23-2.08 (m, 2H), 2.05-1.85 (m, 2H). | MS m/z calcd for $C_{18}H_{21}F_2N_5O_2S$ 409.1 found 410.1 [M + H]$^+$ |
| 49-3 | 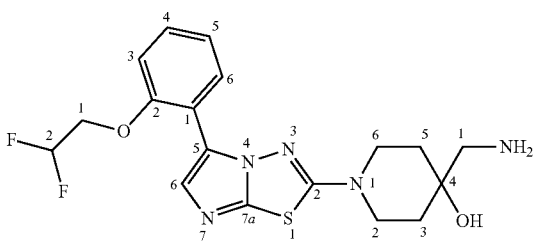<br>4-(aminomethyl)-1-(5-(2-(2,2-difluoroethoxy)phenyl)imidazo[2,1-b][1,3,4]thiadiazol-2-yl)piperidin-4-ol | $^1$H NMR (300 MHz, MeOD-$d_4$) δ 8.34-8.23 (m, 1H), 7.90 (s, 1H), 7.49 (ddd, J = 8.8, 7.4, 1.7 Hz, 1H), 7.29-7.15 (m, 2H), 6.29 (tt, J = 54.6, 3.4 Hz, 1H), 4.43 (td, J = 14.2, 3.4 Hz, 2H), 3.94-3.79 (m, 2H), 3.76-3.55 (m, 2H), 1.90-1.77 (m, 4H). | MS m/z calcd for $C_{18}H_{21}F_2N_5O_2S$ 409.1 found 410.1 [M + H]$^+$ |

| Example/ Compound Number | Structure | NMR | LC-MS |
|---|---|---|---|
| 50-4 | 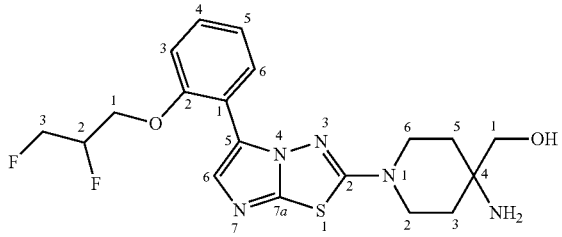<br>(4-amino-1-(5-(2-(2,3-difluoropropoxy) phenyl)imidazo[2,1-b][1,3,4]thiadiazol-2-yl) piperidin-4-yl)methanol | $^1$H NMR (400 MHz, MeOD-d$_4$) δ 8.23 (dd, J = 7.8, 1.7 Hz, 1H), 7.92 (s, 1H), 7.53-7.45 (m, 1H), ), 7.24 (dd, J = 8.5, 1.0 Hz, 1H), 7.18 (td, J = 7.6, 1.0 Hz, 1H), 4.86-4.58 (m, 3H), 4.55-4.32 (m, 3H), 3.94-3.82 (m, 2H), 3.80 (s, 2H), 3.64 (ddd, J = 13.7, 9.7, 3.8 Hz, 2H), 2.21-2.08 (m, 2H), 1.99 (ddd, J = 14.1, 9.7, 4.7 Hz, 2H). | MS m/z calcd for C$_{19}$H$_{23}$F$_2$N$_5$O$_2$S 423.2 found 424.1 [M + H]$^+$ |
| 50-5 | 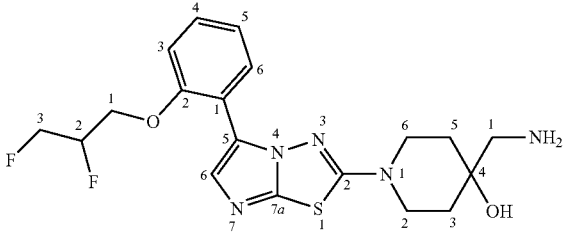<br>4-(aminomethyl)-1-(5-(2-(2,3-difluoropropoxy)phenyl)imidazo[2,1-b] [1,3,4]thiadiazol-2-yl)piperidin-4-ol | $^1$H NMR (300 MHz, MeOD-d$_4$) δ 8.22 (dd, J = 7.8, 1.6 Hz, 1H), 7.90 (s, 1H), 7.52-7.44 (m, 1H), 7.25-7.13 (m, 2H), 4.77-4.56 (m, 2H), 4.52-4.29 (m, 3H), 3.90-3.78 (m, 2H), 3.71-3.59 (m, 2H), 2.98 (s, 2H), 1.88-1.77 (m, 4H). | MS m/z calcd for C$_{19}$H$_{23}$F$_2$N$_5$O$_2$S 423.2 found 424.2 [M + H]$^+$ |
| 51-5 | 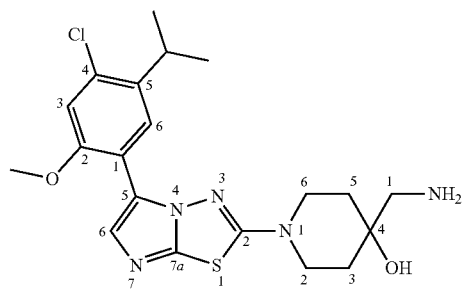<br>4-(aminomethyl)-1-(5-(4-chloro-5-isopropyl-2-methoxyphenyl)imidazo [2,1-b][1,3,4]thiadiazol-2-yl)piperidin-4-ol | $^1$H NMR (400 MHz, MeOD-d$_4$) δ 8.46 (s, 1H), 7.97 (s, 1H), 7.23 (s, 1H), 3.99 (s, 3H), 3.92-3.85 (m, 2H), 3.76-3.65 (m, 2H), 3.44 (p, J = 6.8 Hz, 1H), 3.01 (s, 2H), 1.92-1.80 (m, 4H), 1.31 (d, J = 6.8 Hz, 6H) | MS m/z calcd for C$_{20}$H$_{26}$ClN$_5$O$_2$S 435.2 found 436.2 [M + H]$^+$ |

Compound 53-0: tert-butyl 4-amino-1-thia-8-azaspiro[4.5]decane-8-carboxylate 1,1-dioxide

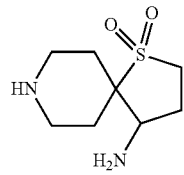

Compound 53-0 was prepared in the following way:

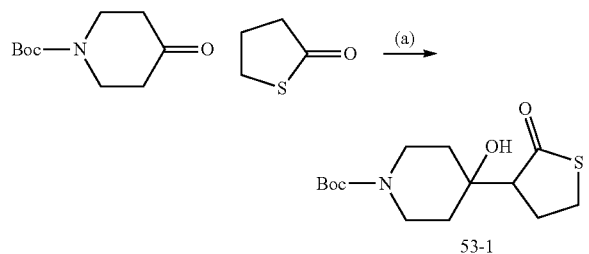

To a suspension of dihydrothiophen-2(3H)-one (0.123 g, 1.20 mmol) in THF (3 mL), LiHMDS (1.2 mL, 1.23 mmol) was added at −78° C. and stirred for 1 hour. Then tert-butyl 4-oxopiperidine-1-carboxylate (0.200. g, 1.0 mmol) in THF (3 mL) was added to the reaction mixture at −78° C. and stirred at same temperature for 2 hours. The reaction mixture was quenched with sat. NH$_4$Cl solution and extracted with EtOAc (20 mL). The organic layer was washed with brine and dried over Na$_2$SO$_4$ and concentrated in vacuo. The crude product was purified by normal phase chromatography with a running gradient of 30-40% EtOAc/n-hexane to afford 0.155 g of Compound 53-1 as a solid. $^1$H NMR (300 MHz, CDCl$_3$) δ 3.92 (br s, 2H), 3.75-3.59 (m, 1H), 3.32-3.21 (m, 2H), 3.13 (s, 2H), 2.65 (s, 9H). LC-MS=202.10 [M+H]$^+$ (De-Boc), retention time=1.48 minutes.

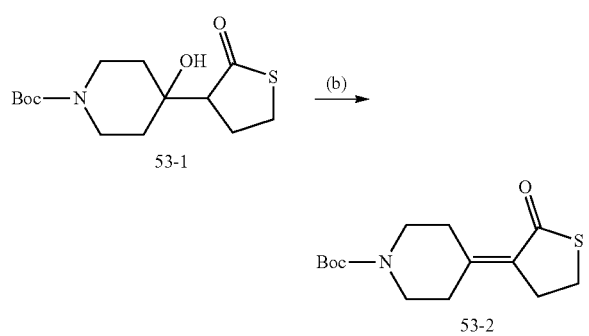

To a suspension of Compound 53-1 (0.150 g, 0.497 mmol) in DCM (5 mL), Et$_3$N (0.69 mL, 4.97 mmol) and MsCl (0.077 mL, 0.995 mmol) were added at 0° C. The reaction allowed to reach the room temperature and stirred for 18 hours. The reaction mixture was quenched with sat. NaHCO$_3$ solution and extracted with DCM (10 mL). The organic layer was washed with brine and dried over Na$_2$SO$_4$ and concentrated in vacuo. The crude product was purified by normal phase chromatography with a running gradient of 30-40% EtOAc/n-hexane to afford 0.080 g of Compound 53-2 as a colorless liquid. $^1$H NMR (300 MHz, CDCl$_3$) δ 3.54 (t, J=5.9 Hz, 2H), 3.44 (t, J=5.9 Hz, 2H), 3.29-3.22 (m, 2H), 3.05-2.94 (m, 4H), 2.34 (t, J=6.0 Hz, 2H), 1.47 (s, 9H). LC-MS=284.05 [M+H]$^+$, retention time=1.64 minutes.

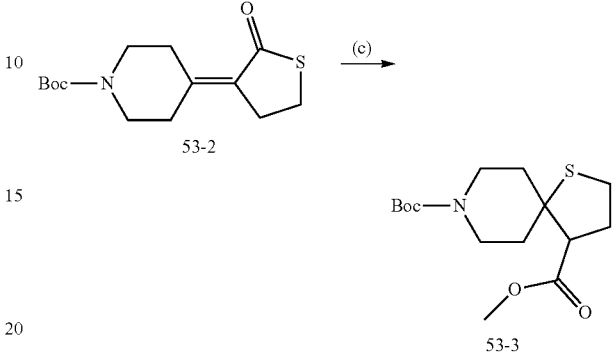

To a suspension of Compound 53-2 (0.3 g, 1.06 mmol) in MeOH (3 mL), Et$_3$N (0.297 mL, 2.12 mmol) was added. The reaction mixture was heated at 70° C. for 32 hours. The reaction was concentrated in vacuo. The crude product was purified by normal phase chromatography with a running gradient of 5-10% EtOAc/n-hexane to afford 0.56 g of Compound 53-3 as a colorless liquid. $^1$H NMR (400 MHz, CDCl$_3$) δ 4.13 (s, 2H), 3.73 (s, 3H), 3.05-2.94 (m, 2H), 2.94-2.84 (m, 2H), 2.77 (dd, J=10.8, 6.2 Hz, 1H), 2.52-2.31 (m, 2H), 2.21-2.09 (m, 1H), 1.68 (t, J=12.9 Hz, 2H), 1.46 (s, 10H).

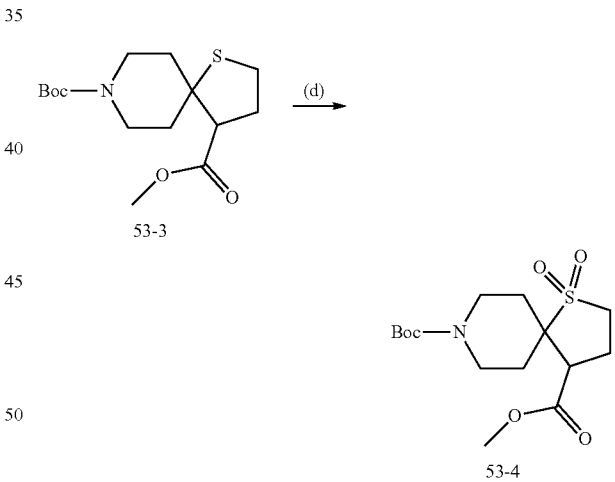

To a suspension of Compound 53-3 (0.050 g, 0.158 mmol) in DCM (3 mL), mCPBA (0.070 g, 0.317 mmol) was added portionwise at 0° C. and the reaction mixture was stirred at room temperature for 1 hour. The reaction mixture was quenched with sat. NaHCO$_3$ and aqueous Na$_2$SO$_3$ and extracted twice with DCM (10 mL). The organic layer was washed with brine and dried over Na$_2$SO$_4$ and concentrated in vacuo. The crude product was purified by normal phase chromatography with a running gradient of 50-70% EtOAc/n-hexane to afford 0.034 g of Compound 53-4 as a colourless liquid. $^1$H NMR (400 MHz, CDCl$_3$) δ 3.94 (s, 2H), 3.76 (s, 3H), 3.43 (s, 1H), 3.35 (ddd, J=13.4, 9.4, 4.0 Hz, 1H), 3.23 (s, 1H), 3.09 (dt, J=13.4, 9.0 Hz, 1H), 2.99 (dd, J=11.1, 6.3 Hz, 1H), 2.45 (ddt, J=14.0, 11.2, 9.3 Hz, 1H), 2.24 (dddd, J=14.0, 8.8, 6.3, 4.0 Hz, 2H), 2.15-2.02 (m, 3H), 1.45 (s, 9H).

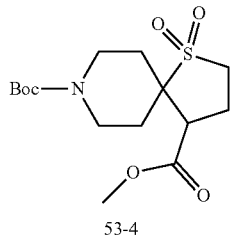

53-4

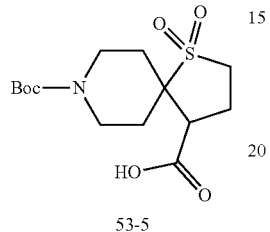

53-5

To a suspension of Compound 53-4 (0.56 g. 1.61 mmol) in THF:H₂O (6 mL, 1:1), LiOH H₂O (0.135 g, 3.22 mmol) was added at 0° C. and the reaction mixture was stirred at room temperature for 3 hours. The reaction mixture was acidified with sat. citric acid to pH=4 and extracted twice with DCM (20 mL). The combined organic layers were washed with brine and dried over Na₂SO₄ and concentrated in vacuo to afford 0.4 g of Compound 53-5 as a solid. ¹H NMR (300 MHz, DMSO-d₆) δ 3.79 (d, J=13.2 Hz, 2H), 3.52-3.34 (m, 2H), 3.25-3.08 (m, 2H), 2.94 (dd, J=10.4, 7.1 Hz, 1H), 2.22-2.16 (m, 1H), 2.10-1.95 (m, 4H), 1.57 (ddd, J=15.0, 11.2, 4.9 Hz, 1H), 1.39 (s, 9H).

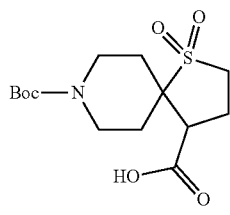

53-5

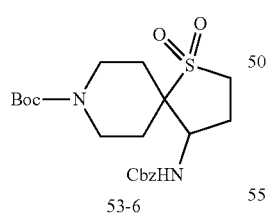

53-6

To a solution of Compound 53-5 (0.5 g, 1.49 mmol) in PhMe (30 mL) and Et₃N (0.313 mL, 2.24 mmol), diphenyl phosphoryl azide (0.619 g, 2.24 mmol) was added dropwise at room temperature. Then reaction heated at 110° C. for 1.5 hours. The reaction was cooled to room temperature and BnOH (0.486 g, 4.49 mmol) was added dropwise and stirred at 100° C. for 10 hours. The reaction mixture was quenched by sat. Na₂CO₃ and extracted with EtOAc. The combined organic layers were dried over Na₂SO₄ and concentrated in vacuo. The crude was purified by normal phase chromatography with a running gradient of 40-70% EtOAc/n-hexane to afford 0.350 g of Compound 53-6 as a solid. ¹H NMR (400 MHz, CDCl₃) δ 7.42-7.29 (m, 5H), 5.11 (ABq, J=12.0 Hz, 2H), 3.71 (brs, 1H), 3.56 (brs, 2H), 3.26-3.10 (m, 2H), 2.18-2.06 (m, 2H), 1.98-1.87 (m, 2H), 1.80-1.75 (m, 2H), 1.68-1.64 (m, 2H), 1.45 (s, 9H)).

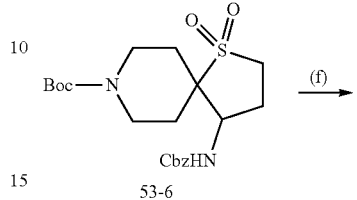

53-6

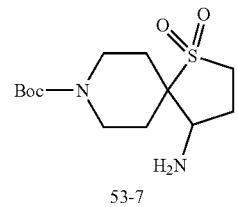

53-7

To a solution of Compound 53-6 (350 mg, 0.79 mmol) in THF (30.0 mL), 10% Pd—C (70 mg) was added under H₂. The reaction was stirred for 10 hours. The reaction mixture was filtered on CELITE pad and concentrated in vacuo to afford 250 mg of Compound 53-7. LC-MS=249 M-tBu+H]⁺, retention time=1.27 minutes;

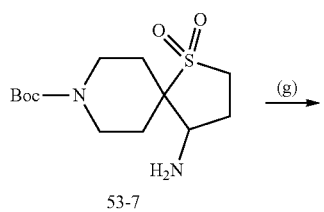

53-7

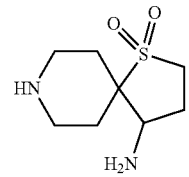

53

To a solution of Compound 53-7 in dioxane, 4 M HCl in dioxane was added dropwise at 0° C. for 5 minutes. Then it was allowed to stir at room temperature for 2 hours. The reaction was concentrated in vacuo to afford 30 mg of Compound 53. LC-MS=205.10 [M+H]⁺, retention time=0.10 minutes.

Compound 54-0: tert-butyl(4-(methoxymethyl)piperidin-4-yl)carbamate

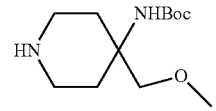 [SMILES: COCC1(NC(=O)OC(C)(C)C)CCNCC1]

Compound 54-0 was prepared in the following way:

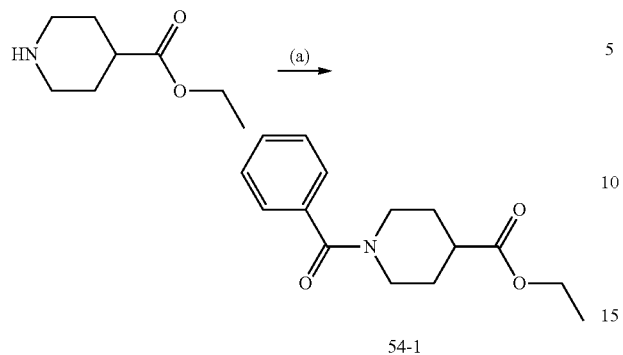

To a solution of ethyl piperidine-4-carboxylate (10.0 g, 63.61 mmol) in DCM (100 mL), TEA (19.3 g 190.84 mmol) was added at 0° C. After 15 minutes, benzoyl chloride (9.84 g, 69.97 mmol) was added dropwise at 0° C. Then the reaction was allowed to reach the room temperature for 16 hours. The reaction mixture was quenched with ice cooled $H_2O$ and extracted with DCM. The combined organic layers were washed with 2 N HCl, followed by brine and dried over $Na_2SO_4$, concentrated in vacuo to afford 13.0 g of Compound 54-1. $^1$H NMR (300 MHz, CDCl$_3$) δ 7.46-7.33 (m, 5H), 4.53 (s, 1H), 4.15 (q, J=7.1 Hz, 2H), 3.75 (s, 1H), 3.04 (s, 2H), 2.57 (tt, J=10.7, 4.0 Hz, 1H), 2.12-1.55 (m, 4H), 1.26 (t, J=7.1 Hz, 3H). LC-MS=262.1 [M+H]$^+$, retention time=0.83 minutes.

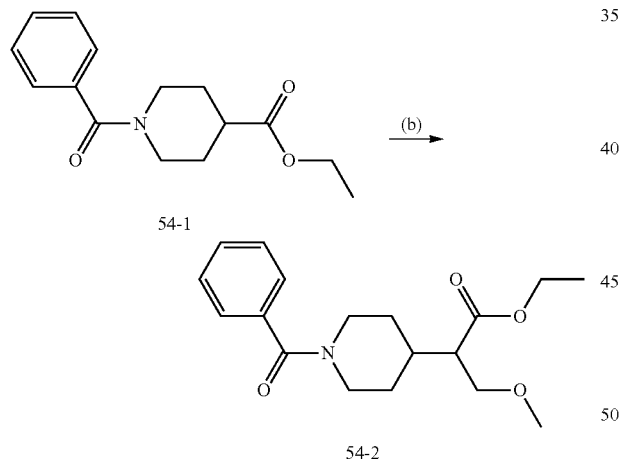

To a solution of diisopropyl amine (2.50 g, 24.491 mmol) in THF (20 mL) at −78° C., n-BuLi (2.5 M in n-hexane-9.20 mL, 22.960 mmol) was added dropwise, The reaction was allowed to reach 0° C. for 10 minutes. Then the reaction was cooled to −78° C. and Compound 54-1 (4 g, 15.307 mmol) in THF (10 mL) was added dropwise. After 1 hour at −78° C., bromo(methoxy)methane (2.50 g, 19.899 mmol) was added dropwise at −78° C. and the reaction was allowed to reach the room temperature for 16 hours. The reaction mixture was quenched with sat. NH$_4$Cl in H$_2$O and extracted with EtOAc and the combined organic layers were dried over Na$_2$SO$_4$ and concentrated in vacuo. The crude material was purified by normal phase chromatography with a running gradient of 30-40% EtOAc/n-hexane to afford 3.50 g of Compound 54-2 as a colourless sticky mass. $^1$H NMR (300 MHz, CDCl$_3$) δ 7.46-7.33 (m, 5H), 4.53 (s, 1H), 4.15 (q, J=7.1 Hz, 2H), 3.75 (s, 1H), 3.04 (s, 2H), 2.57 (tt, J=10.7, 4.0 Hz, 1H), 2.12-1.55 (m, 4H), 1.26 (t, J=7.1 Hz, 3H). LC-MS=306.05 [M+H]$^+$, retention time=1.49 minutes.

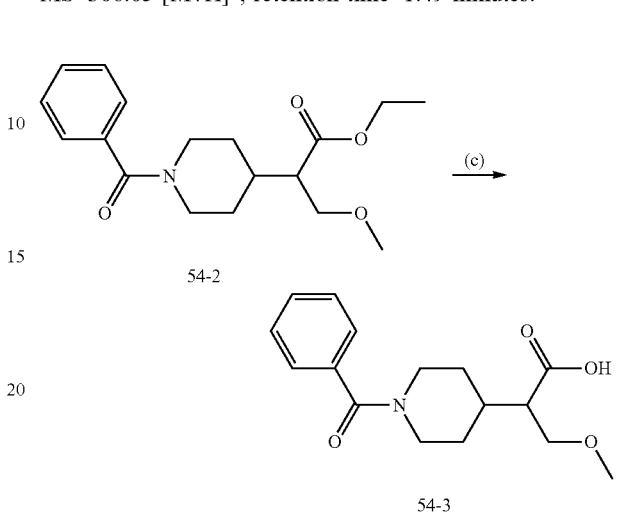

To a solution of Compound 54-2 (3.50 g, 11.462 mmol) in EtOH (35 mL), NaOH (687 mg, 17.192 mmol) in H$_2$O (2.8 mL) was added at room temperature and stirred for 8 hours at 50° C., then stirred for 48 hours at room temperature. The reaction mixture was acidified with KHSO$_4$ and extracted with EtOAc. The combined organic layers were washed with brine solution, dried over Na$_2$SO$_4$ and concentrated in vacuo to afford 3.0 g of Compound 54-3 as a white sticky mass. LC-MS=278.15 [M+H]$^+$, retention time=1.37 minutes.

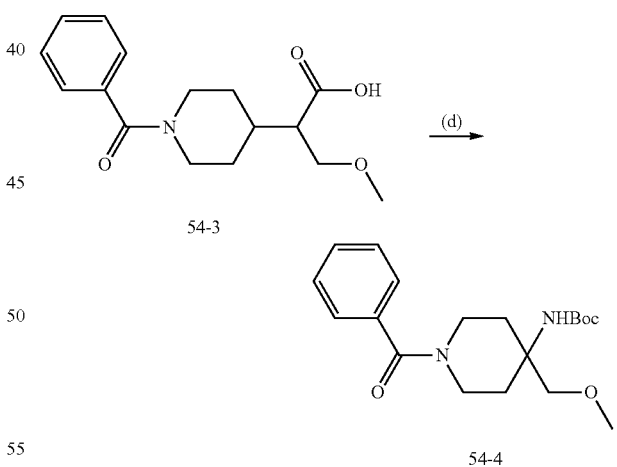

To a solution of Compound 54-3 (1.0 g, 3.61 mmol) and Et$_3$N (1.09 g, 10.830 mmol) in PhMe (10 mL), diphenyl phosphoryl azide (1.19 g, 4.332 mmol) was added dropwise at room temperature. The reaction was stirred for 3 hours at a reflux. The reaction mixture was diluted with EtOAc and washed with water, followed by sat. solution of Na$_2$CO$_3$ and brine, dried over Na$_2$SO$_4$ and concentrated in vacuo. The resulting residue was taken in THF (10 mL) and KO$^t$Bu (810 mg, 7.220 mmol) was added at room temperature. The reaction was stirred for 20 minutes at room temperature. The reaction mixture was quenched by sat. solution of NH₄Cl extracted with EtOAc. The combined organic layers were dried over Na₂SO₄ and concentrated in vacuo. The crude material was purified by normal phase chromatography with a running gradient of 30-40% EtOAc/n-hexane to afford 600 mg of Compound 54-4 as a colourless sticky product. LC-MS=349.15 [M+H]⁺, retention time=1.50 minutes.

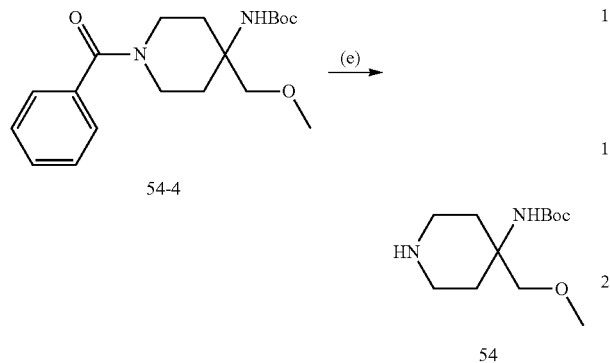

To a solution of Compound 54-4 (350 mg, 1.004 mmol) in EtOH (4.5 mL), NaOH (241 mg, 6.026 mmol) in H₂O (1 mL) was added at room temperature and stirred for 16 hours at 90° C. The reaction mixture was concentrated in vacuo. The resulting residue was diluted with EtOAc and washed with water, dried over Na₂SO₄ and concentrated in vacuo to afford 250 mg of Compound 54 as a colourless sticky product. LC-MS=245.20 [M+H]⁺, retention time=1.23 minutes.

Compound 55-0: tert-butyl (3-(2-hydroxypropan-2-yl)pyrrolidin-3-yl)carbamate

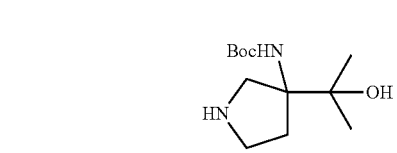

Compound 55-0 was prepared in the following way:

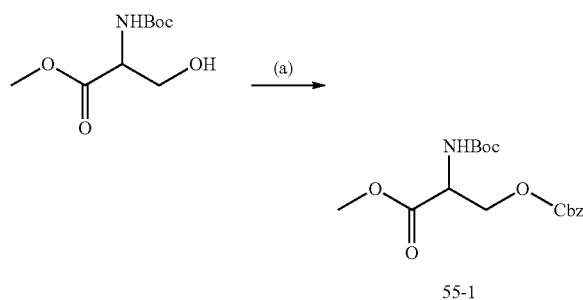

To a solution of Methyl (tert-butoxycarbonyl)serinate (10.00 g, 45.639 mmol) in DCM (100 mL), pyridine (4.43 mL, 57.222 mmol) and Cbz-Cl (50% in PhMe, 14.22 mL, 50.203 mmol) were added slowly over a period of 30 minutes at −50° C. The reaction was then stirred at room temperature for 16 hours. The reaction mixture was diluted with DCM (100 mL) and with 20% citric acid solution (500 mL). The aqueous layer was extracted twice with DCM (500 mL). The combined organic layers were washed with 5% NaHCO₃ solution and brine (200 mL), dried over Na₂SO₄ and concentrated in vacuo. The product was purified by normal phase chromatography with a running gradient of 20% EtOAc/n-hexane to afford 12.50 g of Compound 55-1 as a solid. ¹H NMR (400 MHz, CDCl₃) δ 7.38 (d, J=5.1 Hz, 5H), 5.38-5.25 (m, 1H), 5.15 (s, 2H), 4.63-4.48 (m, 2H), 4.41 (dd, J=10.8, 3.4 Hz, 1H), 3.74 (s, 3H), 1.44 (s, 9H). LC-MS=254.1 [M-100]⁺ (De-Boc), retention time=1.31 minutes.

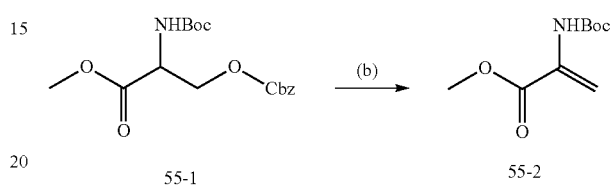

To a solution of Compound 55-1 (6.00 g, 16.989 mmol) in N,N-dimethylformamide (60 mL), K₂CO₃ (4.695 g, 33.979 mmol) was added slowly over a period of 5 minutes at room temperature. The reaction was then stirred at 65° C. for 3 hours. The reaction mixture was diluted with H₂O (500 mL) and extracted twice with EtOAc (100 mL). The combined organic layers were washed with brine solution (300 mL), dried over Na₂SO₄ and concentrated in vacuo. The product was purified by normal phase chromatography with a running gradient of 10% EtOAc/hexane to afford 3.00 g of Compound 55-2 as a colourless liquid. ¹H NMR (400 MHz, DMSO-d₆) δ 8.34 (s, 1H), 7.46-7.32 (m, 1H), 5.65 (s, 1H), 5.49 (s, 1H), 3.72 (s, 3H), 1.41 (s, 9H). LC-MS=102.1 [M-100]⁺ (De-Boc), retention time=1.28 minutes.

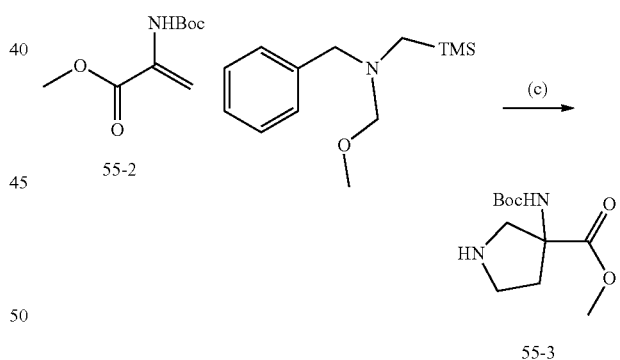

To a solution of Compound 55-2 (3.7 g, 18.398 mmol) and N-benzyl-1-methoxy-N-((trimethylsilyl)methyl)methanamine (4.36 g, 18.398 mmol) in DCM (30 mL), TFA (0.1 mL) was added slowly over a period of 5 minutes at 0° C. Then the reaction was stirred at room temperature for 16 hours. The reaction mixture was diluted with H₂O (50 mL) and extracted twice with DCM (50 mL). The combined organic layers were washed with aqueous NaHCO₃ and brine (50 mL), the organic layer was dried over Na₂SO₄ and concentrated in vacuo. The product was purified by normal phase chromatography with a running gradient of 20% EtOAc/n-hexane to afford 1.90 g of Compound 55-3 as a yellow liquid. ¹H NMR (400 MHz, CDCl₃) δ 7.39-7.27 (m, 5H), 3.73 (s, 3H), 3.64 (q, J=13.0 Hz, 2H), 2.88 (s, 1H), 2.81

(d, J=10.3 Hz, 1H), 2.67-2.52 (m, 2H), 2.08-1.93 (m, 1H), 1.58 (s, 1H), 1.42 (s, 9H). LC-MS=335.2 [M+H]⁺, retention time=1.04 minutes.

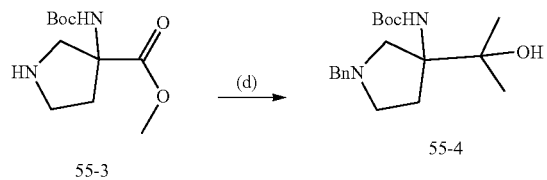 [SMILES: COC(=O)C1(NC(=O)OC(C)(C)C)CCNC1 ; CC(C)(C)OC(=O)NC1(C(C)(C)O)CCN(Cc2ccccc2)C1]

To a solution of Compound 55-3 (1.9 g, 5.685 mmol) in anhydrous THF (25 mL), a solution of 3 M MeMgBr in Et₂O (9.475 mL, 28.426 mmol) was added slowly over a period of 5 minutes at 0° C. Then the reaction was stirred at room temperature for 1 hour. The reaction mixture was quenched with sat. NH₄Cl solution (20 mL), diluted with H₂O (60 mL) and extracted twice with EtOAc (30 mL). The combined organic layers were washed with brine (20 mL), dried over Na₂SO₄ and concentrated in vacuo. The product was purified by normal phase chromatography with a running gradient of 1-2% MeOH/DCM to afford 900 mg of Compound 55-4 as a yellow liquid. ¹H NMR (400 MHz, CDCl₃) δ 7.39-7.12 (m, 5H), 4.85 (s, 1H), 3.67-3.51 (m, 2H), 2.90 (d, J=10.6 Hz, 1H), 2.77-2.58 (m, 2H), 2.55 (d, J=10.1 Hz, 1H), 2.34-2.18 (m, 1H), 1.91-1.78 (m, 1H), 1.40 (s, 9H), 1.18 (s, 3H), 1.16 (s, 3H). LC-MS=335.1 [M+H]⁺, retention time=1.08 minutes.

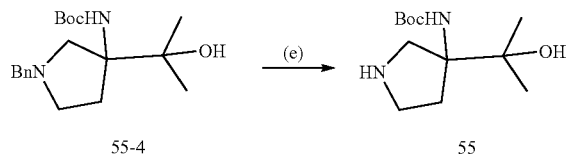 [SMILES: CC(C)(C)OC(=O)NC1(C(C)(C)O)CCN(Cc2ccccc2)C1 ; CC(C)(C)OC(=O)NC1(C(C)(C)O)CCNC1]

To a solution of Compound 55-4 (900 g, 2.692 mmol) in MeOH (20 mL), 10% Pd/C, 50% moisture (1.432 g, 13.463 mmol) was added slowly at 30° C. The reaction was stirred at room temperature for 1 hour under H₂ (60 psi). The reaction mixture was filtered through CELITE pad. The filtrate was concentrated in vacuo to afford 640 mg of Compound 55 as a yellow liquid. ¹H NMR (400 MHz, DMSO-d₆) δ 4.92 (s, 1H), 3.31 (s, 2H), 2.99-2.77 (m, 3H), 2.72-2.62 (m, 1H), 2.02-1.80 (m, 2H), 1.38 (s, 9H), 1.16-0.99 (m, 6H). LC-MS=245.1 [M+H]⁺, retention time=1.00 minutes.

Compound 56-0:3-azido-4-methylpiperidin-4-ol

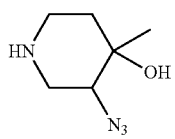

The Compound 56-0 was prepared in the following way:

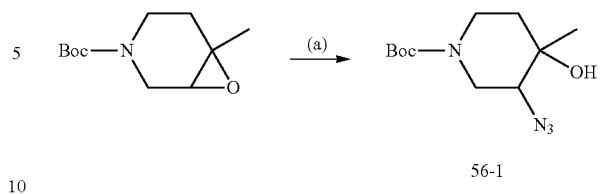

A solution of tert-butyl 6-methyl-7-oxa-3-azabicyclo[4.1.0]heptane-3-carboxylate (500 mg, 2.344 mmol) in MeOH (10 mL) and H₂O (2 mL) was treated with NaN₃ (762 mg, 11.72 mmol) and NH₄Cl (251 mg, 4.69 mmol). The reaction was heated to 65° C. for 18 hours. The reaction mixture was concentrated in vacuo and diluted with DCM, filtered through a phase separator and concentrated in vacuo to give 544 mg of an oil of Compound 56-1.

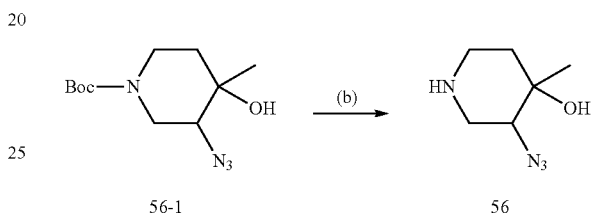

A mixture of Compound 56-1 (200 mg, 0.780 mmol) in HCl in dioxane (1 mL, 4.00 mmol) was stirred at room temperature for 1 hour. The reaction mixture was dried under N₂ stream to afford 204.8 mg of Compound 56.

Compound 57-0:
(3R,4r,5S)-4-amino-4-methylpiperidine-3,5-diol

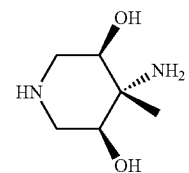

Compound 57-0 was prepared in the following way:

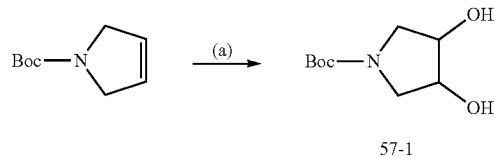 [SMILES: CC(C)(C)OC(=O)N1CC=CC1 ; CC(C)(C)OC(=O)N1CC(O)C(O)C1]

A solution of tert-butyl 2,5-dihydro-1H-pyrrole-1-carboxylate (5 g, 29.5 mmol) in THF (110 mL) was cooled to 0° C. and NMO (3.46 g, 29.5 mmol) and osmium(VIII) oxide (4.64 ml, 0.591 mmol) (4% solution in water) were added. The reaction mixture was stirred at room temperature under N₂ for 18 hours. The reaction mixture was concentrated in vacuo and the resulting residue was diluted with aq. 5% sodium sulfite (100 mL). The mixture was stirred at room temperature for 30 minutes and then was extracted with EtOAc. The combined organic layers were washed brine, dried over MgSO₄, filtered and concentrated in vacuo.

The crude was purified by normal phase chromatography with a running gradient of 20-100% EtOAc/heptane to afford 4.31 g of Compound 57-1 as an oil.

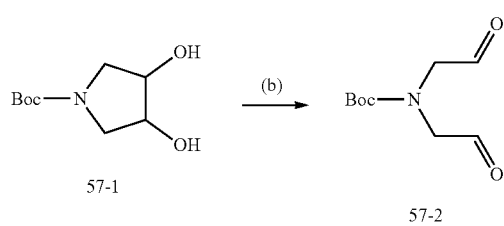 [SMILES: CC(C)(C)OC(=O)N1CC(O)C(O)C1 ; CC(C)(C)OC(=O)N(CC=O)CC=O]

A solution of Compound 57-1 (4.31 g, 21.21 mmol) in THF (35.4 mL) was cooled to 0° C. and a solution consisting of NaIO$_4$ (4.54 g, 21.21 mmol) in H$_2$O (26.4 mL) was added dropwise at 0° C. The resulting white suspension was stirred at room temperature for 1 hour. The reaction mixture was filtrated and washed with THF (40 mL). The filtrate was concentrated in vacuo to afford 4.27 g of Compound 57-2 as a colourless solution.

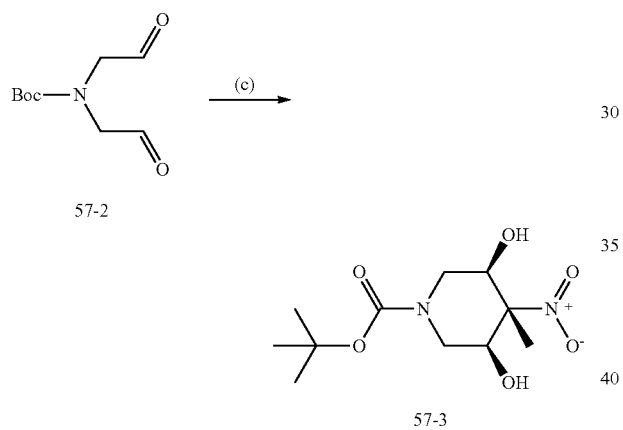

A solution of Compound 57-2 (4.27 g, 21.22 mmol) and nitroethane (1.517 mL, 21.22 mmol) in MeOH (7.66 mL) was cooled to 0° C. and a solution consisting of Na$_2$CO$_3$ (2.249 g, 21.22 mmol) in H$_2$O (26.3 mL) was added dropwise at 0° C. The reaction mixture was stirred at room temperature for 1 hour and then was quenched with sat. NH$_4$Cl. The pH was set to 4 with 1 N HCl. This mixture was extracted with EtOAc. The combined organic layers were washed with sat. NH$_4$Cl, dried over Na$_2$SO$_4$, filtrated and concentrated in vacuo. The crude was purified by normal phase chromatography with a running gradient of 5-50% EtOAc/heptane to afford 1.74 g of Compound 57-3.

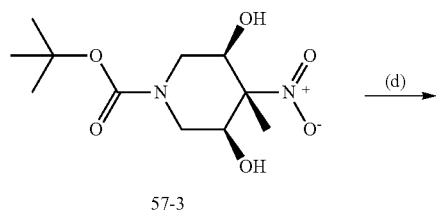

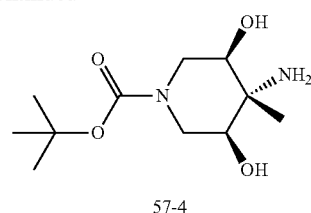

To a solution of Compound 57-3 (300 mg, 1.086 mmol) and Zn (1136 mg, 17.37 mmol) in MeOH (4 mL), acetic acid (0.622 mL, 10.86 mmol) was added dropwise. The reaction mixture was stirred at room temperature for 3 days and then was filtered through CELITE pad. The resulting solution was concentrated in vacuo. The crude was purified by normal phase chromatography with a running gradient of 0-100% EtOAC/heptanes and then 0-20% MeOH/DCM to afford 74 mg of Compound 57-4. LC-MS=247.4 [M+H]$^+$.

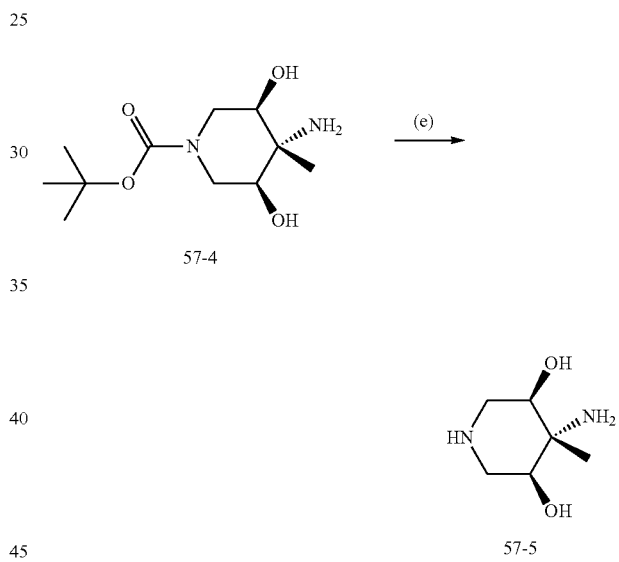

A mixture of Compound 57-4 (74 mg, 0.300 mmol) and HCl in dioxane (1 mL, 4.00 mmol) was stirred at room temperature for 1 hour. The reaction mixture was dried under N$_2$ stream to afford 62 mg of Compound 57.

Compound 58-0: tert-butyl((3S,4S)-3-(hydroxymethyl)piperidin-4-yl)carbamate

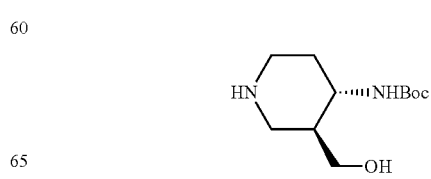

Compound 58-0 was prepared in the following way:

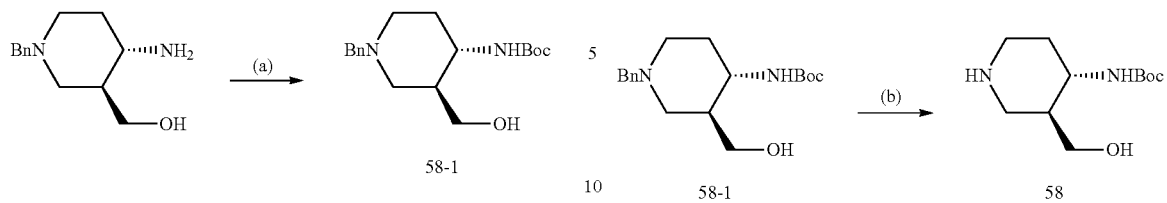

To a mixture of ((3S,4S)-4-aminopiperidin-3-yl)methanol (2.8 g, 12.71 mmol) in THF (20 mL) and H$_2$O (20 mL), Boc$_2$O (11.1 g, 50.83 mmol) was added. Then the reaction was stirred at room temperature for 2 hours. The reaction mixture concentrated to remove THF. The mixture was washed with water and extracted twice with EtOAc. The combined organic layers were driver over Na$_2$SO$_4$, filtered and concentrated in vacuo. The crude product was purified by normal phase chromatography with a running gradient of Petroleum ether:EtOAc 5:1 to 1:3 to afford 2.1 g of Compound 58-1 as a solid. $^1$H NMR (400 MHz, DMSO-d$_6$) δ 7.38-7.18 (m, 5H), 6.75 (brd, J=8.8 Hz, 1H), 4.28 (t, J=5.1 Hz, 1H), 3.47-3.36 (m, 1H), 3.18-2.92 (m, 3H), 2.80-2.63 (m, 1H), 1.96-1.82 (m, 1H), 1.74-1.62 (m, 2H), 1.59-1.51 (m, 1H), 1.44 (dd, J=3.6, 11.9 Hz, 1H), 1.39-1.29 (m, 9H).

To a solution of Compound 58-1 (2.1 g, 6.55 mmol) in MeOH (60 mL), Pd/C (700 mg, 10%) was added under H$_2$. The reaction mixture was stirred at room temperature under H$_2$ for 2 hours. The mixture was filtered and the filtrate was concentrated in vacuo. The crude product was purified by reverse phase chromatography to afford 924.7 mg of Compound 58 as an oil. $^1$H NMR (400 MHz, MeOD-d$_4$) δ 3.59 (brd, J=9.9 Hz, 1H), 3.52-3.41 (m, 1H), 3.32 (brs, 2H), 3.19 (brd, J=10.1 Hz, 1H), 3.09-2.99 (m, 1H), 2.60 (brt, J=11.9 Hz, 1H), 2.48 (brt, J=12.0 Hz, 1H), 1.87 (brd, J=11.7 Hz, 1H), 1.51-1.37 (m, 12H).

The following compounds were prepared by the same route used for Compound 4:

| Example/ Compound Number | Structure | NMR | LC-MS |
|---|---|---|---|
| 53-8 | 4-amino-8-(5-(6-isopropyl-2-methoxypyridin-3-yl)imidazo[2,1-b][1,3,4]thiadiazol-2-yl)-1-thia-8-azaspiro[4.5]decane 1,1-dioxide | $^1$H NMR (400 MHz, CDCl$_3$) δ 8.47 (d, J = 7.7 Hz, 1H), 7.70 (s, 1H), 6.83 (d, J = 7.7 Hz 1H), 4.06 (s, 3H), 3.91-3.75 (m, 3H), 3.66 (ddd, J = 13.9, 12.0, 3.1 Hz, 1H), 3.40-3.25 (m, 2H), 3.16 (dt, J = 13.6, 8.7 Hz, 1H), 2.97 (m, 1H), 2.45-2.32 (m, 1H), 2.26 (dd, J = 14.3, 2.1 Hz, 1H), 2.19-1.85 (m 4H), 1.30 (s, 3H), 1.29 (s, 3H). | MS m/z calcd for C$_{21}$H$_{28}$N$_6$O$_3$S$_2$ 476.2 found 477.2 [M + H]$^+$ |
| 54-5 | 1-(5-(4-fluoro-2-methoxyphenyl)imidazo[2,1-b][1,3,4]thiadiazol-2-yl)-4-(methoxymethyl)piperidin-4-amine | $^1$H NMR (400 MHz, MeOD-d$_4$) δ 8.29 (dd, J = 8.7, 6.5 Hz, 1H), 7.92 (s, 1H), 7.04 (dd, J = 11.0, 2.4 Hz, 1H), 6.93-6.84 (m, 1H), 3.98 (s, 3H), 3.89 (d, J = 13.7 Hz, 2H), 3.69 (s, 2H), 3.64 (d, J = 10.6 Hz, 2H), 3.50 (s, 3H), 2.22-1.94 (m, 4H). | MS m/z calcd for C$_{18}$H$_{22}$FN$_5$O$_2$S 391.2 found 392.2 [M + H]$^+$ |

| Example/ Compound Number | Structure | NMR | LC-MS |
|---|---|---|---|
| 55-5 | 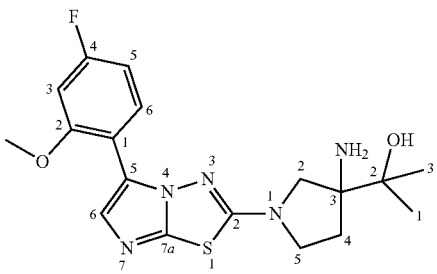<br>2-(3-amino-1-(5-(4-fluoro-2-methoxyphenyl)imidazo[2,1-b][1,3,4]thiadiazol-2-yl)pyrrolidin-3-yl)propan-2-ol | $^1$H NMR (400 MHz, DMSO-d$_6$) δ 8.52-8.31 (m, 2H), 8.21 (dd, J = 8.8, 6.8 Hz, 1H), 7.75-7.61 (m, 1H), 7.13 (dd, J = 11.4, 2.6 Hz, 1H), 6.96 (td, J = 8.6, 2.5 Hz, 1H), 3.92 (s, 3H), 3.88 (d, J = 12.0 Hz, 1H), 3.85-3.74 (m, 1H), 3.74-3.56 (m, 2H), 2.47-2.35 (m, 1H), 2.24-2.06 (m, 1H), 1.28 (s, 6H). | MS m/z calcd for C$_{18}$H$_{22}$FN$_5$O$_2$S 391.2 found 392.2 [M + H]$^+$ |
| 56-2 | 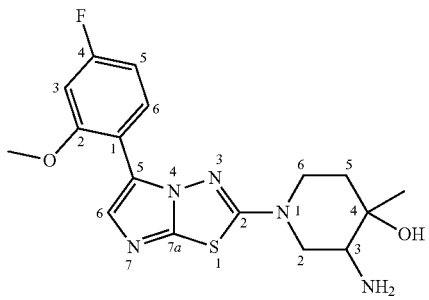<br>3-amino-1-(5-(4-fluoro-2-methoxyphenyl)imidazo[2,1-b][1,3,4]thiadiazol-2-yl)-4-methylpiperidin-4-ol | $^1$H NMR (500 MHz, DMSO-d$_6$) δ 8.15 (dd, J = 8.7, 6.8 Hz, 1H), 7.97 (s, 3H), 7.48 (s, 1H), 7.08 (dd, J = 11.4, 2.5 Hz, 1H), 6.90 (td, J = 8.4, 2.6 Hz, 1H), 3.90 (s, 3H), 3.80-3.75 (m, 1H), 3.75-3.68 (m, 2H), 3.15 (dd, J = 12.4, 10.3 Hz, 2H), 1.90 (d, J = 13.2 Hz, 1H), 1.83 (dt, J = 12.9, 6.5 Hz, 1H), 1.30 (s, 3H). | MS m/z calcd for C$_{17}$H$_{20}$FN$_5$O$_2$S 377.1 found 378.3 [M + H]$^+$ |
| 57-4 | 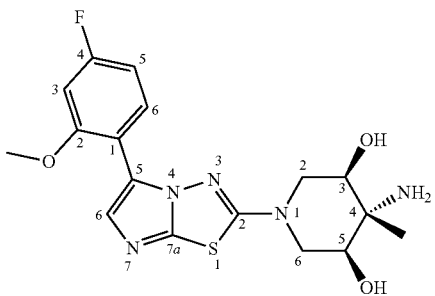<br>(3R,4r,5S)-4-amino-1-(5-(4-fluoro-2-methoxyphenyl)imidazo[2,1-b][1,3,4]thiadiazol-2-yl)-4-methylpiperidine-3,5-diol | $^1$H NMR (500 MHz, DMSO-d$_6$) δ 8.12 (dd, J = 8.7, 6.8 Hz, 1H), 7.96 (s, 3H), 7.50 (s, 1H), 7.09 (dd, J = 11.4, 2.5 Hz, 1H), 6.90 (td, J = 8.4, 2.5 Hz, 1H), 3.91 (s, 3H), 3.71 (d, J = 9.5 Hz, 4H), 3.19 (t, J = 13.2 Hz, 2H), 1.21 (s, 3H). | MS m/z calcd for C$_{17}$H$_{20}$FN$_5$O$_3$S 393.1 found 394.1 [M + H]$^+$ |

| Example/Compound Number | Structure | NMR | LC-MS |
|---|---|---|---|
| 58-2 | 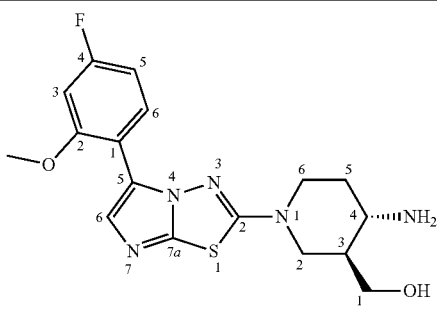<br>((3S,4S)-4-amino-1-(5-(4-fluoro-2-methoxyphenyl)imidazo[2,1-b][1,3,4]thiadiazol-2-yl)piperidin-3-yl)methanol | $^1$H NMR (500 MHz, DMSO-$d_6$) δ 8.30-8.10 (m, 4H), 7.64 (s, 1H), 7.12 (dd, J = 11.3, 2.5 Hz, 1H), 6.94 (td, J = 8.4, 2.4 Hz, 1H), 3.92 (s, 5H), 3.60 (ddt, J = 16.8, 11.3, 5.6 Hz, 2H), 3.36-3.22 (m, 2H), 3.12 (t, J = 12.2 Hz, 1H), 2.18-2.09 (m, 1H), 1.94 (td, J = 10.1, 4.9 Hz, 1H), 1.76-1.64 (m, 1H). | MS m/z calcd for $C_{17}H_{20}FN_5O_2S$ 377.1 found 378.3 [M + H]$^+$ |

Assays

Compounds of the invention can be assayed to measure their capacity to inhibit proliferation of parasitemia in infected red blood cells. The proliferation is quantified by the addition of SYBR Green I (INVITROGEN)® dye which has a high affinity for double stranded DNA.

The following assay illustrates the invention without in any way limiting the scope of the invention. This parasite proliferation assay measures the increase in parasite DNA content using a DNA intercalating dye, SYBR Green®.

3D7 P. falciparum strain is grown in complete culturing media until parasitemia reaches 3% to 8% with O+ human erythrocytes. 20 µl of screening media is dispensed into 384 well assay plates. 50 nl of compounds of the invention (in DMSO), including antimalarial controls (mefloquine, pyrimethamine and artemisinin), are then transferred into the assay plates, as well as DMSO alone to serve as a negative control for inhibition. Then 30 µl of a suspension of a3D7 P. falciparum infected erythrocytes in screening media is dispensed into the assay plates such that the final hematocrit is 2.5% with a final parasitemia of 0.3%. The plates are placed in a37° C. incubator for 72 hours in a low oxygen environment containing 93% $N_2$, 4% $CO_2$, and 3% $O_2$ gas mixture. 10 µl of lysis buffer (saponin, triton-X, EDTA) containing a 10× solution of SYBR Green I® in RPMI media is dispensed into the plates. The plates are lidded and kept at room temperature overnight for the lysis of the infected red blood cells. The fluorescence intensity is measured (excitation 425 nm, emission 530 nm) using the Envision™ system (Perkin Elmer). The percentage inhibition of 50%, $EC_{50}$, is calculated for each compound.

Biological activity in for certain examples is represented in the table below wherein: +>EC50 0.1 µM; EC50 0.1 µM>++>EC50 0.01 µM; +++<EC50 0.01 µM.

| MALARIA PLASMODIUM FALCIPARUM 3D7 ASSAY DATA: | |
|---|---|
| Compound/Example Number | Pf3D7 ($EC_{50}$ µM) |
| 4-102 | ++ |
| 4-101 | ++ |
| 4-100 | +++ |
| 4-99 | ++ |
| 4-98 | ++ |
| 4-97 | ++ |
| 4-96 | + |
| 4-95 | ++ |
| 4-94 | +++ |
| 4-93 | +++ |
| 4-92 | ++ |
| 4-91 | ++ |
| 4-90 | ++ |
| 4-89 | ++ |
| 4-89 | ++ |
| 4-88 | ++ |
| 4-87 | +++ |
| 4-86 | + |
| 4-85 | ++ |
| 4-84 | ++ |
| 4-83 | ++ |
| 4-82 | ++ |
| 4-81 | ++ |
| 4-80 | ++ |
| 4-79 | ++ |
| 4-78 | ++ |
| 4-77 | ++ |
| 4-76 | ++ |
| 4-75 | ++ |
| 4-74 | ++ |
| 4-73 | ++ |
| 4-72 | ++ |
| 4-71 | +++ |
| 4-70 | + |
| 4-69 | ++ |
| 4-68 | ++ |
| 4-67 | ++ |
| 4-66 | ++ |
| 4-65 | ++ |
| 4-64 | ++ |
| 4-63 | +++ |
| 4-62 | ++ |
| 4-61 | ++ |
| 4-60 | +++ |
| 4-59 | ++ |
| 4-58 | ++ |
| 4-57 | ++ |

MALARIA PLASMODIUM FALCIPARUM
3D7 ASSAY DATA:

| Compound/Example Number | Pf3D7 (EC$_{50}$ μM) |
|---|---|
| 4-56 | +++ |
| 4-55 | ++ |
| 4-54 | ++ |
| 4-53 | ++ |
| 4-52 | ++ |
| 4-51 | ++ |
| 4-50 | ++ |
| 4-49 | ++ |
| 4-48 | ++ |
| 4-47 | ++ |
| 4-46 | ++ |
| 4-45 | ++ |
| 4-44 | ++ |
| 4-43 | ++ |
| 4-42 | ++ |
| 4-41 | +++ |
| 4-40 | ++ |
| 4-39 | ++ |
| 4-38 | ++ |
| 4-37 | ++ |
| 4-36 | ++ |
| 4-35 | ++ |
| 4-34 | ++ |
| 4-33 | ++ |
| 4-32 | ++ |
| 4-31 | ++ |
| 4-30 | +++ |
| 4-29 | ++ |
| 4-28 | ++ |
| 4-27 | ++ |
| 4-26 | ++ |
| 4-25 | ++ |
| 4-24 | ++ |
| 4-23 | ++ |
| 4-22 | ++ |
| 4-21 | +++ |
| 4-20 | ++ |
| 4-19 | ++ |
| 4-18 | ++ |
| 4-17 | ++ |
| 4-16 | ++ |
| 4-15 | ++ |
| 4-14 | ++ |
| 4-13 | ++ |
| 4-12 | ++ |
| 4-11 | ++ |
| 4-10 | ++ |
| 4-9 | ++ |
| 4-8 | +++ |
| 4-7 | ++ |
| 4-6 | ++ |
| 4-5 | ++ |
| 4-4 | ++ |
| 4-3 | ++ |
| 4-2 | ++ |
| 4-0 | +++ |
| 5-4 | ++ |
| 5-3 | ++ |
| 5-2 | ++ |
| 5-0 | ++ |
| 6-6 | ++ |
| 6-5 | +++ |
| 6-0 | ++ |
| 7-6 | ++ |
| 7-5 | ++ |
| 7-4 | ++ |
| 7-3 | ++ |
| 7-2 | ++ |
| 7-0 | ++ |
| 8-0 | + |
| 9-0 | ++ |
| 10-0 | ++ |
| 11-0 | ++ |
| 12-4 | ++ |
| 12-3 | ++ |
| 12-0 | ++ |
| 13-0 | ++ |
| 14-0 | ++ |
| 15-2 | ++ |
| 15-0 | ++ |
| 16-0 | ++ |
| 17-0 | ++ |
| 18-8 | ++ |
| 18-7 | ++ |
| 18-6 | +++ |
| 18-0 | ++ |
| 19-15 | ++ |
| 19-14 | ++ |
| 19-13 | ++ |
| 19-12 | ++ |
| 19-11 | +++ |
| 19-10 | +++ |
| 19-9 | ++ |
| 19-0 | ++ |
| 20-3 | ++ |
| 20-0 | ++ |
| 21-0 | ++ |
| 22-0 | ++ |
| 23-0 | ++ |
| 24-0 | + |
| 25-0 | ++ |
| 26-0 | ++ |
| 27-0 | ++ |
| 28-0 | ++ |
| 29-0 | ++ |
| 30-22 | ++ |
| 30-21 | +++ |
| 30-20 | +++ |
| 30-19 | +++ |
| 30-18 | +++ |
| 30-17 | +++ |
| 30-16 | +++ |
| 30-0 | +++ |
| 31-10 | +++ |
| 31-9 | +++ |
| 31-8 | ++ |
| 31-0 | ++ |
| 32-13 | +++ |
| 32-0 | +++ |
| 33-0 | +++ |
| 34-0 | +++ |
| 35-6 | ++ |
| 35-5 | +++ |
| 35-0 | +++ |
| 36-0 | +++ |
| 37-2 | +++ |
| 38-2 | +++ |
| 39-5 | ++ |
| 39-4 | ++ |
| 39-3 | +++ |
| 39-2 | +++ |
| 40-2 | + |
| 41-4 | ++ |
| 41-3 | ++ |
| 42-4 | ++ |
| 43-3 | ++ |
| 44-3 | ++ |
| 45-3 | ++ |
| 46-3 | ++ |
| 47-3 | ++ |
| 48-3 | ++ |
| 48-2 | ++ |
| 49-3 | ++ |
| 49-2 | ++ |
| 50-5 | ++ |
| 50-4 | ++ |

-continued

MALARIA PLASMODIUM FALCIPARUM 3D7 ASSAY DATA:

| Compound/Example Number | Pf3D7 (EC$_{50}$ µM) |
|---|---|
| 51-5 | ++ |
| 53-8 | + |
| 54-5 | ++ |
| 55-5 | ++ |
| 56-2 | ++ |
| 57-4 | + |
| 58-2 | ++ |

Kinase Biological Selectivity Assay

Compounds were screened against human kinases using KINOMESCAN (DiscoverX) (Fabian, M. A. et al. Nat. Biotechnol. 23, 329-336 (2005); Karaman, M. W. et al. Nat. Biotechnol. 26, 127-132 (2008); Carter, T. A. et al. Proc. Natl. Acad. Sci. USA. 102, 11011-11016 (2005)). For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. Binding constants (Kds) were calculated with a standard dose-response curve using the Hill equation:

Response=Background+(Signal−Background)/[1+
(KdHill Slope/DoseHill Slope)]

(Hill, A. V. J. Physiol. (Lond.). 40, iv-vii (1910); Levenberg, K. A Q. Appl. Math. 2, 164-168 (1944)). The Hill Slope was set to −1. Curves were fitted using a non-linear least square fit with the Levenberg-Marquardt algorithm. Biological activity for certain examples is represented in the table below wherein: +>EC50 100 nM; EC$_{50}$ 100 nM>++ >EC$_{50}$ 10 nM; +++<EC$_{50}$ 10 nM.

FLT3, PIK3, and PIM1 KINASE IC50 DATA FOR SELECTED COMPOUNDS

| Compound/Example | FLT3 Biochemical Kd (nM) | PIK3CA Biochemical Kd (nM) | PIM Biochemical Kd (nM) | Plasmodium falciparum 3D7 Cell EC50 (nM) |
|---|---|---|---|---|
| 4-97 | + | + | + | +++ |
| 4-79 | + | + | + | +++ |
| 4-78 | ++ | + | + | +++ |
| 4-76 | + | + | + | +++ |
| 4-73 | + | + | + | +++ |
| 4-66 | + | + | ++ | +++ |
| 4-63 | + | + | + | ++++ |
| 4-50 | + | + | + | +++ |
| 4-40 | ++ | + | + | +++ |
| 4-35 | ++ | + | + | +++ |
| 4-34 | + | + | + | +++ |
| 4-32 | + | + | + | +++ |
| 4-24 | + | + | + | +++ |
| 4-13 | + | + | + | +++ |
| 4-0 | + | + | + | ++++ |
| 30-20 | + | + | + | ++++ |
| 30-19 | + | + | + | ++++ |
| 30-16 | + | + | + | ++++ |
| 30-0 | + | + | + | ++++ |
| 39-2 | + | + | + | ++++ |

As shown in the Tables above, compounds of the invention have on target EC$_{50}$s of 0.1 µM or less, with off-target EC50s of 1000 nM, or more. Compounds of the invention can significantly delay the increase in parasitemia.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula Ic:

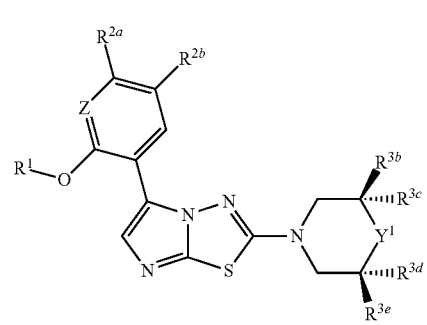

wherein:
Z is N;
Y is C(OH)CH$_2$NH$_2$
R$^1$ is C$_{1-4}$alkyl;
R$^{2a}$ is C$_{1-4}$alkyl;
R$^{2b}$ is hydrogen;
R$^{3a}$ is selected from amino, —CO—C$_{1-4}$alkyl, and 3-6 member, saturated, unsaturated or partially unsaturated heterocyclic ring containing up to three heteroatoms selected from N, NR$_{30}$, S(O)$_{0-2}$ and O, wherein the heterocyclic ring of R$^{3a}$ is unsubstituted or substituted with 1 or 2 hydroxy or amino;

R³ᵇ, R³ᶜ, R³ᵈ, and R³ᵉ is each independently selected from hydrogen, $C_{1-4}$alkyl, amino, —$X^1$—$R^{3a}$, —NH—$X^1$—$R^{3a}$, hydroxy-substituted-$C_{1-4}$alkyl, $C_{1-4}$alkoxy-substituted-$C_{1-4}$alkyl, hydroxy, oxo, halo, —$X^1$—$CO_2H$, —$X^1$—$CO_2NH_2$, —$X^1$—$SO_2C_{1-4}$alkyl, —$X^1$—$SO_2N(C_{1-4}$alkyl$)_2$, and —$X^1$—$C_{3-6}$-cycloalkyl;

$X^1$ is selected from a bond and $C_{1-4}$alkylene; or a pharmaceutically acceptable salt thereof.

2. A compound selected from any one of Examples 4-0 to 58-2:

4-(aminomethyl)-1-(5-(6-isopropyl-2-methoxypyridin-3-yl)imidazo[2,1-b][1,3,4]thiadiazol-2-yl)piperidin-4-ol; 3-(aminomethyl)-1-(5-(2-methoxy-4-methylphenyl)imidazo[2,1-b][1,3,4]thiadiazol-2-yl)pyrrolidin-3-ol; (4-(5-(2-methoxy-4-methylphenyl)imidazo[2,1-b][1,3,4]thiadiazol-2-yl)piperazin-2-yl)methanol; (4-amino-1-(5-(2-methoxy-4-methylphenyl)imidazo[2,1-b][1,3,4]thiadiazol-2-yl)piperidin-4-yl)methanol; (3S,5S)-5-amino-1-(5-(4-fluoro-2-methoxyphenyl)imidazo[2,1-b][1,3,4]thiadiazol-2-yl)piperidin-3-ol; 3-(aminomethyl)-1-(5-(6-isopropyl-2-methoxypyridin-3-yl)imidazo[2,1-b][1,3,4]thiadiazol-2-yl)azetidin-3-ol; 4-(aminomethyl)-1-(5-(5-chloro-4-fluoro-2-methoxyphenyl)imidazo[2,1-b][1,3,4]thiadiazol-2-yl)piperidin-4-ol; 4-(aminomethyl)-1-(5-(2-ethoxy-5-methylphenyl)imidazo[2,1-b][1,3,4]thiadiazol-2-yl)piperidin-4-ol; 2-(5-(4-fluoro-2-methoxyphenyl)imidazo[2,1-b][1,3,4]thiadiazol-2-yl)-5-oxa-2,8-diazaspiro[3.5]nonane; 8-(5-(2-methoxy-4-methylphenyl)imidazo[2,1-b][1,3,4]thiadiazol-2-yl)-1-oxa-8-azaspiro[4.5]decan-3-amine; 4-(aminomethyl)-1-(5-(5-fluoro-2-methoxyphenyl)imidazo[2,1-b][1,3,4]thiadiazol-2-yl)piperidin-4-ol; 9-(5-(4-fluoro-2-methoxyphenyl)imidazo[2,1-b][1,3,4]thiadiazol-2-yl)-1-oxa-4,9-diazaspiro[5.5]undecane; 4-(aminomethyl)-1-(5-(2-methoxy-6-methylpyridin-3-yl)imidazo[2,1-b][1,3,4]thiadiazol-2-yl)piperidin-4-ol; 4-(aminomethyl)-1-(5-(3-chloro-2-methoxyphenyl)imidazo[2,1-b][1,3,4]thiadiazol-2-yl)piperidin-4-ol; 4-(aminomethyl)-1-(5-(4-cyclopropyl-2-methoxyphenyl)imidazo[2,1-b][1,3,4]thiadiazol-2-yl)piperidin-4-ol; (3S,4R)-4-amino-1-(5-(4-fluoro-2-methoxyphenyl)imidazo[2,1-b][1,3,4]thiadiazol-2-yl)piperidin-3-ol; (3R,4S)-4-amino-1-(5-(4-fluoro-2-methoxyphenyl)imidazo[2,1-b][1,3,4]thiadiazol-2-yl)piperidin-3-ol; 4-(aminomethyl)-1-(5-(3,5-difluoro-2-methoxyphenyl)imidazo[2,1-b][1,3,4]thiadiazol-2-yl)piperidin-4-ol; 4-(aminomethyl)-1-(5-(2,3-dihydrobenzofuran-7-yl)imidazo[2,1-b][1,3,4]thiadiazol-2-yl)piperidin-4-ol; 4-(aminomethyl)-1-(5-(2-methoxy-3-methylphenyl)imidazo[2,1-b][1,3,4]thiadiazol-2-yl)piperidin-4-ol; (R)-1-(1-(5-(6-isopropyl-2-methoxypyridin-3-yl)imidazo[2,1-b][1,3,4]thiadiazol-2-yl)pyrrolidin-3-yl)cyclopropan-1-amine; (4-((cyclopropylmethyl)amino)-1-(5-(2-methoxy-4-methylphenyl)imidazo[2,1-b][1,3,4]thiadiazol-2-yl)piperidin-4-yl)methanol; 4-(aminomethyl)-1-(5-(2-methoxy-3-(trifluoromethyl)phenyl)imidazo[2,1-b][1,3,4]thiadiazol-2-yl)piperidin-4-ol; 2-(4-(5-(2-methoxy-4-methylphenyl)imidazo[2,1-b][1,3,4]thiadiazol-2-yl)piperazin-2-yl)ethan-1-ol; 3-(aminomethyl)-1-(5-(2-methoxy-4-methylphenyl)imidazo[2,1-b][1,3,4]thiadiazol-2-yl)azetidin-3-ol; (3S,4R)-3-fluoro-1-(5-(4-fluoro-2-methoxyphenyl)imidazo[2,1-b][1,3,4]thiadiazol-2-yl)piperidin-4-amine; (3R,4S)-3-fluoro-1-(5-(4-fluoro-2-methoxyphenyl)imidazo[2,1-b][1,3,4]thiadiazol-2-yl)piperidin-4-amine; (3S,4R)-4-amino-1-(5-(6-isopropyl-2-methoxypyridin-3-yl)imidazo[2,1-b][1,3,4]thiadiazol-2-yl)pyrrolidin-3-ol; (4-(5-(6-isopropyl-2-methoxypyridin-3-yl)imidazo[2,1-b][1,3,4]thiadiazol-2-yl)piperazin-2-yl)methanol; 8-(5-(6-isopropyl-2-methoxypyridin-3-yl)imidazo[2,1-b][1,3,4]thiadiazol-2-yl)-1-oxa-8-azaspiro[4.5]decan-3-amine; 8-(5-(4-fluoro-2-methoxyphenyl)imidazo[2,1-b][1,3,4]thiadiazol-2-yl)-1-oxa-8-azaspiro[4.5]decan-3-amine; 4-(aminomethyl)-1-(5-(2-ethoxy-4-(trifluoromethyl)phenyl)imidazo[2,1-b][1,3,4]thiadiazol-2-yl)piperidin-4-ol; 3-(aminomethyl)-1-(5-(2-methoxy-6-methylpyridin-3-yl)imidazo[2,1-b][1,3,4]thiadiazol-2-yl)pyrrolidin-3-ol; 4-(aminomethyl)-1-(5-(4-chloro-2-(2-methoxyethoxy)phenyl)imidazo[2,1-b][1,3,4]thiadiazol-2-yl)piperidin-4-ol; (S)-3-(aminomethyl)-1-(5-(4-fluoro-2-methoxyphenyl)imidazo[2,1-b][1,3,4]thiadiazol-2-yl)pyrrolidin-3-ol; (R)-3-(aminomethyl)-1-(5-(4-fluoro-2-methoxyphenyl)imidazo[2,1-b][1,3,4]thiadiazol-2-yl)pyrrolidin-3-ol; 4-(aminomethyl)-1-(5-(4-fluoro-2-(trifluoromethoxy)phenyl)imidazo[2,1-b][1,3,4]thiadiazol-2-yl)piperidin-4-ol; 4-(aminomethyl)-1-(5-(3-fluoro-2-methoxy-4-methylphenyl)imidazo[2,1-b][1,3,4]thiadiazol-2-yl)piperidin-4-ol; 4-(aminomethyl)-1-(5-(2-(cyclopropylmethoxy)-4-fluorophenyl)imidazo[2,1-b][1,3,4]thiadiazol-2-yl)piperidin-4-ol; 4-(aminomethyl)-1-(5-(4-fluoro-2-methoxyphenyl)imidazo[2,1-b][1,3,4]thiadiazol-2-yl)piperidin-4-ol; 4-(aminomethyl)-1-(5-(4-fluoro-5-isopropyl-2-methoxyphenyl)imidazo[2,1-b][1,3,4]thiadiazol-2-yl)piperidin-4-ol; 8-(5-(2-methoxy-6-methylpyridin-3-yl)imidazo[2,1-b][1,3,4]thiadiazol-2-yl)-1-oxa-8-azaspiro[4.5]decan-3-amine; (4-amino-1-(5-(4-chloro-2-methoxyphenyl)imidazo[2,1-b][1,3,4]thiadiazol-2-yl)piperidin-4-yl)methanol; 4-(aminomethyl)-1-(5-(2,3-dihydrobenzo[b][1,4]dioxin-5-yl)imidazo[2,1-b][1,3,4]thiadiazol-2-yl)piperidin-4-ol; 2-(5-(4-fluoro-2-methoxyphenyl)imidazo[2,1-b][1,3,4]thiadiazol-2-yl)-2-azaspiro[3.3]heptan-5-amine; (4-(aminomethyl)-1-(5-(4-fluoro-2-methoxyphenyl)imidazo[2,1-b][1,3,4]thiadiazol-2-yl)piperidin-4-yl)methanol; 4-(aminomethyl)-1-(5-(2-ethoxyphenyl)imidazo[2,1-b][1,3,4]thiadiazol-2-yl)piperidin-4-ol; 4-(aminomethyl)-1-(5-(2-methoxypyridin-3-yl)imidazo[2,1-b][1,3,4]thiadiazol-2-yl)piperidin-4-ol; (S)-(3-amino-1-(5-(4-fluoro-2-methoxyphenyl)imidazo[2,1-b][1,3,4]thiadiazol-2-yl)pyrrolidin-3-yl)methanol; (R)-(3-amino-1-(5-(4-fluoro-2-methoxyphenyl)imidazo[2,1-b][1,3,4]thiadiazol-2-yl)pyrrolidin-3-yl)methanol; (3R,5R)-5-fluoro-1-(5-(4-fluoro-2-methoxyphenyl)imidazo[2,1-b][1,3,4]thiadiazol-2-yl)piperidin-3-amine; (3R,4R)-4-amino-1-(5-(4-fluoro-2-methoxyphenyl)imidazo[2,1-b][1,3,4]thiadiazol-2-yl)piperidin-3-ol; (3S,4S)-4-amino-1-(5-(4-fluoro-2-methoxyphenyl)imidazo[2,1-b][1,3,4]thiadiazol-2-yl)piperidin-3-ol; 1-(5-(2-methoxy-4-methylphenyl)imidazo[2,1-b][1,3,4]thiadiazol-2-yl)-3-methylpyrrolidin-3-amine; 1-(5-(2-methoxy-6-methylpyridin-3-yl)imidazo[2,1-b][1,3,4]thiadiazol-2-yl)-3-methylpyrrolidin-3-amine; 1-(5-(6-isopropyl-2-methoxypyridin-3-yl)imidazo[2,1-b][1,3,4]thiadiazol-2-yl)-3-methylpyrrolidin-3-amine; 2-((1-(5-(6-isopropyl-2-methoxypyridin-3-yl)imidazo[2,1-b][1,3,4]thiadiazol-2-yl)piperidin-4-yl)amino)ethan-1-ol; 4-(aminomethyl)-1-(5-(2-methoxy-4-(trifluoromethyl)phenyl)imidazo[2,1-b][1,3,4]thiadiazol-2-yl)piperidin-4-ol; 4-amino-1-(5-(4-fluoro-2-methoxyphenyl)imidazo[2,1-b][1,3,4]thiadiazol-2-yl)pyrrolidin-3-ol; 4-(aminomethyl)-1-(5-(3,4-difluoro-2-methoxyphenyl)imidazo[2,1-b][1,3,4]thiadiazol-2-yl)piperidin-4-ol; (3S,4R)-4-amino-1-(5-(4-fluoro-2-methoxyphenyl)imidazo[2,1-b][1,3,4]thiadiazol-2-yl)pyrrolidin-3-ol; (3S,4R)-4-amino-1-(5-(4-fluoro-2-methoxyphenyl)imidazo[2,1-b][1,3,4]thiadiazol-2-yl)pyrrolidin-3-ol; 4-(aminomethyl)-1-(5-(4-chloro-2-methoxyphenyl)imidazo[2,1-b][1,3,4]thiadiazol-2-yl)piperidin-4-ol; 4-(aminomethyl)-1-(5-(4,5-difluoro-2-methoxyphenyl)imidazo[2,1-b][1,3,4]thiadiazol-2-yl)

piperidin-4-ol; (R)-(3-amino-1-(5-(2-ethoxy-4-fluorophenyl)imidazo[2,1-b][1,3,4]thiadiazol-2-yl)pyrrolidin-3-yl)methanol; (S)-(3-amino-1-(5-(2-ethoxy-4-fluorophenyl)imidazo[2,1-b][1,3,4]thiadiazol-2-yl)pyrrolidin-3-yl)methanol; 4-(aminomethyl)-1-(5-(2-methoxy-4,5-dimethylphenyl)imidazo[2,1-b][1,3,4]thiadiazol-2-yl)piperidin-4-ol; (3S,4R)-3-amino-1-(5-(4-fluoro-2-methoxyphenyl)imidazo[2,1-b][1,3,4]thiadiazol-2-yl)piperidin-4-ol; (3R,4S)-3-amino-1-(5-(4-fluoro-2-methoxyphenyl)imidazo[2,1-b][1,3,4]thiadiazol-2-yl)piperidin-4-ol; 2-(4-(5-(6-isopropyl-2-methoxypyridin-3-yl)imidazo[2,1-b][1,3,4]thiadiazol-2-yl)piperazin-1-yl)ethan-1-ol; 3-(aminomethyl)-1-(5-(6-isopropyl-2-methoxypyridin-3-yl)imidazo[2,1-b][1,3,4]thiadiazol-2-yl)pyrrolidin-3-ol; 4-(aminomethyl)-1-(5-(2-methoxy-4-(tetrahydro-2H-pyran-4-yl)phenyl)imidazo[2,1-b][1,3,4]thiadiazol-2-yl)piperidin-4-ol; 4-(2-(4-(aminomethyl)-4-hydroxypiperidin-1-yl)imidazo[2,1-b][1,3,4]thiadiazol-5-yl)-3-methoxybenzonitrile; 4-(aminomethyl)-1-(5-(2,6-dimethoxypyridin-3-yl)imidazo[2,1-b][1,3,4]thiadiazol-2-yl)piperidin-4-ol; (4-amino-1-(5-(4-chloro-2-(2-methoxyethoxy)phenyl)imidazo[2,1-b][1,3,4]thiadiazol-2-yl)piperidin-4-yl)methanol; 3-(aminomethyl)-1-(5-(4-fluoro-2-methoxyphenyl)imidazo[2,1-b][1,3,4]thiadiazol-2-yl)azetidin-3-ol; 4-(aminomethyl)-1-(5-(2-ethoxy-4-fluorophenyl)imidazo[2,1-b][1,3,4]thiadiazol-2-yl)piperidin-4-ol; 4-(aminomethyl)-1-(5-(6-isopropyl-2-(2-methoxyethoxy)pyridin-3-yl)imidazo[2,1-b][1,3,4]thiadiazol-2-yl)piperidin-4-ol; 4-(aminomethyl)-1-(5-(3-fluoro-2-methoxyphenyl)imidazo[2,1-b][1,3,4]thiadiazol-2-yl)piperidin-4-ol; 4-(aminomethyl)-1-(5-(3-methoxynaphthalen-2-yl)imidazo[2,1-b][1,3,4]thiadiazol-2-yl)piperidin-4-ol; (3S,4S)-3-amino-1-(5-(4-fluoro-2-methoxyphenyl)imidazo[2,1-b][1,3,4]thiadiazol-2-yl)piperidin-4-ol; (3R,4R)-3-amino-1-(5-(4-fluoro-2-methoxyphenyl)imidazo[2,1-b][1,3,4]thiadiazol-2-yl)piperidin-4-ol; (4aR,8aR)-6-(5-(2-methoxy-4-methylphenyl)imidazo[2,1-b][1,3,4]thiadiazol-2-yl)octahydro-2H-pyrido[4,3-b][1,4]oxazine; 1-(5-(6-isopropyl-2-methoxypyridin-3-yl)imidazo[2,1-b][1,3,4]thiadiazol-2-yl)-[1,3'-biazetidin]-3-ol; (4-amino-1-(5-(6-isopropyl-2-methoxypyridin-3-yl)imidazo[2,1-b][1,3,4]thiadiazol-2-yl)piperidin-4-yl)methanol; 4-(aminomethyl)-1-(5-(5-chloro-2-methoxyphenyl)imidazo[2,1-b][1,3,4]thiadiazol-2-yl)piperidin-4-ol; 4-(aminomethyl)-1-(5-(2-methoxyphenyl)imidazo[2,1-b][1,3,4]thiadiazol-2-yl)piperidin-4-ol; 4-(aminomethyl)-1-(5-(4-fluoro-2-isopropoxyphenyl)imidazo[2,1-b][1,3,4]thiadiazol-2-yl)piperidin-4-ol; 4-(1-(5-(6-isopropyl-2-methoxypyridin-3-yl)imidazo[2,1-b][1,3,4]thiadiazol-2-yl)piperidin-4-yl)morpholine; 4-(aminomethyl)-1-(5-(2-(trifluoromethoxy)phenyl)imidazo[2,1-b][1,3,4]thiadiazol-2-yl)piperidin-4-ol; 3-(aminomethyl)-1-(5-(2-ethoxy-4-fluorophenyl)imidazo[2,1-b][1,3,4]thiadiazol-2-yl)pyrrolidin-3-ol; 1-(1-(5-(6-isopropyl-2-methoxypyridin-3-yl)imidazo[2,1-b][1,3,4]thiadiazol-2-yl)piperidin-4-yl)azetidin-3-ol; 4-(aminomethyl)-1-(5-(2-methoxy-6-(trifluoromethyl)pyridin-3-yl)imidazo[2,1-b][1,3,4]thiadiazol-2-yl)piperidin-4-ol; (4-(aminomethyl)-1-(5-(2-methoxy-4-methylphenyl)imidazo[2,1-b][1,3,4]thiadiazol-2-yl)piperidin-4-yl)methanol; 4-(1-(5-(6-isopropyl-2-methoxypyridin-3-yl)imidazo[2,1-b][1,3,4]thiadiazol-2-yl)piperidin-4-yl)thiomorpholine 1,1-dioxide; (4-amino-1-(5-(2-methoxy-6-methylpyridin-3-yl)imidazo[2,1-b][1,3,4]thiadiazol-2-yl)piperidin-4-yl)methanol; (4-amino-1-(5-(4-fluoro-2-methoxyphenyl)imidazo[2,1-b][1,3,4]thiadiazol-2-yl)piperidin-4-yl)methanol; 4-(aminomethyl)-1-(5-(4-fluoro-2-methoxy-5-methylphenyl)imidazo[2,1-b][1,3,4]thiadiazol-2-yl)piperidin-4-ol; (4-amino-1-(5-(2-ethoxy-4-fluorophenyl)imidazo[2,1-b][1,3,4]thiadiazol-2-yl)piperidin-4-yl)methanol; 4-(aminomethyl)-1-(5-(2,4-dimethoxyphenyl)imidazo[2,1-b][1,3,4]thiadiazol-2-yl)piperidin-4-ol; N-((3aR,7aR)-2-(5-(4-fluoro-2-methoxyphenyl)imidazo[2,1-b][1,3,4]thiadiazol-2-yl)octahydro-3aH-pyrrolo[3,4-c]pyridin-3a-yl)acetamide; 2-(5-(2-methoxy-4-methylphenyl)imidazo[2,1-b][1,3,4]thiadiazol-2-yl)-5-oxa-2,7-diazaspiro[3.4]oct-6-en-6-amine; 8-(5-(4-fluoro-2-methoxyphenyl)imidazo[2,1-b][1,3,4]thiadiazol-2-yl)-1-oxa-3,8-diazaspiro[4.5]dec-2-en-2-amine; 8-(5-(4-fluoro-2-methoxyphenyl)imidazo[2,1-b][1,3,4]thiadiazol-2-yl)-3-oxa-1,8-diazaspiro[4.5]dec-1-en-2-amine; 8-(5-(2-methoxy-4-methylphenyl)imidazo[2,1-b][1,3,4]thiadiazol-2-yl)-1-oxa-3,8-diazaspiro[4.5]dec-2-en-2-amine; (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol; (3aS,5S,6S,7aR)-6-amino-2-(5-(6-isopropyl-2-methoxypyridin-3-yl)imidazo[2,1-b][1,3,4]thiadiazol-2-yl)octahydro-1H-isoindol-5-ol; (3aS,5S,6S,7aR)-6-amino-2-(5-(4-fluoro-2-methoxyphenyl)imidazo[2,1-b][1,3,4]thiadiazol-2-yl)octahydro-1H-isoindol-5-ol; (9-(5-(4-fluoro-2-methoxyphenyl)imidazo[2,1-b][1,3,4]thiadiazol-2-yl)-2-oxa-9-azaspiro[5.5]und;ecan-3-yl)methanamine; (3-amino-1-(5-(6-isopropyl-2-methoxypyridin-3-yl)imidazo[2,1-b][1,3,4]thiadiazol-2-yl)azetidin-3-yl)methanol; (3-fluoro-1-(5-(4-fluoro-2-methoxyphenyl)imidazo[2,1-b][1,3,4]thiadiazol-2-yl)piperidin-3-yl)methanamine; (8-(5-(4-fluoro-2-methoxyphenyl)imidazo[2,1-b][1,3,4]thiadiazol-2-yl)-1-oxa-8-azaspiro[4.5]decan-2-yl)methanamine; 2-(5-(4-fluoro-2-methoxyphenyl)imidazo[2,1-b][1,3,4]thiadiazol-2-yl)-5-oxa-2-azaspiro[3.4]octan-7-amine; (3S,4S)-8-(5-(4-fluoro-2-methoxyphenyl)imidazo[2,1-b][1,3,4]thiadiazol-2-yl)-3-methyl-2-oxa-8-azaspiro[4.5]decan-4-amine; 4-(aminomethyl)-1-(5-(2-(dimethylamino)-6-methylpyridin-3-yl)imidazo[2,1-b][1,3,4]thiadiazol-2-yl)piperidin-4-ol; 4-(aminomethyl)-1-(5-(6-methyl-2-(methylthio)pyridin-3-yl)imidazo[2,1-b][1,3,4]thiadiazol-2-yl)piperidin-4-ol; 3-(aminomethyl)-1-(5-(4-fluoro-2-methoxyphenyl)imidazo[2,1-b][1,3,4]thiadiazol-2-yl)piperidin-3-ol; 8-(5-(4-fluoro-2-methoxyphenyl)imidazo[2,1-b][1,3,4]thiadiazol-2-yl)-2-oxa-8-azaspiro[4.5]decan-4-amine; 3-amino-1-(9-(5-(4-fluoro-2-methoxyphenyl)imidazo[2,1-b][1,3,4]thiadiazol-2-yl)-1,4,9-triazaspiro[5.5]undecan-4-yl)-3-methylbutan-1-one; 5-(6-isopropyl-2-methoxypyridin-3-yl)-2-(1,4,9-triazaspiro[5.5]undecan-9-yl)imidazo[2,1-b][1,3,4]thiadiazole; 5-(4-fluoro-2-methoxyphenyl)-2-(1,4,9-triazaspiro[5.5]undecan-9-yl)imidazo[2,1-b][1,3,4]thiadiazole; 1-(5-(4-fluoro-2-methoxyphenyl)imidazo[2,1-b][1,3,4]thiadiazol-2-yl)-4-(morpholinomethyl)piperidin-4-amine; 7-(5-(4-fluoro-2-methoxyphenyl)imidazo[2,1-b][1,3,4]thiadiazol-2-yl)-5,6,7,8-tetrahydroimidazo[1,5-a]pyrazin-3-amine; (1-(5-(4-fluoro-2-methoxyphenyl)imidazo[2,1-b][1,3,4]thiadiazol-2-yl)-4-((oxetan-3-ylmethyl)amino)piperidin-4-yl)methanol; (1-(5-(4-fluoro-2-methoxyphenyl)imidazo[2,1-b][1,3,4]thiadiazol-2-yl)-4-((2-morpholinoethyl)amino)piperidin-4-yl)methanol; 4-((3-aminopropyl)amino)-1-(5-(4-fluoro-2-methoxyphenyl)imidazo[2,1-b][1,3,4]thiadiazol-2-yl)piperidin-4-yl)methanol; 6-(aminomethyl)-2-(5-(4-fluoro-2-methoxyphenyl)imidazo[2,1-b][1,3,4]thiadiazol-2-yl)-2-azaspiro[3.3]heptan-6-ol; (S)-3-(aminomethyl)-1-(5-(6-isopropyl-2-methoxypyridin-3-yl)imidazo[2,1-b][1,3,4]thiadiazol-2-yl)pyrrolidin-3-ol; (R)-3-(aminomethyl)-1-(5-(6-isopropyl-2-methoxypyridin-3-yl)imidazo[2,1-b][1,3,4]thiadiazol-2-yl)pyrrolidin-3-ol; (S)-3-(aminomethyl)-1-(5-

(2-methoxy-6-methylpyridin-3-yl)imidazo[2,1-b][1,3,4]thiadiazol-2-yl)pyrrolidin-3-ol; (R)-3-(aminomethyl)-1-(5-(2-methoxy-6-methylpyridin-3-yl)imidazo[2,1-b][1,3,4]thiadiazol-2-yl)pyrrolidin-3-ol; 3-(aminomethyl)-1-(5-(6-isopropyl-2-methoxypyridin-3-yl)imidazo[2,1-b][1,3,4]thiadiazol-2-yl)pyrrolidin-3-ol; (3S,4S)-4-amino-1-(5-(2-methoxy-4-methylphenyl)imidazo[2,1-b][1,3,4]thiadiazol-2-yl)-4-methylpiperidin-3-ol; (3R,4R)-4-amino-1-(5-(2-methoxy-4-methylphenyl)imidazo[2,1-b][1,3,4]thiadiazol-2-yl)-4-methylpiperidin-3-ol; (3R,4R)-4-amino-1-(5-(6-isopropyl-2-methoxypyridin-3-yl)imidazo[2,1-b][1,3,4]thiadiazol-2-yl)-4-methylpiperidin-3-ol; (3S,4S)-4-amino-1-(5-(6-isopropyl-2-methoxypyridin-3-yl)imidazo[2,1-b][1,3,4]thiadiazol-2-yl)-4-methylpiperidin-3-ol; (3R,4R)-4-amino-1-(5-(4-fluoro-2-methoxyphenyl)imidazo[2,1-b][1,3,4]thiadiazol-2-yl)-4-methylpiperidin-3-ol; (3S,4S)-4-amino-1-(5-(4-fluoro-2-methoxyphenyl)imidazo[2,1-b][1,3,4]thiadiazol-2-yl)-4-methylpiperidin-3-ol; (3R,4R)-4-amino-1-(5-(2-methoxy-6-methylpyridin-3-yl)imidazo[2,1-b][1,3,4]thiadiazol-2-yl)-4-methylpiperidin-3-ol; (3S,4S)-4-amino-1-(5-(2-methoxy-6-methylpyridin-3-yl)imidazo[2,1-b][1,3,4]thiadiazol-2-yl)-4-methylpiperidin-3-ol; (3S,4S)-3-amino-1-(5-(4-fluoro-2-methoxyphenyl)imidazo[2,1-b][1,3,4]thiadiazol-2-yl)-4-methylpiperidin-4-ol; (3R,4R)-3-amino-1-(5-(4-fluoro-2-methoxyphenyl)imidazo[2,1-b][1,3,4]thiadiazol-2-yl)-4-methylpiperidin-4-ol; (3R,4R)-4-amino-1-(5-(4-fluoro-2-methoxyphenyl)imidazo[2,1-b][1,3,4]thiadiazol-2-yl)-4-methylpiperidin-3-ol; 4-(aminomethyl)-1-(5-(4-fluoro-2-methoxyphenyl)imidazo[2,1-b][1,3,4]thiadiazol-2-yl)piperidine-4-carboxamide; N-((1-aminocyclopropyl)methyl)-4-(aminomethyl)-1-(5-(4-fluoro-2-methoxyphenyl)imidazo[2,1-b][1,3,4]thiadiazol-2-yl)piperidine-4-carboxamide; N-(2-amino-2-methylpropyl)-8-(5-(4-fluoro-2-methoxyphenyl)imidazo[2,1-b][1,3,4]thiadiazol-2-yl)-1-thia-8-azaspiro[4.5]decane-4-carboxamide 1,1-dioxide; 2-(4-amino-1-(5-(4-fluoro-2-methoxyphenyl)imidazo[2,1-b][1,3,4]thiadiazol-2-yl)piperidin-4-yl)propan-2-ol; 2-(4-amino-1-(5-(4-fluoro-2-methoxyphenyl)imidazo[2,1-b][1,3,4]thiadiazol-2-yl)piperidin-4-yl)propan-2-ol; 4-(aminomethyl)-1-(5-(4-(1-hydroxycyclobutyl)-2-methoxyphenyl)imidazo[2,1-b][1,3,4]thiadiazol-2-yl)piperidin-4-ol; ((1-(5-(4-fluoro-2-methoxyphenyl)imidazo[2,1-b][1,3,4]thiadiazol-2-yl)-4-((methylsulfonyl)methyl)piperidin-4-yl)methanamine; 1-(4-(aminomethyl)-1-(5-(4-fluoro-2-methoxyphenyl)imidazo[2,1-b][1,3,4]thiadiazol-2-yl)piperidin-4-yl)-N,N-dimethylmethanesulfonamide; ((3R,5S)-5-amino-1-(5-(4-fluoro-2-methoxyphenyl)imidazo[2,1-b][1,3,4]thiadiazol-2-yl)piperidin-3-ol; (4S,4aS,7aS)-6-(5-(2-ethoxy-6-isopropylpyridin-3-yl)imidazo[2,1-b][1,3,4]thiadiazol-2-yl)octahydropyrano[2,3-c]pyrrol-4-amine; (4S,4aS,7aR)-6-(5-(2-methoxy-4-(trifluoromethyl)phenyl)imidazo[2,1-b][1,3,4]thiadiazol-2-yl)octahydropyrano[2,3-c]pyrrol-4-amine; (4R,4aS,7aR)-6-(5-(2-methoxy-4-(trifluoromethyl)phenyl)imidazo[2,1-b][1,3,4]thiadiazol-2-yl)octahydropyrano[2,3-c]pyrrol-4-amine; (4S,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (4R,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (4S,4aR,7aR)-6-(5-(4-fluoro-2-methoxyphenyl)imidazo[2,1-b][1,3,4]thiadiazol-2-yl)octahydropyrano[2,3-c]pyrrol-4-amine; (4R,4aS,7aR)-6-(5-(4-fluoro-2-methoxyphenyl)imidazo[2,1-b][1,3,4]thiadiazol-2-yl)octahydropyrano[2,3-c]pyrrol-4-amine; ((4S,4aS,7aR)-6-(5-(4-fluoro-2-methoxyphenyl)imidazo[2,1-b][1,3,4]thiadiazol-2-yl)octahydropyrano[2,3-c]pyrrol-4-amine; (4S,4aS,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (4R,4aR,7aS)-6-(5-(6-isopropyl-2-methoxypyridin-3-yl)imidazo[2,1-b][1,3,4]thiadiazol-2-yl)octahydropyrano[2,3-c]pyrrol-4-amine; 4S,4aR,7aR)-6-(5-(6-isopropyl-2-methoxypyridin-3-yl)imidazo[2,1-b][1,3,4]thiadiazol-2-yl)octahydropyrano[2,3-c]pyrrol-4-amine; (3aS,5R,7R,7aR)-7-amino-2-(5-(6-isopropyl-2-methoxypyridin-3-yl)imidazo[2,1-b][1,3,4]thiadiazol-2-yl)octahydro-1H-isoindol-5-ol; (3aR,4S,5S,7aS)-4-amino-2-(5-(6-isopropyl-2-methoxypyridin-3-yl)imidazo[2,1-b][1,3,4]thiadiazol-2-yl)octahydro-1H-isoindol-5-ol; (3aR,4S,5R,7aS)-4-amino-2-(5-(2-methoxy-6-methylpyridin-3-yl)imidazo[2,1-b][1,3,4]thiadiazol-2-yl)octahydro-1H-isoindol-5-ol; (3aR,4S,5R,7aS)-4-amino-2-(5-(6-isopropyl-2-methoxypyridin-3-yl)imidazo[2,1-b][1,3,4]thiadiazol-2-yl)octahydro-1H-isoindol-5-ol; (3aR,4S,5R,7aS)-4-amino-2-(5-(4-fluoro-2-methoxyphenyl)imidazo[2,1-b][1,3,4]thiadiazol-2-yl)octahydro-1H-isoindol-5-ol; (3aR,4R,7aS)-2-(5-(6-isopropyl-2-methoxypyridin-3-yl)imidazo[2,1-b][1,3,4]thiadiazol-2-yl)-2,3,3a,4,7,7a-hexahydro-1H-isoindol-4-amine: 4-(aminomethyl)-1-(5-(4-chloro-5-fluoro-2-methoxyphenyl)imidazo[2,1-b][1,3,4]thiadiazol-2-yl)piperidin-4-ol; 4-(aminomethyl)-1-(5-(2-isopropoxy-6-isopropylpyridin-3-yl)imidazo[2,1-b][1,3,4]thiadiazol-2-yl)piperidin-4-ol; 4-(aminomethyl)-1-(5-(2-ethoxy-6-isopropylpyridin-3-yl)imidazo[2,1-b][1,3,4]thiadiazol-2-yl)piperidin-4-ol; (4-amino-1-(5-(2-ethoxy-6-isopropylpyridin-3-yl)imidazo[2,1-b][1,3,4]thiadiazol-2-yl)piperidin-4-yl)methanol; 3-(aminomethyl)-1-(5-(2-ethoxy-6-isopropylpyridin-3-yl)imidazo[2,1-b][1,3,4]thiadiazol-2-yl)azetidin-3-ol; (4-amino-1-(5-(4-(1,2-difluoroethyl)-2-methoxyphenyl)imidazo[2,1-b][1,3,4]thiadiazol-2-yl)piperidin-4-yl)methanol; 4-(aminomethyl)-1-(5-(2-(2-hydroxyethoxy)-6-isopropylpyridin-3-yl)imidazo[2,1-b][1,3,4]thiadiazol-2-yl)piperidin-4-ol; (4-amino-1-(5-(4-(1,2-difluoroethyl)-2-methoxyphenyl)imidazo[2,1-b][1,3,4]thiadiazol-2-yl)piperidin-4-yl)methanol; 4-(aminomethyl)-1-(5-(4-(1,2-difluoroethyl)-2-methoxyphenyl)imidazo[2,1-b][1,3,4]thiadiazol-2-yl)piperidin-4-ol; 4-(aminomethyl)-1-(5-(2-(2,2-difluoroethoxy)phenyl)imidazo[2,1-b][1,3,4]thiadiazol-2-yl)piperidin-4-ol; 4-(aminomethyl)-1-(5-(4-isopropyl-2-methoxyphenyl)imidazo[2,1-b][1,3,4]thiadiazol-2-yl)piperidin-4-ol; 4-(aminomethyl)-1-(5-(2-ethoxy-4-isopropylphenyl)imidazo[2,1-b][1,3,4]thiadiazol-2-yl)piperidin-4-ol; 4-(aminomethyl)-1-(5-(2-methoxy-4-(tetrahydrofuran-3-yl)phenyl)imidazo[2,1-b][1,3,4]thiadiazol-2-yl)piperidin-4-ol; 4-(aminomethyl)-1-(5-(2-methoxy-4-(1-methoxycyclopropyl)phenyl)imidazo[2,1-b][1,3,4]thiadiazol-2-yl)piperidin-4-ol; 4-(aminomethyl)-1-(5-(2-methoxy-4-(1-methoxycyclobutyl)phenyl)imidazo[2,1-b][1,3,4]thiadiazol-2-yl)piperidin-4-ol; (4-amino-1-(5-(2-(2-fluoroethoxy)phenyl)imidazo[2,1-b][1,3,4]thiadiazol-2-yl)piperidin-4-yl)methanol; 4-(aminomethyl)-1-(5-(2-(2-fluoroethoxy)phenyl)imidazo[2,1-b][1,3,4]thiadiazol-2-yl)piperidin-4-ol; (4-amino-1-(5-(2-(2,2-difluoroethoxy)phenyl)imidazo[2,1-b][1,3,4]thiadiazol-2-yl)piperidin-4-yl)methanol; 4-(aminomethyl)-1-(5-(2-(2,2-difluoroethoxy)phenyl)imidazo[2,1-b][1,3,4]thiadiazol-2-yl)piperidin-4-ol; (4-amino-1-(5-(2-(2,3-difluoropropoxy)phenyl)imidazo[2,1-b][1,3,4]thiadiazol-2-yl)piperidin-4-yl)methanol; 4-(aminomethyl)-1-(5-(2-(2,3-difluoropropoxy)phenyl)imidazo[2,1-b][1,3,4]thiadiazol-2-yl)piperidin-4-ol; 4-(aminomethyl)-1-(5-(4-chloro-5-isopropyl-2-methoxyphenyl)imidazo[2,1-b][1,3,4]thiadiazol-2-yl)piperidin-4-ol; 4-amino-8-(5-(6-isopropyl-2-methoxypyridin-3-yl)imidazo[2,1-b][1,3,4]thiadiazol-2-yl)-1-thia-8-azaspiro[4.5]decane 1,1-dioxide;

1-(5-(4-fluoro-2-methoxyphenyl)imidazo[2,1-b][1,3,4]thiadiazol-2-yl)-4-(methoxymethyl)piperidin-4-amine; 2-(3-amino-1-(5-(4-fluoro-2-methoxyphenyl)imidazo[2,1-b][1,3,4]thiadiazol-2-yl)pyrrolidin-3-yl)propan-2-ol; 3-amino-1-(5-(4-fluoro-2-methoxyphenyl)imidazo[2,1-b][1,3,4]thiadiazol-2-yl)-4-methylpiperidin-4-ol; (3R,4r,5S)-4-amino-1-(5-(4-fluoro-2-methoxyphenyl)imidazo[2,1-b][1,3,4]thiadiazol-2-yl)-4-methylpiperidine-3,5-diol; and ((3S,4S)-4-amino-1-(5-(4-fluoro-2-methoxyphenyl)imidazo[2,1-b][1,3,4]thiadiazol-2-yl)piperidin-3-yl)methanol.

3. The compound according to claim 1 wherein the compound has the structure:

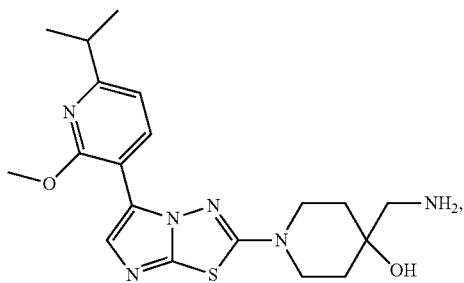 [SMILES: COc1nc(C(C)C)ccc1-c1cnc2sc(N3CCC(O)(CN)CC3)nn12]

or a pharmaceutically acceptable salt thereof.

4. The compound according to claim 3 wherein the compound is the adipate salt form in a 2 to 1 ratio of the compound to adipic acid.

5. A solid or salt form A of the compound according to claim 4 characterized by an X ray diffraction pattern having three or more peaks at 2θ values selected from 3.56, 7.15, and 17.87±0.2°2θ.

6. A solid or salt form B of the compound according to claim 4 characterized by an X ray diffraction pattern having three or more peaks at 2θ values selected from 9.40, 10.93, and 19.33±0.2°2θ.

7. A method of preventing or treating a *Plasmodium* related disease comprising administering to a subject in need thereof a therapeutically effective amount of the compound according to claim 1, or a pharmaceutically acceptable salt thereof; optionally in combination with a second agent.

8. The method according to claim 7, wherein the *Plasmodium* related disease is malaria.

9. The method according to claim 7, wherein the second agent is selected from a kinase inhibitor, an anti-malarial drug and an anti-inflammatory agent.

10. The method according to claim 9, wherein the anti-malarial drug is selected from proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, KAE-609 and KAF-156.

11. The method according to claim 7, wherein the compound according to claim 1 is administered prior to, simultaneously with, or after the second agent.

12. The method according to claim 7, wherein said subject is a human.

* * * * *